US012453697B2

(12) United States Patent
Wardell et al.

(10) Patent No.: US 12,453,697 B2
(45) Date of Patent: *Oct. 28, 2025

(54) PROCESSES FOR PRODUCTION OF TUMOR INFILTRATING LYMPHOCYTES AND USES OF THE SAME IN IMMUNOTHERAPY

(71) Applicant: Iovance Biotherapeutics, Inc., San Carlos, CA (US)

(72) Inventors: Seth Wardell, Tampa, FL (US); Maritza Lienlaf Moreno, Tampa, FL (US)

(73) Assignee: Iovance Biotherapeutics, Inc., San Carlos, CA (US)

( * ) Notice: Subject to any disclaimer, the term of this patent is extended or adjusted under 35 U.S.C. 154(b) by 972 days.

This patent is subject to a terminal disclaimer.

(21) Appl. No.: 17/290,708

(22) PCT Filed: Nov. 4, 2019

(86) PCT No.: PCT/US2019/059718

§ 371 (c)(1),
(2) Date: Apr. 30, 2021

(87) PCT Pub. No.: WO2020/096988

PCT Pub. Date: May 14, 2020

(65) Prior Publication Data

US 2022/0090018 A1 Mar. 24, 2022

Related U.S. Application Data

(60) Provisional application No. 62/903,585, filed on Sep. 20, 2019, provisional application No. 62/755,954, filed on Nov. 5, 2018.

(51) Int. Cl.

| | |
|---|---|
| ***C12N 5/0783*** | (2010.01) |
| ***A61K 9/00*** | (2006.01) |
| ***A61K 35/17*** | (2025.01) |
| ***A61K 38/20*** | (2006.01) |
| ***A61K 40/11*** | (2025.01) |
| ***A61K 40/42*** | (2025.01) |
| ***A61P 35/00*** | (2006.01) |
| *C07K 16/28* | (2006.01) |

(52) U.S. Cl.

CPC ........ *A61K 9/0019* (2013.01); *A61K 38/2013* (2013.01); *A61K 40/11* (2025.01); *A61K 40/42* (2025.01); *A61P 35/00* (2018.01); *C12N 5/0638* (2013.01); *C07K 16/2809* (2013.01); *C12N 2501/2302* (2013.01); *C12N 2502/11* (2013.01)

(58) Field of Classification Search

CPC .... A61P 35/00; A61K 39/4644; A61K 9/0019
See application file for complete search history.

(56) References Cited

U.S. PATENT DOCUMENTS

| | | | |
|---|---|---|---|
| 4,766,106 | A | 8/1988 | Katre et al. |
| 4,897,355 | A | 1/1990 | Eppstein et al. |
| 4,902,502 | A | 2/1990 | Nitecki et al. |
| 5,019,034 | A | 5/1991 | Weaver et al. |
| 5,089,261 | A | 2/1992 | Nitecki et al. |
| 5,126,132 | A | 6/1992 | Rosenberg |
| 5,128,257 | A | 7/1992 | Baer |
| 5,137,817 | A | 8/1992 | Busta et al. |
| 5,173,158 | A | 12/1992 | Schmukler |
| 5,206,344 | A | 4/1993 | Katre et al. |
| 5,232,856 | A | 8/1993 | Firth |
| 5,273,525 | A | 12/1993 | Hofmann |
| 5,279,833 | A | 1/1994 | Rose |
| 5,304,120 | A | 4/1994 | Crandell et al. |
| 5,318,514 | A | 6/1994 | Hofmann |
| 5,443,983 | A | 8/1995 | Ochoa et al. |
| 5,593,875 | A | 1/1997 | Wurm et al. |
| 5,766,902 | A | 6/1998 | Craig et al. |
| 5,849,902 | A | 12/1998 | Arrow et al. |
| 5,908,635 | A | 6/1999 | Thierry |
| 5,928,893 | A | 7/1999 | Kang et al. |
| 6,010,613 | A | 1/2000 | Walters et al. |
| 6,025,337 | A | 2/2000 | Truong et al. |
| 6,056,938 | A | 5/2000 | Unger et al. |
| 6,078,490 | A | 6/2000 | Walters |
| 6,110,490 | A | 8/2000 | Thierry |

(Continued)

FOREIGN PATENT DOCUMENTS

| | | | |
|---|---|---|---|
| CN | 102816734 | A | 12/2012 |
| CN | 106244538 | A | 12/2016 |

(Continued)

OTHER PUBLICATIONS

Rosenberg et al., Clin Cancer Res. 2011;17(13): 4550-7. (Year: 2011).*

Sadeghi et al. Large-scale bioreactor expansion of tumor-infiltrating lymphocytes. J Immunological Methods. 2011; 364: 94-100. (Year: 2011).*

Frank et al., Stable tumor-infiltrating lymphocytes (TIL) phenotype following cryopreservation. J ImmunoTherapy of Cancer. 2016; 4(Suppl 1):82, p. 20. (Year: 2016).*

Maecker et al. Impact of cryopreservation on tetramer, cytokine flow cytometry, and ELISPOT. BMC Immunology 2005, 6:17, p. 1-14. (Year: 2005).*

(Continued)

*Primary Examiner* — James D Schultz
*Assistant Examiner* — Jianjian Zhu
(74) *Attorney, Agent, or Firm* — Lei Xu

(57) ABSTRACT

The present invention provides improved and/or shortened methods for expanding TILs and producing therapeutic populations of TILs, including novel methods for expanding TIL populations in a closed system that lead to improved efficacy, improved phenotype, and increased metabolic health of the TILs in a shorter time period, while allowing for reduced microbial contamination as well as decreased costs. Such TILs find use in therapeutic treatment regimens.

22 Claims, 125 Drawing Sheets

Specification includes a Sequence Listing.

(56) References Cited

U.S. PATENT DOCUMENTS

| | | | |
|---|---|---|---|
| 6,210,669 | B1 | 4/2001 | Aruffo et al. |
| 6,303,121 | B1 | 10/2001 | Kwon |
| 6,352,694 | B1 | 3/2002 | June et al. |
| 6,362,325 | B1 | 3/2002 | Kwon |
| 6,410,517 | B1 | 6/2002 | Truong et al. |
| 6,475,994 | B2 | 11/2002 | Tomalia et al. |
| 6,479,626 | B1 | 11/2002 | Kim et al. |
| 6,489,458 | B2 | 12/2002 | Hackett et al. |
| 6,534,055 | B1 | 3/2003 | June et al. |
| 6,534,261 | B1 | 3/2003 | Cox, III et al. |
| 6,534,484 | B1 | 3/2003 | Wheeler et al. |
| 6,569,997 | B1 | 5/2003 | Kwon |
| 6,607,882 | B1 | 8/2003 | Cox, III et al. |
| 6,627,442 | B1 | 9/2003 | Humeau et al. |
| 6,706,289 | B2 | 3/2004 | Lewis et al. |
| 6,746,838 | B1 | 6/2004 | Choo et al. |
| 6,794,136 | B1 | 9/2004 | Eisenberg et al. |
| 6,824,978 | B1 | 11/2004 | Cox, III et al. |
| 6,866,997 | B1 | 3/2005 | Choo et al. |
| 6,867,041 | B2 | 3/2005 | Berenson et al. |
| 6,887,466 | B2 | 5/2005 | June et al. |
| 6,887,673 | B2 | 5/2005 | Kunkel et al. |
| 6,903,185 | B2 | 6/2005 | Kim et al. |
| 6,905,680 | B2 | 6/2005 | June et al. |
| 6,905,681 | B1 | 6/2005 | June et al. |
| 6,905,685 | B2 | 6/2005 | Kwon |
| 6,933,113 | B2 | 8/2005 | Case et al. |
| 6,974,863 | B2 | 12/2005 | Kwon |
| 6,979,539 | B2 | 12/2005 | Cox, III et al. |
| 7,013,219 | B2 | 3/2006 | Case et al. |
| 7,030,215 | B2 | 4/2006 | Liu et al. |
| 7,144,575 | B2 | 12/2006 | June et al. |
| 7,175,843 | B2 | 2/2007 | June et al. |
| 7,189,705 | B2 | 3/2007 | Lam et al. |
| 7,220,719 | B2 | 5/2007 | Case et al. |
| 7,232,566 | B2 | 6/2007 | June et al. |
| 7,241,573 | B2 | 7/2007 | Choo et al. |
| 7,241,574 | B2 | 7/2007 | Choo et al. |
| 7,288,638 | B2 | 10/2007 | Jure-Kunkel et al. |
| 7,479,269 | B2 | 1/2009 | June et al. |
| 7,504,101 | B2 | 3/2009 | Weinberg |
| 7,550,140 | B2 | 6/2009 | Bakker et al. |
| 7,572,631 | B2 | 8/2009 | Berenson et al. |
| 7,585,849 | B2 | 9/2009 | Liu et al. |
| 7,595,376 | B2 | 9/2009 | Kim et al. |
| 7,622,444 | B2 | 11/2009 | Weinberg |
| 7,687,070 | B2 | 3/2010 | Gebeyehu et al. |
| 7,696,175 | B2 | 4/2010 | Epstein et al. |
| 7,943,743 | B2 | 5/2011 | Korman et al. |
| 7,951,365 | B2 | 5/2011 | Winqvist et al. |
| 7,960,515 | B2 | 6/2011 | Min et al. |
| 7,961,515 | B2 | 6/2011 | Kato et al. |
| 8,007,785 | B2 | 8/2011 | Winqvist et al. |
| 8,008,449 | B2 | 8/2011 | Korman et al. |
| 8,034,334 | B2 | 10/2011 | Dudley et al. |
| 8,133,983 | B2 | 3/2012 | Bakker et al. |
| 8,206,702 | B2 | 6/2012 | Winqvist et al. |
| 8,211,424 | B2 | 7/2012 | Winqvist et al. |
| 8,211,425 | B2 | 7/2012 | Winqvist et al. |
| 8,236,930 | B2 | 8/2012 | Min et al. |
| 8,287,857 | B2 | 10/2012 | Dudley et al. |
| 8,337,850 | B2 | 12/2012 | Ahrens et al. |
| 8,383,099 | B2 | 2/2013 | Dudley et al. |
| 8,450,460 | B2 | 5/2013 | Hill et al. |
| 8,586,526 | B2 | 11/2013 | Gregory et al. |
| 8,617,884 | B2 | 12/2013 | Berenson et al. |
| 8,697,359 | B1 | 4/2014 | Zhang |
| 8,771,945 | B1 | 7/2014 | Zhang |
| 8,795,965 | B2 | 8/2014 | Zhang |
| 8,809,050 | B2 | 8/2014 | Vera et al. |
| 8,821,867 | B2 | 9/2014 | Ahrens et al. |
| 8,865,406 | B2 | 10/2014 | Zhang et al. |
| 8,871,445 | B2 | 10/2014 | Cong et al. |
| 8,889,356 | B2 | 11/2014 | Zhang |
| 8,895,308 | B1 | 11/2014 | Zhang et al. |
| 8,906,616 | B2 | 12/2014 | Zhang et al. |
| 8,921,519 | B2 | 12/2014 | Hill et al. |
| 8,932,814 | B2 | 1/2015 | Cong et al. |
| 8,945,839 | B2 | 2/2015 | Zhang |
| 8,956,860 | B2 | 2/2015 | Vera et al. |
| 8,993,233 | B2 | 3/2015 | Zhang et al. |
| 8,999,641 | B2 | 4/2015 | Zhang et al. |
| 9,006,399 | B2 | 4/2015 | Liu et al. |
| 9,028,824 | B2 | 5/2015 | Min et al. |
| 9,074,185 | B2 | 7/2015 | Dudley et al. |
| 9,080,171 | B2 | 7/2015 | Khvorova et al. |
| 9,163,085 | B2 | 10/2015 | Liu et al. |
| 9,340,599 | B2 | 5/2016 | Hill et al. |
| 9,359,420 | B2 | 6/2016 | Hill et al. |
| 9,468,678 | B2 | 10/2016 | Ahrens et al. |
| 9,476,028 | B2 | 10/2016 | Karlsson-Parra et al. |
| 9,528,088 | B2 | 12/2016 | Berenson et al. |
| 9,687,510 | B2 | 6/2017 | Borrello et al. |
| 9,790,490 | B2 | 10/2017 | Zhang et al. |
| 9,844,569 | B2 | 12/2017 | Gros et al. |
| 9,914,783 | B1 | 3/2018 | Afar et al. |
| 10,130,659 | B2 | 11/2018 | Wardell |
| 10,363,273 | B2 | 7/2019 | Wardell |
| 10,517,894 | B2 | 12/2019 | Frank |
| 10,537,595 | B2 | 1/2020 | Wardell |
| 10,653,723 | B1 | 5/2020 | Wardell |
| 10,905,718 | B2 | 2/2021 | Wardell |
| 10,918,666 | B2 | 2/2021 | Wardell |
| 10,933,094 | B2 | 3/2021 | Wardell |
| 10,946,044 | B2 | 3/2021 | Wardell |
| 10,946,045 | B2 | 3/2021 | Wardell |
| 10,953,046 | B2 | 3/2021 | Wardell |
| 10,953,047 | B2 | 3/2021 | Wardell |
| 11,013,770 | B1 | 5/2021 | Wardell |
| 11,026,974 | B2 | 6/2021 | Frank |
| 11,168,303 | B2 | 11/2021 | Wardell |
| 11,168,304 | B2 | 11/2021 | Wardell |
| 11,220,670 | B2 | 1/2022 | Simpson-Abelson |
| 11,254,913 | B1 | 2/2022 | Wardell |
| 11,293,009 | B2 | 4/2022 | Simpson-Abelson |
| 11,351,198 | B2 | 6/2022 | Frank |
| 11,357,841 | B2 | 6/2022 | Ritthipichai |
| 11,401,503 | B2 * | 8/2022 | Rosenberg ............. A61K 40/11 |
| 11,401,507 | B2 | 8/2022 | Simpson-Abelson |
| 11,433,097 | B2 | 9/2022 | Fardis |
| 11,517,592 | B1 | 12/2022 | Wardell |
| 11,529,372 | B1 | 12/2022 | Wardell |
| 11,541,077 | B2 | 1/2023 | Wardell |
| 11,631,483 | B2 | 4/2023 | Brooks |
| 11,713,446 | B2 | 8/2023 | Chartier-Courtaud |
| 11,819,517 | B2 | 11/2023 | Wardell |
| 2005/0095244 | A1 | 5/2005 | Jure-Kunkel et al. |
| 2005/0106717 | A1 | 5/2005 | Wilson et al. |
| 2010/0136030 | A1 | 6/2010 | Salah-Eddine et al. |
| 2011/0027218 | A1 | 2/2011 | Hill et al. |
| 2011/0039914 | A1 | 2/2011 | Pavco et al. |
| 2011/0052530 | A1 | 3/2011 | Dudley et al. |
| 2011/0111494 | A1 | 5/2011 | Hill et al. |
| 2011/0136228 | A1 | 6/2011 | Vera et al. |
| 2011/0201118 | A1 | 8/2011 | Yang et al. |
| 2012/0244133 | A1 | 9/2012 | Rosenberg et al. |
| 2013/0102075 | A1 | 4/2013 | Vera et al. |
| 2013/0115617 | A1 | 5/2013 | Wilson |
| 2013/0117869 | A1 | 5/2013 | Duchateau et al. |
| 2013/0131141 | A1 | 5/2013 | Khvorova et al. |
| 2013/0131142 | A1 | 5/2013 | Libertine et al. |
| 2013/0315884 | A1 | 11/2013 | Galetto |
| 2014/0227237 | A1 | 8/2014 | June et al. |
| 2014/0328791 | A1 | 11/2014 | Bossard et al. |
| 2014/0377284 | A1 | 12/2014 | Simons et al. |
| 2014/0377739 | A1 | 12/2014 | Welch et al. |
| 2015/0110734 | A1 | 4/2015 | Hill et al. |
| 2015/0126709 | A1 | 5/2015 | Hill et al. |
| 2015/0126710 | A1 | 5/2015 | Hill et al. |
| 2015/0132288 | A1 | 5/2015 | Simons et al. |
| 2015/0175966 | A1 | 6/2015 | Vera et al. |
| 2015/0190506 | A1 | 7/2015 | Cheung et al. |
| 2015/0203871 | A1 | 7/2015 | Juillerat et al. |
| 2015/0320798 | A1 | 11/2015 | Borrello et al. |

(56) References Cited

U.S. PATENT DOCUMENTS

| | | | |
|---|---|---|---|
| 2016/0010058 | A1 | 1/2016 | Gros et al. |
| 2016/0120906 | A1 | 5/2016 | Galetto et al. |
| 2016/0208216 | A1 | 7/2016 | Vera et al. |
| 2016/0215262 | A1 | 7/2016 | Powell |
| 2016/0304873 | A1 | 10/2016 | Wolfson et al. |
| 2017/0044496 | A1 | 2/2017 | Sarnaik et al. |
| 2017/0081635 | A1 | 3/2017 | Sarnaik et al. |
| 2017/0107490 | A1 | 4/2017 | Maeurer |
| 2017/0114321 | A1 | 4/2017 | Berenson et al. |
| 2017/0152478 | A1 | 6/2017 | Rosenberg et al. |
| 2017/0258838 | A1 | 9/2017 | Borrello et al. |
| 2018/0127715 | A1 | 5/2018 | Veerapathran et al. |
| 2018/0148690 | A1 | 5/2018 | Gros et al. |
| 2018/0187150 | A1 | 7/2018 | De Larichaudy |
| 2018/0207201 | A1 | 7/2018 | Wardell et al. |
| 2018/0228841 | A1 | 8/2018 | Frank et al. |
| 2018/0280436 | A1 | 10/2018 | Wardell et al. |
| 2019/0000070 | A1 | 1/2019 | De Larichaudy et al. |
| 2019/0062706 | A1 | 2/2019 | Almaasbak et al. |
| 2019/0136186 | A1 | 5/2019 | Germeroth et al. |

FOREIGN PATENT DOCUMENTS

| | | | |
|---|---|---|---|
| CN | 106591232 | A | 4/2017 |
| CN | 107384867 | A | 11/2017 |
| EP | 0672141 | B1 | 5/2003 |
| EP | 1539929 | B1 | 4/2013 |
| EP | 2925329 | A1 | 10/2015 |
| EP | 3188740 | A1 | 7/2017 |
| EP | 3365434 | A1 | 8/2018 |
| EP | 3368659 | A1 | 9/2018 |
| EP | 3487990 | A1 | 5/2019 |
| TW | 201839129 | A | 11/2018 |
| WO | WO 90/14074 | A1 | 11/1990 |
| WO | WO 91/16024 | A1 | 10/1991 |
| WO | WO 91/17424 | A1 | 11/1991 |
| WO | WO 95/12673 | A1 | 5/1995 |
| WO | WO 95/21925 | A1 | 8/1995 |
| WO | WO 98/13526 | A1 | 4/1998 |
| WO | WO 1998/030679 | A1 | 7/1998 |
| WO | WO 2004031370 | A1 | 4/2004 |
| WO | WO 2006/121810 | A2 | 11/2006 |
| WO | WO 2008/025516 | A2 | 3/2008 |
| WO | WO 2009/007120 | A2 | 1/2009 |
| WO | WO 2009040789 | A2 | 4/2009 |
| WO | WO 2009045457 | A2 | 4/2009 |
| WO | WO 2009102427 | A2 | 8/2009 |
| WO | WO 2010/003766 | A2 | 1/2010 |
| WO | WO 2010/010051 | A1 | 1/2010 |
| WO | WO 2010033246 | A1 | 3/2010 |
| WO | WO 2010033247 | A2 | 3/2010 |
| WO | WO 2010/042433 | A1 | 4/2010 |
| WO | WO 2010/078966 | A1 | 7/2010 |
| WO | WO 2011072088 | A2 | 6/2011 |
| WO | WO 2011119852 | A1 | 9/2011 |
| WO | WO 2011119887 | A1 | 9/2011 |
| WO | WO 2012/027328 | A2 | 3/2012 |
| WO | WO 2012/032433 | A1 | 3/2012 |
| WO | WO 2012065086 | A1 | 5/2012 |
| WO | WO 2012129201 | A1 | 9/2012 |
| WO | WO 2012/177788 | A1 | 12/2012 |
| WO | WO 2013/028231 | A1 | 2/2013 |
| WO | WO 2013/038191 | A2 | 3/2013 |
| WO | WO 2013/057500 | A1 | 4/2013 |
| WO | WO 2013/059343 | A1 | 4/2013 |
| WO | WO 2013/088147 | A1 | 6/2013 |
| WO | WO 2013/173835 | A1 | 11/2013 |
| WO | WO 2013/188427 | A1 | 12/2013 |
| WO | WO 2014/148895 | A1 | 9/2014 |
| WO | WO 2014210036 | A1 | 12/2014 |
| WO | WO 2015009604 | A1 | 1/2015 |
| WO | WO 2015/119923 | A1 | 8/2015 |
| WO | WO 2015157636 | A1 | 10/2015 |
| WO | WO 2015/189357 | A1 | 12/2015 |
| WO | WO 2015188839 | A1 | 12/2015 |
| WO | WO 2015189356 | A1 | 12/2015 |
| WO | WO 2016/053338 | A1 | 4/2016 |
| WO | WO 2016/096903 | A1 | 6/2016 |
| WO | WO 2017/008063 | A1 | 1/2017 |
| WO | WO 2017001784 | A1 | 1/2017 |
| WO | WO 2017048614 | A1 | 3/2017 |
| WO | WO 2017070151 | A1 | 4/2017 |
| WO | WO 2017/123663 | A1 | 7/2017 |
| WO | WO 2018005712 | A1 | 1/2018 |
| WO | WO 2018/081473 | A1 | 5/2018 |
| WO | WO 2018/081789 | A8 | 5/2018 |
| WO | WO 2018102761 | A1 | 6/2018 |
| WO | WO 2018129332 | A1 | 7/2018 |
| WO | WO 2018170188 | A2 | 9/2018 |
| WO | WO 2018182817 | A1 | 10/2018 |
| WO | WO 2018209115 | A1 | 11/2018 |

OTHER PUBLICATIONS

Piscopo et al. Bioengineering Solutions for Manufacturing Challenges in CAR T Cells. Biotechnol. J. 2018; 13: 1700095, p. 1-10. (Year: 2018).*

Chacon et al, Manipulating the Tumor Microenvironment Ex Vivo for Enhanced Expansion of Tumor-Infiltrating Lymphocytes for Adoptive Cell Therapy. Clin Cancer Res; 2015; 21(3); 611-21. (Year: 2015).*

Hopewell et al. Tumor-infiltrating lymphocytes: Streamlining a complex manufacturing process. Cytotherapy, 2019; 21: 307-314. (Year: 2019).*

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes inPatients with Metastatic Melanoma: Intent-to-Treat Analysis and Efficacy after Failure to Prior Immunotherapies"; Clin Cancer Res, 19(17):0F1-0F9 (2013).

Donia M, et al.. Simplified protocol for clinical-grade tumor-infiltrating lymphocyte manufacturing with use of the Wave bioreactor. Cytotherapy. Aug. 2014;16(8):1117-20.

Donia, et al., "Characterization and Comparison of 'Standard' and 'Young' Tumour-Infiltrating Lymphocytes for Adoptive Cell Therapy at a Danish Translational Research Institution"; Scandinavian Journal of Immunology, 75, 157-157 (2012).

Dudley et al., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al.,"Cancer Regression and Autoimmunity in Patients After Clonal Repopulation with Antitumor Lymphocytes", Science, Oct. 2002, 298, 850-54.

International Search Report and Written Opinion for International Patent Application No. PCT/US2018/012633 dated May 25, 2018, 14 pages.

He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.

Jin et al., "Simplified method of the growth of human tumor infiltrating lymphocytes in gas-permiable flasks to numbers needed for patient treatment", J. Immunotherapy, 2012, 35:283-292.

Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65.

Massaro A. F. et al., Solid-phase anti-CD3 antibody activation of murine tumor-infiltrating lymphocytes. Cancer Res, May 1, 1990, vol. 50, No. 9, pp. 2587-2592.

Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.

(56) References Cited

OTHER PUBLICATIONS

Rosenberg SA, Dudley ME. "Adoptive cell therapy for the treatment of patients with metastatic melanoma", Curr Opin Immunol. Apr. 2009;21(2):233-40.
Rosenberg, "IL-2: The First Effective Immunotherapy for Human Cancer," The Journal of Immunology, col. 192, No. 12, Jun. 6, 2014.
Sadeghi, et al., "Rapid expansion of T cells: Effects of culture and cryopreservation and improtance of short-term cell recovery", Acta Oncologica 2013, 52, 978-986.
Somerville RP, et al., "Clinical scale rapid expansion of lymphocytes for adoptive cell transfer therapy in the WAVE® bioreactor", J Transl Med. Apr. 4, 2012;10:69.
Tran et al., "Minimally Cultured tumor-infiltrating lymphocytes display optimal characteristics for adoptive cell therapy", J. Immunother., Oct. 2008; 31(8), 742-751.
Search Reported dated Feb. 2022 for Singapore Patent Application No. 11202104615V, 3 pages.
Ye, Q. et al.; "Engineered artificial antigen presenting cells facilitate direct and efficient expansion of tumor infiltrating lymphocytes", Journal of Translational Medicine, 2011, 9:131.
Akkök, C. A. et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.
Andersen, Rikke et al. "Long-Lasting Complete Responses in Patients with Metastatic Melanoma after Adoptive Cell Therapy with Tumor-Infiltrating Lymphocytes and an Attenuated IL2 Regimen." Clinical cancer research : an official journal of the American Association for Cancer Research vol. 22,15 (2016): 3734-45. doi:10.1158/1078-0432.CCR-15-1879.
Axelsson et al., "Cryopreserved peripheral blood mononuclear cells are suitable for the assessment of immunological markers in type 1 diabetic children", Cryobiology, Aug. 2008, 57, 201-208.
Bajgain, P. et al., "Optimizing the production of suspension cells using the G-Rex "M" series", Molecular Therapy—Methods and Clinical Development, vol. 1, Jan. 1, 2014.
Baruch et al., "Adoptive T cell therapy: An overview of obstacles and opportunities : ACT Obstacles and Opportunities", Cancer, vol. 123, No. S11, May 19, 2017, pp. 2154-2162.
Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.
Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS One, vol. 8, No. 4, Apr. 1, 2013, 25 pages.
Chang C.-H. et al., "Metabolic competition in the tumor microenvironment is a driver of cancer progression", Cell., Sep. 10, 2015, vol. 162, No. 6, pp. 1229-1241.
Chang et al., "Emerging concepts in immunotherapy T-cell metabolism as a therapeutic target", Nat. Immunol., Apr. 2016, 17(4), 364-368.
Dudley et al., "CD8+ Enriched "Young" Tumor Infiltrating Lymphocytes Can Mediate Regression of Metastatic Melanoma" Clin Cancer Res, 16:6122-6131 (2010).
Dudley, et al., "Adoptive Cell Therapy for Patients with Metastatic Melanoma: Evaluation of Intensive Myeloablative Chemoradiation Preparative Regimens" , J. Clin. Oncol., Nov. 2008, 26(32), 5233-39.
Forget et al., "Activation and propagation of tumor infiltrating lymphocytes on clinical-grade designer artificial antigen presenting cells for adoptive immunotherapy of melanoma", Journal of Immunotherapy, vol. 37 No. 9, Nov. 1, 2014, pp. 448-460.
Forget, Marie-Andrée et al. "The beneficial effects of a gas-permeable flask for expansion of Tumor-Infiltrating lymphocytes as reflected in their mitochondrial function and respiration capacity." Oncoimmunology vol. 5,2 e1057386. Jun. 5, 2015, doi:10.1080/2162402X.2015.1057386.
Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.
Garaud, Soizic et al. "A simple and rapid protocol to non-enzymatically dissociate fresh human tissues for the analysis of infiltrating lymphocytes." Journal of visualized experiments : JoVE ,94 52392. Dec. 6, 2014, doi:10.3791/52392.
Gassner, et al., "Fludarabine modulates composition and function of the T Cell pool in patients with chronic lymphocytic leukaemia", Cancer. Immunol. Immunother., 2011, 60, 75-85.
Gattinoni, et al., "Adoptive immunotherapy for cancer: building on success", Nat. Rev. Immunol. May 2006, 6(5), 383-393.
Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014.98.
Glassman, A B, and C E Bennett. "Cryopreservation of human lymphocytes: a brief review and evaluation of an automated liquid nitrogen freezer." Transfusion vol. 19,2 (1979): 178-81. doi:10.1046/j.1537-2995.1979.19279160289.x.
Goff et al., "Tumor Infiltrating Lymphocyte Therapy for Metastatic Melanoma: Analysis of Tumors Resected for TIL", J. Immunother, Oct. 2010, 33(8), 840-847.
Goff SL, et al., "Randomized, Prospective Evaluation Comparing Intensity of Lymphodepletion Before Adoptive Transfer of Tumor-Infiltrating Lymphocytes for Patients With Metastatic Melanoma", J Clin Oncol. Jul. 10, 2016;34(20):2389-79.
Hall et al., "Expansion of tumor-infiltrating lymphocytes (TIL) from human pancreatic tumors", Journal for ImmunoTherapy of Cancer, vol. 4, No. 1, pp. 1-12.
Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.
Henning AL,et al.. Measurement of T-Cell Telomere Length Using Amplified-Signal FISH Staining and Flow Cytometry. Curr Protoc Cytom. Jan. 5, 2017;79:7.47.1-7.47.10. doi:10.1002/cpcy.11. PubMed PMID 28055115.
Hernandez-Chacon et al., "Costimulation through the CD137/4-1BB Pathway Protects Human Melanoma Tumor-infiltrating Lymphocytes from Activation-induced Cell Death and Enhances Anti-tumor Effector Function", Journal of Immuno Therapy, vol. 34, No. 3, Apr. 1, 2011, pp. 236-250.
Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.
Huang et al., "Survival, Persistence, and Progressive Differentiation of Adoptively Transferred Tumor-Reactive T Cells Associated with Tumor Regression"; J. Immunother, 28(3), 258-267 (2005).
Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.
International Search Report and Written Opinion for International Patent Application No. PCT/US2017/058610 dated Mar. 8, 2018, 13 pages.
International Search Report and Written Opinion for International Patent Application No. PCT/US2018/040474 dated Nov. 14, 2018, 17 pages.
Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI.0b013e318209c94c.
Iyer, R.K. et al., "Industrializing Autologous Adoptive Immunotherapies: Manufacturing Advances and Challenges", Frontiers in Medicine, vol. 5, May 23, 2018.

(56) References Cited

OTHER PUBLICATIONS

Jin et al., "Enhanced clinical-scale manufacturing of TCR transduced T-cells using closed culture system modules", Journal of Transactional Medicine, col. 16. No. 1, Jan. 24, 2018.
Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Lee et al., "Tumor-Infiltrating Lymphocytes in Melanoma", Curr Oncol Rep. Aug. 2012, 14, 468-474.
Merhavi-Shoham et al., "Adoptive Cell Therapy for Metastatic Melanoma", Cancer Journal, vol. 23, No. 1, Jan. 1, 2017.
Mullinax et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.
Muranski, et al., "Increased intensity lymphodepletion and adoptive immunotherapy—how far can we go?", Nat. Clin. Pract. Oncol., Dec. 2006, 3, 668-681.
Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.
Riddell, et al., "Restoration of Viral Immunity in Immunodeficient Humans by the Adoptive Transfer of T Cell Clones", Science, Jul. 1992, 257, 238-41.
Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Rosenberg, S A et al. "A new approach to the adoptive immunotherapy of cancer with tumor-infiltrating lymphocytes." Science (New York, N.Y.) vol. 233,4770 (1986): 1318-21. doi: 10.1126/science.3489291.
Rosenberg, S A et al. "Treatment of patients with metastatic melanoma with autologous tumor-infiltrating lymphocytes and interleukin 2." Journal of the National Cancer Institute vol. 86,15 (1994): 1159-66. doi:10.1093/jnci/86.15.1159.
Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi:10.1056/NEJM198812223192527.
Rufer N, et al., "Telomere length dynamics in human lymphocyte subpopulations measured by flow cytometry", Nat Biotechnol. Aug. 1998; 16(8):743-7. PubMed PMID: 9702772.
Shen X,et al.. Persistence of tumor infiltrating lymphocytes in adoptive immunotherapy correlates with telomere length. J Immunother. Jan. 2007;30(1):123-9. PubMed PMID:17198091; PubMed Central PMCID: PMC2151201.
Tsoukas et al., "Activation of resting T lymphocytes by anti-CD3 (T3) antibodies in the absence of monocytes", J. Immunol. 1985, 135, 1719.
Van den Bossche, J. et al. "Metabolic Characterization of Polarized M1 and M2 Bone Marrow-derived Macrophages Using Real-time Extracellular Flux Analysis." Journal of visualized experiments : JoVE , 105 53424. Nov. 28, 2015, doi:10.3791/53424.
Wang & Riviere, "Manufacture of tumor- and virus-specific T lymphocytes for adoptive cell therapies", Cancer Gene Therapy, 2015, 22: 85-94.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Wilson Wolf—Superior Cell Culture Devices, G-Rex, Oct. 31, 2016.
Ye, et al., "Engineered Artificial antigen presenting cells facilitate direct and efficient expansion of tumor infiltrating lymphocytes", J. Translat. Med. 2011, 9(131), 13 pages.
Zhou J, et al.. Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central PMCID: PMC135131.
Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).
Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.
Schiltz, P M et al. "Characterization of tumor-infiltrating lymphocytes derived from human tumors for use as adoptive immunotherapy of cancer." Journal of immunotherapy (Hagerstown, Md. : 1997) vol. 20,5 (1997): 377-86. doi:10.1097/00002371-199709000-00007.
Spiess, P J et al. "In vivo antitumor activity of tumor-infiltrating lymphocytes expanded in recombinant interleukin-2." Journal of the National Cancer Institute vol. 79,5 (1987): 1067-75.
Wu, Richard et al. "Adoptive T-cell therapy using autologous tumor-infiltrating lymphocytes for metastatic melanoma: current status and future outlook." Cancer journal (Sudbury, Mass.) vol. 18,2 (2012): 160-75. doi:10.1097/PPO.0b013e31824d4465.
Meng, Qingda et al. "Expansion of Tumor-reactive T Cells From Patients With Pancreatic Cancer." Journal of immunotherapy (Hagerstown, Md. : 1997) vol. 39,2 (2016): 81-9. doi:10.1097/CJI.0000000000000111.
Peng, Weiyi et al. "PD-1 blockade enhances T-cell migration to tumors by elevating IFN-γ inducible chemokines." Cancer research vol. 72,20 (2012): 5209-18. doi:10.1158/0008-5472.CAN-12-1187.
NCT03374839, ClinicalTrials.gov.
Katz, Steven C et al. "Phase I Hepatic Immunotherapy for Metastases Study of Intra-Arterial Chimeric Antigen Receptor-Modified T-cell Therapy for CEA+ Liver Metastases." Clinical cancer research : an official journal of the American Association for Cancer Research vol. 21,14 (2015): 3149-59. doi:10.1158/1078-0432.CCR-14-1421.
Grimm, E. et al., Characterization of interleukin-2-initiated versus OKT3-initiated human tumor infiltrating lymphocytes from glioblastoma multiforme: growth characteristics, cytolytic activity, and cell phenotype, Cancer Immunol. Immunother., Nov. 1, 1991, 32(6):391-399.
Rohaan, M. et al., "Adoptive transfer of tumor-infiltrating lymphocytes in melanoma: a viable treatment option," Journal for Immuno Therapy of Cancer, 2018, 6:102, pp. 1-16.
Hege, K. et al., "Safety, tumor trafficking and immunogenicity of chimeric antigen receptor (CAR)-T cells specific for TAG-72 in colorectal cancer," Journal for ImmunoTherapy of Cancer, 2017, 5:22, pp. 1-14.
OriGen Biomedical, "PermaLife Cell Culture Bags," 2017, 2 pages.
Ahmad, Z. et al., "scFv Antibody: Principles and Clinical Application," Clin. & Dev. Immunol., 2012, 980250, doi:10.1155/2012/980250, 15 pages.
Augustyns, K., et al., "Incorporation of hexose nucleoside analogues into oligonucleotides: synthesis, base-pairing properties and enzymatic stability," Nucl. Acids. Res., 1992, 20(18):4711-4716.
Beane, J. et al., "Clinical Scale Zinc Finger Nuclease-mediated Gene Editing of PD-1 in Tumor Infiltrating Lymphocytes for the Treatment of Metastatic Melanoma," Molecular Therapy, Aug. 2015, 23(8):1380-1390.
Bergan, R. et al., "Electroporation enhances c-myc antisense oligodeoxynucleotide efficacy," Nucleic Acids Research, 1993, 21(15):3567-3573.
Byrne, M. et al., "Novel Hydrophobically Modified Asymmetric RNAi Compounds (sd-rxRNA) Demonstrate Robust Efficacy in the Eye," J. Ocular Pharmacology and Therapeutics, 2013, 00:00, 1-10.
Cepko, C. et al., "Transduction of Genes Using Retrovirus Vectors," Current Protocols in Molecular Biology, 1996, 9.9.1-9.9.16.

(56) References Cited

OTHER PUBLICATIONS

Chen, C. et al., "High-Efficiency Transformation of Mammalian Cells by Plasmid DNA," Molecular and Cellular Biology, Aug. 1987, 7(8):2745-2752.
Cieri, N. et al., "IL-7 and IL-15 instruct the generation of human memory stem T cells from naive precursors," Blood, Jan. 24, 2013, 121(4):573-584.
Cox, D. et al., "Therapeutic Genome Editing: Prospects and Challenges," Nat. Med., Feb. 2015, 21(2):121-131.
Curti, B. et al., "OX40 is a potent immune stimulating target in late stage cancer patients," Dec. 15, 2013, Cancer Res., 73(24):7189-7198.
Damsky, W. et al., "Mouse melanoma models and cell lines," Pigment Cell Melanoma Res., 2010, 23:853-859.
De Marco, A., "Biotechnological applications of recombinant single-domain antibody fragments," Microbial Cell Factories, 2011, 10:44, 1-14.
Dull T. et al., "A Third-Generation Lentivirus Vector with a Conditional Packaging System," Journal of Virology, Nov. 1998, 72(11):8463-8471.
Eton, O. et al., "A Phase II Study of 'Decrescendo' Interleukin-2 plus Interferon-α-2a in Patients with Progressive Metastatic Melanoma after Chemotherapy," Cancer, Apr. 1, 2000, 88(7):1703-1709.
Fantozzi, A. et al., "Mouse models of breast cancer metastasis," Breast Cancer Research, 2006, 8:212, pp. 1-11.
FDA, "Guidance, Compliance & Regulatory Information (Biologics)," https://www.fda.gov/vaccines-blood-biologics/guidance-compliance-regulatory-information-biologics, 4 pages.
FDA, "Tissue Guidances," http://www.fda.gov/cber/guidelines.htm, 3 pages.
Felgner, P. et al., "Lipofection: A highly efficient, lipid-mediated DNA-transfection procedure," Proc. Natl. Acad. Sci. USA, Nov. 1987, 84:7413-7417.
Fisher, T. et al., "Targeting of 4-1BB by monoclonal antibody PF-05082566 enhances T-cell function and promotes anti-tumor activity," Cancer Immunolog. & Immunother., 2012, 61:1721- 1733.
Fong, M. et al., "Ovarian cancer mouse models: a summary of current models and their limitations," Journal of Ovarian Research, 2009, 2:12, pp. 1-8.
Fry, T. et al., "Interleukin-7: from bench to clinic," Blood, Jun. 1, 2002, 99(11):3892-3904.
Gattinoni, L. et al., "Wnt signaling arrests effector T cell differentiation and generates $CD8^+$ memory stem cells," Nat. Med., Jul. 2009, 15(7):808-813.
Gattinoni, L. et al., "A human memory T-cell subset with stem cell-like properties," Nat. Med., 2011, 17(10):1290-1297.
Gattinoni, L. et al., "Paths to stemness: building the ultimate antitumour T cell," Nat. Rev. Cancer, Oct. 2012, 12(10):671-684.
Gieffers, C. et al., "APG350 Induces Superior Clustering of TRAIL Receptors and Shows Therapeutic Antitumor Efficacy Independent of Cross-Linking via Fcγ Receptors," Mol. Cancer Therapeutics, Dec. 2013, 12(12):2735-2747.
Graham, F. L. et al., "A New Technique for the Assay of Infectivity of Human Adenovirus 5 DNA," Virology, 1973, 52:456-467.
Griesbeck, M. et al., "Sex Differences in Plasmacytoid Dendritic Cell Levels of IRF5 Drive Higher IFN-a Production in Women," The Journal of Immunology, 2015, 195:5327-5336.
Hackett, P. et al., "A Transposon and Transposase System for Human Application," Molecular Therapy, Apr. 2010, 18(4):674-683.
Herreros-Villanueva, M. et al., "Mouse models of pancreatic cancer," World of Gastroenterol, Mar. 28, 2012, 18(12):1286-1294.
Jaeger, H. et al., "Physics of the Granular State," Science, Mar. 20, 1992, 255:1523-1531.
Kandoth, C. et al., "Integrated genomic characterization of endometrial carcinoma," Nature, May 2, 2013, 497(7447):67-73.
Khvorova et al., "The chemical evolution of oligonucleotide therapies of clinical utility," Nat. Biotechnol., Mar. 2017, 35(3):238-248.
Kim, S., "Animal Models of Cancer in the Head and Neck Region," Clinical and Experimental Otorhinolaryngology, Jun. 2009, 2(2):55-60.
Lee, D. et al., "4-1BB Signaling Activates the T Cell Factor 1 Effector/b-Catenin Pathway with Delayed Kinetics via ERK Signaling and Delayed PI3K/AKT Activation to Promote the Proliferation of $CD8^+$ T Cells," Plos One, Jul. 2013, 8(7):e69677, 11 pages.
Levine, B. et al., "Gene transfer in humans using a conditionally replicating lentiviral vector," PNAS, Nov. 14, 2006, 103(46):17372-17377.
Ligtenberg, M. et al., "Self-Delivering RNAi Targeting PD-1 Improves Tumor-Specific T Cell Functionality for Adoptive Cell Therapy of Malignant Melanoma," Mol. Therapy, Jun. 2018, 26(6):1482-1493.
Malek, T., "The Biology of Interleukin-2," Annu. Rev. Immunol., 2008, 26:453-79.
Meuwissen, R., et al., "Mouse models for human lung cancer," Genes & Development, 2005, 19:643-664.
Monnier, P. et al., "In Vivo Applications of Single Chain Fv (Variable Domain) (scFv) Fragments," Antibodies, 2013, 2:193-208.
Musin, O., "The problem of the twenty-five spheres," Russ. Math. Surv., 2003, 58:794-795.
Mullany, L. et al., "Minireview: Animal Models and Mechanisms of Ovarian Cancer Development," Endocrinology, 2012, 153:1585-1592.
NIH—U.S. National Library of Medicine, "A Study of PF-05082566 as a Single Agent and in Combination With Rituximab," ClinicalTrials.gov Identifier: NCT01307267, Mar. 17, 2020, 27 pages.
NIH—U.S. National Library of Medicine, "Safety, Tolerability, Pharmacokinetics, and Immunoregulatory Study of Urelumab (BMS-663513) in Subjects With Advanced and/or Metastatic Solid Tumors and Relapsed/Refractory B-cell Non-Hodgkin's Lymphoma," ClinicalTrials.gov Identifier: NCT01471210, Apr. 19, 2017, 12 pages.
NIH—U.S. National Library of Medicine, "Combination Study of Urelumab and Rituximab in Patients With B-cell Non-Hodgkins Lymphoma," ClinicalTrials.gov Identifier: NCT01775631, Mar. 31, 2017, 10 pages.
NIH—U.S. National Library of Medicine, "Combination Study of Urelumab and Cetuximab in Patients With Advanced/Metastatic Colorectal Cancer or Advanced/Metastatic Head and Neck Cancer," ClinicalTrials.gov Identifier: NCT02110082, Apr. 19, 2017, 11 pages.
NIH—U.S. National Library of Medicine, "An Investigational Immuno-therapy Study to Determine the Safety of Urelumab Given in Combination With Nivolumab in Solid Tumors and B-cell Non-Hodgkin's Lymphoma," ClinicalTrials.gov Identifier: NCT02253992, Oct. 5, 2020, 11 pages.
NIH—U.S. National Library of Medicine, "Study of OX40 Agonist PF-04518600 Alone and in Combination With 4-1BB Agonist PF-05082566," ClinicalTrials.gov Identifier: NCT02315066, Apr. 21, 2022, 39 pages.
NIH—U.S. National Library of Medicine, "A Phase 1 Study of MEDI0562 in Adult Subjects With Selected Advanced Solid Tumors," ClinicalTrials.gov Identifier: NCT02318394, Mar. 31, 2017, 10 pages.
NIH—U.S. National Library of Medicine, "A Study of PF-05082566 In Combination With Mogamulizumab in Patients With Advanced Solid Tumors," ClinicalTrials.gov Identifier: NCT02444793, Feb. 27, 2019, 22 pages.
NIH—U.S. National Library of Medicine, "A Study of Avelumab in Combination With Other Cancer Immunotherapies in Advanced Malignancies (JAVELIN Medley)," ClinicalTrials.gov Identifier: NCT02554812, Jun. 23, 2023, 8 pages.
NIH—U.S. National Library of Medicine, "Combination Study of Urelumab and Rituximab in Patients With B-cell Non-Hodgkins Lymphoma," ClinicalTrials.gov Identifier: NCT02705482, Mar. 31, 2017, 10 pages.
Nelson, B., "IL-2, Regulatory T Cells, and Tolerance," J. Immunol., 2004, 172:3983-3988.
O'Day, S. et al., "Advantages of Concurrent Biochemistry Modified by Decrescendo Interleukin-2, Granulocyte Colony-Stimulating Fac-

(56) References Cited

OTHER PUBLICATIONS tor, and Tamoxifen for Patients With Metastatic Melanoma," J. Clin. Oncol., Sep. 1999, 17(9):2752-2761.
Pfeifer, G. et al., "Mutations induced by ultraviolet light," Mutation Research, 2005, 571:19-31.
Pleasance, E. et al., "A small cell lung cancer genome reports complex tobacco exposure signatures," Nature, Jan. 14, 2010, 463(7278):184-190.
Roberts, S. et al. "An APOBEC Cytidine Deaminase Mutagenesis Pattern is Widespread in Human Cancers," Nat. Gen., Sep. 2013, 45(9):970-976.
Rose, J K et al., "A new cationic liposome reagent mediating nearly quantitative transfection of animal cells," Biotechniques, Apr. 1991, 10(4):520-525.
Ruby, C. et al., "OX40-Enhanced Tumor Rejection and Effector T Cell Differentiation Decreases with Age," J. Immunol., 2009, 182:1481-1489.
Sage, E., "Distribution and Repair of Photolesions in DNA: Genetic Consequences and the Role of Sequence Context," Photochemistry and Photobiology, 1993, 57(1):163-174.
Sano, D. et al., "Xenograft models of head and neck cancers," Head & Neck Oncology, 2009, 1:32, pp. 1-6.
Santegoets, S. et al., "IL-21 promotes the expansion of $CD27^+$ CD28+ tumor infiltrating lymphocytes with high cytotoxic potential and low collateral expansion of regulatory T cells," Journal of Translational Medicine, 2013, 11:37, pp. 1-10.
Segal, N. et al., "Results from an Integrated Safety Analysis of Urelumab, an Agonist Anti-CD137 Monoclonal Antibody," Clin. Cancer Res., Apr. 15, 2017, 23(8):1929-1936.
Sharei, A. et al., "A vector-free microfluidic platform for intracellular delivery," PNAS, Feb. 5, 2013, 110(6):2082-2087.
Sharei, A. et al., "Ex Vivo Cytosolic Delivery of Functional Macromolecules to Immune Cells," PLOS One, 2015, 10(4):e0118803, pp. 1-12.
Smith, C. et al., "Ex vivo expansion of human T cells for adoptive immunotherapy using the novel Xeno-free CTS Immune Cell Serum Replacement," Clinical & Translational Immunology, 2015, 4(e31), doi:10.1038/cti.2014.31.
Spolski, R. et al., "Interleukin-21: a double-edged sword with therapeutic potential," Nature Reviews—Drug Discovery, May 2014, 13:379-395.
Steinke, J. et al., "Th2 cytokines and asthma Interleukin-4: its role in the pathogenesis of asthma, and targeting it for asthma treatment with interleukin-4 receptor antagonists," Respir. Res., 2001, 2:66-70.
Swartz, M. et al., "Tumor Microenvironment Complexity: Emerging Roles in Cancer Therapy," Cancer Res., May 15, 2012, 72(10):2473-2480.
The Cancer Genome Atlas Network, "Comprehensive molecular characterization of human colon and rectal cancer," Nature, 2012, 487:330-337.
Tsong, T., "Electroporation of cell membranes," Biophys. J., Aug. 1991, 60:297-306.
Weinberg, A. et al., "Anti-OX40 (CD134) Administration to Non-human Primates: Immunostimulatory Effects and Toxicokinetic Study," J. Immunother. Nov./Dec. 2006, 29(6):575-585.
Wigler, M. et al., "DNA-mediated transfer of the adenine phosphoribosyltransferase locus into mammalian cells," Proc. Natl. Acad. Sci. USA, Mar. 1979, 76(3):1373-1376.
Zufferey, R. et al., "Multiply attenuated lentiviral vector achieves efficient gene delivery in vivo," Nature Biotechnology, Sep. 1997, 15:871-875.

* cited by examiner

| Process 2A: about 22 days from Steps A - E | Process GEN 3: about 14-18 days from Steps A - E |
| --- | --- |
| **STEP A**<br>Obtain Patient Tumor Sample<br>(optionally can be frozen before Step B; optionally tumor sample can be a core/small biopsy) | **STEP A**<br>Obtain Patient Tumor Sample<br>(optionally can be frozen before Step B) |
| **STEP B**<br>First Expansion<br>(physical fragmentation to at least 40 fragments per container grown for about 3 days to 14 days with media comprising IL-2) | **STEP B**<br>Priming First Expansion<br>(physical fragmentation of up to 60 fragments per container grown for about 1 days to 7/8 days with media comprising IL-2, OKT-3, and optionally antigen-presenting feeder cells) |
| **STEP C**<br>First Expansion to Second Expansion Transition<br>(Step B TILs directly move to Step D, optionally on Step B day 11) | **STEP C**<br>Priming First Expansion to Rapid Second Expansion Transition<br>(Step B TILs directly move to Step D on day 7/8) |
| **STEP D**<br>Second Expansion<br>(TILs grown in growth media medium comprising IL-2, OKT-3, and antigen-presenting feeder cells in a closed container) | **STEP D**<br>Rapid Second Expansion<br>(TILs grown in growth media medium comprising IL-2, OKT-3, and 2X antigen-presenting feeder cells; Days 10-11 scale up and add additional IL-2) |
| **STEP E**<br>Harvest TILS from Step D<br>(TILs harvested via closed system) | **STEP E**<br>Harvest TILS from Step D |
| **STEP F**<br>Final Formulation and/or Transfer to Infusion Bag<br>(optionally cryopreserve) | **STEP F**<br>Final Formulation and/or Transfer to Infusion Bag<br>(optionally cryopreserve) |

FIG. 1A

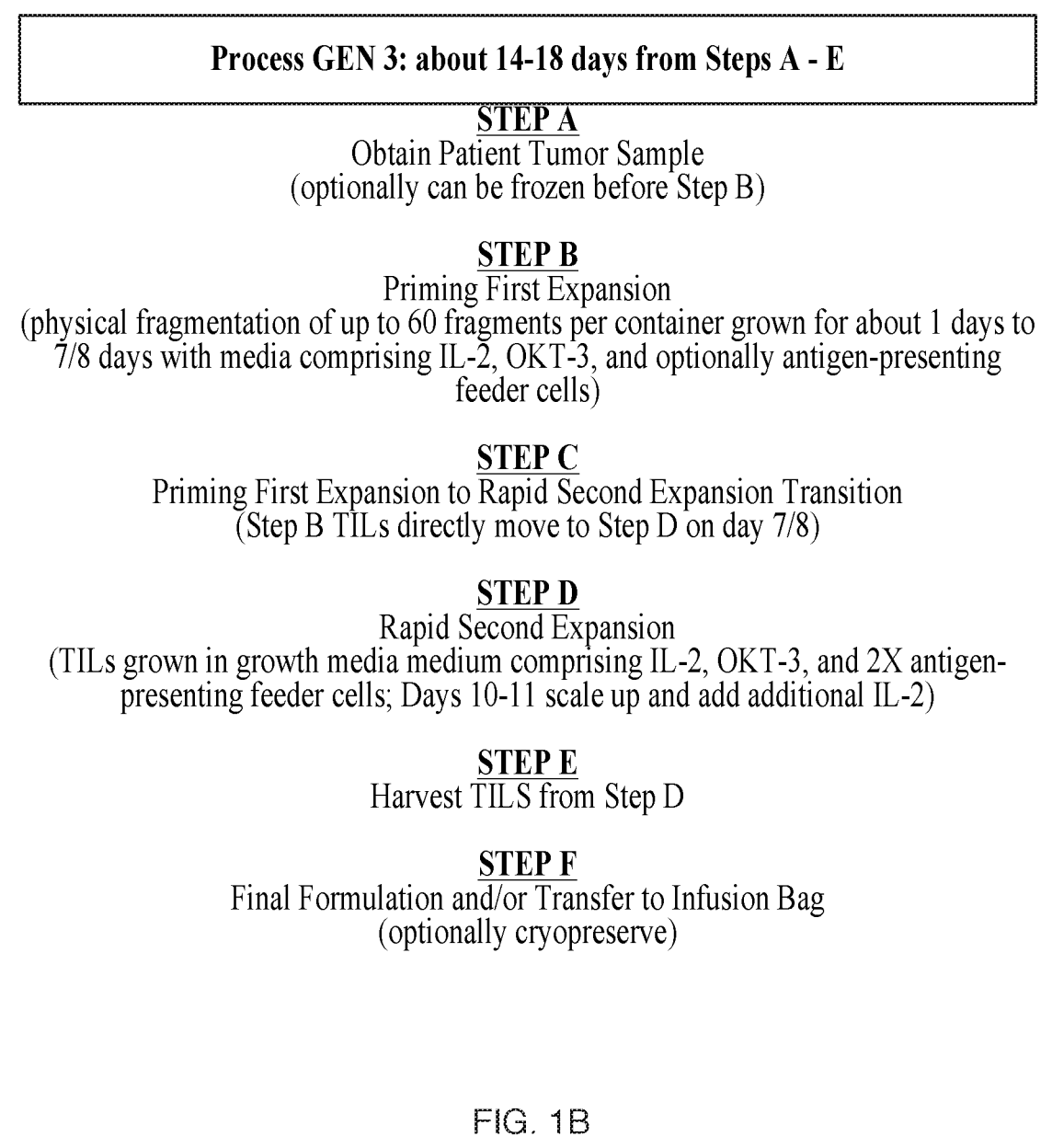

Process GEN 3: about 14-18 days from Steps A - E

STEP A
Obtain Patient Tumor Sample
(optionally can be frozen before Step B)

STEP B
Priming First Expansion
(physical fragmentation of up to 60 fragments per container grown for about 1 days to 7/8 days with media comprising IL-2, OKT-3, and optionally antigen-presenting feeder cells)

STEP C
Priming First Expansion to Rapid Second Expansion Transition
(Step B TILs directly move to Step D on day 7/8)

STEP D
Rapid Second Expansion
(TILs grown in growth media medium comprising IL-2, OKT-3, and 2X antigen-presenting feeder cells; Days 10-11 scale up and add additional IL-2)

STEP E
Harvest TILS from Step D

STEP F
Final Formulation and/or Transfer to Infusion Bag
(optionally cryopreserve)

FIG. 1B

| Embodiment GEN 3.0: about 14-18 days from Steps A-E | Embodiment GEN 3.1 control: about 14-18 days from Steps A - E | Embodiment GEN 3.1 Test/F: about 14-18 days from Steps A - E |
|---|---|---|
| **STEP A** Obtain Patient Tumor Sample (optionally can be frozen before Step B) | **STEP A** Obtain Patient Tumor Sample (optionally can be frozen before Step B) | **STEP A** Obtain Patient Tumor Sample (optionally can be frozen before Step B) |
| **STEP B** Priming First Expansion (physical fragmentation of up to 60 fragments per container grown for about 1 days to 7/8 days with media comprising IL-2) | **STEP B** Priming First Expansion (physical fragmentation of up to 60 fragments per container grown for about 1 days to 7/8 days with media comprising IL-2, and OKT-3) | **STEP B** Priming First Expansion (physical fragmentation of up to 60 fragments per container grown for about 1 days to 7/8 days with media comprising IL-2, OKT-3, and antigen-presenting feeder cells) |
| **STEP C** Priming First Expansion to Rapid Second Expansion Transition (Step B TILs directly move to Step D on day 7/8) | **STEP C** Priming First Expansion to Rapid Second Expansion Transition (Step B TILs directly move to Step D on day 7/8) | **STEP C** Priming First Expansion to Rapid Second Expansion Transition (Step B TILs directly move to Step D on day 7/8) |
| **STEP D** Rapid Second Expansion (TILs grown in growth media medium comprising IL-2, OKT-3, and antigen-presenting feeder cells; Days 10-11 scale up and add additional IL-2) | **STEP D** Rapid Second Expansion (TILs grown in growth media medium comprising IL-2, OKT-3, and 2X antigen-presenting feeder cells; Days 10-11 scale up and add additional IL-2) | **STEP D** Rapid Second Expansion (TILs grown in growth media medium comprising IL-2, OKT-3, and 2X antigen-presenting feeder cells; Days 10-11 scale up and add additional IL-2) |
| **STEP E** Harvest TILS from Step D | **STEP E** Harvest TILS from Step D | **STEP E** Harvest TILS from Step D |
| **STEP F** Final Formulation and/or Transfer to Infusion Bag (optionally cryopreserve) | **STEP F** Final Formulation and/or Transfer to Infusion Bag (optionally cryopreserve) | **STEP F** Final Formulation and/or Transfer to Infusion Bag (optionally cryopreserve) |

FIG. 1C

Modified Gen 2-like Process: about 22 days from Steps A - E

STEP A
Obtain Patient Tumor Sample
(optionally can be frozen before Step B;
optionally tumor sample can be a core/small biopsy)

STEP B1
Initial Culture
physical fragmentation of up to 60 tumor fragments or up to 10 cores/small biopsies per container, TILs grown for 3 days in growth medium comprising IL-2

STEP B2
Priming First Expansion
TILs grown for 8 days in growth medium comprising IL-2, OKT-3, and antigen-presenting feeder cells)

STEP C
Priming First Expansion to Rapid Second Expansion Transition
(Step B TILs directly move to Step D on day 11)

STEP D
Rapid Second Expansion
(volume reduced; TILs grown in growth media medium comprising IL-2, OKT-3, and 50X antigen-presenting feeder cells; Day 16 scale up and add additional IL-2)

STEP E
Harvest TILS from Step D

STEP F
Final Formulation and/or Transfer to Infusion Bag
(optionally cryopreserve)

FIG. 1D

| Tumor ID | L4054 | | L4055 | | M1085T | |
|---|---|---|---|---|---|---|
| Process | Gen 2 | Gen 3 | Gen 2 | Gen 3 | Gen 2 | Gen 3 |
| # Fragments | 21 | 21 | 24 | 24 | 16 | 16 |

| Tumor ID | L4054 | | L4055 | | M1085T | |
|---|---|---|---|---|---|---|
| Process | Gen 2 | Gen 3 | Gen 2 | Gen 3 | Gen 2 | Gen 3 |
| # Fragments | 21 | 21 | 24 | 24 | 16 | 16 |

A
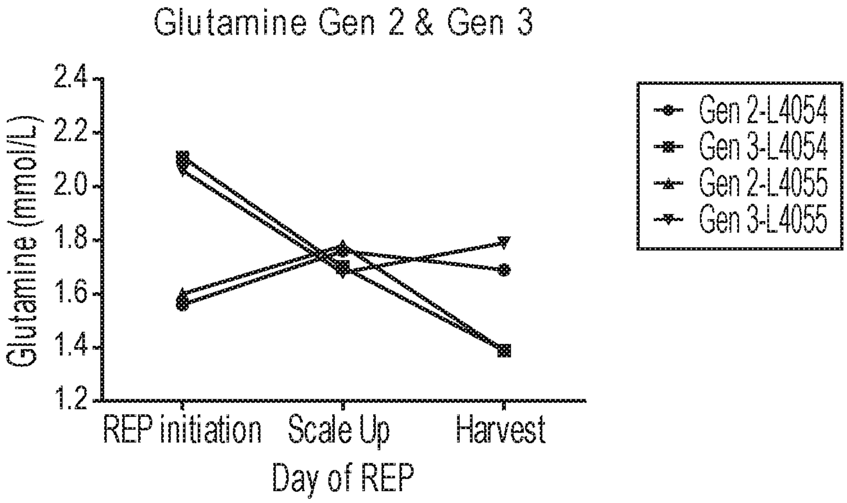
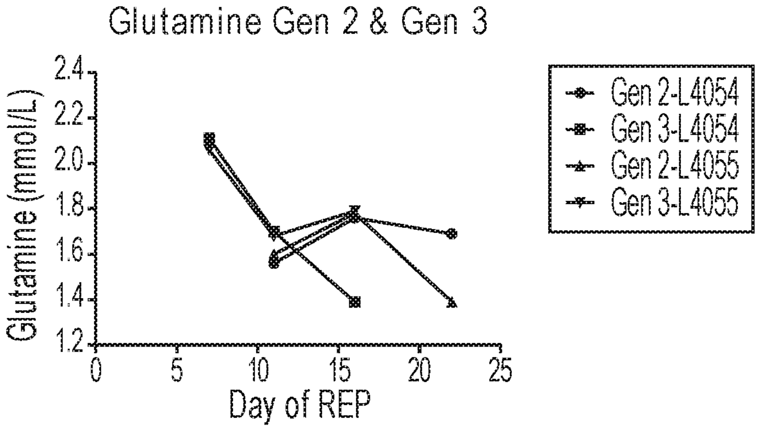
FIG. 10A

B
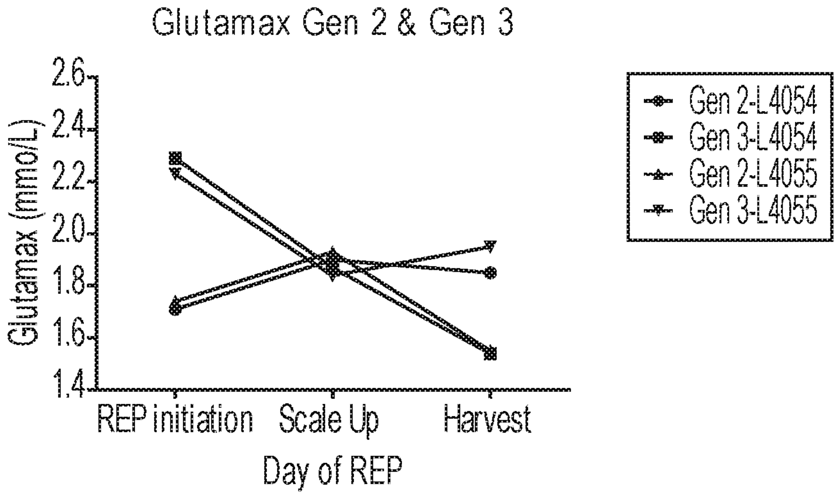
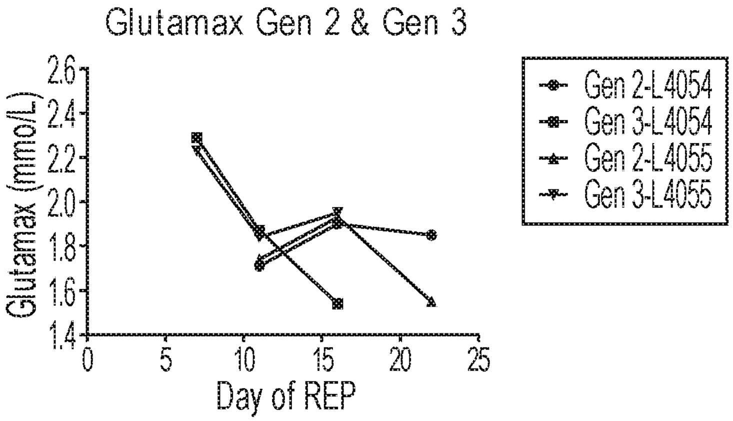
FIG. 10B

C
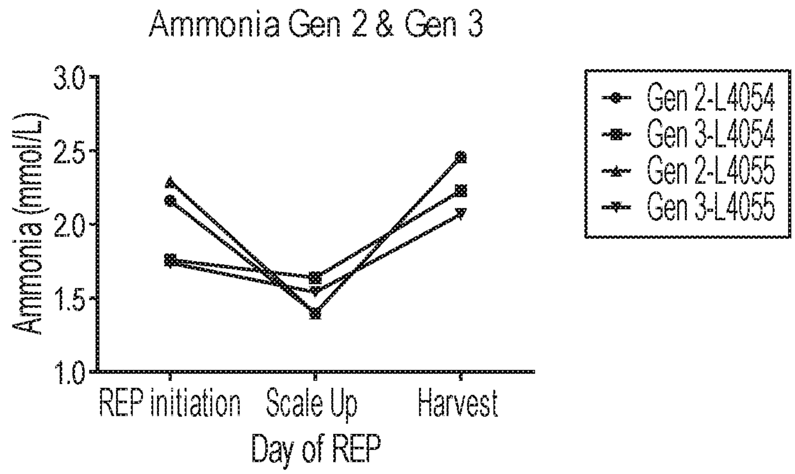
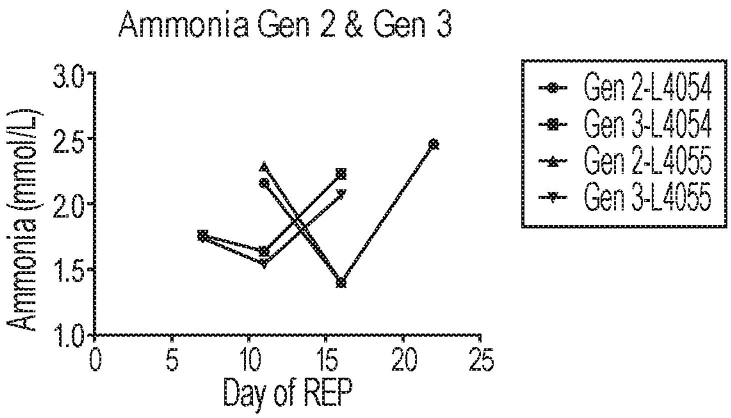
FIG. 10C

| # uCDR3 (% Overlap) | All uCDR3's | | Top 80% uCDR3's | |
|---|---|---|---|---|
| | Gen 2 | Gen 3 | Gen 2 | Gen 3 |
| Gen 2-L4054 | 8915 | 4355 (48.85%) | 205 | 199 (97.07%) |
| Gen 3-L4054 | - | 18130 | - | 223 |

- 199 sequences are shared between Gen 3 and Gen 2 final product, corresponding to 97.07% of top 80% of unique CDR3 sequences from Gen 2 shared with Gen 3 final product.

| # uCDR3 (% Overlap) | All uCDR3's | | Top 80% uCDR3's | |
|---|---|---|---|---|
| | Gen 2 | Gen 3 | Gen 2 | Gen 3 |
| Gen 2-L4055 | 12996 | 6599 (50.77%) | 1843 | 1833 (99.45%) |
| Gen 3-L4055 | - | 27246 | - | 2616 |

- 1833 sequences are shared between Gen 3 and Gen 2 final product, corresponding to 99.45% of top 80% of unique CDR3 sequences from Gen 2 shared with Gen 3 final product.

| Volume (mL) | | Count 1 (cells/mL) | Count 2 (cells/mL) | Count 3 (cells/mL) | Average (cells/mL) | Total Cells Average*Volume |
|---|---|---|---|---|---|---|
| 188 | Total | 2.46E+05 | 2.28E+05 | 2.31E+05 | 2.35E+05 | 4.42E+07 |
| | Live | 2.37E+05 | 2.27E+05 | 2.26E+05 | 2.30E+05 | 4.32E+07 |
| | Dead | 9.26E+03 | 7.03E+02 | 4.63E+03 | 4.86E+03 | 9.14E+05 |
| | % Viability | 96.20% | 99.70% | 98.00% | 97.97% | |
| 188 | Total | 8.26E+04 | 8.00E+04 | 7.66E+04 | 7.97E+04 | 1.50E+07 |
| | Live | 7.60E+04 | 7.54E+04 | 6.89E+04 | 7.34E+04 | 1.38E+07 |
| | Dead | 6.61E+03 | 4.63E+03 | 7.73E+03 | 6.32E+03 | 1.19E+06 |
| | % Viability | 92.00% | 94.20% | 89.90% | 92.03% | |
| 200 | Total | 2.44E+04 | 4.20E+04 | 1.05E+04 | 2.56E+04 | 5.13E+06 |
| | Live | 1.74E+04 | 2.80E+04 | 7.03E+03 | 1.75E+04 | 3.50E+06 |
| | Dead | 7.03E+03 | 1.40E+04 | 3.48E+03 | 8.17E+03 | 1.63E+06 |
| | % Viability | 71.20% | 66.70% | 66.90% | 68.27% | |

FIG. 16

| ID | Volume (mL) | | Count 1 (cells/mL) | Count 3 (cells/mL) | Count 2 (cells/mL) | Average (cells/mL) | Total Cells Average*Volume |
|---|---|---|---|---|---|---|---|
| Gen 3 #L4054 First Round | 1000 | Total | 9.11E+05 | 1.01E+06 | 1.08E+06 | 1.00E+06 | 1.00E+09 |
| | | Live | 8.60E+05 | 9.34E+05 | 1.01E+06 | 9.35E+05 | 9.35E+08 |
| | | Dead | 5.09E+04 | 7.49E+04 | 6.74E+04 | 6.44E+04 | 6.44E+07 |
| | | % Viability | 94.40% | 92.60% | 93.70% | 93.57% | |
| Gen 3 #L4055 Second Round | 1000 | Total | 8.56E+05 | 9.04E+05 | 8.81E+05 | 8.80E+05 | 8.80E+08 |
| | | Live | 8.24E+05 | 8.67E+05 | 8.42E+05 | 8.44E+05 | 8.44E+08 |
| | | Dead | 3.17E+04 | 3.70E+04 | 3.87E+04 | 3.58E+04 | 3.58E+07 |
| | | % Viability | 96.30% | 95.90% | 95.60% | 95.93% | |
| Gen 3 #M1085T | 200 | Total | 2.32E+06 | 2.25E+06 | | 2.29E+06 | 4.57E+08 |
| | | Live | 1.68E+06 | 1.57E+06 | | 1.63E+06 | 3.25E+08 |
| | | Dead | 6.41E+05 | 6.79E+05 | | 6.60E+05 | 1.32E+08 |
| | | % Viability | 72.40% | 69.90% | | 71.15% | |
| Gen 2 #L4054 First Round | 142 | Total | 1.08E+06 | 9.84E+05 | 1.00E+06 | 1.02E+06 | 1.45E+08 |
| | | Live | 1.06E+06 | 9.71E+05 | 9.79E+05 | 1.00E+06 | 1.42E+08 |
| | | Dead | 2.05E+04 | 1.26E+04 | 2.12E+04 | 1.81E+04 | 2.57E+06 |
| | | % Viability | 98.10% | 98.70% | 97.90% | 98.23% | |
| Gen 2 #L4055 Second Round | 96 | Total | 2.93E+05 | 3.05E+05 | 2.64E+05 | 2.87E+05 | 2.76E+07 |
| | | Live | 2.88E+05 | 2.96E+05 | 2.55E+05 | 2.80E+05 | 2.68E+07 |
| | | Dead | 4.72E+03 | 9.14E+03 | 8.26E+03 | 7.37E+03 | 7.08E+05 |
| | | % Viability | 98.40% | 97.00% | 96.90% | 97.43% | |
| Gen 2 #M1085T | 200 | Total | 9.10E+04 | 5.60E+04 | | 7.35E+04 | 1.47E+07 |
| | | Live | 8.05E+04 | 4.21E+04 | | 6.13E+04 | 1.23E+07 |
| | | Dead | 1.04E+04 | 1.39E+04 | | 1.22E+04 | 2.43E+06 |
| | | % Viability | 88.50% | 75.20% | | 81.85% | |

FIG. 17

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4054 First Round -pre LOVO | 1243.1 | Total | 1.40E+07 | 1.46E+07 | | 1.43E+07 | 1.78E+10 |
| | | Live | 1.32E+07 | 1.35E+07 | | 1.34E+07 | 1.66E+10 |
| | | Dead | 8.47E+05 | 1.12E+06 | | 9.84E+05 | 1.22E+09 |
| | | % Viability | 94.00% | 92.40% | | 93.20% | |
| Gen 3 #L4054 First Round -post LOVO | 330 | Total | 6.35E+07 | 6.07E+07 | | 6.21E+07 | 2.05E+10 |
| | | Live | 5.72E+07 | 5.44E+07 | | 5.58E+07 | 1.84E+10 |
| | | Dead | 6.35E+06 | 6.27E+06 | | 6.31E+06 | 2.08E+09 |
| | | % Viability | 90.00% | 89.70% | | 89.85% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #L4055 Second Round -pre LOVO | 1032.6 | Total | 9.49E+06 | 1.05E+07 | | 1.00E+07 | 1.03E+10 |
| | | Live | 8.90E+06 | 9.79E+06 | | 9.35E+06 | 9.65E+09 |
| | | Dead | 5.85E+05 | 6.75E+05 | | 6.30E+05 | 6.51E+08 |
| | | % Viability | 93.80% | 93.60% | | 93.70% | |
| Gen 3 #L4055 Second Round -post LOVO | 330 | Total | 3.31E+07 | 2.82E+07 | 3.18E+07 | 3.07E+07 | 1.01E+10 |
| | | Live | 2.85E+07 | 2.46E+07 | 2.77E+07 | 2.66E+07 | 8.67E+09 |
| | | Dead | 4.56+06 | 3.61+06 | 4.12E+06 | 4.09E+06 | 1.35E+09 |
| | | % Viability | 86.20% | 87.20% | 87.10% | 86.70% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3 #M1085T pre-LOVO | 5000 | Total | 2.26E+06 | 2.64E+06 | | 2.45E+06 | 1.23E+10 |
| | | Live | 1.97E+06 | 2.31E+06 | | 2.14E+06 | 1.07E+10 |
| | | Dead | 2.85E+05 | 3.30E+05 | | 3.08E+05 | 1.54E+09 |
| | | % Viability | 87.40% | 87.50% | | 87.45% | |
| Gen 3 #M1085T post LOVO pre CS10 addition | 150 | Total | 6.27E+07 | 5.44E+07 | | 5.86E+07 | 8.78E+09 |
| | | Live | 5.50E+07 | 4.74E+07 | | 5.12E+07 | 7.68E+09 |
| | | Dead | 7.70E+06 | 6.96E+06 | | 7.33E+06 | 1.10E+09 |
| | | % Viability | 87.70% | 87.20% | | 87.45% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round | 913 | Total | 3.53E+06 | 4.30E+06 | | 3.92E+06 | 3.57E+09 |
| | | Live | 3.35E+06 | 4.00E+06 | | 3.68E+06 | 3.36E+09 |
| | | Dead | 1.75E+05 | 3.03E+05 | | 2.39E+05 | 2.18E+08 |
| | | % Viability | 95.00% | 93.00% | | 94.00% | |
| Gen 2 #L4055 Second Round | 292 | Total | 1.29E+07 | 1.36E+07 | | 1.33E+07 | 3.87E+09 |
| | | Live | 1.16E+07 | 1.23E+07 | | 1.20E+07 | 3.49E+09 |
| | | Dead | 1.27E+06 | 1.23E+06 | | 1.25E+06 | 3.65E+08 |
| | | % Viability | 90.10% | 90.90% | | 90.50% | |
| Gen 2 #M1085T | 369 | Total | 6.75E+06 | 6.98E+06 | | 6.87E+06 | 2.53E+09 |
| | | Live | 5.22E+06 | 5.58E+06 | | 5.40E+06 | 1.99E+09 |
| | | Dead | 1.54E+06 | 1.40E+06 | | 1.47E+06 | 5.42E+08 |
| | | % Viability | 77.20% | 79.90% | | 78.55% | |

FIG. 18

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4054 First Round -pre LOVO | 1385.7 | Total | 3.55E+07 | 4.12E+07 | 4.03E+07 | 3.90E+07 | 5.40E+10 |
| | | Live | 3.26E+07 | 3.73E+07 | 3.67E+07 | 3.55E+07 | 4.92E+10 |
| | | Dead | 2.93E+06 | 3.87E+06 | 3.59E+06 | 3.46E+06 | 4.80E+09 |
| | | % Viability | 91.70% | 90.60% | 91.10% | 91.13% | |
| Gen 2 #L4054 First Round -post LOVO | 330 | Total | 1.70E+08 | 1.79E+08 | 1.68E+08 | 1.72E+08 | 5.69E+10 |
| | | Live | 1.49E+08 | 1.58E+08 | 1.48E+08 | 1.52E+08 | 5.01E+10 |
| | | Dead | 2.16E+07 | 2.04E+07 | 2.00E+07 | 2.07E+07 | 6.82E+09 |
| | | % Viability | 87.30% | 88.60% | 88.10% | 87.95% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #L4055 First Round -pre LOVO | 1968.2 | Total | 3.15E+07 | 2.51E+07 | 2.97E+07 | 2.88E+07 | 5.66E+10 |
| | | Live | 2.89E+07 | 2.25E+07 | 2.72E+07 | 2.62E+07 | 5.16E+10 |
| | | Dead | 2.57E+06 | 2.61E+06 | 2.52E+06 | 2.57E+06 | 5.05E+09 |
| | | % Viability | 91.80% | 89.60% | 91.50% | 90.97% | |
| Gen 2 #L4055 First Round -post LOVO | 330 | Total | 2.33E+08 | 1.89E+08 | 1.53E+08 | 1.92E+08 | 6.33E+10 |
| | | Live | 2.03E+08 | 1.66E+08 | 1.33E+08 | 1.67E+08 | 5.52E+10 |
| | | Dead | 3.00E+07 | 2.24E+07 | 1.94E+07 | 2.39E+07 | 7.90E+09 |
| | | % Viability | 87.10% | 88.10% | 87.30% | 87.50% | |

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 2 #M1085T-pre LOVO | N/S | Total | | | | #DIV/0! | #DIV/0! |
| | | Live | | | | #DIV/0! | #DIV/0! |
| | | Dead | | | | #DIV/0! | #DIV/0! |
| | | % Viability | | | | #DIV/0! | |
| Gen 2 #M1085T - post LOVO pre CS10 addition | 150 | Total | 8.51E+07 | 9.05E+07 | | 8.78E+07 | 1.32E+10 |
| | | Live | 7.33E+07 | 7.79E+07 | | 7.56E+07 | 1.13E+10 |
| | | Dead | 1.18E+07 | 1.26E+07 | | 1.22E+07 | 1.83E+09 |
| | | % Viability | 86.10% | 86.10% | | 86.10% | |

For L4054 Gen 2, post LOVO count was extrapolated to 4 flasks, because was the total number of the study. 1 flask was contaminated, and the extrapolation was done for total = 6.67e+10

FIG. 19

| | S1/S2/All/Live \| Freq. of Parent (%) | S1/S2/All/Live/CD14+ \| Freq. of Parent (%) | S1/S2/All/Live/CD14-/CD3-/NK \| Freq. of null (%) | S1/S2/All/Live/CD14-/CD19 \| Freq. of null (%) | S1/S2/All/Live/CD14-/TCRab \| Freq. of null (%) | S1/S2/All/Live/CD14-/TCRab/CD4 \| Freq. of null (%) | S1/S2/All/Live/CD14-/TCRab/CD4/CD27 \| Freq. of null (%) | S1/S2/All/Live/CD14-/TCRab/CD4/CD28 \| Freq. of null (%) | S1/S2/All/Live/CD14-/TCRab/CD4/CD56 \| Freq. of null (%) | S1/S2/All/Live/CD14-/TCRab/CD4/CD57 \| Freq. of null (%) | S1/S2/All/Live/CD14-/TCRab/CD4/Q1: CCR7-PE-A-, CD45RA-AF700-A+ \| Freq. of Parent (%) | S1/S2/All/Live/CD14-/TCRab/CD4/Q2: CCR7-PE-A+, CD45RA-AF700-A+ \| Freq. of Parent (%) | S1/S2/All/Live/CD14-/TCRab/CD4/Q3: CCR7-PE-A+, CD45RA-AF700-A- \| Freq. of Parent (%) | S1/S2/All/Live/CD14-/TCRab/CD4/Q4: CCR7-PE-A-, CD45RA-AF700-A- \| Freq. of Parent (%) | S1/S2/All/Live/CD14-/TCRab/CD4/Q5: CD62L-B421-A-, CD45RA-AF700-A+ \| Freq. of Parent (%) | S1/S2/All/Live/CD14-/TCRab/CD4/Q6: CD62L-B421-A+, CD45RA-AF700-A+ \| Freq. of Parent (%) | S1/S2/All/Live/CD14-/TCRab/CD4/Q7: CD62L-B421-A+, CD45RA-AF700-A- \| Freq. of Parent (%) | S1/S2/All/Live/CD14-/TCRab/CD4/Q8: CD62L-B421-A-, CD45RA-AF700-A- \| Freq. of Parent (%) |
|---|---|---|---|---|---|---|---|---|---|---|---|---|---|---|---|---|---|---|
| | | | | | | | | | | | TEMRA | NAÏVE | CM | EM | TEMRA | NAÏVE | CM | EM |
| A1 gen2 1st.fcs | 87.2 | 1.77E-03 | 0.66 | 0 | 98.9 | 60.6 | 3.35 | 60.1 | 0.06 | 5.34 | 0.25 | 0.073 | 3.37 | 96.3 | 0.056 | 0.032 | 21.1 | 78.8 |
| A2 gen2 2nd.fcs | 73.5 | 0 | 0.12 | 0 | 99.7 | 83.1 | 7.94 | 82.6 | 0.14 | 6.18 | 0.16 | 0.047 | 2.39 | 97.4 | 0.036 | 0.014 | 8.3 | 91.6 |
| A3 gen3 1st.fcs | 90.4 | 0 | 0.197 | 1.72e-03 | 98.8 | 49.1 | 4.5 | 48.9 | 0.18 | 4.02 | 0.2 | 0.059 | 2.29 | 97.5 | 0.059 | 0.049 | 30.7 | 69.2 |
| A4 gen3 2nd.fcs | 72.1 | 2.56E-03 | 0.44 | 0.018 | 99.3 | 64.4 | 6.27 | 64 | 0.26 | 4.3 | 0.25 | 0.18 | 7.12 | 92.5 | 0.12 | 0.072 | 20.1 | 79.7 |
| A5 PBMC.fcs | 93.7 | 6.07 | 11.6 | 6.12 | 70.9 | 41.1 | 35.6 | 40.4 | 0.041 | 0.31 | 0.91 | 36.1 | 16.2 | 46.9 | 11.4 | 23.1 | 16.4 | 49.1 |

d area was include to make the graph
TCRab+ are = CD3+

| S1/S2/All/Live/CD14-/TCRab/CD8 \| Freq. of null (%) | S1/S2/All/Live/CD14-/TCRab/CD8/CD27 \| Freq. of null (%) | S1/S2/All/Live/CD14-/TCRab/CD8/CD28 \| Freq. of null (%) | S1/S2/All/Live/CD14-/TCRab/CD8/CD56 \| Freq. of null (%) | S1/S2/All/Live/CD14-/TCRab/CD8/CD57 \| Freq. of null (%) | S1/S2/All/Live/CD14-/TCRab/CD8/Q1: CCR7-PE-A-, CD45RA-AF700-A+ \| Freq. of Parent (%) | S1/S2/All/Live/CD14-/TCRab/CD8/Q2: CCR7-PE-A+, CD45RA-AF700-A+ \| Freq. of Parent (%) | S1/S2/All/Live/CD14-/TCRab/CD8/Q3: CCR7-PE-A+, CD45RA-AF700-A- \| Freq. of Parent (%) | S1/S2/All/Live/CD14-/TCRab/CD8/Q4: CCR7-PE-A-, CD45RA-AF700-A- \| Freq. of Parent (%) | S1/S2/All/Live/CD14-/TCRab/CD8/Q5: CD62L-BV421-A-, CD45RA-AF700-A+ \| Freq. of Parent (%) | S1/S2/All/Live/CD14-/TCRab/CD8/Q6: CD62L-BV421-A+, CD45RA-AF700-A+ \| Freq. of Parent (%) | S1/S2/All/Live/CD14-/TCRab/CD8/Q7: CD62L-BV421-A+, CD45RA-AF700-A- \| Freq. of Parent (%) | S1/S2/All/Live/CD14-/TCRab/CD8/Q8: CD62L-BV421-A-, CD45RA-AF700-A- \| Freq. of Parent (%) | S1/S2/All/Live/CD14-/TCRgd \| Freq. of Parent (%) |
|---|---|---|---|---|---|---|---|---|---|---|---|---|---|
| | | | | | TEMRA | NAÏVE | CM | EM | TEMRA | NAÏVE | CM | EM | |
| 37.9 | 3.25 | 37.3 | 0.41 | 2.31 | 0.028 | 0 | 4.24 | 95.7 | 0.033 | 9.37E-03 | 14.1 | 85.9 | 0 |
| 16.1 | 1.08 | 15.8 | 0.67 | 0.17 | 0.042 | 0.014 | 4.76 | 95.2 | 0.071 | 0.014 | 5.24 | 94.7 | 0 |
| 49.2 | 4.83 | 48.5 | 0.71 | 1.53 | 0.056 | 6.97E-03 | 3.11 | 96.8 | 0.077 | 0.017 | 25.5 | 74.4 | 0 |
| 34.6 | 2.46 | 34 | 1.57 | 0.5 | 0.18 | 0.13 | 10.2 | 89.5 | 0.29 | 0.044 | 10.6 | 89.1 | 0 |
| 29.6 | 25.8 | 27.4 | 0.75 | 2.81 | 8.05 | 40.9 | 3.02 | 48 | 22.3 | 27.1 | 6.23 | 44.3 | 0 |

FIG. 20

| | | | | | | |
|---|---|---|---|---|---|---|
| | CD3/CD4 | | | | | |
| | CD38 | HLA-DR | CCR7- CD45RA+ | CCR7+CD45RA+ | CCR7+ CD45RA- | CCR7-CD45RA- |
| GEN 3-Day 16-Harvest | 42.4 | 95.2 | 4.96 | 0.7 | 1.22 | 93.1 |
| GEN 2-D22-Harvest | 50.4 | 98 | 0.61 | 0.13 | 0.3 | 99 |

| | | | | | | | |
|---|---|---|---|---|---|---|---|
| CD3 | CD3/CD8 | | | | | | |
| CD8 | CD38 | HLA-DR | CCR7-CD45RA+ | CCR7+CD45RA+ | CCR7+CD45RA- | CCR7-CD45RA- | |
| | 77.6 | 83.2 | 90.3 | 20.5 | 0.013 | 0.06 | 79.5 |
| | 54.3 | 88 | 83.2 | 4.24 | 0.026 | 1.05 | 94.7 |

FIG. 21

| | | | | CD4 | | | | | | | | | | | |
|---|---|---|---|---|---|---|---|---|---|---|---|---|---|---|---|
| | CD3+ | | CD4+ | 2B4+ | BTLA+ | CD103+ | CD25+ | CD69+ | CD95+ | CXCR3+ | KLRG1+ | LAG3+ | PD1+ | TIGIT+ | TIM3+ |
| Gen 2-L4054 | | | | 0.61 | 99.50 | 1.05 | 14.80 | 43.20 | 99.40 | 52.90 | 2.65 | 5.36 | 81.20 | 88.40 | 78.60 |
| Gen 3-L4054 | | | | 1.11 | 99.50 | 2.28 | 21.70 | 45.40 | 99.70 | 56.90 | 8.06 | 5.07 | 76.70 | 74.10 | 79.30 |
| Gen 2-L4055 | | | | 1.61 | 98.60 | 1.56 | 23.10 | 51.10 | 99.80 | 63.30 | 3.86 | 15.30 | 77.60 | 86.00 | 79.50 |
| Gen 3-L4055 | | | | 3.57 | 99.30 | 2.61 | 54.40 | 57.00 | 99.90 | 48.00 | 8.02 | 10.80 | 61.40 | 47.50 | 84.60 |
| | | | | | | | | | | | | | | | |
| | | | | | | | | | | | | | | | |
| | | | | | | | | | | | | | | | |
| | | | | CD8 | | | | | | | | | | | |
| Gen 2-L4054 | | | CD8+ | 2B4+ | BTLA4+ | CD103+ | CD25+ | CD95+ | CD69+ | CXCR3+ | KLRG1+ | LAG3+ | PD1+ | TIGIT+ | TIM3+ |
| Gen 3-L4054 | | | | 35.20 | 99.50 | 74.90 | 11.80 | 99.80 | 58.30 | 99.10 | 8.03 | 33.10 | 80.60 | 99.10 | 88.30 |
| Gen 2-L4055 | | | | 45.50 | 99.60 | 62.40 | 12.10 | 99.90 | 54.00 | 99.30 | 13.40 | 22.10 | 64.90 | 98.50 | 87.50 |
| Gen 3-L4055 | | | | 40.60 | 98.20 | 19.50 | 32.00 | 99.70 | 75.50 | 96.80 | 22.80 | 27.40 | 28.10 | 92.30 | 75.10 |
| | | | | 62.80 | 99.20 | 29.20 | 45.50 | 99.70 | 58.80 | 99.60 | 13.10 | 16.60 | 34.10 | 71.70 | 63.60 |

FIG. 22

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | TIL- Gen 2-stimulated | TIL- Gen 2-stimulated | TIL- Gen 2-stimulated | TIL- Gen 2-Un-stimulated | TIL- Gen 2-Un-stimulated | TIL- Gen 2-Un-stimulated | MC-Stimulated xG2 | MC-Stimulated xG2 | MC-Stimulated xG2 | Well ID |
| | 1000 | 1000 | 1000 | 3 | 3 | 3 | 3 | 3 | 3 | 3 | 3 | 3 | Conc/Dil |
| B | STD2 | STD2 | STD2 | TIL- Gen 2-stimulated | TIL- Gen 2-stimulated | TIL- Gen 2-stimulated | TIL- Gen 2-Un stimulated | TIL- Gen 2-Un stimulated | TIL- Gen 2-Un stimulated | MC-Stimulated xG2 | MC-Stimulated xG2 | MC-Stimulated xG2 | Well ID |
| | 500 | 500 | 500 | 9 | 9 | 9 | 9 | 9 | 9 | 9 | 9 | 9 | Conc/Dil |
| C | STD3 | STD3 | STD3 | TIL- Gen 2-stimulated | TIL- Gen 2-stimulated | TIL- Gen 2-stimulated | TIL- Gen 2-Un-stimulated | TIL- Gen 2-Un-stimulated | TIL- Gen 2-Un-stimulated | MC-Unstimulated xG2 | MC-Unstimulated xG2 | MC-Unstimulated xG2 | Well ID |
| | 250 | 250 | 250 | 27 | 27 | 27 | 27 | 27 | 27 | 3 | 3 | 3 | Conc/Dil |
| D | STD4 | STD4 | STD4 | TIL- Gen 2-stimulated | TIL- Gen 2-stimulated | TIL- Gen 2-stimulated | TIL- Gen 2-Un stimulated | TIL- Gen 2-Un stimulated | TIL- Gen 2-Un stimulated | MC-Unstimulated xG2 | MC-Unstimulated xG2 | MC-Unstimulated xG2 | Well ID |
| | 125 | 125 | 125 | 81 | 81 | 81 | 81 | 81 | 81 | 9 | 9 | 9 | Conc/Dil |
| E | STD5 | STD5 | STD5 | TIL- Gen 3-stimulated | TIL- Gen 3-stimulated | TIL- Gen 3-stimulated | TIL- Gen 3-Un-stimulated | TIL- Gen 3-Un-stimulated | TIL- Gen 3-Un-stimulated | MC-Stimulated xG3 | MC-Stimulated xG3 | MC-Stimulated xG3 | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | TIL- Gen 3-stimulated | TIL- Gen 3-stimulated | TIL- Gen 3-stimulated | TIL- Gen 3-Un stimulated | TIL- Gen 3-Un stimulated | TIL- Gen 3-Un stimulated | MC-Stimulated xG3 | MC-Stimulated xG3 | MC-Stimulated xG3 | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | TIL- Gen 3-stimulated | TIL- Gen 3-stimulated | TIL- Gen 3-stimulated | TIL- Gen 3-Un-stimulated | TIL- Gen 3-Un-stimulated | TIL- Gen 3-Un-stimulated | MC-Unstimulated xG3 | MC-Unstimulated xG3 | MC-Unstimulated xG3 | Well ID |
| | 15.6 | 15.6 | 15.6 | 27 | 27 | 27 | 27 | 27 | 27 | 3 | 3 | 3 | Conc/Dil |
| H | STD8 | STD8 | STD8 | TIL- Gen 3-stimulated | TIL- Gen 3-stimulated | TIL- Gen 3-stimulated | TIL- Gen 3-Un stimulated | TIL- Gen 3-Un stimulated | TIL- Gen 3-Un stimulated | MC-Unstimulated xG3 | MC-Unstimulated xG3 | MC-Unstimulated xG3 | Well ID |
| | 0 | 0 | 0 | 81 | 81 | 81 | 81 | 81 | 81 | 9 | 9 | 9 | Conc/Dil |
| 22.6 | | | | | | | | | | | | | |
| 22.6 | | | | | | | | | | | | | |

FIG. 23A

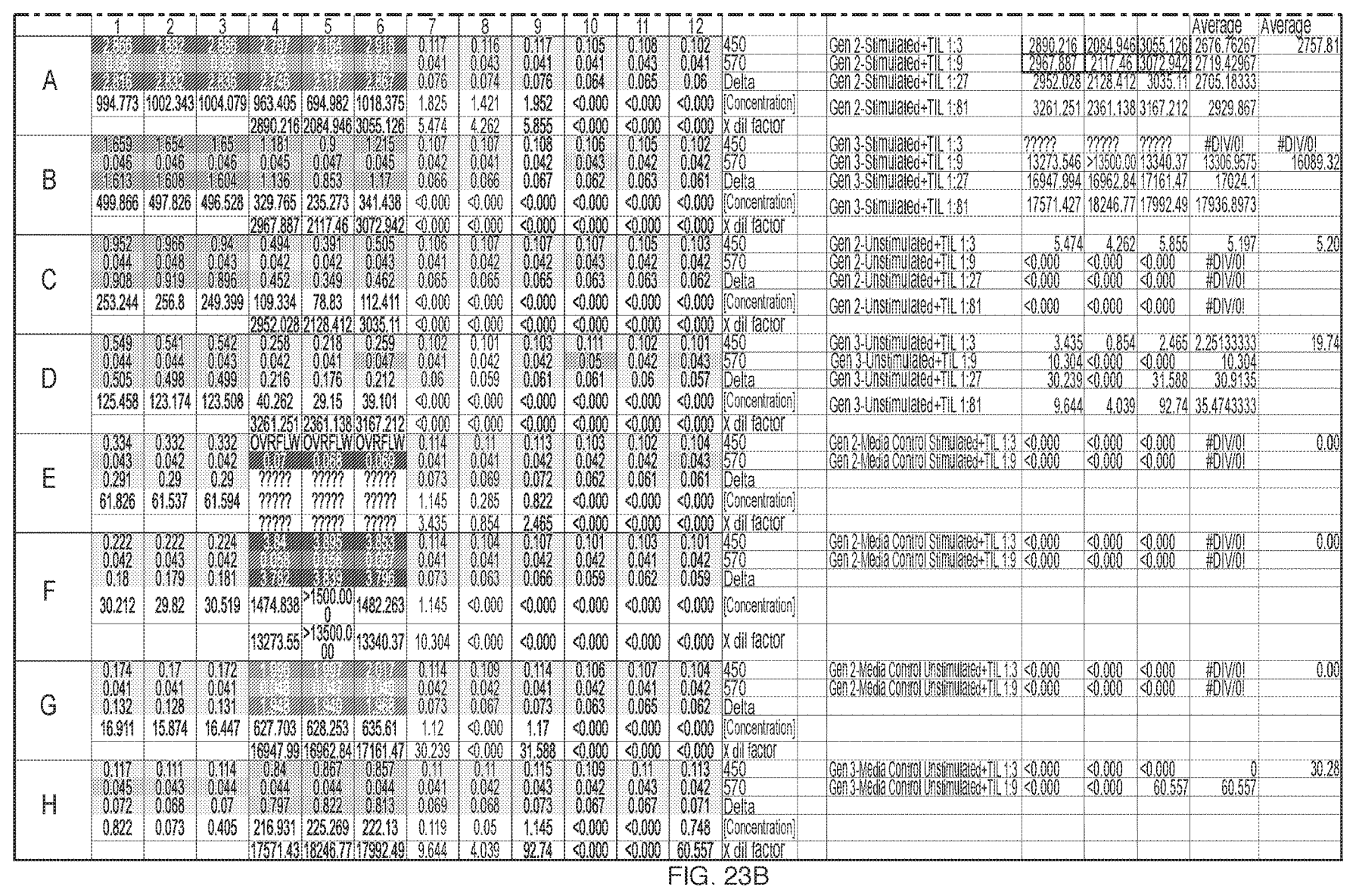

| | 1 | 2 | 3 | 4 | 5 | 6 | 7 | 8 | 9 | 10 | 11 | 12 | | | | | | Average | Average |
|---|---|---|---|---|---|---|---|---|---|---|---|---|---|---|---|---|---|---|---|
| A | [illegible] | [illegible] | [illegible] | [illegible] | [illegible] | [illegible] | 0.117 | 0.116 | 0.117 | 0.105 | 0.108 | 0.102 | 450 | Gen 2-Stimulated+TIL 1:3 | 2890.216 | 2084.946 | 3055.126 | 2676.76267 | 2757.81 |
| | [illegible] | [illegible] | [illegible] | [illegible] | [illegible] | [illegible] | 0.041 | 0.043 | 0.041 | 0.041 | 0.043 | 0.041 | 570 | Gen 2-Stimulated+TIL 1:9 | 2967.887 | 2117.46 | 3072.942 | 2719.42967 | |
| | [illegible] | [illegible] | [illegible] | [illegible] | [illegible] | [illegible] | 0.076 | 0.074 | 0.076 | 0.064 | 0.065 | 0.06 | Delta | Gen 2-Stimulated+TIL 1:27 | 2952.028 | 2128.412 | 3035.11 | 2705.18333 | |
| | 994.773 | 1002.343 | 1004.079 | 963.405 | 694.982 | 1018.375 | 1.825 | 1.421 | 1.952 | <0.000 | <0.000 | <0.000 | [Concentration] | Gen 2-Stimulated+TIL 1:81 | 3261.251 | 2361.138 | 3167.212 | 2929.867 | |
| | | | | 2890.216 | 2084.946 | 3055.126 | 5.474 | 4.262 | 5.855 | <0.000 | <0.000 | <0.000 | X dil factor | | | | | | |
| B | 1.659 | 1.654 | 1.65 | 1.181 | 0.9 | 1.215 | 0.107 | 0.107 | 0.108 | 0.106 | 0.105 | 0.102 | 450 | Gen 3-Stimulated+TIL 1:3 | ????? | ????? | ????? | #DIV/0! | #DIV/0! |
| | 0.046 | 0.046 | 0.046 | 0.045 | 0.047 | 0.045 | 0.042 | 0.041 | 0.042 | 0.043 | 0.042 | 0.042 | 570 | Gen 3-Stimulated+TIL 1:9 | 13273.546 | >13500.00 | 13340.37 | 13306.9575 | 16089.32 |
| | 1.613 | 1.608 | 1.604 | 1.136 | 0.853 | 1.17 | 0.066 | 0.066 | 0.067 | 0.062 | 0.063 | 0.061 | Delta | Gen 3-Stimulated+TIL 1:27 | 16947.994 | 16962.84 | 17161.47 | 17024.1 | |
| | 499.866 | 497.826 | 496.528 | 329.765 | 235.273 | 341.438 | <0.000 | <0.000 | <0.000 | <0.000 | <0.000 | <0.000 | [Concentration] | Gen 3-Stimulated+TIL 1:81 | 17571.427 | 18246.77 | 17992.49 | 17936.8973 | |
| | | | | 2967.887 | 2117.46 | 3072.942 | <0.000 | <0.000 | <0.000 | <0.000 | <0.000 | <0.000 | X dil factor | | | | | | |
| C | 0.952 | 0.966 | 0.94 | 0.494 | 0.391 | 0.505 | 0.106 | 0.107 | 0.107 | 0.107 | 0.105 | 0.103 | 450 | Gen 2-Unstimulated+TIL 1:3 | 5.474 | 4.262 | 5.855 | 5.197 | 5.20 |
| | 0.044 | 0.048 | 0.043 | 0.042 | 0.042 | 0.043 | 0.041 | 0.042 | 0.042 | 0.043 | 0.042 | 0.042 | 570 | Gen 2-Unstimulated+TIL 1:9 | <0.000 | <0.000 | <0.000 | #DIV/0! | |
| | 0.908 | 0.919 | 0.896 | 0.452 | 0.349 | 0.462 | 0.065 | 0.065 | 0.065 | 0.063 | 0.063 | 0.062 | Delta | Gen 2-Unstimulated+TIL 1:27 | <0.000 | <0.000 | <0.000 | #DIV/0! | |
| | 253.244 | 256.8 | 249.399 | 109.334 | 78.83 | 112.411 | <0.000 | <0.000 | <0.000 | <0.000 | <0.000 | <0.000 | [Concentration] | Gen 2-Unstimulated+TIL 1:81 | <0.000 | <0.000 | <0.000 | #DIV/0! | |
| | | | | 2952.028 | 2128.412 | 3035.11 | <0.000 | <0.000 | <0.000 | <0.000 | <0.000 | <0.000 | X dil factor | | | | | | |
| D | 0.549 | 0.541 | 0.542 | 0.258 | 0.218 | 0.259 | 0.102 | 0.101 | 0.103 | 0.111 | 0.102 | 0.101 | 450 | Gen 3-Unstimulated+TIL 1:3 | 3.435 | 0.854 | 2.465 | 2.25133333 | 19.74 |
| | 0.044 | 0.044 | 0.043 | 0.042 | 0.041 | 0.047 | 0.041 | 0.042 | 0.042 | 0.05 | 0.042 | 0.043 | 570 | Gen 3-Unstimulated+TIL 1:9 | 10.304 | <0.000 | <0.000 | 10.304 | |
| | 0.505 | 0.498 | 0.499 | 0.216 | 0.176 | 0.212 | 0.06 | 0.059 | 0.061 | 0.061 | 0.06 | 0.057 | Delta | Gen 3-Unstimulated+TIL 1:27 | 30.239 | <0.000 | 31.588 | 30.9135 | |
| | 125.458 | 123.174 | 123.508 | 40.262 | 29.15 | 39.101 | <0.000 | <0.000 | <0.000 | <0.000 | <0.000 | <0.000 | [Concentration] | Gen 3-Unstimulated+TIL 1:81 | 9.644 | 4.039 | 92.74 | 35.4743333 | |
| | | | | 3261.251 | 2361.138 | 3167.212 | <0.000 | <0.000 | <0.000 | <0.000 | <0.000 | <0.000 | X dil factor | | | | | | |
| E | 0.334 | 0.332 | 0.332 | OVRFLW | OVRFLW | OVRFLW | 0.114 | 0.11 | 0.113 | 0.103 | 0.102 | 0.104 | 450 | Gen 2-Media Control Stimulated+TIL 1:3 | <0.000 | <0.000 | <0.000 | #DIV/0! | 0.00 |
| | 0.043 | 0.042 | 0.042 | [illegible] | [illegible] | [illegible] | 0.041 | 0.041 | 0.042 | 0.042 | 0.042 | 0.043 | 570 | Gen 2-Media Control Stimulated+TIL 1:9 | <0.000 | <0.000 | <0.000 | #DIV/0! | |
| | 0.291 | 0.29 | 0.29 | ????? | ????? | ????? | 0.073 | 0.069 | 0.072 | 0.062 | 0.061 | 0.061 | Delta | | | | | | |
| | 61.826 | 61.537 | 61.594 | ????? | ????? | ????? | 1.145 | 0.285 | 0.822 | <0.000 | <0.000 | <0.000 | [Concentration] | | | | | | |
| | | | | ????? | ????? | ????? | 3.435 | 0.854 | 2.465 | <0.000 | <0.000 | <0.000 | X dil factor | | | | | | |
| F | 0.222 | 0.222 | 0.224 | [illegible] | [illegible] | [illegible] | 0.114 | 0.104 | 0.107 | 0.101 | 0.103 | 0.101 | 450 | Gen 2-Media Control Stimulated+TIL 1:3 | <0.000 | <0.000 | <0.000 | #DIV/0! | 0.00 |
| | 0.042 | 0.043 | 0.042 | [illegible] | [illegible] | [illegible] | 0.041 | 0.041 | 0.042 | 0.042 | 0.041 | 0.042 | 570 | Gen 2-Media Control Stimulated+TIL 1:9 | <0.000 | <0.000 | <0.000 | #DIV/0! | |
| | 0.18 | 0.179 | 0.181 | [illegible] | [illegible] | [illegible] | 0.073 | 0.063 | 0.066 | 0.059 | 0.062 | 0.059 | Delta | | | | | | |
| | 30.212 | 29.82 | 30.519 | 1474.838 | >1500.000 | 1482.263 | 1.145 | <0.000 | <0.000 | <0.000 | <0.000 | <0.000 | [Concentration] | | | | | | |
| | | | | 13273.55 | >13500.000 | 13340.37 | 10.304 | <0.000 | <0.000 | <0.000 | <0.000 | <0.000 | X dil factor | | | | | | |
| G | 0.174 | 0.17 | 0.172 | [illegible] | [illegible] | [illegible] | 0.114 | 0.109 | 0.114 | 0.106 | 0.107 | 0.104 | 450 | Gen 2-Media Control Unstimulated+TIL 1:3 | <0.000 | <0.000 | <0.000 | #DIV/0! | 0.00 |
| | 0.041 | 0.041 | 0.041 | [illegible] | [illegible] | [illegible] | 0.042 | 0.042 | 0.041 | 0.042 | 0.041 | 0.042 | 570 | Gen 2-Media Control Unstimulated+TIL 1:9 | <0.000 | <0.000 | <0.000 | #DIV/0! | |
| | 0.132 | 0.128 | 0.131 | [illegible] | [illegible] | [illegible] | 0.073 | 0.067 | 0.073 | 0.063 | 0.065 | 0.062 | Delta | | | | | | |
| | 16.911 | 15.874 | 16.447 | 627.703 | 628.253 | 635.61 | 1.12 | <0.000 | 1.17 | <0.000 | <0.000 | <0.000 | [Concentration] | | | | | | |
| | | | | 16947.99 | 16962.84 | 17161.47 | 30.239 | <0.000 | 31.588 | <0.000 | <0.000 | <0.000 | X dil factor | | | | | | |
| H | 0.117 | 0.111 | 0.114 | 0.84 | 0.867 | 0.857 | 0.11 | 0.11 | 0.115 | 0.109 | 0.11 | 0.113 | 450 | Gen 3-Media Control Unstimulated+TIL 1:3 | <0.000 | <0.000 | <0.000 | 0 | 30.28 |
| | 0.045 | 0.043 | 0.044 | 0.044 | 0.044 | 0.044 | 0.041 | 0.042 | 0.043 | 0.042 | 0.043 | 0.042 | 570 | Gen 3-Media Control Unstimulated+TIL 1:9 | <0.000 | <0.000 | 60.557 | 60.557 | |
| | 0.072 | 0.068 | 0.07 | 0.797 | 0.822 | 0.813 | 0.069 | 0.068 | 0.073 | 0.067 | 0.067 | 0.071 | Delta | | | | | | |
| | 0.822 | 0.073 | 0.405 | 216.931 | 225.269 | 222.13 | 0.119 | 0.05 | 1.145 | <0.000 | <0.000 | 0.748 | [Concentration] | | | | | | |
| | | | | 17571.43 | 18246.77 | 17992.49 | 9.644 | 4.039 | 92.74 | <0.000 | <0.000 | 60.557 | X dil factor | | | | | | |

FIG. 23B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | TIL- Gen 2- stimulated | TIL- Gen 2- stimulated | TIL- Gen 2- stimulated | TIL- Gen 2-Un- stimulated | TIL- Gen 2-Un- stimulated | TIL- Gen 2-Un- stimulated | MC- Stimulate d xG2 | MC- Stimulate d xG2 | MC- Stimulate d xG2 | Well ID |
| | 1000 | 1000 | 1000 | 3 | 3 | 3 | 3 | 3 | 3 | 3 | 3 | 3 | Conc/Dil |
| B | STD2 | STD2 | STD2 | TIL- Gen 2- stimulated | TIL- Gen 2- stimulated | TIL- Gen 2- stimulated | TIL- Gen 2-Un stimulated | TIL- Gen 2-Un stimulated | TIL- Gen 2-Un stimulated | MC- Stimulate d xG2 | MC- Stimulate d xG2 | MC- Stimulate d xG2 | Well ID |
| | 500 | 500 | 500 | 9 | 9 | 9 | 9 | 9 | 9 | 9 | 9 | 9 | Conc/Dil |
| C | STD3 | STD3 | STD3 | TIL- Gen 2- stimulated | TIL- Gen 2- stimulated | TIL- Gen 2- stimulated | TIL- Gen 2-Un- stimulated | TIL- Gen 2-Un- stimulated | TIL- Gen 2-Un- stimulated | MC- Unstimula ted xG2 | MC- Unstimula ted xG2 | MC- Unstimula ted xG2 | Well ID |
| | 250 | 250 | 250 | 27 | 27 | 27 | 27 | 27 | 27 | 3 | 3 | 3 | Conc/Dil |
| D | STD4 | STD4 | STD4 | TIL- Gen 2- stimulated | TIL- Gen 2- stimulated | TIL- Gen 2- stimulated | TIL- Gen 2-Un stimulated | TIL- Gen 2-Un stimulated | TIL- Gen 2-Un stimulated | MC- Unstimula ted xG2 | MC- Unstimula ted xG2 | MC- Unstimula ted xG2 | Well ID |
| | 125 | 125 | 125 | 81 | 81 | 81 | 81 | 81 | 81 | 9 | 9 | 9 | Conc/Dil |
| E | STD5 | STD5 | STD5 | TIL- Gen 3- stimulated | TIL- Gen 3- stimulated | TIL- Gen 3- stimulated | TIL- Gen 3-Un- stimulated | TIL- Gen 3-Un- stimulated | TIL- Gen 3-Un- stimulated | MC- Stimulate d xG3 | MC- Stimulate d xG3 | MC- Stimulate d xG3 | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | TIL- Gen 3- stimulated | TIL- Gen 3- stimulated | TIL- Gen 3- stimulated | TIL- Gen 3-Un stimulated | TIL- Gen 3-Un stimulated | TIL- Gen 3-Un stimulated | MC- Stimulate d xG3 | MC- Stimulate d xG3 | MC- Stimulate d xG3 | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | TIL- Gen 3- stimulated | TIL- Gen 3- stimulated | TIL- Gen 3- stimulated | TIL- Gen 3-Un- stimulated | TIL- Gen 3-Un- stimulated | TIL- Gen 3-Un- stimulated | MC- Unstimula ted xG3 | MC- Unstimula ted xG3 | MC- Unstimula ted xG3 | Well ID |
| | 15.6 | 15.6 | 15.6 | 27 | 27 | 27 | 27 | 27 | 27 | 3 | 3 | 3 | Conc/Dil |
| H | STD8 | STD8 | STD8 | TIL- Gen 3- stimulated | TIL- Gen 3- stimulated | TIL- Gen 3- stimulated | TIL- Gen 3-Un stimulated | TIL- Gen 3-Un stimulated | TIL- Gen 3-Un stimulated | MC- Unstimula ted xG3 | MC- Unstimula ted xG3 | MC- Unstimula ted xG3 | Well ID |
| | 0 | 0 | 0 | 81 | 81 | 81 | 81 | 81 | 81 | 9 | 9 | 9 | Conc/Dil |
| 22.9 | | | | | | | | | | | | | |
| 22.9 | | | | | | | | | | | | | |

FIG. 24A

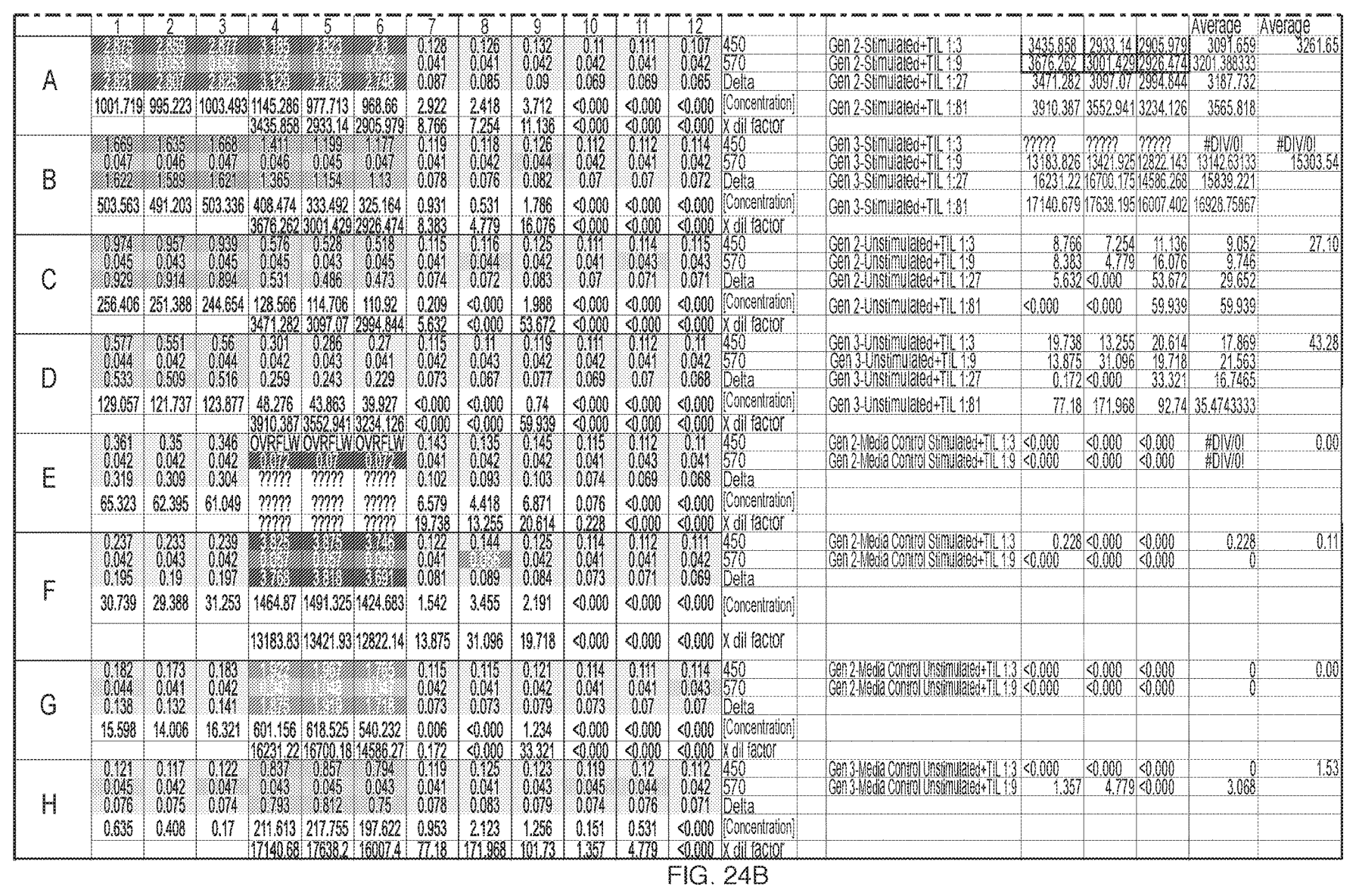

| | 1 | 2 | 3 | 4 | 5 | 6 | 7 | 8 | 9 | 10 | 11 | 12 | | | | | | Average | Average |
|---|---|---|---|---|---|---|---|---|---|---|---|---|---|---|---|---|---|---|---|
| A | [illegible] | [illegible] | [illegible] | [illegible] | [illegible] | [illegible] | 0.128 | 0.126 | 0.132 | 0.11 | 0.111 | 0.107 | 450 | Gen 2-Stimulated+TIL 1:3 | 3435.858 | 2933.14 | 2905.979 | 3091.659 | 3261.65 |
| | [illegible] | [illegible] | [illegible] | [illegible] | [illegible] | [illegible] | 0.041 | 0.041 | 0.042 | 0.042 | 0.041 | 0.042 | 570 | Gen 2-Stimulated+TIL 1:9 | 3676.262 | 3001.429 | 2926.474 | 3201.388333 | |
| | [illegible] | [illegible] | [illegible] | [illegible] | [illegible] | [illegible] | 0.087 | 0.085 | 0.09 | 0.069 | 0.069 | 0.065 | Delta | Gen 2-Stimulated+TIL 1:27 | 3471.282 | 3097.07 | 2994.844 | 3187.732 | |
| | 1001.719 | 995.223 | 1003.493 | 1145.286 | 977.713 | 968.66 | 2.922 | 2.418 | 3.712 | <0.000 | <0.000 | <0.000 | [Concentration] | Gen 2-Stimulated+TIL 1:81 | 3910.387 | 3552.941 | 3234.126 | 3565.818 | |
| | | | | 3435.858 | 2933.14 | 2905.979 | 8.766 | 7.254 | 11.136 | <0.000 | <0.000 | <0.000 | X dil factor | | | | | | |
| B | 1.669 | 1.635 | 1.668 | 1.411 | 1.199 | 1.177 | 0.119 | 0.118 | 0.126 | 0.112 | 0.112 | 0.114 | 450 | Gen 3-Stimulated+TIL 1:3 | ????? | ????? | ????? | #DIV/0! | #DIV/0! |
| | 0.047 | 0.046 | 0.047 | 0.046 | 0.045 | 0.047 | 0.041 | 0.042 | 0.044 | 0.042 | 0.041 | 0.042 | 570 | Gen 3-Stimulated+TIL 1:9 | 13183.826 | 13421.925 | 12822.143 | 13142.63133 | 15303.54 |
| | 1.622 | 1.589 | 1.621 | 1.365 | 1.154 | 1.13 | 0.078 | 0.076 | 0.082 | 0.07 | 0.07 | 0.072 | Delta | Gen 3-Stimulated+TIL 1:27 | 16231.22 | 16700.175 | 14586.268 | 15839.221 | |
| | 503.563 | 491.203 | 503.336 | 408.474 | 333.492 | 325.164 | 0.931 | 0.531 | 1.786 | <0.000 | <0.000 | <0.000 | [Concentration] | Gen 3-Stimulated+TIL 1:81 | 17140.679 | 17638.195 | 16007.402 | 16928.75867 | |
| | | | | 3676.262 | 3001.429 | 2926.474 | 8.383 | 4.779 | 16.076 | <0.000 | <0.000 | <0.000 | X dil factor | | | | | | |
| C | 0.974 | 0.957 | 0.939 | 0.576 | 0.528 | 0.518 | 0.115 | 0.116 | 0.125 | 0.111 | 0.114 | 0.115 | 450 | Gen 2-Unstimulated+TIL 1:3 | 8.766 | 7.254 | 11.136 | 9.052 | 27.10 |
| | 0.045 | 0.043 | 0.045 | 0.045 | 0.043 | 0.045 | 0.041 | 0.044 | 0.042 | 0.041 | 0.043 | 0.043 | 570 | Gen 2-Unstimulated+TIL 1:9 | 8.383 | 4.779 | 16.076 | 9.746 | |
| | 0.929 | 0.914 | 0.894 | 0.531 | 0.486 | 0.473 | 0.074 | 0.072 | 0.083 | 0.07 | 0.071 | 0.071 | Delta | Gen 2-Unstimulated+TIL 1:27 | 5.632 | <0.000 | 53.672 | 29.652 | |
| | 256.406 | 251.388 | 244.654 | 128.566 | 114.706 | 110.92 | 0.209 | <0.000 | 1.988 | <0.000 | <0.000 | <0.000 | [Concentration] | Gen 2-Unstimulated+TIL 1:81 | <0.000 | <0.000 | 59.939 | 59.939 | |
| | | | | 3471.282 | 3097.07 | 2994.844 | 5.632 | <0.000 | 53.672 | <0.000 | <0.000 | <0.000 | X dil factor | | | | | | |
| D | 0.577 | 0.551 | 0.56 | 0.301 | 0.286 | 0.27 | 0.115 | 0.11 | 0.119 | 0.111 | 0.112 | 0.11 | 450 | Gen 3-Unstimulated+TIL 1:3 | 19.738 | 13.255 | 20.614 | 17.869 | 43.28 |
| | 0.044 | 0.042 | 0.044 | 0.042 | 0.043 | 0.041 | 0.042 | 0.043 | 0.042 | 0.042 | 0.041 | 0.042 | 570 | Gen 3-Unstimulated+TIL 1:9 | 13.875 | 31.096 | 19.718 | 21.563 | |
| | 0.533 | 0.509 | 0.516 | 0.259 | 0.243 | 0.229 | 0.073 | 0.067 | 0.077 | 0.069 | 0.07 | 0.068 | Delta | Gen 3-Unstimulated+TIL 1:27 | 0.172 | <0.000 | 33.321 | 16.7465 | |
| | 129.057 | 121.737 | 123.877 | 48.276 | 43.863 | 39.927 | <0.000 | <0.000 | 0.74 | <0.000 | <0.000 | <0.000 | [Concentration] | Gen 3-Unstimulated+TIL 1:81 | 77.18 | 171.968 | 92.74 | 35.4743333 | |
| | | | | 3910.387 | 3552.941 | 3234.126 | <0.000 | <0.000 | 59.939 | <0.000 | <0.000 | <0.000 | X dil factor | | | | | | |
| E | 0.361 | 0.35 | 0.346 | OVRFLW | OVRFLW | OVRFLW | 0.143 | 0.135 | 0.145 | 0.115 | 0.112 | 0.11 | 450 | Gen 2-Media Control Stimulated+TIL 1:3 | <0.000 | <0.000 | <0.000 | #DIV/0! | 0.00 |
| | 0.042 | 0.042 | 0.042 | [illegible] | [illegible] | [illegible] | 0.041 | 0.042 | 0.042 | 0.041 | 0.043 | 0.041 | 570 | Gen 2-Media Control Stimulated+TIL 1:9 | <0.000 | <0.000 | <0.000 | #DIV/0! | |
| | 0.319 | 0.309 | 0.304 | ????? | ????? | ????? | 0.102 | 0.093 | 0.103 | 0.074 | 0.069 | 0.068 | Delta | | | | | | |
| | 65.323 | 62.395 | 61.049 | ????? | ????? | ????? | 6.579 | 4.418 | 6.871 | 0.076 | <0.000 | <0.000 | [Concentration] | | | | | | |
| | | | | ????? | ????? | ????? | 19.738 | 13.255 | 20.614 | 0.228 | <0.000 | <0.000 | X dil factor | | | | | | |
| F | 0.237 | 0.233 | 0.239 | [illegible] | [illegible] | [illegible] | 0.122 | 0.144 | 0.125 | 0.114 | 0.112 | 0.111 | 450 | Gen 2-Media Control Stimulated+TIL 1:3 | 0.228 | <0.000 | <0.000 | 0.228 | 0.11 |
| | 0.042 | 0.043 | 0.042 | [illegible] | [illegible] | [illegible] | 0.041 | [illegible] | 0.042 | 0.041 | 0.041 | 0.042 | 570 | Gen 2-Media Control Stimulated+TIL 1:9 | <0.000 | <0.000 | <0.000 | 0 | |
| | 0.195 | 0.19 | 0.197 | [illegible] | [illegible] | [illegible] | 0.081 | 0.089 | 0.084 | 0.073 | 0.071 | 0.069 | Delta | | | | | | |
| | 30.739 | 29.388 | 31.253 | 1464.87 | 1491.325 | 1424.683 | 1.542 | 3.455 | 2.191 | <0.000 | <0.000 | <0.000 | [Concentration] | | | | | | |
| | | | | 13183.83 | 13421.93 | 12822.14 | 13.875 | 31.096 | 19.718 | <0.000 | <0.000 | <0.000 | X dil factor | | | | | | |
| G | 0.182 | 0.173 | 0.183 | [illegible] | [illegible] | [illegible] | 0.115 | 0.115 | 0.121 | 0.114 | 0.111 | 0.114 | 450 | Gen 2-Media Control Unstimulated+TIL 1:3 | <0.000 | <0.000 | <0.000 | 0 | 0.00 |
| | 0.044 | 0.041 | 0.042 | [illegible] | [illegible] | [illegible] | 0.042 | 0.041 | 0.042 | 0.041 | 0.041 | 0.043 | 570 | Gen 2-Media Control Unstimulated+TIL 1:9 | <0.000 | <0.000 | <0.000 | 0 | |
| | 0.138 | 0.132 | 0.141 | [illegible] | [illegible] | [illegible] | 0.073 | 0.073 | 0.079 | 0.073 | 0.07 | 0.07 | Delta | | | | | | |
| | 15.598 | 14.006 | 16.321 | 601.156 | 618.525 | 540.232 | 0.006 | <0.000 | 1.234 | <0.000 | <0.000 | <0.000 | [Concentration] | | | | | | |
| | | | | 16231.22 | 16700.18 | 14586.27 | 0.172 | <0.000 | 33.321 | <0.000 | <0.000 | <0.000 | X dil factor | | | | | | |
| H | 0.121 | 0.117 | 0.122 | 0.837 | 0.857 | 0.794 | 0.119 | 0.125 | 0.123 | 0.119 | 0.12 | 0.112 | 450 | Gen 3-Media Control Unstimulated+TIL 1:3 | <0.000 | <0.000 | <0.000 | 0 | 1.53 |
| | 0.045 | 0.042 | 0.047 | 0.043 | 0.045 | 0.043 | 0.041 | 0.041 | 0.043 | 0.045 | 0.044 | 0.042 | 570 | Gen 3-Media Control Unstimulated+TIL 1:9 | 1.357 | 4.779 | <0.000 | 3.068 | |
| | 0.076 | 0.075 | 0.074 | 0.793 | 0.812 | 0.75 | 0.078 | 0.083 | 0.079 | 0.074 | 0.076 | 0.071 | Delta | | | | | | |
| | 0.635 | 0.408 | 0.17 | 211.613 | 217.755 | 197.622 | 0.953 | 2.123 | 1.256 | 0.151 | 0.531 | <0.000 | [Concentration] | | | | | | |
| | | | | 17140.68 | 17638.2 | 16007.4 | 77.18 | 171.968 | 101.73 | 1.357 | 4.779 | <0.000 | X dil factor | | | | | | |

FIG. 24B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 1000 | 1000 | 1000 | 3 | 3 | 3 | 3 | 3 | 3 | 3 | 3 | 3 | Conc/Dil |
| B | STD2 | STD2 | STD2 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 500 | 500 | 500 | 9 | 9 | 9 | 9 | 9 | 9 | 9 | 9 | 9 | Conc/Dil |
| C | STD3 | STD3 | STD3 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 250 | 250 | 250 | 27 | 27 | 27 | 27 | 27 | 27 | 27 | 27 | 27 | Conc/Dil |
| D | STD4 | STD4 | STD4 | 2A-BEAD+TIL | 2A-BEAD+TIL | 2A-BEAD+TIL | 2A-MC | 2A-MC | 2A-MC | 2A-Un-stimulated | 2A-Un-stimulated | 2A-Un-stimulated | Well ID |
| | 125 | 125 | 125 | 81 | 81 | 81 | 81 | 81 | 81 | 81 | 81 | 81 | Conc/Dil |
| E | STD5 | STD5 | STD5 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 15.6 | 15.6 | 15.6 | 27 | 27 | 27 | 27 | 27 | 27 | 27 | 27 | 27 | Conc/Dil |
| H | STD8 | STD8 | STD8 | 2A-BEAD+TIL | 2A-BEAD+TIL | 2A-BEAD+TIL | 2B-Un-stimulated | 2B-Un-stimulated | 2B-Un-stimulated | 2B-MC | 2B-MC | 2B-MC | Well ID |
| | 0 | 0 | 0 | 81 | 81 | 81 | 81 | 81 | 81 | 81 | 81 | 81 | Conc/Dil |
| 24.1 | | | | | | | | | | | | | |
| 24.1 | | | | | | | | | | | | | |

FIG. 25A

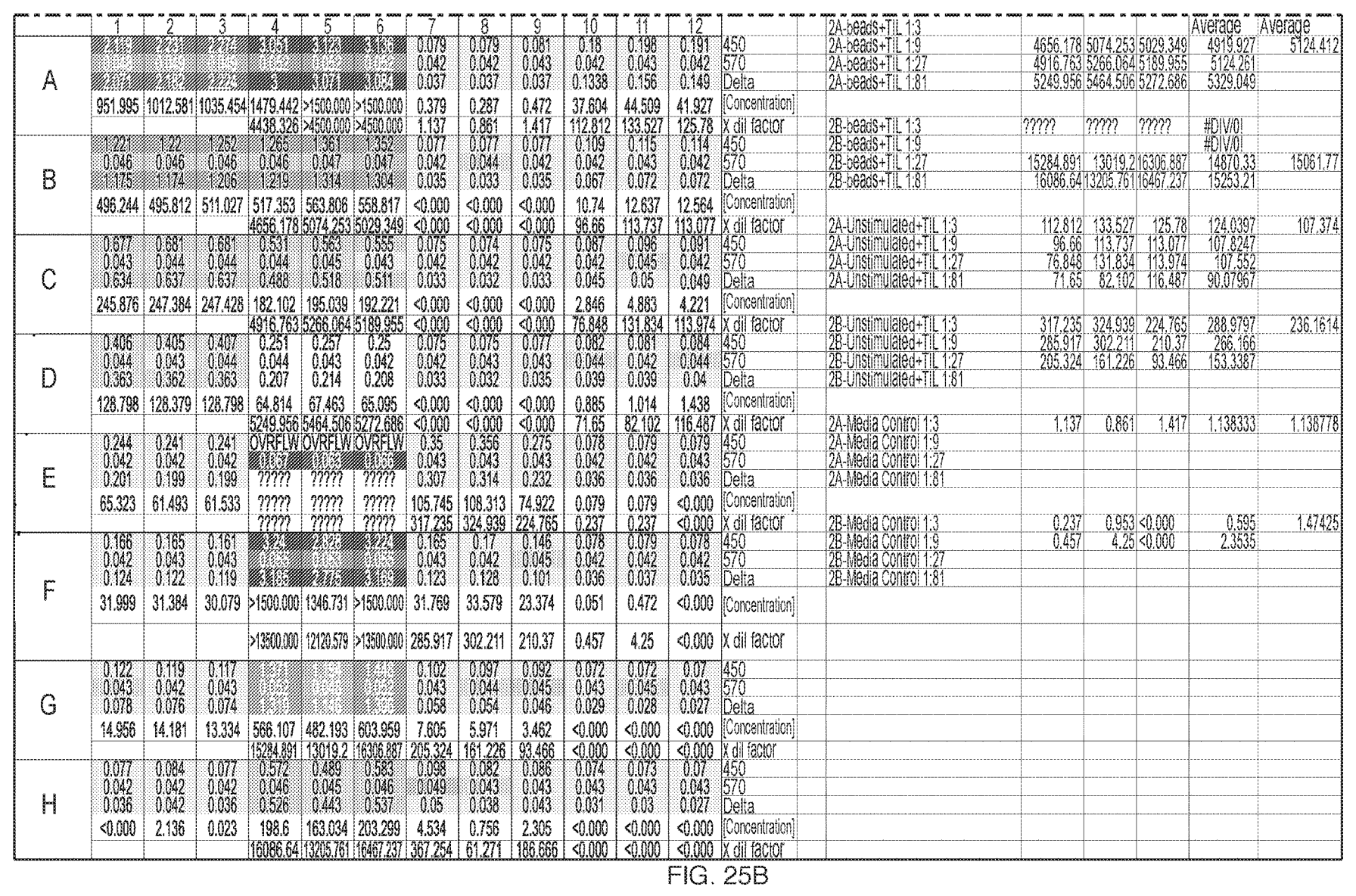

| | 1 | 2 | 3 | 4 | 5 | 6 | 7 | 8 | 9 | 10 | 11 | 12 | | 2A-beads+TIL 1:3 | | | | Average | Average |
|---|---|---|---|---|---|---|---|---|---|---|---|---|---|---|---|---|---|---|---|
| A | 2.119 | 2.231 | 2.274 | 3.051 | 3.123 | 3.136 | 0.079 | 0.079 | 0.081 | 0.18 | 0.198 | 0.191 | 450 | 2A-beads+TIL 1:9 | 4656.178 | 5074.253 | 5029.349 | 4919.927 | 5124.412 |
| | [illegible] | [illegible] | [illegible] | [illegible] | [illegible] | [illegible] | 0.042 | 0.042 | 0.043 | 0.042 | 0.043 | 0.042 | 570 | 2A-beads+TIL 1:27 | 4916.763 | 5266.064 | 5189.955 | 5124.261 | |
| | 2.071 | 2.182 | 2.224 | 3 | 3.071 | 3.084 | 0.037 | 0.037 | 0.037 | 0.1338 | 0.156 | 0.149 | Delta | 2A-beads+TIL 1:81 | 5249.956 | 5464.506 | 5272.686 | 5329.049 | |
| | 951.995 | 1012.581 | 1035.454 | 1479.442 | >1500.000 | >1500.000 | 0.379 | 0.287 | 0.472 | 37.604 | 44.509 | 41.927 | [Concentration] | | | | | | |
| | | | | 4438.326 | >4500.000 | >4500.000 | 1.137 | 0.861 | 1.417 | 112.812 | 133.527 | 125.78 | X dil factor | 2B-beads+TIL 1:3 | ????? | ????? | ????? | #DIV/0! | |
| B | 1.221 | 1.22 | 1.252 | 1.265 | 1.361 | 1.352 | 0.077 | 0.077 | 0.077 | 0.109 | 0.115 | 0.114 | 450 | 2B-beads+TIL 1:9 | | | | #DIV/0! | |
| | 0.046 | 0.046 | 0.046 | 0.046 | 0.047 | 0.047 | 0.042 | 0.044 | 0.042 | 0.042 | 0.043 | 0.042 | 570 | 2B-beads+TIL 1:27 | 15284.891 | 13019.2 | 16306.887 | 14870.33 | 15061.77 |
| | 1.175 | 1.174 | 1.206 | 1.219 | 1.314 | 1.304 | 0.035 | 0.033 | 0.035 | 0.067 | 0.072 | 0.072 | Delta | 2B-beads+TIL 1:81 | 16086.64 | 13205.761 | 16467.237 | 15253.21 | |
| | 496.244 | 495.812 | 511.027 | 517.353 | 563.806 | 558.817 | <0.000 | <0.000 | <0.000 | 10.74 | 12.637 | 12.564 | [Concentration] | | | | | | |
| | | | | 4656.178 | 5074.253 | 5029.349 | <0.000 | <0.000 | <0.000 | 96.66 | 113.737 | 113.077 | X dil factor | 2A-Unstimulated+TIL 1:3 | 112.812 | 133.527 | 125.78 | 124.0397 | 107.374 |
| C | 0.677 | 0.681 | 0.681 | 0.531 | 0.563 | 0.555 | 0.075 | 0.074 | 0.075 | 0.087 | 0.096 | 0.091 | 450 | 2A-Unstimulated+TIL 1:9 | 96.66 | 113.737 | 113.077 | 107.8247 | |
| | 0.043 | 0.044 | 0.044 | 0.044 | 0.045 | 0.043 | 0.042 | 0.042 | 0.042 | 0.042 | 0.045 | 0.042 | 570 | 2A-Unstimulated+TIL 1:27 | 76.848 | 131.834 | 113.974 | 107.552 | |
| | 0.634 | 0.637 | 0.637 | 0.488 | 0.518 | 0.511 | 0.033 | 0.032 | 0.033 | 0.045 | 0.05 | 0.049 | Delta | 2A-Unstimulated+TIL 1:81 | 71.65 | 82.102 | 116.487 | 90.07967 | |
| | 245.876 | 247.384 | 247.428 | 182.102 | 195.039 | 192.221 | <0.000 | <0.000 | <0.000 | 2.846 | 4.883 | 4.221 | [Concentration] | | | | | | |
| | | | | 4916.763 | 5266.064 | 5189.955 | <0.000 | <0.000 | <0.000 | 76.848 | 131.834 | 113.974 | X dil factor | 2B-Unstimulated+TIL 1:3 | 317.235 | 324.939 | 224.765 | 288.9797 | 236.1614 |
| D | 0.406 | 0.405 | 0.407 | 0.251 | 0.257 | 0.25 | 0.075 | 0.075 | 0.077 | 0.082 | 0.081 | 0.084 | 450 | 2B-Unstimulated+TIL 1:9 | 285.917 | 302.211 | 210.37 | 266.166 | |
| | 0.044 | 0.043 | 0.044 | 0.044 | 0.043 | 0.042 | 0.042 | 0.043 | 0.043 | 0.044 | 0.042 | 0.044 | 570 | 2B-Unstimulated+TIL 1:27 | 205.324 | 161.226 | 93.466 | 153.3387 | |
| | 0.363 | 0.362 | 0.363 | 0.207 | 0.214 | 0.208 | 0.033 | 0.032 | 0.035 | 0.039 | 0.039 | 0.04 | Delta | 2B-Unstimulated+TIL 1:81 | | | | | |
| | 128.798 | 128.379 | 128.798 | 64.814 | 67.463 | 65.095 | <0.000 | <0.000 | <0.000 | 0.885 | 1.014 | 1.438 | [Concentration] | | | | | | |
| | | | | 5249.956 | 5464.506 | 5272.686 | <0.000 | <0.000 | <0.000 | 71.65 | 82.102 | 116.487 | X dil factor | 2A-Media Control 1:3 | 1.137 | 0.861 | 1.417 | 1.138333 | 1.138778 |
| E | 0.244 | 0.241 | 0.241 | OVRFLW | OVRFLW | OVRFLW | 0.35 | 0.356 | 0.275 | 0.078 | 0.079 | 0.079 | 450 | 2A-Media Control 1:9 | | | | | |
| | 0.042 | 0.042 | 0.042 | [illegible] | [illegible] | [illegible] | 0.043 | 0.043 | 0.043 | 0.042 | 0.042 | 0.043 | 570 | 2A-Media Control 1:27 | | | | | |
| | 0.201 | 0.199 | 0.199 | ????? | ????? | ????? | 0.307 | 0.314 | 0.232 | 0.036 | 0.036 | 0.036 | Delta | 2A-Media Control 1:81 | | | | | |
| | 65.323 | 61.493 | 61.533 | ????? | ????? | ????? | 105.745 | 108.313 | 74.922 | 0.079 | 0.079 | <0.000 | [Concentration] | | | | | | |
| | | | | ????? | ????? | ????? | 317.235 | 324.939 | 224.765 | 0.237 | 0.237 | <0.000 | X dil factor | 2B-Media Control 1:3 | 0.237 | 0.953 | <0.000 | 0.595 | 1.47425 |
| F | 0.166 | 0.165 | 0.161 | [illegible] | [illegible] | [illegible] | 0.165 | 0.17 | 0.146 | 0.078 | 0.079 | 0.078 | 450 | 2B-Media Control 1:9 | 0.457 | 4.25 | <0.000 | 2.3535 | |
| | 0.042 | 0.043 | 0.043 | [illegible] | [illegible] | [illegible] | 0.043 | 0.042 | 0.045 | 0.042 | 0.042 | 0.042 | 570 | 2B-Media Control 1:27 | | | | | |
| | 0.124 | 0.122 | 0.119 | [illegible] | [illegible] | [illegible] | 0.123 | 0.128 | 0.101 | 0.036 | 0.037 | 0.035 | Delta | 2B-Media Control 1:81 | | | | | |
| | 31.999 | 31.384 | 30.079 | >1500.000 | 1346.731 | >1500.000 | 31.769 | 33.579 | 23.374 | 0.051 | 0.472 | <0.000 | [Concentration] | | | | | | |
| | | | | >13500.000 | 12120.579 | >13500.000 | 285.917 | 302.211 | 210.37 | 0.457 | 4.25 | <0.000 | X dil factor | | | | | | |
| G | 0.122 | 0.119 | 0.117 | [illegible] | [illegible] | [illegible] | 0.102 | 0.097 | 0.092 | 0.072 | 0.072 | 0.07 | 450 | | | | | | |
| | 0.043 | 0.042 | 0.043 | [illegible] | [illegible] | [illegible] | 0.043 | 0.044 | 0.045 | 0.043 | 0.045 | 0.043 | 570 | | | | | | |
| | 0.078 | 0.076 | 0.074 | [illegible] | [illegible] | [illegible] | 0.058 | 0.054 | 0.046 | 0.029 | 0.028 | 0.027 | Delta | | | | | | |
| | 14.956 | 14.181 | 13.334 | 566.107 | 482.193 | 603.959 | 7.605 | 5.971 | 3.462 | <0.000 | <0.000 | <0.000 | [Concentration] | | | | | | |
| | | | | 15284.891 | 13019.2 | 16306.887 | 205.324 | 161.226 | 93.466 | <0.000 | <0.000 | <0.000 | X dil factor | | | | | | |
| H | 0.077 | 0.084 | 0.077 | 0.572 | 0.489 | 0.583 | 0.098 | 0.082 | 0.086 | 0.074 | 0.073 | 0.07 | 450 | | | | | | |
| | 0.042 | 0.042 | 0.042 | 0.046 | 0.045 | 0.046 | 0.049 | 0.043 | 0.043 | 0.043 | 0.043 | 0.043 | 570 | | | | | | |
| | 0.036 | 0.042 | 0.036 | 0.526 | 0.443 | 0.537 | 0.05 | 0.038 | 0.043 | 0.031 | 0.03 | 0.027 | Delta | | | | | | |
| | <0.000 | 2.136 | 0.023 | 198.6 | 163.034 | 203.299 | 4.534 | 0.756 | 2.305 | <0.000 | <0.000 | <0.000 | [Concentration] | | | | | | |
| | | | | 16086.64 | 13205.761 | 16467.237 | 367.254 | 61.271 | 186.666 | <0.000 | <0.000 | <0.000 | X dil factor | | | | | | |

FIG. 25B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 2000 | STD1 2000 | STD1 2000 | Gen 3-D7 1ST RUN | Gen 3-D7 1ST RUN | Gen 3-D7 1ST RUN | Gen 3-D7 2ND RUN | Gen 3-D7 2ND RUN | Gen 3-D7 2ND RUN | | | | Well ID<br>Conc/Dil |
| B | STD2 1000 | STD2 1000 | STD2 1000 | Gen 3-D11 1ST RUN | Gen 3-D11 1ST RUN | Gen 3-D11 1ST RUN | Gen 3-D11 2ND RUN | Gen 3-D11 2ND RUN | Gen 3-D11 2ND RUN | | | | Well ID<br>Conc/Dil |
| C | STD3 500 | STD3 500 | STD3 500 | Gen 3-D16 1ST RUN | Gen 3-D16 1ST RUN | Gen 3-D16 1ST RUN | Gen 3-D16 2ND RUN | Gen 3-D16 2ND RUN | Gen 3-D16 2ND RUN | | | | Well ID<br>Conc/Dil |
| D | STD4 250 | STD4 250 | STD4 250 | Gen 2-D11 1ST RUN | Gen 2-D11 1ST RUN | Gen 2-D11 1ST RUN | Gen 2-D11 2ND RUN | Gen 2-D11 2ND RUN | Gen 2-D11 2ND RUN | | | | Well ID<br>Conc/Dil |
| E | STD5 125 | STD5 125 | STD5 125 | Gen 2-D16 1ST RUN | Gen 2-D16 1ST RUN | Gen 2-D16 1ST RUN | Gen 2-D16 2ND RUN | Gen 2-D16 2ND RUN | Gen 2-D16 2ND RUN | | | | Well ID<br>Conc/Dil |
| F | STD6 62.5 | STD6 62.5 | STD6 62.5 | Gen 2-D22 1ST RUN | Gen 2-D22 1ST RUN | Gen 2-D22 1ST RUN | Gen 2-D22 2ND RUN | Gen 2-D22 2ND RUN | Gen 2-D22 2ND RUN | | | | Well ID<br>Conc/Dil |
| G | STD7 31.3 | STD7 31.3 | STD7 31.3 | Empty | Empty | Empty | Empty | Empty | Empty | | | | Well ID<br>Conc/Dil |
| H | STD8 0 | STD8 0 | STD8 0 | Empty | Empty | Empty | Empty | Empty | Empty | | | | Well ID<br>Conc/Dil |
| 22 | | | | | | | | | | | | | |
| 22 | | | | | | | | | | | | | |

FIG. 26A

| | 1 | 2 | 3 | 4 | 5 | 6 | 7 | 8 | 9 | 10 | 11 | 12 | | | | | | | | | | |
|---|---|---|---|---|---|---|---|---|---|---|---|---|---|---|---|---|---|---|---|---|---|---|
| A | 2.223 | 2.297 | 2.239 | 0.218 | 0.22 | 0.215 | 0.187 | 0.187 | 0.184 | | | | 450 | | Dilution Factor=100 | | | | | | | |
| | 0.052 | 0.052 | 0.053 | 0.043 | 0.042 | 0.043 | 0.044 | 0.043 | 0.051 | | | | 570 | | | | | | | | | |
| | 2.171 | 2.246 | 2.186 | 0.175 | 0.177 | 0.172 | 0.143 | 0.145 | 0.133 | | | | Delta | | | Reading A | Reading B | Reading C | Reading A*100 | Reading B*100 | Reading C*100 | Average |
| | 1970.541 | 2046.905 | 1987.758 | 124.53 | 126.082 | 121.662 | 99.302 | 100.904 | 92.083 | | | | [Concentration] | | Gen 3 Rep initiation 1st run | 124.530 | 126.082 | 121.662 | 12453.0 | 12608.2 | 12166.2 | 12409.1 |
| B | 1.095 | 1.291 | 1.276 | 0.415 | 0.412 | 0.435 | 0.394 | 0.392 | 0.356 | | | | 450 | | Gen 3 Scale up 1st run | 282.400 | 280.328 | 299.854 | 28240.0 | 28032.8 | 29985.4 | 28752.7 |
| | 0.057 | 0.057 | 0.047 | 0.043 | 0.043 | 0.043 | 0.043 | 0.044 | 0.044 | | | | 570 | | Gen 3 Harvest 1st run | 252.774 | 247.768 | 250.557 | 25277.4 | 24776.8 | 25055.7 | 25036.6 |
| | 1.038 | 1.234 | 1.229 | 0.372 | 0.369 | 0.393 | 0.351 | 0.348 | 0.312 | | | | Delta | | | | | | | | | |
| | 877.734 | 1051.728 | 1047.027 | 282.4 | 280.328 | 299.854 | 264.954 | 262.893 | 233.453 | | | | [Concentration] | | Gen 2 Rep initiation 1st run | 79.199 | 77.702 | 93.523 | 7919.9 | 7770.2 | 9352.3 | 8347.5 |
| C | 0.683 | 0.683 | 0.68 | 0.379 | 0.372 | 0.376 | 0.356 | 0.338 | 0.33 | | | | 450 | | Gen 2 Scale up 1st run | 136.754 | 131.526 | 131.682 | 13675.4 | 13152.6 | 13168.2 | 13332.1 |
| | 0.045 | 0.044 | 0.044 | 0.043 | 0.043 | 0.043 | 0.043 | 0.043 | 0.043 | | | | 570 | | Gen 2 Harvest 1st run | 117.564 | 130.125 | 121.895 | 11756.4 | 13012.5 | 12189.5 | 12319.5 |
| | 0.638 | 0.639 | 0.637 | 0.336 | 0.33 | 0.333 | 0.313 | 0.295 | 0.287 | | | | Delta | | | | | | | | | |
| | 510.008 | 510.619 | 508.261 | 252.774 | 247.768 | 250.557 | 233.9443 | 219.211 | 212.888 | | | | [Concentration] | | | | | | | | | |
| D | 0.37 | 0.38 | 0.382 | 0.162 | 0.156 | 0.177 | 0.155 | 0.15 | 0.149 | | | | 450 | | Gen 3 Rep initiation 2nd run | 99.302 | 100.904 | 92.083 | 9930.2 | 10090.4 | 9208.3 | 9743.0 |
| | 0.043 | 0.045 | 0.043 | 0.046 | 0.042 | 0.042 | 0.043 | 0.044 | 0.043 | | | | 570 | | Gen 3 Scale up 2nd run | 264.954 | 262.893 | 233.453 | 26495.4 | 26289.3 | 23345.3 | 25376.7 |
| | 0.328 | 0.335 | 0.338 | 0.116 | 0.114 | 0.135 | 0.112 | 0.106 | 0.106 | | | | Delta | | Gen 3 Harvest 2nd run | 233.943 | 219.211 | 212.888 | 23394.3 | 21921.1 | 21288.8 | 22201.4 |
| | 246.046 | 252.035 | 254.91 | 79.199 | 77.702 | 93.523 | 76.431 | 71.588 | 71.737 | | | | [Concentration] | | | | | | | | | |
| E | 0.216 | 0.219 | 0.22 | 0.235 | 0.227 | 0.228 | 0.253 | 0.231 | 0.222 | | | | 450 | | Gen 2 Rep initiation 2nd run | 76.431 | 71.588 | 71.737 | 7643.1 | 7158.8 | 7173.7 | 7325.2 |
| | 0.043 | 0.043 | 0.045 | 0.044 | 0.043 | 0.043 | 0.048 | 0.045 | 0.045 | | | | 570 | | Gen 2 Scale up 2nd run | 147.807 | 132.695 | 125.539 | 14780.7 | 13269.5 | 12553.9 | 13534.7 |
| | 0.173 | 0.176 | 0.175 | 0.191 | 0.185 | 0.185 | 0.205 | 0.186 | 0.177 | | | | Delta | | Gen 2 Harvest 2nd run | 139.491 | 135.738 | 149.459 | 13949.1 | 13573.8 | 14945.9 | 14156.3 |
| | 122.514 | 124.995 | 123.909 | 136.754 | 131.526 | 131.682 | 147.807 | 132.695 | 125.539 | | | | [Concentration] | | | | | | | | | |
| F | 0.137 | 0.132 | 0.133 | 0.21 | 0.227 | 0.216 | 0.238 | 0.233 | 0.253 | | | | 450 | | | | | | | | | |
| | 0.047 | 0.043 | 0.044 | 0.043 | 0.044 | 0.044 | 0.043 | 0.043 | 0.045 | | | | 570 | | | | | | | | | |
| | 0.089 | 0.089 | 0.089 | 0.166 | 0.183 | 0.172 | 0.195 | 0.19 | 0.207 | | | | Delta | | | | | | | | | |
| | 59.482 | 58.969 | 59.116 | 117.564 | 130.125 | 121.895 | 139.491 | 135.738 | 149.459 | | | | [Concentration] | | | | | | | | | |
| G | 0.088 | 0.088 | 0.089 | 2.265 | 2.329 | 2.22 | 2.225 | 2.175 | 2.239 | | | | 450 | | | | | | | | | |
| | 0.042 | 0.043 | 0.043 | 0.05 | 0.05 | 0.049 | 0.051 | 0.052 | 0.053 | | | | 570 | | | | | | | | | |
| | 0.046 | 0.046 | 0.046 | 2.215 | 2.28 | 2.171 | 2.174 | 2.122 | 2.186 | | | | Delta | | | | | | | | | |
| | 28.375 | 28.237 | 28.514 | 2014.9 | 2081.651 | 1970.439 | 1973.799 | 1920.845 | 1986.127 | | | | [Concentration] | | | | | | | | | |
| H | 0.05 | 0.048 | 0.048 | 2.272 | 2.267 | 2.213 | 2.244 | 2.254 | 2.248 | | | | 450 | | | | | | | | | |
| | 0.043 | 0.042 | 0.041 | 0.05 | 0.05 | 0.052 | 0.057 | 0.052 | 0.059 | | | | 570 | | | | | | | | | |
| | 0.007 | 0.006 | 0.007 | 2.223 | 2.217 | 2.161 | 2.187 | 2.202 | 2.189 | | | | Delta | | | | | | | | | |
| | 3.1 | 2.399 | 2.573 | 2023.073 | 2016.943 | 1960.16 | 1986.84 | 2002.036 | 1988.165 | | | | [Concentration] | | | | | | | | | |

FIG. 26B

| Sample number # | Description | Glucose (g/L) | Lactate (g/L) | Ammonia (mmol/L) | Glutamine (mmol/L) | Glutamax (mmol/L) | Glutamax-Glutamine (mmol/L) |
|---|---|---|---|---|---|---|---|
| 1 | Gen 2-Rep initiation First Round #L4054 | 1.78 | 0.14 | 2.16 | 1.56 | 1.71 | 0.16 |
| 2 | Gen 2-Scale Up First Round #L4054 | 1.36 | 0.89 | 1.40 | 1.76 | 1.90 | 0.15 |
| 3 | Gen 2-Harvest First Round #L4054 | 0.83 | 1.68 | 2.46 | 1.69 | 1.85 | 0.17 |
| 4 | Gen 3-REP initiation First Round #L4054 | 1.68 | 0.29 | 1.76 | 2.11 | 2.29 | 0.18 |
| 5 | Gen 3-Scale Up First Round #L4054 | 1.28 | 0.94 | 1.64 | 1.70 | 1.87 | 0.16 |
| 6 | Gen 3-Harvest First Round #L4054 | 1.07 | 1.53 | 2.23 | 1.39 | 1.54 | 0.14 |
| | | | | | | | |
| 7 | Gen 2-Rep initiation Second Round #L4055 | 1.91 | 0.08 | 2.29 | 1.60 | 1.74 | 0.14 |
| 8 | Gen 2-Scale up Second Round #L4055 | 1.61 | 0.77 | 1.40 | 1.78 | 1.93 | 0.15 |
| 9 | Gen 2-Harvest Second Round #L4055 | 0.85 | 1.86 | 2.46 | 1.39 | 1.55 | 0.16 |
| 10 | Gen 3-REP initiation Second Round #L4055 | 1.77 | 0.18 | 1.74 | 2.06 | 2.23 | 0.17 |
| 11 | Gen 3-Scale up Second Round #L4055 | 1.60 | 0.72 | 1.54 | 1.68 | 1.84 | 0.15 |
| 12 | Gen 3-Harvest Second Round #L4055 | 1.44 | 1.32 | 2.07 | 1.79 | 1.95 | 0.16 |

FIG. 27

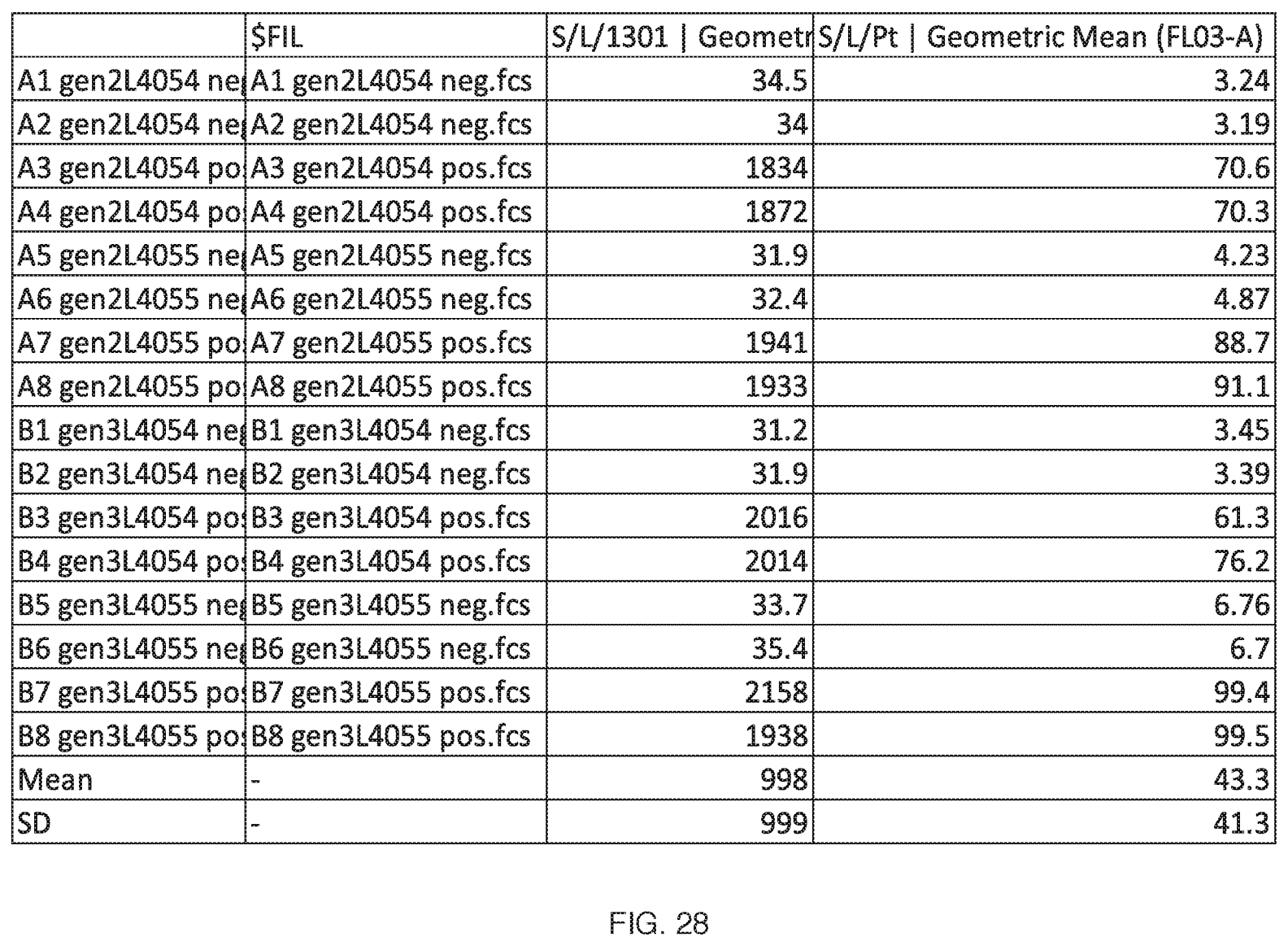

| | $FIL | S/L/1301 \| Geometr | S/L/Pt \| Geometric Mean (FL03-A) |
|---|---|---|---|
| A1 gen2L4054 ne | A1 gen2L4054 neg.fcs | 34.5 | 3.24 |
| A2 gen2L4054 ne | A2 gen2L4054 neg.fcs | 34 | 3.19 |
| A3 gen2L4054 po | A3 gen2L4054 pos.fcs | 1834 | 70.6 |
| A4 gen2L4054 po | A4 gen2L4054 pos.fcs | 1872 | 70.3 |
| A5 gen2L4055 ne | A5 gen2L4055 neg.fcs | 31.9 | 4.23 |
| A6 gen2L4055 ne | A6 gen2L4055 neg.fcs | 32.4 | 4.87 |
| A7 gen2L4055 po | A7 gen2L4055 pos.fcs | 1941 | 88.7 |
| A8 gen2L4055 po | A8 gen2L4055 pos.fcs | 1933 | 91.1 |
| B1 gen3L4054 ne | B1 gen3L4054 neg.fcs | 31.2 | 3.45 |
| B2 gen3L4054 ne | B2 gen3L4054 neg.fcs | 31.9 | 3.39 |
| B3 gen3L4054 po | B3 gen3L4054 pos.fcs | 2016 | 61.3 |
| B4 gen3L4054 po | B4 gen3L4054 pos.fcs | 2014 | 76.2 |
| B5 gen3L4055 ne | B5 gen3L4055 neg.fcs | 33.7 | 6.76 |
| B6 gen3L4055 ne | B6 gen3L4055 neg.fcs | 35.4 | 6.7 |
| B7 gen3L4055 po | B7 gen3L4055 pos.fcs | 2158 | 99.4 |
| B8 gen3L4055 po | B8 gen3L4055 pos.fcs | 1938 | 99.5 |
| Mean | - | 998 | 43.3 |
| SD | - | 999 | 41.3 |

FIG. 28

| Study | Sample | Sample id | Species | Chain | Reads | CDR3 | Unique CDR3 | D50 |
|---|---|---|---|---|---|---|---|---|
| 20180511_Study1_FCA | Gen2-L4054 | 59990 | TRB | h | 1181732 | 1181732 | 8915 | 0 |
| 20180511_Study1_FCA | Gen3-L4054 | 59991 | TRB | h | 1145697 | 1145697 | 18130 | 0 |
| 20180511_Study1_FCA | Gen2-L4055 | 59987 | TRB | h | 1166465 | 1166465 | 12996 | 0.1 |
| 20180511_Study1_FCA | Gen3-L4055 | 59982 | TRB | h | 1059985 | 1059985 | 27246 | 0.9 |

FIG. 29

| STEP | Gen 2 | Gen 2.1 | Gen 3.0 Optimized |
|---|---|---|---|
| **Pre REP- day 0** | ≤ 50 fragments/ 1 G-Rex 100MCS - **11 days** | ≤ 180 fragments/ 3 G-Rex, Pre-formulated CM1 warmed media 100MCS - **11 days** | ***Fresh or Frozen Tumor*** Whole tumor with ≤ 30 fragments up to 60 fragments per 1 G-Rex. 100MCS (up to 4 G-Rex), preformulated warmed media - **7 days. Pre REP, Feeders 2.5 E8 cells + OKT-3 (30ng/mL)** |
| **REP Initiation** | Direct to REP- Day 11- **<200 E6 TIL** 1 G-Rex 500MCS | Direct to REP- Day 11- **<200 E6 TIL** Pre-formulated CM2 warmed media in one G-Rex 500MCS | Direct to REP - Day **7-all cells TIL- same G-Rex 100MCS (100MCS up to 4 GREX), Standard media or Defined Media (Serum free). Addition Feeders 5 E8 cells +OKT-3 (30ng/mL)** |
| **TIL propagation or Scale up** | 1 to 5 G-REX 500MCS **Split day 16** | 2 to 5 G-REX 500MCS Pre-formulated CM4 warmed media **Split day 16** | From G-REX 100MCS transfer TIL suspension to G-REX 500MCS, up to 4 GREX 500 MCS- Standard media or Defined Media (Serum Free) **Scale up on day 10 or 11** |
| **Harvest** | **Harvest day 22,** LOVO-automated cell washer | **Harvest day 22,** LOVO-automated cell washer (5 wash cycle) | **Harvest day 14 or 16** LOVO- automated cell washer (5 wash cycle) |
| **Final formulation** | Cryopreserved Product 300IU/ml IL2- CS10 in $LN_2$, multiple aliquots | Cryopreserved Product 300IU/ml IL2- CS10 in $LN_2$, multiple aliquots | Cryopreserved Product 300IU/ml IL-2- CS10 in $LN_2$, multiple aliquots |
| **Process time** | **22 days** | **22 days** | **16 days** |

FIG. 31

| Process Day | Conditions | Gen 3.1 |
|---|---|---|
| Day 0- pre REP initiation | Media CM1 | 500 mL |
| | IL-2 (6000 IU/mL) | + |
| | OKT-3 (30ng/mL) | + |
| | Feeders (250 E+06) | + |

| Process Day | Conditions | Gen 3.1 |
|---|---|---|
| Day 7- REP initiation | Media CM2 | 500 mL |
| | IL-2 (6000 IU/mL) | + |
| | OKT-3 (30ng/mL) added on Day 7 | + |
| | Feeders Added on Day 7 | 500 E06 |
| | Total Feeders at Day | 750 E+06 |

| Process Day | Conditions | Gen 3.1 |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

FIG. 32

| Process Comparison | Key Process Changes | Benefit |
|---|---|---|
| **Gen 2 : Gen 2.1** | • Initiate process with two flasks instead of one flask<br>• Divide REP initiation feeder layer between 2 G-Rex500MCS Flasks<br>• Pre-formulate media and warm prior to use | • Potential doubling of final cell count (dose with increased TIL repertoire.<br>• Process redundancy throughout process |
| **Gen 2.1 : Gen 3.1** | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

FIG. 33

| Process Comparison | Key Process Changes | Desired Improvement | Criteria for Success | Outcome |
|---|---|---|---|---|
| Gen 2 : Gen 3.0 | • 14-16 days<br>• Initiate REP with fragments up to 4 flask.<br>• 100MCS scales to 500MCS | • Increased potency<br>• Improved phenotype<br>• Decreased process time | • Increase potency as measured by INF-g ✓<br>• Comparable phenotype ✓<br>• Comparable Dose ✓<br>• Comparable purity ✓ (feeder cell)<br>• Maintain clonal diversity ✓ | • Potency increased over Gen2<br>• Improved expression of CD28 on CD8 cells<br>• Maximum capacity of flask reached by day 16 on Gen 3.1<br>• Reduced feeder cell usage<br>• Increased diversity |

FIG. 34

| Process | Gen 2 | Gen 3 |
|---|---|---|
| L4054 | Standard Media | Standard Media |
| L4055 | Standard Media | Standard Media |
| M1085T | Standard Media | Standard Media |

| Process | Gen 3 | Gen 3.1 control | Gen 3.1 |
|---|---|---|---|
| L4063 | Standard Media | Standard Media | Standard Media |
| L4064 | Defined Media | Defined Media | Defined Media |

Standard Media:
Pre REP· CM1
REP initiation CM2
Split or Scale up CM4

Defined Media:
CTS Optimizer (Serum Free Media) in each day of the process

FIG. 35

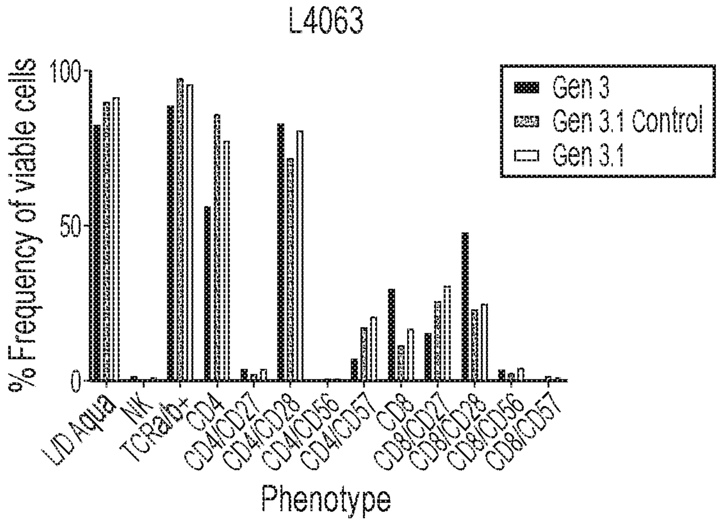
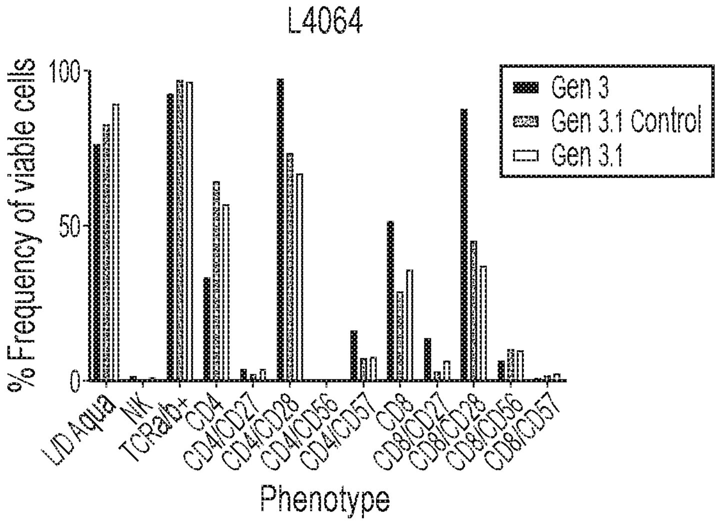
| **Tumor ID** | **L4063 Standard media** | | | **L4064 Defined media** | | |
|---|---|---|---|---|---|---|
| **Process** | **Gen 3.0** | **Gen 3.1 Control** | **Gen 3.1** | **Gen 3.0** | **Gen 3.1 Control** | **Gen 3.1** |
| # Fragments | 53 | 53 | 53 | 21 | 21 | 21 |
| **Tumor ID** | **L4063 in Standard Media** | | | **L4064 in CTS Optimizer Media** | | |
|---|---|---|---|---|---|---|
| Process | **Gen 3.0** | **Gen 3.1 Control** | **Gen 3.1 Test** | **Gen 3.0** | **Gen 3.1 Control** | **Gen 3.1 Test** |
| Number of fragments | **53** | **53** | **53** | **21** | **21** | **21** |
| Average TVC per fragment | 1.37E+08 | 3.19E+08 | 3.53E+08 | 5.90E+08 | 7.57E+08 | 9.29E+08 |
| % viability at Harvest | 79.53% | 89.43% | 94.80% | 88.80% | 81.90% | 84.90% |
| **TVC Harvest** | **7.26E+09** | **1.69E+10** | **1.87E+10 *** | **1.24E+10** | **1.59E+10** | **1.95E+10 *** |
FIG. 36

L4063- Standard Media:

L4064- Defined Media

| Process Day | Conditions | Gen 3.0 | Gen 3.1 CT (control) | Gen 3.1 F |
|---|---|---|---|---|
| Day 0- pre REP initiation | Media CM1 | 500 mL | 500 mL | 500 mL |
| | IL-2 (6000 IU/mL) | + | + | + |
| | OKT-3 (30ng/mL) | - | + | + |
| | Feeders (250 E+06) | - | - | + |

| Conditions on Day 0 | Gen 3.0 | Gen 3.1 (control) | Gen 3.1 |
|---|---|---|---|
| Media | 500 mL | 500 mL | 500 mL |
| IL-2 (6E+06) | + | + | + |
| OKT-3 (30ng/mL) | - | + | + |
| Feeders (250 E+06) | - | - | + |

| Number of uCDR3 (% Overlap) | All uCDR3's | | | Top 80% uCDR3's | | |
|---|---|---|---|---|---|---|
| | Gen 3.0 | Gen 3.1 Control | Gen 3.1 | Gen 3.0 | Gen 3.1 control | Gen 3.1 |
| Gen 3.0 | 14005 | 3240 (23) | 2959 (21) | 1105 | 1000 (90) | 975 (88) |
| Gen 3.1 control | - | 18149 | - | - | 2438 | - |
| Gen 3.1 | - | - | 17181 | - | - | 2332 |

| Conditions on Day 0 | Gen 3.0 | Gen 3.1 (control) | Gen 3.1 |
|---|---|---|---|
| Media | 500 mL | 500 mL | 500 mL |
| IL-2 (6E+06) | + | + | + |
| OKT-3 (30ng/mL) | - | + | + |
| Feeders (250 E+06) | - | - | + |

| Number of uCDR3 (% Overlap) | All uCDR3's | | | Top 80% uCDR3's | | |
|---|---|---|---|---|---|---|
| | Gen 3.0 | Gen 3.1 Control | Gen 3.1 | Gen 3.0 | Gen 3.1 control | Gen 3.1 |
| Gen 3.0 | 15107 | 5486 (36) | 5541 (37) | 2479 | 2186 (88) | 2163 (87) |
| Gen 3.1 control | - | 21460 | - | - | 3247 | - |
| Gen 3.1 | - | - | 21503 | - | - | 3264 |

| Process Day | Conditions | Gen 3.1 Test |
|---|---|---|
| Day 0- pre REP initiation | Media CM1 | 500 mL |
| | IL-2 (6000 IU/mL) | + |
| | OKT-3 (15 ug) | + |
| | Feeders (250 E+06) | + |

| Process Day | Conditions | Gen 3.1 Test |
|---|---|---|
| Day 7- REP initiation | Media CM2 | 500 mL |
| | IL-2 (6000 IU/mL) | + |
| | OKT-3 (30 ug) added on Day 7 | + |
| | Feeders Added on Day 7 | 500 E06 |
| | Total Feeders at Day | 750 E+06 |

| Process Day | Conditions | Gen 3.1 Test |
|---|---|---|
| Day 9-11 - Scale Up | From G-REX 100MCS transfer TIL suspension to 1 G-REX 500MCS (up to 3 GREX 500MCS) | Yes |
| Day 16 - Harvest | LOVO- automated cell washer | Yes |

FIG. 44

| Tumor ID | L4063 in Standard Media | | | L4064 in CTS Optimizer Media | | |
|---|---|---|---|---|---|---|
| Process | Gen 3.0 | Gen 3.1 Control | Gen 3.1 Test | Gen 3.0 | Gen 3.1 Control | Gen 3.1 Test |
| Number of fragments | **53** | **53** | **53** | **21** | **21** | **21** |
| Average TVC per fragment | 1.37E+08 | 3.19E+08 | 3.53E+08 | 5.90E+08 | 7.57E+08 | 9.29E+08 |
| % viability at Harvest | 79.53% | 89.43% | 94.80% | 88.80% | 81.90% | 84.90% |
| **TVC Harvest** | **7.26E+09** | **1.69E+10** | **1.87E+10 *** | **1.24E+10** | **1.59E+10** | **1.95E+10 *** |

FIG. 45

| Tumor ID | L4063 Standard media | | | L4064 Defined media | | |
|---|---|---|---|---|---|---|
| **Process** | **Gen 3.0** | **Gen 3.1 Control** | **Gen 3.1** | **Gen 3.0** | **Gen 3.1 Control** | **Gen 3.1** |
| # Fragments | 53 | 53 | 53 | 21 | 21 | 21 |

| Process Day | Conditions | Gen 3.0 | Gen 3.1 Control | Gen 3.1 Test |
|---|---|---|---|---|
| Day 0- pre REP initiation | Media CM1 | 500 mL | 500 mL | 500 mL |
| | IL-2 (6000 IU/mL) | + | + | + |
| | OKT-3 (30ng/mL) | - | + | + |
| | Feeders (250 E+06) | - | - | + |

| | Gen 2 | Gen 3 |
|---|---|---|
| Total Culture Time | 22d | 16-17d |
| Pre-REP | | |
| Fragments/flask | ≤60 fragments in 1 flask | ≤60 fragments/flask in up to 4 flasks |
| Media volume | 1L - Single addition | 1L – 2 x 500mL additions |
| Target preREP cell numbers | ≤200e6 TIL | All cells carried through continuous process |
| Screening | No screen | No screen |
| Selection of flasks | No selection | Bac-T sterility, visual inspection for contaminants |
| REP / Scale up | | |
| Feeders | | Reduced by ≥40% |
| Media | Contains HSAB | Defined |
| Scale up | Pooled culture<br>Volume reduce to 500mL on Day 5 split up to 5 flasks (2500 cm2) | Flasks scaled linearly and treated as subcomponents |
| OKT3 | 150ug | ≤180ug at max scale |
| IL2 | High dose | High dose |
| Number of flasks | 1-5 | 1-4 |
| Harvest-Volume reduction | Closed 10:1 | Closed 10:1 |
| Concentrate/Wash | LOVO 100:1 | LOVO 1000:1 |
| Formulation | 1:1 CS10 (5% DMSO) | 1:1 CS10 (5% DMSO) |
| Shipment | Vapor phase LN | Vapor phase LN |
| Infusion | Thawed IV gravity | Thawed IV gravity |

FIG. 57A

| | Gen 2 | Gen 3 |
|---|---|---|
| Total Culture Time | 22d | 16 |
| Fragment Culture | | |
| Fragments/flask | ≤60 fragments in 1 flask | ≤60 fragments/flask in up to 4 flasks |
| Media volume | 1L - Single addition | 1L – 2 x 500mL additions |
| Target preREP cell numbers | ≤200e6 TIL | All cells carried through continuous process |
| Screening | No screen | No screen |
| Selection of flasks | No selection | Bac-T sterility, visual inspection for contaminants |
| REP / Scale up | | |
| Feeders | | Reduced by ≥40% |
| Media | Contains HSAB | Defined |
| Scale up | Pooled culture<br>Volume reduce to 500mL on Day 5 split up to 5 flasks (2500 cm2) | Flasks scaled linearly and treated as subcomponents |
| OKT3 | 150ug | ≤180ug at max scale |
| IL2 | High dose | High dose |
| Number of flasks | 1-5 | 1-4 |
| Harvest-Volume reduction | Closed 10:1 | Closed 10:1 |
| Concentrate/Wash | LOVO 100:1 | LOVO 1000:1 |
| Formulation | 1:1 CS10 (5% DMSO) | 1:1 CS10 (5% DMSO) |
| Shipment | Vapor phase LN | Vapor phase LN |
| Infusion | Thawed IV gravity | Thawed IV gravity |

FIG. 57B

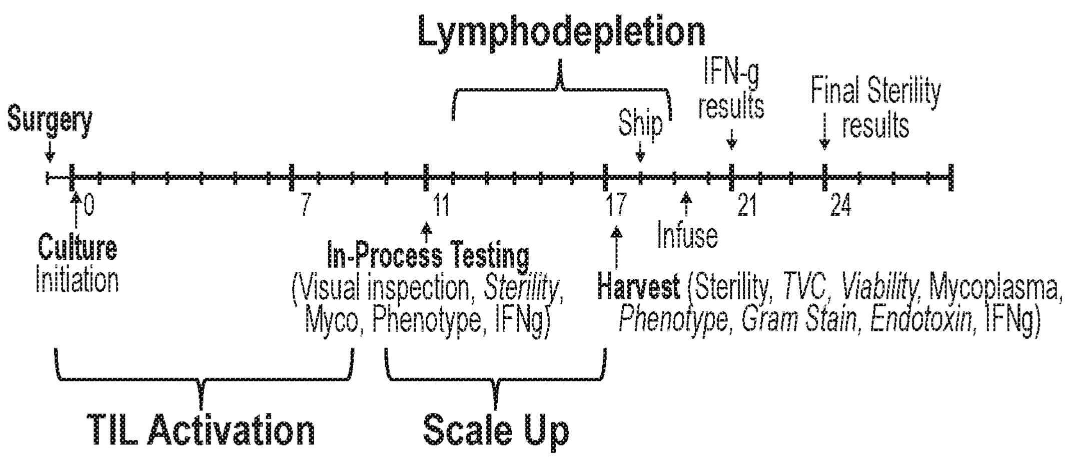

LD on:
Day 10-11 Viability
Day 10-11 Phenotype
Day 10-11 myco
Day 10-11 IFNg*

Release for infusion on:
*Gram Stain*
*Day 10-11 Sterility*
*Day 16-17 Mycoplasma*
*Day 16-17 Endotoxin*
*Day 16-17 Phenotyping*
*Day 16-17 TVC count*
*Day 16-17 Viability*

Final Release (CoA)
Day 16-17 Frozen:Thawed IFNg (ELISA)
Day 16-17 Endotoxin
Day 16-17 Phenotyping
Day 16-17 TVC count
Day 16-17 Viability
Day 16-17 Sterility

* Restimulation for ELISA on Day 10-11 will be from a fresh / frozen in-process sample reportable On Day 14

FIG. 58

Data Summary of testing Day 16/17

| Testing Parameter | 1st Eng. Run Day 17 10 March 2019 | 2nd Eng. Run Day 17 11 March 2019 | 3rd Eng. Run Day 17 25 March 2019 | Gen 2 (n=47) | | |
|---|---|---|---|---|---|---|
| | | | | Mean | Median | Stdev |
| Pre-LOVO TVC | 17.3E+09 | 46.1E+09 | | | | |
| Pre-LOVO % Viability | 90.5% | 94.3% | | | | |
| Post-LOVO TVC | 17.9E+09 | 59.4E+09 | 48.2E+09 | | | |
| Post-LOVO % Viability | 85.3% | 90.7% | 89% | | | |
| TVC Post LOVO % Recovery | 103.5% | 128.9% | | | | |
| %CD45+/CD3+ | 88.0% | 98.3% | | | | |
| IFNγ (pg/mL) | 11,618 | 19,235 | | 10,005 | 9,637 | 5,128 |
| GrzB (pg/mL) | 11,326 | 27,441 | | 19,929 | 16,040 | |
| Sterility | Pending (*) | Pending (*) | | | | |
| Endotoxin (total EU units) | 154.2 EU | 195.9 EU | | | | |
| Mycoplasma | Negative | Negative | | | | |
| Gram Staining | No organisms detected | No organisms detected | | | | |

FIG. 60

*Adds up to entire TIL sample (100% Live, CD14-, except for monocytes)*

| Characteristic | Eng run #1 | Eng run #2 |
|---|---|---|
| NK cells (CD3-CD56+) (%) | 10.9 | 1.5 |
| B cells (CD3-CD19+) (%) | 0.2 | 0.2 |
| Monocytes (CD14+) (%) | 0.0 | 0.0 |
| TCRαβ (%) | 87.1 | 96.3 |
| TCRγδ (%) | 1.2 | 1.6 |
| Sum | 99.4 | 99.6 |

*Adds up to 100% TCRab*

| Characteristic | Eng run #1 | Eng run #2 |
|---|---|---|
| Naive: CCR7+CD45RA+ (%) | 0.0 | 0.1 |
| T-EM: CCR7-CD45RA-(%) | 92.2 | 84.4 |
| T-CM: CCR7+CD45RA-(%) | 7.7 | 15.5 |
| T-EFF/TEMRA: CCR7-CD45RA+(%) | 0.1 | 0.1 |
| Sum | 100.0 | 100.0 |

*Adds up to 100% Live, CD14-*

| Characteristic | Eng run #1 | Eng run #2 |
|---|---|---|
| TCRαβ+ CD4+ (%) | 89.6 | 71.8 |
| TCRαβ+ CD8+ (%) | 10.0 | 27.8 |
| Sum | 99.6 | 99.6 |

FIG. 61

*Adds up to entire TIL sample (100% Live, CD14-, except for monocytes)*

| Characteristic | PD run #1 L4063 | PD run #2 L4064 |
|---|---|---|
| NK cells (CD3-CD56+) (%) | 1.04 | 0.52 |
| B cells (CD3-CD19+) (%) | 0.0076 | 0.013 |
| Monocytes (CD14+) (%) | 0.032 | 0.043 |
| TCRαβ (%) | 95.5 | 96.7 |
| TCRγδ (%) | 2 | 1.86 |
| Sum | 98.6 | 99.14 |

*Adds up to 100% TCRab*

| Characteristic | PD run #1 L4063 | PD run #2 L4064 |
|---|---|---|
| Naive: CCR7+CD45RA+ (%) | 0.35 | 0.07 |
| T-EM: CCR7-CD45RA-(%) | 97.4 | 96.7 |
| T-CM: CCR7+CD45RA-(%) | 1.39 | 2.78 |
| T-EFF/TEMRA: CCR7-CD45RA+(%) | 0.88 | 0.44 |
| Sum | 100.0 | 100.0 |

| Characteristic | PD run #1 L4063 | PD run #2 L4064 |
|---|---|---|
| TCRαβ$^+$ CD4$^+$ (%) | 77.5 | 57.4 |
| TCRαβ$^+$ CD8$^+$ (%) | 16.8 | 36.1 |
| Sum | 94.3 | 93.5 |

FIG. 62

| Characteristic | OV-8025 | | | OV-8026 | | | OV-8028 | | | OV-8022 | | |
|---|---|---|---|---|---|---|---|---|---|---|---|---|
| | FRER* | Gen 2^Y | Gen 3.1 | FRER^Y | Gen 2 | Gen 3.1 | FRER | Gen 2^Y | Gen 3.1 | FRER | Gen 2^Y | Gen 3.1* |
| **Purity** | | | | | | | | | | | | |
| T cells ($CD45^+CD3^+$) (%) | - | - | 99.2 | - | 75.1 | 97.5 | 97 | - | 97.6 | 53.6 | 16.4 | - |
| NK cells ($CD3^-CD56^+$) (%) | - | - | 0.2 | - | 8.4 | 1.1 | 0.4 | - | 0.1 | 44.6 | 81.1 | - |
| B cells (CD3-CD19+) (%) | - | - | 0 | - | 2.1 | 0 | 0 | - | 0 | 1.3 | 3.3 | - |
| Monocytes (CD14+) (%) | - | - | 0 | - | 0.2 | 0 | 0 | - | 0 | 2 | 0.1 | - |
| **Identity T cells** | | | | | | | | | | | | |
| TCR αβ (%) | - | - | 98.8 | - | 71.9 | 96.4 | 98.7 | - | 99.4 | 52.2 | 12.4 | - |
| TCR γδ (%) | - | - | 0.3 | - | 0.8 | 0.6 | 0 | - | 0.1 | 0.1 | 0 | - |
| $CD3^+ CD4^+$ (%) | - | - | 85.7 | - | 63.1 | 81.5 | 81.8 | - | 92.3 | 77.3 | 48.6 | - |
| $CD3^+ CD8^+$ (%) | - | - | 12 | - | 23 | 14.4 | 15.5 | - | 5.2 | 16.6 | 26.1 | - |
| **Memory Phenotype-TCRαβ+** | | | | | | | | | | | | |
| Naive: CCR7+CD45RA+ (%) | - | - | 0 | - | 0.4 | 0 | 2.1 | - | 0 | 0 | 0.1 | - |
| T-EM: CCR7-CD45RA-(%) | - | - | 98.5 | - | 88.7 | 97.5 | 93.6 | - | 97.1 | 89.1 | 93.8 | - |
| T-CM: CCR7+CD45RA-(%) | - | - | 1 | - | 7.5 | 0.6 | 1.9 | - | 2.5 | 0.1 | 0 | - |
| T-EFF/TEMRA: CCR7-CD45RA+(%) | - | - | 0.4 | - | 3.4 | 1.8 | 2.4 | - | 0.3 | 10.8 | 6.1 | - |

FR ER, Frozen tumor, Early REP
*, Condition not test
Y, Sampling issue, low TVC count or non-viable cells on thawing

FIG. 63

<table>
<tr><th>Characteristic</th><th>Hierarchy</th><th>Eng run #1</th><th>Eng run #2</th></tr>
<tr><td>NK cells (CD3-CD56+) (%)</td><td>S1/S2/All/Live/CD14-/CD3-/NK | Freq. of null (%)</td><td>10.9</td><td>1.5</td></tr>
<tr><td>B cells (CD3-CD19+) (%)</td><td>S1/S2/All/Live/CD14-/CD19 | Freq. of null (%)</td><td>0.2</td><td>0.2</td></tr>
<tr><td>Monocytes (CD14+) (%)</td><td>S1/S2/All/Live/CD14+ | Freq. of Parent (%)</td><td>0.0</td><td>0.0</td></tr>
<tr><td>TCRαβ (%)</td><td>S1/S2/All/Live/CD14-/TCRab | Freq. of null (%)</td><td>87.1</td><td>96.3</td></tr>
<tr><td>TCRγδ (%)</td><td>S1/S2/All/Live/CD14-/TCRgd | Freq. of null (%)</td><td>1.2</td><td>1.6</td></tr>
<tr><td>TCRαβ+CD4+ (%)</td><td>S1/S2/All/Live/CD14-/TCRab/CD4 | Freq. of Parent (%)</td><td>89.6</td><td>71.8</td></tr>
<tr><td>TCRαβ+CD8+ (%)</td><td>S1/S2/All/Live/CD14-/TCRab/CD8 | Freq. of Parent (%)</td><td>10.0</td><td>27.8</td></tr>
<tr><td>Naïve: CCR7+CD45RA+ (%)</td><td>S1/S2/All/Live/CD14-/TCRab/Q2: CCR7+, CD45RA+ | Freq. of Parent (%)</td><td>0.0</td><td>0.1</td></tr>
<tr><td>T-EM: CCR7-CD45RA-(%)</td><td>S1/S2/All/Live/CD14-/TCRab/Q4: CCR7-, CD45RA- | Freq. of Parent (%)</td><td>92.2</td><td>84.4</td></tr>
<tr><td>T-CM: CCR7+CD45RA-(%)</td><td>S1/S2/All/Live/CD14-/TCRab/Q3: CCR7+, CD45RA- | Freq. of Parent (%)</td><td>7.7</td><td>15.5</td></tr>
<tr><td>T-EFF/TEMRA: CCR7-CD45RA+(%)</td><td>S1/S2/All/Live/CD14-/TCRab/Q1: CCR7-, CD45RA+ | Freq. of Parent (%)</td><td>0.1</td><td>0.1</td></tr>
<tr><td>Naïve: CD62L+CD45RA+ (%)</td><td>S1/S2/All/Live/CD14-/TCRab/Q6: CD62L+, CD45RA+ | Freq. of Parent (%)</td><td>0.2</td><td>0.1</td></tr>
<tr><td>T-EM: CD62L-CD45RA-(%)</td><td>S1/S2/All/Live/CD14-/TCRab/Q8: CD62L-, CD45RA- | Freq. of Parent (%)</td><td>47.7</td><td>49.5</td></tr>
<tr><td>T-CM: CD62L+CD45RA-(%)</td><td>S1/S2/All/Live/CD14-/TCRab/Q7: CD62L+, CD45RA- | Freq. of Parent (%)</td><td>52.1</td><td>50.4</td></tr>
<tr><td>T-EFF/TEMRA: CD62L-CD45RA+(%)</td><td>S1/S2/All/Live/CD14-/TCRab/Q5: CD62L-, CD45RA+ | Freq. of Parent (%)</td><td>0.1</td><td>0.0</td></tr>
</table>

**Adds up to CD3+CD45+ %*

| Characteristic | Eng run #1 | Eng run #2 |
|---|---|---|
| TCRαβ (%) | 87.1 | 96.3 |
| TCRγδ (%) | 1.2 | 1.6 |
| Sum | 88.3 | 97.9 |

FIG. 64

| Characteristic | Hierarchy | CD4+ | | CD8+ | |
|---|---|---|---|---|---|
| | | Eng run #1 | Eng run #2 | Eng run #1 | Eng run #2 |
| **CD27+ (%)** | S1/S2/All/Live/CD14-/TCRab/CD4 or CD8/CD4+/8+CD27+ \| Freq. of Parent (%) | 0.7 | 2.0 | 2.1 | 12.7 |
| **CD28+ (%)** | S1/S2/All/Live/CD14-/TCRab/CD4 or CD8/CD4+/8+CD28+ \| Freq. of Parent (%) | 41.2 | 50.1 | 3.6 | 13.9 |
| **CD57+ (%)** | S1/S2/All/Live/CD14-/TCRab/CD4+/8+CD57+ \| Freq. of Parent (%) | 1.0 | 6.9 | 0.1 | 3.7 |
| **2B4+ (%)** | S/S/Live/CD3/CD4 or CD8/btla \| Freq. of Parent (%) | 4.5 | 5.5 | 69.1 | 55.7 |
| **BTLA4+ (%)** | S/S/Live/CD3/CD4 or CD8/2b4 \| Freq. of Parent (%) | 67.5 | 86.1 | 79.6 | 89.1 |
| **CCR4+ (%)** | S/S/Live/CD3/CD4 or CD8/CCR4+ \| Freq. of Parent (%) | 94.1 | 93.6 | 84.2 | 96.6 |
| **CD25+ (%)** | S/S/Live/CD3/CD4 or CD8/CD25 \| Freq. of Parent (%) | 63.1 | 61.0 | 47.5 | 51.8 |
| **CD69+ (%)** | S/S/Live/CD3/CD4 or CD8/CD69 \| Freq. of Parent (%) | 47.0 | 22.8 | 45.4 | 25.8 |
| **CD95+ (%)** | S/S/Live/CD3/CD4 or CD8/CD95 \| Freq. of Parent (%) | 99.2 | 98.1 | 99.1 | 97.6 |
| **CD103+ (%)** | S/S/Live/CD3/CD4 or CD8/CD103 \| Freq. of Parent (%) | 4.2 | 10.7 | 25.0 | 36.9 |
| **CXCR3+ (%)** | S/S/Live/CD3/CD4 or CD8/CXCR3 \| Freq. of Parent (%) | 58.1 | 76.7 | 89.3 | 88.3 |
| **KLRG1+ (%)** | S/S/Live/CD3/CD4 or CD8/KLRG1 \| Freq. of Parent (%) | 0.3 | 8.9 | 3.1 | 35.8 |
| **LAG3+ (%)** | S/S/Live/CD3/CD4 or CD8/Lag3 \| Freq. of Parent (%) | 5.0 | 3.3 | 19.4 | 21.2 |
| **PD1+ (%)** | S/S/Live/CD3/CD4 or CD8/PD1 \| Freq. of Parent (%) | 29.3 | 22.1 | 11.2 | 7.2 |
| **TIGIT+ (%)** | S/S/Live/CD3/CD4 or CD8/Tigit \| Freq. of Parent (%) | 68.1 | 53.2 | 74.9 | 65.8 |
| **TIM3+ (%)** | S/S/Live/CD3/CD4 or CD8/TIM3 \| Freq. of Parent (%) | 93.6 | 81.8 | 91.2 | 84.4 |

FIG. 65

| | 1:100 Stim/1:50 Unstim | | | 1:200 Stim/1:100 Unstim | | | 1:400 Stim/1:200 Unstim | | | | | |
|---|---|---|---|---|---|---|---|---|---|---|---|---|
| Sample | 1 | 2 | 3 | 4 | 5 | 6 | 7 | 8 | 9 | Avg | Stim-Unstim | Fold Induction |
| Eng 1 Stimulated | 13001.49 | 16033.00 | 14083.24 | 11008.85 | 15254.59 | 12534.24 | 9985.83 | 14237.22 | 11669.82 | 13089.81 | 11325.97 | 7.42 |
| Eng 1 Unstimulated | 2155.31 | 2445.64 | 2108.37 | 1727.43 | 1982.96 | 1566.52 | 1119.057 | 1611.132 | 1158.179 | 1763.84 | | |
| Eng 1 Stimulated Ctrl | 26491.92 | 31766.20 | 31601.13 | 26385.05 | 30852.42 | 29752.34 | 26175.43 | 33462.43 | 29728.52 | 29579.49 | 13486.52 | 1.84 |
| Eng 1 Unstimulated Ctrl | 16209.90 | 16478.69 | 16936.51 | 15659.69 | 16385.60 | 17083.36 | 15419.07 | 15683.49 | 14980.40 | 16092.97 | | |

| | 1:100 Stim/1:50 Unstim | | | 1:200 Stim/1:100 Unstim | | | 1:400 Stim/1:200 Unstim | | | | | |
|---|---|---|---|---|---|---|---|---|---|---|---|---|
| Sample | 1 | 2 | 3 | 4 | 5 | 6 | 7 | 8 | 9 | Avg | Stim-Unstim | Fold Induction |
| Eng 2 Stimulated | 31509.54 | 30435.33 | 33822.81 | 27299.28 | 29091.87 | 29432.13 | 29027.45 | 30685.94 | 31138.70 | 30271.45 | 27441.29 | 10.70 |
| Eng 2 Unstimulated | 3236.50 | 3442.58 | 3630.97 | 2764.12 | 2839.66 | 2892.96 | 2047.795 | 2291.994 | 2324.838 | 2830.16 | | |
| Eng 2 Stimulated Ctrl | 21515.93 | 20346.31 | 19425.54 | 18299.25 | 17398.91 | 18131.38 | 18825.27 | 18412.15 | 18278.94 | 18959.30 | 6189.32 | 1.48 |
| Eng 2 Unstimulated Ctrl | 13716.23 | 13445.80 | 13563.89 | 12782.28 | 12678.37 | 13122.65 | 11898.75 | 11675.48 | 12046.29 | 12769.97 | | |

FIG. 66

| STEP | Gen 2 | Gen 2.1 | Gen 3.0 |
|---|---|---|---|
| **Pre REP-day 0** | ≤ 50 fragments/ 1 G-Rex 100MCS - **11 days** | ≤ 180 fragments/ 3 G-Rex, Pre-formulated CM1 warmed media 100MCS - **11 days** | ***Fresh or Frozen Tumor*** Whole tumor with ≤ 30 fragments up to 60 fragments per 1 G-Rex. 100MCS (up to 4 G-Rex), preformulated warmed media - **7 days. Pre REP, Feeders 250e6 cells + OKT-3 (15ug)** |
| **REP Initiation** | Direct to REP- Day 11- **<200e$^6$ TIL** 1 G-Rex 500MCS | Direct to REP- Day 11- **<200 e$^6$ TIL** Pre-formulated CM2 warmed media in one G-Rex 500MCS | Direct to REP - Day **7-all cells TIL- same G-Rex 100MCS (100MCS up to 4 GREX), Standard media or Defined Media (Serum free). Addition Feeders 500e6 cells +OKT-3 (30ug)** |
| **TIL propagation or Scale up** | 1 to 5 G-REX 500MCS **Split day 16** | 2 to 5 G-REX 500MCS Pre-formulated CM4 warmed media **Split day 16** | From G-REX 100MCS transfer TIL suspension to G-REX 500MCS, up to 4 GREX 500 MCS- Standard media or Defined Media (Serum Free) **Scale up on day 10 or 11** |
| **Harvest** | **Harvest day 22,** LOVO-automated cell washer | **Harvest day 22,** LOVO-automated cell washer (5 wash cycle) | **Harvest day 14 or 16** LOVO- automated cell washer (5 wash cycle) |
| **Final formulation** | Cryopreserved Product 300IU/ml IL2- CS10 in $LN_2$, multiple aliquots | Cryopreserved Product 300IU/ml IL2- CS10 in $LN_2$, multiple aliquots | Cryopreserved Product 300IU/ml IL2-CS10 in $LN_2$, multiple aliquots |
| **Process time** | **22 days** | **22 days** | **16 days** |

FIG. 69

| Process Comparison | Process Changes | Differences |
|---|---|---|
| **Gen 2 : Gen 2.1** | • Initiate process with two flasks instead of one flask<br>• Divide REP initiation feeder layer between 2 G-Rex500MCS Flasks<br>• Pre-formulate media and warm prior to use | • Potential doubling of final cell count (dose) with increased TIL repertoire.<br>• Process redundancy throughout process |
| **Gen 2.1 : Gen 3.1** | • Fresh or Frozen tumor<br>• 14-16 day process (from 22 day)<br>• Reduce total feeder layer on process<br>• Feeder layer and OKT3 present at Day 0<br>• REP initiated with fragments<br>• 100MCS scales to 500MCS<br>• Scales to multiple pre-REP flasks<br>• Standard Media and Defined Media (Serum Free) | • Increased potency<br>• Improved phenotype<br>• Decreased process time<br>• Reduced reagent testing<br>• Decreased process variability<br>• Defined reagents<br>• Increased repertoire<br>• Reduce impurities (feeder)<br>• Comparable or Higher Dose. |

FIG. 70

| Process Day | Conditions | Gen 3.0 | Gen 3.1 control | Gen 3.1 Test |
|---|---|---|---|---|
| **Day 0 :** Tumor Fragment Isolation and Activation | Media (*) | 500 mL | 500 mL | 500 mL |
| | IL-2 | 6000 IU/mL | 6000 IU/mL | 6000 IU/mL |
| | OKT-3 | - | 15 ug | 15 ug |
| | Feeders | - | - | 2.5E+06 |
| **Process Day** | **Conditions** | **Gen 3.0** | **Gen 3.1 control** | **Gen 3.1 Test** |
| **Day 7 - 8 :** TIL Culture Reactivation | Media (*) | 500 mL | 500 mL | 500 mL |
| | IL-2 | 6000 IU/mL | 6000 IU/mL | 6000 IU/mL |
| | OKT-3 | 30 ug | 30 ug | 30 ug |
| | Feeders | 1 E+09 | 500 E+06 | 500E+06 |
| | Total Feeders added through Day 7 | 1 E+09 | 500 E+06 | 750E+06 |
| **Process Day** | **Conditions** | **Gen 3.0** | **Gen 3.1 control** | **Gen 3.1 Test** |
| **Day 10-11 : Culture Scale Up** | From GREX 100 transfer whole TIL suspension to 1 GREX 500 containing 4L media with IL-2 (3000 IU/mL) | | | |
| **Process Day** | **Conditions** | **Gen 3.0** | **Gen 3.1 control** | **Gen 3.1 Test** |
| **Day 16-17: Harvest/Wash/Formulate** | LOVO automated cell washer and cryopreservation with CS10. | | | |

(*) Media can be standard media or CTS serum free media.

FIG. 71

| Process Day | L4063 in Standard Media | | | L4064 in Serum Free Media | | |
|---|---|---|---|---|---|---|
| | Gen 3.0 | Gen 3.1 Control | Gen 3.1 Test | Gen 3.0 | Gen 3.1 Control | Gen 3.1 Test |
| Number of fragments | **53** | **53** | **53** | **21** | **21** | **21** |
| Average TVC at harvest per fragment | 1.37E+08 | 3.19E+08 | 3.53E+08 | 5.90E+08 | 7.57E+08 | 9.29E+08 |
| TVC day 7 (*) | 2.59E+07 | 6.43E+07 | 1.45E+08 | 7.35E+06 | 9.28E+07 | 1.39E+08 |
| TVC day 10/11 (*) | 6.07E+08 | 1.66E+09 | 1.83E+09 | 7.48E+08 | 1.28E+09 | 1.72E+09 |
| TVC harvest day 16/17 | 7.26E+09 | 1.69E+10 | 1.87E+10 | 1.24E+10 | 1.59E+10 | 1.95E+10 |
| Fold Expansion (day 10 or 11 / day 7) | **23.4** | **25.8** | **12.6** | **101.8** | **13.8** | **12.4** |
| Fold Expansion (Harvest day 16 / day 7) | **280.3** | **262.8** | **129.0** | **1687.1** | **171.3** | **140.3** |

(*) Cell counts for Day 7 and Day 10/11 were taken FIO. Based on the design of the process, samples were pulled directly from each flask after swirling its contents without volume reduction. As such, analysis and conclusions of cell count data from these samples is limited by the nature of the sampling methodology.

FIG. 73

| | L4063 in Standard media | | | L4064 in CTS Serum Free media | | |
|---|---|---|---|---|---|---|
| Process Day | Gen 3.0 | Gen 3.1 Control | Gen 3.1 Test | Gen 3.0 | Gen 3.1 Control | Gen 3.1 Test |
| Reactivation | 74.6% | 92.1% | 88.7% | 88.0% | 92.8% | 95.0% |
| Scale up | 92.1% | 95.4% | 94.0% | 90.4% | 94.3% | 95.1% |
| Harvest | 79.5% | 89.4% | 94.8% | 88.8% | 81.9% | 84.9% |

FIG. 74

| Tumor ID | L4063 in Standard media | | | L4064 in CTS Serum Free media | | |
|---|---|---|---|---|---|---|
| Markers | Gen 3.0 | Gen 3.1 Control | Gen 3.1 Test | Gen 3.0 | Gen 3.1 Control | Gen 3.1 Test |
| L/D Aqua | 82.2 | 89.4 | 91.0 | 76.6 | 83.1 | 89.5 |
| NK | 1.3 | 0.4 | 1.0 | 2.5 | 0.2 | 0.5 |
| TCRa/b+ | 88.6 | 97.5 | 95.5 | 93.0 | 97.3 | 96.7 |
| CD4 | 56.4 | 85.8 | 77.5 | 33.8 | 64.8 | 57.4 |
| CD4/CD27 | 3.8 | 2.1 | 3.4 | 6.7 | 0.7 | 2.2 |
| CD4/CD28 | 82.7 | 71.8 | 80.2 | 97.5 | 73.5 | 66.8 |
| CD4/CD56 | 0.4 | 0.5 | 0.7 | 0.5 | 0.5 | 0.3 |
| CD4/CD57 | 6.7 | 17.0 | 20.5 | 16.0 | 7.6 | 8.0 |
| CD8 | 29.6 | 11.2 | 16.8 | 51.9 | 28.9 | 36.1 |
| CD8/CD27 | 15.0 | 25.6 | 30.5 | 14.1 | 3.3 | 6.7 |
| CD8/CD28 | 47.5 | 23.0 | 24.5 | 88.0 | 45.1 | 37.3 |
| CD8/CD56 | 3.3 | 2.3 | 4.2 | 6.6 | 10.3 | 10.0 |
| CD8/CD57 | 0.3 | 1.2 | 1.1 | 1.3 | 0.2 | 2.5 |

FIG. 75

| Tumor ID | L4063 in Standard media | | | L4064 in CTS Serum Free media | | |
|---|---|---|---|---|---|---|
| **Markers** | **Gen 3.0** | **Gen 3.1 Control** | **Gen 3.1 Test** | **Gen 3.0** | **Gen 3.1 Control** | **Gen 3.1 Test** |
| CD/CD4 | 56.4 | 85.8 | 77.5 | 33.8 | 64.8 | 57.4 |
| TEMRA of CD4 | 0.4 | 0.7 | 0.4 | 1.1 | 0.7 | 0.2 |
| NAIVE of CD4 | 0.3 | 0.2 | 0.2 | 0.5 | 0.1 | 0.0 |
| CM of CD4 | 45.6 | 16.8 | 29.3 | 46.3 | 30.6 | 29.9 |
| EM of CD4 | 53.7 | 82.3 | 70.2 | 52.1 | 68.6 | 69.9 |
| | | | | | | |
| CD3/CD8 | 29.6 | 11.2 | 16.8 | 51.9 | 28.9 | 36.1 |
| TEMRA of CD8 | 3.1 | 0.5 | 0.9 | 6.1 | 8.0 | 5.4 |
| NAIVE of CD8 | 0.7 | 0.1 | 0.4 | 2.2 | 0.7 | 1.0 |
| CM of CD8 | 22.0 | 15.8 | 29.7 | 61.9 | 18.9 | 18.2 |
| EM of CD8 | 74.3 | 83.5 | 69.0 | 29.8 | 72.4 | 75.5 |

FIG. 76

| Tumor ID | L4063 in Standard media | | | L4064 in CTS Serum Free media | | |
|---|---|---|---|---|---|---|
| Markers | Gen 3.0 | Gen 3.1 Control | Gen 3.1 Test | Gen 3.0 | Gen 3.1 Control | Gen 3.1 Test |
| 2B4+ | 2.1 | 0.6 | 1.0 | 2.0 | 1.2 | 1.3 |
| BTLA4 | 99.7 | 95.4 | 96.9 | 99.5 | 98.8 | 98.1 |
| CD25+ | 48.6 | 10.5 | 3.9 | 58.2 | 41.7 | 32.1 |
| CD69+ | 27.1 | 37.7 | 21.5 | 39.4 | 35.6 | 30.5 |
| CD95+ | 99.9 | 99.9 | 99.5 | 99.6 | 99.0 | 97.3 |
| CD103+ | 0.7 | 1.2 | 0.4 | 1.4 | 1.3 | 1.2 |
| KLRG1+ | 1.6 | 3.7 | 3.3 | 11.4 | 8.3 | 10.7 |
| LAG3+ | 5.6 | 8.2 | 3.3 | 1.5 | 1.6 | 1.4 |
| PD1+ | 77.4 | 58.4 | 41.6 | 34.1 | 28.4 | 26.7 |
| TIGIT+ | 68.5 | 40.3 | 30.3 | 45.8 | 52.1 | 52.2 |
| TIM3+ | 58.0 | 42.4 | 59.4 | 61.0 | 58.4 | 56.8 |

FIG. 77

| Tumor ID | L4063 in Standard media | | | L4064 in CTS Serum Free media | | |
|---|---|---|---|---|---|---|
| Markers | Gen 3.0 | Gen 3.1 Control | Gen 3.1 Test | Gen 3.0 | Gen 3.1 Control | Gen 3.1 Test |
| 2B4+ | 65.8 | 56.6 | 70.5 | 13.6 | 21.5 | 20.7 |
| BTLA4 | 99.5 | 96.6 | 98.2 | 99.3 | 97.4 | 96.1 |
| CD25+ | 41.4 | 10.5 | 5.9 | 60.6 | 32.0 | 17.1 |
| CD69+ | 44.9 | 28.0 | 20.0 | 33.2 | 30.6 | 22.7 |
| CD95+ | 99.6 | 99.6 | 98.9 | 98.9 | 96.1 | 93.5 |
| CD103+ | 29.4 | 27.9 | 24.5 | 10.9 | 6.0 | 7.3 |
| CXCR3+ | 99.9 | 99.9 | 99.8 | 99.3 | 99.2 | 99.2 |
| KLRG1+ | 7.1 | 4.6 | 6.7 | 13.2 | 14.5 | 14.1 |
| LAG3+ | 28.6 | 22.5 | 11.9 | 2.8 | 1.6 | 1.4 |
| PD1+ | 56.9 | 54.5 | 51.7 | 25.4 | 20.0 | 23.6 |
| TIGIT+ | 90.8 | 93.7 | 93.3 | 92.1 | 90.4 | 90.5 |
| TIM3+ | 66.7 | 49.1 | 58.6 | 65.6 | 46.8 | 43.6 |

FIG. 78

| TIL Characterization | L4063 in Standard media | | | L4064 in CTS Serum Free media | | |
|---|---|---|---|---|---|---|
| | Gen 3.0 | Gen 3.1 Control | Gen 3.1 Test | Gen 3.0 | Gen 3.1 Control | Gen 3.1 Test |
| IFNγ (pg/mL) | 907 | 428 | 2863 | 1485 | 3130 | 3863 |

*Results are reported as mean of triplicate samples from one representative experiment*

FIG. 79

| Process Day | L4063 in Standard media | | | L4064 in CTS Serum Free media | | |
|---|---|---|---|---|---|---|
| | Gen 3.0 | Gen 3.1 Control | Gen 3.1 Test | Gen 3.0 | Gen 3.1 Control | Gen 3.1 Test |
| Reactivation | 12319.6 | 11928.7 | 11786.7 | 5891.6 | 5671.8 | 389.4(1) |
| Scale Up | 32095.1 | 30368.6 | 26145.0 | * | * | * |
| Harvest | 17309.3 | 13828.4 | 16019.2 | 656.0 | 826.2 | 768.9 |

*Results are reported as mean triplicate samples from one representative experiement*

*(*) Spent media from day 10/11 on L4064 was not collected during the execution of the runs.*

*(1) The data for Gen 3.1 Test L4064 on reactivation day was significantly below the corresponding values for Gen 3.1 control and Gen 3.0 conditions. Due to the low amount of sample taken, it was not possible to repeat the assay to verify the accuracy of this number.*

FIG. 80

| Glucose (g/L) | | | | | | |
|---|---|---|---|---|---|---|
| | L4063 in Standard media | | | L4064 in CTS Serum Free media | | |
| Process Day | Gen 3.0 | Gen 3.1 Control | Gen 3.1 Test | Gen 3.0 | Gen 3.1 Control | Gen 3.1 Test |
| Reactivation | 1.8 | 1.7 | 1.4 | 4.3 | 4.1 | 3.8 |
| Scale Up | 1.4 | 0.9 | 0.8 | * | * | * |
| Harvest | 1.5 | 0.9 | 1.0 | 2.8 | 2.1 | 2.2 |

*(*) Spent media from day 10/11 on L4064 was not collected during the execution of the runs.*

FIG. 81

| Lactate (g/L) | | | | | | |
|---|---|---|---|---|---|---|
| | L4063 in Standard media | | | L4064 in CTS Serum Free media | | |
| Process Day | Gen 3.0 | Gen 3.1 Control | Gen 3.1 Test | Gen 3.0 | Gen 3.1 Control | Gen 3.1 Test |
| Reactivation | 0.2 | 0.2 | 0.5 | 0.1 | 0.2 | 0.5 |
| Scale Up | 0.7 | 1.1 | 1.2 | * | * | * |
| Harvest | 1.1 | 1.7 | 1.6 | 1.5 | 2.0 | 1.9 |

*(*) Spent media from day 10/11 on L4064 was not collected during the execution of the runs.*

FIG. 82

| Glutamine (mmol/L) | | | | | | |
|---|---|---|---|---|---|---|
| | L4063 in Standard media | | | L4064 in CTS Serum Free media | | |
| Process Day | Gen 3.0 | Gen 3.1 Control | Gen 3.1 Test | Gen 3.0 | Gen 3.1 Control | Gen 3.1 Test |
| Reactivation | 2.0 | 2.0 | 2.0 | 1.3 | 1.2 | 1.1 |
| Scale Up | 1.7 | 1.1 | 1.1 | * | * | * |
| Harvest | 1.9 | 1.3 | 1.3 | 0.7 | 0.6 | 0.6 |

*(*) Spent media from day 10/11 on L4064 was not collected during the execution of the runs.*

FIG. 83

| Glutamax (mmol/L) | | | | | | |
|---|---|---|---|---|---|---|
| | L4063 in Standard media | | | L4064 in CTS Serum Free media | | |
| Process Day | Gen 3.0 | Gen 3.1 Control | Gen 3.1 Test | Gen 3.0 | Gen 3.1 Control | Gen 3.1 Test |
| Reactivation | 2.2 | 2.2 | 2.2 | 1.4 | 1.3 | 1.2 |
| Scale Up | 1.9 | 1.2 | 1.2 | * | * | * |
| Harvest | 2.1 | 1.5 | 1.5 | 0.8 | 0.7 | 0.7 |

*(*) Spent media from day 10/11 on L4064 was not collected during the execution of the runs.*

FIG. 84

| Ammonia (mmol/L) | | | | | | |
|---|---|---|---|---|---|---|
| | L4063 in Standard media | | | L4064 in CTS Serum Free media | | |
| Process Day | Gen 3.0 | Gen 3.1 Control | Gen 3.1 Test | Gen 3.0 | Gen 3.1 Control | Gen 3.1 Test |
| Reactivation | 1.9 | 1.9 | 2.0 | 0.7 | 0.8 | 0.9 |
| Scale Up | 1.8 | 2.2 | 2.3 | * | * | * |
| Harvest | 2.1 | 2.5 | 2.5 | 1.0 | 1.0 | 0.9 |

*(*) Spent media from day 10/11 on L4064 was not collected during the execution of the runs.*

FIG. 85

| TIL Characterization | L4063 in Standard media | | | L4064 in CTS Serum Free media | | |
|---|---|---|---|---|---|---|
| | Gen 3.0 | Gen 3.1 Control | Gen 3.1 Test | Gen 3.0 | Gen 3.1 Control | Gen 3.1 Test |
| Relative Telomere Length | 7.7 | 6.3 | 6.1 | 6.4 | 6.7 | 6.6 |

FIG. 86

| TIL Characterization | L4063 in Standard media | | | L4064 in CTS Serum Free media | | |
|---|---|---|---|---|---|---|
| | Gen 3.0 | Gen 3.1 Control | Gen 3.1 Test | Gen 3.0 | Gen 3.1 Control | Gen 3.1 Test |
| uCD3 | 14005.0 | 18149.0 | 17181.0 | 15107.0 | 21460.0 | 21503.0 |
| Shanon Entropy Index | 5.9 | 10.8 | 10.5 | 8.5 | 10.7 | 10.4 |

FIG. 87

| Number of u CDR3 (%overlap) L4063 | All uCDR3's | | | Top 80% uCDR3's | | |
|---|---|---|---|---|---|---|
| | Gen 3.0 | Gen 3.1 Control | Gen 3.1 Test | Gen 3.0 | Gen 3.1 Control | Gen 3.1 Test |
| Gen 3.0 | 14005 | 3240 (23%) | 2959 (21%) | 1105 | 1000 (90%) | 975 (88%) |
| Gen 3.1 Control | - | 18149 | - | - | 2437 | - |
| Gen 3.1 Test | - | - | 17181 | - | - | 2331 |

FIG. 89

| Number of u CDR3 (%overlap) L4064 | All uCDR3's | | | Top 80% uCDR3's | | |
|---|---|---|---|---|---|---|
| | Gen 3.0 | Gen 3.1 Control | Gen 3.1 Test | Gen 3.0 | Gen 3.1 Control | Gen 3.1 Test |
| Gen 3.0 | 15107 | 5486 (36%) | 5541 (36%) | 2478 | 2186 (88%) | 2163 (87%) |
| Gen 3.1 Control | - | 21460 | - | - | 3246 | - |
| Gen 3.1 Test | - | - | 21503 | - | - | 3263 |

FIG. 90

| Step | Process Gen 3-Optimized |
| --- | --- |
| **Day 0**<br>**Tumor isolation and Activation** | ≤240 fragments<br>≤60 fragments/flask<br>≤4 flasks<br>≤2L media (500mL/flask)<br>IL-2 (6000IU/mL)<br>$2.5 \times 10^8$ feeder cells/flask<br>15ug OKT3/flask |
| **Day 7 - 8**<br>**Reactivation** | Fresh TIL direct to REP<br>Activate entire culture<br>$5 \times 10^8$ feeder cells<br>30 ug OKT3/flask<br>G-Rex 100MCS<br>Add 500mL media+ IL-2(6000IU/mL) |
| **Day 10 - 11**<br>**Scale up or TIL Sub-culture** | ≤4 G-REX 500MCS<br>Scale up entire culture transferring 1L from GREX 100MCS into GREX 500MCS<br>and add 4L of media +IL-2 (3000 IU/mL) /flask |
| **Day 16 - 17**<br>**Harvest** | Harvest<br>LOVO- automated cell washer<br>Cryopreservation on Plasmalyte 1% HSA: CS10 |

FIG. 92

| Test | Acceptance Criteria | Gen 3.1 Test vs Gen 3.0 Process |
|---|---|---|
| Cell Count (TVC) | Gen 3.1 > 30% to Process Gen 3.0 | Met |
| % Viability | ≥70% Viability | Met |
| Immunophenotyping (%CD3+/ %CD45+) | ≤5% difference between Gen 3.1 and Gen 3.0 process | Met |
| IFNγ secretion | Gen 3.1 ≥ to Process Gen 3.0 | Met |

FIG. 93

Cell counts reactivation Day

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3.0 (A) L4063 | 500 | Total | 7.10E+04 | 6.81E+04 | | 6.96E+04 | 3.48E+07 |
| | | Live | 5.27E+04 | 5.09E+04 | | 5.18E+04 | 2.59E+07 |
| | | Dead | 1.83E+04 | 1.72E+04 | | 1.78E+04 | 8.88E+06 |
| | | % Viability | 74.30% | 74.80% | | 74.55% | |
| Gen 3.1 (A) L4063 | 500 | Total | 1.41E+05 | 1.38E+05 | | 1.40E+05 | 6.98E+07 |
| | | Live | 1.31E+05 | 1.26E+05 | | 1.29E+05 | 6.43E+07 |
| | | Dead | 9.84E+03 | 1.21E+04 | | 1.10E+04 | 5.49E+06 |
| | | % Viability | 93.00% | 91.20% | | 92.10% | |
| Gen 3.1 Test L4063 | 500 | Total | 3.26E+05 | 3.28E+05 | | 3.27E+05 | 1.64E+08 |
| | | Live | 2.83E+05 | 2.96E+05 | | 2.90E+05 | 1.45E+08 |
| | | Dead | 4.25E+04 | 3.16E+04 | | 3.71E+04 | 1.85E+07 |
| | | % Viability | 87.00% | 90.30% | | 88.65% | |
| Gen 3.0 (A) L4064 | 500 | Total | 1.59E+04 | 1.75E+04 | | 1.67E+04 | 8.35E+06 |
| | | Live | 1.39E+04 | 1.44E+04 | | 1.47E+04 | 7.35E+06 |
| | | Dead | 1.98E+03 | 2.02E+03 | | 2.00E+03 | 1.00E+06 |
| | | % Viability | 87.50% | 88.50% | | 88.00% | |
| Gen 3.1 Control L4064 | 500 | Total | 2.02E+05 | 1.98E+05 | | 2.00E+05 | 1.00E+08 |
| | | Live | 1.88E+05 | 1.83E+05 | | 1.86E+05 | 9.28E+07 |
| | | Dead | 1.38E+04 | 1.51E+04 | | 1.45E+04 | 7.23E+06 |
| | | % Viability | 93.20% | 92.40% | | 92.80% | |
| Gen 3.1 TEST L4064 | 500 | Total | 2.70E+05 | 3.15E+05 | | 2.93E+05 | 1.46E+08 |
| | | Live | 2.55E+05 | 3.01E+05 | | 2.78E+05 | 1.39E+08 |
| | | Dead | 1.51E+04 | 1.38E+04 | | 1.45E+04 | 7.23E+06 |
| | | % Viability | 94.40% | 95.60% | | 95.00% | |

FIG. 94

Cell counts Scale Up Day

| ID | Volume (mL) | | Count 1 (cells/mL) | Count 3 (cells/mL) | Count 2 (cells/mL) | Average (cells/mL) | Total Cells Average*Volume |
|---|---|---|---|---|---|---|---|
| Gen 3.0 (A) L4063 | 1000 | Total | 6.57E+05 | 6.61E+05 | | 6.59E+05 | 6.59E+08 |
| | | Live | 6.00E+05 | 6.14E+05 | | 6.07E+05 | 6.07E+08 |
| | | Dead | 5.71E+04 | 4.68E+04 | | 5.20E+04 | 5.20E+07 |
| | | % Viability | 91.30% | 92.90% | | 92.10% | |
| Gen 3.1 Control L4063 | 1000 | Total | 1.66E+06 | 1.82E+06 | | 1.74E+06 | 1.74E+09 |
| | | Live | 1.59E+06 | 1.72E+06 | | 1.66E+06 | 1.66E+09 |
| | | Dead | 7.17E+04 | 9.07E+04 | | 8.12E+04 | 8.12E+07 |
| | | % Viability | 95.70% | 95.00% | | 95.35% | |
| Gen 3.1 Test L4063 | 1000 | Total | 1.88E+06 | 2.00E+06 | | 1.94E+06 | 1.94E+09 |
| | | Live | 1.76E+06 | 1.89E+06 | | 1.83E+06 | 1.83E+09 |
| | | Dead | 1.20E+05 | 1.15E+05 | | 1.18E+05 | 1.18E+08 |
| | | % Viability | 93.60% | 94.30% | | 93.95% | |
| Gen 3.0 (A) L4064 | 1000 | Total | 7.95E+05 | 8.58E+05 | | 8.27E+05 | 8.27E+08 |
| | | Live | 7.17E+05 | 7.78E+05 | | 7.48E+05 | 7.48E+08 |
| | | Dead | 7.85E+04 | 8.05E+04 | | 7.95E+04 | 7.95E+07 |
| | | % Viability | 90.10% | 90.60% | | 90.35% | |
| Gen 3.1 Control L4064 | 1000 | Total | 1.38E+06 | 1.32E+06 | | 1.35E+06 | 1.35E+09 |
| | | Live | 1.31E+06 | 1.24E+06 | | 1.28E+06 | 1.28E+09 |
| | | Dead | 7.20E+04 | 8.13E+04 | | 7.67E+04 | 7.67E+07 |
| | | % Viability | 94.80% | 93.80% | | 94.30% | |
| Gen 3.1 TEST L4064 | 1000 | Total | 1.85E+06 | 1.76E+06 | | 1.81E+06 | 1.81E+09 |
| | | Live | 1.76E+06 | 1.67E+06 | | 1.72E+06 | 1.72E+09 |
| | | Dead | 8.62E+04 | 8.95E+04 | | 8.79E+04 | 8.79E+07 |
| | | % Viability | 95.30% | 94.90% | | 95.10% | |

FIG. 95

Cell counts Harvest L4063

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3.0 (A) L4063 pre LOVO | 602.4 | Total | 1.68E+07 | 1.70E+07 | | 1.69E+07 | 1.02E+10 |
| | | Live | 1.52E+07 | 1.54E+07 | | 1.53E+07 | 9.22E+09 |
| | | Dead | 1.60E+06 | 1.64E+06 | | 1.63E+06 | 9.79E+08 |
| | | % Viability | 90.50% | 90.30% | | 90.40% | |
| Gen 3.1 Control L4063 pre LOVO | 497 1 | Total | 3.39E+07 | 3.90E+07 | | 3.65E+07 | 1.81E+10 |
| | | Live | 3.25E+07 | 3.73E+07 | | 3.49E+07 | 1.73E+10 |
| | | Dead | 1.41E+06 | 1.63E+06 | | 1.52E+06 | 7.56E+08 |
| | | % Viability | 95.80% | 95.80% | | 95.80% | |
| Gen 3.1 Test L4063 pre LOVO | 552.3 | Total | 3.71E+07 | 3.62E+07 | | 3.67E+07 | 2.02E+10 |
| | | Live | 3.56E+07 | 3.51E+07 | | 3.54E+07 | 1.95E+10 |
| | | Dead | 1.50E+06 | 1.09E+06 | | 1.30E+06 | 7.15E+08 |
| | | % Viability | 96.00% | 97.00% | | 96.50% | |
| Gen 3.0 (A) L4063 post LOVO | 165 | Total | 5.37E+07 | 5.73E+07 | 5.50E+07 | 5.53E+07 | 9.13E+09 |
| | | Live | 4.32E+07 | 4.52E+07 | 4.36E+07 | 4.40E+07 | 7.26E+09 |
| | | Dead | 1.04E+07 | 1.21E+07 | 1.14E+07 | 1.13E+07 | 1.86E+09 |
| | | % Viability | 80.50% | 78.80% | 79.30% | 79.53% | |
| Gen 3.1 Control L4063 post LOVO | 165 | Total | 1.21E+08 | 1.01E+08 | 1.22E+08 | 1.15E+08 | 1.89E+10 |
| | | Live | 1.10E+08 | 8.85E+07 | 1.09E+08 | 1.03E+08 | 1.69E+10 |
| | | Dead | 1.11E+07 | 1.23E+07 | 1.27E+07 | 1.20E+07 | 1.99E+09 |
| | | % Viability | 90.90% | 87.80% | 89.60% | 89.43% | |
| Gen 3.1 TEST L4063 post LOVO | 175 | Total | 1.05E+08 | 1.20E+08 | | 1.13E+08 | 1.97E+10 |
| | | Live | 9.93E+07 | 1.14E+08 | | 1.07E+08 | 1.87E+10 |
| | | Dead | 5.51E+06 | 6.14E+06 | | 5.83E+06 | 1.02E+09 |
| | | % Viability | 94.70% | 94.90% | | 94.80% | |

FIG. 96

Cell counts Harvest L4064

| ID | Volume (mL) | | Count 1 (cells/mL) | Count 2 (cells/mL) | Count 3 (cells/mL) | Average (cells/mL) | Total Cells Average*Volume |
|---|---|---|---|---|---|---|---|
| Gen 3.0 (A) L4064 pre LOVO | 641.3 | Total | 1.99E+07 | 1.94E+07 | | 1.97E+07 | 1.26E+10 |
| | | Live | 1.83E+07 | 1.94E+07 | | 1.89E+07 | 1.21E+10 |
| | | Dead | 1.60E+06 | 1.68E+06 | | 1.64E+06 | 1.05E+09 |
| | | % Viability | 92.00% | 92.00% | | 92.00% | |
| Gen 3.1 Control L4064 pre LOVO | 493.4 | Total | 3.98E+07 | 3.87E+07 | | 3.93E+07 | 1.94E+10 |
| | | Live | 3.65E+07 | 3.55E+07 | | 3.60E+07 | 1.78E+10 |
| | | Dead | 3.31E+06 | 3.22E+06 | | 3.27E+06 | 1.61E+09 |
| | | % Viability | 91.70% | 91.70% | | 91.70% | |
| Gen 3.1 Test L4064 pre LOVO | 593.4 | Total | 3.92E+07 | 3.79E+07 | | 3.86E+07 | 2.29E+10 |
| | | Live | 3.67E+07 | 3.54E+07 | | 3.61E+07 | 2.14E+10 |
| | | Dead | 2.55E+06 | 2.50E+06 | | 2.53E+06 | 1.50E+09 |
| | | % Viability | 93.50% | 93.40% | | 93.45% | |
| Gen 3.0 (A) L4064 post LOVO | 165 | Total | 8.58E+07 | 8.34E+07 | | 8.46E+07 | 1.40E+10 |
| | | Live | 7.56E+07 | 7.46E+07 | | 7.51E+07 | 1.24E+10 |
| | | Dead | 1.02E+07 | 8.79E+06 | | 9.50E+06 | 1.57E+09 |
| | | % Viability | 88.10% | 89.50% | | 88.80% | |
| Gen 3.1 Control L4064 post LOVO | 165 | Total | 1.13E+08 | 1.22E+08 | 1.15E+08 | 1.18E+08 | 1.94E+10 |
| | | Live | 9.21E+07 | 1.01E+08 | 9.45E+07 | 9.66E+07 | 1.59E+10 |
| | | Dead | 2.14E+07 | 2.13E+07 | 2.07E+07 | 2.14E+07 | 3.52E+09 |
| | | % Viability | 81.20% | 82.60% | 82.10% | 81.90% | |
| Gen 3.1 TEST L4064 post LOVO | 165 | Total | 1.33E+08 | 1.45E+08 | | 1.39E+08 | 2.29E+10 |
| | | Live | 1.14E+08 | 1.22E+08 | | 1.18E+08 | 1.95E+10 |
| | | Dead | 1.94E+07 | 2.26E+07 | | 2.10E+07 | 3.47E+09 |
| | | % Viability | 85.40% | 84.40% | | 84.90% | |

FIG. 97

| | S1/S2/All/Live/CD14-/TCRab/CD4/CD27 \| Freq. of Parent (%) | S1/S2/All/Live/CD14-/TCRab/CD4/CD28 \| Freq. of Parent (%) | S1/S2/All/Live/CD14-/TCRab/CD4/CD56 \| Freq. of Parent (%) | S1/S2/All/Live/CD14-/TCRab/CD4/CD57 \| Freq. of Parent (%) | S1/S2/All/Live/CD14-/TCRab/CD8/CD27 \| Freq. of Parent (%) | S1/S2/All/Live/CD14-/TCRab/CD8/CD28 \| Freq. of Parent (%) | S1/S2/All/Live/CD14-/TCRab/CD8/CD56 \| Freq. of Parent (%) | S1/S2/All/Live/CD14-/TCRab/CD8/CD57 \| Freq. of Parent (%) |
|---|---|---|---|---|---|---|---|---|
| | CD4+/CD27 | CD4+/CD28 | CD4+/CD56 | CD4+/CD57 | CD8+/CD27 | CD8+/CD28 | CD8+/CD56 | CD8+/CD57 |
| L4063-Gen 3.0 | 3.8 | 82.7 | 0.42 | 6.7 | 15 | 47.5 | 3.29 | 0.28 |
| L4063-Gen 3.1 CT | 2.08 | 71.8 | 0.53 | 17 | 25.6 | 23 | 2.33 | 1.18 |
| L4063-Gen 3.1+Feeders | 3.35 | 80.2 | 0.69 | 20.5 | 30.5 | 24.5 | 4.19 | 1.07 |
| L4064-Gen 3.0 | 6.66 | 97.5 | 0.54 | 16 | 14.1 | 88 | 6.62 | 1.29 |
| L4064-Gen 3.1 CT | 0.72 | 73.5 | 0.54 | 7.58 | 3.3 | 45.1 | 10.3 | 1.95 |
| L4063-Gen 3.1+Feeders | 2.24 | 66.8 | 0.34 | 7.98 | 6.69 | 37.3 | 9.98 | 2.54 |

FIG. 98

| | | S1/S2/All/Live \| Freq. of Parent (%) | S1/S2/All/Live/ CD14- \| Freq. of Parent (%) | S1/S2/All/Live/ CD14-/CD8-/NK \| Freq. of null (%) | S1/S2/All/Live/ CD14-/CD19 \| Freq. of null (%) | S1/S2/All/Live/ CD14-/TCRab \| Freq. of null (%) | S1/S2/All/Live/ CD14-/TCRab/ CD4 \| Freq. of null (%) | S1/S2/All/Live/ CD14-/TCRab/ CD4/CD27 \| Freq. of null (%) | S1/S2/All/Live/ CD14-/TCRab/ CD4/CD28 \| Freq. of null (%) | S1/S2/All/Live/ CD14-/TCRab/ CD4/CD56 \| Freq. of null (%) | S1/S2/All/Live/ CD14-/TCRab/ CD4/CD57 \| Freq. of null (%) |
|---|---|---|---|---|---|---|---|---|---|---|---|
| | | L/D | CD34+ | NK | CD19 | TCRa/b+ | TCRa/b+ /CD4+ | TCRa/b+ /CD4+ /CD27 | TCRa/b+ /CD4+ /CD28 | TCRa/b+ /CD4+ /CD56 | TCRa/b+ /CD4+ /CD57 |
| L4063-Gen 3.0 | C10 10.tcx | 82.2 | 0.13 | 1.3 | 0.083 | 88.6 | 56.4 | 2.34 | 46.6 | 0.24 | 3.78 |
| L4063-Gen 3.1 CT | C11 11.tcx | 83.4 | 0.035 | 0.15 | 0.033 | 97.5 | 85.8 | 1.78 | 61.6 | 0.46 | 14.6 |
| L4063-Gen 3.1+Feeders | C12 12.tcx | 91 | 0.032 | 1.04 | 0.007% | 95.5 | 77.5 | 2.6 | 62.1 | 0.54 | 15.9 |
| L4064-Gen 3.0 | D1 13.tcx | 76.6 | 0.18 | 2.45 | 0.11 | 93 | 33.8 | 2.25 | 32.9 | 0.18 | 5.4 |
| L4064-Gen 3.1 CT | D2 14.tcx | 83.1 | 0.068 | 0.23 | 0.011 | 97.3 | 64.8 | 0.46 | 47.6 | 0.35 | 4.91 |
| L4063-Gen 3.1+Feeders | D3 15.tcx | 89.5 | 0.043 | 0.52 | 0.023 | 96.7 | 57.4 | 1.28 | 38.4 | 0.2 | 4.58 |

| | S1/S2/All/Live/ CD14-/TCRab/CD4/ Q1: CCR7-PE-A-, CD45RA-AF700-A+ \| Freq. of Parent (%) | S1/S2/All/Live/ CD14-/TCRab/CD4/ Q2: CCR7-PE-A+, CD45RA-AF700-A+ \| Freq. of Parent (%) | S1/S2/All/Live/ CD14-/TCRab/CD4/ Q3: CCR7-PE-A-, CD45RA-AF700-A- \| Freq. of Parent (%) | S1/S2/All/Live/ CD14-/TCRab/CD4/ Q4: CCR7-PE-A-, CD45RA-AF700-A- \| Freq. of Parent (%) | S1/S2/All/Live/ CD14-/TCRab/CD4/ Q5: CD62L-DV421-A+, CD45RA-AF700-A+ \| Freq. of Parent (%) | S1/S2/All/Live/ CD14-/TCRab/CD4/ Q6: CD62L-DV421-A+, CD45RA-AF700-A+ \| Freq. of Parent (%) | S1/S2/All/Live/ CD14-/TCRab/CD4/ Q7: CD62L-DV421-A+, CD45RA-AF700-A- \| Freq. of Parent (%) | S1/S2/All/Live/ CD14-/TCRab/CD4/ Q8: CD62L-DV421-A-, CD45RA-AF700-A- \| Freq. of Parent (%) |
|---|---|---|---|---|---|---|---|---|
| | TEMRA | NAIVE | CM | EM | TEMRA | NAIVE | CM | EM |
| L4063-Gen 3.0 | 0.58 | 0.77 | 11.2 | 87.4 | 0.36 | 0.26 | 45.6 | 53.7 |
| L4063-Gen 3.1 CT | 1.22 | 0.8 | 1.56 | 94.4 | 0.66 | 0.22 | 16.8 | 82.3 |
| L4063-Gen 3.1+Feeders | 0.88 | 0.35 | 1.39 | 97.4 | 0.36 | 0.17 | 29.3 | 70.2 |
| L4064-Gen 3.0 | 1.47 | 1.3 | 14.2 | 83 | 1.09 | 0.53 | 46.3 | 52.1 |
| L4064-Gen 3.1 CT | 0.41 | 0.096 | 5.28 | 94.2 | 0.73 | 0.11 | 30.6 | 68.6 |
| L4063-Gen 3.1+Feeders | 0.44 | 0.07 | 2.78 | 95.7 | 0.37 | 0.035 | 29.9 | 69.9 |

| | S1/S2/All/Live/ CD14-/TCRab/CD8/ Q1: CCR7-PE-A-, CD45RA-AF700-A+ \| Freq. of Parent (%) | S1/S2/All/Live/ CD14-/TCRab/CD8/ Q2: CCR7-PE-A+, CD45RA-AF700-A+ \| Freq. of Parent (%) | S1/S2/All/Live/ CD14-/TCRab/CD8/ Q3: CCR7-PE-A-, CD45RA-AF700-A- \| Freq. of Parent (%) | S1/S2/All/Live/ CD14-/TCRab/CD8/ Q4: CCR7-PE-A-, CD45RA-AF700-A- \| Freq. of Parent (%) | S1/S2/All/Live/ CD14-/TCRab/CD8/ Q5: CD62L-DV421-A+, CD45RA-AF700-A+ \| Freq. of Parent (%) | S1/S2/All/Live/ CD14-/TCRab/CD8/ Q6: CD62L-DV421-A+, CD45RA-AF700-A+ \| Freq. of Parent (%) | S1/S2/All/Live/ CD14-/TCRab/CD8/ Q7: CD62L-DV421-A+, CD45RA-AF700-A- \| Freq. of Parent (%) | S1/S2/All/Live/ CD14-/TCRab/CD8/ Q8: CD62L-DV421-A-, CD45RA-AF700-A- \| Freq. of Parent (%) | S1/S2/All/Live/ CD14-/TCRgd \| Freq. of Parent (%) |
|---|---|---|---|---|---|---|---|---|---|
| | TEMRA | NAIVE | CM | EM | TEMRA | NAIVE | CM | EM | |
| L4063-Gen 3.0 | 1.72 | 1.54 | 18.1 | 79.1 | 3.06 | 0.67 | 32 | 74.3 | 6.47 |
| L4063-Gen 3.1 CT | 1.65 | 0.62 | 3.39 | 94.3 | 0.52 | 0.097 | 15.8 | 83.5 | 1.11 |
| L4063-Gen 3.1+Feeders | 2.65 | 0.73 | 1.66 | 95 | 0.89 | 0.41 | 29.7 | 789 | 2 |
| L4064-Gen 3.0 | 6.49 | 4.31 | 10.9 | 70.3 | 6.05 | 3.31 | 61.9 | 39.8 | 2.36 |
| L4064-Gen 3.1 CT | 6.3 | 0.59 | 7.15 | 86 | 8 | 0.72 | 18.9 | 72.4 | 1.68 |
| L4063-Gen 3.1+Feeders | 5.83 | 0.22 | 3.17 | 90.8 | 5.38 | 0.96 | 18.2 | 75.5 | 1.86 |

FIG. 99

| | | S/S/All/Live/CD3/CD4/284 \| Freq. of Parent (%) | S/S/All/Live/CD3/BTLA \| Freq. of Parent (%) | S/S/All/Live/CD3/CD4/CD25 \| Freq. of Parent (%) | S/S/All/Live/CD3/CD4/CD69 \| Freq. of Parent (%) | S/S/All/Live/CD3/CD4/CD95 \| Freq. of Parent (%) | S/S/All/Live/CD3/CD4/CD103 \| Freq. of Parent (%) | S/S/All/Live/CD3/CD4/KLRG1+ \| Freq. of Parent (%) | S/S/All/Live/CD3/CD4/LAG3 \| Freq. of Parent (%) | S/S/All/Live/CD3/CD4/PD1 \| Freq. of Parent (%) |
|---|---|---|---|---|---|---|---|---|---|---|
| | | | | | | CD4 | | | | |
| | | 284+ | BTLA | CD25+ | CD69+ | CD95+ | CD103+ | KLRG1+ | LAG3+ | PD1+ |
| L4063-Gen 3.0 | G10 10.fcs | 2.1 | 99.7 | 48.6 | 27.1 | 99.9 | 0.69 | 1.61 | 5.57 | 77.4 |
| L4063-Gen 3.1 CT | G11 11.fcs | 0.62 | 95.4 | 10.5 | 37.7 | 99.9 | 1.15 | 3.7 | 8.24 | 58.4 |
| L4063-Gen 3.1+Feeders | G12 12.fcs | 0.95 | 96.9 | 3.89 | 21.5 | 99.5 | 0.43 | 3.32 | 3.28 | 41.6 |
| L4064-Gen 3.0 | H1 13.fcs | 2 | 99.5 | 58.2 | 39.4 | 99.6 | 1.44 | 11.4 | 1.49 | 34.1 |
| L4064-Gen 3.1 CT | H2 14.fcs | 1.18 | 98.8 | 41.7 | 35.6 | 99 | 1.25 | 8.3 | 1.6 | 28.4 |
| L4063-Gen 3.1+Feeders | H3 15.fcs | 1.26 | 98.1 | 32.1 | 30.5 | 97.3 | 1.19 | 10.7 | 1.42 | 26.7 |

| S/S/All/Live/CD3/CD4/tigit \| Freq. of Parent (%) | S/S/All/Live/CD3/CD4/tigit \| Freq. of Parent (%) |
|---|---|
| CD4+ | CD4+ |
| TIGIT+ | TIM3+ |
| 68.5 | 58 |
| 40.3 | 42.4 |
| 30.3 | 59.4 |
| 45.8 | 61 |
| 52.1 | 58.4 |
| 52.2 | 56.8 |

FIG. 100

| S/S/All/Live/CD3/ CD8/284 \| Freq. of Parent (%) | S/S/All/Live/CD3/ CD8/BTLA \| Freq. of Parent (%) | S/S/All/Live/CD3/ CD8/CD25 \| Freq. of Parent (%) | S/S/All/Live/CD3/ CD8/CD69 \| Freq. of Parent (%) | S/S/All/Live/CD3/ CD8/CD95 \| Freq. of Parent (%) | S/S/All/Live/CD3/ CD8/CD103 \| Freq. of Parent (%) | S/S/All/Live/CD3/ CD8/CXCR3 \| Freq. of Parent (%) | S/S/All/Live/CD3/ CD8/KLRG1 \| Freq. of Parent (%) | S/S/All/Live/CD3/ CD8/LAG3 \| Freq. of Parent (%) | S/S/All/Live/CD3 /CD8/PD1 \| Freq. of Parent (%) |
|---|---|---|---|---|---|---|---|---|---|
| | | | | CD8+ | | | | | |
| **284+** | **BTLA** | **CD25+** | **CD69+** | **CD95+** | **CD103+** | **CXCR3** | **KLRG1** | **LAG3** | **PD1** |
| 2.1 | 2.1 | 99.7 | 48.6 | 27.1 | 99.9 | 0.69 | 1.61 | 5.57 | 77.4 |
| 0.62 | 0.62 | 95.4 | 10.5 | 37.7 | 99.9 | 1.15 | 3.7 | 8.24 | 58.4 |
| 0.95 | 0.95 | 96.9 | 3.89 | 21.5 | 99.5 | 0.43 | 3.32 | 3.28 | 41.6 |
| 2 | 2 | 99.5 | 58.2 | 39.4 | 99.6 | 1.44 | 11.4 | 1.49 | 34.1 |
| 1.18 | 1.18 | 98.8 | 41.7 | 35.6 | 99 | 1.25 | 8.3 | 1.6 | 28.4 |
| 1.26 | 1.26 | 98.1 | 32.1 | 30.5 | 97.3 | 1.19 | 10.7 | 1.42 | 26.7 |

| S/S/All/Live/CD3/ CD8/tigit \| Freq. of Parent (%) | S/S/All/Live/CD3/ CD8/tim3 \| Freq. of Parent (%) |
|---|---|
| **CD8** | **CD8** |
| **TIGIT** | **TIM3** |
| 90.8 | 66.7 |
| 93.7 | 49.1 |
| 93.3 | 58.6 |
| 92.1 | 65.6 |
| 90.4 | 46.8 |
| 90.5 | 43.6 |

FIG. 101

IFN-γ production Data Figure 7-L4063

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | TIL- Gen 3.0-A- stimulated | TIL- Gen 3.0-A- stimulated | TIL- Gen 3.0-A- stimulated | TIL- Gen 3.1-B- stimulated | TIL- Gen 3.1-B- stimulated | TIL- Gen 3.1-B- stimulated | TIL- Gen 3.1-C- stimulated | TIL- Gen 3.1-C- stimulated | TIL- Gen 3.1-C- stimulated | Well ID |
| | 1000 | 1000 | 1000 | 3 | 3 | 3 | 3 | 3 | 3 | 3 | 3 | 3 | Conc/Dil |
| B | STD2 | STD2 | STD2 | TIL- Gen 3.0-A- stimulated | TIL- Gen 3.0-A- stimulated | TIL- Gen 3.0-A- stimulated | TIL- Gen 3.1-B- stimulated | TIL- Gen 3.1-B- stimulated | TIL- Gen 3.1-B- stimulated | TIL- Gen 3.1-C- stimulated | TIL- Gen 3.1-C- stimulated | TIL- Gen 3.1-C- stimulated | Well ID |
| | 500 | 500 | 500 | 9 | 9 | 9 | 9 | 9 | 9 | 9 | 9 | 9 | Conc/Dil |
| C | STD3 | STD3 | STD3 | TIL- Gen 3.0-A- stimulated | TIL- Gen 3.0-A- stimulated | TIL- Gen 3.0-A- stimulated | TIL- Gen 3.1-B- stimulated | TIL- Gen 3.1-B- stimulated | TIL- Gen 3.1-B- stimulated | TIL- Gen 3.1-C- stimulated | TIL- Gen 3.1-C- stimulated | TIL- Gen 3.1-C- stimulated | Well ID |
| | 250 | 250 | 250 | 27 | 27 | 27 | 27 | 27 | 27 | 27 | 27 | 27 | Conc/Dil |
| D | STD4 | STD4 | STD4 | TIL- Gen 3.0-A- stimulated | TIL- Gen 3.0-A- stimulated | TIL- Gen 3.0-A- stimulated | TIL- Gen 3.1-B- stimulated | TIL- Gen 3.1-B- stimulated | TIL- Gen 3.1-B- stimulated | TIL- Gen 3.1-C- stimulated | TIL- Gen 3.1-C- stimulated | TIL- Gen 3.1-C- stimulated | Well ID |
| | 125 | 125 | 125 | 81 | 81 | 81 | 81 | 81 | 81 | 81 | 81 | 81 | Conc/Dil |
| E | STD5 | STD5 | STD5 | TIL- Gen 3.0-A-Un- stimulated | TIL- Gen 3.0-A-Un- stimulated | TIL- Gen 3.0-A-Un- stimulated | TIL- Gen 3.1-B-Un- stimulated | TIL- Gen 3.1-B-Un- stimulated | TIL- Gen 3.1-B-Un- stimulated | TIL- Gen 3.1-C-Un- stimulated | TIL- Gen 3.1-C-Un- stimulated | TIL- Gen 3.1-C-Un- stimulated | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | TIL- Gen 3.0-A-Un- stimulated | TIL- Gen 3.0-A-Un- stimulated | TIL- Gen 3.0-A-Un- stimulated | TIL- Gen 3.1-B-Un- stimulated | TIL- Gen 3.1-B-Un- stimulated | TIL- Gen 3.1-B-Un- stimulated | TIL- Gen 3.1-C-Un- stimulated | TIL- Gen 3.1-C-Un- stimulated | TIL- Gen 3.1-C-Un- stimulated | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | TIL- Gen 3.0-A-Un- stimulated | TIL- Gen 3.0-A-Un- stimulated | TIL- Gen 3.0-A-Un- stimulated | TIL- Gen 3.1-B-Un- stimulated | TIL- Gen 3.1-B-Un- stimulated | TIL- Gen 3.1-B-Un- stimulated | TIL- Gen 3.1-C-Un- stimulated | TIL- Gen 3.1-c-Un- stimulated | TIL- Gen 3.1-c-Un- stimulated | Well ID |
| | 15.6 | 15.6 | 15.6 | 27 | 27 | 27 | 27 | 27 | 27 | 27 | 27 | 27 | Conc/Dil |
| H | STD8 | STD8 | STD8 | TIL- Gen 3.0-A-Un- stimulated | TIL- Gen 3.0-A-Un- stimulated | TIL- Gen 3.0-A-Un- stimulated | TIL- Gen 3.1-B-Un- stimulated | TIL- Gen 3.1-B-Un- stimulated | TIL- Gen 3.1-B-Un- stimulated | TIL- Gen 3.1-c-Un- stimulated | TIL- Gen 3.1-c-Un- stimulated | TIL- Gen 3.1-c-Un- stimulated | Well ID |
| | 0 | 0 | 0 | 81 | 81 | 81 | 81 | 81 | 81 | 81 | 81 | 81 | Conc/Dil |
| 22.4 | | | | | | | | | | | | | |
| 22.4 | | | | | | | | | | | | | |

TIL- Gen 3.0-A-Gen 3.0
TIL- Gen 3.1-B-Gen 3.1 Control
TIL- Gen 3.1-C-Gen 3.1 Test

FIG. 102A

| | 1 | 2 | 3 | 4 | 5 | 6 | 7 | 8 | 9 | 10 | 11 | 12 | |
|---|---|---|---|---|---|---|---|---|---|---|---|---|---|
| A | 3.405 | 3.397 | 3.403 | 1.442 | 1.299 | 1.259 | 0.728 | 0.783 | 0.787 | 3.154 | 3.319 | 3.099 | 450 |
| | 0.047 | 0.049 | 0.054 | 0.049 | 0.048 | 0.045 | 0.044 | 0.045 | 0.043 | 0.057 | 0.057 | 0.077 | 570 |
| | 3.359 | 3.347 | 3.349 | 1.393 | 1.252 | 1.223 | 0.684 | 0.738 | 0.744 | [illegible] | 3.352 | 3.023 | Delta |
| | 1002.565 | 997.786 | 998.498 | 334.562 | 295.824 | 288.115 | 149.315 | 162.815 | 164.235 | 895.979 | 958.429 | 867.067 | [Concentration] |
| | | | | 1003.686 | 887.473 | 864.346 | 447.944 | 488.444 | 492.706 | 2687.938 | 2875.286 | 2601.171 | X dil factor |
| B | [illegible] | [illegible] | [illegible] | 0.585 | 0.504 | 0.493 | 0.308 | 0.325 | 0.338 | 1.37 | 1.4553 | 1.298 | 450 |
| | 0.049 | 0.052 | 0.05 | 0.046 | 0.045 | 0.044 | 0.045 | 0.044 | 0.04 | 0.04 | 0.043 | 0.045 | 570 |
| | [illegible] | [illegible] | [illegible] | 0.54 | 0.459 | 0.449 | 0.253 | 0.281 | 0.299 | 1.33 | 1.41 | 1.252 | Delta |
| | 488.001 | 508.782 | 507.605 | 113.947 | 94.422 | 92.089 | 47.659 | 51.958 | 56.14 | 317.208 | 339.278 | 296.013 | [Concentration] |
| | | | | 1025.524 | 845.796 | 828.801 | 428.928 | 467.618 | 505.257 | 2854.874 | 3053.502 | 2664.121 | X dil factor |
| C | 1.108 | 1.123 | 1.127 | 0.269 | 0.244 | 0.241 | 0.171 | 0.192 | 0.179 | 0.552 | 0.571 | 0.524 | 450 |
| | 0.045 | 0.045 | 0.047 | 0.043 | 0.042 | 0.044 | 0.043 | 0.047 | 0.041 | 0.045 | 0.045 | 0.045 | 570 |
| | 1.062 | 1.077 | 1.08 | 0.226 | 0.202 | 0.197 | 0.128 | 0.145 | 0.138 | 0.506 | 0.526 | 0.479 | Delta |
| | 245.406 | 249.416 | 250.019 | 38.873 | 33.123 | 32.029 | 15.474 | 19.579 | 17.877 | 105.831 | 110.648 | 99.215 | [Concentration] |
| | | | | 1049.571 | 894.323 | 864.792 | 417.785 | 528.537 | 482.676 | 2857.431 | 2987.505 | 2678.8 | X dil factor |
| D | 0.635 | 0.625 | 0.641 | 0.161 | 0.147 | 0.143 | 0.135 | 0.125 | 0.127 | 0.253 | 0.274 | 0.259 | 450 |
| | 0.052 | 0.044 | 0.052 | 0.042 | 0.043 | 0.042 | 0.056 | 0.045 | 0.048 | 0.045 | 0.044 | 0.048 | 570 |
| | 0.583 | 0.581 | 0.589 | 0.119 | 0.134 | 0.102 | 0.079 | 0.08 | 0.079 | 0.218 | 0.23 | 0.211 | Delta |
| | 124.607 | 123.9 | 125.852 | 13.279 | 9.768 | 9.154 | 3.452 | 3.753 | 3.628 | 36.973 | 39.87 | 35.405 | [Concentration] |
| | | | | 1075.611 | 792.798 | 741.476 | 279.628 | 304.005 | 293.856 | 2994.798 | 3229.505 | 2867.785 | X dil factor |
| E | 0.368 | 0.377 | 0.368 | 0.117 | 0.115 | 0.114 | 0.108 | 0.104 | 0.107 | 0.107 | 0.101 | 0.097 | 450 |
| | 0.043 | 0.044 | 0.044 | 0.045 | 0.041 | 0.042 | 0.047 | 0.044 | 0.048 | 0.053 | 0.047 | 0.043 | 570 |
| | 0.325 | 0.333 | 0.324 | 0.072 | 0.074 | 0.072 | 0.051 | 0.05 | 0.059 | 0.053 | 0.054 | 0.054 | Delta |
| | 62.49 | 64.276 | 62.276 | 1.881 | 2.214 | 1.676 | <0.000 | <0.000 | <0.000 | <0.000 | <0.000 | <0.000 | [Concentration] |
| | | | | 5.644 | 6.641 | 5.029 | <0.000 | <0.000 | <0.000 | <0.000 | <0.000 | <0.000 | X dil factor |
| F | 0.242 | 0.247 | 0.239 | 0.1 | 0.122 | 0.102 | 0.097 | 0.095 | 0.096 | 0.101 | 0.094 | 0.099 | 450 |
| | 0.044 | 0.044 | 0.043 | 0.041 | 0.042 | 0.042 | 0.043 | 0.042 | 0.044 | 0.049 | 0.042 | 0.043 | 570 |
| | 0.198 | 0.203 | 0.196 | 0.059 | 0.06 | 0.06 | 0.053 | 0.054 | 0.062 | 0.053 | 0.052 | 0.056 | Delta |
| | 32.291 | 33.432 | 31.72 | <0.000 | <0.000 | <0.000 | <0.000 | <0.000 | <0.000 | <0.000 | <0.000 | <0.000 | [Concentration] |
| | | | | <0.000 | <0.000 | <0.000 | <0.000 | <0.000 | <0.000 | <0.000 | <0.000 | <0.000 | X dil factor |
| G | 0.186 | 0.187 | 0.172 | 0.102 | 0.096 | 0.098 | 0.095 | 0.09 | 0.091 | 0.09 | 0.093 | 0.099 | 450 |
| | 0.056 | 0.055 | 0.043 | 0.047 | 0.041 | 0.042 | 0.041 | 0.042 | 0.045 | 0.043 | 0.042 | 0.044 | 570 |
| | 0.13 | 0.132 | 0.129 | 0.055 | 0.055 | 0.056 | 0.054 | 0.048 | 0.047 | 0.047 | 0.061 | 0.056 | Delta |
| | 15.979 | 16.58 | 15.666 | <0.000 | <0.000 | <0.000 | <0.000 | <0.000 | <0.000 | <0.000 | <0.000 | <0.000 | [Concentration] |
| | | | | <0.000 | <0.000 | <0.000 | <0.000 | <0.000 | <0.000 | <0.000 | <0.000 | <0.000 | X dil factor |
| H | 0.106 | 0.107 | 0.1 | 0.102 | 0.1 | 0.1 | 0.1 | 0.099 | 0.098 | 0.1 | 0.095 | 0.098 | 450 |
| | 0.045 | 0.045 | 0.044 | 0.041 | 0.042 | 0.042 | 0.041 | 0.042 | 0.043 | 0.043 | 0.043 | 0.044 | 570 |
| | 0.062 | 0.062 | 0.056 | 0.061 | 0.058 | 0.058 | 0.059 | 0.058 | 0.055 | 0.056 | 0.052 | 0.053 | Delta |
| | <0.000 | <0.000 | <0.000 | <0.000 | <0.000 | <0.000 | <0.000 | <0.000 | <0.000 | <0.000 | <0.000 | <0.000 | [Concentration] |
| | | | | <0.000 | <0.000 | <0.000 | <0.000 | <0.000 | <0.000 | <0.000 | <0.000 | <0.000 | X dil factor |

| | Dilution | Reading A | Reading B | Reading C | Average | Average |
|---|---|---|---|---|---|---|
| TIL- Gen 3.0-A-stimulated | 3 | 1003.686 | 887.473 | 864.345 | 918.5 | 906.5 |
| | 9 | 1025.524 | 849.796 | 828.801 | 901.4 | |
| | 27 | 1049.571 | 894.323 | 864.792 | 936.2 | |
| | 81 | 1075.611 | 792.798 | 741.476 | 870.0 | |
| TIL- Gen 3.1-Control -stimulated | 3 | 447.944 | 488.444 | 492.706 | 476.4 | 428.1 |
| | 9 | 428.928 | 467.618 | 505.257 | 457.3 | |
| | 27 | 417.785 | 528.637 | 482.676 | 476.4 | |
| | 81 | 279.628 | 304.005 | 293.856 | 292.5 | |
| TIL- Gen 3.1-Test-stimulated | 3 | 2687.938 | 2875.286 | 2601.171 | 2721.5 | 2862.7 |
| | 9 | 2854.874 | 3053.502 | 2664.121 | 2857.9 | |
| | 27 | 2857.431 | 2987.505 | 2678.8 | 2841.2 | |
| | 81 | 2994.798 | 3229.505 | 2867.786 | 3030.7 | |
| TIL- Gen 3.0-A-Unstimulated | 3 | 5.644 | 6.641 | 5.029 | 5.8 | 5.8 |
| | 9 | 0 | 0 | 0 | 0.0 | |
| | 27 | 0 | 0 | 0 | 0.0 | |
| | 81 | 0 | 0 | 0 | 0.0 | |
| TIL- Gen 3.1-Control -Unstimulated | 3 | 0 | 0 | 0 | 0.0 | 0.0 |
| | 9 | 0 | 0 | 0 | 0.0 | |
| | 27 | 0 | 0 | 0 | 0.0 | |
| | 81 | 0 | 0 | 0 | 0.0 | |
| TIL- Gen 3.1-Test-Unstimulated | 3 | 0 | 0 | 0 | 0.0 | 0.0 |
| | 9 | 0 | 0 | 0 | 0.0 | |
| | 27 | 0 | 0 | 0 | 0.0 | |
| | 81 | 0 | 0 | 0 | 0.0 | |

FIG. 102B

IFN-γ production Data Figure 7-L4063

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 | STD1 | STD1 | TIL- Gen 3.0-A-stimulated | TIL- Gen 3.0-A-stimulated | TIL- Gen 3.0-A-stimulated | TIL- Gen 3.1-B-stimulated | TIL- Gen 3.1-B-stimulated | TIL- Gen 3.1-B-stimulated | TIL- Gen 3.1-C-stimulated | TIL- Gen 3.1-C-stimulated | TIL- Gen 3.1-C-stimulated | Well ID |
| | 1000 | 1000 | 1000 | 3 | 3 | 3 | 3 | 3 | 3 | 3 | 3 | 3 | Conc/Dil |
| B | STD2 | STD2 | STD2 | TIL- Gen 3.0-A-stimulated | TIL- Gen 3.0-A-stimulated | TIL- Gen 3.0-A-stimulated | TIL- Gen 3.1-B-stimulated | TIL- Gen 3.1-B-stimulated | TIL- Gen 3.1-B-stimulated | TIL- Gen 3.1-C-stimulated | TIL- Gen 3.1-C-stimulated | TIL- Gen 3.1-C-stimulated | Well ID |
| | 500 | 500 | 500 | 9 | 9 | 9 | 9 | 9 | 9 | 9 | 9 | 9 | Conc/Dil |
| C | STD3 | STD3 | STD3 | TIL- Gen 3.0-A-stimulated | TIL- Gen 3.0-A-stimulated | TIL- Gen 3.0-A-stimulated | TIL- Gen 3.1-B-stimulated | TIL- Gen 3.1-B-stimulated | TIL- Gen 3.1-B-stimulated | TIL- Gen 3.1-C-stimulated | TIL- Gen 3.1-C-stimulated | TIL- Gen 3.1-C-stimulated | Well ID |
| | 250 | 250 | 250 | 27 | 27 | 27 | 27 | 27 | 27 | 27 | 27 | 27 | Conc/Dil |
| D | STD4 | STD4 | STD4 | TIL- Gen 3.0-A-stimulated | TIL- Gen 3.0-A-stimulated | TIL- Gen 3.0-A-stimulated | TIL- Gen 3.1-B-stimulated | TIL- Gen 3.1-B-stimulated | TIL- Gen 3.1-B-stimulated | TIL- Gen 3.1-C-stimulated | TIL- Gen 3.1-C-stimulated | TIL- Gen 3.1-C-stimulated | Well ID |
| | 125 | 125 | 125 | 81 | 81 | 81 | 81 | 81 | 81 | 81 | 81 | 81 | Conc/Dil |
| E | STD5 | STD5 | STD5 | TIL- Gen 3.0-A-Un-stimulated | TIL- Gen 3.0-A-Un-stimulated | TIL- Gen 3.0-A-Un-stimulated | TIL- Gen 3.1-B-Un-stimulated | TIL- Gen 3.1-B-Un-stimulated | TIL- Gen 3.1-B-Un-stimulated | TIL- Gen 3.1-C-Un-stimulated | TIL- Gen 3.1-C-Un-stimulated | TIL- Gen 3.1-C-Un-stimulated | Well ID |
| | 62.5 | 62.5 | 62.5 | 3 | 3 | 3 | 3 | 3 | 3 | 3 | 3 | 3 | Conc/Dil |
| F | STD6 | STD6 | STD6 | TIL- Gen 3.0-A-Un-stimulated | TIL- Gen 3.0-A-Un-stimulated | TIL- Gen 3.0-A-Un-stimulated | TIL- Gen 3.1-B-Un-stimulated | TIL- Gen 3.1-B-Un-stimulated | TIL- Gen 3.1-B-Un-stimulated | TIL- Gen 3.1-C-Un-stimulated | TIL- Gen 3.1-C-Un-stimulated | TIL- Gen 3.1-C-Un-stimulated | Well ID |
| | 31.3 | 31.3 | 31.3 | 9 | 9 | 9 | 9 | 9 | 9 | 9 | 9 | 9 | Conc/Dil |
| G | STD7 | STD7 | STD7 | TIL- Gen 3.0-A-Un-stimulated | TIL- Gen 3.0-A-Un-stimulated | TIL- Gen 3.0-A-Un-stimulated | TIL- Gen 3.1-B-Un-stimulated | TIL- Gen 3.1-B-Un-stimulated | TIL- Gen 3.1-B-Un-stimulated | TIL- Gen 3.1-C-Un-stimulated | TIL- Gen 3.1-C-Un-stimulated | TIL- Gen 3.1-C-Un-stimulated | Well ID |
| | 15.6 | 15.6 | 15.6 | 27 | 27 | 27 | 27 | 27 | 27 | 27 | 27 | 27 | Conc/Dil |
| H | STD8 | STD8 | STD8 | TIL- Gen 3.0-A-Un-stimulated | TIL- Gen 3.0-A-Un-stimulated | TIL- Gen 3.0-A-Un-stimulated | TIL- Gen 3.1-B-Un-stimulated | TIL- Gen 3.1-B-Un-stimulated | TIL- Gen 3.1-B-Un-stimulated | TIL- Gen 3.1-C-Un-stimulated | TIL- Gen 3.1-C-Un-stimulated | TIL- Gen 3.1-C-Un-stimulated | Well ID |
| | 0 | 0 | 0 | 81 | 81 | 81 | 81 | 81 | 81 | 81 | 81 | 81 | Conc/Dil |
| 22.6 | | | | | | | | | | | | | |
| 22.6 | | | | | | | | | | | | | |

TIL- Gen 3.0-A-Gen 3.0
TIL- Gen 3.1-B-Gen 3.1 Control
TIL- Gen 3.1-C-Gen 3.1 Test

FIG. 103A

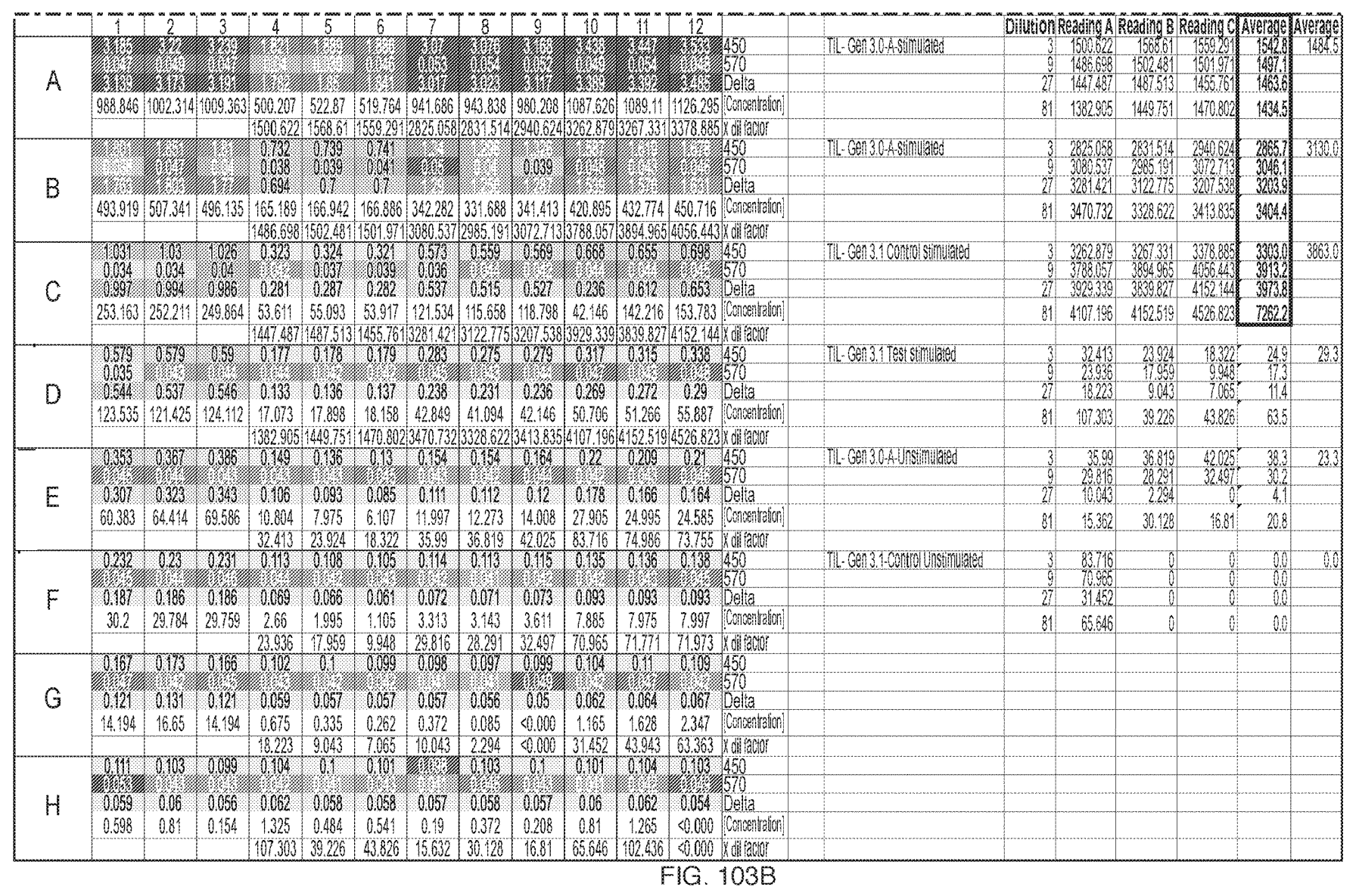

| | 1 | 2 | 3 | 4 | 5 | 6 | 7 | 8 | 9 | 10 | 11 | 12 | | | Dilution | Reading A | Reading B | Reading C | Average | Average |
|---|---|---|---|---|---|---|---|---|---|---|---|---|---|---|---|---|---|---|---|---|
| A | 3.185 | 3.22 | 3.239 | [illegible] | [illegible] | [illegible] | 3.07 | 3.076 | 3.168 | 3.438 | 3.447 | 3.533 | 450 | TIL- Gen 3.0-A-stimulated | 3 | 1500.622 | 1568.61 | 1559.291 | 1542.8 | 1484.5 |
| | 0.047 | 0.049 | 0.047 | [illegible] | [illegible] | 0.046 | 0.053 | 0.054 | 0.052 | 0.049 | 0.054 | [illegible] | 570 | | 9 | 1486.698 | 1502.481 | 1501.971 | 1497.1 | |
| | 3.139 | 3.173 | 3.191 | [illegible] | [illegible] | [illegible] | 3.017 | 3.023 | 3.117 | 3.389 | 3.392 | 3.485 | Delta | | 27 | 1447.487 | 1487.513 | 1455.761 | 1463.6 | |
| | 988.846 | 1002.314 | 1009.363 | 500.207 | 522.87 | 519.764 | 941.686 | 943.838 | 980.208 | 1087.626 | 1089.11 | 1126.295 | [Concentration] | | 81 | 1382.905 | 1449.751 | 1470.802 | 1434.5 | |
| | | | | 1500.622 | 1568.61 | 1559.291 | 2825.058 | 2831.514 | 2940.624 | 3262.879 | 3267.331 | 3378.885 | X dil factor | | | | | | | |
| B | [illegible] | [illegible] | [illegible] | 0.732 | 0.739 | 0.741 | [illegible] | [illegible] | [illegible] | [illegible] | [illegible] | [illegible] | 450 | TIL- Gen 3.0-A-stimulated | 3 | 2825.058 | 2831.514 | 2940.624 | 2865.7 | 3130.0 |
| | [illegible] | 0.047 | [illegible] | 0.038 | 0.039 | 0.041 | [illegible] | [illegible] | 0.039 | [illegible] | [illegible] | [illegible] | 570 | | 9 | 3080.537 | 2985.191 | 3072.713 | 3046.1 | |
| | [illegible] | [illegible] | [illegible] | 0.694 | 0.7 | 0.7 | [illegible] | [illegible] | [illegible] | [illegible] | [illegible] | [illegible] | Delta | | 27 | 3281.421 | 3122.775 | 3207.538 | 3203.9 | |
| | 493.919 | 507.341 | 496.135 | 165.189 | 166.942 | 166.886 | 342.282 | 331.688 | 341.413 | 420.895 | 432.774 | 450.716 | [Concentration] | | 81 | 3470.732 | 3328.622 | 3413.835 | 3404.4 | |
| | | | | 1486.698 | 1502.481 | 1501.971 | 3080.537 | 2985.191 | 3072.713 | 3788.057 | 3894.965 | 4056.443 | X dil factor | | | | | | | |
| C | 1.031 | 1.03 | 1.026 | 0.323 | 0.324 | 0.321 | 0.573 | 0.559 | 0.569 | 0.668 | 0.655 | 0.698 | 450 | TIL- Gen 3.1 Control stimulated | 3 | 3262.879 | 3267.331 | 3378.885 | 3303.0 | 3863.0 |
| | 0.034 | 0.034 | 0.04 | [illegible] | 0.037 | 0.039 | 0.036 | [illegible] | [illegible] | [illegible] | [illegible] | [illegible] | 570 | | 9 | 3788.057 | 3894.965 | 4056.443 | 3913.2 | |
| | 0.997 | 0.994 | 0.986 | 0.281 | 0.287 | 0.282 | 0.537 | 0.515 | 0.527 | 0.236 | 0.612 | 0.653 | Delta | | 27 | 3929.339 | 3839.827 | 4152.144 | 3973.8 | |
| | 253.163 | 252.211 | 249.864 | 53.611 | 55.093 | 53.917 | 121.534 | 115.658 | 118.798 | 42.146 | 142.216 | 153.783 | [Concentration] | | 81 | 4107.196 | 4152.519 | 4526.823 | 7262.2 | |
| | | | | 1447.487 | 1487.513 | 1455.761 | 3281.421 | 3122.775 | 3207.538 | 3929.339 | 3839.827 | 4152.144 | X dil factor | | | | | | | |
| D | 0.579 | 0.579 | 0.59 | 0.177 | 0.178 | 0.179 | 0.283 | 0.275 | 0.279 | 0.317 | 0.315 | 0.338 | 450 | TIL- Gen 3.1 Test stimulated | 3 | 32.413 | 23.924 | 18.322 | 24.9 | 29.3 |
| | 0.035 | [illegible] | [illegible] | [illegible] | [illegible] | [illegible] | [illegible] | [illegible] | [illegible] | [illegible] | [illegible] | [illegible] | 570 | | 9 | 23.936 | 17.959 | 9.948 | 17.3 | |
| | 0.544 | 0.537 | 0.546 | 0.133 | 0.136 | 0.137 | 0.238 | 0.231 | 0.236 | 0.269 | 0.272 | 0.29 | Delta | | 27 | 18.223 | 9.043 | 7.065 | 11.4 | |
| | 123.535 | 121.425 | 124.112 | 17.073 | 17.898 | 18.158 | 42.849 | 41.094 | 42.146 | 50.706 | 51.266 | 55.887 | [Concentration] | | 81 | 107.303 | 39.226 | 43.826 | 63.5 | |
| | | | | 1382.905 | 1449.751 | 1470.802 | 3470.732 | 3328.622 | 3413.835 | 4107.196 | 4152.519 | 4526.823 | X dil factor | | | | | | | |
| E | 0.353 | 0.367 | 0.386 | 0.149 | 0.136 | 0.13 | 0.154 | 0.154 | 0.164 | 0.22 | 0.209 | 0.21 | 450 | TIL- Gen 3.0-A-Unstimulated | 3 | 35.99 | 36.819 | 42.025 | 38.3 | 23.3 |
| | [illegible] | [illegible] | [illegible] | [illegible] | [illegible] | [illegible] | [illegible] | [illegible] | [illegible] | [illegible] | [illegible] | [illegible] | 570 | | 9 | 29.816 | 28.291 | 32.497 | 30.2 | |
| | 0.307 | 0.323 | 0.343 | 0.106 | 0.093 | 0.085 | 0.111 | 0.112 | 0.12 | 0.178 | 0.166 | 0.164 | Delta | | 27 | 10.043 | 2.294 | 0 | 4.1 | |
| | 60.383 | 64.414 | 69.586 | 10.804 | 7.975 | 6.107 | 11.997 | 12.273 | 14.008 | 27.905 | 24.995 | 24.585 | [Concentration] | | 81 | 15.362 | 30.128 | 16.81 | 20.8 | |
| | | | | 32.413 | 23.924 | 18.322 | 35.99 | 36.819 | 42.025 | 83.716 | 74.986 | 73.755 | X dil factor | | | | | | | |
| F | 0.232 | 0.23 | 0.231 | 0.113 | 0.108 | 0.105 | 0.114 | 0.113 | 0.115 | 0.135 | 0.136 | 0.138 | 450 | TIL- Gen 3.1-Control Unstimulated | 3 | 83.716 | 0 | 0 | 0.0 | 0.0 |
| | [illegible] | [illegible] | [illegible] | [illegible] | [illegible] | [illegible] | [illegible] | [illegible] | [illegible] | [illegible] | [illegible] | [illegible] | 570 | | 9 | 70.965 | 0 | 0 | 0.0 | |
| | 0.187 | 0.186 | 0.186 | 0.069 | 0.066 | 0.061 | 0.072 | 0.071 | 0.073 | 0.093 | 0.093 | 0.093 | Delta | | 27 | 31.452 | 0 | 0 | 0.0 | |
| | 30.2 | 29.784 | 29.759 | 2.66 | 1.995 | 1.105 | 3.313 | 3.143 | 3.611 | 7.885 | 7.975 | 7.997 | [Concentration] | | 81 | 65.646 | 0 | 0 | 0.0 | |
| | | | | 23.936 | 17.959 | 9.948 | 29.816 | 28.291 | 32.497 | 70.965 | 71.771 | 71.973 | X dil factor | | | | | | | |
| G | 0.167 | 0.173 | 0.166 | 0.102 | 0.1 | 0.099 | 0.098 | 0.097 | 0.099 | 0.104 | 0.11 | 0.109 | 450 | | | | | | | |
| | [illegible] | [illegible] | [illegible] | [illegible] | [illegible] | [illegible] | [illegible] | [illegible] | [illegible] | [illegible] | [illegible] | [illegible] | 570 | | | | | | | |
| | 0.121 | 0.131 | 0.121 | 0.059 | 0.057 | 0.057 | 0.057 | 0.056 | 0.05 | 0.062 | 0.064 | 0.067 | Delta | | | | | | | |
| | 14.194 | 16.65 | 14.194 | 0.675 | 0.335 | 0.262 | 0.372 | 0.085 | <0.000 | 1.165 | 1.628 | 2.347 | [Concentration] | | | | | | | |
| | | | | 18.223 | 9.043 | 7.065 | 10.043 | 2.294 | <0.000 | 31.452 | 43.943 | 63.363 | X dil factor | | | | | | | |
| H | 0.111 | 0.103 | 0.099 | 0.104 | 0.1 | 0.101 | [illegible] | 0.103 | 0.1 | 0.101 | 0.104 | 0.103 | 450 | | | | | | | |
| | [illegible] | [illegible] | [illegible] | [illegible] | [illegible] | [illegible] | [illegible] | [illegible] | [illegible] | [illegible] | [illegible] | [illegible] | 570 | | | | | | | |
| | 0.059 | 0.06 | 0.056 | 0.062 | 0.058 | 0.058 | 0.057 | 0.058 | 0.057 | 0.06 | 0.062 | 0.054 | Delta | | | | | | | |
| | 0.598 | 0.81 | 0.154 | 1.325 | 0.484 | 0.541 | 0.19 | 0.372 | 0.208 | 0.81 | 1.265 | <0.000 | [Concentration] | | | | | | | |
| | | | | 107.303 | 39.226 | 43.826 | 15.632 | 30.128 | 16.81 | 65.646 | 102.436 | <0.000 | X dil factor | | | | | | | |

FIG. 103B

| | 1 | 2 | 3 | 4 | 5 | 6 | 7 | 8 | 9 | 10 | 11 | 12 | |
|---|---|---|---|---|---|---|---|---|---|---|---|---|---|
| A | STD1 2000 | STD1 2000 | STD1 2000 | Gen 3.1 Test-D7 L4063 | Gen 3.1 Test-D7 L4063 | Gen 3.1 Test-D7 L4063 | Gen 3.1 Test-D16 L4063 | Gen 3.1 Test-D16 L4063 | Gen 3.1 Test-D16 L4063 | Empty | Empty | Empty | Well ID Conc/Dil |
| B | STD2 1000 | STD2 1000 | STD2 1000 | Gen 3.1 Control-D7 L4063 L4063 | Gen 3.1 Control-D7 L4063 L4063 | Gen 3.1 Control-D7 L4063 L4063 | Gen 3.0-D7 L4064 | Gen 3.0-D7 L4064 | Gen 3.0-D7 L4064 | Empty | Empty | Empty | Well ID Conc/Dil |
| C | STD3 500 | STD3 500 | STD3 500 | Gen 3.0-D7 L4063 | Gen 3.0-D7 L4063 | Gen 3.0-D7 L4063 | Gen 3.1 Control-D7 L4064 | Gen 3.1 Control-D7 L4064 | Gen 3.1 Control-D7 L4064 | Empty | Empty | Empty | Well ID Conc/Dil |
| D | STD4 250 | STD4 250 | STD4 250 | Gen 3.0-D11 L4063 | Gen 3.0-D11 L4063 | Gen 3.0-D11 L4063 | Gen 3.1 Test-D7 L4064 | Gen 3.1 Test-D7 L4064 | Gen 3.1 Test-D7 L4064 | Empty | Empty | Empty | Well ID Conc/Dil |
| E | STD5 125 | STD5 125 | STD5 125 | Gen 3.1 Control-D11 L4063 | Gen 3.1 Control-D11 L4063 | Gen 3.1 Control-D11 L4063 | Gen 3.0-D16 L4064 | Gen 3.0-D16 L4064 | Gen 3.0-D16 L4064 | Empty | Empty | Empty | Well ID Conc/Dil |
| F | STD6 62.5 | STD6 62.5 | STD6 62.5 | Gen 3.1 Test-D11 L4063 | Gen 3.1 Test-D11 L4063 | Gen 3.1 Test-D11 L4063 | Gen 3.1 Control-D16 L4064 | Gen 3.1 Control-D16 L4064 | Gen 3.1 Control-D16 L4064 | Empty | Empty | Empty | Well ID Conc/Dil |
| G | STD7 31.3 | STD7 31.3 | STD7 31.3 | Gen 3.0-D16 L4063 | Gen 3.0-D16 L4063 | Gen 3.0-D16 L4063 | Gen 3.1 Test-D16 L4063 | Gen 3.1 Test-D16 L4063 | Gen 3.1 Test-D16 L4063 | Empty | Empty | Empty | Well ID Conc/Dil |
| H | STD8 0 | STD8 0 | STD8 0 | Gen 3.1 Control-D16 L4063 | Gen 3.1 Control-D16 L4063 | Gen 3.1 Control-D16 L4063 | Empty | Empty | Empty | Empty | Empty | Empty | Well ID Conc/Dil |
| 23 | | | | | | | | | | | | | |
| 23 | | | | | | | | | | | | | |

D7=Day 7= Rep Initiation
D11= Day 11= Scale up
D16= Day 16= Harvest

FIG. 104A

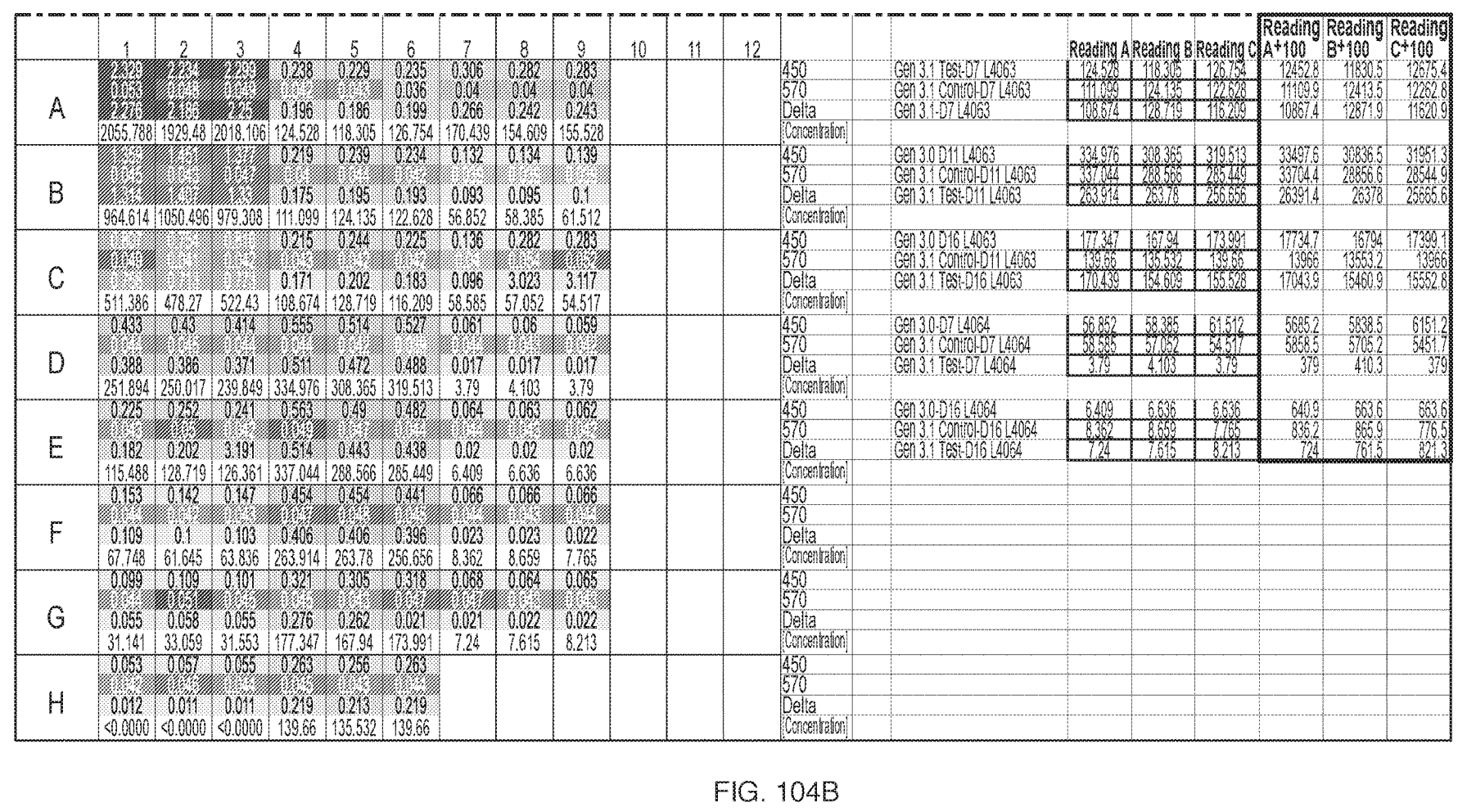

| | 1 | 2 | 3 | 4 | 5 | 6 | 7 | 8 | 9 | 10 | 11 | 12 | | | Reading A | Reading B | Reading C | Reading A*100 | Reading B*100 | Reading C*100 |
|---|---|---|---|---|---|---|---|---|---|---|---|---|---|---|---|---|---|---|---|---|
| A | 2.329 | 2.234 | 2.299 | 0.238 | 0.229 | 0.235 | 0.306 | 0.282 | 0.283 | | | | 450 | Gen 3.1 Test-D7 L4063 | 124.528 | 118.305 | 126.754 | 12452.8 | 11830.5 | 12675.4 |
| | 0.053 | 0.049 | 0.049 | [illegible] | [illegible] | 0.036 | 0.04 | 0.04 | 0.04 | | | | 570 | Gen 3.1 Control-D7 L4063 | 111.099 | 124.135 | 122.628 | 11109.9 | 12413.5 | 12262.8 |
| | 2.276 | 2.186 | 2.25 | 0.196 | 0.186 | 0.199 | 0.266 | 0.242 | 0.243 | | | | Delta | Gen 3.1-D7 L4063 | 108.674 | 128.719 | 116.209 | 10867.4 | 12871.9 | 11620.9 |
| | 2055.788 | 1929.48 | 2018.106 | 124.528 | 118.305 | 126.754 | 170.439 | 154.609 | 155.528 | | | | [Concentration] | | | | | | | |
| B | [illegible] | [illegible] | [illegible] | 0.219 | 0.239 | 0.234 | 0.132 | 0.134 | 0.139 | | | | 450 | Gen 3.0 D11 L4063 | 334.976 | 308.365 | 319.513 | 33497.6 | 30836.5 | 31951.3 |
| | [illegible] | [illegible] | [illegible] | [illegible] | [illegible] | [illegible] | [illegible] | [illegible] | [illegible] | | | | 570 | Gen 3.1 Control-D11 L4063 | 337.044 | 288.566 | 285.449 | 33704.4 | 28856.6 | 28544.9 |
| | [illegible] | [illegible] | [illegible] | 0.175 | 0.195 | 0.193 | 0.093 | 0.095 | 0.1 | | | | Delta | Gen 3.1 Test-D11 L4063 | 263.914 | 263.78 | 256.656 | 26391.4 | 26378 | 25665.6 |
| | 964.614 | 1050.496 | 979.308 | 111.099 | 124.135 | 122.628 | 56.852 | 58.385 | 61.512 | | | | [Concentration] | | | | | | | |
| C | [illegible] | [illegible] | [illegible] | 0.215 | 0.244 | 0.225 | 0.136 | 0.282 | 0.283 | | | | 450 | Gen 3.0 D16 L4063 | 177.347 | 167.94 | 173.991 | 17734.7 | 16794 | 17399.1 |
| | 0.049 | [illegible] | [illegible] | [illegible] | [illegible] | [illegible] | [illegible] | [illegible] | [illegible] | | | | 570 | Gen 3.1 Control-D11 L4063 | 139.66 | 135.532 | 139.66 | 13966 | 13553.2 | 13966 |
| | [illegible] | [illegible] | [illegible] | 0.171 | 0.202 | 0.183 | 0.096 | 3.023 | 3.117 | | | | Delta | Gen 3.1 Test-D16 L4063 | 170.439 | 154.609 | 155.528 | 17043.9 | 15460.9 | 15552.8 |
| | 511.386 | 478.27 | 522.43 | 108.674 | 128.719 | 116.209 | 58.585 | 57.052 | 54.517 | | | | [Concentration] | | | | | | | |
| D | 0.433 | 0.43 | 0.414 | 0.555 | 0.514 | 0.527 | 0.061 | 0.06 | 0.059 | | | | 450 | Gen 3.0-D7 L4064 | 56.852 | 58.385 | 61.512 | 5685.2 | 5838.5 | 6151.2 |
| | [illegible] | [illegible] | [illegible] | [illegible] | [illegible] | [illegible] | [illegible] | [illegible] | [illegible] | | | | 570 | Gen 3.1 Control-D7 L4064 | 58.585 | 57.052 | 54.517 | 5858.5 | 5705.2 | 5451.7 |
| | 0.388 | 0.386 | 0.371 | 0.511 | 0.472 | 0.488 | 0.017 | 0.017 | 0.017 | | | | Delta | Gen 3.1 Test-D7 L4064 | 3.79 | 4.103 | 3.79 | 379 | 410.3 | 379 |
| | 251.894 | 250.017 | 239.849 | 334.976 | 308.365 | 319.513 | 3.79 | 4.103 | 3.79 | | | | [Concentration] | | | | | | | |
| E | 0.225 | 0.252 | 0.241 | 0.563 | 0.49 | 0.482 | 0.064 | 0.063 | 0.062 | | | | 450 | Gen 3.0-D16 L4064 | 6.409 | 6.636 | 6.636 | 640.9 | 663.6 | 663.6 |
| | [illegible] | 0.05 | [illegible] | 0.049 | [illegible] | [illegible] | [illegible] | [illegible] | [illegible] | | | | 570 | Gen 3.1 Control-D16 L4064 | 8.362 | 8.659 | 7.765 | 836.2 | 865.9 | 776.5 |
| | 0.182 | 0.202 | 3.191 | 0.514 | 0.443 | 0.438 | 0.02 | 0.02 | 0.02 | | | | Delta | Gen 3.1 Test-D16 L4064 | 7.24 | 7.615 | 8.213 | 724 | 761.5 | 821.3 |
| | 115.488 | 128.719 | 126.361 | 337.044 | 288.566 | 285.449 | 6.409 | 6.636 | 6.636 | | | | [Concentration] | | | | | | | |
| F | 0.153 | 0.142 | 0.147 | 0.454 | 0.454 | 0.441 | 0.066 | 0.066 | 0.066 | | | | 450 | | | | | | | |
| | [illegible] | [illegible] | [illegible] | [illegible] | [illegible] | [illegible] | [illegible] | [illegible] | [illegible] | | | | 570 | | | | | | | |
| | 0.109 | 0.1 | 0.103 | 0.406 | 0.406 | 0.396 | 0.023 | 0.023 | 0.022 | | | | Delta | | | | | | | |
| | 67.748 | 61.645 | 63.836 | 263.914 | 263.78 | 256.656 | 8.362 | 8.659 | 7.765 | | | | [Concentration] | | | | | | | |
| G | 0.099 | 0.109 | 0.101 | 0.321 | 0.305 | 0.318 | 0.068 | 0.064 | 0.065 | | | | 450 | | | | | | | |
| | [illegible] | 0.051 | [illegible] | [illegible] | [illegible] | [illegible] | [illegible] | [illegible] | [illegible] | | | | 570 | | | | | | | |
| | 0.055 | 0.058 | 0.055 | 0.276 | 0.262 | 0.021 | 0.021 | 0.022 | 0.022 | | | | Delta | | | | | | | |
| | 31.141 | 33.059 | 31.553 | 177.347 | 167.94 | 173.991 | 7.24 | 7.615 | 8.213 | | | | [Concentration] | | | | | | | |
| H | 0.053 | 0.057 | 0.055 | 0.263 | 0.256 | 0.263 | | | | | | | 450 | | | | | | | |
| | [illegible] | [illegible] | [illegible] | [illegible] | [illegible] | [illegible] | | | | | | | 570 | | | | | | | |
| | 0.012 | 0.011 | 0.011 | 0.219 | 0.213 | 0.219 | | | | | | | Delta | | | | | | | |
| | <0.0000 | <0.0000 | <0.0000 | 139.66 | 135.532 | 139.66 | | | | | | | [Concentration] | | | | | | | |

FIG. 104B

| Sample number # | Description Gen 3.1 Optimization | Glucose (g/L) | Lactate (g/L) | Ammonia (mmol/L) | Glutamine (mmol/L) | Glutamax (mmol/L) | Glutamax-Glutamine (mmol/L) |
|---|---|---|---|---|---|---|---|
| 13 | Gen 3.0-Day 16 First Round #L4063 | 1.52 | 1.07 | 2.06 | 1.91 | 2.11 | 0.20 |
| 14 | Gen 3.1 Control-Day 16 First Round #L4063 | 0.90 | 1.74 | 2.50 | 1.34 | 1.49 | 0.15 |
| 15 | Gen 3.1 Test-Day 16 First Round #L4063 | 0.96 | 1.64 | 2.49 | 1.33 | 1.47 | 0.14 |
| 16 | Gen 3.0-Day 11 First Round #L4063 | 1.42 | 0.70 | 1.83 | 1.70 | 1.86 | 0.16 |
| 17 | Gen 3.1 Control-Day 11 First Round #L4063 | 0.90 | 1.08 | 2.24 | 1.07 | 1.19 | 0.11 |
| 18 | Gen 3.1 Test-Day 11 First Round #L4063 | 0.84 | 1.21 | 2.25 | 1.11 | 1.23 | 0.12 |
| 19 | Gen 3.0-Day 7 First Round #L4063 | 1.76 | 0.20 | 1.88 | 2.04 | 2.23 | 0.19 |
| 20 | Gen 3.1 Control-Day 7 First Round #L4063 | 1.73 | 0.22 | 1.86 | 2.00 | 2.19 | 0.19 |
| 21 | Gen 3.1 Test-Day 7 First Round #L4063 | 1.41 | 0.50 | 1.96 | 1.98 | 2.15 | 0.17 |
| | | | | | | | |
| 22 | Gen 3.0 Day 16 Second Round #L4064 | 2.76 | 1.52 | 1.00 | 0.68 | 0.77 | 0.09 |
| 23 | Gen 3.1 Control-Day 16 Second Round #L4064 | 2.14 | 1.95 | 0.99 | 0.64 | 0.73 | 0.08 |
| 24 | Gen 3.1 Test-Day 16 Second Round #L4064 | 2.20 | 1.89 | 0.94 | 0.64 | 0.71 | 0.07 |
| 25 | Gen 3.0-Day 7 Second Round #L4064 | 4.26 | 0.08 | 0.71 | 1.29 | 1.43 | 0.14 |
| 26 | Gen 3.1 Control-Day 7 Second Round #L4064 | 4.14 | 0.22 | 0.78 | 1.17 | 1.29 | 0.12 |
| 27 | Gen 3.1 Test-Day 7 Second Round #L4064 | 3.82 | 0.49 | 0.89 | 1.09 | 1.20 | 0.11 |

FIG. 105

| Order | Name | | Geometric Mean Probe-fitc-A | Geometric Mean Probe-fitc-A | Average 1301 | Average T | Length relative to 1301 | |
|---|---|---|---|---|---|---|---|---|
| A1 | Gen 3.0-L4063 | A1 10.1.fcs | 86 | 42.5 | | | | |
| A2 | | A2 10.2.fcs | 85.4 | 42.3 | 85.7 | 42.4 | | |
| A3 | | A3 10.3.fcs | 4585 | 207 | | | | |
| A4 | | A4 10.4.fcs | 4389 | 216 | 4487 | 211.5 | 7.684093 | |
| A5 | Gen 3.1 Control-L4063 | A5 11.1.fcs | 82.7 | 33.3 | | | | |
| A6 | | A6 11.2.fcs | 86 | 32.9 | 84.35 | 33.1 | | |
| A7 | | A7 11.3.fcs | 4696 | 180 | | | | |
| A8 | | A8 11.4.fcs | 4641 | 175 | 4668.5 | 177.5 | 6.299968 | |
| B1 | Gen 3.1 Test-L4063 | B1 12.1.fcs | 95.1 | 28.8 | | | | |
| B2 | | B2 12.2.fcs | 84.7 | 26.7 | 89.9 | 27.75 | | |
| B3 | | B3 12.3.fcs | 4764 | 169 | | | | |
| B4 | | B4 12.4.fcs | 4800 | 174 | 4782 | 171.5 | 6.12732 | |
| B5 | Gen 3.0 -L4064 | B5 13.1.fcs | 101 | 40.3 | | | | |
| B6 | | B6 13.2.fcs | 89.6 | 34.1 | 95.3 | 37.2 | | |
| B7 | | B7 13.3.fcs | 4300 | 174 | | | | |
| B8 | | B8 13.4.fcs | 4367 | 172 | 4333.5 | 173 | 6.408381 | |
| C1 | Gen 3.1 Control-L4064 | C1 14.1.fcs | 92.1 | 31.1 | | | | |
| C2 | | C2 14.2.fcs | 88.6 | 29.6 | 90.35 | 30.35 | | |
| C3 | | C3 14.3.fcs | 4111 | 169 | | | | |
| C4 | | C4 14.4.fcs | 4443 | 172 | 4277 | 170.5 | 6.69509 | |
| C5 | Gen 3.1 Test-L4064 | C5 15.1.fcs | 89.7 | 25.7 | | | | |
| C6 | | C6 15.2.fcs | 85.7 | 24.7 | 87.7 | 25.2 | | |
| C7 | | C7 15.3.fcs | 4342 | 172 | | | | |
| C8 | | C8 15.4.fcs | 4560 | 166 | 4451 | 169 | 6.591341 | |

FIG. 106

Shared Frequencies

| Subject | Original Sample | uCDR3 count | Compared Sample | uCDR3 count | shared uCDR3 count | uCDR3 count |
|---|---|---|---|---|---|---|
| L4063 | L63GA | 14005 | L63GB | 18149 | 3240 | 23.13459479 |
| L4063 | L63GA | 14005 | L63GC | 17181 | 2959 | 21.12816851 |
| L4063 | L63GA | 15107 | L64GB | 21460 | 5486 | 36.31429139 |
| L4063 | L63GA | 15107 | L64GC | 21503 | 5541 | 36.67836102 |

Code:
L63GA = L4063 Gen 3.0
L63GB = L4063 Gen 3.1 control
L63GC = L4063 Gen 3.1 Test L64GA = L4064 Gen 3.0
L64GB = L4064 Gen 3.1 control
L64GC = L4064 Gen 3.1 Test

Top 80%

| Subject | sample1 | uCDR3 count | sample2 | uCDR3 count | shared uCDR3 count | % shared of col B |
|---|---|---|---|---|---|---|
| L4063 | L63GA | 1104 | L63GB | 2437 | 1000 | 90.57971 |
| L4063 | L63GA | 1104 | L63GC | 2331 | 975 | 88.31522 |
| L4064 | L64GA | 2478 | L64GB | 3246 | 2186 | 88.2163 |
| L4064 | L64GA | 2478 | L64GC | 3263 | 2163 | 87.28814 |

Code:
L63GA = L4063 Gen 3.0
L63GB = L4063 Gen 3.1 control
L63GC = L4063 Gen 3.1 Test L64GA = L4064 Gen 3.0
L64GB = L4064 Gen 3.1 control
L64GC = L4064 Gen 3.1 Test

FIG. 107

Shannon Diversity

Only 6 samples were included in the Shannon diversity graph for Gen 3.1 Optimization L4063 Gen 3.1 = L4063 Gen 3.0
L4063 Gen 3.2 = L4063 Gen 3.1 control
L4063 Gen 3.3 = L4063 Gen 3.1 Test L4064 Gen 3.1 = L4064 Gen 3.0
L4064 Gen 3.2 = L4064 Gen 3.1 control
L4064 Gen 3.3 = L4064 Gen 3.1 Test

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

FIG. 109

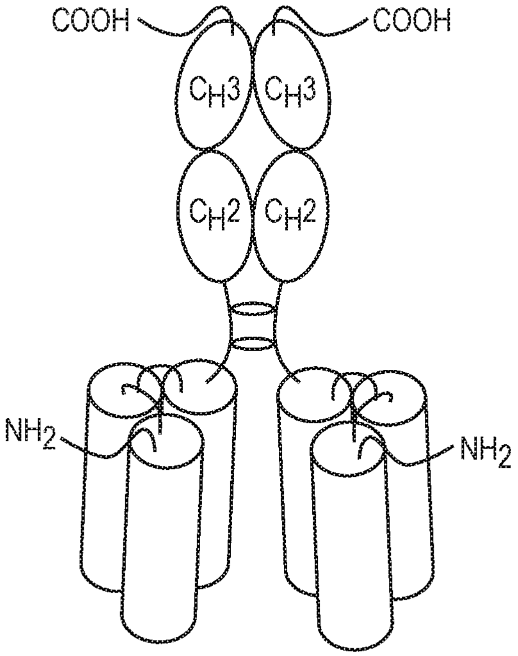
Structure I-A
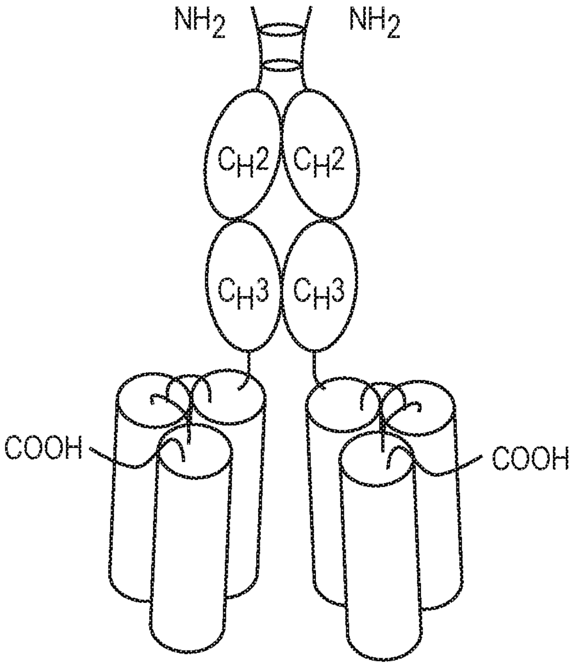
Structure I-B
FIG. 110

SEQUENCE LISTING

```
<160> NUMBER OF SEQ ID NOS: 126

<210> SEQ ID NO 1
<211> LENGTH: 450
<212> TYPE: PRT
<213> ORGANISM: Artificial Sequence
<220> FEATURE:
<223> OTHER INFORMATION: Muromonab heavy chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala Lys Thr Thr Ala Pro Ser Val Tyr
        115                 120                 125

Pro Leu Ala Pro Val Cys Gly Gly Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
```

```
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 2
<211> LENGTH: 213
<212> TYPE: PRT
<213> ORGANISM: Artificial Sequence
<220> FEATURE:
<223> OTHER INFORMATION: Muromonab light chain

<400> SEQUENCE: 2

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
```

```
                85                  90                  95

Phe Gly Ser Gly Thr Lys Leu Glu Ile Asn Arg Ala Asp Thr Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210


<210> SEQ ID NO 3
<211> LENGTH: 134
<212> TYPE: PRT
<213> ORGANISM: Artificial Sequence
<220> FEATURE:
<223> OTHER INFORMATION: recombinant human IL-2 (rhIL-2)

<400> SEQUENCE: 3

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130


<210> SEQ ID NO 4
<211> LENGTH: 132
<212> TYPE: PRT
<213> ORGANISM: Artificial Sequence
<220> FEATURE:
<223> OTHER INFORMATION: Aldesleukin

<400> SEQUENCE: 4

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30
```

Pro Lys Leu Thr Arg Met Leu Thr Phe Lys Phe Tyr Met Pro Lys Lys
35 40 45

Ala Thr Glu Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 5
<211> LENGTH: 130
<212> TYPE: PRT
<213> ORGANISM: Artificial Sequence
<220> FEATURE:
<223> OTHER INFORMATION: recombinant human IL-4 (rhIL-4)

<400> SEQUENCE: 5

Met His Lys Cys Asp Ile Thr Leu Gln Glu Ile Ile Lys Thr Leu Asn
1 5 10 15

Ser Leu Thr Glu Gln Lys Thr Leu Cys Thr Glu Leu Thr Val Thr Asp
20 25 30

Ile Phe Ala Ala Ser Lys Asn Thr Thr Glu Lys Glu Thr Phe Cys Arg
35 40 45

Ala Ala Thr Val Leu Arg Gln Phe Tyr Ser His His Glu Lys Asp Thr
50 55 60

Arg Cys Leu Gly Ala Thr Ala Gln Gln Phe His Arg His Lys Gln Leu
65 70 75 80

Ile Arg Phe Leu Lys Arg Leu Asp Arg Asn Leu Trp Gly Leu Ala Gly
85 90 95

Leu Asn Ser Cys Pro Val Lys Glu Ala Asn Gln Ser Thr Leu Glu Asn
100 105 110

Phe Leu Glu Arg Leu Lys Thr Ile Met Arg Glu Lys Tyr Ser Lys Cys
115 120 125

Ser Ser
130

<210> SEQ ID NO 6
<211> LENGTH: 153
<212> TYPE: PRT
<213> ORGANISM: Artificial Sequence
<220> FEATURE:
<223> OTHER INFORMATION: recombinant human IL-7 (rhIL-7)

<400> SEQUENCE: 6

Met Asp Cys Asp Ile Glu Gly Lys Asp Gly Lys Gln Tyr Glu Ser Val
1 5 10 15

Leu Met Val Ser Ile Asp Gln Leu Leu Asp Ser Met Lys Glu Ile Gly
20 25 30

Ser Asn Cys Leu Asn Asn Glu Phe Asn Phe Phe Lys Arg His Ile Cys
35 40 45

Asp Ala Asn Lys Glu Gly Met Phe Leu Phe Arg Ala Ala Arg Lys Leu
50 55 60

Arg Gln Phe Leu Lys Met Asn Ser Thr Gly Asp Phe Asp Leu His Leu
65 70 75 80

Leu Lys Val Ser Glu Gly Thr Thr Ile Leu Leu Asn Cys Thr Gly Gln
85 90 95

Val Lys Gly Arg Lys Pro Ala Ala Leu Gly Glu Ala Gln Pro Thr Lys
100 105 110

Ser Leu Glu Glu Asn Lys Ser Leu Lys Glu Gln Lys Lys Leu Asn Asp
115 120 125

Leu Cys Phe Leu Lys Arg Leu Leu Gln Glu Ile Lys Thr Cys Trp Asn
130 135 140

Lys Ile Leu Met Gly Thr Lys Glu His
145 150

<210> SEQ ID NO 7
<211> LENGTH: 115
<212> TYPE: PRT
<213> ORGANISM: Artificial Sequence
<220> FEATURE:
<223> OTHER INFORMATION: recombinant human IL-15 (rhIL-15)

<400> SEQUENCE: 7

Met Asn Trp Val Asn Val Ile Ser Asp Leu Lys Lys Ile Glu Asp Leu
1 5 10 15

Ile Gln Ser Met His Ile Asp Ala Thr Leu Tyr Thr Glu Ser Asp Val
20 25 30

His Pro Ser Cys Lys Val Thr Ala Met Lys Cys Phe Leu Leu Glu Leu
35 40 45

Gln Val Ile Ser Leu Glu Ser Gly Asp Ala Ser Ile His Asp Thr Val
50 55 60

Glu Asn Leu Ile Ile Leu Ala Asn Asn Ser Leu Ser Ser Asn Gly Asn
65 70 75 80

Val Thr Glu Ser Gly Cys Lys Glu Cys Glu Glu Leu Glu Glu Lys Asn
85 90 95

Ile Lys Glu Phe Leu Gln Ser Phe Val His Ile Val Gln Met Phe Ile
100 105 110

Asn Thr Ser
115

<210> SEQ ID NO 8
<211> LENGTH: 132
<212> TYPE: PRT
<213> ORGANISM: Artificial Sequence
<220> FEATURE:
<223> OTHER INFORMATION: recombinant human IL-21 (rhIL-21)

<400> SEQUENCE: 8

Met Gln Asp Arg His Met Ile Arg Met Arg Gln Leu Ile Asp Ile Val
1 5 10 15

Asp Gln Leu Lys Asn Tyr Val Asn Asp Leu Val Pro Glu Phe Leu Pro
20 25 30

Ala Pro Glu Asp Val Glu Thr Asn Cys Glu Trp Ser Ala Phe Ser Cys
35 40 45

Phe Gln Lys Ala Gln Leu Lys Ser Ala Asn Thr Gly Asn Asn Glu Arg
50 55 60

Ile Ile Asn Val Ser Ile Lys Lys Leu Lys Arg Lys Pro Pro Ser Thr
65 70 75 80

Asn Ala Gly Arg Arg Gln Lys His Arg Leu Thr Cys Pro Ser Cys Asp

```
                85                  90                  95

Ser Tyr Glu Lys Lys Pro Pro Lys Glu Phe Leu Glu Arg Phe Lys Ser
            100                 105                 110

Leu Leu Gln Lys Met Ile His Gln His Leu Ser Ser Arg Thr His Gly
        115                 120                 125

Ser Glu Asp Ser
    130


<210> SEQ ID NO 9
<211> LENGTH: 255
<212> TYPE: PRT
<213> ORGANISM: Artificial Sequence
<220> FEATURE:
<223> OTHER INFORMATION: human 4-1BB, Tumor necrosis factor receptor
      superfamily, member 9 (Homo sapiens)

<400> SEQUENCE: 9

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255


<210> SEQ ID NO 10
<211> LENGTH: 256
<212> TYPE: PRT
<213> ORGANISM: Artificial Sequence
<220> FEATURE:
<223> OTHER INFORMATION: murine 4-1BB, Tumor necrosis factor receptor
      superfamily, member 9 (Mus musculus)
```

<400> SEQUENCE: 10

Met Gly Asn Asn Cys Tyr Asn Val Val Val Ile Val Leu Leu Leu Val
1 5 10 15

Gly Cys Glu Lys Val Gly Ala Val Gln Asn Ser Cys Asp Asn Cys Gln
20 25 30

Pro Gly Thr Phe Cys Arg Lys Tyr Asn Pro Val Cys Lys Ser Cys Pro
35 40 45

Pro Ser Thr Phe Ser Ser Ile Gly Gly Gln Pro Asn Cys Asn Ile Cys
50 55 60

Arg Val Cys Ala Gly Tyr Phe Arg Phe Lys Lys Phe Cys Ser Ser Thr
65 70 75 80

His Asn Ala Glu Cys Glu Cys Ile Glu Gly Phe His Cys Leu Gly Pro
85 90 95

Gln Cys Thr Arg Cys Glu Lys Asp Cys Arg Pro Gly Gln Glu Leu Thr
100 105 110

Lys Gln Gly Cys Lys Thr Cys Ser Leu Gly Thr Phe Asn Asp Gln Asn
115 120 125

Gly Thr Gly Val Cys Arg Pro Trp Thr Asn Cys Ser Leu Asp Gly Arg
130 135 140

Ser Val Leu Lys Thr Gly Thr Thr Glu Lys Asp Val Val Cys Gly Pro
145 150 155 160

Pro Val Val Ser Phe Ser Pro Ser Thr Thr Ile Ser Val Thr Pro Glu
165 170 175

Gly Gly Pro Gly Gly His Ser Leu Gln Val Leu Thr Leu Phe Leu Ala
180 185 190

Leu Thr Ser Ala Leu Leu Leu Ala Leu Ile Phe Ile Thr Leu Leu Phe
195 200 205

Ser Val Leu Lys Trp Ile Arg Lys Lys Phe Pro His Ile Phe Lys Gln
210 215 220

Pro Phe Lys Lys Thr Thr Gly Ala Ala Gln Glu Glu Asp Ala Cys Ser
225 230 235 240

Cys Arg Cys Pro Gln Glu Glu Glu Gly Gly Gly Gly Gly Tyr Glu Leu
245 250 255

<210> SEQ ID NO 11
<211> LENGTH: 441
<212> TYPE: PRT
<213> ORGANISM: Artificial Sequence
<220> FEATURE:
<223> OTHER INFORMATION: heavy chain for utomilumab

<400> SEQUENCE: 11

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Ser Phe Ser Thr Tyr
20 25 30

Trp Ile Ser Trp Val Arg Gln Met Pro Gly Lys Gly Leu Glu Trp Met
35 40 45

Gly Lys Ile Tyr Pro Gly Asp Ser Tyr Thr Asn Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Gly Tyr Gly Ile Phe Asp Tyr Trp Gly Gln Gly Thr Leu Val

```
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440
```

<210> SEQ ID NO 12
<211> LENGTH: 214
<212> TYPE: PRT
<213> ORGANISM: Artificial Sequence
<220> FEATURE:
<223> OTHER INFORMATION: light chain for utomilumab

<400> SEQUENCE: 12

```
Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
```

```
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 13
<211> LENGTH: 116
<212> TYPE: PRT
<213> ORGANISM: Artificial Sequence
<220> FEATURE:
<223> OTHER INFORMATION: heavy chain variable region for utomilumab

<400> SEQUENCE: 13

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
            20                  25                  30

Trp Ile Ser Trp Val Arg Gln Met Pro Gly Lys Gly Leu Glu Trp Met
        35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
            100                 105                 110

Thr Val Ser Ser
        115


<210> SEQ ID NO 14
<211> LENGTH: 108
<212> TYPE: PRT
<213> ORGANISM: Artificial Sequence
<220> FEATURE:
<223> OTHER INFORMATION: light chain variable region for utomilumab
```

<400> SEQUENCE: 14

```
Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
            100                 105
```

<210> SEQ ID NO 15
<211> LENGTH: 6
<212> TYPE: PRT
<213> ORGANISM: Artificial Sequence
<220> FEATURE:
<223> OTHER INFORMATION: heavy chain CDR1 for utomilumab

<400> SEQUENCE: 15

```
Ser Thr Tyr Trp Ile Ser
1               5
```

<210> SEQ ID NO 16
<211> LENGTH: 17
<212> TYPE: PRT
<213> ORGANISM: Artificial Sequence
<220> FEATURE:
<223> OTHER INFORMATION: heavy chain CDR2 for utomilumab

<400> SEQUENCE: 16

```
Lys Ile Tyr Pro Gly Asp Ser Tyr Thr Asn Tyr Ser Pro Ser Phe Gln
1               5                   10                  15

Gly
```

<210> SEQ ID NO 17
<211> LENGTH: 8
<212> TYPE: PRT
<213> ORGANISM: Artificial Sequence
<220> FEATURE:
<223> OTHER INFORMATION: heavy chain CDR3 for utomilumab

<400> SEQUENCE: 17

```
Arg Gly Tyr Gly Ile Phe Asp Tyr
1               5
```

<210> SEQ ID NO 18
<211> LENGTH: 11
<212> TYPE: PRT
<213> ORGANISM: Artificial Sequence
<220> FEATURE:
<223> OTHER INFORMATION: light chain CDR1 for utomilumab

<400> SEQUENCE: 18

```
Ser Gly Asp Asn Ile Gly Asp Gln Tyr Ala His
1               5                   10
```

<210> SEQ ID NO 19
<211> LENGTH: 7
<212> TYPE: PRT
<213> ORGANISM: Artificial Sequence
<220> FEATURE:
<223> OTHER INFORMATION: light chain CDR2 for utomilumab

<400> SEQUENCE: 19

Gln Asp Lys Asn Arg Pro Ser
1               5

<210> SEQ ID NO 20
<211> LENGTH: 11
<212> TYPE: PRT
<213> ORGANISM: Artificial Sequence
<220> FEATURE:
<223> OTHER INFORMATION: light chain CDR3 for utomilumab

<400> SEQUENCE: 20

Ala Thr Tyr Thr Gly Phe Gly Ser Leu Ala Val
1               5                   10

<210> SEQ ID NO 21
<211> LENGTH: 448
<212> TYPE: PRT
<213> ORGANISM: Artificial Sequence
<220> FEATURE:
<223> OTHER INFORMATION: heavy chain for urelumab

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 22
<211> LENGTH: 216
<212> TYPE: PRT
<213> ORGANISM: Artificial Sequence
<220> FEATURE:
<223> OTHER INFORMATION: light chain for urelumab

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Cys Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160
```

Ser Gln Glu Ser Val Thr Glu Gln Asp Ser Lys Asp Ser Thr Tyr Ser
165 170 175

Leu Ser Ser Thr Leu Thr Leu Ser Lys Ala Asp Tyr Glu Lys His Lys
180 185 190

Val Tyr Ala Cys Glu Val Thr His Gln Gly Leu Ser Ser Pro Val Thr
195 200 205

Lys Ser Phe Asn Arg Gly Glu Cys
210 215

<210> SEQ ID NO 23
<211> LENGTH: 120
<212> TYPE: PRT
<213> ORGANISM: Artificial Sequence
<220> FEATURE:
<223> OTHER INFORMATION: variable heavy chain for urelumab

<400> SEQUENCE: 23

Met Lys His Leu Trp Phe Phe Leu Leu Leu Val Ala Ala Pro Arg Trp
1 5 10 15

Val Leu Ser Gln Val Gln Leu Gln Gln Trp Gly Ala Gly Leu Leu Lys
20 25 30

Pro Ser Glu Thr Leu Ser Leu Thr Cys Ala Val Tyr Gly Gly Ser Phe
35 40 45

Ser Gly Tyr Tyr Trp Ser Trp Ile Arg Gln Ser Pro Glu Lys Gly Leu
50 55 60

Glu Trp Ile Gly Glu Ile Asn His Gly Gly Tyr Val Thr Tyr Asn Pro
65 70 75 80

Ser Leu Glu Ser Arg Val Thr Ile Ser Val Asp Thr Ser Lys Asn Gln
85 90 95

Phe Ser Leu Lys Leu Ser Ser Val Thr Ala Ala Asp Thr Ala Val Tyr
100 105 110

Tyr Cys Ala Arg Asp Tyr Gly Pro
115 120

<210> SEQ ID NO 24
<211> LENGTH: 110
<212> TYPE: PRT
<213> ORGANISM: Artificial Sequence
<220> FEATURE:
<223> OTHER INFORMATION: variable light chain for urelumab

<400> SEQUENCE: 24

Met Glu Ala Pro Ala Gln Leu Leu Phe Leu Leu Leu Leu Trp Leu Pro
1 5 10 15

Asp Thr Thr Gly Glu Ile Val Leu Thr Gln Ser Pro Ala Thr Leu Ser
20 25 30

Leu Ser Pro Gly Glu Arg Ala Thr Leu Ser Cys Arg Ala Ser Gln Ser
35 40 45

Val Ser Ser Tyr Leu Ala Trp Tyr Gln Gln Lys Pro Gly Gln Ala Pro
50 55 60

Arg Leu Leu Ile Tyr Asp Ala Ser Asn Arg Ala Thr Gly Ile Pro Ala
65 70 75 80

Arg Phe Ser Gly Ser Gly Ser Gly Thr Asp Phe Thr Leu Thr Ile Ser
85 90 95

Ser Leu Glu Pro Glu Asp Phe Ala Val Tyr Tyr Cys Gln Gln
100 105 110

<210> SEQ ID NO 25
<211> LENGTH: 5
<212> TYPE: PRT
<213> ORGANISM: Artificial Sequence
<220> FEATURE:
<223> OTHER INFORMATION: heavy chain CDR1 for urelumab

<400> SEQUENCE: 25

Gly Tyr Tyr Trp Ser
1               5

<210> SEQ ID NO 26
<211> LENGTH: 16
<212> TYPE: PRT
<213> ORGANISM: Artificial Sequence
<220> FEATURE:
<223> OTHER INFORMATION: heavy chain CDR2 for urelumab

<400> SEQUENCE: 26

Glu Ile Asn His Gly Gly Tyr Val Thr Tyr Asn Pro Ser Leu Glu Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: heavy chain CDR3 for urelumab

<400> SEQUENCE: 27

Asp Tyr Gly Pro Gly Asn Tyr Asp Trp Tyr Phe Asp Leu
1               5                   10

<210> SEQ ID NO 28
<211> LENGTH: 11
<212> TYPE: PRT
<213> ORGANISM: Artificial Sequence
<220> FEATURE:
<223> OTHER INFORMATION: light chain CDR1 for urelumab

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: light chain CDR2 for urelumab

<400> SEQUENCE: 29

Asp Ala Ser Asn Arg Ala Thr
1               5

<210> SEQ ID NO 30
<211> LENGTH: 11
<212> TYPE: PRT
<213> ORGANISM: Artificial Sequence
<220> FEATURE:
<223> OTHER INFORMATION: light chain CDR3 for urelumab

<400> SEQUENCE: 30

Gln Gln Arg Ser Asp Trp Pro Pro Ala Leu Thr
1               5                   10

<210> SEQ ID NO 31

```
<211> LENGTH: 230
<212> TYPE: PRT
<213> ORGANISM: Artificial Sequence
<220> FEATURE:
<223> OTHER INFORMATION: Fc domain

<400> SEQUENCE: 31

Lys Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230


<210> SEQ ID NO 32
<211> LENGTH: 22
<212> TYPE: PRT
<213> ORGANISM: Artificial Sequence
<220> FEATURE:
<223> OTHER INFORMATION: linker

<400> SEQUENCE: 32

Gly Gly Pro Gly Ser Ser Lys Ser Cys Asp Lys Thr His Thr Cys Pro
1               5                   10                  15

Pro Cys Pro Ala Pro Glu
            20


<210> SEQ ID NO 33
<211> LENGTH: 22
<212> TYPE: PRT
<213> ORGANISM: Artificial Sequence
<220> FEATURE:
<223> OTHER INFORMATION: linker

<400> SEQUENCE: 33
```

```
Gly Gly Ser Gly Ser Ser Lys Ser Cys Asp Lys Thr His Thr Cys Pro
1               5                   10                  15

Pro Cys Pro Ala Pro Glu
            20


<210> SEQ ID NO 34
<211> LENGTH: 27
<212> TYPE: PRT
<213> ORGANISM: Artificial Sequence
<220> FEATURE:
<223> OTHER INFORMATION: linker

<400> SEQUENCE: 34

Gly Gly Pro Gly Ser Ser Ser Ser Ser Ser Ser Lys Ser Cys Asp Lys
1               5                   10                  15

Thr His Thr Cys Pro Pro Cys Pro Ala Pro Glu
            20                  25


<210> SEQ ID NO 35
<211> LENGTH: 27
<212> TYPE: PRT
<213> ORGANISM: Artificial Sequence
<220> FEATURE:
<223> OTHER INFORMATION: linker

<400> SEQUENCE: 35

Gly Gly Ser Gly Ser Ser Ser Ser Ser Ser Ser Lys Ser Cys Asp Lys
1               5                   10                  15

Thr His Thr Cys Pro Pro Cys Pro Ala Pro Glu
            20                  25


<210> SEQ ID NO 36
<211> LENGTH: 29
<212> TYPE: PRT
<213> ORGANISM: Artificial Sequence
<220> FEATURE:
<223> OTHER INFORMATION: linker

<400> SEQUENCE: 36

Gly Gly Pro Gly Ser Ser Ser Ser Ser Ser Ser Ser Ser Lys Ser Cys
1               5                   10                  15

Asp Lys Thr His Thr Cys Pro Pro Cys Pro Ala Pro Glu
            20                  25


<210> SEQ ID NO 37
<211> LENGTH: 29
<212> TYPE: PRT
<213> ORGANISM: Artificial Sequence
<220> FEATURE:
<223> OTHER INFORMATION: linker

<400> SEQUENCE: 37

Gly Gly Ser Gly Ser Ser Ser Ser Ser Ser Ser Ser Ser Lys Ser Cys
1               5                   10                  15

Asp Lys Thr His Thr Cys Pro Pro Cys Pro Ala Pro Glu
            20                  25


<210> SEQ ID NO 38
<211> LENGTH: 24
<212> TYPE: PRT
<213> ORGANISM: Artificial Sequence
<220> FEATURE:
<223> OTHER INFORMATION: linker

<400> SEQUENCE: 38
```

Gly Gly Pro Gly Ser Ser Gly Ser Gly Ser Ser Asp Lys Thr His Thr
1 5 10 15

Cys Pro Pro Cys Pro Ala Pro Glu
20

<210> SEQ ID NO 39
<211> LENGTH: 23
<212> TYPE: PRT
<213> ORGANISM: Artificial Sequence
<220> FEATURE:
<223> OTHER INFORMATION: linker

<400> SEQUENCE: 39

Gly Gly Pro Gly Ser Ser Gly Ser Gly Ser Asp Lys Thr His Thr Cys
1 5 10 15

Pro Pro Cys Pro Ala Pro Glu
20

<210> SEQ ID NO 40
<211> LENGTH: 21
<212> TYPE: PRT
<213> ORGANISM: Artificial Sequence
<220> FEATURE:
<223> OTHER INFORMATION: linker

<400> SEQUENCE: 40

Gly Gly Pro Ser Ser Ser Gly Ser Asp Lys Thr His Thr Cys Pro Pro
1 5 10 15

Cys Pro Ala Pro Glu
20

<210> SEQ ID NO 41
<211> LENGTH: 25
<212> TYPE: PRT
<213> ORGANISM: Artificial Sequence
<220> FEATURE:
<223> OTHER INFORMATION: linker

<400> SEQUENCE: 41

Gly Gly Ser Ser Ser Ser Ser Ser Ser Ser Gly Ser Asp Lys Thr His
1 5 10 15

Thr Cys Pro Pro Cys Pro Ala Pro Glu
20 25

<210> SEQ ID NO 42
<211> LENGTH: 246
<212> TYPE: PRT
<213> ORGANISM: Artificial Sequence
<220> FEATURE:
<223> OTHER INFORMATION: Fc domain

<400> SEQUENCE: 42

Met Glu Thr Asp Thr Leu Leu Leu Trp Val Leu Leu Leu Trp Val Pro
1 5 10 15

Ala Gly Asn Gly Asp Lys Thr His Thr Cys Pro Pro Cys Pro Ala Pro
20 25 30

Glu Leu Leu Gly Gly Pro Ser Val Phe Leu Phe Pro Pro Lys Pro Lys
35 40 45

Asp Thr Leu Met Ile Ser Arg Thr Pro Glu Val Thr Cys Val Val Val
50 55 60

Asp Val Ser His Glu Asp Pro Glu Val Lys Phe Asn Trp Tyr Val Asp
65 70 75 80

```
Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Glu Glu Met Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly
                245


<210> SEQ ID NO 43
<211> LENGTH: 11
<212> TYPE: PRT
<213> ORGANISM: Artificial Sequence
<220> FEATURE:
<223> OTHER INFORMATION: linker

<400> SEQUENCE: 43

Ser Gly Ser Gly Ser Gly Ser Gly Ser Gly Ser
1               5                   10


<210> SEQ ID NO 44
<211> LENGTH: 12
<212> TYPE: PRT
<213> ORGANISM: Artificial Sequence
<220> FEATURE:
<223> OTHER INFORMATION: linker

<400> SEQUENCE: 44

Ser Ser Ser Ser Ser Ser Gly Ser Gly Ser Gly Ser
1               5                   10


<210> SEQ ID NO 45
<211> LENGTH: 16
<212> TYPE: PRT
<213> ORGANISM: Artificial Sequence
<220> FEATURE:
<223> OTHER INFORMATION: linker

<400> SEQUENCE: 45

Ser Ser Ser Ser Ser Ser Gly Ser Gly Ser Gly Ser Gly Ser Gly Ser
1               5                   10                  15


<210> SEQ ID NO 46
<211> LENGTH: 254
<212> TYPE: PRT
<213> ORGANISM: Artificial Sequence
<220> FEATURE:
```

<223> OTHER INFORMATION: 4-1BBL

<400> SEQUENCE: 46

Met Glu Tyr Ala Ser Asp Ala Ser Leu Asp Pro Glu Ala Pro Trp Pro
1 5 10 15

Pro Ala Pro Arg Ala Arg Ala Cys Arg Val Leu Pro Trp Ala Leu Val
20 25 30

Ala Gly Leu Leu Leu Leu Leu Leu Leu Ala Ala Ala Cys Ala Val Phe
35 40 45

Leu Ala Cys Pro Trp Ala Val Ser Gly Ala Arg Ala Ser Pro Gly Ser
50 55 60

Ala Ala Ser Pro Arg Leu Arg Glu Gly Pro Glu Leu Ser Pro Asp Asp
65 70 75 80

Pro Ala Gly Leu Leu Asp Leu Arg Gln Gly Met Phe Ala Gln Leu Val
85 90 95

Ala Gln Asn Val Leu Leu Ile Asp Gly Pro Leu Ser Trp Tyr Ser Asp
100 105 110

Pro Gly Leu Ala Gly Val Ser Leu Thr Gly Gly Leu Ser Tyr Lys Glu
115 120 125

Asp Thr Lys Glu Leu Val Val Ala Lys Ala Gly Val Tyr Tyr Val Phe
130 135 140

Phe Gln Leu Glu Leu Arg Arg Val Val Ala Gly Glu Gly Ser Gly Ser
145 150 155 160

Val Ser Leu Ala Leu His Leu Gln Pro Leu Arg Ser Ala Ala Gly Ala
165 170 175

Ala Ala Leu Ala Leu Thr Val Asp Leu Pro Pro Ala Ser Ser Glu Ala
180 185 190

Arg Asn Ser Ala Phe Gly Phe Gln Gly Arg Leu Leu His Leu Ser Ala
195 200 205

Gly Gln Arg Leu Gly Val His Leu His Thr Glu Ala Arg Ala Arg His
210 215 220

Ala Trp Gln Leu Thr Gln Gly Ala Thr Val Leu Gly Leu Phe Arg Val
225 230 235 240

Thr Pro Glu Ile Pro Ala Gly Leu Pro Ser Pro Arg Ser Glu
245 250

<210> SEQ ID NO 47
<211> LENGTH: 168
<212> TYPE: PRT
<213> ORGANISM: Artificial Sequence
<220> FEATURE:
<223> OTHER INFORMATION: 4-1BBL soluble domain

<400> SEQUENCE: 47

Leu Arg Gln Gly Met Phe Ala Gln Leu Val Ala Gln Asn Val Leu Leu
1 5 10 15

Ile Asp Gly Pro Leu Ser Trp Tyr Ser Asp Pro Gly Leu Ala Gly Val
20 25 30

Ser Leu Thr Gly Gly Leu Ser Tyr Lys Glu Asp Thr Lys Glu Leu Val
35 40 45

Val Ala Lys Ala Gly Val Tyr Tyr Val Phe Phe Gln Leu Glu Leu Arg
50 55 60

Arg Val Val Ala Gly Glu Gly Ser Gly Ser Val Ser Leu Ala Leu His
65 70 75 80

Leu Gln Pro Leu Arg Ser Ala Ala Gly Ala Ala Ala Leu Ala Leu Thr
85 90 95

```
Val Asp Leu Pro Pro Ala Ser Ser Glu Ala Arg Asn Ser Ala Phe Gly
            100                 105                 110

Phe Gln Gly Arg Leu Leu His Leu Ser Ala Gly Gln Arg Leu Gly Val
        115                 120                 125

His Leu His Thr Glu Ala Arg Ala Arg His Ala Trp Gln Leu Thr Gln
    130                 135                 140

Gly Ala Thr Val Leu Gly Leu Phe Arg Val Thr Pro Glu Ile Pro Ala
145                 150                 155                 160

Gly Leu Pro Ser Pro Arg Ser Glu
                165


<210> SEQ ID NO 48
<211> LENGTH: 118
<212> TYPE: PRT
<213> ORGANISM: Artificial Sequence
<220> FEATURE:
<223> OTHER INFORMATION: variable heavy chain for 4B4-1-1 version 1

<400> SEQUENCE: 48

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Val Leu Glu Trp Ile
        35                  40                  45

Gly Glu Ile Asn Pro Gly Asn Gly His Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Thr Thr Ala Arg Gly Phe Ala Tyr Trp Gly Gln Gly
            100                 105                 110

Thr Leu Val Thr Val Ser
        115


<210> SEQ ID NO 49
<211> LENGTH: 107
<212> TYPE: PRT
<213> ORGANISM: Artificial Sequence
<220> FEATURE:
<223> OTHER INFORMATION: variable light chain for 4B4-1-1 version 1

<400> SEQUENCE: 49

Asp Ile Val Met Thr Gln Ser Pro Ala Thr Gln Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asp Gly His Ser Phe Pro Pro
                85                  90                  95

Thr Phe Gly Gly Gly Thr Lys Leu Glu Ile Lys
```

100 105

<210> SEQ ID NO 50
<211> LENGTH: 119
<212> TYPE: PRT
<213> ORGANISM: Artificial Sequence
<220> FEATURE:
<223> OTHER INFORMATION: variable heavy chain for 4B4-1-1 version 2

<400> SEQUENCE: 50

Gln Val Gln Leu Gln Gln Pro Gly Ala Glu Leu Val Lys Pro Gly Ala
1 5 10 15

Ser Val Lys Leu Ser Cys Lys Ala Ser Gly Tyr Thr Phe Ser Ser Tyr
20 25 30

Trp Met His Trp Val Lys Gln Arg Pro Gly Gln Val Leu Glu Trp Ile
35 40 45

Gly Glu Ile Asn Pro Gly Asn Gly His Thr Asn Tyr Asn Glu Lys Phe
50 55 60

Lys Ser Lys Ala Thr Leu Thr Val Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Ser Phe Thr Thr Ala Arg Gly Phe Ala Tyr Trp Gly Gln Gly
100 105 110

Thr Leu Val Thr Val Ser Ala
115

<210> SEQ ID NO 51
<211> LENGTH: 108
<212> TYPE: PRT
<213> ORGANISM: Artificial Sequence
<220> FEATURE:
<223> OTHER INFORMATION: variable light chain for 4B4-1-1 version 2

<400> SEQUENCE: 51

Asp Ile Val Met Thr Gln Ser Pro Ala Thr Gln Ser Val Thr Pro Gly
1 5 10 15

Asp Arg Val Ser Leu Ser Cys Arg Ala Ser Gln Thr Ile Ser Asp Tyr
20 25 30

Leu His Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Gly Ser Asp Phe Thr Leu Ser Ile Asn Ser Val Glu Pro
65 70 75 80

Glu Asp Val Gly Val Tyr Tyr Cys Gln Asp Gly His Ser Phe Pro Pro
85 90 95

Thr Phe Gly Gly Gly Thr Lys Leu Glu Ile Lys Arg
100 105

<210> SEQ ID NO 52
<211> LENGTH: 120
<212> TYPE: PRT
<213> ORGANISM: Artificial Sequence
<220> FEATURE:
<223> OTHER INFORMATION: variable heavy chain for H39E3-2

<400> SEQUENCE: 52

Met Asp Trp Thr Trp Arg Ile Leu Phe Leu Val Ala Ala Ala Thr Gly
1 5 10 15

Ala His Ser Glu Val Gln Leu Val Glu Ser Gly Gly Gly Leu Val Gln
20 25 30

Pro Gly Gly Ser Leu Arg Leu Ser Cys Ala Ala Ser Gly Phe Thr Phe
35 40 45

Ser Asp Tyr Trp Met Ser Trp Val Arg Gln Ala Pro Gly Lys Gly Leu
50 55 60

Glu Trp Val Ala Asp Ile Lys Asn Asp Gly Ser Tyr Thr Asn Tyr Ala
65 70 75 80

Pro Ser Leu Thr Asn Arg Phe Thr Ile Ser Arg Asp Asn Ala Lys Asn
85 90 95

Ser Leu Tyr Leu Gln Met Asn Ser Leu Arg Ala Glu Asp Thr Ala Val
100 105 110

Tyr Tyr Cys Ala Arg Glu Leu Thr
115 120

<210> SEQ ID NO 53
<211> LENGTH: 109
<212> TYPE: PRT
<213> ORGANISM: Artificial Sequence
<220> FEATURE:
<223> OTHER INFORMATION: variable light chain for H39E3-2

<400> SEQUENCE: 53

Met Glu Ala Pro Ala Gln Leu Leu Phe Leu Leu Leu Leu Trp Leu Pro
1 5 10 15

Asp Thr Thr Gly Asp Ile Val Met Thr Gln Ser Pro Asp Ser Leu Ala
20 25 30

Val Ser Leu Gly Glu Arg Ala Thr Ile Asn Cys Lys Ser Ser Gln Ser
35 40 45

Leu Leu Ser Ser Gly Asn Gln Lys Asn Tyr Leu Trp Tyr Gln Gln Lys
50 55 60

Pro Gly Gln Pro Pro Lys Leu Leu Ile Tyr Tyr Ala Ser Thr Arg Gln
65 70 75 80

Ser Gly Val Pro Asp Arg Phe Ser Gly Ser Gly Ser Gly Thr Asp Phe
85 90 95

Thr Leu Thr Ile Ser Ser Leu Gln Ala Glu Asp Val Ala
100 105

<210> SEQ ID NO 54
<211> LENGTH: 277
<212> TYPE: PRT
<213> ORGANISM: Artificial Sequence
<220> FEATURE:
<223> OTHER INFORMATION: human OX40 (Homo sapiens)

<400> SEQUENCE: 54

Met Cys Val Gly Ala Arg Arg Leu Gly Arg Gly Pro Cys Ala Ala Leu
1 5 10 15

Leu Leu Leu Gly Leu Gly Leu Ser Thr Val Thr Gly Leu His Cys Val
20 25 30

Gly Asp Thr Tyr Pro Ser Asn Asp Arg Cys Cys His Glu Cys Arg Pro
35 40 45

Gly Asn Gly Met Val Ser Arg Cys Ser Arg Ser Gln Asn Thr Val Cys
50 55 60

Arg Pro Cys Gly Pro Gly Phe Tyr Asn Asp Val Val Ser Ser Lys Pro
65 70 75 80

Cys Lys Pro Cys Thr Trp Cys Asn Leu Arg Ser Gly Ser Glu Arg Lys

```
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275
```

<210> SEQ ID NO 55
<211> LENGTH: 272
<212> TYPE: PRT
<213> ORGANISM: Artificial Sequence
<220> FEATURE:
<223> OTHER INFORMATION: murine OX40 (Mus musculus)

<400> SEQUENCE: 55

```
Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
```

```
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270
```

<210> SEQ ID NO 56
<211> LENGTH: 451
<212> TYPE: PRT
<213> ORGANISM: Artificial Sequence
<220> FEATURE:
<223> OTHER INFORMATION: heavy chain for tavolixizumab

<400> SEQUENCE: 56

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

```
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 57
<211> LENGTH: 214
<212> TYPE: PRT
<213> ORGANISM: Artificial Sequence
<220> FEATURE:
<223> OTHER INFORMATION: light chain for tavolixizumab

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 58
<211> LENGTH: 118
<212> TYPE: PRT
<213> ORGANISM: Artificial Sequence
<220> FEATURE:
<223> OTHER INFORMATION: heavy chain variable region for tavolixizumab

<400> SEQUENCE: 58

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95

Arg Tyr Lys Tyr Asp Tyr Asp Gly Gly His Ala Met Asp Tyr Trp Gly
            100                 105                 110

Gln Gly Thr Leu Val Thr
        115


<210> SEQ ID NO 59
<211> LENGTH: 108
<212> TYPE: PRT
<213> ORGANISM: Artificial Sequence
<220> FEATURE:
<223> OTHER INFORMATION: light chain variable region for tavolixizumab

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg
            100                 105


<210> SEQ ID NO 60
<211> LENGTH: 9
```

<212> TYPE: PRT
<213> ORGANISM: Artificial Sequence
<220> FEATURE:
<223> OTHER INFORMATION: heavy chain CDR1 for tavolixizumab

<400> SEQUENCE: 60

Gly Ser Phe Ser Ser Gly Tyr Trp Asn
1               5

<210> SEQ ID NO 61
<211> LENGTH: 13
<212> TYPE: PRT
<213> ORGANISM: Artificial Sequence
<220> FEATURE:
<223> OTHER INFORMATION: heavy chain CDR2 for tavolixizumab

<400> SEQUENCE: 61

Tyr Ile Gly Tyr Ile Ser Tyr Asn Gly Ile Thr Tyr His
1               5                   10

<210> SEQ ID NO 62
<211> LENGTH: 14
<212> TYPE: PRT
<213> ORGANISM: Artificial Sequence
<220> FEATURE:
<223> OTHER INFORMATION: heavy chain CDR3 for tavolixizumab

<400> SEQUENCE: 62

Arg Tyr Lys Tyr Asp Tyr Asp Gly Gly His Ala Met Asp Tyr
1               5                   10

<210> SEQ ID NO 63
<211> LENGTH: 8
<212> TYPE: PRT
<213> ORGANISM: Artificial Sequence
<220> FEATURE:
<223> OTHER INFORMATION: light chain CDR1 for tavolixizumab

<400> SEQUENCE: 63

Gln Asp Ile Ser Asn Tyr Leu Asn
1               5

<210> SEQ ID NO 64
<211> LENGTH: 11
<212> TYPE: PRT
<213> ORGANISM: Artificial Sequence
<220> FEATURE:
<223> OTHER INFORMATION: light chain CDR2 for tavolixizumab

<400> SEQUENCE: 64

Leu Leu Ile Tyr Tyr Thr Ser Lys Leu His Ser
1               5                   10

<210> SEQ ID NO 65
<211> LENGTH: 8
<212> TYPE: PRT
<213> ORGANISM: Artificial Sequence
<220> FEATURE:
<223> OTHER INFORMATION: light chain CDR3 for tavolixizumab

<400> SEQUENCE: 65

Gln Gln Gly Ser Ala Leu Pro Trp
1               5

<210> SEQ ID NO 66
<211> LENGTH: 444
<212> TYPE: PRT

<213> ORGANISM: Artificial Sequence
<220> FEATURE:
<223> OTHER INFORMATION: heavy chain for 11D4

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
```

```
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440


<210> SEQ ID NO 67
<211> LENGTH: 214
<212> TYPE: PRT
<213> ORGANISM: Artificial Sequence
<220> FEATURE:
<223> OTHER INFORMATION: light chain for 11D4

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 68
<211> LENGTH: 118
<212> TYPE: PRT
<213> ORGANISM: Artificial Sequence
<220> FEATURE:
<223> OTHER INFORMATION: heavy chain variable region for 11D4

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ser Met Asn Trp Val Arg Gln Ala Pro Gly Lys Gly Leu Glu Trp Val
35 40 45

Ser Tyr Ile Ser Ser Ser Ser Ser Thr Ile Asp Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Ala Arg Glu Ser Gly Trp Tyr Leu Phe Asp Tyr Trp Gly Gln Gly Thr
100 105 110

Leu Val Thr Val Ser Ser
115

<210> SEQ ID NO 69
<211> LENGTH: 107
<212> TYPE: PRT
<213> ORGANISM: Artificial Sequence
<220> FEATURE:
<223> OTHER INFORMATION: light chain variable region for 11D4

<400> SEQUENCE: 69

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Glu Lys Ala Pro Lys Ser Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Pro
85 90 95

Thr Phe Gly Gly Gly Thr Lys Val Glu Ile Lys
100 105

<210> SEQ ID NO 70
<211> LENGTH: 5
<212> TYPE: PRT
<213> ORGANISM: Artificial Sequence
<220> FEATURE:
<223> OTHER INFORMATION: heavy chain CDR1 for 11D4

<400> SEQUENCE: 70

Ser Tyr Ser Met Asn
1 5

<210> SEQ ID NO 71
<211> LENGTH: 17
<212> TYPE: PRT
<213> ORGANISM: Artificial Sequence
<220> FEATURE:
<223> OTHER INFORMATION: heavy chain CDR2 for 11D4

<400> SEQUENCE: 71

Tyr Ile Ser Ser Ser Ser Ser Thr Ile Asp Tyr Ala Asp Ser Val Lys
1 5 10 15

Gly

<210> SEQ ID NO 72

<211> LENGTH: 9
<212> TYPE: PRT
<213> ORGANISM: Artificial Sequence
<220> FEATURE:
<223> OTHER INFORMATION: heavy chain CDR3 for 11D4

<400> SEQUENCE: 72

Glu Ser Gly Trp Tyr Leu Phe Asp Tyr
1               5

<210> SEQ ID NO 73
<211> LENGTH: 11
<212> TYPE: PRT
<213> ORGANISM: Artificial Sequence
<220> FEATURE:
<223> OTHER INFORMATION: light chain CDR1 for 11D4

<400> SEQUENCE: 73

Arg Ala Ser Gln Gly Ile Ser Ser Trp Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: light chain CDR2 for 11D4

<400> SEQUENCE: 74

Ala Ala Ser Ser Leu Gln Ser
1               5

<210> SEQ ID NO 75
<211> LENGTH: 9
<212> TYPE: PRT
<213> ORGANISM: Artificial Sequence
<220> FEATURE:
<223> OTHER INFORMATION: light chain CDR3 for 11D4

<400> SEQUENCE: 75

Gln Gln Tyr Asn Ser Tyr Pro Pro Thr
1               5

<210> SEQ ID NO 76
<211> LENGTH: 450
<212> TYPE: PRT
<213> ORGANISM: Artificial Sequence
<220> FEATURE:
<223> OTHER INFORMATION: heavy chain for 18D8

<400> SEQUENCE: 76

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp

```
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ala Pro Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 77
<211> LENGTH: 213
<212> TYPE: PRT
<213> ORGANISM: Artificial Sequence
<220> FEATURE:
<223> OTHER INFORMATION: light chain for 18D8

<400> SEQUENCE: 77

Glu Ile Val Val Thr Gln Ser Pro Ala Thr Leu Ser Leu Ser Pro Gly
```

```
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 78
<211> LENGTH: 124
<212> TYPE: PRT
<213> ORGANISM: Artificial Sequence
<220> FEATURE:
<223> OTHER INFORMATION: heavy chain variable region for 18D8

<400> SEQUENCE: 78

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120


<210> SEQ ID NO 79
<211> LENGTH: 106
<212> TYPE: PRT
```

<213> ORGANISM: Artificial Sequence
<220> FEATURE:
<223> OTHER INFORMATION: light chain variable region for 18D8

<400> SEQUENCE: 79

Glu Ile Val Val Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Thr
85 90 95

Phe Gly Gln Gly Thr Lys Val Glu Ile Lys
100 105

<210> SEQ ID NO 80
<211> LENGTH: 5
<212> TYPE: PRT
<213> ORGANISM: Artificial Sequence
<220> FEATURE:
<223> OTHER INFORMATION: heavy chain CDR1 for 18D8

<400> SEQUENCE: 80

Asp Tyr Ala Met His
1 5

<210> SEQ ID NO 81
<211> LENGTH: 17
<212> TYPE: PRT
<213> ORGANISM: Artificial Sequence
<220> FEATURE:
<223> OTHER INFORMATION: heavy chain CDR2 for 18D8

<400> SEQUENCE: 81

Gly Ile Ser Trp Asn Ser Gly Ser Ile Gly Tyr Ala Asp Ser Val Lys
1 5 10 15

Gly

<210> SEQ ID NO 82
<211> LENGTH: 15
<212> TYPE: PRT
<213> ORGANISM: Artificial Sequence
<220> FEATURE:
<223> OTHER INFORMATION: heavy chain CDR3 for 18D8

<400> SEQUENCE: 82

Asp Gln Ser Thr Ala Asp Tyr Tyr Phe Tyr Tyr Gly Met Asp Val
1 5 10 15

<210> SEQ ID NO 83
<211> LENGTH: 11
<212> TYPE: PRT
<213> ORGANISM: Artificial Sequence
<220> FEATURE:
<223> OTHER INFORMATION: light chain CDR1 for 18D8

<400> SEQUENCE: 83

Arg Ala Ser Gln Ser Val Ser Ser Tyr Leu Ala 1 5 10

<210> SEQ ID NO 84
<211> LENGTH: 7
<212> TYPE: PRT
<213> ORGANISM: Artificial Sequence
<220> FEATURE:
<223> OTHER INFORMATION: light chain CDR2 for 18D8

<400> SEQUENCE: 84

Asp Ala Ser Asn Arg Ala Thr
1 5

<210> SEQ ID NO 85
<211> LENGTH: 8
<212> TYPE: PRT
<213> ORGANISM: Artificial Sequence
<220> FEATURE:
<223> OTHER INFORMATION: light chain CDR3 for 18D8

<400> SEQUENCE: 85

Gln Gln Arg Ser Asn Trp Pro Thr
1 5

<210> SEQ ID NO 86
<211> LENGTH: 120
<212> TYPE: PRT
<213> ORGANISM: Artificial Sequence
<220> FEATURE:
<223> OTHER INFORMATION: heavy chain variable region for Hu119-122

<400> SEQUENCE: 86

Glu Val Gln Leu Val Glu Ser Gly Gly Gly Leu Val Gln Pro Gly Gly
1 5 10 15

Ser Leu Arg Leu Ser Cys Ala Ala Ser Glu Tyr Glu Phe Pro Ser His
20 25 30

Asp Met Ser Trp Val Arg Gln Ala Pro Gly Lys Gly Leu Glu Leu Val
35 40 45

Ala Ala Ile Asn Ser Asp Gly Gly Ser Thr Tyr Tyr Pro Asp Thr Met
50 55 60

Glu Arg Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Tyr Asp Asp Tyr Tyr Ala Trp Phe Ala Tyr Trp Gly Gln
100 105 110

Gly Thr Met Val Thr Val Ser Ser
115 120

<210> SEQ ID NO 87
<211> LENGTH: 111
<212> TYPE: PRT
<213> ORGANISM: Artificial Sequence
<220> FEATURE:
<223> OTHER INFORMATION: light chain variable region for Hu119-122

<400> SEQUENCE: 87

Glu Ile Val Leu Thr Gln Ser Pro Ala Thr Leu Ser Leu Ser Pro Gly
1 5 10 15

Glu Arg Ala Thr Leu Ser Cys Arg Ala Ser Lys Ser Val Ser Thr Ser
20 25 30

Gly Tyr Ser Tyr Met His Trp Tyr Gln Gln Lys Pro Gly Gln Ala Pro

```
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110


<210> SEQ ID NO 88
<211> LENGTH: 5
<212> TYPE: PRT
<213> ORGANISM: Artificial Sequence
<220> FEATURE:
<223> OTHER INFORMATION: heavy chain CDR1 for Hu119-122

<400> SEQUENCE: 88

Ser His Asp Met Ser
1               5


<210> SEQ ID NO 89
<211> LENGTH: 17
<212> TYPE: PRT
<213> ORGANISM: Artificial Sequence
<220> FEATURE:
<223> OTHER INFORMATION: heavy chain CDR2 for Hu119-122

<400> SEQUENCE: 89

Ala Ile Asn Ser Asp Gly Gly Ser Thr Tyr Tyr Pro Asp Thr Met Glu
1               5                   10                  15

Arg


<210> SEQ ID NO 90
<211> LENGTH: 11
<212> TYPE: PRT
<213> ORGANISM: Artificial Sequence
<220> FEATURE:
<223> OTHER INFORMATION: heavy chain CDR3 for Hu119-122

<400> SEQUENCE: 90

His Tyr Asp Asp Tyr Tyr Ala Trp Phe Ala Tyr
1               5                   10


<210> SEQ ID NO 91
<211> LENGTH: 15
<212> TYPE: PRT
<213> ORGANISM: Artificial Sequence
<220> FEATURE:
<223> OTHER INFORMATION: light chain CDR1 for Hu119-122

<400> SEQUENCE: 91

Arg Ala Ser Lys Ser Val Ser Thr Ser Gly Tyr Ser Tyr Met His
1               5                   10                  15


<210> SEQ ID NO 92
<211> LENGTH: 7
<212> TYPE: PRT
<213> ORGANISM: Artificial Sequence
<220> FEATURE:
<223> OTHER INFORMATION: light chain CDR2 for Hu119-122

<400> SEQUENCE: 92

Leu Ala Ser Asn Leu Glu Ser
```

1 5

<210> SEQ ID NO 93
<211> LENGTH: 9
<212> TYPE: PRT
<213> ORGANISM: Artificial Sequence
<220> FEATURE:
<223> OTHER INFORMATION: light chain CDR3 for Hu119-122

<400> SEQUENCE: 93

Gln His Ser Arg Glu Leu Pro Leu Thr
1 5

<210> SEQ ID NO 94
<211> LENGTH: 122
<212> TYPE: PRT
<213> ORGANISM: Artificial Sequence
<220> FEATURE:
<223> OTHER INFORMATION: heavy chain variable region for Hu106-222

<400> SEQUENCE: 94

Gln Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr Asp Tyr
20 25 30

Ser Met His Trp Val Arg Gln Ala Pro Gly Gln Gly Leu Lys Trp Met
35 40 45

Gly Trp Ile Asn Thr Glu Thr Gly Glu Pro Thr Tyr Ala Asp Asp Phe
50 55 60

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Asn Pro Tyr Tyr Asp Tyr Val Ser Tyr Tyr Ala Met Asp Tyr Trp
100 105 110

Gly Gln Gly Thr Thr Val Thr Val Ser Ser
115 120

<210> SEQ ID NO 95
<211> LENGTH: 107
<212> TYPE: PRT
<213> ORGANISM: Artificial Sequence
<220> FEATURE:
<223> OTHER INFORMATION: light chain variable region for Hu106-222

<400> SEQUENCE: 95

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Thr Ala
20 25 30

Val Ala Trp Tyr Gln Gln Lys Pro Gly Lys Ala Pro Lys Leu Leu Ile
35 40 45

Tyr Ser Ala Ser Tyr Leu Tyr Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln His Tyr Ser Thr Pro Arg
85 90 95

Thr Phe Gly Gln Gly Thr Lys Leu Glu Ile Lys
100 105

<210> SEQ ID NO 96
<211> LENGTH: 5
<212> TYPE: PRT
<213> ORGANISM: Artificial Sequence
<220> FEATURE:
<223> OTHER INFORMATION: heavy chain CDR1 for Hu106-222

<400> SEQUENCE: 96

Asp Tyr Ser Met His
1               5

<210> SEQ ID NO 97
<211> LENGTH: 17
<212> TYPE: PRT
<213> ORGANISM: Artificial Sequence
<220> FEATURE:
<223> OTHER INFORMATION: heavy chain CDR2 for Hu106-222

<400> SEQUENCE: 97

Trp Ile Asn Thr Glu Thr Gly Glu Pro Thr Tyr Ala Asp Asp Phe Lys
1               5                   10                  15

Gly

<210> SEQ ID NO 98
<211> LENGTH: 13
<212> TYPE: PRT
<213> ORGANISM: Artificial Sequence
<220> FEATURE:
<223> OTHER INFORMATION: heavy chain CDR3 for Hu106-222

<400> SEQUENCE: 98

Pro Tyr Tyr Asp Tyr Val Ser Tyr Tyr Ala Met Asp Tyr
1               5                   10

<210> SEQ ID NO 99
<211> LENGTH: 11
<212> TYPE: PRT
<213> ORGANISM: Artificial Sequence
<220> FEATURE:
<223> OTHER INFORMATION: light chain CDR1 for Hu106-222

<400> SEQUENCE: 99

Lys Ala Ser Gln Asp Val Ser Thr Ala Val Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: light chain CDR2 for Hu106-222

<400> SEQUENCE: 100

Ser Ala Ser Tyr Leu Tyr Thr
1               5

<210> SEQ ID NO 101
<211> LENGTH: 9
<212> TYPE: PRT
<213> ORGANISM: Artificial Sequence
<220> FEATURE:
<223> OTHER INFORMATION: light chain CDR3 for Hu106-222

<400> SEQUENCE: 101

Gln Gln His Tyr Ser Thr Pro Arg Thr 1 5

<210> SEQ ID NO 102
<211> LENGTH: 183
<212> TYPE: PRT
<213> ORGANISM: Artificial Sequence
<220> FEATURE:
<223> OTHER INFORMATION: OX40L

<400> SEQUENCE: 102

Met Glu Arg Val Gln Pro Leu Glu Glu Asn Val Gly Asn Ala Ala Arg
1 5 10 15

Pro Arg Phe Glu Arg Asn Lys Leu Leu Leu Val Ala Ser Val Ile Gln
20 25 30

Gly Leu Gly Leu Leu Leu Cys Phe Thr Tyr Ile Cys Leu His Phe Ser
35 40 45

Ala Leu Gln Val Ser His Arg Tyr Pro Arg Ile Gln Ser Ile Lys Val
50 55 60

Gln Phe Thr Glu Tyr Lys Lys Glu Lys Gly Phe Ile Leu Thr Ser Gln
65 70 75 80

Lys Glu Asp Glu Ile Met Lys Val Gln Asn Asn Ser Val Ile Ile Asn
85 90 95

Cys Asp Gly Phe Tyr Leu Ile Ser Leu Lys Gly Tyr Phe Ser Gln Glu
100 105 110

Val Asn Ile Ser Leu His Tyr Gln Lys Asp Glu Glu Pro Leu Phe Gln
115 120 125

Leu Lys Lys Val Arg Ser Val Asn Ser Leu Met Val Ala Ser Leu Thr
130 135 140

Tyr Lys Asp Lys Val Tyr Leu Asn Val Thr Thr Asp Asn Thr Ser Leu
145 150 155 160

Asp Asp Phe His Val Asn Gly Gly Glu Leu Ile Leu Ile His Gln Asn
165 170 175

Pro Gly Glu Phe Cys Val Leu
180

<210> SEQ ID NO 103
<211> LENGTH: 131
<212> TYPE: PRT
<213> ORGANISM: Artificial Sequence
<220> FEATURE:
<223> OTHER INFORMATION: OX40L soluble domain

<400> SEQUENCE: 103

Ser His Arg Tyr Pro Arg Ile Gln Ser Ile Lys Val Gln Phe Thr Glu
1 5 10 15

Tyr Lys Lys Glu Lys Gly Phe Ile Leu Thr Ser Gln Lys Glu Asp Glu
20 25 30

Ile Met Lys Val Gln Asn Asn Ser Val Ile Ile Asn Cys Asp Gly Phe
35 40 45

Tyr Leu Ile Ser Leu Lys Gly Tyr Phe Ser Gln Glu Val Asn Ile Ser
50 55 60

Leu His Tyr Gln Lys Asp Glu Glu Pro Leu Phe Gln Leu Lys Lys Val
65 70 75 80

Arg Ser Val Asn Ser Leu Met Val Ala Ser Leu Thr Tyr Lys Asp Lys
85 90 95

Val Tyr Leu Asn Val Thr Thr Asp Asn Thr Ser Leu Asp Asp Phe His
100 105 110

```
Val Asn Gly Gly Glu Leu Ile Leu Ile His Gln Asn Pro Gly Glu Phe
        115                 120                 125

Cys Val Leu
    130


<210> SEQ ID NO 104
<211> LENGTH: 128
<212> TYPE: PRT
<213> ORGANISM: Artificial Sequence
<220> FEATURE:
<223> OTHER INFORMATION: OX40L soluble domain (alternative)

<400> SEQUENCE: 104

Tyr Pro Arg Ile Gln Ser Ile Lys Val Gln Phe Thr Glu Tyr Lys Lys
1               5                   10                  15

Glu Lys Gly Phe Ile Leu Thr Ser Gln Lys Glu Asp Glu Ile Met Lys
            20                  25                  30

Val Gln Asn Asn Ser Val Ile Ile Asn Cys Asp Gly Phe Tyr Leu Ile
        35                  40                  45

Ser Leu Lys Gly Tyr Phe Ser Gln Glu Val Asn Ile Ser Leu His Tyr
    50                  55                  60

Gln Lys Asp Glu Glu Pro Leu Phe Gln Leu Lys Lys Val Arg Ser Val
65                  70                  75                  80

Asn Ser Leu Met Val Ala Ser Leu Thr Tyr Lys Asp Lys Val Tyr Leu
                85                  90                  95

Asn Val Thr Thr Asp Asn Thr Ser Leu Asp Asp Phe His Val Asn Gly
            100                 105                 110

Gly Glu Leu Ile Leu Ile His Gln Asn Pro Gly Glu Phe Cys Val Leu
        115                 120                 125


<210> SEQ ID NO 105
<211> LENGTH: 120
<212> TYPE: PRT
<213> ORGANISM: Artificial Sequence
<220> FEATURE:
<223> OTHER INFORMATION: variable heavy chain for 008

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser
        115                 120


<210> SEQ ID NO 106
<211> LENGTH: 108
<212> TYPE: PRT
<213> ORGANISM: Artificial Sequence
```

<220> FEATURE:
<223> OTHER INFORMATION: variable light chain for 008

<400> SEQUENCE: 106

Asp Ile Val Met Thr Gln Ser Pro Asp Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Ala Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gln Gln Tyr
85 90 95

Tyr Asn His Pro Thr Thr Phe Gly Gln Gly Thr Lys
100 105

<210> SEQ ID NO 107
<211> LENGTH: 120
<212> TYPE: PRT
<213> ORGANISM: Artificial Sequence
<220> FEATURE:
<223> OTHER INFORMATION: variable heavy chain for 011

<400> SEQUENCE: 107

Glu Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asp Tyr
20 25 30

Thr Met Asn Trp Val Arg Gln Ala Pro Gly Lys Gly Leu Glu Trp Val
35 40 45

Ser Ser Ile Ser Gly Gly Ser Thr Tyr Tyr Ala Asp Ser Arg Lys Gly
50 55 60

Arg Phe Thr Ile Ser Arg Asp Asn Ser Lys Asn Thr Leu Tyr Leu Gln
65 70 75 80

Met Asn Asn Leu Arg Ala Glu Asp Thr Ala Val Tyr Tyr Cys Ala Arg
85 90 95

Asp Arg Tyr Phe Arg Gln Gln Asn Ala Phe Asp Tyr Trp Gly Gln Gly
100 105 110

Thr Leu Val Thr Val Ser Ser Ala
115 120

<210> SEQ ID NO 108
<211> LENGTH: 108
<212> TYPE: PRT
<213> ORGANISM: Artificial Sequence
<220> FEATURE:
<223> OTHER INFORMATION: variable light chain for 011

<400> SEQUENCE: 108

Asp Ile Val Met Thr Gln Ser Pro Asp Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Ala Gly Gln Ser
35 40 45

```
Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys
            100                 105


<210> SEQ ID NO 109
<211> LENGTH: 120
<212> TYPE: PRT
<213> ORGANISM: Artificial Sequence
<220> FEATURE:
<223> OTHER INFORMATION: variable heavy chain for 021

<400> SEQUENCE: 109

Glu Val Gln Leu Val Glu Ser Gly Gly Gly Leu Val Gln Pro Arg Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ile Thr Leu Pro Asn Ala Leu Asp Tyr Trp Gly
            100                 105                 110

Gln Gly Thr Leu Val Thr Val Ser
        115                 120


<210> SEQ ID NO 110
<211> LENGTH: 108
<212> TYPE: PRT
<213> ORGANISM: Artificial Sequence
<220> FEATURE:
<223> OTHER INFORMATION: variable light chain for 021

<400> SEQUENCE: 110

Asp Ile Gln Met Thr Gln Ser Pro Val Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Lys Ser Asn Pro Pro Thr Phe Gly Gln Gly Thr Lys
            100                 105


<210> SEQ ID NO 111
```

```
<211> LENGTH: 120
<212> TYPE: PRT
<213> ORGANISM: Artificial Sequence
<220> FEATURE:
<223> OTHER INFORMATION: variable heavy chain for 023

<400> SEQUENCE: 111

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
            100                 105                 110

Gly Thr Leu Val Thr Val Ser Ser
        115                 120


<210> SEQ ID NO 112
<211> LENGTH: 108
<212> TYPE: PRT
<213> ORGANISM: Artificial Sequence
<220> FEATURE:
<223> OTHER INFORMATION: variable light chain for 023

<400> SEQUENCE: 112

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg
            100                 105


<210> SEQ ID NO 113
<211> LENGTH: 119
<212> TYPE: PRT
<213> ORGANISM: Artificial Sequence
<220> FEATURE:
<223> OTHER INFORMATION: heavy chain variable region

<400> SEQUENCE: 113

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

```
Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
        115


<210> SEQ ID NO 114
<211> LENGTH: 108
<212> TYPE: PRT
<213> ORGANISM: Artificial Sequence
<220> FEATURE:
<223> OTHER INFORMATION: light chain variable region

<400> SEQUENCE: 114

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105


<210> SEQ ID NO 115
<211> LENGTH: 121
<212> TYPE: PRT
<213> ORGANISM: Artificial Sequence
<220> FEATURE:
<223> OTHER INFORMATION: heavy chain variable region

<400> SEQUENCE: 115

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110
```

```
Ala Gly Thr Thr Val Thr Val Ser Pro
        115                 120


<210> SEQ ID NO 116
<211> LENGTH: 108
<212> TYPE: PRT
<213> ORGANISM: Artificial Sequence
<220> FEATURE:
<223> OTHER INFORMATION: light chain variable region

<400> SEQUENCE: 116

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105


<210> SEQ ID NO 117
<211> LENGTH: 122
<212> TYPE: PRT
<213> ORGANISM: Artificial Sequence
<220> FEATURE:
<223> OTHER INFORMATION: heavy chain variable region of humanized
      antibody

<400> SEQUENCE: 117

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120


<210> SEQ ID NO 118
<211> LENGTH: 122
<212> TYPE: PRT
<213> ORGANISM: Artificial Sequence
<220> FEATURE:
<223> OTHER INFORMATION: heavy chain variable region of humanized
      antibody
```

<400> SEQUENCE: 118

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120

<210> SEQ ID NO 119
<211> LENGTH: 107
<212> TYPE: PRT
<213> ORGANISM: Artificial Sequence
<220> FEATURE:
<223> OTHER INFORMATION: light chain variable region of humanized antibody

<400> SEQUENCE: 119

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 120
<211> LENGTH: 107
<212> TYPE: PRT
<213> ORGANISM: Artificial Sequence
<220> FEATURE:
<223> OTHER INFORMATION: light chain variable region of humanized antibody

<400> SEQUENCE: 120

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Leu Tyr Thr Gly Val Pro Asp Arg Phe Thr Gly

```
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105


<210> SEQ ID NO 121
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 121

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Asp Asp Tyr Tyr Ala Trp Phe Ala Tyr Trp Gly Gln
            100                 105                 110

Gly Thr Leu Val Thr Val Ser Ala
        115                 120


<210> SEQ ID NO 122
<211> LENGTH: 120
<212> TYPE: PRT
<213> ORGANISM: Artificial Sequence
<220> FEATURE:
<223> OTHER INFORMATION: heavy chain variable region of humanized
      antibody

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
```

115 120

<210> SEQ ID NO 123
<211> LENGTH: 111
<212> TYPE: PRT
<213> ORGANISM: Artificial Sequence
<220> FEATURE:
<223> OTHER INFORMATION: light chain variable region of humanized antibody

<400> SEQUENCE: 123

Asp Ile Val Leu Thr Gln Ser Pro Ala Ser Leu Ala Val Ser Leu Gly
1 5 10 15

Gln Arg Ala Thr Ile Ser Cys Arg Ala Ser Lys Ser Val Ser Thr Ser
20 25 30

Gly Tyr Ser Tyr Met His Trp Tyr Gln Gln Lys Pro Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Gly Thr Asp Phe Thr Leu Asn Ile His
65 70 75 80

Pro Val Glu Glu Glu Asp Ala Ala Thr Tyr Tyr Cys Gln His Ser Arg
85 90 95

Glu Leu Pro Leu Thr Phe Gly Ala Gly Thr Lys Leu Glu Leu Lys
100 105 110

<210> SEQ ID NO 124
<211> LENGTH: 111
<212> TYPE: PRT
<213> ORGANISM: Artificial Sequence
<220> FEATURE:
<223> OTHER INFORMATION: light chain variable region of humanized antibody

<400> SEQUENCE: 124

Glu Ile Val Leu Thr Gln Ser Pro Ala Thr Leu Ser Leu Ser Pro Gly
1 5 10 15

Glu Arg Ala Thr Leu Ser Cys Arg Ala Ser Lys Ser Val Ser Thr Ser
20 25 30

Gly Tyr Ser Tyr Met His Trp Tyr Gln Gln Lys Pro Gly Gln Ala Pro
35 40 45

Arg Leu Leu Ile Tyr Leu Ala Ser Asn Leu Glu Ser Gly Val Pro Ala
50 55 60

Arg Phe Ser Gly Ser Gly Ser Gly Thr Asp Phe Thr Leu Thr Ile Ser
65 70 75 80

Ser Leu Glu Pro Glu Asp Phe Ala Val Tyr Tyr Cys Gln His Ser Arg
85 90 95

Glu Leu Pro Leu Thr Phe Gly Gly Gly Thr Lys Val Glu Ile Lys
100 105 110

<210> SEQ ID NO 125
<211> LENGTH: 138
<212> TYPE: PRT
<213> ORGANISM: Artificial Sequence
<220> FEATURE:
<223> OTHER INFORMATION: heavy chain variable region

<400> SEQUENCE: 125

Met Tyr Leu Gly Leu Asn Tyr Val Phe Ile Val Phe Leu Leu Asn Gly
1 5 10 15

```
Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser
    130                 135


<210> SEQ ID NO 126
<211> LENGTH: 126
<212> TYPE: PRT
<213> ORGANISM: Artificial Sequence
<220> FEATURE:
<223> OTHER INFORMATION: light chain variable region

<400> SEQUENCE: 126

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
        115                 120                 125
```

PROCESSES FOR PRODUCTION OF TUMOR INFILTRATING LYMPHOCYTES AND USES OF THE SAME IN IMMUNOTHERAPY

CROSS REFERENCE TO RELATED APPLICATIONS

This application claims priority to U.S. Provisional Patent Application No. 62/775,954, filed on Nov. 5, 2018, U.S. and U.S. Provisional Patent Application No. 62/903,585, filed on Sep. 20, 2019, which are hereby incorporated by reference in their entirety.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma. Current infusion acceptance parameters rely on readouts of the composition of TILs (e.g., CD28, CD8, or CD4 positivity) and on fold expansion and viability of the REP product.

Current TIL manufacturing processes are limited by length, cost, sterility concerns, and other factors described herein. There is an urgent need to provide TIL manufacturing processes and therapies based on such processes that are characterized by improved cost-effectiveness and scalability in manufacturing and more potent anti-cancer phenotypes of TIL preparations produced for treatment of human patients at multiple clinical centers. The present invention meets this need by providing a novel TIL expansion process which includes antigen-presenting feeder cells from the initiation of expansion, in order to prime the TILs for expansion, rather than a tradition pre-REP expansion step, thus allowing for a substantial reduction in overall time for the expansion process.

BRIEF SUMMARY OF THE INVENTION

The present invention provides improved and/or shortened methods for expanding TILs and producing therapeutic populations of TILs.

The present invention provides a method for expanding tumor infiltrating lymphocytes (TILs) into a therapeutic population of TILs comprising:

(a) obtaining and/or receiving a first population of TILs from a tumor resected from a subject by processing a tumor sample obtained from the subject into multiple tumor fragments;
(b) performing a priming first expansion by culturing the first population of TILs in a cell culture medium comprising IL-2, optionally OKT-3, and optionally antigen presenting cells (APCs) to produce a second population of TILs, wherein the priming first expansion is performed in a container comprising a first gas-permeable surface area, wherein the priming first expansion is performed for first period of about 1 to 7/8 days to obtain the second population of TILs, wherein the second population of TILs is greater in number than the first population of TILs;
(c) performing a rapid second expansion by supplementing the cell culture medium of the second population of TILs with additional IL-2, OKT-3, and APCs, to produce a third population of TILs, wherein the number of APCs added in the rapid second expansion is at least twice the number of APCs added in step (b), wherein the rapid second expansion is performed for a second period of about 1 to 11 days to obtain the third population of TILs, wherein the third population of TILs is a therapeutic population of TILs, wherein the rapid second expansion is performed in a container comprising a second gas-permeable surface area;
(d) harvesting the therapeutic population of TILs obtained from step (c); and
(e) transferring the harvested TIL population from step (d) to an infusion bag.

The present invention provides a method for expanding tumor infiltrating lymphocytes (TILs) into a therapeutic population of TILs comprising:

(a) obtaining and/or receiving a first population of TILs from a tumor resected from a subject by processing a tumor sample obtained from the subject into multiple tumor fragments;
(b) performing a priming first expansion by culturing the first population of TILs in a cell culture medium comprising IL-2, optionally OKT-3, and optionally comprising antigen presenting cells (APCs), to produce a second population of TILs, wherein the priming first expansion is performed for a first period of about 1 to 7/8 days to obtain the second population of TILs, wherein the second population of TILs is greater in number than the first population of TILs;
(c) performing a rapid second expansion by contacting the second population of TILs with a cell culture medium comprising IL-2, OKT-3, and APCs, to produce a third population of TILs, wherein the rapid second expansion is performed for a second period of about 1 to 11 days to obtain the third population of TILs, wherein the third population of TILs is a therapeutic population of TILs; and
(d) harvesting the therapeutic population of TILs obtained from step (c).

In some embodiments, "obtaining" indicates the TILs employed in the method and/or process can be derived directly from the sample (including from a surgical resection, needle biopsy, core biopsy, small biopsy, or other sample) as part of the method and/or process steps. In some embodiments, 'receiving" indicates the TILs employed in the method and/or process can be derived indirectly from the sample (including from a surgical resection, needle biopsy, core biopsy, small biopsy, or other sample) and then employed in the method and/or process, (for example, where step (a) begins will TILs that have already been derived from the sample by a separate process not included in part (a), such TILs could be referred to as "received").

In some embodiments of the method, in step (b) the cell culture medium further comprises antigen-presenting cells (APCs), and wherein the number of APCs in the culture medium in step (c) is greater than the number of APCs in the culture medium in step (b).

The present invention provides a method for expanding tumor infiltrating lymphocytes (TILs) into a therapeutic population of TILs comprising:

(a) performing a priming first expansion by culturing a first population of TILs, said first population of TILs obtainable by processing a tumor sample from a tumor resected from a subject into multiple tumor fragments, in a cell culture medium comprising IL-2, optionally OKT-3, and optionally antigen presenting cells (APCs) to produce a second population of TILs, wherein the priming first expansion is performed in a container comprising a first gas-permeable surface area, wherein the priming first expansion is performed for first period of about 1 to 7/8 days to obtain the second population of TILs, wherein the second population of TILs is greater in number than the first population of TILs;

(b) performing a rapid second expansion by contacting the second population of TILs to a cell culture medium of the second population of TILs with additional IL-2, OKT-3, and APCs, to produce a third population of TILs, wherein the number of APCs in the rapid second expansion is at least twice the number of APCs in step (a), wherein the rapid second expansion is performed for a second period of about 1 to 11 days to obtain the third population of TILs, wherein the third population of TILs is a therapeutic population of TILs, wherein the rapid second expansion is performed in a container comprising a second gas-permeable surface area; and (c) harvesting the therapeutic population of TILs obtained from step (b).

The present invention also provides a method for expanding tumor infiltrating lymphocytes (TILs) into a therapeutic population of TILs comprising:

(a) performing a priming first expansion by culturing a first population of TILs in a cell culture medium comprising IL-2, optionally OKT-3, and optionally comprising antigen presenting cells (APCs), to produce a second population of TILs, wherein the priming first expansion is performed for a first period of about 1 to 7/8 days to obtain the second population of TILs, wherein the second population of TILs is greater in number than the first population of TILs;

(b) performing a rapid second expansion by contacting the second population of TILs with a cell culture medium comprising IL-2, OKT-3, and APCs, to produce a third population of TILs, wherein the rapid second expansion is performed for a second period of about 1 to 11 days to obtain the third population of TILs, wherein the third population of TILs is a therapeutic population of TILs; and (c) harvesting the therapeutic population of TILs obtained from step (b).

In some embodiments of the method, in step (a) the cell culture medium further comprises antigen-presenting cells (APCs), and wherein the number of APCs in the culture medium in step (c) is greater than the number of APCs in the culture medium in step (b).

In some embodiments, the ratio of the number of APCs in the rapid second expansion to the number of APCs in the priming first expansion is selected from a range of from about 1.5:1 to about 20:1.

In some embodiments, the ratio of the number of APCs in the rapid second expansion to the number of APCs in the priming first expansion is in a range of from about 1.5:1 to about 10:1.

In some embodiments, the ratio of the number of APCs in the rapid second expansion to the number of APCs in the priming first expansion is in a range of from about 2:1 to about 5:1.

In some embodiments, the ratio of the number of APCs in the rapid second expansion to the number of APCs in the priming first expansion is in a range of from about 2:1 to about 3:1.

In some embodiments, the ratio of the number of APCs in the rapid second expansion to the number of APCs in the priming first expansion is about 2:1.

In some embodiments, the number of APCs in the priming first expansion is selected from the range of about $1.0\times10^6$ APCs/cm$^2$ to about $4.5\times10^6$ APCs/cm$^2$, and wherein the number of APCs in the rapid second expansion is selected from the range of about $2.5\times10^6$ APCs/cm$^2$ to about $7.5\times10^6$ APCs/cm$^2$.

In some embodiments, the number of APCs in the priming first expansion is selected from the range of about $1.5\times10^6$ APCs/cm$^2$ to about $3.5\times10^6$ APCs/cm$^2$, and wherein the number of APCs in the rapid second expansion is selected from the range of about $3.5\times10^6$ APCs/cm$^2$ to about $6.0\times10^6$ APCs/cm$^2$.

In some embodiments, the number of APCs in the priming first expansion is selected from the range of about $2.0\times10^6$ APCs/cm$^2$ to about $3.0\times10^6$ APCs/cm$^2$, and wherein the number of APCs in the rapid second expansion is selected from the range of about $4.0\times10^6$ APCs/cm$^2$ to about $5.5\times10^6$ APCs/cm$^2$.

In some embodiments, the number of APCs in the priming first expansion is selected from the range of about $1\times10^8$ APCs to about $3.5\times10^8$ APCs, and wherein the number of APCs in the rapid second expansion is selected from the range of about $3.5\times10^8$ APCs to about $1\times10^9$ APCs.

In some embodiments, the number of APCs in the priming first expansion is selected from the range of about $1.5\times10^8$ APCs to about $3\times10^8$ APCs, and wherein the number of APCs in the rapid second expansion is selected from the range of about $4\times10^8$ APCs to about $7.5\times10^8$ APCs.

In some embodiments, the number of APCs in the priming first expansion is selected from the range of about $2\times10^8$ APCs to about $2.5\times10^8$ APCs, and wherein the number of APCs in the rapid second expansion is selected from the range of about $4.5\times10^8$ APCs to about $5.5\times10^8$ APCs.

In some embodiments, about $2.5\times10^8$ APCs are added to the priming first expansion and $5\times10^8$ APCs are added to the rapid second expansion.

In some embodiments, the ratio of the number of TILs in the second population of TILs to the number of TILs in the first population of TILs is about 1.5:1 to about 100:1.

In some embodiments, the ratio of the number of TILs in the second population of TILs to the number of TILs in the first population of TILs is about 50:1.

In some embodiments, the ratio of the number of TILs in the second population of TILs to the number of TILs in the first population of TILs is about 25:1.

In some embodiments, the ratio of the number of TILs in the second population of TILs to the number of TILs in the first population of TILs is about 20:1.

In some embodiments, the ratio of the number of TILs in the second population of TILs to the number of TILs in the first population of TILs is about 10:1.

In some embodiments, the second population of TILs is at least 50-fold greater in number than the first population of TILs.

In some embodiments, the method comprises performing, after the step of harvesting the therapeutic population of TILs, the additional step of:

transferring the harvested therapeutic population of TILs to an infusion bag.

In some embodiments, the multiple tumor fragments are distributed into a plurality of separate containers, in each of which separate containers the second population of TILs is obtained from the first population of TILs in the step of the priming first expansion, and the third population of TILs is obtained from the second population of TILs in the step of the rapid second expansion, and wherein the therapeutic population of TILs obtained from the third population of TILs is collected from each of the plurality of containers and combined to yield the harvested TIL population.

In some embodiments, the plurality of separate containers comprises at least two separate containers.

In some embodiments, the plurality of separate containers comprises from two to twenty separate containers.

In some embodiments, the plurality of separate containers comprises from two to ten separate containers.

In some embodiments, the plurality of separate containers comprises from two to five separate containers.

In some embodiments, each of the separate containers comprises a first gas-permeable surface area.

In some embodiments, the multiple tumor fragments are distributed in a single container.

In some embodiments, the single container comprises a first gas-permeable surface area.

In some embodiments, the step of the priming first expansion the cell culture medium comprises antigen-presenting cells (APCs) and the APCs are layered onto the first gas-permeable surface area at an average thickness of about one cell layer to about three cell layers.

In some embodiments, the step of the priming first expansion the APCs are layered onto the first gas-permeable surface area at an average thickness of about 1.5 cell layers to about 2.5 cell layers.

In some embodiments, the step of the priming first expansion the APCs are layered onto the first gas-permeable surface area at an average thickness of about 2 cell layers.

In some embodiments, the step of the rapid second expansion the APCs are layered onto the first gas-permeable surface area at a thickness of about 3 cell layers to about 5 cell layers.

In some embodiments, the rapid second expansion the APCs are layered onto the first gas-permeable surface area at a thickness of about 3.5 cell layers to about 4.5 cell layers.

In some embodiments, the rapid second expansion the APCs are layered onto the first gas-permeable surface area at a thickness of about 4 cell layers.

In some embodiments, the step of the priming first expansion the priming first expansion is performed in a first container comprising a first gas-permeable surface area and in the step of the rapid second expansion the rapid second expansion is performed in a second container comprising a second gas-permeable surface area.

In some embodiments, the second container is larger than the first container.

In some embodiments, the step of the priming first expansion the cell culture medium comprises antigen-presenting cells (APCs) and the APCs are layered onto the first gas-permeable surface area at an average thickness of about one cell layer to about three cell layers.

In some embodiments, the step of the priming first expansion the APCs are layered onto the first gas-permeable surface area at an average thickness of about 1.5 cell layers to about 2.5 cell layers.

In some embodiments, the step of the priming first expansion the APCs are layered onto the first gas-permeable surface area at an average thickness of about 2 cell layers.

In some embodiments, the rapid second expansion the APCs are layered onto the second gas-permeable surface area at an average thickness of about 3 cell layers to about 5 cell layers.

In some embodiments, the rapid second expansion the APCs are layered onto the second gas-permeable surface area at an average thickness of about 3.5 cell layers to about 4.5 cell layers.

In some embodiments, the step of the rapid second expansion the APCs are layered onto the second gas-permeable surface area at an average thickness of about 4 cell layers.

In some embodiments, for each container in which the priming first expansion is performed on a first population of TILs the rapid second expansion is performed in the same container on the second population of TILs produced from such first population of TILs.

In some embodiments, each container comprises a first gas-permeable surface area.

In some embodiments, the step of the priming first expansion the cell culture medium comprises antigen-presenting cells (APCs) and the APCs are layered onto the first gas-permeable surface area at an average thickness of from about one cell layer to about three cell layers.

In some embodiments, the step of the priming first expansion the APCs are layered onto the first gas-permeable surface area at an average thickness of from about 1.5 cell layers to about 2.5 cell layers.

In some embodiments, the step of the priming first expansion the APCs are layered onto the first gas-permeable surface area at an average thickness of about 2 cell layers.

In some embodiments, the step of the rapid second expansion the APCs are layered onto the first gas-permeable surface area at an average thickness of about 3 cell layers to about 5 cell layers.

In some embodiments, the step of the rapid second expansion the APCs are layered onto the first gas-permeable surface area at an average thickness of about 3.5 cell layers to about 4.5 cell layers.

In some embodiments, the step of the rapid second expansion the APCs are layered onto the first gas-permeable surface area at an average thickness of about 4 cell layers.

In some embodiments, wherein for each container in which the priming first expansion is performed on a first population of TILs in the step of the priming first expansion the first container comprises a first surface area, the cell culture medium comprises antigen-presenting cells (APCs), and the APCs are layered onto the first gas-permeable surface area, and wherein the ratio of the average number of layers of APCs layered in the step of the priming first expansion to the average number of layers of APCs layered in the step of the rapid second expansion is selected from the range of about 1:1.1 to about 1:10.

In some embodiments, the ratio of the average number of layers of APCs layered in the step of the priming first expansion to the average number of layers of APCs layered in the step of the rapid second expansion is selected from the range of about 1:1.2 to about 1:8.

In some embodiments, the ratio of the average number of layers of APCs layered in the step of the priming first expansion to the average number of layers of APCs layered in the step of the raid second expansion is selected from the range of about 1:1.3 to about 1:7.

In some embodiments, the ratio of the average number of layers of APCs layered in the step of the priming first expansion to the average number of layers of APCs layered in the step of the rapid second expansion is selected from the range of about 1:1.4 to about 1:6.

In some embodiments, the ratio of the average number of layers of APCs layered in the step of the priming first expansion to the average number of layers of APCs layered in the step of the rapid second expansion is selected from the range of about 1:1.5 to about 1:5.

In some embodiments, the ratio of the average number of layers of APCs layered in the step of the priming first expansion to the average number of layers of APCs layered in the step of the rapid second expansion is selected from the range of about 1:1.6 to about 1:4.

In some embodiments, the ratio of the average number of layers of APCs layered in the step of the priming first expansion to the average number of layers of APCs layered in the step of the rapid second expansion is selected from the range of about 1:1.7 to about 1:3.5.

In some embodiments, the ratio of the average number of layers of APCs layered in the step of the priming first expansion to the average number of layers of APCs layered in the step of the rapid second expansion is selected from the range of about 1:1.8 to about 1:3.

In some embodiments, the ratio of the average number of layers of APCs layered in the step of the priming first expansion to the average number of layers of APCs layered in the step of the rapid second expansion is selected from the range of about 1:1.9 to about 1:2.5.

In some embodiments, the ratio of the average number of layers of APCs layered in the step of the priming first expansion to the average number of layers of APCs layered in the step of the rapid second expansion is about 1:2.

In some embodiments, after 2 to 3 days in the step of the rapid second expansion, the cell culture medium is supplemented with additional IL-2.

In some embodiments, the method further comprises cryopreserving the harvested TIL population in the step of harvesting the therapeutic population of TILs using a cryopreservation process.

In some embodiments, the method further comprises the step of cryopreserving the infusion bag.

In some embodiments, the cryopreservation process is performed using a 1:1 ratio of harvested TIL population to cryopreservation media.

In some embodiments, the antigen-presenting cells are peripheral blood mononuclear cells (PBMCs).

In some embodiments, the PBMCs are irradiated and allogeneic.

In some embodiments, the step of the priming first expansion the cell culture medium comprises peripheral blood mononuclear cells (PBMCs), and wherein the total number of PBMCs added to the cell culture medium in the step of the priming first expansion is about $2.5\times10^8$.

In some embodiments, the step of the rapid second expansion the antigen-presenting cells (APCs) in the cell culture medium are peripheral blood mononuclear cells (PBMCs), and wherein the total number of PBMCs added to the cell culture medium in the step of the rapid second expansion is about $5\times10^8$.

In some embodiments, the e antigen-presenting cells are artificial antigen-presenting cells.

In some embodiments, the harvesting in the step of harvesting the therapeutic population of TILs is performed using a membrane-based cell processing system.

In some embodiments, the harvesting in step harvesting the therapeutic population of TILs is performed using a LOVO cell processing system.

In some embodiments, the multiple fragments comprise about 60 fragments per container in the step of the priming first expansion, wherein each fragment has a volume of about 27 $mm^3$.

In some embodiments, the multiple fragments comprise about 30 to about 60 fragments with a total volume of about 1300 $mm^3$ to about 1500 $mm^3$.

In some embodiments, the multiple fragments comprise about 50 fragments with a total volume of about 1350 $mm^3$.

In some embodiments, the multiple fragments comprise about 50 fragments with a total mass of about 1 gram to about 1.5 grams.

In some embodiments, the cell culture medium is provided in a container selected from the group consisting of a G-container and a Xuri cellbag.

In some embodiments, the IL-2 concentration is about 10,000 IU/mL to about 5,000 IU/mL.

In some embodiments, the IL-2 concentration is about 6,000 IU/mL.

In some embodiments, the infusion bag in the step of transferring the harvested therapeutic population of TILs to an infusion bag is a HypoThermosol-containing infusion bag.

In some embodiments, the cryopreservation media comprises dimethlysulfoxide (DMSO).

In some embodiments, the cryopreservation media comprises 7% to 10% DMSO.

In some embodiments, the first period in the step of the priming first expansion and the second period in the step of the rapid second expansion are each individually performed within a period of 5 days, 6 days, or 7 days.

In some embodiments, the first period in the step of the priming first expansion is performed within a period of 5 days, 6 days, or 7 days.

In some embodiments, the second period in the step of the rapid second expansion is performed within a period of 7 days, 8 days, or 9 days.

In some embodiments, the first period in the step of the priming first expansion and the second period in the step of the rapid second expansion are each individually performed within a period of 7 days.

In some embodiments, the steps of the priming first expansion through the harvesting of the therapeutic population of TILs are performed within a period of about 14 days to about 16 days.

In some embodiments, the steps of the priming first expansion through the harvesting of the therapeutic population of TILs are performed within a period of about 15 days to about 16 days.

In some embodiments, the steps of the priming first expansion through the harvesting of the therapeutic population of TILs are performed within a period of about 14 days.

In some embodiments, the steps of the priming first expansion through the harvesting of the therapeutic population of TILs are performed within a period of about 15 days.

In some embodiments, the steps the priming first expansion through the harvesting of the therapeutic population of TILs are performed within a period of about 16 days.

In some embodiments, the method further comprises the step of cryopreserving the harvested therapeutic population of TILs using a cryopreservation process, wherein steps of the priming first expansion through the harvesting of the therapeutic population of TILs and cryopreservation are performed in 16 days or less.

In some embodiments, the therapeutic population of TILs harvested in the step of harvesting of the therapeutic population of TILs comprises sufficient TILs for a therapeutically effective dosage of the TILs.

In some embodiments, the number of TILs sufficient for a therapeutically effective dosage is from about $2.3\times10^{10}$ to about $13.7\times10^{10}$.

In some embodiments, the third population of TILs in the step of the rapid second expansion provides for increased efficacy, increased interferon-gamma production, and/or increased polyclonality.

In some embodiments, the third population of TILs in the step of the rapid second expansion provides for at least a one-fold to five-fold or more interferon-gamma production as compared to TILs prepared by a process longer than 18 days.

In some embodiments, the effector T cells and/or central memory T cells obtained from the third population of TILs in the step of the rapid second expansion exhibit increased CD8 and CD28 expression relative to effector T cells and/or central memory T cells obtained from the second population of TILs in the step of the priming first expansion.

In some embodiments, the therapeutic population of TILs from the step of the harvesting of the therapeutic population of TILs are infused into a patient.

The present invention also provides a method for treating a subject with cancer, the method comprising administering expanded tumor infiltrating lymphocytes (TILs) comprising:

(a) obtaining and/or receiving a first population of TILs from a tumor resected from a subject by processing a tumor sample obtained from the subject into multiple tumor fragments;

(b) performing a priming first expansion by culturing the first population of TILs in a cell culture medium comprising IL-2, optionally OKT-3, and optionally antigen presenting cells (APCs) to produce a second population of TILs, wherein the priming first expansion is performed in a container comprising a first gas-permeable surface area, wherein the priming first expansion is performed for about 1 to 7/8 days to obtain the second population of TILs, wherein the second population of TILs is at least 50-fold greater in number than the first population of TILs;

(c) performing a rapid second expansion by supplementing the cell culture medium of the second population of TILs with additional IL-2, OKT-3, and APCs, to produce a third population of TILs, wherein the number of APCs added to the rapid second expansion is at least twice the number of APCs added in step (b), wherein the rapid second expansion is performed for about 1 to 11 days to obtain the third population of TILs, wherein the third population of TILs is a therapeutic population of TILs, wherein the rapid second expansion is performed in a container comprising a second gas-permeable surface area;

(d) harvesting the therapeutic population of TILs obtained from step (c);

(e) transferring the harvested TIL population from step (d) to an infusion bag; and (f) administering a therapeutically effective dosage of the TILs from step (e) to the subject.

In some embodiments, the number of TILs sufficient for administering a therapeutically effective dosage in step (f) is from about $2.3\times10^{10}$ to about $13.7\times10^{10}$.

In some embodiments, the antigen presenting cells (APCs) are PBMCs.

In some embodiments, prior to administering a therapeutically effective dosage of TIL cells in step (f), a non-myeloablative lymphodepletion regimen has been administered to the patient.

In some embodiments, the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In some embodiments, the method further comprises the step of treating the patient with a high-dose IL-2 regimen starting on the day after administration of the TIL cells to the patient in step (f).

In some embodiments, the high-dose IL-2 regimen comprises 600,000 or 720,000 IU/kg administered as a 15-minute bolus intravenous infusion every eight hours until tolerance.

In some embodiments, the e third population of TILs in step (b) provides for increased efficacy, increased interferon-gamma production, and/or increased polyclonality.

In some embodiments, the third population of TILs in step (c) provides for at least a one-fold to five-fold or more interferon-gamma production as compared to TILs prepared by a process longer than 16 days.

In some embodiments, the effector T cells and/or central memory T cells obtained from the third population of TILs in step (c) exhibit increased CD8 and CD28 expression relative to effector T cells and/or central memory T cells obtained from the second population of cells in step (b).

In some embodiments, the cancer is a solid tumor.

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma.

In some embodiments, the cancer is selected from the group consisting of melanoma, HNSCC, cervical cancers, NSCLC, glioblastoma (including GBM), and gastrointestinal cancer.

In some embodiments, the cancer is melanoma.

In some embodiments, the cancer is HNSCC.

In some embodiments, the cancer is a cervical cancer.

In some embodiments, the cancer is NSCLC.

In some embodiments, the cancer is glioblastoma (including GBM).

In some embodiments, the cancer is gastrointestinal cancer.

In some embodiments, the cancer is a hypermutated cancer.

In some embodiments, the cancer is a pediatric hypermutated cancer.

In some embodiments, the container is a closed container.

In some embodiments, the container is a G-container.

In some embodiments, the container is a GREX-10.

In some embodiments, the closed container comprises a GREX-100.

In some embodiments, the closed container comprises a GREX-500.

The presenting invention also provides a therapeutic population of tumor infiltrating lymphocytes (TILs) made by the method as disclosed herein.

The presenting invention also provides therapeutic population of tumor infiltrating lymphocytes (TILs) prepared from tumor tissue of a patient, wherein the therapeutic population of TILs provides for increased efficacy, increased interferon-gamma production, and/or increased polyclonality.

In some embodiments, the therapeutic population of TILs as disclosed herein provide for increased interferon-gamma production.

In some embodiments, the therapeutic population of TILs as disclosed herein provide for increased polyclonality.

In some embodiments, the therapeutic population of TILs as disclosed herein provide for increased efficacy.

In some embodiments, the therapeutic population of TILs as described herein is capable of at least one-fold more interferon-gamma production as compared to TILs prepared by a process longer than 16 days.

In some embodiments, the therapeutic population of TILs as described herein is capable of at least two-fold more interferon-gamma production as compared to TILs prepared by a process longer than 16 days.

In some embodiments, the therapeutic population of TILs as described herein is capable of at least three-fold more interferon-gamma production as compared to TILs prepared by a process longer than 16 days.

In some embodiments, the present invention provides a therapeutic population of tumor infiltrating lymphocytes (TILs), wherein the therapeutic population of TILs is capable of at least one-fold more interferon-gamma production as compared to TILs prepared by a process in which the first expansion of TILs is performed without any added antigen-presenting cells (APCs).

In some embodiments, the therapeutic population of TILs as described herein is capable of at least two-fold more interferon-gamma production as compared to TILs prepared by a process in which the first expansion of TILs is performed without any added APCs.

In some embodiments, the therapeutic population of TILs as described herein is capable of at least three-fold more interferon-gamma production as compared to TILs prepared by a process in which the first expansion of TILs is performed without any added APCs.

In some embodiments, the present invention provides a therapeutic population of tumor infiltrating lymphocytes (TILs), wherein the therapeutic population of TILs is capable of at least one-fold more interferon-gamma production as compared to TILs prepared by a process in which the first expansion of TILs is performed without any added OKT3.

In some embodiments, the therapeutic population of TILs as described herein is capable of at least two-fold more interferon-gamma production as compared to TILs prepared by a process in which the first expansion of TILs is performed without any added OKT3.

In some embodiments, the therapeutic population of TILs as described herein is capable of at least three-fold more interferon-gamma production as compared to TILs prepared by a process in which the first expansion of TILs is performed without any added OKT3.

In some embodiments, the present invention provides a therapeutic population of tumor infiltrating lymphocytes (TILs), wherein the therapeutic population of TILs is capable of at least one-fold more interferon-gamma production as compared to TILs prepared by a process in which the first expansion of TILs is performed with no added antigen-presenting cells (APCs) and no added OKT3.

In some embodiments, the therapeutic population of TILs as described herein is capable of at least two-fold more interferon-gamma production as compared to TILs prepared by a process in which the first expansion of TILs is performed with no added antigen-presenting cells (APCs) and no added OKT3.

In some embodiments, the therapeutic population of TILs as described herein is capable of at least three-fold more interferon-gamma production as compared to TILs prepared by a process in which the first expansion of TILs is performed with no added antigen-presenting cells (APCs) and no added OKT3.

The present invention also provides a tumor infiltrating lymphocyte (TIL) composition comprising the therapeutic population of TILs as described herein and a pharmaceutically acceptable carrier.

The present invention also provides a sterile infusion bag comprising the TIL composition as described herein.

The present invention also provides a cryopreserved preparation of the therapeutic population of TILs as described herein.

The present invention also provides a tumor infiltrating lymphocyte (TIL) composition comprising the therapeutic population of TILs as described herein and a cryopreservation media.

In some embodiments, the cryopreservation media contains DMSO.

In some embodiments, the cryopreservation media contains 7-10% DMSO.

The present invention also provides a cryopreserved preparation of the TIL composition as described herein.

In some embodiments, the tumor infiltrating lymphocyte (TIL) composition as described herein is for use as a medicament.

In some embodiments, the tumor infiltrating lymphocyte (TIL) composition as described herein is for use in the treatment of a cancer.

In some embodiments, the tumor infiltrating lymphocyte (TIL) composition as described herein is for use in the treatment of a solid tumor cancer.

In some embodiments, the tumor infiltrating lymphocyte (TIL) composition as described herein for use in treatment of a cancer selected from melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma.

In some embodiments, the tumor infiltrating lymphocyte (TIL) composition as described herein is for use in treatment of a cancer selected from the group consisting of melanoma, HNSCC, cervical cancers, NSCLC, glioblastoma (including GBM), and gastrointestinal cancer.

In some embodiments, the TIL composition as described herein is for use in treatment of a cancer wherein cancer is melanoma.

In some embodiments, the TIL composition as described herein is for use in treatment of a cancer wherein cancer is HNSCC.

In some embodiments, the TIL composition as described herein is for use in treatment of a cancer wherein a cervical cancer.

In some embodiments, the TIL composition as described herein is for use in treatment of a cancer wherein the cancer is NSCLC.

In some embodiments, the TIL composition as described herein is for use in treatment of a cancer wherein the cancer is glioblastoma (including GBM).

In some embodiments, the TIL composition as described herein is for use in treatment of a cancer wherein the cancer is gastrointestinal cancer.

In some embodiments, the TIL composition as described herein is for use in treatment of a cancer wherein the cancer is a hypermutated cancer.

In some embodiments, the TIL composition as described herein is for use in treatment of a cancer wherein the cancer is a pediatric hypermutated cancer.

In some embodiments, the present invention provides for the use of the tumor infiltrating lymphocyte (TIL) composition as described herein in a method of treating cancer in a subject comprising administering a therapeutically effective dosage of the TIL composition to the subject. In some embodiments, the cancer is a solid tumor. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma In some embodiments, the cancer is selected from the group consisting of melanoma, HNSCC, cervical cancers, NSCLC, glioblastoma (including GBM), and gastrointestinal cancer. In some embodiments, the cancer is melanoma. In some embodiments, the cancer is HNSCC. In some embodiments, the cancer is a cervical cancer. In some embodiments, the cancer is NSCLC. In some embodiments, the cancer is glioblastoma (including GBM). In some embodiments, the cancer is gastrointestinal cancer. In some embodiments, the cancer is a hypermutated cancer. In some embodiments, the cancer is a pediatric hypermutated cancer.

In some embodiments, the tumor infiltrating lymphocyte (TIL) composition as described herein is for use in a method of treating cancer in a subject comprising administering a therapeutically effective dosage of the TIL composition to the subject. In some embodiments, the cancer is a solid tumor. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, HNSCC, cervical cancers, NSCLC, glioblastoma (including GBM), and gastrointestinal cancer.

The present invention also provides a method of treating cancer in a subject comprising administering to the subject a therapeutically effective dosage of the tumor infiltrating lymphocyte (TIL) composition as described herein.

In some embodiments, the cancer is a solid tumor.

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma.

In some embodiments, the cancer is selected from the group consisting of melanoma, HNSCC, cervical cancers, NSCLC, glioblastoma (including GBM), and gastrointestinal cancer. In some embodiments, the cancer is melanoma. In some embodiments, the cancer is HNSCC. In some embodiments, the cancer is a cervical cancer. In some embodiments, the cancer is NSCLC. In some embodiments, the cancer is glioblastoma (including GBM). In some embodiments, the cancer is gastrointestinal cancer. In some embodiments, the cancer is a hypermutated cancer. In some embodiments, the cancer is a pediatric hypermutated cancer.

The present invention also provides a method of expanding T cells comprising:

(a) performing a priming first expansion of a first population of T cells obtained from a donor by culturing the first population of T cells to effect growth and to prime an activation of the first population of T cells;

(b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells.

In some embodiments, the priming first expansion of step (a) is performed during a period of up to 7 days.

In some embodiments, the rapid second expansion of step (b) is performed during a period of up to 11 days.

In some embodiments, the rapid second expansion of step (b) is performed during a period of up to 9 days.

In some embodiments, the priming first expansion of step (a) is performed during a period of 7 days and the rapid second expansion of step (b) is performed during a period of 9 days.

In some embodiments, the priming first expansion of step (a) is performed during a period of up to 8 days.

In some embodiments, the rapid second expansion of step (b) is performed during a period of up to 8 days.

In some embodiments, the priming first expansion of step (a) is performed during a period of 8 days and the rapid second expansion of step (b) is performed during a period of 8 days.

In some embodiments of the method, in step (a) the first population of T cells is cultured in a first culture medium comprising OKT-3 and IL-2.

In some embodiments, the first culture medium comprises OKT-3, IL-2 and antigen-presenting cells (APCs).

In some embodiments of the method, in step (b) the first population of T cells is cultured in a second culture medium comprising OKT-3, IL-2 and antigen-presenting cells (APCs).

In some embodiments of the method, in step (a) the first population of T cells is cultured in a first culture medium in a container comprising a first gas-permeable surface, wherein the first culture medium comprises optionally OKT-3, IL-2 and optionally a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In some embodiments, the ratio of the number of APCs in the second population of APCs to the number of APCs in the first population of APCs is about 2:1.

In some embodiments, the number of APCs in the first population of APCs is about $2.5\times10^8$ and the number of APCs in the second population of APCs is about $5\times10^8$.

In some embodiments of the method, in step (a) the first population of APCs is layered onto the first gas-permeable surface at an average thickness of 2 layers of APCs.

In some embodiments of the method, in step (b) the second population of APCs is layered onto the first gas-permeable surface at an average thickness selected from the range of 4 to 8 layers of APCs.

In some embodiments, the ratio of the average number of layers of APCs layered onto the first gas-permeable surface in step (b) to the average number of layers of APCs layered onto the first gas-permeable surface in step (a) is 2:1.

In some embodiments, the APCs are peripheral blood mononuclear cells (PBMCs).

In some embodiments, the APCs comprise PBMCs, wherein the PBMCs are irradiated and exogenous to the donor of the first population of T cells.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the cell culture medium is a defined medium and/or a serum free medium.

In some embodiments, the defined medium comprises (optionally recombinant) transferrin, (optionally recombinant) insulin, and (optionally recombinant) albumin.

In some embodiments, the serum-free or defined medium comprises a basal cell medium and a serum supplement and/or a serum replacement.

In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement is selected from the group consisting of CTS™ OpTmizer T-Cell Expansion Serum Supplement and CTS™ Immune Cell Serum Replacement.

In some embodiments, the cell culture medium comprises one or more albumins or albumin substitutes.

In some embodiments, the cell culture medium comprises one or more amino acids.

In some embodiments, the cell culture medium comprises one or more vitamins, one or more transferrins or transferrin substitutes.

In some embodiments, the cell culture medium comprises one or more antioxidants, one or more insulins or insulin substitutes.

In some embodiments, the cell culture medium comprises one or more collagen precursors, one or more antibiotics, and one or more trace elements. In In some embodiments, the cell culture medium comprises albumin.

In some embodiments, the cell culture medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^+$, $Al^{3+}$, $Ba^{2+}$, $Cd^{2+}$, $Co^{2+}$, $Cr^{3"}$, $Ge^{4+}$, $Se^{4+}$, Br, T, $Mn^{2+}$, P, $Si^{4+}$, $V^{5+}$, $Mo^{6+}$, $Ni^{2+}$, $Rb^+$, $Sn^{2+}$ and $Zr^{4+}$.

In some embodiments, the cell culture medium further comprises L-glutamine, sodium bicarbonate and/or 2-mercaptoethanol.

In some embodiments, the cell culture medium comprises a total serum replacement concentration (vol %) of from about 1%, 2%, 3%, 4%, 5%, 6%, 7%, 8%, 9%, 10%, 11%, 12%, 13%, 14%, 15%, 16%, 17%, 18%, 19%, or 20% by volume of the cell culture medium.

In some embodiments, the cell culture medium comprises a total serum replacement concentration of about 3%, about 5%, or about 10% of the total volume of the cell culture medium.

In some embodiments, the cell culture medium further comprises glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM.

In some embodiments, the cell culture medium further comprises glutamine (i.e., GlutaMAX®) at a concentration of about 2 mM.

In some embodiments, the cell culture medium further comprises 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM.

In some embodiments, the cell culture medium further comprises 2-mercaptoethanol at a concentration of about 55 mM.

In some embodiments, the cell culture medium comprises the defined media described in International PCT Publication No. WO/1998/030679.

In some embodiments, the cell culture medium comprises glycine in the range of from about 5-200 mg/L, L-histidine in the range of from about 5-250 mg/L, L-isoleucine in the range of from about 5-300 mg/L, L-methionine in the range of from about 5-200 mg/L, L-phenylalanine in the range of from about 5-400 mg/L, L-proline in the range of from about 1-1000 mg/L, L-hydroxyproline in the range of from about 1-45 mg/L, L-serine in the range of from about 1-250 mg/L, L-threonine in the range of from about 10-500 mg/L, L-tryptophan in the range of from about 2-110 mg/L, L-tyrosine in the range of from about 3-175 mg/L, L-valine in the range of from about 5-500 mg/L, thiamine in the range of from about 1-20 mg/L, reduced glutathione in the range of from about 1-20 mg/L, L-ascorbic acid-2-phosphate in the range of from about 1-200 mg/L, iron saturated transferrin in the range of from about 1-50 mg/L, insulin in the range of from about 1-100 mg/L, sodium selenite in the range of from about 0.000001-0.0001 mg/L, and/or albumin (e.g., AlbuMAX® I) in the range of from about 5000-50,000 mg/L.

In some embodiments, the cell culture medium comprises one or more of the non-trace element moiety ingredients in the defined medium are present in the concentration ranges listed in the column under the heading "Concentration Range in 1× Medium" in Table A provided herein.

In some embodiments, the osmolarity of the cell culture medium is between about 260 and 350 mOsmol.

In some embodiments, the cell culture medium further comprises about 3.7 g/L, or about 2.2 g/L sodium bicarbonate.

In some embodiments, the cell culture medium further comprises L-glutamine (final concentration of about 2 mM), one or more antibiotics, non-essential amino acids (NEAA; final concentration of about 100 μM), and/or 2-mercaptoethanol (final concentration of about 100 μM).

In some embodiments, the cell culture medium in the first and/or second gas permeable container lacks beta-mercaptoethanol (BME or βME; also known as 2-mercaptoethanol, CAS 60-24-2).

In some embodiments, the cell culture medium comprises CTS OpTmizer T-Cell Expansion SFM, 3% CTS Immune Cell Serum Replacement, 55 mM BME, and optionally glutamine.

In some embodiments, the cell culture medium comprises CTS™OpTmizer™ T-Cell Expansion Basal Medium supplemented with CTS™ OpTmizer™ T-Cell Expansion Supplement (26 mL/L), and 3% CTS™ Immune Cell SR, and 2 mM Glutamax, optionally further comprising 6,000 IU/mL of IL-2.

In some embodiments, the cell culture medium comprises CTS™OpTmizer™ T-Cell Expansion Basal Medium supplemented with CTS™ OpTmizer™ T-Cell Expansion Supplement (26 mL/L), and 3% CTS™ Immune Cell SR, 2 mM Glutamax, and optionally further comprising 3,000 IU/mL of IL-2.

The present invention also provides a tumor infiltrating lymphocyte (TIL) composition comprising:

- i) a therapeutic population of tumor infiltrating lymphocytes (TILs), and
- ii) defined medium or serum free medium optionally comprising (optionally recombinant) transferrin, (optionally recombinant) insulin, and (optionally recombinant) albumin.

The present invention also provides an expanded tumor infiltrating lymphocyte (TIL) composition comprising:

- i) a therapeutic population of tumor infiltrating lymphocytes (TILs), and
- ii) defined medium or serum free medium optionally comprising (optionally recombinant) transferrin, (optionally recombinant) insulin, and (optionally recombinant) albumin.

In some embodiments, the defined medium or serum free medium comprises (optionally recombinant) transferrin, (optionally recombinant) insulin, and (optionally recombinant) albumin.

In some embodiments, the defined medium or serum free medium comprises a basal cell medium and a serum supplement and/or a serum replacement.

In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement is selected from the group consisting of CTS™ OpTmizer T-Cell Expansion Serum Supplement and CTS™ Immune Cell Serum Replacement.

In some embodiments, the defined medium or serum free medium comprises one or more albumins or albumin substitutes.

In some embodiments, the defined medium or serum free medium comprises one or more amino acids.

In some embodiments, the defined medium or serum free medium comprises one or more vitamins, one or more transferrins or transferrin substitutes.

In some embodiments, the defined medium or serum free medium comprises one or more antioxidants, one or more insulins or insulin substitutes.

In some embodiments, the defined medium or serum free medium comprises one or more collagen precursors, one or more antibiotics, and one or more trace elements.

In some embodiments, the defined medium or serum free medium comprises albumin.

In some embodiments, the defined medium or serum free medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3''}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$.

In some embodiments, the defined medium or serum free medium further comprises L-glutamine, sodium bicarbonate and/or 2-mercaptoethanol.

In some embodiments, the defined medium or serum free medium comprises a total serum replacement concentration (vol %) of from about 1%, 2%, 3%, 4%, 5%, 6%, 7%, 8%, 9%, 10%, 11%, 12%, 13%, 14%, 15%, 16%, 17%, 18%, 19%, or 20% by volume of the cell culture medium.

In some embodiments, the defined medium or serum free medium comprises a total serum replacement concentration of about 3%, about 5%, or about 10% of the total volume of the cell culture medium.

In some embodiments, the defined medium or serum free medium further comprises glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM.

In some embodiments, the defined medium or serum free medium further comprises glutamine (i.e., GlutaMAX®) at a concentration of about 2 mM.

In some embodiments, the defined medium or serum free medium further comprises 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM.

In some embodiments, the defined medium or serum free medium further comprises 2-mercaptoethanol at a concentration of about 55 mM.

In some embodiments, the defined medium or serum free medium comprises the defined media described in International PCT Publication No. WO/1998/030679.

In some embodiments, the defined medium or serum free medium comprises glycine in the range of from about 5-200 mg/L, L-histidine in the range of from about 5-250 mg/L, L-isoleucine in the range of from about 5-300 mg/L, L-methionine in the range of from about 5-200 mg/L, L-phenylalanine in the range of from about 5-400 mg/L, L-proline in the range of from about 1-1000 mg/L, L-hydroxyproline in the range of from about 1-45 mg/L, L-serine in the range of from about 1-250 mg/L, L-threonine in the range of from about 10-500 mg/L, L-tryptophan in the range of from about 2-110 mg/L, L-tyrosine in the range of from about 3-175 mg/L, L-valine in the range of from about 5-500 mg/L, thiamine in the range of from about 1-20 mg/L, reduced glutathione in the range of from about 1-20 mg/L, L-ascorbic acid-2-phosphate in the range of from about 1-200 mg/L, iron saturated transferrin in the range of from about 1-50 mg/L, insulin in the range of from about 1-100 mg/L, sodium selenite in the range of from about 0.000001-0.0001 mg/L, and/or albumin (e.g., AlbuMAX® I) in the range of from about 5000-50,000 mg/L.

In some embodiments, the defined medium or serum free medium comprises one or more of the non-trace element moiety ingredients in the defined medium are present in the concentration ranges listed in the column under the heading "Concentration Range in 1× Medium" in Table A provided herein.

In some embodiments, the osmolarity of the defined medium or serum free medium is between about 260 and 350 mOsmol.

In some embodiments, the defined medium or serum free medium further comprises about 3.7 g/L, or about 2.2 g/L sodium bicarbonate.

In some embodiments, the defined medium or serum free medium further comprises L-glutamine (final concentration of about 2 mM), one or more antibiotics, non-essential amino acids (NEAA; final concentration of about 100 μM), and/or 2-mercaptoethanol (final concentration of about 100 μM).

In some embodiments, the defined medium or serum free medium in the first and/or second gas permeable container lacks beta-mercaptoethanol (BME or βME; also known as 2-mercaptoethanol, CAS 60-24-2).

In some embodiments, the cell culture medium comprises CTS OpTmizer T-Cell Expansion SFM, 3% CTS Immune Cell Serum Replacement, 55 mM BME, and optionally glutamine.

In some embodiments, the cell culture medium comprises CTS™OpTmizer™ T-Cell Expansion Basal Medium supplemented with CTS™ OpTmizer™ T-Cell Expansion Supplement (26 mL/L), and 3% CTS™ Immune Cell SR, and 2 mM Glutamax, optionally further comprising 6,000 IU/mL of IL-2.

In some embodiments, the cell culture medium comprises CTS™OpTmizer™ T-Cell Expansion Basal Medium supplemented with CTS™ OpTmizer™ T-Cell Expansion Supplement (26 mL/L), and 3% CTS™ Immune Cell SR, 2 mM Glutamax, and optionally further comprising 3,000 IU/mL of IL-2.

In some embodiments, the population of TILs is a therapeutic population of TILs.

In some embodiments, the therapeutic population of TILs exhibits a rise in serum IFN-γ, wherein the rise in IFN-γ is greater than 200 pg/ml, greater than 250 pg/ml, greater than 300 pg/ml, greater than 350 pg/ml, greater than 400 pg/ml, greater than 450 pg/ml, greater than 500 pg/ml, greater than 550 pg/ml, greater than 600 pg/ml, greater than 650 pg/ml, greater than 700 pg/ml, greater than 750 pg/ml, greater than 800 pg/ml, greater than 850 pg/ml, greater than 900 pg/ml, greater than 950 pg/ml, or greater than 1000 pg/ml.

BRIEF DESCRIPTION OF THE DRAWINGS

FIG. 1A-1C: A) Shows a comparison between the 2A process (approximately 22-day process) and an embodiment of the Gen 3 process for TIL manufacturing (approximately 14-days to 16-days process). B) Exemplary Process Gen3 chart providing an overview of Steps A through F (approximately 14-days to 16-days process). C) Chart providing three exemplary Gen 3 processes with an overview of Steps A through F (approximately 14-days to 16-days process) for each of the three process variations.

FIG. 10: A) Quantification of L-glutamine in spent media for L4054 and L4055. B) Quantification of Glutamax in spent media for L4054 and L4055. C) Quantification of ammonia in spent media for L4054 and L4055.

FIG. 16: Raw data for cell counts Day 7-Gen 3 REP initiation presented in Table 22 (see Example 5 below).

FIG. 17: Raw data for cell counts Day 11-Gen 2 REP initiation and Gen 3 Scale Up presented in Table 22 (see Example 5 below).

FIG. 18: Raw data for cell counts Day 16-Gen 2 Scale Up and Gen 3 Harvest (e.g., day 16) presented in Table 23 (see Example 5 below).

FIG. 19: Raw data for cell counts Day 22-Gen 2 Harvest (e.g., day 22) presented in Table 23 (see Example 5 below). For L4054 Gen 2, post LOVO count was extrapolated to 4 flasks, because was the total number of the study. 1 flask was contaminated, and the extrapolation was done for total=6.67E+10.

FIG. 20: Raw data for flow cytometry results depicted in FIGS. 3A, 4A, and 4B.

FIG. 21: Raw data for flow cytometry results depicted in FIGS. 3C and 4C.

FIG. 22: Raw data for flow cytometry results depicted in FIGS. 5 and 6.

FIG. 23: Raw data for IFNγ production assay results for L4054 samples depicted in FIG. 7.

FIG. 24: Raw data for IFNγ production assay results for L4055 samples depicted in FIG. 7.

FIG. 25: Raw data for IFNγ production assay results for M1085T samples depicted in FIG. 7.

FIG. 26: Raw data for IL-2 ELISA assay results depicted in FIG. 8.

FIG. 27: Raw data for the metabolic substrate and metabolic analysis results presented in FIGS. 9 and 10.

FIG. 28: Raw data for the relative telomere length analysis results presented in FIG. 11.

FIG. 29: Raw data for the unique CD3 sequence and clonal diversity analyses results presented in FIGS. 12 and 15.

FIG. 31: Table describing various features of embodiments of the Gen 2, Gen 2.1 and Gen 3.0 process.

FIG. 32: Overview of the media conditions for an embodiment of the Gen 3 process, referred to as Gen 3.1.

FIG. 33: Table describing various features of embodiments of the Gen 2, Gen 2.1 and Gen 3.0 process.

FIG. 34: Table comparing various features of embodiments of the Gen 2 and Gen 3.0 processes.

FIG. 35: Table providing media uses in the various embodiments of the described expansion processes.

FIG. 36: Phenotype comparison: Gen 3.0 and Gen 3.1 embodiments of the process showed comparable CD28, CD27, and CD57 expression. Gen 3.1 Test (which includes the addition of OKT-3 and feeders on Day 0) reached maximum capacity of the flask at harvest.

FIG. 44: Provides a process overview for an exemplary embodiment (Gen 3.1 Test) of the Gen 3.1 process (a 16 day process).

FIG. 45: Provides data from TIL proliferation, average total viable cell counts per tumor fragment, percent viability at Harvest Day and total viable cell counts (TVC) at Harvest Day for exemplary embodiments of the Gen 3 process (Gen 3.0, Gen 3.1 Control, Gen 3.1 Test). Gen 3.1 Test (which includes the addition of OKT-3 and feeders on Day 0) reached maximum capacity of the flask at harvest. If a maximum of 4 flasks are initiated on day 0, each TVC harvest should be multiplied by 4.

FIG. 57A-57B: Comparison tables for exemplary Gen 2 and exemplary Gen 3 processes with exemplary differences highlighted.

FIG. 58: Schematic of an exemplary embodiment of the Gen 3 process (a 16/17 day process) preparation timeline.

FIG. 60: Summary of data from Day 16/17 of three engineering runs of an exemplary Gen 3 process embodiment.

FIG. 61: Data regarding the extended phenotype of TIL: shown are the differentiation characteristics against TIL identity (ID) specifications for cells produced by two engineering runs of an exemplary Gen 3 process embodiment.

FIG. 62: Data regarding the extended phenotype of TIL expanded from lung tumors: shown are the differentiation characteristics against TIL identity (ID) specifications for cells produced by two process development (PD) runs of an exemplary Gen 3 process embodiment using lung tumor tissues.

FIG. 63: Data regarding the extended phenotype (purity, identity and memory) of TIL expanded from ovarian tumors: shown are the purity, identity and memory phenotypic characteristics of cells expanded from ovarian tumors using exemplary Gen 2, Gen 3.1, and FR ER (Frozen tumor, Early REP) process embodiments; * indicates condition not tested; $^{Y}$ indicates sampling issue, low TVC count or non-viable cells on thawing.

FIG. 64: Shown is the gating strategy for characterization of TIL (gating hierarchy is shown) and data regarding the extended phenotypic characteristics of cells produced by two engineering runs of an exemplary Gen 3 process embodiment.

FIG. 65: Shown is the gating strategy for characterization of TIL (gating hierarchy is shown) and data regarding the extended phenotypic characteristics of the CD4+ subpopulation and the CD8+ subpopulation of cells produced by two engineering runs of an exemplary Gen 3 process embodiment.

FIG. 66: Shown are data regarding Granzyme B ELISA analysis of cells produced by two engineering runs of an exemplary Gen 3 process embodiment.

FIG. 69: Comparison of Gen 2, Gen 2.1 and an embodiment of the Gen 3 process (a 16 day process).

FIG. 70: Comparison of Gen 2, Gen 2.1 and an embodiment of the Gen 3 process (a 16 day process).

FIG. 71: Gen 3 embodiment components.

FIG. 73: Total viable cell count and fold expansion are presented for exemplary Gen 3 embodiments (Gen 3.0, Gen 3.1 Control and Gen 3.1 Test) using standard cell culture media and serum free cell culture media.

FIG. 74: % viability scores upon reactivation, culture scale up and TIL harvest are presented for exemplary Gen 3 embodiments (Gen 3.0, Gen 3.1 Control and Gen 3.1 Test) using standard cell culture media and serum free cell culture media.

Figure 2:
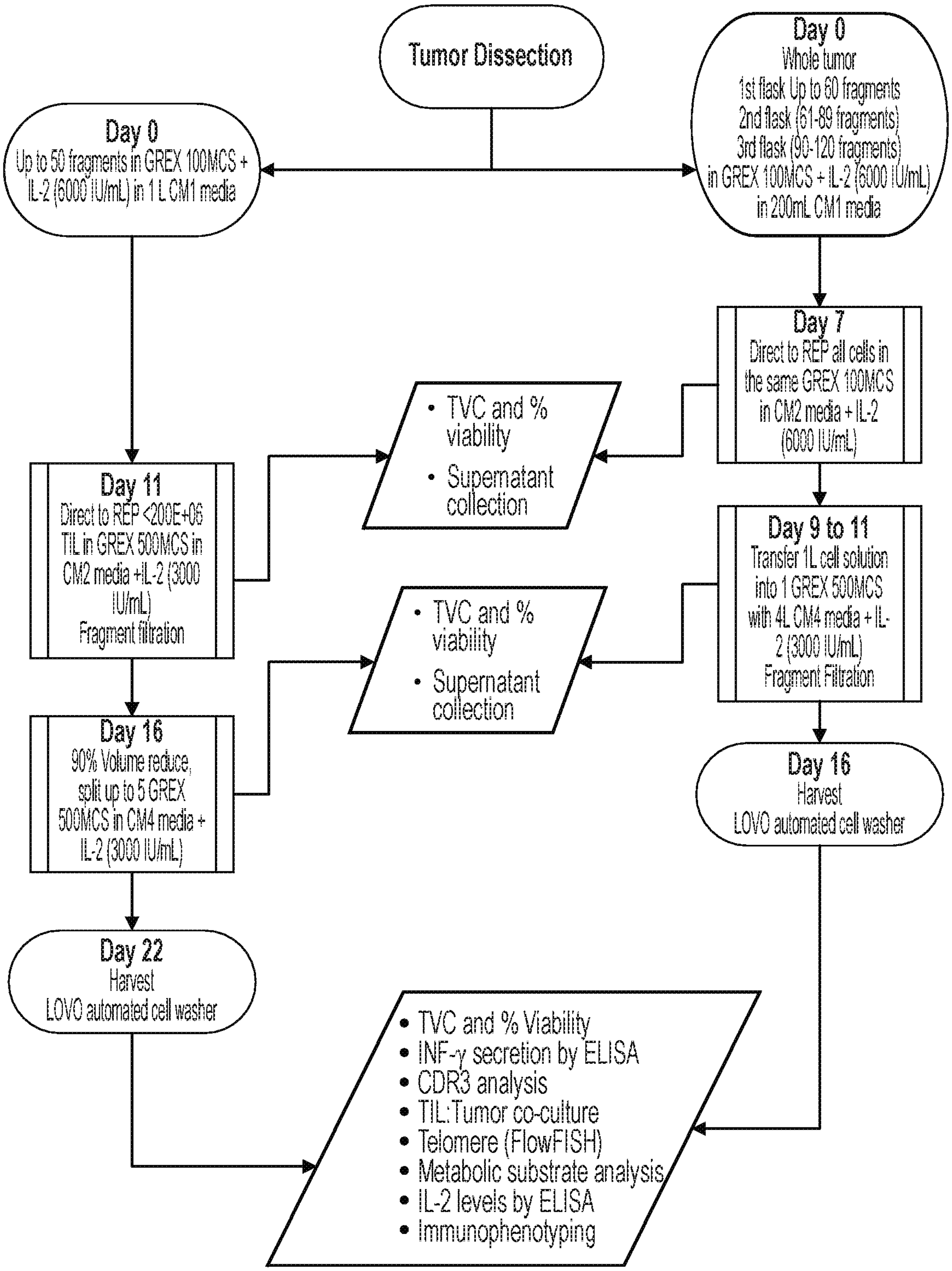
FIG. 2: Provides an experimental flow chart for comparability between GEN 2 (process 2A) versus GEN 3.

FIG. 75: Presented is phenotypic characterization of final TIL product produced by processing L4063 and L4064 tumor samples in exemplary Gen 3 processes (Gen 3.0, Gen 3.1 Control and Gen 3.1 Test) using standard cell culture media and CTS serum free cell culture media.

FIG. 76: Presented is memory marker analysis of TIL product produced by processing L4063 and L4064 tumor samples in exemplary Gen 3 processes (Gen 3.0, Gen 3.1 Control and Gen 3.1 Test) using standard cell culture media and CTS serum free cell culture media.

FIG. 77: Presented are activation and exhaustion markers of TIL produced by processing L4063 and L4064 tumor samples in exemplary Gen 3 processes (Gen 3.0, Gen 3.1 Control and Gen 3.1 Test) using standard cell culture media and CTS serum free cell culture media followed by CD4+ gated cell sorting.

FIG. 78: Presented are activation and exhaustion markers of TIL produced by processing L4063 and L4064 tumor samples in exemplary Gen 3 processes (Gen 3.0, Gen 3.1 Control and Gen 3.1 Test) using standard cell culture media and CTS serum free cell culture media followed by CD8+ gated cell sorting.

FIG. 79: Presented are IFN-γ production (pg/mL) scores for final TIL product produced by processing L4063 and L4064 tumor samples in exemplary Gen 3 processes (Gen 3.0, Gen 3.1 Control and Gen 3.1 Test) using standard cell culture media and CTS serum free cell culture media.

FIG. 80: Presented is IL-2 concentration (pg/mL) analysis of spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 81: Presented is concentration of glucose (g/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 82: Presented is concentration of lactate (g/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 83: Presented is concentration of glutamine (mmol/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 84: Presented is concentration of glutamax (mmol/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media.

FIG. 85: Presented is concentration of ammonia (mmol/L) in spent media (collected upon reactivation, culture scale up and TIL harvest) from processing L4063 and L4064 tumor samples in exemplary Gen 3 processes (Gen 3.0, Gen 3.1 Control and Gen 3.1 Test) using standard cell culture media and CTS serum free cell culture media. Telomere length analysis on exemplary embodiments of the Gen 3 process (Gen 3.0, Gen 3.1 Control, Gen 3.1 Test). Telomere length analysis for cells yielded by tumor identification numbers L4063 and L4064: the relative telomere length (RTL) value indicates the average telomere fluorescence per chromosome/genome in cells produced by the Gen 3.0, Gen 3.1 Control and Gen 3.1 Test processes over the telomere fluorescence per chromosome/genome in the control cells line (1301 Leukemia cell line) using DAKO kit.

FIG. 86: Telomere length analysis on TIL produced by exemplary embodiments of the Gen 3 process (Gen 3.0, Gen 3.1 Control, Gen 3.1 Test) using standard cell culture media and CTS serum free cell culture media. Telomere length analysis for cells yielded by tumor identification numbers L4063 and L4064: the relative telomere length (RTL) value indicates the average telomere fluorescence per chromosome/genome in cells produced by the Gen 3.0, Gen 3.1 Control and Gen 3.1 Test processes over the telomere fluorescence per chromosome/genome in the control cells line (1301 Leukemia cell line) using DAKO kit.

FIG. 87: TCR Vβ repertoire summary for TIL produced by exemplary embodiments of the Gen 3 process (Gen 3.0, Gen 3.1 Control, Gen 3.1 Test) using standard cell culture media and CTS serum free cell culture media. Described is the clonality of TIL for final TIL product yielded by tumor identification numbers L4063 and L4064 produced by the Gen 3.0, Gen 3.1 Control and Gen 3.1 Test processes as measured by the TCR repertoire of unique CDR3 sequences.

Figure 88:
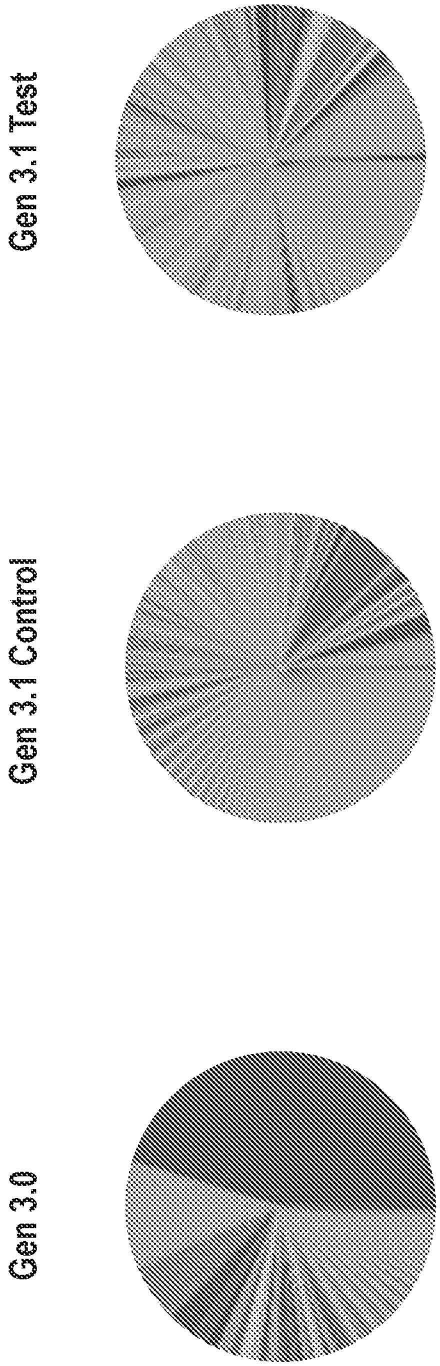

FIG. 88: Comparison of TIL produced by exemplary embodiments of the Gen 3 process (Gen 3.0, Gen 3.1 Control, Gen 3.1 Test) with respect to frequency of unique CDR3 sequences in TIL harvested product from processing of L4063 tumor samples.

FIG. 89: Comparison of TIL produced by exemplary embodiments of the Gen 3 process (Gen 3.0, Gen 3.1 Control, Gen 3.1 Test) with respect to percentage shared unique CDR3 sequences in TIL harvested cell product from processing of L4063 tumor samples: 975 sequences are shared between Gen 3.0 and Gen 3.1 Test final product, equivalent to 88% of top 80% of unique CDR3 sequences from Gen 3.0 shared with Gen 3.1 Test final product.

FIG. 90: Comparison of TIL produced by exemplary embodiments of the Gen 3 process (Gen 3.0, Gen 3.1 Control, Gen 3.1 Test) with respect to percentage shared unique CDR3 sequences in TIL harvested cell product for from processing of L4064 tumor samples: 2163 sequences are shared between Gen 3.0 and Gen 3.1 Test final product, equivalent to 87% of top 80% of unique CDR3 sequences from Gen 3.0 shared with Gen 3.1 Test final product.

Figure 91:
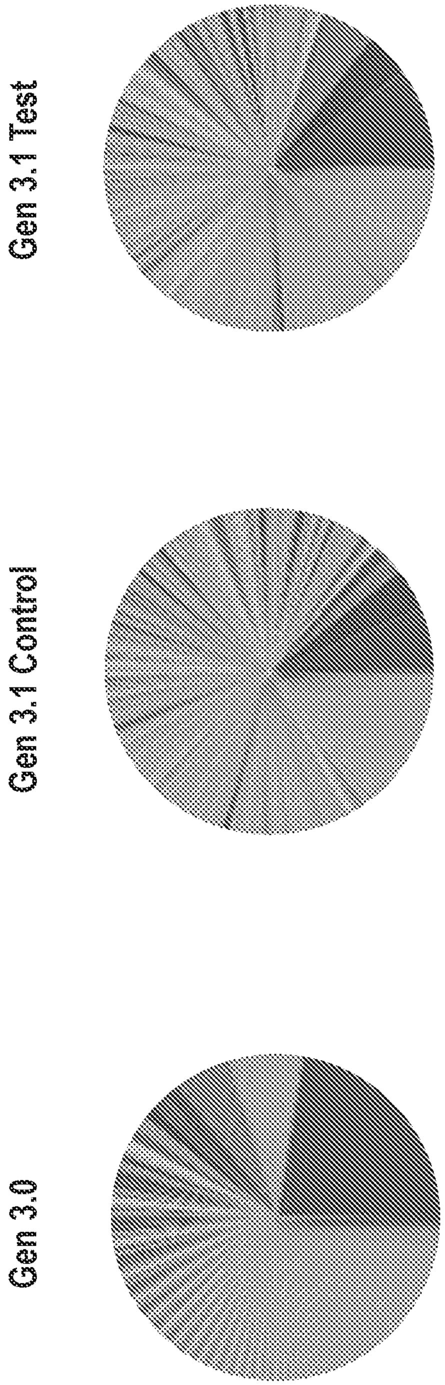

FIG. 91: Comparison of TIL produced by exemplary embodiments of the Gen 3 process (Gen 3.0, Gen 3.1 Control, Gen 3.1 Test) with respect to frequency of unique CDR3 sequences in TIL harvested product from processing of L4064 tumor samples.

FIG. 92: Shown are the components of an exemplary embodiment of the Gen 3 process (Gen 3-Optimized, a 16-17 day process).

FIG. 93: Acceptance criteria table.

FIG. 94: Cell counts reactivation Day.

FIG. 95: Cell counts Scale Up Day.

FIG. 96: Cell counts Harvest L4063.

FIG. 97: Cell counts Harvest L4064.

FIG. 98: Flow data.

FIG. 99: Flow data.

FIG. 100: Flow data.

FIG. 101: Flow data.

Figure 7:
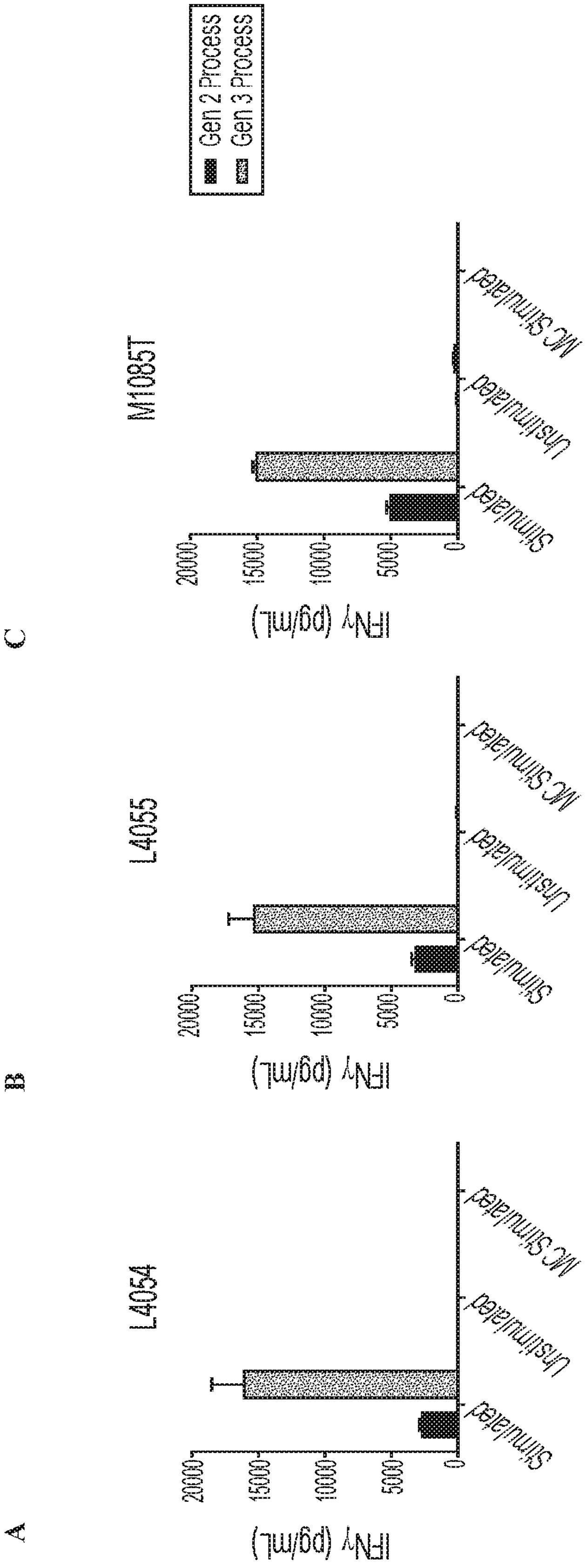
FIG. 7: IFNγ production (pg/mL): (A) L4054, (B) L4055, and (C) M1085T for the Gen 2 and Gen 3 processes: Each bar represented here is mean+SEM for IFNγ levels of stimulated, unstimulated, and media control. Optical density measured at 450 nm.

FIG. 102: IFN-γ production Data Figure 7-L4063.

FIG. 103: Data IFN-γ production Figure 7-L4064.

FIG. 104: ELISA analysis of IL-2 concentration data.

FIG. 105: Metabolic data summary table.

FIG. 106: Summary data.

FIG. 107: Summary data.

Figure 108:
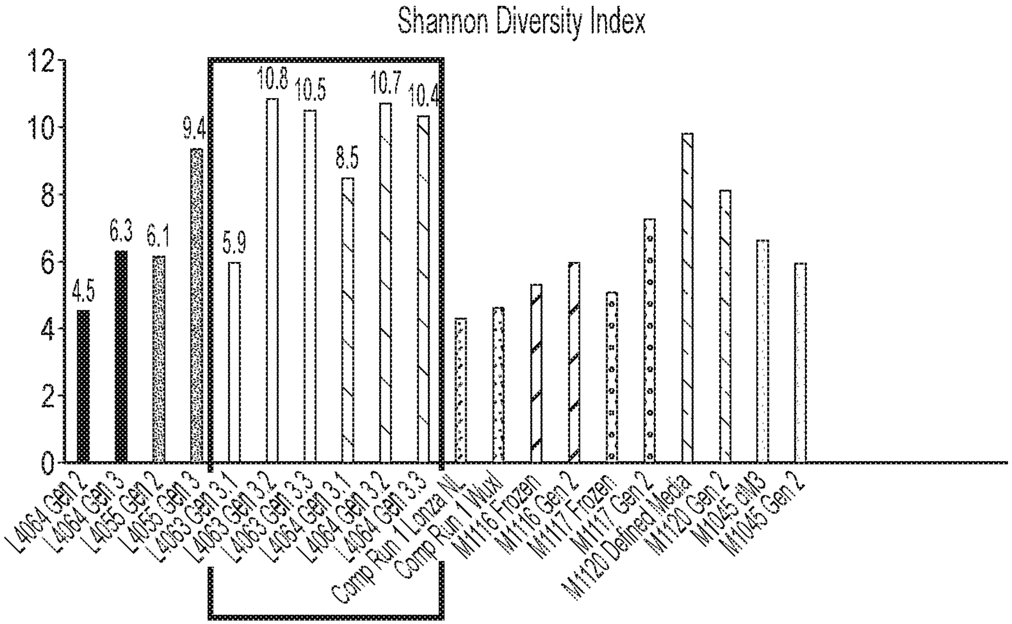

FIG. 108: Shannon diversity index.

FIG. 109: Exemplary Process 2A chart providing an overview of Steps A through F.

FIG. 110: Provides the structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including CH3 and CH2 domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a VH and a VL chain connected by a linker that may comprise hydrophilic residues and Gly and Ser sequences for flexibility, as well as Glu and Lys for solubility.

Figure 111:
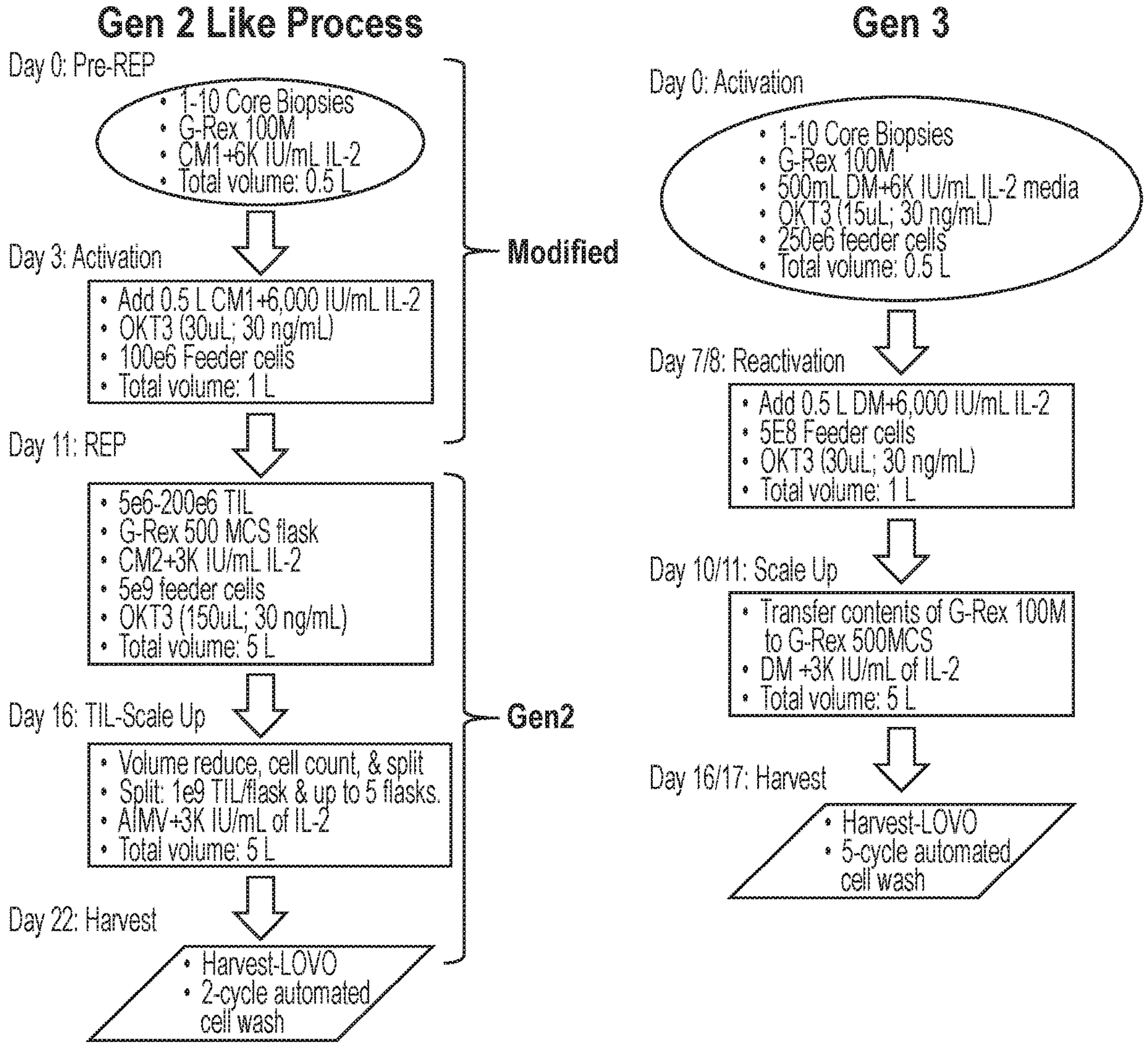

FIG. 111: Overview of Gen 2 and Gen 3 processes using biopsy samples.

Figure 112:
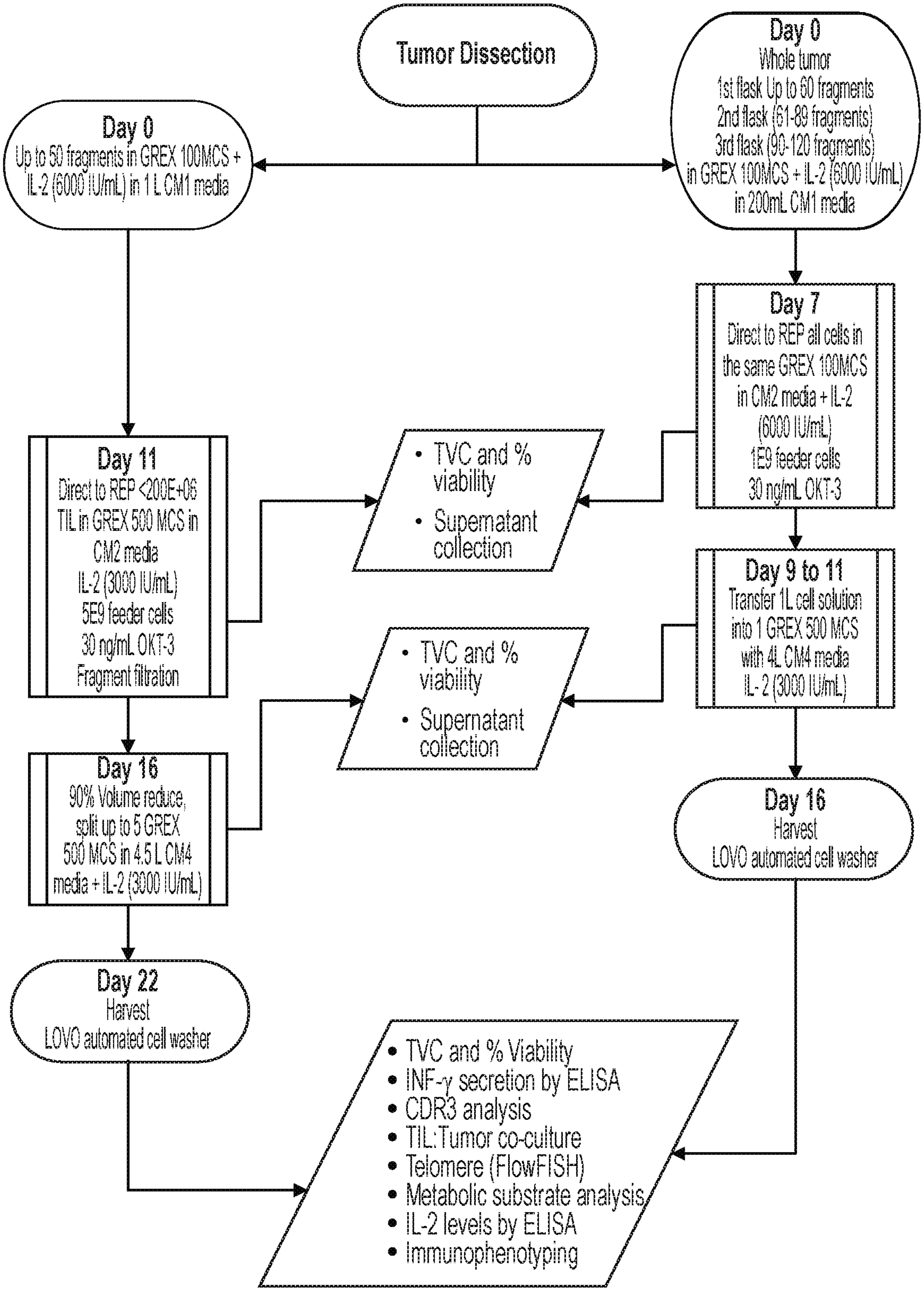

FIG. 112: Exemplary embodiment of Gen 3 processes.

BRIEF DESCRIPTION OF THE SEQUENCE LISTING

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

SEQ ID NO:9 is the amino acid sequence of human 4-1BB.

SEQ ID NO:10 is the amino acid sequence of murine 4-1BB.

SEQ ID NO:11 is the heavy chain for the 4-1BB agonist monoclonal antibody utomilumab (PF-05082566).

SEQ ID NO:12 is the light chain for the 4-1BB agonist monoclonal antibody utomilumab (PF-05082566).

SEQ ID NO:13 is the heavy chain variable region (VH) for the 4-1BB agonist monoclonal antibody utomilumab (PF-05082566).

SEQ ID NO:14 is the light chain variable region (VL) for the 4-1BB agonist monoclonal antibody utomilumab (PF-05082566).

SEQ ID NO:15 is the heavy chain CDR1 for the 4-1BB agonist monoclonal antibody utomilumab (PF-05082566).

SEQ ID NO:16 is the heavy chain CDR2 for the 4-1BB agonist monoclonal antibody utomilumab (PF-05082566).

SEQ ID NO:17 is the heavy chain CDR3 for the 4-1BB agonist monoclonal antibody utomilumab (PF-05082566).

SEQ ID NO:18 is the light chain CDR1 for the 4-1BB agonist monoclonal antibody utomilumab (PF-05082566).

SEQ ID NO:19 is the light chain CDR2 for the 4-1BB agonist monoclonal antibody utomilumab (PF-05082566).

SEQ ID NO:20 is the light chain CDR3 for the 4-1BB agonist monoclonal antibody utomilumab (PF-05082566).

SEQ ID NO:21 is the heavy chain for the 4-1BB agonist monoclonal antibody urelumab (BMS-663513).

SEQ ID NO:22 is the light chain for the 4-1BB agonist monoclonal antibody urelumab (BMS-663513).

SEQ ID NO:23 is the heavy chain variable region ($V_H$) for the 4-1BB agonist monoclonal antibody urelumab (BMS-663513).

SEQ ID NO:24 is the light chain variable region ($V_L$) for the 4-1BB agonist monoclonal antibody urelumab (BMS-663513).

SEQ ID NO:25 is the heavy chain CDR1 for the 4-1BB agonist monoclonal antibody urelumab (BMS-663513).

SEQ ID NO:26 is the heavy chain CDR2 for the 4-1BB agonist monoclonal antibody urelumab (BMS-663513).

SEQ ID NO:27 is the heavy chain CDR3 for the 4-1BB agonist monoclonal antibody urelumab (BMS-663513).

SEQ ID NO:28 is the light chain CDR1 for the 4-1BB agonist monoclonal antibody urelumab (BMS-663513).

SEQ ID NO:29 is the light chain CDR2 for the 4-1BB agonist monoclonal antibody urelumab (BMS-663513).

SEQ ID NO:30 is the light chain CDR3 for the 4-1BB agonist monoclonal antibody urelumab (BMS-663513).

SEQ ID NO:31 is an Fc domain for a TNFRSF agonist fusion protein.

SEQ ID NO:32 is a linker for a TNFRSF agonist fusion protein.

SEQ ID NO:33 is a linker for a TNFRSF agonist fusion protein.

SEQ ID NO:34 is a linker for a TNFRSF agonist fusion protein.

SEQ ID NO:35 is a linker for a TNFRSF agonist fusion protein.

SEQ ID NO:36 is a linker for a TNFRSF agonist fusion protein.

SEQ ID NO:37 is a linker for a TNFRSF agonist fusion protein.

SEQ ID NO:38 is a linker for a TNFRSF agonist fusion protein.

SEQ ID NO:39 is a linker for a TNFRSF agonist fusion protein.

SEQ ID NO:40 is a linker for a TNFRSF agonist fusion protein.

SEQ ID NO:41 is a linker for a TNFRSF agonist fusion protein.

SEQ ID NO:42 is an Fc domain for a TNFRSF agonist fusion protein.

SEQ ID NO:43 is a linker for a TNFRSF agonist fusion protein.

SEQ ID NO:44 is a linker for a TNFRSF agonist fusion protein.

SEQ ID NO:45 is a linker for a TNFRSF agonist fusion protein.

SEQ ID NO:46 is a 4-1BB ligand (4-1BBL) amino acid sequence.

SEQ ID NO:47 is a soluble portion of 4-1BBL polypeptide.

SEQ ID NO:48 is a heavy chain variable region ($V_H$) for the 4-1BB agonist antibody 4B4-1-1 version 1.

SEQ ID NO:49 is a light chain variable region ($V_L$) for the 4-1BB agonist antibody 4B4-1-1 version 1.

SEQ ID NO:50 is a heavy chain variable region ($V_H$) for the 4-1BB agonist antibody 4B4-1-1 version 2.

SEQ ID NO:51 is a light chain variable region ($V_L$) for the 4-1BB agonist antibody 4B4-1-1 version 2.

SEQ ID NO:52 is a heavy chain variable region ($V_H$) for the 4-1BB agonist antibody H39E3-2.

SEQ ID NO:53 is a light chain variable region ($V_L$) for the 4-1BB agonist antibody
H39E3-2.

SEQ ID NO:54 is the amino acid sequence of human OX40.

SEQ ID NO:55 is the amino acid sequence of murine OX40.

SEQ ID NO:56 is the heavy chain for the OX40 agonist monoclonal antibody tavolixizumab (MEDI-0562).

SEQ ID NO:57 is the light chain for the OX40 agonist monoclonal antibody tavolixizumab (MEDI-0562).

SEQ ID NO:58 is the heavy chain variable region ($V_H$) for the OX40 agonist monoclonal antibody tavolixizumab (MEDI-0562).

SEQ ID NO:59 is the light chain variable region ($V_L$) for the OX40 agonist monoclonal antibody tavolixizumab (MEDI-0562).

SEQ ID NO:60 is the heavy chain CDR1 for the OX40 agonist monoclonal antibody tavolixizumab (MEDI-0562).

SEQ ID NO:61 is the heavy chain CDR2 for the OX40 agonist monoclonal antibody tavolixizumab (MEDI-0562).

SEQ ID NO:62 is the heavy chain CDR3 for the OX40 agonist monoclonal antibody tavolixizumab (MEDI-0562).

SEQ ID NO:63 is the light chain CDR1 for the OX40 agonist monoclonal antibody tavolixizumab (MEDI-0562).

SEQ ID NO:64 is the light chain CDR2 for the OX40 agonist monoclonal antibody tavolixizumab (MEDI-0562).

SEQ ID NO:65 is the light chain CDR3 for the OX40 agonist monoclonal antibody tavolixizumab (MEDI-0562).

SEQ ID NO:66 is the heavy chain for the OX40 agonist monoclonal antibody 11D4.

SEQ ID NO:67 is the light chain for the OX40 agonist monoclonal antibody 11D4.

SEQ ID NO:68 is the heavy chain variable region ($V_H$) for the OX40 agonist monoclonal antibody 11D4.

SEQ ID NO:69 is the light chain variable region ($V_L$) for the OX40 agonist monoclonal antibody 11D4.

SEQ ID NO:70 is the heavy chain CDR1 for the OX40 agonist monoclonal antibody 11D4.

SEQ ID NO:71 is the heavy chain CDR2 for the OX40 agonist monoclonal antibody 11D4.

SEQ ID NO:72 is the heavy chain CDR3 for the OX40 agonist monoclonal antibody 11D4.

SEQ ID NO:73 is the light chain CDR1 for the OX40 agonist monoclonal antibody 11D4.

SEQ ID NO:74 is the light chain CDR2 for the OX40 agonist monoclonal antibody 11D4.

SEQ ID NO:75 is the light chain CDR3 for the OX40 agonist monoclonal antibody 11D4.

SEQ ID NO:76 is the heavy chain for the OX40 agonist monoclonal antibody 18D8.

SEQ ID NO:77 is the light chain for the OX40 agonist monoclonal antibody 18D8.

SEQ ID NO:78 is the heavy chain variable region ($V_H$) for the OX40 agonist monoclonal antibody 18D8.

SEQ ID NO:79 is the light chain variable region ($V_L$) for the OX40 agonist monoclonal antibody 18D8.

SEQ ID NO:80 is the heavy chain CDR1 for the OX40 agonist monoclonal antibody 18D8.

SEQ ID NO:81 is the heavy chain CDR2 for the OX40 agonist monoclonal antibody 18D8.

SEQ ID NO:82 is the heavy chain CDR3 for the OX40 agonist monoclonal antibody 18D8.

SEQ ID NO:83 is the light chain CDR1 for the OX40 agonist monoclonal antibody 18D8.

SEQ ID NO:84 is the light chain CDR2 for the OX40 agonist monoclonal antibody 18D8.

SEQ ID NO:85 is the light chain CDR3 for the OX40 agonist monoclonal antibody 18D8.

SEQ ID NO:86 is the heavy chain variable region ($V_H$) for the OX40 agonist monoclonal antibody Hu119-122.

SEQ ID NO:87 is the light chain variable region ($V_L$) for the OX40 agonist monoclonal antibody Hu119-122.

SEQ ID NO:88 is the heavy chain CDR1 for the OX40 agonist monoclonal antibody Hu119-122.

SEQ ID NO:89 is the heavy chain CDR2 for the OX40 agonist monoclonal antibody Hu119-122.

SEQ ID NO:90 is the heavy chain CDR3 for the OX40 agonist monoclonal antibody Hu119-122.

SEQ ID NO:91 is the light chain CDR1 for the OX40 agonist monoclonal antibody Hu119-122.

SEQ ID NO:92 is the light chain CDR2 for the OX40 agonist monoclonal antibody Hu119-122.

SEQ ID NO:93 is the light chain CDR3 for the OX40 agonist monoclonal antibody Hu119-122.

SEQ ID NO:94 is the heavy chain variable region ($V_H$) for the OX40 agonist monoclonal antibody Hu106-222.

SEQ ID NO:95 is the light chain variable region ($V_L$) for the OX40 agonist monoclonal antibody Hu106-222.

SEQ ID NO:96 is the heavy chain CDR1 for the OX40 agonist monoclonal antibody Hu106-222.

SEQ ID NO:97 is the heavy chain CDR2 for the OX40 agonist monoclonal antibody Hu106-222.

SEQ ID NO:98 is the heavy chain CDR3 for the OX40 agonist monoclonal antibody Hu106-222.

SEQ ID NO:99 is the light chain CDR1 for the OX40 agonist monoclonal antibody Hu106-222.

SEQ ID NO:100 is the light chain CDR2 for the OX40 agonist monoclonal antibody Hu106-222.

SEQ ID NO:101 is the light chain CDR3 for the OX40 agonist monoclonal antibody Hu106-222.

SEQ ID NO:102 is an OX40 ligand (OX40L) amino acid sequence.

SEQ ID NO:103 is a soluble portion of OX40L polypeptide.

SEQ ID NO:104 is an alternative soluble portion of OX40L polypeptide.

SEQ ID NO:105 is the heavy chain variable region ($V_H$) for the OX40 agonist monoclonal antibody 008.

SEQ ID NO:106 is the light chain variable region ($V_L$) for the OX40 agonist monoclonal antibody 008.

SEQ ID NO:107 is the heavy chain variable region ($V_H$) for the OX40 agonist monoclonal antibody 011.

SEQ ID NO:108 is the light chain variable region ($V_L$) for the OX40 agonist monoclonal antibody 011.

SEQ ID NO:109 is the heavy chain variable region ($V_H$) for the OX40 agonist monoclonal antibody 021.

SEQ ID NO:110 is the light chain variable region ($V_L$) for the OX40 agonist monoclonal antibody 021.

SEQ ID NO:111 is the heavy chain variable region ($V_H$) for the OX40 agonist monoclonal antibody 023.

SEQ ID NO:112 is the light chain variable region ($V_L$) for the OX40 agonist monoclonal antibody 023.

SEQ ID NO:113 is the heavy chain variable region ($V_H$) for an OX40 agonist monoclonal antibody.

SEQ ID NO:114 is the light chain variable region ($V_L$) for an OX40 agonist monoclonal antibody.

SEQ ID NO:115 is the heavy chain variable region ($V_H$) for an OX40 agonist monoclonal antibody.

SEQ ID NO:116 is the light chain variable region ($V_L$) for an OX40 agonist monoclonal antibody.

SEQ ID NO:117 is the heavy chain variable region ($V_H$) for a humanized OX40 agonist monoclonal antibody.

SEQ ID NO:118 is the heavy chain variable region ($V_H$) for a humanized OX40 agonist monoclonal antibody.

SEQ ID NO:119 is the light chain variable region ($V_L$) for a humanized OX40 agonist monoclonal antibody.

SEQ ID NO:120 is the light chain variable region ($V_L$) for a humanized OX40 agonist monoclonal antibody.

SEQ ID NO:121 is the heavy chain variable region ($V_H$) for a humanized OX40 agonist monoclonal antibody.

SEQ ID NO:122 is the heavy chain variable region ($V_H$) for a humanized OX40 agonist monoclonal antibody.

SEQ ID NO:123 is the light chain variable region ($V_L$) for a humanized OX40 agonist monoclonal antibody.

SEQ ID NO:124 is the light chain variable region ($V_L$) for a humanized OX40 agonist monoclonal antibody.

SEQ ID NO:125 is the heavy chain variable region ($V_H$) for an OX40 agonist monoclonal antibody.

SEQ ID NO:126 is the light chain variable region ($V_L$) for an OX40 agonist monoclonal antibody.

DETAILED DESCRIPTION OF THE INVENTION

I. Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly obtained" or "freshly isolated"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion. In some embodiments, REP expansion is done to provide populations of $2.3\times10^{10}$-$13.7\times10^{10}$.

By "cryopreserved TILs" herein is meant that TILs, either primary, bulk, or expanded (REP TILs), are treated and stored in the range of about −150° C. to −60° C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 ($CCR7^{hi}$) and CD62L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 ($CCR7^{lo}$) and are heterogeneous or low for CD62L expression) ($CD62L^{lo}$. The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perforin.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is not opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The term "fine needle aspirate" or FNA refers to a type of biopsy procedure that can be employed for sampling or diagnostic procedures, including tumor sampling, in which a sample is taken but the tumor is not removed or resected. In fine needle aspiration, a hollow needle, for example 25-18 gauge, is inserted into the tumor or into an area containing the tumor and fluid and cells (including tissue) are obtained for further analysis or expansion, as described herein. With an FNA, the cells are removed without preserving the histological architecture of the tissue cells. An FNA can comprise TILs. In some instances, a fine needle aspiration biopsy is performed using an ultrasound-guided fine needle aspiration biopsy needle. FNA needles are commercially available from Becton Dickinson, Covidien, and the like.

The term "core biopsy" or "core needle biopsy" refers to a type of biopsy procedure that can be employed for sampling or diagnostic procedures, including tumor sampling, in which a sample is taken but the tumor is not removed or resected. In a core biopsy, a hollow needle, for example 16-11 gauge, is inserted into the tumor or into an area containing the tumor and fluid and cells (including tissue) are obtained for further analysis or expansion, as described herein. With a core biopsy, the cells can be removed with some preservation of the histological architecture of the tissue cells, given the larger needle size as compared to a FNA. The core biopsy needle is generally of a gauge size that is able to preserve at least some portion of the histological architecture of the tumor. A core biopsy can comprise TILs. In some instances, a core needle biopsy is performed using a biopsy instrument, a vacuum-assisted core-needle biopsy instrument, a steretactically guided core-needle biopsy instrument, an ultrasound-guided core-needle biopsy instrument, an MRI-guided core-needle biopsy instrument commercially available from Bard Medical, Becton Dickinson, and the like.

The terms "peripheral blood mononuclear cells" and "PBMCs" refers to a peripheral blood cell having a round nucleus, including lymphocytes (T cells, B cells, NK cells) and monocytes. When used as antigen-presenting cells (PBMCs are a type of antigen-presenting cell), the peripheral blood mononuclear cells are irradiated allogeneic peripheral blood mononuclear cells.

The terms "peripheral blood lymphocytes" and "PBLs" refer to T cells expanded from peripheral blood. In some embodiments, PBLs are separated from whole blood or apheresis product from a donor. In some embodiments, PBLs are separated from whole blood or apheresis product from a donor by positive or negative selection of a T cell phenotype, such as the T cell phenotype of CD3+CD45+.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

Amino acid sequences of muromonab.

| Identifier | Sequence (One-Letter Amino Acid Symbols) | |
|---|---|---|
| SEQ ID NO: 1 | QVQLQQSGAE LARPGASVKM SCKASGYTFT RYTMHWVKQR PGQGLEWIGY INPSRGYTNY | 60 |
| Muromonab | NQKFKDKATL TTDKSSSTAY MQLSSLTSED SAVYYCARYY DDHYCLDYWG QGTTLTVSSA | 120 |
| heavy chain | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 | QIVLTQSPAI MSASPGEKVT MTCSASSSVS YMNWYQQKSG TSPKRWIYDT SKLASGVPAH | 60 |
| Muromonab | FRGSGSGTSY SLTISGMEAE DAATYYCQQW SSNPFTFGSG TKLEINRADT APTVSIFPPS | 120 |
| light chain | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, *J. Immunol.* 2004, 172, 3983-88 and Malek, *Annu. Rev. Immunol.* 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELLGRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, *Respir. Res.* 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and $IgG_1$ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, *Blood* 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of recombinant human IL-7 suitable for use in the invention is given in Table 2 (SEQ ID NO:6).

The term "IL-15" (also referred to herein as "IL15") refers to the T cell growth factor known as interleukin-15, and includes all forms of IL-2 including human and mammalian

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG | 60 |
| | NNERIINVSI KKLKRKPPST NAGRRQKHRL TCPSCDSYEK KPPKEFLERF KSLLQKMIHQ | 120 |
| | HLSSRTHGSE DS | 132 |

forms, conservative amino acid substitutions, glycoforms, biosimilars, and variants thereof. IL-15 is described, e.g., in Fehniger and Caligiuri, *Blood* 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, *Nat. Rev. Drug. Disc.* 2014, 13, 379-95, the disclosure of which is incorporated by reference herein. IL-21 is primarily produced by natural killer T cells and activated human $CD4^+$ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "a tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^7$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically modified cytotoxic lymphocytes) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy", "hematologic malignancy" or terms of correlative meaning refer to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs). TILs obtained from liquid tumors, including liquid tumors circulating in peripheral blood, may also be referred to herein as PBLs. The terms MIL, TIL, and PBL are used interchangeably herein and differ only based on the tissue type from which the cells are derived.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.,* 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as “immunosuppressive conditioning”) on the patient prior to the introduction of the rTILs of the invention.

The terms “co-administration,” “co-administering,” “administered in combination with,” “administering in combination with,” “simultaneous,” and “concurrent,” as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term “effective amount” or “therapeutically effective amount” refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms “treatment”, “treating”, “treat”, and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. “Treatment”, as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. “Treatment” is also meant to encompass delivery of an agent in order to provide for a pharmacologic effect, even in the absence of a disease or condition. For example, “treatment” encompasses delivery of a composition that can elicit an immune response or confer immunity in the absence of a disease condition, e.g., in the case of a vaccine.

The term “heterologous” when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms “sequence identity,” “percent identity,” and “sequence percent identity” (or synonyms thereof, e.g., “99% identical”) in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term “variant” encompasses but is not limited to proteins, antibodies or fusion proteins which comprise an amino acid sequence which differs from the amino acid sequence of a reference protein, antibody or fusion protein by way of one or more substitutions, deletions and/or additions at certain positions within or adjacent to the amino acid sequence of the reference antibody, protein, or fusion protein. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody, protein, or fusion protein. The term variant also includes pegylated antibodies or proteins.

By “tumor infiltrating lymphocytes” or “TILs” herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. “Primary TILs” are those that are obtained from patient tissue samples as outlined herein (sometimes referred to as “freshly obtained” or “freshly isolated”), and “secondary TILs” are any TIL cell populations that have been expanded or proliferated as discussed herein, including, but not limited to bulk TILs, expanded TILs (“REP TILs”) as well as “reREP TILs” as discussed herein. reREP TILs can include for example second expansion TILs or second additional expansion TILs (such as, for example, those described in Step D of FIG. 1, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL. TILS may be considered potent if, for example, interferon (IFNγ) release is greater than about 50 pg/mL, greater than about 100 pg/mL, greater than about 150 pg/mL, or greater than about 200 pg/mL, greater than about 300 pg/mL, greater than about 400 pg/mL, greater than about 500 pg/mL, greater than about 600 pg/mL, greater than about 700 pg/mL, greater than about 800 pg/mL, greater than about 900 pg/mL, greater than about 1000 pg/mL.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

II. TIL Manufacturing Processes (Embodiments of GEN3 Processes, Optionally Including Defined Media)

Without being limited to any particular theory, it is believed that the priming first expansion that primes an activation of T cells followed by the rapid second expansion that boosts the activation of T cells as described in the methods of the invention allows the preparation of expanded T cells that retain a "younger" phenotype, and as such the expanded T cells of the invention are expected to exhibit greater cytotoxicity against cancer cells than T cells expanded by other methods. In particular, it is believed that an activation of T cells that is primed by exposure to an anti-CD3 antibody (e.g. OKT-3), IL-2 and optionally antigen-presenting cells (APCs) and then boosted by subsequent exposure to additional anti-CD-3 antibody (e.g. OKT-3), IL-2 and APCs as taught by the methods of the invention limits or avoids the maturation of T cells in culture, yielding a population of T cells with a less mature phenotype, which T cells are less exhausted by expansion in culture and exhibit greater cytotoxicity against cancer cells. In some embodiments, the step of rapid second expansion is split into a plurality of steps to achieve a scaling up of the culture by: (a) performing the rapid second expansion by culturing T cells in a small scale culture in a first container, e.g., a G-REX 100MCS container, for a period of about 3 to 4 days, and then (b) effecting the transfer of the T cells in the small scale culture to a second container larger than the first container, e.g., a G-REX 500MCS container, and culturing the T cells from the small scale culture in a larger scale culture in the second container for a period of about 4 to 7 days. In some embodiments, the step of rapid expansion is split into a plurality of steps to achieve a scaling out of the culture by: (a) performing the rapid second expansion by culturing T cells in a first small scale culture in a first container, e.g., a G-REX 100MCS container, for a period of about 3 to 4 days, and then (b) effecting the transfer and apportioning of the T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the T cells from first small scale culture transferred to such second container is cultured in a second small scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100MCS container, for a period of about 3 to 4 days, and then (b) effecting the transfer and apportioning of the T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the T cells from the small scale culture transferred to such second container is cultured in a larger scale culture for a period of about 4 to 7 days. In some embodiments, the step of rapid expansion is split into a plurality of steps to achieve a scaling out and scaling up of the culture by: (a) performing the rapid second expansion by culturing T cells in a small scale culture in a first container, e.g., a G-REX 100MCS container, for a period of about 4 days, and then (b) effecting the transfer and apportioning of the T cells from the small scale culture into and amongst 2, 3 or 4 second containers that are larger in size than the first container, e.g., G-REX 500MCS containers, wherein in each second container the portion of the T cells from the small scale culture transferred to such second container is cultured in a larger scale culture for a period of about 5 days.

In some embodiments, the rapid second expansion is performed after the activation of T cells effected by the priming first expansion begins to decrease, abate, decay or subside.

In some embodiments, the rapid second expansion is performed after the activation of T cells effected by the priming first expansion has decreased by at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

In some embodiments, the rapid second expansion is performed after the activation of T cells effected by the priming first expansion has decreased by a percentage in the range of at or about 1% to 100%.

In some embodiments, the rapid second expansion is performed after the activation of T cells effected by the priming first expansion has decreased by a percentage in the range of at or about 1% to 10%, 10% to 20%, 20% to 30%, 30% to 40%, 40% to 50%, 50% to 60%, 60% to 70%, 70% to 80%, 80% to 90%, or 90% to 100%.

In some embodiments, the rapid second expansion is performed after the activation of T cells effected by the priming first expansion has decreased by at least at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

In some embodiments, the rapid second expansion is performed after the activation of T cells effected by the priming first expansion has decreased by up to at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In some embodiments, the decrease in the activation of T cells effected by the priming first expansion is determined by a reduction in the amount of interferon gamma released by the T cells in response to stimulation with antigen.

In some embodiments, the priming first expansion of T cells is performed during a period of up to at or about 7 days or about 8 days.

In some embodiments, the priming first expansion of T cells is performed during a period of up to at or about 1 day, 2 days, 3 days, 4 days, 5 days, 6 days, 7 days, or 8 days.

In some embodiments, the priming first expansion of T cells is performed during a period of 1 day, 2 days, 3 days, 4 days, 5 days, 6 days, 7 days, or 8 days.

In some embodiments, the rapid second expansion of T cells is performed during a period of up to at or about 11 days.

In some embodiments, the rapid second expansion of T cells is performed during a period of up to at or about 1 day, 2 days, 3 days, 4 days, 5 days, 6 days, 7 days, 8 days, 9 days, 10 days or 11 days.

In some embodiments, the rapid second expansion of T cells is performed during a period of 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 7 days and the rapid second expansion of T cells is performed during a period of from at or about 1 day to at or about 11 days.

In some embodiments, the priming first expansion of T cells is performed during a period of up to at or about 1 day, 2 days, 3 days, 4 days, 5 days, 6 days, 7 days, or 8 days and the rapid second expansion of T cells is performed during a period of up to at or about 1 day, 2 days, 3 days, 4 days, 5 days, 6 days, 7 days, 8 days, 9 days, 10 days or 11 days.

In some embodiments, the priming first expansion of T cells is performed during a period of from at or about 1 day to at or about 8 days and the rapid second expansion of T cells is performed during a period of from at or about 1 day to at or about 9 days.

In some embodiments, the priming first expansion of T cells is performed during a period of 8 days and the rapid second expansion of T cells is performed during a period of 9 days.

In some embodiments, the priming first expansion of T cells is performed during a period of from at or about 1 day to at or about 7 days and the rapid second expansion of T cells is performed during a period of from at or about 1 day to at or about 9 days.

In some embodiments, the priming first expansion of T cells is performed during a period of 7 days and the rapid second expansion of T cells is performed during a period of 9 days.

In some embodiments, the T cells are tumor infiltrating lymphocytes (TILs).

In some embodiments, the T cells are marrow infiltrating lymphocytes (MILs).

In some embodiments, the T cells are peripheral blood lymphocytes (PBLs).

In some embodiments, the T cells are obtained from a donor suffering from a cancer.

In some embodiments, the T cells are TILs obtained from a tumor excised from a patient suffering from a cancer.

In some embodiments, the T cells are MILs obtained from bone marrow of a patient suffering from a hematologic malignancy.

In some embodiments, the T cells are PBLs obtained from peripheral blood mononuclear cells (PBMCs) from a donor. In some embodiments, the donor is suffering from a cancer. In some embodiments, the cancer is the cancer is selected from the group consisting of melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HN- SCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy.

In certain aspects of the present disclosure, immune effector cells, e.g., T cells, can be obtained from a unit of blood collected from a subject using any number of techniques known to the skilled artisan, such as FICOLL separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. In one aspect, T cells are isolated from peripheral blood lymphocytes by lysing the red blood cells and depleting the monocytes, for example, by centrifugation through a PERCOLL gradient or by counterflow centrifugal elutriation.

In some embodiments, the T cells are PBLs separated from whole blood or apheresis product enriched for lymphocytes from a donor. In some embodiments, the donor is suffering from a cancer. In some embodiments, the cancer is the cancer is selected from the group consisting of melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, and renal cell carcinoma. In some embodiments, the donor is suffering from a tumor. In some embodiments, the tumor is a liquid tumor. In some embodiments, the tumor is a solid tumor. In some embodiments, the donor is suffering from a hematologic malignancy. In some embodiments, the PBLs are isolated from whole blood or apheresis product enriched for lymphocytes by using positive or negative selection methods, i.e., removing the PBLs using a marker(s), e.g., CD3+ CD45+, for T cell phenotype, or removing non-T cell phenotype cells, leaving PBLs. In other embodiments, the PBLs are isolated by gradient centrifugation. Upon isolation of PBLs from donor tissue, the priming first expansion of PBLs can be initiated by seeding a suitable number of isolated PBLs (in some embodiments, approximately $1\times10^7$ PBLs) in the priming first expansion culture according to the priming first expansion step of any of the methods described herein.

Figure 30:
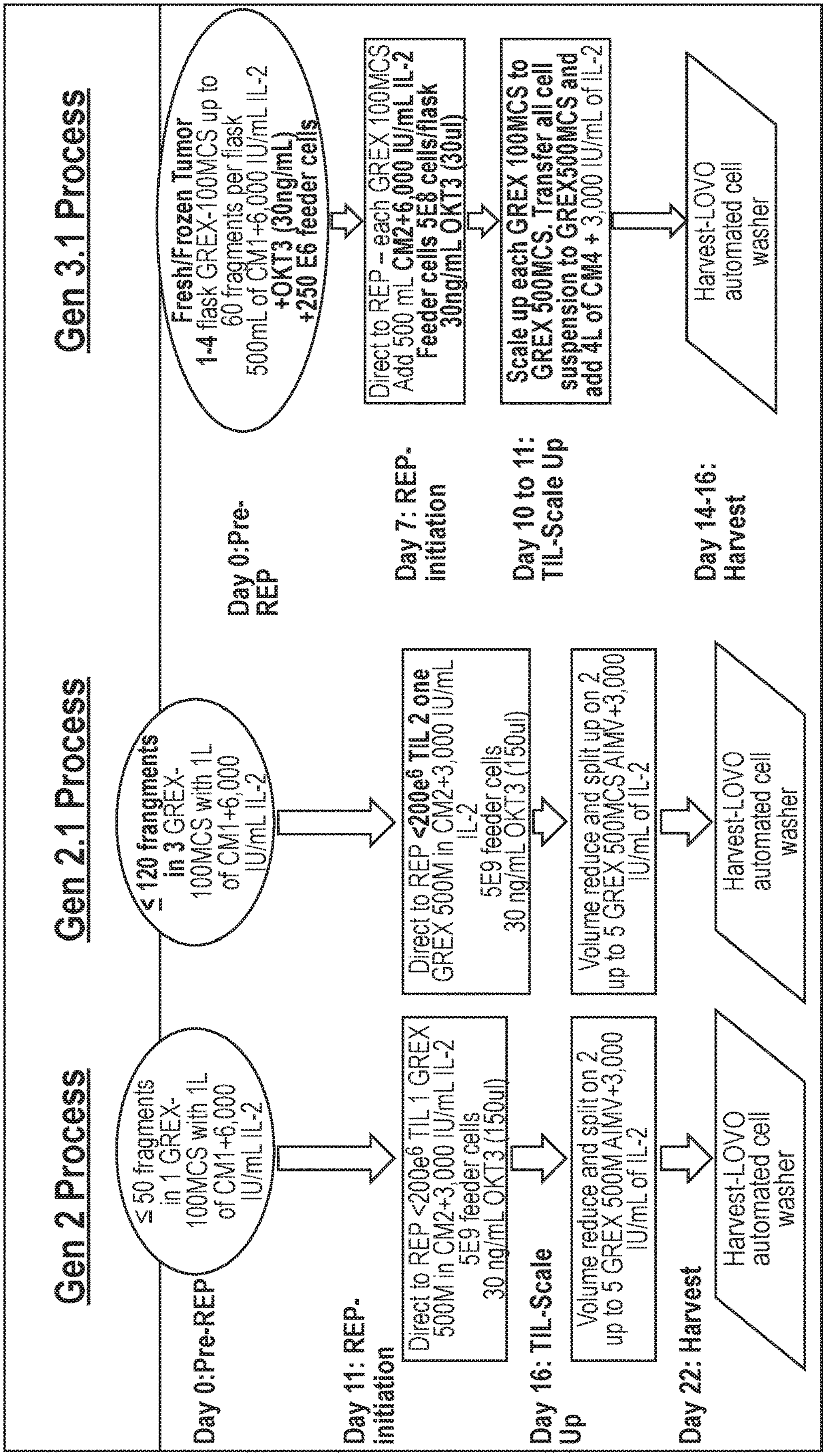
FIG. 30: Shows a comparison between various Gen 2 (2A process) and the Gen 3.1 process embodiment.
Figure 37:
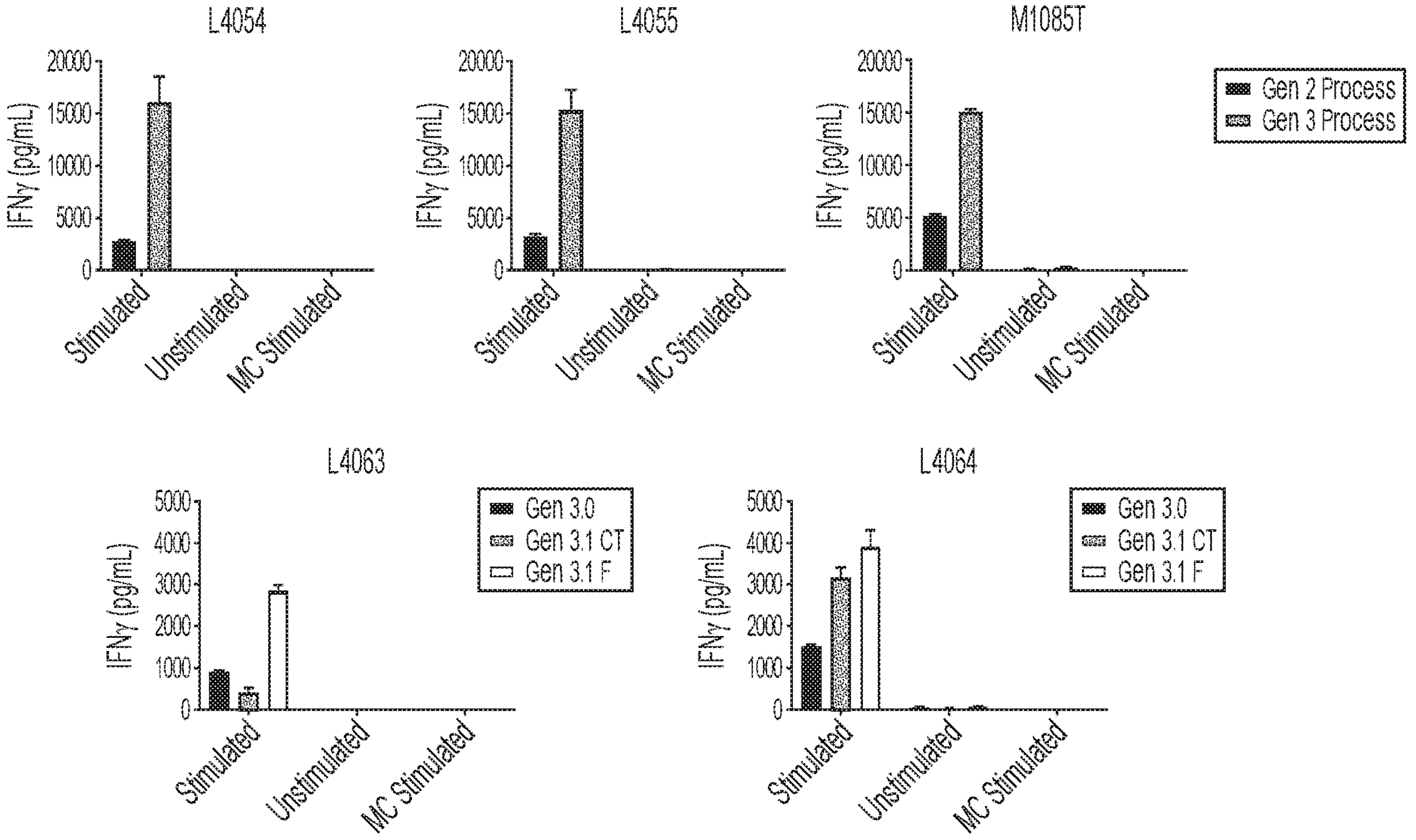
FIG. 37: Higher production of IFNγ on Gen 3 final product. IFNγ analysis (by ELISA) was assessed in the culture frozen supernatant to compared both processes. For each tumor overnight stimulation with coated anti-CD3 plate, using fresh TIL product on each Gen 2 (e.g., day 22) and Gen 3 process (e.g., day 16). Each bar represents here are IFNγlevels of stimulated, unstimulated and media control.
Figure 38:
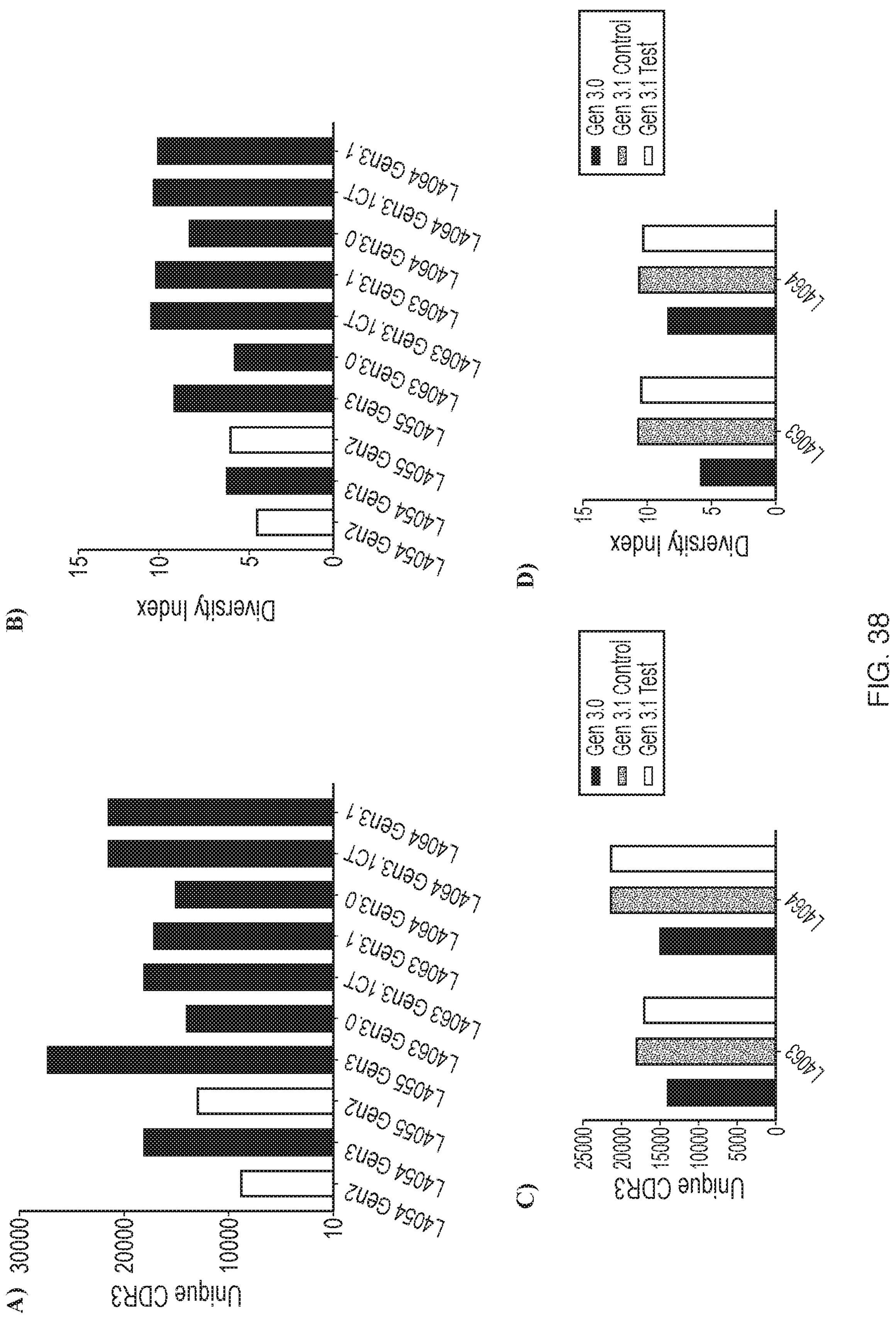
FIG. 38: A) Unique CDR3 sequence analysis for TIL final product: Columns show the number of unique TCR B clonotypes identified from $1\times10^6$ cells collected on Gen 2 (e.g., day 22) and Gen 3 process (e.g., day 14-16). Gen 3 shows higher clonal diversity compared to Gen 2 based on the number of unique peptide CDRs within the sample. B) Diversity Index for TIL final product: Shanon entropy diversity index is a more reliable a common metric for comparison. Gen 3 showed a slightly higher diversity than Gen 2. C) Unique CDR3 sequence analysis for TIL final product on L4063 and L4064 under Gen 3, Gen 3.1 control and Gen 3.1 test processes. Columns show the number of unique TCR B clonotypes identified from $1\times10^6$ cells collected on Harvest day 16, for Gen 3 and Gen 3.1 processes. Gen 3.1 showed a slightly higher clonal diversity compared to Gen 3 based on the number of unique peptide CDRs within the sample. D) Diversity Index for TIL final product on L4063 and L4064 under Gen 3. Gen 3.1 control and Gen 3.1 Test processes. Shannon entropy diversity index is a more reliable and common metric for comparison. Gen 3.1 conditions on L4063 and L4064 showed a slightly higher diversity than Gen 3 process.
Figure 39:
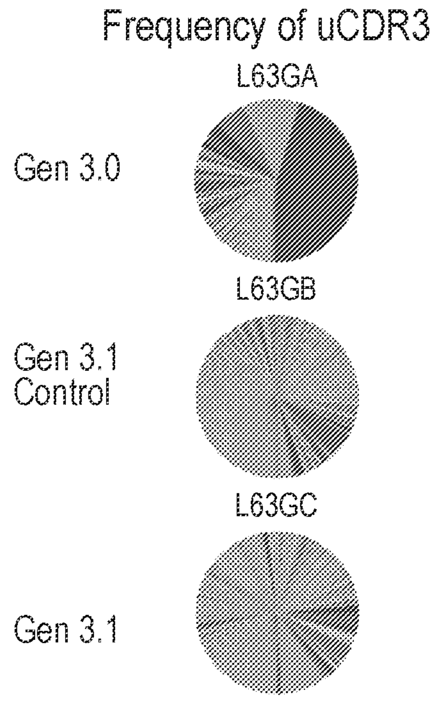
FIG. 39: 199 sequences are shared between Gen 3 and Gen 2 final product, corresponding to 97.07% of top 80% of unique CDR3 sequences from Gen 2 shared with Gen 3 final product.
Figure 40:
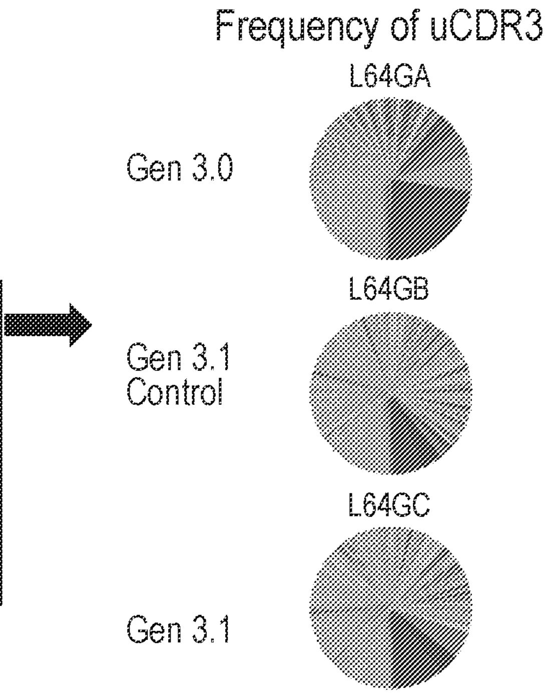
FIG. 40: 1833 sequences are shared between Gen 3 and Gen 2 final product, corresponding to 99.45% of top 80% of unique CDR3 sequences from Gen 2 shared with Gen 3 final product.
Figure 41:
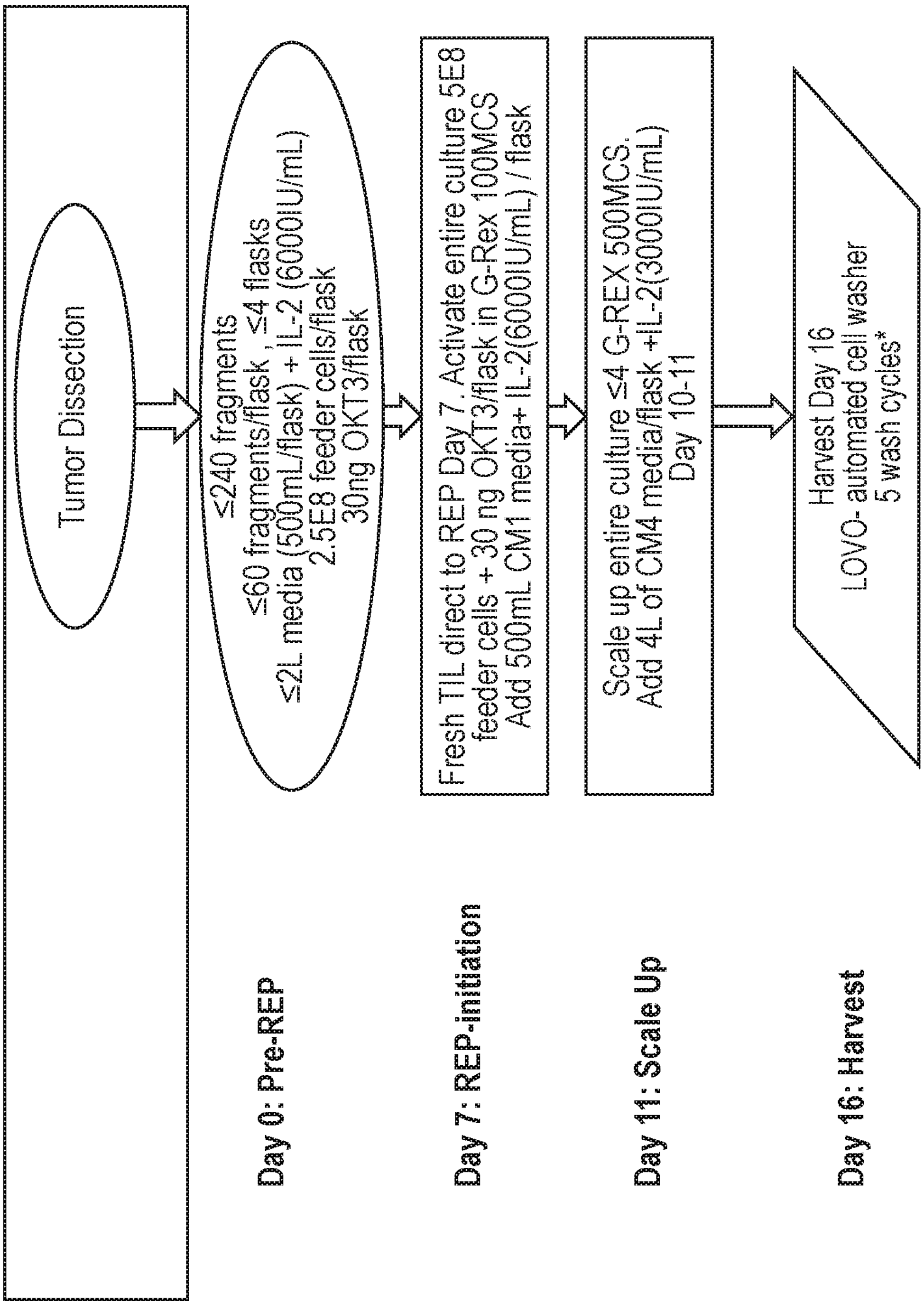
FIG. 41: Schematic of an exemplary embodiment of the Gen 3 process (a 16-day process).

An exemplary TIL process known as process 3 (also referred to herein as GEN3) containing some of these features is depicted in FIG. 1 (in particular, e.g., FIG. 1B and/or FIG. 1C), and some of the advantages of this embodiment of the present invention over process 2A are described in FIGS. 1, 2, 30, and 31 (in particular, e.g., FIG. 1B and/or FIG. 1C). Two embodiments of process 3 are shown in FIGS. 1 and 30 (in particular, e.g., FIG. 1B and/or FIG. 1C). Process 2A or Gen 2 is also described in U.S. Patent Publication No. 2018/.0280436, incorporated by reference herein in its entirety.

As discussed and generally outlined herein, TILs are taken from a patient sample and manipulated to expand their number prior to transplant into a patient using the TIL expansion process described herein and referred to as Gen 3. In some embodiments, the TILs may be optionally genetically manipulated as discussed below. In some embodiments, the TILs may be cryopreserved prior to or after expansion. Once thawed, they may also be restimulated to increase their metabolism prior to infusion into a patient.

In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is shortened to 1 to 8 days and the rapid second expansion (including processes referred to herein as Rapid Expansion Protocol (REP) as well as processes shown in FIG. 1 (in particular, e.g., FIG. 1B and/or FIG. 1C) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is shortened to 1 to 8 days and the rapid second expansion (including processes referred to herein as Rapid Expansion Protocol (REP) as well as processes shown in FIG. 1 (in particular, e.g., FIG. 1B and/or FIG. 1C) as Step D) is shortened to 1 to 8 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is shortened to 1 to 7 days and the rapid second expansion (including processes referred to herein as Rapid Expansion Protocol (REP) as well as processes shown in FIG. 1 (in particular, e.g., FIG. 1B and/or FIG. 1C) as Step D) is shortened to 1 to 9 days, as discussed in detail below as well as in the examples and figures. In some embodiments, the priming first expansion (including processes referred herein as the pre-Rapid Expansion (Pre-REP), as well as processes shown in FIG. 1 (in particular, e.g., FIG. 1B and/or FIG. 1C) as Step B) is 1 to 7 days and the rapid second expansion (including processes referred to herein as Rapid Expansion Protocol (REP) as well as processes shown in FIG. 1 (in particular, e.g., FIG. 1B and/or FIG. 1C) as Step D) is 1 to 10 days, as discussed in detail below as well as in the examples and figures. In some embodiments, the priming first expansion (for example, an expansion described as Step B in FIG. 1 (in particular, e.g., FIG. 1B and/or FIG. 1C) is shortened to 8 days and the rapid second expansion (for example, an expansion as described in Step D in FIG. 1 (in particular, e.g., FIG. 1B and/or FIG. 1C) is 7 to 9 days. In some embodiments, the priming first expansion (for example, an expansion described as Step B in FIG. 1 (in particular, e.g., FIG. 1B and/or FIG. 1C) is 8 days and the rapid second expansion (for example, an expansion as described in Step D in FIG. 1 (in particular, e.g., FIG. 1B and/or FIG. 1C) is 8 to 9 days. In some embodiments, the priming first expansion (for example, an expansion described as Step B in FIG. 1 (in particular, e.g., FIG. 1B and/or FIG. 1C) is shortened to 7 days and the rapid second expansion (for example, an expansion as described in Step D in FIG. 1 (in particular, e.g., FIG. 1B and/or FIG. 1C) is 7 to 8 days. In some embodiments, the priming first expansion (for example, an expansion described as Step B in FIG. 1 (in particular, e.g., FIG. 1B and/or FIG. 1C) is shortened to 8 days and the rapid second expansion (for example, an expansion as described in Step D in FIG. 1 (in particular, e.g., FIG. 1B and/or FIG. 1C) is 8 days. In some embodiments, the priming first expansion (for example, an expansion described as Step B in FIG. 1 (in particular, e.g., FIG. 1B and/or FIG. 1C) is 8 days and the rapid second expansion (for example, an expansion as described in Step D in FIG. 1 (in particular, e.g., FIG. 1B and/or FIG. 1C) is 9 days. In some embodiments, the priming first expansion (for example, an expansion described as Step B in FIG. 1 (in particular, e.g., FIG. 1B and/or FIG. 1C) is 8 days and the rapid second expansion (for example, an expansion as described in Step D in FIG. 1 (in particular, e.g., FIG. 1B and/or FIG. 1C) is 10 days. In some embodiments, the priming first expansion (for example, an expansion described as Step B in FIG. 1 (in particular, e.g., FIG. 1B and/or FIG. 1C) is 7 days and the rapid second expansion (for example, an expansion as described in Step D in FIG. 1 (in particular, e.g., FIG. 1B and/or FIG. 1C) is 7 to 10 days. In some embodiments, the priming first expansion (for example, an expansion described as Step B in FIG. 1 (in particular, e.g., FIG. 1B and/or FIG. 1C) is 7 days and the rapid second expansion (for example, an expansion as described in Step D in FIG. 1 (in particular, e.g., FIG. 1B and/or FIG. 1C) is 8 to 10 days. In some embodiments, the priming first expansion (for example, an expansion described as Step B in FIG. 1 (in particular, e.g., FIG. 1B and/or FIG. 1C) is 7 days and the rapid second expansion (for example, an expansion as described in Step D in FIG. 1 (in particular, e.g., FIG. 1B and/or FIG. 1C) is 9 to 10 days. In some embodiments, the priming first expansion (for example, an expansion described as Step B in FIG. 1 (in particular, e.g., FIG. 1B and/or FIG. 1C) is shortened to 7 days and the rapid second expansion (for example, an expansion as described in Step D in FIG. 1 (in particular, e.g., FIG. 1B and/or FIG. 1C) is 7 to 9 days. In some embodiments, the combination of the priming first expansion and rapid second expansion (for example, expansions described as Step B and Step D in FIG. 1 (in particular, e.g., FIG. 1B and/or FIG. 1C) is 14-16 days, as discussed in detail below and in the examples and figures. Particularly, it is considered that certain embodiments of the present invention comprise a priming first expansion step in which TILs are activated by exposure to an anti-CD3 antibody, e.g., OKT-3 in the presence of IL-2 or exposure to an antigen in the presence of at least IL-2 and an anti-CD3 antibody e.g. OKT-3. In certain embodiments, the TILs which are activated in the priming first expansion step as described above are a first population of TILs i.e., which are a primary cell population.

The "Step" Designations A, B, C, etc., below are in reference to the non-limiting example in FIG. 1 (in particular, e.g., FIG. 1B and/or FIG. 1C) and in reference to certain non-limiting embodiments described herein. The ordering of the Steps below and in FIG. 1 (in particular, e.g., FIG. 1B and/or FIG. 1C) is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample ("primary TILs") or from circulating lymphocytes, such as peripheral blood lymphocytes, including peripheral blood lymphocytes having TIL-like characteristics, and are then expanded into a larger population for further manipulation as described herein, optionally cryopreserved, and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma. In some embodiments, useful TILs are obtained from malignant melanoma tumors, as these have been reported to have particularly high levels of TILs.

Once obtained, the tumor sample is generally fragmented using sharp dissection into small pieces of between 1 to about 8 $mm^3$, with from about 2-3 $mm^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% CO2, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

As indicated above, in some embodiments, the TILs are derived from solid tumors. In some embodiments, the solid tumors are not fragmented. In some embodiments, the solid tumors are not fragmented and are subjected to enzymatic digestion as whole tumors. In some embodiments, the tumors are digested in in an enzyme mixture comprising collagenase, DNase, and hyaluronidase. In some embodiments, the tumors are digested in in an enzyme mixture comprising collagenase, DNase, and hyaluronidase for 1-2 hours. In some embodiments, the tumors are digested in in an enzyme mixture comprising collagenase, DNase, and hyaluronidase for 1-2 hours at 37° C., 5% $CO_2$. In some embodiments, the tumors are digested in in an enzyme mixture comprising collagenase, DNase, and hyaluronidase for 1-2 hours at 37° C., 5% $CO_2$ with rotation. In some embodiments, the tumors are digested overnight with constant rotation. In some embodiments, the tumors are digested overnight at 37° C., 5% $CO_2$ with constant rotation. In some embodiments, the whole tumor is combined with the enzymes to form a tumor digest reaction mixture.

In some embodiments, the tumor is reconstituted with the lyophilized enzymes in a sterile buffer. In some embodiments, the buffer is sterile HBSS.

In some embodiments, the enxyme mixture comprises collagenase. In some embodiments, the collagenase is collagenase IV. In some embodiments, the working stock for the collagenase is a 100 mg/ml 10× working stock.

In some embodiments, the enzyme mixture comprises DNAse. In some embodiments, the working stock for the DNAse is a 10,000 IU/ml 10× working stock.

In some embodiments, the enzyme mixture comprises hyaluronidase. In some embodiments, the working stock for the hyaluronidase is a 10-mg/ml 10× working stock.

In some embodiments, the enzyme mixture comprises 10 mg/ml collagenase, 1000 IU/ml DNAse, and 1 mg/ml hyaluronidase.

In some embodiments, the enzyme mixture comprises 10 mg/ml collagenase, 500 IU/ml DNAse, and 1 mg/ml hyaluronidase.

In general, the cell suspension obtained from the tumor is called a "primary cell population" or a "freshly obtained" or a "freshly isolated" cell population. In certain embodiments, the freshly obtained cell population of TILs is exposed to a cell culture medium comprising antigen presenting cells, IL-12 and OKT-3.

In some embodiments, fragmentation includes physical fragmentation, including, for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 1 (in particular, e.g., FIG. 1B and/or FIG. 1C). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the step of fragmentation is an in vitro or ex-vivo process. In some embodiments, the tumor is fragmented and 10, 20, 30, 40 or more fragments or pieces are placed in each container for the priming first expansion. In some embodiments, the tumor is fragmented and 30 or 40 fragments or pieces are placed in each container for the priming first expansion. In some embodiments, the tumor is fragmented and 40 fragments or pieces are placed in each container for the priming first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$. In some embodiments, the tumor fragments are 1-4 mm×1-4 mm×1-4 mm. In some embodiments, the tumor fragments are 1 mm×1 mm×1 mm. In some embodiments, the tumor fragments are 2 mm×2 mm×2 mm. In some embodiments, the tumor fragments are 3 mm×3 mm×3 mm. In some embodiments, the tumor fragments are 4 mm×4 mm×4 mm.

In some embodiments, the tumors are fragmented in order to minimize the amount of hemorrhagic, necrotic, and/or fatty tissues on each piece. In some embodiments, the tumors are fragmented in order to minimize the amount of hemorrhagic tissue on each piece. In some embodiments, the tumors are fragmented in order to minimize the amount of necrotic tissue on each piece. In some embodiments, the tumors are fragmented in order to minimize the amount of fatty tissue on each piece. In certain embodiments, the step of fragmentation of the tumor is an in vitro or ex-vivo method.

In some embodiments, the tumor fragmentation is performed in order to maintain the tumor internal structure. In some embodiments, the tumor fragmentation is performed without preforming a sawing motion with a scalpel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the cell suspension prior to the priming first expansion step is called a "primary cell population" or a "freshly obtained" or "freshly isolated" cell population.

In some embodiments, cells can be optionally frozen after sample isolation (e.g., after obtaining the tumor sample and/or after obtaining the cell suspension from the tumor sample) and stored frozen prior to entry into the expansion described in Step B, which is described in further detail below, as well as exemplified in FIG. 1 (in particular, e.g., FIG. 1B and/or FIG. 1C).

1. Core/Small Biopsy Derived TILS

In some embodiments, TILs are initially obtained from a patient tumor sample ("primary TILs") obtained by a core biopsy or similar procedure and then expanded into a larger population for further manipulation as described herein, optionally cryopreserved, and optionally evaluated for phenotype and metabolic parameters.

In some embodiments, a patient tumor sample may be obtained using methods known in the art, generally via small biopsy, core biopsy, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. In some embodiments, the sample can be from multiple small tumor samples or biopsies. In some embodiments, the sample can comprise multiple tumor samples from a single tumor from the same patient. In some embodiments, the sample can comprise multiple tumor samples from one, two, three, or four tumors from the same patient. In some embodiments, the sample can comprise multiple tumor samples from multiple tumors from the same patient. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, the cancer is selected from cervical cancer, head and neck cancer (including, for example, head and neck squamous cell carcinoma (HNSCC)), glioblastoma (GBM), gastrointestinal cancer, ovarian cancer, sarcoma, pancreatic cancer, bladder cancer, breast cancer, triple negative breast cancer, and non-small cell lung carcinoma (NSCLC). In some embodiments, useful TILs are obtained from malignant melanoma tumors, as these have been reported to have particularly high levels of TILs.

In general, the cell suspension obtained from the tumor core or fragment is called a "primary cell population" or a "freshly obtained" or a "freshly isolated" cell population. In certain embodiments, the freshly obtained cell population of TILs is exposed to a cell culture medium comprising antigen presenting cells, IL-2 and OKT-3.

In some embodiments, if the tumor is metastatic and the primary lesion has been efficiently treated/removed in the past, removal of one of the metastatic lesions may be needed. In some embodiments, the least invasive approach is to remove a skin lesion, or a lymph node on the neck or axillary area when available. In some embodiments, a skin lesion is removed or small biopsy thereof is removed. In some embodiments, a lymph node or small biopsy thereof is removed. In some embodiments, a lung or liver metastatic lesion, or an intra-abdominal or thoracic lymph node or small biopsy can thereof can be employed.

In some embodiments, the tumor is a melanoma. In some embodiments, the small biopsy for a melanoma comprises a mole or portion thereof.

In some embodiments, the small biopsy is a punch biopsy. In some embodiments, the punch biopsy is obtained with a circular blade pressed into the skin. In some embodiments, the punch biopsy is obtained with a circular blade pressed into the skin. around a suspicious mole. In some embodiments, the punch biopsy is obtained with a circular blade pressed into the skin, and a round piece of skin is removed. In some embodiments, the small biopsy is a punch biopsy and round portion of the tumor is removed.

In some embodiments, the small biopsy is an excisional biopsy. In some embodiments, the small biopsy is an excisional biopsy and the entire mole or growth is removed. In some embodiments, the small biopsy is an excisional biopsy and the entire mole or growth is removed along with a small border of normal-appearing skin.

In some embodiments, the small biopsy is an incisional biopsy. In some embodiments, the small biopsy is an incisional biopsy and only the most irregular part of a mole or growth is taken. In some embodiments, the small biopsy is an incisional biopsy and the incisional biopsy is used when other techniques can't be completed, such as if a suspicious mole is very large.

In some embodiments, the small biopsy is a lung biopsy. In some embodiments, the small biopsy is obtained by bronchoscopy. Generally, bronchoscopy, the patient is put under anesthesia, and a small tool goes through the nose or mouth, down the throat, and into the bronchial passages, where small tools are used to remove some tissue. In some embodiments, where the tumor or growth cannot be reached via bronchoscopy, a transthoracic needle biopsy can be employed. Generally, for a transthoracic needle biopsy, the patient is also under anesthesia and a needle is inserted through the skin directly into the suspicious spot to remove a small sample of tissue. In some embodiments, a transthoracic needle biopsy may require interventional radiology (for example, the use of x-rays or CT scan to guide the needle). In some embodiments, the small biopsy is obtained by needle biopsy. In some embodiments, the small biopsy is obtained endoscopic ultrasound (for example, an endoscope with a light and is placed through the mouth into the esophagus). In some embodiments, the small biopsy is obtained surgically.

In some embodiments, the small biopsy is a head and neck biopsy. In some embodiments, the small biopsy is an incisional biopsy. In some embodiments, the small biopsy is an incisional biopsy, wherein a small piece of tissue is cut from an abnormal-looking area. In some embodiments, if the abnormal region is easily accessed, the sample may be taken without hospitalization. In some embodiments, if the tumor is deeper inside the mouth or throat, the biopsy may need to be done in an operating room, with general anesthesia. In some embodiments, the small biopsy is an excisional biopsy. In some embodiments, the small biopsy is an excisional biopsy, wherein the whole area is removed. In some embodiments, the small biopsy is a fine needle aspiration (FNA). In some embodiments, the small biopsy is a fine needle aspiration (FNA), wherein a very thin needle attached to a syringe is used to extract (aspirate) cells from a tumor or lump. In some embodiments, the small biopsy is a punch biopsy. In some embodiments, the small biopsy is a punch biopsy, wherein punch forceps are used to remove a piece of the suspicious area.

In some embodiments, the small biopsy is a cervical biopsy. In some embodiments, the small biopsy is obtained via colposcopy. Generally, colposcopy methods employ the use of a lighted magnifying instrument attached to magnifying binoculars (a colposcope) which is then used to biopsy a small section of the surface of the cervix. In some embodiments, the small biopsy is a conization/cone biopsy. In some embodiments, the small biopsy is a conization/cone biopsy, wherein an outpatient surgery may be needed to remove a larger piece of tissue from the cervix. In some embodiments, the cone biopsy, in addition to helping to confirm a diagnosis, a cone biopsy can serve as an initial treatment.

The term “solid tumor” refers to an abnormal mass of tissue that usually does not contain cysts or liquid areas. Solid tumors may be benign or malignant. The term “solid tumor cancer refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer, glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

In some embodiments, the sample from the tumor is obtained as a fine needle aspirate (FNA), a core biopsy, a small biopsy (including, for example, a punch biopsy). In some embodiments, sample is placed first into a G-Rex 10. In some embodiments, sample is placed first into a G-Rex 10 when there are 1 or 2 core biopsy and/or small biopsy samples. In some embodiments, sample is placed first into a G-Rex 100 when there are 3, 4, 5, 6, 8, 9, or 10 or more core biopsy and/or small biopsy samples. In some embodiments, sample is placed first into a G-Rex 500 when there are 3, 4, 5, 6, 8, 9, or 10 or more core biopsy and/or small biopsy samples.

The FNA can be obtained from a tumor selected from the group consisting of lung, melanoma, head and neck, cervical, ovarian, pancreatic, glioblastoma, colorectal, and sarcoma. In some embodiments, the FNA is obtained from a lung tumor, such as a lung tumor from a patient with non-small cell lung cancer (NSCLC). In some cases, the patient with NSCLC has previously undergone a surgical treatment.

TILs described herein can be obtained from an FNA sample. In some cases, the FNA sample is obtained or isolated from the patient using a fine gauge needle ranging from an 18 gauge needle to a 25 gauge needle. The fine gauge needle can be 18 gauge, 19 gauge, 20 gauge, 21 gauge, 22 gauge, 23 gauge, 24 gauge, or 25 gauge. In some embodiments, the FNA sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In some cases, the TILs described herein are obtained from a core biopsy sample. In some cases, the core biopsy sample is obtained or isolated from the patient using a surgical or medical needle ranging from an 11 gauge needle to a 16 gauge needle. The needle can be 11 gauge, 12 gauge, 13 gauge, 14 gauge, 15 gauge, or 16 gauge. In some embodiments, the core biopsy sample from the patient can contain at least 400,000 TILs, e.g., 400,000 TILs, 450,000 TILs, 500,000 TILs, 550,000 TILs, 600,000 TILs, 650,000 TILs, 700,000 TILs, 750,000 TILs, 800,000 TILs, 850,000 TILs, 900,000 TILs, 950,000 TILs, or more.

In general, the harvested cell suspension is called a “primary cell population” or a “freshly harvested” cell population.

In some embodiments, the TILs are not obtained from tumor digests. In some embodiments, the solid tumor cores are not fragmented.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

2. Methods of Expanding Peripheral Blood Lymphocytes (PBLs) from Peripheral Blood PBL Method 1. In an embodiment of the invention, PBLs are expanded using the processes described herein. In an embodiment of the invention, the method comprises obtaining a PBMC sample from whole blood. In an embodiment, the method comprises enriching T-cells by isolating pure T-cells from PBMCs using negative selection of a non-CD19+ fraction. In an embodiment, the method comprises enriching T-cells by isolating pure T-cells from PBMCs using magnetic bead-based negative selection of a non-CD19+ fraction.

In an embodiment of the invention, PBL Method 1 is performed as follows: On Day 0, a cryopreserved PBMC sample is thawed and PBMCs are counted. T-cells are isolated using a Human Pan T-Cell Isolation Kit and LS columns (Miltenyi Biotec).

PBL Method 2. In an embodiment of the invention, PBLs are expanded using PBL Method 2, which comprises obtaining a PBMC sample from whole blood. The T-cells from the PBMCs are enriched by incubating the PBMCs for at least three hours at 37° C. and then isolating the non-adherent cells.

In an embodiment of the invention, PBL Method 2 is performed as follows: On Day 0, the cryopreserved PMBC sample is thawed and the PBMC cells are seeded at 6 million cells per well in a 6 well plate in CM-2 media and incubated for 3 hours at 37 degrees Celsius. After 3 hours, the non-adherent cells, which are the PBLs, are removed and counted.

PBL Method 3. In an embodiment of the invention, PBLs are expanded using PBL Method 3, which comprises obtaining a PBMC sample from peripheral blood. B-cells are isolated using a CD19+ selection and T-cells are selected using negative selection of the non-CD19+ fraction of the PBMC sample.

In an embodiment of the invention, PBL Method 3 is performed as follows: On Day 0, cryopreserved PBMCs derived from peripheral blood are thawed and counted. CD19+ B-cells are sorted using a CD19 Multisort Kit, Human (Miltenyi Biotec). Of the non-CD19+ cell fraction, T-cells are purified using the Human Pan T-cell Isolation Kit and LS Columns (Miltenyi Biotec).

In an embodiment, PBMCs are isolated from a whole blood sample. In an embodiment, the PBMC sample is used as the starting material to expand the PBLs. In an embodiment, the sample is cryopreserved prior to the expansion process. In another embodiment, a fresh sample is used as the starting material to expand the PBLs. In an embodiment of the invention, T-cells are isolated from PBMCs using methods known in the art. In an embodiment, the T-cells are isolated using a Human Pan T-cell isolation kit and LS columns. In an embodiment of the invention, T-cells are isolated from PBMCs using antibody selection methods known in the art, for example, CD19 negative selection.

In an embodiment of the invention, the PBMC sample is incubated for a period of time at a desired temperature effective to identify the non-adherent cells. In an embodiment of the invention, the incubation time is about 3 hours. In an embodiment of the invention, the temperature is about 37° Celsius. The non-adherent cells are then expanded using the process described above.

In some embodiments, the PBMC sample is from a subject or patient who has been optionally pre-treated with a regimen comprising a kinase inhibitor or an ITK inhibitor. In some embodiments, the tumor sample is from a subject or patient who has been pre-treated with a regimen comprising a kinase inhibitor or an ITK inhibitor. In some embodiments, the PBMC sample is from a subject or patient who has been pre-treated with a regimen comprising a kinase inhibitor or an ITK inhibitor, has undergone treatment for at least 1 month, at least 2 months, at least 3 months, at least 4 months, at least 5 months, at least 6 months, or 1 year or more. In another embodiment, the PBMCs are derived from a patient who is currently on an ITK inhibitor regimen, such as ibrutinib.

In some embodiments, the PBMC sample is from a subject or patient who has been pre-treated with a regimen comprising a kinase inhibitor or an ITK inhibitor and is refractory to treatment with a kinase inhibitor or an ITK inhibitor, such as ibrutinib.

In some embodiments, the PBMC sample is from a subject or patient who has been pre-treated with a regimen comprising a kinase inhibitor or an ITK inhibitor but is no longer undergoing treatment with a kinase inhibitor or an ITK inhibitor. In some embodiments, the PBMC sample is from a subject or patient who has been pre-treated with a regimen comprising a kinase inhibitor or an ITK inhibitor but is no longer undergoing treatment with a kinase inhibitor or an ITK inhibitor and has not undergone treatment for at least 1 month, at least 2 months, at least 3 months, at least 4 months, at least 5 months, at least 6 months, or at least 1 year or more. In another embodiment, the PBMCs are derived from a patient who has prior exposure to an ITK inhibitor, but has not been treated in at least 3 months, at least 6 months, at least 9 months, or at least 1 year.

In an embodiment of the invention, at Day 0, cells are selected for CD19+ and sorted accordingly. In an embodiment of the invention, the selection is made using antibody binding beads. In an embodiment of the invention, pure T-cells are isolated on Day 0 from the PBMCs.

In an embodiment of the invention, for patients that are not pre-treated with ibrutinib or other ITK inhibitor, 10-15 ml of Buffy Coat will yield about $5\times10^9$ PBMC, which, in turn, will yield about $5.5\times10^7$ PBLs.

In an embodiment of the invention, for patients that are pre-treated with ibrutinib or other ITK inhibitor, the expansion process will yield about $20\times10^9$ PBLs. In an embodiment of the invention, $40.3\times10^6$ PBMCs will yield about $4.7\times10^5$ PBLs.

In any of the foregoing embodiments, PBMCs may be derived from a whole blood sample, by apheresis, from the buffy coat, or from any other method known in the art for obtaining PBMCs.

3. Methods of Expanding Marrow Infiltrating Lymphocytes (MILs) from PBMCs Derived from Bone Marrow MIL Method 3. In an embodiment of the invention, the method comprises obtaining PBMCs from the bone marrow. On Day 0, the PBMCs are selected for CD3+/CD33+/CD20+/CD14+ and sorted, and the non-CD3+/CD33+/CD20+/CD14+ cell fraction is sonicated and a portion of the sonicated cell fraction is added back to the selected cell fraction.

In an embodiment of the invention, MIL Method 3 is performed as follows: On Day 0, a cryopreserved sample of PBMCs is thawed and PBMCs are counted. The cells are stained with CD3, CD33, CD20, and CD14 antibodies and sorted using a S3e cell sorted (Bio-Rad). The cells are sorted into two fractions—an immune cell fraction (or the MIL fraction) (CD3+CD33+CD20+CD14+) and an AML blast cell fraction (non-CD3+CD33+CD20+CD14+).

In an embodiment of the invention, PBMCs are obtained from bone marrow. In an embodiment, the PBMCs are obtained from the bone marrow through apheresis, aspiration, needle biopsy, or other similar means known in the art. In an embodiment, the PBMCs are fresh. In another embodiment, the PBMCs are cryopreserved.

In an embodiment of the invention, MILs are expanded from 10-50 ml of bone marrow aspirate. In an embodiment of the invention, 10 ml of bone marrow aspirate is obtained from the patient. In another embodiment, 20 ml of bone marrow aspirate is obtained from the patient. In another embodiment, 30 ml of bone marrow aspirate is obtained from the patient. In another embodiment, 40 ml of bone marrow aspirate is obtained from the patient. In another embodiment, 50 ml of bone marrow aspirate is obtained from the patient.

In an embodiment of the invention, the number of PBMCs yielded from about 10-50 ml of bone marrow aspirate is about $5\times10^7$ to about $10\times10^7$ PBMCs. In another embodiment, the number of PMBCs yielded is about $7\times10^7$ PBMCs.

In an embodiment of the invention, about $5\times10^7$ to about $10\times10^7$ PBMCs, yields about $0.5\times10^6$ to about $1.5\times10^6$ MILs. In an embodiment of the invention, about $1\times10^6$ MILs is yielded.

In an embodiment of the invention, $12\times10^6$ PBMC derived from bone marrow aspirate yields approximately $1.4\times10^5$ MILs.

In any of the foregoing embodiments, PBMCs may be derived from a whole blood sample, from bone marrow, by apheresis, from the buffy coat, or from any other method known in the art for obtaining PBMCs.

B. Step B: Priming First Expansion

In some embodiments, the present methods provide for younger TILs, which may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology,* 75:157-167 (2012); Dudley et al., *Clin Cancer Res,* 16:6122-6131 (2010); Huang et al., *J Immunother,* 28(3):258-267 (2005); Besser et al., *Clin Cancer Res,* 19(17):OF1-OF9 (2013); Besser et al., *J Immunother* 32:415-423 (2009); Robbins, et al., *J Immunol* 2004;

173:7125-7130; Shen et al., *J Immunother,* 30:123-129 (2007); Zhou, et al., *J Immunother,* 28:53-62 (2005); and Tran, et al., *J Immunother,* 31:742-751 (2008), all of which are incorporated herein by reference in their entireties.

After dissection or digestion of tumor fragments and/or tumor fragments, for example such as described in Step A of FIG. 1 (in particular, e.g., FIG. 1B and/or FIG. 1C), the resulting cells are cultured in serum containing IL-2, OKT-3, and feeder cells (e.g., antigen-presenting feeder cells), under conditions that favor the growth of TILs over tumor and other cells. In some embodiments, the IL-2, OKT-3, and feeder cells are added at culture initiation along with the tumor digest and/or tumor fragments (e.g., at Day 0). In some embodiments, the tumor digests and/or tumor fragments are incubated in a container with up to 60 fragments per container and with 6000 IU/mL of IL-2. In some embodiments, this primary cell population is cultured for a period of days, generally from 1 to 8 days, resulting in a bulk TIL population, generally about $1\times10^8$ bulk TIL cells. In some embodiments, this primary cell population is cultured for a period of days, generally from 1 to 7 days, resulting in a bulk TIL population, generally about $1\times10^8$ bulk TIL cells. In some embodiments, priming first expansion occurs for a period of 1 to 8 days, resulting in a bulk TIL population, generally about $1\times10^8$ bulk TIL cells. In some embodiments, priming first expansion occurs for a period of 1 to 7 days, resulting in a bulk TIL population, generally about $1\times10^8$ bulk TIL cells. In some embodiments, this priming first expansion occurs for a period of 5 to 8 days, resulting in a bulk TIL population, generally about $1\times10^8$ bulk TIL cells. In some embodiments, this priming first expansion occurs for a period of 5 to 7 days, resulting in a bulk TIL population, generally about $1\times10^8$ bulk TIL cells. In some embodiments, this priming first expansion occurs for a period of about 6 to 8 days, resulting in a bulk TIL population, generally about $1\times10^8$ bulk TIL cells. In some embodiments, this priming first expansion occurs for a period of about 6 to 7 days, resulting in a bulk TIL population, generally about $1\times10^8$ bulk TIL cells. In some embodiments, this priming first expansion occurs for a period of about 7 to 8 days, resulting in a bulk TIL population, generally about $1\times10^8$ bulk TIL cells. In some embodiments, this priming first expansion occurs for a period of about 7 days, resulting in a bulk TIL population, generally about $1\times10^8$ bulk TIL cells. In some embodiments, this priming first expansion occurs for a period of about 8 days, resulting in a bulk TIL population, generally about $1\times10^8$ bulk TIL cells.

In a preferred embodiment, expansion of TILs may be performed using a priming first expansion step (for example such as those described in Step B of FIG. 1 (in particular, e.g., FIG. 1B and/or FIG. 1C), which can include processes referred to as pre-REP or priming REP and which contains feeder cells from Day 0 and/or from culture initiation) as described below and herein, followed by a rapid second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein. In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin.

In some embodiments, there are less than or equal to 240 tumor fragments. In some embodiments, there are less than or equal to 240 tumor fragments placed in less than or equal to 4 containers. In some embodiments, the containers are GREX100 MCS flasks. In some embodiments, less than or equal to 60 tumor fragments are placed in 1 container. In some embodiments, each container comprises less than or equal to 500 mL of media per container. In some embodiments, the media comprises IL-2. In some embodiments, the media comprises 6000 IU/mL of IL-2. In some embodiments, the media comprises antigen-presenting feeder cells (also referred to herein as "antigen-presenting cells"). In some embodiments, the media comprises $2.5\times10^8$ antigen-presenting feeder cells per container. In some embodiments, the media comprises OKT-3. In some embodiments, the media comprises 30 ng/mL of OKT-3 per container. In some embodiments, the container is a GREX100 MCS flask. In some embodiments, the media comprises 6000 IU/mL of IL-2, 30 ng of OKT-3, and $2.5\times10^8$ antigen-presenting feeder cells. In some embodiments, the media comprises 6000 IU/mL of IL-2, 30 ng/mL of OKT-3, and $2.5\times10^8$ antigen-presenting feeder cells per container.

After preparation of the tumor fragments, the resulting cells (i.e., fragments which is a primary cell population) are cultured in media containing IL-2, antigen-presenting feeder cells and OKT-3 under conditions that favor the growth of TILs over tumor and other cells and which allow for TIL priming and accelerated growth from initiation of the culture on Day 0. In some embodiments, the tumor digests and/or tumor fragments are incubated in with 6000 IU/mL of IL-2, as well as antigen-presenting feeder cells and OKT-3. This primary cell population is cultured for a period of days, generally from 1 to 8 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, this primary cell population is cultured for a period of days, generally from 1 to 7 days, resulting in a bulk TIL population, generally about $1\times10^8$ bulk TIL cells. In some embodiments, the growth media during the priming first expansion comprises IL-2 or a variant thereof, as well as antigen-presenting feeder cells and OKT-3. In some embodiments, the IL-2 is recombinant human IL-2 (rhIL-2). In some embodiments the IL-2 stock solution has a specific activity of 20-30$\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of 4-8$\times10^6$ IU/mg of IL-2. In some embodiments, the IL-2 stock solution has a final concentration of 5-7$\times10^6$ IU/mg of IL-2. In some embodiments, the IL-2 stock solution has a final concentration of $6\times10^6$ IU/mg of IL-2. In some embodiments, the IL-2 stock solution is prepare as described in Example C. In some embodiments, the priming first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the priming first expansion culture media comprises about 9,000 IU/mL of IL-2 to about 5,000 IU/mL of IL-2. In some embodiments, the priming first expansion culture media comprises about 8,000 IU/mL of IL-2 to about 6,000 IU/mL of IL-2. In some embodiments, the priming first expansion culture media comprises about 7,000 IU/mL of IL-2 to about 6,000 IU/mL of IL-2. In some embodiments, the priming first expansion culture media comprises about 6,000 IU/mL of IL-2. In an embodiment, the cell culture medium further comprises IL-2. In some embodiments, the priming first expansion cell culture medium comprises about 3000 IU/mL of IL-2. In an embodiment, the priming first expansion cell culture medium further comprises IL-2. In a preferred embodiment, the priming first expansion cell culture medium comprises about 3000 IU/mL of IL-2. In an embodiment, the priming first expansion cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the priming first expansion cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, priming first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the priming first expansion culture media comprises about 500 IU/mL of IL-15 to about 100 IU/mL of IL-15. In some embodiments, the priming first expansion culture media comprises about 400 IU/mL of IL-15 to about 100 IU/mL of IL-15. In some embodiments, the priming first expansion culture media comprises about 300 IU/mL of IL-15 to about 100 IU/mL of IL-15. In some embodiments, the priming first expansion culture media comprises about 200 IU/mL of IL-15. In some embodiments, the priming first expansion cell culture medium comprises about 180 IU/mL of IL-15. In an embodiment, the priming first expansion cell culture medium further comprises IL-15. In a preferred embodiment, the priming first expansion cell culture medium comprises about 180 IU/mL of IL-15.

In some embodiments, priming first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the priming first expansion culture media comprises about 20 IU/mL of IL-21 to about 0.5 IU/mL of IL-21. In some embodiments, the priming first expansion culture media comprises about 15 IU/mL of IL-21 to about 0.5 IU/mL of IL-21. In some embodiments, the priming first expansion culture media comprises about 12 IU/mL of IL-21 to about 0.5 IU/mL of IL-21. In some embodiments, the priming first expansion culture media comprises about 10 IU/mL of IL-21 to about 0.5 IU/mL of IL-21. In some embodiments, the priming first expansion culture media comprises about 5 IU/mL of IL-21 to about 1 IU/mL of IL-21. In some embodiments, the priming first expansion culture media comprises about 2 IU/mL of IL-21. In some embodiments, the priming first expansion cell culture medium comprises about 1 IU/mL of IL-21. In some embodiments, the priming first expansion cell culture medium comprises about 0.5 IU/mL of IL-21. In an embodiment, the cell culture medium further comprises IL-21. In a preferred embodiment, the priming first expansion cell culture medium comprises about 1 IU/mL of IL-21.

In an embodiment, the priming first expansion cell culture medium comprises OKT-3 antibody. In some embodiments, the priming first expansion cell culture medium comprises about 30 ng/mL of OKT-3 antibody. In an embodiment, the priming first expansion cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 15 ng/ml and 30 ng/mL of OKT-3 antibody. In an embodiment, the cell culture medium comprises 30 ng/mL of OKT-3 antibody. In some embodiments, the OKT-3 antibody is muromonab.

TABLE 3

Amino acid sequences of muromonab (exemplary OKT-3 antibody)

| Identifier | Sequence (One-Letter Amino Acid Symbols) | |
|---|---|---|
| SEQ ID NO: 1 | QVQLQQSGAE LARPGASVKM SCKASGYTFT RYTMHWVKQR PGQGLEWIGY INPSRGYTNY | 60 |
| Muromonab | NQKFKDKATL TTDKSSSTAY MQLSSLTSED SAVYYCARYY DDHYCLDYWG QGTTLTVSSA | 120 |
| heavy chain | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 | QIVLTQSPAI MSASPGEKVT MTCSASSSVS YMNWYQQKSG TSPKRWIYDT SKLASGVPAH | 60 |
| Muromonab | FRGSGSGTSY SLTISGMEAE DAATYYCQQW SSNPFTFGSG TKLEINRADT APTVSIFPPS | 120 |
| light chain | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

In some embodiments, the priming first expansion cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the priming first expansion cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist. In some embodiments, in addition to one or more TNFRSF agonists, the priming first expansion cell culture medium further comprises IL-2 at an initial concentration of about 6000 IU/mL and OKT-3 antibody at an initial concentration of about 30 ng/mL, and wherein the one or more TNFRSF agonists comprises a 4-1BB agonist.

In some embodiments, the priming first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In some embodiments, the CM is the CM1 described in the Examples, see, Example A. In some embodiments, the priming first expansion occurs in an initial cell culture medium or a first cell culture medium. In some embodiments, the priming first expansion culture medium or the initial cell culture medium or the first cell culture medium comprises IL-2, OKT-3 and antigen-presenting feeder cells (also referred to herein as feeder cells).

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium CTS™ OpTmizer™ T-Cell Expansion SFM, CTS™ AIM-V Medium, CTS™ AIM-V SFM, LymphoONE™ T-Cell Expansion Xeno-Free Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3''}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM. In some embodiments, the final concentration of 2-mercaptoethanol in the media is 55 μM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, histidine, L-isoleucine, L-methionine, L-phenylalanine, L-proline, hydroxyproline, L-serine, L-threonine, L-tryptophan, Z tyrosine L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3"}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium. Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 1 to 8 days, as discussed in the examples and figures. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 2 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 3 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 4 to 8 days, as discussed in the examples and figures. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 1 to 7 days, as discussed in the examples and figures. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 2 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 2 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 3 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 3 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 4 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 4 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 5 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 5 to 7 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 6 to 8 days. In some embodiments, the priming first expansion (including processes such as for example those described in Step B of FIG. 1 (in particular, e.g., FIG. 1B and/or FIG. 1C), which can include those sometimes referred to as the pre-REP or priming REP) process is 6 to 7 days. In some embodiments, the priming first expansion (including processes such as for example those provided in Step B of FIG. 1 (in particular, e.g., FIG. 1B and/or FIG. 1C), which can include those sometimes referred to as the pre-REP or priming REP) process is 7 to 8 days. In some embodiments, the priming first expansion (including processes such as for example those provided in Step B of FIG. 1 (in particular, e.g., FIG. 1B and/or FIG. 1C), which can include those sometimes referred to as the pre-REP or priming REP) process is 8 days. In some embodiments, the priming first expansion (including processes such as for example those provided in Step B of FIG. 1 (in particular, e.g., FIG. 1B and/or FIG. 1C), which can include those sometimes referred to as the pre-REP or priming REP) process is 7 days.

In some embodiments, the priming first TIL expansion can proceed for 1 days to 8 days from when fragmentation occurs and/or when the first priming expansion step is initiated. In some embodiments, the priming first TIL expansion can proceed for 1 days to 7 days from when fragmentation occurs and/or when the first priming expansion step is initiated. In some embodiments, the priming first TIL expansion can proceed for 2 days to 8 days from when fragmentation occurs and/or when the first priming expansion step is initiated. In some embodiments, the priming first TIL expansion can proceed for 2 days to 7 days from when fragmentation occurs and/or when the first priming expansion step is initiated. In some embodiments, the priming first TIL expansion can proceed for 3 days to 8 days from when fragmentation occurs and/or when the first priming expansion step is initiated. In some embodiments, the priming first TIL expansion can proceed for 3 days to 7 days from when fragmentation occurs and/or when the first priming expansion step is initiated. In some embodiments, the priming first TIL expansion can proceed for 4 days to 8 days from when fragmentation occurs and/or when the first priming expansion step is initiated. In some embodiments, the priming first TIL expansion can proceed for 4 days to 7 days from when fragmentation occurs and/or when the first priming expansion step is initiated. In some embodiments, the priming first TIL expansion can proceed for 5 days to 8 days from when fragmentation occurs and/or when the first priming expansion step is initiated. In some embodiments, the priming first TIL expansion can proceed for 5 days to 7 days from when fragmentation occurs and/or when the first priming expansion step is initiated. In some embodiments, the priming first TIL expansion can proceed for 6 days to 8 days from when fragmentation occurs and/or when the first priming expansion step is initiated. In some embodiments, the priming first TIL expansion can proceed for 6 days to 7 days from when fragmentation occurs and/or when the first priming expansion step is initiated. In some embodiments, the priming first TIL expansion can proceed for 7 to 8 days from when fragmentation occurs and/or when the first priming expansion step is initiated. In some embodiments, the priming first TIL expansion can proceed for 8 days from when fragmentation occurs and/or when the first priming expansion step is initiated. In some embodiments, the priming first TIL expansion can proceed for 7 days from when fragmentation occurs and/or when the first priming expansion step is initiated.

In some embodiments, the priming first expansion of the TILs can proceed for 1 day, 2 days, 3 days, 4 days, 5 days, 6 days, 7 days, or 8 days. In some embodiments, the first TIL expansion can proceed for 1 day to 8 days. In some embodiments, the first TIL expansion can proceed for 1 day to 7 days. In some embodiments, the first TIL expansion can proceed for 2 days to 8 days. In some embodiments, the first TIL expansion can proceed for 2 days to 7 days. In some embodiments, the first TIL expansion can proceed for 3 days to 8 days. In some embodiments, the first TIL expansion can proceed for 3 days to 7 days. In some embodiments, the first TIL expansion can proceed for 4 days to 8 days. In some embodiments, the first TIL expansion can proceed for 4 days to 7 days. In some embodiments, the first TIL expansion can proceed for 5 days to 8 days. In some embodiments, the first TIL expansion can proceed for 5 days to 7 days. In some embodiments, the first TIL expansion can proceed for 6 days to 8 days. In some embodiments, the first TIL expansion can proceed for 6 days to 7 days. In some embodiments, the first TIL expansion can proceed for 7 to 8 days. In some embodiments, the first TIL expansion can proceed for 8 days. In some embodiments, the first TIL expansion can proceed for 7 days.

In some embodiments, a combination of IL-2, IL-7, IL-15, and/or IL-21 are employed as a combination during the priming first expansion. In some embodiments, IL-2, IL-7, IL-15, and/or IL-21 as well as any combinations thereof can be included during the priming first expansion, including, for example during Step B processes according to FIG. 1 (in particular, e.g., FIG. 1B and/or FIG. 1C), as well as described herein. In some embodiments, a combination of IL-2, IL-15, and IL-21 are employed as a combination during the priming first expansion. In some embodiments, IL-2, IL-15, and IL-21 as well as any combinations thereof can be included during Step B processes according to FIG. 1 (in particular, e.g., FIG. 1B and/or FIG. 1C) and as described herein.

In some embodiments, the priming first expansion, for example, Step B according to FIG. 1 (in particular, e.g., FIG. 1B and/or FIG. 1C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-10 or a G-REX-100. In some embodiments, the bioreactor employed is a G-REX-100. In some embodiments, the bioreactor employed is a G-REX-10.

1. Feeder Cells and Antigen Presenting Cells

In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 4-8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 4-7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 5-8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 5-7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 6-8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during days 6-7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during day 7 or 8. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during day 7. In an embodiment, the priming first expansion procedures described herein (for example including expansion such as those described in Step B from FIG. 1 (in particular, e.g., FIG. 1B and/or FIG. 1C), as well as those referred to as pre-REP or priming REP) does not require feeder cells (also referred to herein as "antigen-presenting cells") at the initiation of the TIL expansion, but rather are added during the priming first expansion at any time during day 8.

In an embodiment, the priming first expansion procedures described herein (for example including expansion such as those described in Step B from FIG. 1 (in particular, e.g., FIG. 1B and/or FIG. 1C), as well as those referred to as pre-REP or priming REP) require feeder cells (also referred to herein as "antigen-presenting cells") at the initiation of the TIL expansion and during the priming first expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In some embodiments, $2.5\times10^8$ feeder cells are used during the priming first expansion. In some embodiments, $2.5\times10^8$ feeder cells per container are used during the priming first expansion. In some embodiments, $2.5\times10^8$ feeder cells per GREX-10 are used during the priming first expansion. In some embodiments, $2.5\times10^8$ feeder cells per GREX-100 are used during the priming first expansion.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 14 is less than the initial viable cell number put into culture on day 0 of the priming first expansion.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 30 ng/ml OKT3 antibody and 3000 IU/ml IL-2. In some embodiments, the PBMCs are cultured in the presence of 30 ng/ml OKT3 antibody and 6000 IU/ml IL-2.

In some embodiments, PBMCs are considered replication incompetent and acceptable for use in the TIL expansion procedures described herein if the total number of viable cells, cultured in the presence of OKT3 and IL-2, on day 7 have not increased from the initial viable cell number put into culture on day 0 of the priming first expansion. In some embodiments, the PBMCs are cultured in the presence of 5-60 ng/mL OKT3 antibody and 1000-6000 IU/mL IL-2. In some embodiments, the PBMCs are cultured in the presence of 10-50 ng/mL OKT3 antibody and 2000-5000 IU/mL IL-2. In some embodiments, the PBMCs are cultured in the presence of 20-40 ng/mL OKT3 antibody and 2000-4000 IU/mL IL-2. In some embodiments, the PBMCs are cultured in the presence of 25-35 ng/mL OKT3 antibody and 2500-3500 IU/mL IL-2. In some embodiments, the PBMCs are cultured in the presence of 30 ng/mL OKT3 antibody and 6000 IU/mL IL-2. In some embodiments, the PBMCs are cultured in the presence of 15 ng/mL OKT3 antibody and 3000 IU/ml IL-2. In some embodiments, the PBMCs are cultured in the presence of 15 ng/mL OKT3 antibody and 6000 IU/mL IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the priming first expansion procedures described herein require a ratio of about $2.5\times10^8$ feeder cells to about $100\times10^6$ TILs. In another embodiment, the priming first expansion procedures described herein require a ratio of about $2.5\times10^8$ feeder cells to about $50\times10^6$ TILs. In yet another embodiment, the priming first expansion described herein require about $2.5\times10^8$ feeder cells to about $25\times10^6$ TILs. In yet another embodiment, the priming first expansion described herein require about $2.5\times10^8$ feeder cells. In yet another embodiment, the priming first expansion requires one-fourth, one-third, five-twelfths, or one-half of the number of feeder cells used in the rapid second expansion.

In some embodiments, the media in the priming first expansion comprises IL-2. In some embodiments, the media in the priming first expansion comprises 6000 IU/mL of IL-2. In some embodiments, the media in the priming first expansion comprises antigen-presenting feeder cells. In some embodiments, the media in the priming first expansion comprises $2.5\times10^8$ antigen-presenting feeder cells per container. In some embodiments, the media in the priming first expansion comprises OKT-3. In some embodiments, the media comprises 30 ng of OKT-3 per container. In some embodiments, the container is a GREX100 MCS flask. In some embodiments, the media comprises 6000 IU/mL of IL-2, 30 ng/mL of OKT-3, and $2.5\times10^8$ antigen-presenting feeder cells. In some embodiments, the media comprises 6000 IU/mL of IL-2, 30 ng/mL of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container. In some embodiments, the media comprises 500 mL of culture medium and 15 μg of OKT-3 per container. In some embodiments, the container is a GREX100 MCS flask. In some embodiments, the media comprises 500 mL of culture medium and 6000 IU/mL of IL-2, 30 ng/mL ng of OKT-3, and $2.5\times10^8$ antigen-presenting feeder cells. In some embodiments, the media comprises 500 mL of culture medium and 6000 IU/mL of IL-2, 15 μg of OKT-3, and $2.5\times10^8$ antigen-presenting feeder cells per container. In some embodiments, the media comprises 500 mL of culture medium and 15 μg of OKT-3 per $2.5\times10^8$ antigen-presenting feeder cells per container.

In an embodiment, the priming first expansion procedures described herein require an excess of feeder cells over TILs during the second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the priming first expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the priming first expansion of TILs is additionally possible, with combinations of two or more of IL-2, IL-15 and IL-21 as is generally outlined in International Publication No. WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

TABLE 4

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |

TABLE 4-continued

Amino acid sequences of interleukins.

| Identifier | Sequence (One-Letter Amino Acid Symbols) | |
|---|---|---|
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG | 60 |
| | NNERIINVSI KKLKRKPPST NAGRRQKHRL TCPSCDSYEK KPPKEFLERF KSLLQKMIHQ | 120 |
| | HLSSRTHGSE DS | 132 |

C. Step C: Priming First Expansion to Rapid Second Expansion Transition

In some cases, the bulk TIL population obtained from the priming first expansion (which can include expansions sometimes referred to as pre-REP), including, for example the TIL population obtained from for example, Step B as indicated in FIG. 1 (in particular, e.g., FIG. 1B and/or FIG. 1C), can be subjected to a rapid second expansion (which can include expansions sometimes referred to as Rapid Expansion Protocol (REP)) and then cryopreserved as discussed below. Similarly, in the case where genetically modified TILs will be used in therapy, the expanded TIL population from the priming first expansion or the expanded TIL population from the rapid second expansion can be subjected to genetic modifications for suitable treatments prior to the expansion step or after the priming first expansion and prior to the rapid second expansion.

In some embodiments, the TILs obtained from the priming first expansion (for example, from Step B as indicated in FIG. 1 (in particular, e.g., FIG. 1B and/or FIG. 1C) are stored until phenotyped for selection. In some embodiments, the TILs obtained from the priming first expansion (for example, from Step B as indicated in FIG. 1 (in particular, e.g., FIG. 1B and/or FIG. 1C) are not stored and proceed directly to the rapid second expansion. In some embodiments, the TILs obtained from the priming first expansion are not cryopreserved after the priming first expansion and prior to the rapid second expansion. In some embodiments, the transition from the priming first expansion to the second expansion occurs at about 2 days, 3 days, 4, days, 5 days, 6 days, 7 days, or 8 days from when tumor fragmentation occurs and/or when the first priming expansion step is initiated. In some embodiments, the transition from the priming first expansion to the rapid second expansion occurs at about 3 days to 7 days from when fragmentation occurs and/or when the first priming expansion step is initiated. In some embodiments, the transition from the priming first expansion to the rapid second expansion occurs at about 3 days to 8 days from when fragmentation occurs and/or when the first priming expansion step is initiated. In some embodiments, the transition from the priming first expansion to the second expansion occurs at about 4 days to 7 days from when fragmentation occurs and/or when the first priming expansion step is initiated. In some embodiments, the transition from the priming first expansion to the second expansion occurs at about 4 days to 8 days from when fragmentation occurs and/or when the first priming expansion step is initiated. In some embodiments, the transition from the priming first expansion to the second expansion occurs at about 5 days to 7 days from when fragmentation occurs and/or when the first priming expansion step is initiated. In some embodiments, the transition from the priming first expansion to the second expansion occurs at about 5 days to 8 days from when fragmentation occurs and/or when the first priming expansion step is initiated. In some embodiments, the transition from the priming first expansion to the second expansion occurs at about 6 days to 7 days from when fragmentation occurs and/or when the first priming expansion step is initiated. In some embodiments, the transition from the priming first expansion to the second expansion occurs at about 6 days to 8 days from when fragmentation occurs and/or when the first priming expansion step is initiated. In some embodiments, the transition from the priming first expansion to the second expansion occurs at about 7 days to 8 days from when fragmentation occurs and/or when the first priming expansion step is initiated. In some embodiments, the transition from the priming first expansion to the second expansion occurs at about 7 days from when fragmentation occurs and/or when the first priming expansion step is initiated. In some embodiments, the transition from the priming first expansion to the second expansion occurs at about 8 days from when fragmentation occurs and/or when the first priming expansion step is initiated.

In some embodiments, the transition from the priming first expansion to the rapid second expansion occurs at 1 day, 2 days, 3 days, 4 days, 5 days, 6 days, 7 days, or 8 days from when fragmentation occurs and/or when the first priming expansion step is initiated. In some embodiments, the transition from the priming first expansion to the rapid second expansion occurs 1 day to 7 days from when fragmentation occurs and/or when the first priming expansion step is initiated. In some embodiments, the transition from the priming first expansion to the rapid second expansion occurs 1 day to 8 days from when fragmentation occurs and/or when the first priming expansion step is initiated. In some embodiments, the transition from the priming first expansion to the second expansion occurs 2 days to 7 days from when fragmentation occurs and/or when the first priming expansion step is initiated. In some embodiments, the transition from the priming first expansion to the second expansion occurs 2 days to 8 days from when fragmentation occurs and/or when the first priming expansion step is initiated. In some embodiments, the transition from the priming first expansion to the second expansion occurs 3 days to 7 days from when fragmentation occurs and/or when the first priming expansion step is initiated. In some embodiments, the transition from the priming first expansion to the second expansion occurs 3 days to 8 days from when fragmentation occurs and/or when the first priming expansion step is initiated. In some embodiments, the transition from the priming first expansion to the rapid second expansion occurs 4 days to 7 days from when fragmentation occurs and/or when the first priming expansion step is initiated. In some embodiments, the transition from the priming first expansion to the rapid second expansion occurs 4 days to 8 days from when fragmentation occurs and/or when the first priming expansion step is initiated. In some embodiments, the transition from the priming first expansion to the rapid second expansion occurs 5 days to 7 days from when fragmentation occurs and/or when the first priming expansion step is initiated. In some embodiments, the transition from the priming first expansion to the rapid second expansion occurs 5 days to 8 days from when fragmentation occurs and/or when the first priming expansion step is initiated. In some embodiments, the transition from the priming first expansion to the rapid second expansion occurs 6 days to 7 days from when fragmentation occurs and/or when the first priming expansion step is initiated. In some embodiments, the transition from the priming first expansion to the rapid second expansion occurs 6 days to 8 days from when fragmentation occurs and/or when the first priming expansion step is initiated. In some embodiments, the transition from the priming first expansion to the rapid second expansion occurs 7 days to 8 days from when fragmentation occurs and/or when the first priming expansion step is initiated. In some embodiments, the transition from the priming first expansion to the rapid second expansion occurs 7 days from when fragmentation occurs and/or when the first priming expansion step is initiated. In some embodiments, the transition from the priming first expansion to the rapid second expansion occurs 8 days from when fragmentation occurs and/or when the first priming expansion step is initiated.

In some embodiments, the TILs are not stored after the primary first expansion and prior to the rapid second expansion, and the TILs proceed directly to the rapid second expansion (for example, in some embodiments, there is no storage during the transition from Step B to Step D as shown in FIG. 1 (in particular, e.g., FIG. 1B and/or FIG. 1C). In some embodiments, the transition occurs in closed system, as described herein. In some embodiments, the TILs from the priming first expansion, the second population of TILs, proceeds directly into the rapid second expansion with no transition period.

In some embodiments, the transition from the priming first expansion to the rapid second expansion, for example, Step C according to FIG. 1 (in particular, e.g., FIG. 1B and/or FIG. 1C), is performed in a closed system bioreactor. In some embodiments, a closed system is employed for the TIL expansion, as described herein. In some embodiments, a single bioreactor is employed. In some embodiments, the single bioreactor employed is for example a GREX-10 or a GREX-100. In some embodiments, the closed system bioreactor is a single bioreactor. In some embodiments, the transition from the priming first expansion to the rapid second expansion involves a scale-up in container size. In some embodiments, the priming first expansion is performed in a smaller container than the rapid second expansion. In some embodiments, the priming first expansion is performed in a GREX-100 and the rapid second expansion is performed in a GREX-500.

D. Step D: Rapid Second Expansion

In some embodiments, the TIL cell population is further expanded in number after harvest and the priming first expansion, after Step A and Step B, and the transition referred to as Step C, as indicated in FIG. 1 (in particular, e.g., FIG. 1B and/or FIG. 1C). This further expansion is referred to herein as the rapid second expansion, which can include expansion processes generally referred to in the art as a rapid expansion process (Rapid Expansion Protocol or REP; as well as processes as indicated in Step D of FIG. 1 (in particular, e.g., FIG. 1B and/or FIG. 1C). The rapid second expansion is generally accomplished using a culture media comprising a number of components, including feeder cells, a cytokine source, and an anti-CD3 antibody, in a gas-permeable container. In some embodiments, 1 day, 2 days, 3 days, or 4 days after initiation of the rapid second expansion (i.e., at days 8, 9, 10, or 11 of the overall Gen 3 process), the TILs are transferred to a larger volume container.

In some embodiments, the rapid second expansion (which can include expansions sometimes referred to as REP; as well as processes as indicated in Step D of FIG. 1 (in particular, e.g., FIG. 1B and/or FIG. 1C) of TIL can be performed using any TIL flasks or containers known by those of skill in the art. In some embodiments, the second TIL expansion can proceed for 1 day, 2 days, 3 days, 4, days, 5 days, 6 days, 7 days, 8 days, 9 days or 10 days after initiation of the rapid second expansion. In some embodiments, the second TIL expansion can proceed for about 1 days to about 9 days after initiation of the rapid second expansion. In some embodiments, the second TIL expansion can proceed for about 1 days to about 10 days after initiation of the rapid second expansion. In some embodiments, the second TIL expansion can proceed for about 2 days to about 9 days after initiation of the rapid second expansion. In some embodiments, the second TIL expansion can proceed for about 2 days to about 10 days after initiation of the rapid second expansion. In some embodiments, the second TIL expansion can proceed for about 3 days to about 9 days after initiation of the rapid second expansion. In some embodiments, the second TIL expansion can proceed for about 3 days to about 10 days after initiation of the rapid second expansion. In some embodiments, the second TIL expansion can proceed for about 4 days to about 9 days after initiation of the rapid second expansion. In some embodiments, the second TIL expansion can proceed for about 4 days to about 10 days after initiation of the rapid second expansion. In some embodiments, the second TIL expansion can proceed for about 5 days to about 9 days after initiation of the rapid second expansion. In some embodiments, the second TIL expansion can proceed for about 5 days to about 10 days after initiation of the rapid second expansion. In some embodiments, the second TIL expansion can proceed for about 6 days to about 9 days after initiation of the rapid second expansion. In some embodiments, the second TIL expansion can proceed for about 6 days to about 10 days after initiation of the rapid second expansion. In some embodiments, the second TIL expansion can proceed for about 7 days to about 9 days after initiation of the rapid second expansion. In some embodiments, the second TIL expansion can proceed for about 7 days to about 10 days after initiation of the rapid second expansion. In some embodiments, the second TIL expansion can proceed for about 8 days to about 9 days after initiation of the rapid second expansion. In some embodiments, the second TIL expansion can proceed for about 8 days to about 10 days after initiation of the rapid second expansion. In some embodiments, the second TIL expansion can proceed for about 9 days to about 10 days after initiation of the rapid second expansion. In some embodiments, the second TIL expansion can proceed for about 1 day after initiation of the rapid second expansion. In some embodiments, the second TIL expansion can proceed for about 2 days after initiation of the rapid second expansion. In some embodiments, the second TIL expansion can proceed for about 3 days after initiation of the rapid second expansion. In some embodiments, the second TIL expansion can proceed for about 4 days after initiation of the rapid second expansion. In some embodiments, the second TIL expansion can proceed for about 5 days after initiation of the rapid second expansion. In some embodiments, the second TIL expansion can proceed for about 6 days after initiation of the rapid second expansion. In some embodiments, the second TIL expansion can proceed for about 7 days after initiation of the rapid second expansion. In some embodiments, the second TIL expansion can proceed for about 8 days after initiation of the rapid second expansion. In some embodiments, the second TIL expansion can proceed for about 9 days after initiation of the rapid second expansion. In some embodiments, the second TIL expansion can proceed for about 10 days after initiation of the rapid second expansion.

In an embodiment, the rapid second expansion can be performed in a gas permeable container using the methods of the present disclosure (including, for example, expansions referred to as REP; as well as processes as indicated in Step D of FIG. 1 (in particular, e.g., FIG. 1B and/or FIG. 1C). In some embodiments, the TILs are expanded in the rapid second expansion in the presence of IL-2, OKT-3, and feeder cells (also referred herein as "antigen-presenting cells"). In some embodiments, the TILs are expanded in the rapid second expansion in the presence of IL-2, OKT-3, and feeder cells, wherein the feeder cells are added to a final concentration that is twice, 2.4 times, 2.5 times, 3 times, 3.5 times or 4 times the concentration of feeder cells present in the priming first expansion. For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 ng/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In an embodiment, the cell culture medium comprises between 30 ng/ml and 60 ng/mL of OKT-3 antibody. In an embodiment, the cell culture medium comprises about 60 ng/mL OKT-3. In some embodiments, the OKT-3 antibody is muromonab.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media in the rapid second expansion comprises $7.5\times10^8$ antigen-presenting feeder cells per container. In some embodiments, the media in the rapid second expansion comprises OKT-3. In some embodiments, the in the rapid second expansion media comprises 500 mL of culture medium and 30 μg of OKT-3 per container. In some embodiments, the container is a GREX100 MCS flask. In some embodiments, the in the rapid second expansion media comprises 6000 IU/mL of IL-2, 60 ng/mL of OKT-3, and $7.5\times10^8$ antigen-presenting feeder cells. In some embodiments, the media comprises 500 mL of culture medium and 6000 IU/mL of IL-2, 30 μg of OKT-3, and $7.5\times10^8$ antigen-presenting feeder cells per container.

In some embodiments, the media in the rapid second expansion comprises IL-2. In some embodiments, the media comprises 6000 IU/mL of IL-2. In some embodiments, the media in the rapid second expansion comprises antigen-presenting feeder cells. In some embodiments, the media comprises between $5\times10^8$ and $7.5\times10^8$ antigen-presenting feeder cells per container. In some embodiments, the media in the rapid second expansion comprises OKT-3. In some embodiments, the media in the rapid second expansion comprises 500 mL of culture medium and 30 μg of OKT-3 per container. In some embodiments, the container is a GREX100 MCS flask. In some embodiments, the media in the rapid second expansion comprises 6000 IU/mL of IL-2, 60 ng/mL of OKT-3, and between $5\times10^8$ and $7.5\times10^8$ antigen-presenting feeder cells. In some embodiments, the media in the rapid second expansion comprises 500 mL of culture medium and 6000 IU/mL of IL-2, 30 μg of OKT-3, and between $5\times10^8$ and $7.5\times10^8$ antigen-presenting feeder cells per container.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including, for example during a Step D processes according to FIG. 1 (in particular, e.g., FIG. 1B and/or FIG. 1C), as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 1 (in particular, e.g., FIG. 1B and/or FIG. 1C) and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments, the antigen-presenting feeder cells (APCs) are PBMCs. In an embodiment, the ratio of TILs to PBMCs and/or antigen-presenting cells in the rapid expansion and/or the second expansion is about 1 to 10, about 1 to 15, about 1 to 20, about 1 to 25, about 1 to 30, about 1 to 35, about 1 to 40, about 1 to 45, about 1 to 50, about 1 to 75, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the rapid second expansion is performed in flasks with the bulk TILs being mixed with a 100- or 200-fold excess of inactivated feeder cells, wherein the feeder cell concentration is at least 1.1 times (1.1×), 1.2×, 1.3×, 1.4×, 1.5×, 1.6×, 1.7×, 1.8×, 1.8×, 2×, 2.1×2.2×, 2.3×, 2.4×, 2.5×, 2.6×, 2.7×, 2.8×, 2.9×, 3.0×, 3.1×, 3.2×, 3.3×, 3.4×, 3.5×, 3.6×, 3.7×, 3.8×, 3.9× or 4.0× the feeder cell concentration in the priming first expansion, 30 ng/mL OKT3 anti-CD3 antibody and 6000 IU/mL IL-2 in 150 ml media. Media replacement is done (generally 2/3 media replacement via aspiration of 2/3 of spent media and replacement with an equal volume of fresh media) until the cells are transferred to an alternative growth chamber. Alternative growth chambers include G-REX flasks and gas permeable containers as more fully discussed below.

In some embodiments, the rapid second expansion (which can include processes referred to as the REP process) is 7 to 9 days, as discussed in the examples and figures. In some embodiments, the second expansion is 7 days. In some embodiments, the second expansion is 8 days. In some embodiments, the second expansion is 9 days.

In an embodiment, the second expansion (which can include expansions referred to as REP, as well as those referred to in Step D of FIG. 1 (in particular, e.g., FIG. 1B and/or FIG. 1C) may be performed in 500 mL capacity gas permeable flasks with 100 cm gas-permeable silicon bottoms (G-Rex 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 6000 IU per mL of IL-2, and added back to the original GREX-100 flasks. When TIL are expanded serially in GREX-100 flasks, on day 10 or 11 the TILs can be moved to a larger flask, such as a GREX-500. The cells may be harvested on day 14 of culture. The cells may be harvested on day 15 of culture. The cells may be harvested on day 16 of culture. In some embodiments, media replacement is done until the cells are transferred to an alternative growth chamber. In some embodiments, 2/3 of the media is replaced by aspiration of spent media and replacement with an equal volume of fresh media. In some embodiments, alternative growth chambers include GREX flasks and gas permeable containers as more fully discussed below.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ Optimizer™ Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEW Basal Medium Eagle (BME), RPMI 1640, F-10, F-12, Minimal Essential Medium (αMEM), Glasgow's Minimal Essential Medium (G-MEM), growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3}$", $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific). In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2. In some embodiments, the CTS™ OpTmizer™ T-cell Expansion SFM is supplemented with about 3% of the CTS™ Immune Cell Serum Replacement (SR) (ThermoFisher Scientific) and the final concentration of 2-mercaptoethanol in the media is 55 μM.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-tree supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3"}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hdydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In an embodiment, the rapid second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the rapid second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the standard Cellometer K2 Image Cytometer Automatic Cell Counter protocol.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $7.5\times10^8$ antigen-presenting feeder cells (APCs), as discussed in more detail below. In some embodiments, the rapid second expansion culture medium (e.g., sometimes referred to as CM2 or the second cell culture medium), comprises IL-2, OKT-3, as well as the antigen-presenting feeder cells (APCs), as discussed in more detail below. In some embodiments, the rapid second expansion culture medium (e.g., sometimes referred to as CM2 or the second cell culture medium), comprises 6000 IU/mL IL-2, 30 ug/flask OKT-3, as well as $5\times10^8$ antigen-presenting feeder cells (APCs), as discussed in more detail below.

In some embodiments, the rapid second expansion, for example, Step D according to FIG. 1 (in particular, e.g., FIG. 1B and/or FIG. 1C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

1. Feeder Cells and Antigen Presenting Cells

In an embodiment, the rapid second expansion procedures described herein (for example including expansion such as those described in Step D from FIG. 1 (in particular, e.g., FIG. 1B and/or FIG. 1C), as well as those referred to as REP) require an excess of feeder cells during REP TIL expansion and/or during the rapid second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, which provides an exemplary protocol for evaluating the replication incompetence of irradiate allogeneic PBMCs.

In some embodiments, PBMCs are considered replication incompetent and acceptable for use in the TIL expansion procedures described herein if the total number of viable cells on day 7 or 14 is less than the initial viable cell number put into culture on day 0 of the REP and/or day 0 of the second expansion (i.e., the start day of the second expansion).

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. In some embodiments, the PBMCs are cultured in the presence of 60 ng/ml OKT3 antibody and 6000 IU/ml IL-2. In some embodiments, the PBMCs are cultured in the presence of 60 ng/ml OKT3 antibody and 3000 IU/ml IL-2. In some embodiments, the PBMCs are cultured in the presence of 30 ng/ml OKT3 antibody and 6000 IU/ml IL-2.

In some embodiments, PBMCs are considered replication incompetent and acceptable for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30-60 ng/ml OKT3 antibody and 1000-6000 IU/ml IL-2. In some embodiments, the PBMCs are cultured in the presence of 30-60 ng/ml OKT3 antibody and 2000-5000 IU/ml IL-2. In some embodiments, the PBMCs are cultured in the presence of 30-60 ng/ml OKT3 antibody and 2000-4000 IU/ml IL-2. In some embodiments, the PBMCs are cultured in the presence of 30-60 ng/ml OKT3 antibody and 2500-3500 IU/ml IL-2. In some embodiments, the PBMCs are cultured in the presence of 30-60 ng/ml OKT3 antibody and 6000 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 10, about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $5\times10^8$ feeder cells to about $100\times10^6$ TILs. In an embodiment, the second expansion procedures described herein require a ratio of about $7.5\times10^8$ feeder cells to about $100\times10^6$ TILs. In another embodiment, the second expansion procedures described herein require a ratio of about $5\times10^8$ feeder cells to about $50\times10^6$ TILs. In another embodiment, the second expansion procedures described herein require a ratio of about $7.5\times10^8$ feeder cells to about $50\times10^6$ TILs. In yet another embodiment, the second expansion procedures described herein require about $5\times10^8$ feeder cells to about $25\times10^6$ TILs. In yet another embodiment, the second expansion procedures described herein require about $7.5\times10^8$ feeder cells to about $25\times10^6$ TILs. In yet another embodiment, the rapid second expansion requires twice the number of feeder cells as the rapid second expansion. In yet another embodiment, when the priming first expansion described herein requires about $2.5\times10^8$ feeder cells, the rapid second expansion requires about $5\times10^8$ feeder cells. In yet another embodiment, when the priming first expansion described herein requires about $2.5\times10^8$ feeder cells, the rapid second expansion requires about $7.5\times10^8$ feeder cells. In yet another embodiment, the rapid second expansion requires two times (2.0×), 2.5×, 3.0×, 3.5× or 4.0× the number of feeder cells as the priming first expansion.

In an embodiment, the rapid second expansion procedures described herein require an excess of feeder cells during the rapid second expansion. In many embodiments, the feeder cells are peripheral blood mononuclear cells (PBMCs) obtained from standard whole blood units from allogeneic healthy blood donors. The PBMCs are obtained using standard methods such as Ficoll-Paque gradient separation. In an embodiment, artificial antigen-presenting (aAPC) cells are used in place of PBMCs. In some embodiments, the PBMCs are added to the rapid second expansion at twice the concentration of PBMCs that were added to the priming first expansion.

In general, the allogenic PBMCs are inactivated, either via irradiation or heat treatment, and used in the TIL expansion procedures described herein, including the exemplary procedures described in the figures and examples.

In an embodiment, artificial antigen presenting cells are used in the rapid second expansion as a replacement for, or in combination with, PBMCs.

2. Cytokines

The rapid second expansion methods described herein generally use culture media with high doses of a cytokine, in particular IL-2, as is known in the art.

Alternatively, using combinations of cytokines for the rapid second expansion of TILs is additionally possible, with combinations of two or more of IL-2, IL-15 and IL-21 as is generally outlined in WO 2015/189356 and WO 2015/189357, hereby expressly incorporated by reference in their entirety. Thus, possible combinations include IL-2 and IL-15, IL-2 and IL-21, IL-15 and IL-21, and IL-2, IL-15 and IL-21, with the latter finding particular use in many embodiments. The use of combinations of cytokines specifically favors the generation of lymphocytes, and in particular T-cells as described therein.

E. Step E: Harvest TILS

After the rapid second expansion step, cells can be harvested. In some embodiments the TILs are harvested after one, two, three, four or more expansion steps, for example as provided in FIG. 1 (in particular, e.g., FIG. 1B and/or FIG. 1C). In some embodiments the TILs are harvested after two expansion steps, for example as provided in FIG. 1 (in particular, e.g., FIG. 1B and/or FIG. 1C). In some embodiments the TILs are harvested after two expansion steps, one priming first expansion and one rapid second expansion, for example as provided in FIG. 1 (in particular, e.g., FIG. 1B and/or FIG. 1C).

TILs can be harvested in any appropriate and sterile manner, including, for example by centrifugation. Methods for TIL harvesting are well known in the art and any such known methods can be employed with the present process. In some embodiments, TILS are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing system is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the rapid second expansion, for example, Step D according to FIG. 1 (in particular, e.g., FIG. 1B and/or FIG. 1C), is performed in a closed system bioreactor. In some embodiments, a closed system is employed for the TIL expansion, as described herein. In some embodiments, a bioreactor is employed. In some embodiments, a bioreactor is employed as the container. In some embodiments, the bioreactor employed is for example a G-REX-100 or a G-REX-500. In some embodiments, the bioreactor employed is a G-REX-100. In some embodiments, the bioreactor employed is a G-REX-500.

In some embodiments, Step E according to FIG. 1 (in particular, e.g., FIG. 1B and/or FIG. 1C), is performed according to the processes described herein. In some embodiments, the closed system is accessed via syringes under sterile conditions in order to maintain the sterility and closed nature of the system. In some embodiments, a closed system as described herein is employed.

In some embodiments, TILs are harvested according to the methods described in herein. In some embodiments, TILs between days 14 and 16 are harvested using the methods as described herein. In some embodiments, TILs are harvested at 14 days using the methods as described herein. In some embodiments, TILs are harvested at 15 days using the methods as described herein. In some embodiments, TILs are harvested at 16 days using the methods as described herein.

F. Step F: Final Formulation/Transfer to Infusion Bag

After Steps A through E as provided in an exemplary order in FIG. 1 (in particular, e.g., FIG. 1B and/or FIG. 1C) and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using the methods of the present disclosure are administered to a patient as a pharmaceutical composition. In an embodiment, the pharmaceutical composition is a suspension of TILs in a sterile buffer. TILs expanded as disclosed herein may be administered by any suitable route as known in the art. In some embodiments, the TILs are administered as a single intra-arterial or intravenous infusion, which preferably lasts approximately 30 to 60 minutes. Other suitable routes of administration include intraperitoneal, intrathecal, and intralymphatic.

G. PBMC Feeder Cell Ratios

In some embodiments, the culture media used in expansion methods described herein (see for example, FIG. 1 (in particular, e.g., FIG. 1B and/or FIG. 1C) include an anti-CD3 antibody e.g. OKT-3. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

In an embodiment, the number of PBMC feeder layers is calculated as follows:

A. Volume of a T-cell (10 μm diameter): V=(4/3) $\pi r^3$=523.6 $\mu m^3$

B. Columne of G-Rex 100 (M) with a 40 μm (4 cells) height: V=(4/3) $\pi r^3=4\times10^{12}$ $\mu m^3$ C. Number cell required to fill column B: $4\times10^{12}$ $\mu m^3$/523.6 $\mu m^3$=$7.6\times10^8$ $\mu m^3$*0.64=$4.86\times10^8$ D. Number cells that can be optimally activated in 4D space: $4.86\times10^8/24=20.25\times10^6$ E. Number of feeders and TIL extrapolated to G-Rex 500: TIL: $100\times10^6$ and Feeder: $2.5\times10^9$ In this calculation, an approximation of the number of mononuclear cells required to provide an icosahedral geometry for activation of TIL in a cylinder with a 100 $cm^2$ base is used. The calculation derives the experimental result of ~$5\times10^8$ for threshold activation of T-cells which closely mirrors NCI experimental data.[(1)] (C) The multiplier (0.64) is the random packing density for equivalent spheres as calculated by Jaeger and Nagel in 1992[(2)]. (D) The divisor 24 is the number of equivalent spheres that could contact a similar object in 4 dimensional space "the Newton number."[(3)].

[(1)]Jin, Jianjian, et. al., Simplified Method of the Growth of Human Tumor Infiltrating Lymphocytes (TIL) in Gas-Permeable Flasks to Numbers Needed for Patient Treatment. *J Immunother.* 2012 April; 35(3): 283-292.

[(2)]Jaeger H M, Nagel S R. Physics of the granular state. Science. 1992 Mar. 20; 255(5051):1523-31.

[(3)]O. R. Musin (2003). "The problem of the twenty-five spheres". Russ. Math. Surv. 58 (4): 794-795.

In an embodiment, the number of antigen-presenting feeder cells exogenously supplied during the priming first expansion is approximately one-half the number of antigen-presenting feeder cells exogenously supplied during the rapid second expansion. In certain embodiments, the method comprises performing the priming first expansion in a cell culture medium which comprises approximately 50% fewer antigen presenting cells as compared to the cell culture medium of the rapid second expansion.

In another embodiment, the number of antigen-presenting feeder cells (APCs) exogenously supplied during the rapid second expansion is greater than the number of APCs exogenously supplied during the priming first expansion.

In another embodiment, the ratio of the number of APCs exogenously supplied during the rapid second expansion to the number of APCs exogenously supplied during the priming first expansion is in a range of from at or about 1.1:1 to at or about 20:1.

In another embodiment, the ratio of the number of APCs exogenously supplied during the rapid second expansion to the number of APCs exogenously supplied during the priming first expansion is in a range of from at or about 1.1:1 to at or about 10:1.

In another embodiment, the ratio of the number of APCs exogenously supplied during the rapid second expansion to the number of APCs exogenously supplied during the priming first expansion is in a range of from at or about 1.1:1 to at or about 9:1.

In another embodiment, the ratio of the number of APCs exogenously supplied during the rapid second expansion to the number of APCs exogenously supplied during the priming first expansion is in a range of from at or about 1.1:1 to at or about 8:1.

In another embodiment, the ratio of the number of APCs exogenously supplied during the rapid second expansion to the number of APCs exogenously supplied during the priming first expansion is in a range of from at or about 1.1:1 to at or about 7:1.

In another embodiment, the ratio of the number of APCs exogenously supplied during the rapid second expansion to the number of APCs exogenously supplied during the priming first expansion is in a range of from at or about 1.1:1 to at or about 6:1.

In another embodiment, the ratio of the number of APCs exogenously supplied during the rapid second expansion to the number of APCs exogenously supplied during the priming first expansion is in a range of from at or about 1.1:1 to at or about 5:1.

In another embodiment, the ratio of the number of APCs exogenously supplied during the rapid second expansion to the number of APCs exogenously supplied during the priming first expansion is in a range of from at or about 1.1:1 to at or about 4:1.

In another embodiment, the ratio of the number of APCs exogenously supplied during the rapid second expansion to the number of APCs exogenously supplied during the priming first expansion) is in a range of from at or about 1.1:1 to at or about 3:1.

In another embodiment, the ratio of the number of APCs exogenously supplied during the rapid second expansion to the number of APCs exogenously supplied during the priming first expansion is in a range of from at or about 1.1:1 to at or about 2.9:1.

In another embodiment, the ratio of the number of APCs exogenously supplied during the rapid second expansion to the number of APCs exogenously supplied during the priming first expansion is in a range of from at or about 1.1:1 to at or about 2.8:1.

In another embodiment, the ratio of the number of APCs exogenously supplied during the rapid second expansion to the number of APCs exogenously supplied during the priming first expansion is in a range of from at or about 1.1:1 to at or about 2.7:1.

In another embodiment, the ratio of the number of APCs exogenously supplied during the rapid second expansion to the number of APCs exogenously supplied during the priming first expansion is in a range of from at or about 1.1:1 to at or about 2.6:1.

In another embodiment, the ratio of the number of APCs exogenously supplied during the rapid second expansion to the number of APCs exogenously supplied during the priming first expansion is in a range of from at or about 1.1:1 to at or about 2.5:1.

In another embodiment, the ratio of the number of APCs exogenously supplied during the rapid second expansion to the number of APCs exogenously supplied during the priming first expansion is in a range of from at or about 1.1:1 to at or about 2.4:1.

In another embodiment, the ratio of the number of APCs exogenously supplied during the rapid second expansion to the number of APCs exogenously supplied during the priming first expansion is in a range of from at or about 1.1:1 to at or about 2.3:1.

In another embodiment, the ratio of the number of APCs exogenously supplied during the rapid second expansion to the number of APCs exogenously supplied during the priming first expansion is in a range of from at or about 1.1:1 to at or about 2.2:1.

In another embodiment, the ratio of the number of APCs exogenously supplied during the rapid second expansion to the number of APCs exogenously supplied during the priming first expansion is in a range of from at or about 1.1:1 to at or about 2.1:1.

In another embodiment, the ratio of the number of APCs exogenously supplied during the rapid second expansion to the number of APCs exogenously supplied during the priming first expansion is in a range of from at or about 1.1:1 to at or about 2:1.

In another embodiment, the ratio of the number of APCs exogenously supplied during the rapid second expansion to the number of APCs exogenously supplied during the priming first expansion is in a range of from at or about 2:1 to at or about 10:1.

In another embodiment, the ratio of the number of APCs exogenously supplied during the rapid second expansion to the number of APCs exogenously supplied during the priming first expansion is in a range of from at or about 2:1 to at or about 5:1.

In another embodiment, the ratio of the number of APCs exogenously supplied during the rapid second expansion to the number of APCs exogenously supplied during the priming first expansion is in a range of from at or about 2:1 to at or about 4:1.

In another embodiment, the ratio of the number of APCs exogenously supplied during the rapid second expansion to the number of APCs exogenously supplied during the priming first expansion is in a range of from at or about 2:1 to at or about 3:1.

In another embodiment, the ratio of the number of APCs exogenously supplied during the rapid second expansion to the number of APCs exogenously supplied during the priming first expansion is in a range of from at or about 2:1 to at or about 2.9:1.

In another embodiment, the ratio of the number of APCs exogenously supplied during the rapid second expansion to the number of APCs exogenously supplied during the priming first expansion is in a range of from at or about 2:1 to at or about 2.8:1.

In another embodiment, the ratio of the number of APCs exogenously supplied during the rapid second expansion to the number of APCs exogenously supplied during the priming first expansion is in a range of from at or about 2:1 to at or about 2.7:1.

In another embodiment, the ratio of the number of APCs exogenously supplied during the rapid second expansion to the number of APCs exogenously supplied during the priming first expansion is in a range of from at or about 2:1 to at or about 2.6:1.

In another embodiment, the ratio of the number of APCs exogenously supplied during the rapid second expansion to the number of APCs exogenously supplied during the priming first expansion is in a range of from at or about 2:1 to at or about 2.5:1.

In another embodiment, the ratio of the number of APCs exogenously supplied during the rapid second expansion to the number of APCs exogenously supplied during the priming first expansion is in a range of from at or about 2:1 to at or about 2.4:1.

In another embodiment, the ratio of the number of APCs exogenously supplied during the rapid second expansion to the number of APCs exogenously supplied during the priming first expansion is in a range of from at or about 2:1 to at or about 2.3:1.

In another embodiment, the ratio of the number of APCs exogenously supplied during the rapid second expansion to the number of APCs exogenously supplied during the priming first expansion is in a range of from at or about about 2:1 to at or about 2.2:1.

In another embodiment, the ratio of the number of APCs exogenously supplied during the rapid second expansion to the number of APCs exogenously supplied during the priming first expansion is in a range of from at or about 2:1 to at or about 2.1:1.

In another embodiment, the ratio of the number of APCs exogenously supplied during the rapid second expansion to the number of APCs exogenously supplied during the priming first expansion is at or about 2:1.

In another embodiment, the ratio of the number of APCs exogenously supplied during the rapid second expansion to the number of APCs exogenously supplied during the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs exogenously supplied during the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and the number of APCs exogenously supplied during the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the number of APCs exogenously supplied during the priming first expansion is in the range of at or about $1.5\times10^8$ APCs to at or about $3\times10^8$ APCs, and the number of APCs exogenously supplied during the rapid second expansion is in the range of at or about $4\times10^8$ APCs to at or about $7.5\times10^8$ APCs.

In another embodiment, the number of APCs exogenously supplied during the priming first expansion is in the range of at or about $2\times10^8$ APCs to at or about $2.5\times10^8$ APCs, and the number of APCs exogenously supplied during the rapid second expansion is in the range of at or about $4.5\times10^8$ APCs to at or about $5.5\times10^8$ APCs.

In another embodiment, the number of APCs exogenously supplied during the priming first expansion is at or about $2.5\times10^8$ APCs, and the number of APCs exogenously supplied during the rapid second expansion is at or about $5\times10^8$ APCs.

In an embodiment, the number of APCs (including, for example, PBMCs) added at day 0 of the priming first expansion is approximately one-half of the number of PBMCs added at day 7 of the priming first expansion (e.g., day 7 of the method). In certain embodiments, the method comprises adding antigen presenting cells at day 0 of the priming first expansion to the first population of TILs and adding antigen presenting cells at day 7 to the second population of TILs, wherein the number of antigen presenting cells added at day 0 is approximately 50% of the number of antigen presenting cells added at day 7 of the priming first expansion (e.g., day 7 of the method).

In another embodiment, the number of APCs (including, for example, PBMCs) exogenously supplied at day 7 of the rapid second expansion is greater than the number of PBMCs exogenously supplied at day 0 of the priming first expansion.

In another embodiment, the APCs exogenously supplied in the priming first expansion are seeded in the culture flask at a density in a range of at or about $1.0\times10^6$ APCs/cm$^2$ to at or about $4.5\times10^6$ APCs/cm$^2$.

In another embodiment, the APCs exogenously supplied in the priming first expansion are seeded in the culture flask at a density in a range of at or about $1.5\times10^6$ APCs/cm$^2$ to at or about $3.5\times10^6$ APCs/cm$^2$.

In another embodiment, the APCs exogenously supplied in the priming first expansion are seeded in the culture flask at a density in a range of at or about $2\times10^6$ APCs/cm$^2$ to at or about $3\times10^6$ APCs/cm$^2$.

In another embodiment, the APCs exogenously supplied in the priming first expansion are seeded in the culture flask at a density of at or about $2\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$.

In another embodiment, the APCs exogenously supplied in the rapid second expansion are seeded in the culture flask at a density in a range of at or about $2.5\times10^6$ APCs/cm$^2$ to at or about $7.5\times10^6$ APCs/cm$^2$.

In another embodiment, the APCs exogenously supplied in the rapid second expansion are seeded in the culture flask at a density in a range of at or about $3.5\times10^6$ APCs/cm$^2$ to about $6.0\times10^6$ APCs/cm$^2$.

In another embodiment, the APCs exogenously supplied in the rapid second expansion are seeded in the culture flask at a density in a range of at or about $4.0\times10^6$ APCs/cm$^2$ to about $5.5\times10^6$ APCs/cm$^2$.

In another embodiment, the APCs exogenously supplied in the rapid second expansion are seeded in the culture flask at a density in a range of at or about $4.0\times10^6$ APCs/cm$^2$.

In another embodiment, the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density of at or about $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$ or $4.5\times10^6$ APCs/cm$^2$ and the APCs exogenously supplied in the rapid second expansion are seeded in the culture flask at a density of at or about $2.5\times10^6$ APCs/cm$^2$, $2.6\times10^6$ APCs/cm$^2$, $2.7\times10^6$ APCs/cm$^2$, $2.8\times10^6$, $2.9\times10^6$, $3\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, $5\times10^6$, $5.1\times10^6$, $5.2\times10^6$, $5.3\times10^6$, $5.4\times10^6$, $5.5\times10^6$, $5.6\times10^6$, $5.7\times10^6$, $5.8\times10^6$, $5.9\times10^6$, $6\times10^6$, $6.1\times10^6$, $6.2\times10^6$, $6.3\times10^6$, $6.4\times10^6$, $6.5\times10^6$, $6.6\times10^6$, $6.7\times10^6$, $6.8\times10^6$, $6.9\times10^6$, $7\times10^6$, $7.1\times10^6$, $7.2\times10^6$, $7.3\times10^6$, $7.4\times10^6$ or $7.5\times10^6$ APCs/cm$^2$.

In another embodiment, the APCs exogenously supplied in the priming first expansion are seeded in the culture flask at a density in a range of at or about $1.0\times10^6$ APCs/cm$^2$ to at or about $4.5\times10^6$ APCs/cm$^2$, and the APCs exogenously supplied in the rapid second expansion are seeded in the culture flask at a density in a range of at or about $2.5\times10^6$ APCs/cm$^2$ to at or about $7.5\times10^6$ APCs/cm$^2$.

In another embodiment, the APCs exogenously supplied in the priming first expansion are seeded in the culture flask at a density in a range of at or about $1.5\times10^6$ APCs/cm$^2$ to at or about $3.5\times10^6$ APCs/cm$^2$, and the APCs exogenously supplied in the rapid second expansion are seeded in the culture flask at a density in a range of at or about $3.5\times10^6$ APCs/cm$^2$ to at or about $6\times10^6$ APCs/cm$^2$.

In another embodiment, the APCs exogenously supplied in the priming first expansion are seeded in the culture flask at a density in a range of at or about $2\times10^6$ APCs/cm$^2$ to at or about $3\times10^6$ APCs/cm$^2$, and the APCs exogenously supplied in the rapid second expansion are seeded in the culture flask at a density in a range of at or about $4\times10^6$ APCs/cm$^2$ to at or about $5.5\times10^6$ APCs/cm$^2$.

In another embodiment, the APCs exogenously supplied in the priming first expansion are seeded in the culture flask at a density at or about $2\times10^6$ APCs/cm$^2$ and the APCs exogenously supplied in the rapid second expansion are seeded in the culture flask at a density of at or about $4\times10^6$ APCs/cm$^2$.

In another embodiment, the ratio of the number of APCs (including, for example, PBMCs) exogenously supplied at day 7 of the rapid second expansion to the number of PBMCs exogenously supplied at day 0 of the priming first expansion is in a range of from at or about 1.1:1 to at or about 20:1.

In another embodiment, the ratio of the number of APCs (including, for example, PBMCs) exogenously supplied at day 7 of the rapid second expansion to the number of PBMCs exogenously supplied at day 0 of the priming first expansion is in a range of from at or about 1.1:1 to at or about 10:1.

In another embodiment, the ratio of the number of APCs (including, for example, PBMCs) exogenously supplied at day 7 of the rapid second expansion to the number of PBMCs exogenously supplied at day 0 of the priming first expansion is in a range of from at or about 1.1:1 to at or about 9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 1.1:1 to at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 10:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.9:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.8:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.7:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.6:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.5:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.4:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.3:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is in a range of from at or about 2:1 to at or about 2.1:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 2:1.

In another embodiment, the ratio of the number of APCs (including, for example, PBMCs) exogenously supplied at day 7 of the rapid second expansion to the number of APCs (including, for example, PBMCs) exogenously supplied at day 0 of the priming first expansion is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the number of APCs (including, for example, PBMCs) exogenously supplied at day 0 of the priming first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs (including, for example, PBMCs), and the number of APCs (including, for example, PBMCs) exogenously supplied at day 7 of the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs (including, for example, PBMCs).

In another embodiment, the number of APCs (including, for example, PBMCs) exogenously supplied at day 0 of the priming first expansion is in the range of at or about $1\times10^8$ APCs (including, for example, PBMCs) to at or about $3.5\times10^8$ APCs (including, for example, PBMCs), and the number of APCs (including, for example, PBMCs) exogenously supplied at day 7 of the rapid second expansion is in the range of at or about $3.5\times10^8$ APCs (including, for example, PBMCs) to at or about $1\times10^9$ APCs (including, for example, PBMCs).

In another embodiment, the number of APCs (including, for example, PBMCs) exogenously supplied at day 0 of the priming first expansion is in the range of at or about $1.5\times10^8$ APCs to at or about $3\times10^8$ APCs (including, for example, PBMCs), and the number of APCs (including, for example, PBMCs) exogenously supplied at day 7 of the rapid second expansion is in the range of at or about $4\times10^8$ APCs (including, for example, PBMCs) to at or about $7.5\times10^8$ APCs (including, for example, PBMCs).

In another embodiment, the number of APCs (including, for example, PBMCs) exogenously supplied at day 0 of the priming first expansion is in the range of at or about $2\times10^8$ APCs (including, for example, PBMCs) to at or about $2.5\times10^8$ APCs (including, for example, PBMCs), and the number of APCs (including, for example, PBMCs) exogenously supplied at day 7 of the rapid second expansion is in the range of at or about $4.5\times10^8$ APCs (including, for example, PBMCs) to at or about $5.5\times10^8$ APCs (including, for example, PBMCs).

In another embodiment, the number of APCs (including, for example, PBMCs) exogenously supplied at day 0 of the priming first expansion is at or about $2.5\times10^8$ APCs (including, for example, PBMCs) and the number of APCs (including, for example, PBMCs) exogenously supplied at day 7 of the rapid second expansion is at or about $5\times10^8$ APCs (including, for example, PBMCs).

In an embodiment, the number of layers of APCs (including, for example, PBMCs) added at day 0 of the priming first expansion is approximately one-half of the number of layers of APCs (including, for example, PBMCs) added at day 7 of the rapid second expansion. In certain embodiments, the method comprises adding antigen presenting cell layers at day 0 of the priming first expansion to the first population of TILs and adding antigen presenting cell layers at day 7 to the second population of TILs, wherein the number of antigen presenting cell layer added at day 0 is approximately 50% of the number of antigen presenting cell layers added at day 7.

In another embodiment, the number of layers of APCs (including, for example, PBMCs) exogenously supplied at day 7 of the rapid second expansion is greater than the number of layers of APCs (including, for example, PBMCs) exogenously supplied at day 0 of the priming first expansion.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about 1.5 cell layers to at or about 2.5 cell layers and day 7 of the rapid second expansion occurs in the presence of layered APCs (including, for example, PBMCs) with an average thickness of at or about 3 cell layers.

In another embodiment, day 0 of the priming first expansion occurs in the presence of layered APCs (including, for example, PBMCs) with an average thickness of at or about one cell layer and day 7 of the rapid second expansion occurs in the presence of layered APCs (including, for example, PBMCs) with an average thickness of at or about 2 cell layers.

In another embodiment, day 0 of the priming first expansion occurs in the presence of layered APCs (including, for example, PBMCs) with an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers and day 7 of the rapid second expansion occurs in the presence of layered APCs (including, for example, PBMCs) with an average thickness of at or about 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, day 0 of the priming first expansion occurs in the presence of layered APCs (including, for example, PBMCs) with an average thickness of at or about 1 cell layer to at or about 2 cell layers and day 7 of the rapid second expansion occurs in the presence of layered APCs (including, for example, PBMCs) with an average thickness of at or about 3 cell layers to at or about 10 cell layers.

In another embodiment, day 0 of the priming first expansion occurs in the presence of layered APCs (including, for example, PBMCs) with an average thickness of at or about 2 cell layers to at or about 3 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 2 cell layers and day 7 of the rapid second expansion occurs in the presence of layered APCs (including, for example, PBMCs) with an average thickness of at or about 4 cell layers to at or about 8 cell layers.

In another embodiment, day 0 of the priming first expansion occurs in the presence of layered APCs (including, for example, PBMCs) with an average thickness of at or about 1, 2 or 3 cell layers and day 7 of the rapid second expansion occurs in the presence of layered APCs (including, for example, PBMCs) with an average thickness of at or about 3, 4, 5, 6, 7, 8, 9 or 10 cell layers.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:10.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.1 to at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.2 to at or about 1:8.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.3 to at or about 1:7.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.4 to at or about 1:6.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.5 to at or about 1:5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.6 to at or about 1:4.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.7 to at or about 1:3.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.8 to at or about 1:3.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in the range of at or about 1:1.9 to at or about 1:2.5.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is at or about 1:2.

In another embodiment, day 0 of the priming first expansion occurs in the presence of layered APCs (including, for example, PBMCs) with a first average thickness equal to a first number of layers of APCs (including, for example, PBMCs) and day 7 of the rapid second expansion occurs in the presence of layered APCs (including, for example, PBMCs) with a second average thickness equal to a second number of layers of APCs (including, for example, PBMCs), wherein the ratio of the first number of layers of APCs (including, for example, PBMCs) to the second number of layers of APCs (including, for example, PBMCs) is in at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In some embodiments, the number of APCs in the priming first expansion is in the range of about $1.0\times10^6$ APCs/cm$^2$ to about $4.5\times10^6$ APCs/cm$^2$, and the number of APCs in the rapid second expansion is in the range of about $2.5\times10^6$ APCs/cm$^2$ to about $7.5\times10^6$ APCs/cm$^2$.

In some embodiments, the number of APCs in the priming first expansion is in the range of about $1.5\times10^6$ APCs/cm$^2$ to about $3.5\times10^6$ APCs/cm$^2$, and the number of APCs in the rapid second expansion is in the range of about $3.5\times10^6$ APCs/cm$^2$ to about $6.0\times10^6$ APCs/cm$^2$.

In some embodiments, the number of APCs in the priming first expansion is in the range of about $2.0\times10^6$ APCs/cm$^2$ to about $3.0\times10^6$ APCs/cm$^2$, and the number of APCs in the rapid second expansion is in the range of about $4.0\times10^6$ APCs/cm$^2$ to about $5.5\times10^6$ APCs/cm$^2$.

H. Optional Cell Medium Components

1. Anti-CD3 Antibodies

In some embodiments, the culture media used in expansion methods described herein (see for example, FIG. 1 (in particular, e.g., FIG. 1B and/or FIG. 1C) include an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

TABLE 5

Amino acid sequences of muromonab (exemplary OKT-3 antibody)

| Identifier | Sequence (One-Letter Amino Acid Symbols) | |
|---|---|---|
| SEQ ID NO: 1 Muromonab heavy chain | QVQLQQSGAE LARPGASVKM SCKASGYTFT RYTMHWVKQR PGQGLEWIGY INPSRGYTNY | 60 |
| | NQKFKDKATL TTDKSSSTAY MQLSSLTSED SAVYYCARYY DDHYCLDYWG QGTTLTVSSA | 120 |
| | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 Muromonab light chain | QIVLTQSPAI MSASPGEKVT MTCSASSSVS YMNWYQQKSG TSPKRWIYDT SKLASGVPAH | 60 |
| | FRGSGSGTSY SLTISGMEAE DAATYYCQQW SSNPFTFGSG TKLEINRADT APTVSIFPPS | 120 |
| | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

2. 4-1BB (CD137) Agonists

In an embodiment, the cell culture medium of the priming first expansion and/or the rapid second expansion comprises a TNFRSF agonist. In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multi specific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., PLOS One 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 6.

4-1BB with a $k_{assoc}$ of about $8\times10^5$ l/M·s or faster, binds to human or murine 4-1BB with a $k_{assoc}$ of about $8.5\times10^5$ l/M·s or faster, binds to human or murine 4-1BB with a $k_{assoc}$ of about $9\times10^5$ l/M·s or faster, binds to human or murine 4-1BB with a $k_{assoc}$ of about $9.5\times10^5$ l/M·s or faster, or binds to human or murine 4-1BB with a $k_{assoc}$ of about $1\times10^6$ l/M·s or faster.

In some embodiments, the compositions, processes and methods described include a 4-1BB agonist that binds to human or murine 4-1BB with a $k_{dissoc}$ of about $2\times10^{-5}$ l/s or slower, binds to human or murine 4-1BB with a $k_{dissoc}$ of about $2.1\times10^{-5}$ l/s or slower, binds to human or murine 4-1BB with a $k_{dissoc}$ of about $2.2\times10^{-5}$ l/s or slower, binds to human or murine 4-1BB with a $k_{dissoc}$ of about $2.3\times10^{-5}$ l/s or slower, binds to human or murine 4-1BB with a $k_{dissoc}$ of about $2.4\times10^{-5}$ l/s or slower, binds to human or murine 4-1BB with a $k_{dissoc}$ of about $2.5\times10^{-5}$ l/s or slower, binds to human or murine 4-1BB with a $k_{dissoc}$ of about $2.6\times10^{-5}$ l/s or slower or binds to human or murine 4-1BB with a $k_{dissoc}$ of about $2.7\times10^{-5}$ l/s or slower, binds to human or murine 4-1BB with a $k_{dissoc}$ of about $2.8\times10^{-5}$ l/s or slower, binds to human or murine 4-1BB with a $k_{dissoc}$ of about $2.9\times10^{-5}$ l/s or slower, or binds to human or murine 4-1BB with a $k_{dissoc}$ of about $3\times10^{-5}$ l/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

TABLE 6

Amino acid sequences of 4-1BB antigens.

| Identifier | Sequence (One-Letter Amino Acid Symbols) |
|---|---|
| SEQ ID NO: 9<br>human 4-1BB,<br>Tumor necrosis<br>factor receptor<br>superfamily,<br>member 9 (*Homo sapiens*) | MGNSCYNIVA TLLLVLNFER TRSLQDPCSN CPAGTFCDNN RNQICSPCPP NSFSSAGGQR 60<br>TCDICRQCKG VFRTRKECSS TSNAECDCTP GFHCLGAGCS MCEQDCKQGQ ELTKKGCKDC 120<br>CFGTFNDQKR GICRPWTNCS LDGKSVLVNG TKERDVVCGP SPADLSPGAS SVTPPAPARE 180<br>PGHSPQIISF FLALTSTALL FLLFFLTLRF SVVKRGRKKL LYIFKQPFMR PVQTTQEEDG 240<br>CSCRFPEEEE GGCEL 255 |
| SEQ ID NO: 10<br>murine 4-1BB,<br>Tumor necrosis<br>factor receptor<br>superfamily,<br>member 9 (*Mus musculus*) | MGNNCYNVVV IVLLLVGCEK VGAVQNSCDN CQPGTFCRKY NPVCKSCPPS TFSSIGGQPN 60<br>CNICRVCAGY FRFKKFCSST HNAECECIEG FHCLGPQCTR CEKDCRPGQE LTKQGCKTCS 120<br>LGTFNDQNGT GVCRPWTNCS LDGRSVLKTG TTEKDVVCGP PVVSFSPSTT ISVTPEGGPG 180<br>GHSLQVLTLF LALTSALLLA LIFITLLFSV LKWIRKKFPH IFKQPFKKTT GAAQEEDACS 240<br>CRCPQEEEGG GGGYEL 256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5\times10^5$ l/M·s or faster, binds to human or murine 4-1BB with a $k_{assoc}$ of about $7.5\times10^5$ l/M·s or faster, binds to human or murine In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 7. Utomilumab comprises glycosylation sites at Asn59 and Asn292; heavy chain intrachain disulfide bridges at positions 22-96 ($V_H$-$V_L$), 143-199 ($C_H1$-$C_L$), 256-316 ($C_H2$) and 362-420 ($C_H3$); light chain intrachain disulfide bridges at positions 22'-87' ($V_H$-$V_L$) and 136'-195' ($C_H1$-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO:14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO:16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 7

Amino acid sequences for 4-1BB agonist antibodies related to utomilumab.

| Identifier | Sequence (One-Letter Amino Acid Symbols) |
|---|---|
| SEQ ID NO: 11 heavy chain for utomilumab | EVQLVQSGAE VKKPGESLRI SCKGSGYSFS TYWISWVRQM PGKGLEWMGK IYPGDSYTNY 60<br>SPSFQGQVTI SADKSISTAY LQWSSLKASD TAMYYCARGY GIFDYWGQGT LVTVSSASTK 120<br>GPSVFPLAPC SRSTSESTAA LGCLVKDYFP EPVTVSWNSG ALTSGVHTFP AVLQSSGLYS 180<br>LSSVVTVPSS NFGTQTYTCN VDHKPSNTKV DKTVERKCCV ECPPCPAPPV AGPSVFLFPP 240 |

TABLE 7-continued

Amino acid sequences for 4-1BB agonist antibodies related to utomilumab.

| Identifier | Sequence (One-Letter Amino Acid Symbols) | |
|---|---|---|
| | KPKDTLMISR TPEVTCVVVD VSHEDPEVQF NWYVDGVEVH NAKTKPREEQ FNSTFRVVSV | 300 |
| | LTVVHQDWLN GKEYKCKVSN KGLPAPIEKT ISKTKGQPRE PQVYTLPPSR EEMTKNQVSL | 360 |
| | TCLVKGFYPS DIAVEWESNG QPENNYKTTP PMLDSDGSFF LYSKLTVDKS RWQQGNVFSC | 420 |
| | SVMHEALHNH YTQKSLSLSP G | 441 |
| SEQ ID NO: 12 light chain for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVLGQ PKAAPSVTLF | 120 |
| | PPSSEELQAN KATLVCLISD FYPGAVTVAW KADSSPVKAG VETTTPSKQS NNKYAASSYL | 180 |
| | SLTPEQWKSH RSYSCQVTHE GSTVEKTVAP TECS | 214 |
| SEQ ID NO: 13 heavy chain variable region for utomilumab | EVQLVQSGAE VKKPGESLRI SCKGSGYSFS TYWISWVRQM PGKGLEWMG KIYPGDSYTN | 60 |
| | YSPSFQGQVT ISADKSISTA YLQWSSLKAS DTAMYYCARG YGIFDYWGQ GTLVTVSS | 118 |
| SEQ ID NO: 14 light chain variable region for utomilumab | SYELTQPPSV SVSPGQTASI TCSGDNIGDQ YAHWYQQKPG QSPVLVIYQD KNRPSGIPER | 60 |
| | FSGSNSGNTA TLTISGTQAM DEADYYCATY TGFGSLAVFG GGTKLTVL | 108 |
| SEQ ID NO: 15 heavy chain CDR1 for utomilumab | STYWIS | 6 |
| SEQ ID NO: 16 heavy chain CDR2 for utomilumab | KIYPGDSYTN YSPSFQG | 17 |
| SEQ ID NO: 17 heavy chain CDR3 for utomilumab | RGYGIFDY | 8 |
| SEQ ID NO: 18 light chain CDR1 for utomilumab | SGDNIGDQYA H | 11 |
| SEQ ID NO: 19 light chain CDR2 for utomilumab | QDKNRPS | 7 |
| SEQ ID NO: 20 light chain CDR3 for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table EE. Urelumab comprises N-glycosylation sites at positions 298 (and 298"); heavy chain intrachain disulfide bridges at positions 22-95 (VH-VL), 148-204 (CH1-CL), 262-322 (CH2) and 368-426 (CH3) (and at positions 22"-95", 148"-204", 262"-322", and 368"-426"); light chain intrachain disulfide bridges at positions 23'-88' (VH-VL) and 136'-196' (CH1-CL) (and at positions 23'"-88'" and 136'"-196'"); interchain heavy chain-heavy chain disulfide bridges at positions 227-227" and 230-230"; and interchain heavy chain-light chain disulfide bridges at 135-216' and 135"-216'". The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., Clin. Cancer Res. 2016. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 8

Amino acid sequences for 4-1BB agonist antibodies related to urelumab.

| Identifier | Sequence (One-Letter Amino Acid Symbols) | |
|---|---|---|
| SEQ ID NO: 21 heavy chain for urelumab | QVQLQQWGAG LLKPSETLSL TCAVYGGSFS GYYWSWIRQS PEKGLEWIGE INHGGYVTYN | 60 |
| | PSLESRVTIS VDTSKNQFSL KLSSVTAADT AVYYCARDYG PGNYDWYFDL WGRGTLVTVS | 120 |
| | SASTKGPSVF PLAPCSRSTS ESTAALGCLV KDYFPEPVTV SWNSGALTSG VHTFPAVLQS | 180 |
| | SGLYSLSSVV TVPSSSLGTK TYTCNVDHKP SNTKVDKRVE SKYGPPCPPC PAPEFLGGPS | 240 |
| | VFLFPPKPKD TLMISRTPEV TCVVVDVSQE DPEVQFNWYV DGVEVHNAKT KPREEQFNST | 300 |
| | YRVVSVLTVL HQDWLNGKEY KCKVSNKGLP SSIEKTISKA KGQPREPQVY TLPPSQEEMT | 360 |
| | KNQVSLTCLV KGFYPSDIAV EWESNGQPEN NYKTTPPVLD SDGSFFLYSR LTVDKSRWQE | 420 |
| | GNVFSCSVMH EALHNHYTQK SLSLSLGK | 448 |
| SEQ ID NO: 22 light chain for urelumab | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPALTF CGGTKVEIKR TVAAPSVFIF | 120 |
| | PPSDEQLKSG TASVVCLLNN FYPREAKVQW KVDNALQSGN SQESVTEQDS KDSTYSLSST | 180 |
| | LTLSKADYEK HKVYACEVTH QGLSSPVTKS FNRGEC | 216 |
| SEQ ID NO: 23 variable heavy chain for urelumab | MKHLWFFLLL VAAPRWVLSQ VQLQQWGAGL LKPSETLSLT CAVYGGSFSG YYWSWIRQSP | 60 |
| | EKGLEWIGEI NHGGYVTYNP SLESRVTISV DTSKNQFSLK LSSVTAADTA VYYCARDYGP | 120 |
| SEQ ID NO: 24 variable light chain for urelumab | MEAPAQLLFL LLLWLPDTTG EIVLTQSPAT LSLSPGERAT LSCRASQSVS SYLAWYQQKP | 60 |
| | GQAPRLLIYD ASNRATGIPA RFSGSGSGTD FTLTISSLEP EDFAVYYCQQ | 110 |

TABLE 8-continued

Amino acid sequences for 4-1BB agonist antibodies related to urelumab.

| Identifier | Sequence (One-Letter Amino Acid Symbols) | |
|---|---|---|
| SEQ ID NO: 25 heavy chain CDR1 for urelumab | GYYWS | 5 |
| SEQ ID NO: 26 heavy chain CDR2 for urelumab | EINHGGYVTY NPSLES | 16 |
| SEQ ID NO: 27 heavy chain CDR3 for urelumab | DYGPGNYDWY FDL | 13 |
| SEQ ID NO: 28 light chain CDR1 for urelumab | RASQSVSSYL A | 11 |
| SEQ ID NO: 29 light chain CDR2 for urelumab | DASNRAT | 7 |
| SEQ ID NO: 30 light chain CDR3 for urelumab | QQRSDWPPAL T | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgGl (BMS-663031)), antibodies disclosed in U.S. Pat. No. 6,887,673 (such as 4E9 or BMS-554271), antibodies disclosed in U.S. Pat. No. 7,214, 493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362, 325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303, 121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof, as provided in FIG. 110:

In structures I-A and I-B, the cylinders refer to individual polypeptide binding domains. Structures I-A and I-B comprise three linearly-linked TNFRSF binding domains derived from e.g., 4-1BBL (4-1BB ligand, CD137 ligand (CD137L), or tumor necrosis factor superfamily member 9 (TNFSF9)) or an antibody that binds 4-1BB, which fold to form a trivalent protein, which is then linked to a second triavelent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 9

Amino acid sequences for TNFRSF agonist fusion proteins, including 4-1BB agonist fusion proteins, with C-terminal Fc-antibody fragment fusion protein design (structure I-A).

| Identifier | Sequence (One-Letter Amino Acid Symbols) | |
|---|---|---|
| SEQ ID NO: 31 Fc domain | KSCDKTHTCP PCPAPELLGG PSVFLFPPKP KDTLMISRTP EVTCVVVDVS HEDPEVKFNW | 60 |
| | YVDGVEVHNA KTKPREEQYN STYRVVSVLT VLHQDWLNGK EYKCKVSNKA LPAPIEKTIS | 120 |
| | KAKGQPREPQ VYTLPPSREE MTKNQVSLTC LVKGFYPSDI AVEWESNGQP ENNYKTTPPV | 180 |
| | LDSDGSFFLY SKLTVDKSRW QQGNVFSCSV MHEALHNHYT QKSLSLSPGK | 230 |
| SEQ ID NO: 32 linker | GGPGSSKSCD KTHTCPPCPA PE | 22 |
| SEQ ID NO: 33 linker | GGSGSSKSCD KTHTCPPCPA PE | 22 |
| SEQ ID NO: 34 linker | GGPGSSSSSS SKSCDKTHTC PPCPAPE | 27 |
| SEQ ID NO: 35 linker | GGSGSSSSSS SKSCDKTHTC PPCPAPE | 27 |
| SEQ ID NO: 36 linker | GGPGSSSSSS SSSKSCDKTH TCPPCPAPE | 29 |
| SEQ ID NO: 37 linker | GGSGSSSSSS SSSKSCDKTH TCPPCPAPE | 29 |
| SEQ ID NO: 38 linker | GGPGSSGSGS SDKTHTCPPC PAPE | 24 |
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 10. If an Fc antibody fragment is fused to the N-terminus of an TNRFSF agonist fusion protein as in structure I-B, the sequence of the Fc module is preferably that shown in SEQ ID NO:42, and the linker sequences are preferably selected from those embodiments set forth in SEQ ID NO:43 to SEQ ID NO:45.

TABLE 10

Amino acid sequences for TNFRSF agonist fusion proteins, including 4-1BB agonist fusion proteins, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 10, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 11, wherein the $V_H$ and $V_L$ domains are connected by a linker.

TABLE 11

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46 4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 47 4-1BBL soluble domain | LRQGMFAQLV AQNVLLIDGP LSWYSDPGLA GVSLTGGLSY KEDTKELVVA KAGVYYVFFQ | 60 |
| | LELRRVVAGE GSGSVSLALH LQPLRSAAGA AALALTVDLP PASSEARNSA FGFQGRLLHL | 120 |
| | SAGQRLGVHL HTEARARHAW QLTQGATVLG LFRVTPEIPA GLPSPRSE | 168 |
| SEQ ID NO: 48 variable heavy chain for 4B4-1-1 version 1 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVS | 118 |
| SEQ ID NO: 49 variable light chain for 4B4-1-1 version 1 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIK | 107 |
| SEQ ID NO: 50 variable heavy chain for 4B4-1-1 version 2 | QVQLQQPGAE LVKPGASVKL SCKASGYTFS SYWMHWVKQR PGQVLEWIGE INPGNGHTNY | 60 |
| | NEKFKSKATL TVDKSSSTAY MQLSSLTSED SAVYYCARSF TTARGFAYWG QGTLVTVSA | 119 |
| SEQ ID NO: 51 variable light chain for 4B4-1-1 version 2 | DIVMTQSPAT QSVTPGDRVS LSCRASQTIS DYLHWYQQKS HESPRLLIKY ASQSISGIPS | 60 |
| | RFSGSGSGSD FTLSINSVEP EDVGVYYCQD GHSFPPTFGG GTKLEIKR | 108 |
| SEQ ID NO: 52 variable heavy chain for H39E3-2 | MDWTWRILFL VAAATGAHSE VQLVESGGGL VQPGGSLRLS CAASGFTFSD YWMSWVRQAP | 60 |
| | GKGLEWVADI KNDGSYTNYA PSLTNRFTIS RDNAKNSLYL QMNSLRAEDT AVYYCARELT | 120 |
| SEQ ID NO: 53 variable light chain for H39E3-2 | MEAPAQLLFL LLLWLPDTTG DIVMTQSPDS LAVSLGERAT INCKSSQSLL SSGNQKNYL | 60 |
| | WYQQKPGQPP KLLIYYASTR QSGVPDRFSG SGSGTDFTLT ISSLQAEDVA | 110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist is BPS Bioscience 4-1BB agonist antibody catalog no. 79097-2, commercially available from BPS Bioscience, San Diego, CA, USA. In an embodiment, the 4-1BB agonist is Creative Biolabs 4-1BB agonist antibody catalog no. MOM-18179, commercially available from Creative Biolabs, Shirley, NY, USA.

3. OX40 (CD134) Agonists

In an embodiment, the TNFRSF agonist is an OX40 (CD134) agonist. The OX40 agonist may be any OX40 binding molecule known in the art. The OX40 binding molecule may be a monoclonal antibody or fusion protein capable of binding to human or mammalian OX40. The OX40 agonists or OX40 binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The OX40 agonist or OX40 binding molecule may have both a heavy and a light chain. As used herein, the term binding molecule also includes antibodies (including full length antibodies), monoclonal antibodies (including full length monoclonal antibodies), polyclonal antibodies, multi specific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to OX40. In an embodiment, the OX40 agonist is an antigen binding protein that is a fully human antibody. In an embodiment, the OX40 agonist is an antigen binding protein that is a humanized antibody. In some embodiments, OX40 agonists for use in the presently disclosed methods and compositions include anti-OX40 antibodies, human anti-OX40 antibodies, mouse anti-OX40 antibodies, mammalian anti-OX40 antibodies, monoclonal anti-OX40 antibodies, polyclonal anti-OX40 antibodies, chimeric anti-OX40 antibodies, anti-OX40 adnectins, anti-OX40 domain antibodies, single chain anti-OX40 fragments, heavy chain anti-OX40 fragments, light chain anti-OX40 fragments, anti-OX40 fusion proteins, and fragments, derivatives, conjugates, variants, or biosimilars thereof. In a preferred embodiment, the OX40 agonist is an agonistic, anti-OX40 humanized or fully human monoclonal antibody (i.e., an antibody derived from a single cell line).

In a preferred embodiment, the OX40 agonist or OX40 binding molecule may also be a fusion protein. OX40 fusion proteins comprising an Fc domain fused to OX40L are described, for example, in Sadun, et al., *J. Immunother.* 2009, 182, 1481-89. In a preferred embodiment, a multimeric OX40 agonist, such as a trimeric or hexameric OX40 agonist (with three or six ligand binding domains), may induce superior receptor (OX40L) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic OX40 antibodies and fusion proteins are known to induce strong immune responses. Curti, et al., *Cancer Res.* 2013, 73, 7189-98. In a preferred embodiment, the OX40 agonist is a monoclonal antibody or fusion protein that binds specifically to OX40 antigen in a manner sufficient to reduce toxicity. In some embodiments, the OX40 agonist is an agonistic OX40 monoclonal antibody or fusion protein that abrogates antibody-dependent cellular toxicity (ADCC), for example NK cell cytotoxicity. In some embodiments, the OX40 agonist is an agonistic OX40 monoclonal antibody or fusion protein that abrogates antibody-dependent cell phagocytosis (ADCP). In some embodiments, the OX40 agonist is an agonistic OX40 monoclonal antibody or fusion protein that abrogates complement-dependent cytotoxicity (CDC). In some embodiments, the OX40 agonist is an agonistic OX40 monoclonal antibody or fusion protein which abrogates Fc region functionality.

In some embodiments, the OX40 agonists are characterized by binding to human OX40 (SEQ ID NO:54) with high affinity and agonistic activity. In an embodiment, the OX40 agonist is a binding molecule that binds to human OX40 (SEQ ID NO:54). In an embodiment, the OX40 agonist is a binding molecule that binds to murine OX40 (SEQ ID NO:55). The amino acid sequences of OX40 antigen to which an OX40 agonist or binding molecule binds are summarized in Table 12.

TABLE 12

| Amino acid sequences of OX40 antigens. | | |
|---|---|---|
| Identifier | Sequence (One-Letter Amino Acid Symbols) | |
| SEQ ID NO: 54 | MCVGARRLGR GPCAALLLLG LGLSTVTGLH CVGDTYPSND RCCHECRPGN GMVSRCSRSQ | 60 |
| human OX40 | NTVCRPCGPG FYNDVVSSKP CKPCTWCNLR SGSERKQLCT ATQDTVCRCR AGTQPLDSYK | 120 |
| (*Homo sapiens*) | PGVDCAPCPP GHFSPGDNQA CKPWTNCTLA GKHTLQPASN SSDAICEDRD PPATQPQETQ | 180 |
| | GPPARPITVQ PTEAWPRTSQ GPSTRPVEVP GGRAVAAILG LGLVLGLLGP LAILLALYLL | 240 |
| | RRDQRLPPDA HKPPGGGSFR TPIQEEQADA HSTLAKI | 277 |
| SEQ ID NO: 55 | MYVWVQQPTA LLLLGLTLGV TARRLNCVKH TYPSGHKCCR ECQPGHGMVS RCDHTRDTLC | 60 |
| murine OX40 | HPCETGFYNE AVNYDTCKQC TQCNHRSGSE LKQNCTPTQD TVCRCRPGTQ PRQDSGYKLG | 120 |
| (*Mus musculus*) | VDCVPCPPGH FSPGNNQACK PWTNCTLSGK QTRHPASDSL DAVCEDRSLL ATLLWETQRP | 180 |
| | TFRPTTVQST TVWPRTSELP SPPTLVTPEG PAFAVLLGLG LGLLAPLTVL LALYLLRKAW | 240 |
| | RLPNTPKPCW GNSFRTPIQE EHTDAHFTLA KI | 272 |

In some embodiments, the compositions, processes and methods described include a OX40 agonist that binds human or murine OX40 with a $K_D$ of about 100 pM or lower, binds human or murine OX40 with a $K_D$ of about 90 pM or lower, binds human or murine OX40 with a $K_D$ of about 80 pM or lower, binds human or murine OX40 with a $K_D$ of about 70 pM or lower, binds human or murine OX40 with a $K_D$ of about 60 pM or lower, binds human or murine OX40 with a $K_D$ of about 50 pM or lower, binds human or murine OX40 with a $K_D$ of about 40 pM or lower, or binds human or murine OX40 with a $K_D$ of about 30 pM or lower.

In some embodiments, the compositions, processes and methods described include a OX40 agonist that binds to human or murine OX40 with a $k_{assoc}$ of about $7.5\times10^5$ 1/M·s or faster, binds to human or murine OX40 with a $k_{assoc}$ of about $7.5\times10^5$ 1/M·s or faster, binds to human or murine OX40 with a $k_{assoc}$ of about $8\times10^5$ 1/M·s or faster, binds to human or murine OX40 with a $k_{assoc}$ of about $8.5\times10^5$ 1/M·s or faster, binds to human or murine OX40 with a $k_{assoc}$ of about $9\times10^5$ 1/M·s or faster, binds to human or murine OX40 with a $k_{assoc}$ of about $9.5\times10^5$ 1/M·s or faster, or binds to human or murine OX40 with a $k_{assoc}$ of about $1\times10^6$ 1/M·s or faster.

In some embodiments, the compositions, processes and methods described include a OX40 agonist that binds to human or murine OX40 with a $k_{dissoc}$ of about $2\times10^{-5}$ 1/s or slower, binds to human or murine OX40 with a $k_{dissoc}$ of about $2.1\times10^{-5}$ 1/s or slower, binds to human or murine OX40 with a $k_{dissoc}$ of about $2.2\times10^{-5}$ 1/s or slower, binds to human or murine OX40 with a $k_{dissoc}$ of about $2.3\times10^{-5}$ 1/s or slower, binds to human or murine OX40 with a $k_{dissoc}$ of about $2.4\times10^{-5}$ 1/s or slower, binds to human or murine OX40 with a $k_{dissoc}$ of about $2.5\times10^{-5}$ 1/s or slower, binds to human or murine OX40 with a $k_{dissoc}$ of about $2.6\times10^{-5}$ 1/s or slower or binds to human or murine OX40 with a $k_{dissoc}$ of about $2.7\times10^{-5}$ 1/s or slower, binds to human or murine OX40 with a $k_{dissoc}$ of about $2.8\times10^{-5}$ 1/s or slower, binds to human or murine OX40 with a $k_{dissoc}$ of about $2.9\times10^{-5}$ 1/s or slower, or binds to human or murine OX40 with a $k_{dissoc}$ of about $3\times10^{-5}$ 1/s or slower.

In some embodiments, the compositions, processes and methods described include OX40 agonist that binds to human or murine OX40 with an $IC_{50}$ of about 10 nM or lower, binds to human or murine OX40 with an $IC_{50}$ of about 9 nM or lower, binds to human or murine OX40 with an $IC_{50}$ of about 8 nM or lower, binds to human or murine OX40 with an $IC_{50}$ of about 7 nM or lower, binds to human or murine OX40 with an $IC_{50}$ of about 6 nM or lower, binds to human or murine OX40 with an $IC_{50}$ of about 5 nM or lower, binds to human or murine OX40 with an $IC_{50}$ of about 4 nM or lower, binds to human or murine OX40 with an $IC_{50}$ of about 3 nM or lower, binds to human or murine OX40 with an $IC_{50}$ of about 2 nM or lower, or binds to human or murine OX40 with an $IC_{50}$ of about 1 nM or lower.

In some embodiments, the OX40 agonist is tavolixizumab, also known as MEDI0562 or MEDI-0562. Tavolixizumab is available from the MedImmune subsidiary of AstraZeneca, Inc. Tavolixizumab is immunoglobulin G1-kappa, anti-[*Homo sapiens* TNFRSF4 (tumor necrosis factor receptor (TNFR) superfamily member 4, OX40, CD134)], humanized and chimeric monoclonal antibody. The amino acid sequences of tavolixizumab are set forth in Table 13. Tavolixizumab comprises N-glycosylation sites at positions 301 and 301", with fucosylated complex bi-antennary CHO-type glycans; heavy chain intrachain disulfide bridges at positions 22-95 ($V_H$-$V_L$), 148-204 ($C_H1$-$C_L$), 265-325 ($C_H2$) and 371-429 ($C_H3$) (and at positions 22"-95", 148"-204", 265"-325", and 371"-429"); light chain intrachain disulfide bridges at positions 23'-88' ($V_H$-$V_L$) and 134'-194' ($C_H1$-$C_L$) (and at positions 23'"-88'" and 134'"-194'"); interchain heavy chain-heavy chain disulfide bridges at positions 230-230" and 233-233"; and interchain heavy chain-light chain disulfide bridges at 224-214' and 224"-214'". Current clinical trials of tavolixizumab in a variety of solid tumor indications include U.S. National Institutes of Health clinicaltrials.gov identifiers NCT02318394 and NCT02705482.

In an embodiment, a OX40 agonist comprises a heavy chain given by SEQ ID NO:56 and a light chain given by SEQ ID NO:57. In an embodiment, a OX40 agonist comprises heavy and light chains having the sequences shown in SEQ ID NO:56 and SEQ ID NO:57, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:56 and SEQ ID NO:57, respectively. In an embodiment, a OX40 agonist comprises heavy and light chains that are each at least 98% identical to the sequences shown in SEQ ID NO:56 and SEQ ID NO:57, respectively. In an embodiment, a OX40 agonist comprises heavy and light chains that are each at least 97% identical to the sequences shown in SEQ ID NO:56 and SEQ ID NO:57, respectively. In an embodiment, a OX40 agonist comprises heavy and light chains that are each at least 96% identical to the sequences shown in SEQ ID NO:56 and SEQ ID NO:57, respectively. In an embodiment, a OX40 agonist comprises heavy and light chains that are each at least 95% identical to the sequences shown in SEQ ID NO:56 and SEQ ID NO:57, respectively.

In an embodiment, the OX40 agonist comprises the heavy and light chain CDRs or variable regions (VRs) of tavolixizumab. In an embodiment, the OX40 agonist heavy chain variable region ($V_H$) comprises the sequence shown in SEQ ID NO:58, and the OX40 agonist light chain variable region ($V_L$) comprises the sequence shown in SEQ ID NO:59, and conservative amino acid substitutions thereof. In an embodiment, a OX40 agonist comprises $V_H$ and $V_L$ regions that are each at least 99% identical to the sequences shown in SEQ ID NO:58 and SEQ ID NO:59, respectively. In an embodiment, a OX40 agonist comprises V14 and $V_L$ regions that are each at least 98% identical to the sequences shown in SEQ ID NO:58 and SEQ ID NO:59, respectively. In an embodiment, a OX40 agonist comprises $V_H$ and $V_L$ regions that are each at least 97% identical to the sequences shown in SEQ ID NO:58 and SEQ ID NO:59, respectively. In an embodiment, a OX40 agonist comprises $V_H$ and $V_L$ regions that are each at least 96% identical to the sequences shown in SEQ ID NO:58 and SEQ ID NO:59, respectively. In an embodiment, a OX40 agonist comprises $V_H$ and $V_L$ regions that are each at least 95% identical to the sequences shown in SEQ ID NO:58 and SEQ ID NO:59, respectively. In an embodiment, an OX40 agonist comprises an scFv antibody comprising $V_H$ and $V_L$ regions that are each at least 99% identical to the sequences shown in SEQ ID NO:58 and SEQ ID NO:59.

In an embodiment, a OX40 agonist comprises heavy chain CDR1, CDR2 and CDR3 domains having the sequences set forth in SEQ ID NO:60, SEQ ID NO:61, and SEQ ID NO:62, respectively, and conservative amino acid substitutions thereof, and light chain CDR1, CDR2 and CDR3 domains having the sequences set forth in SEQ ID NO:63, SEQ ID NO:64, and SEQ ID NO:65, respectively, and conservative amino acid substitutions thereof.

In an embodiment, the OX40 agonist is a OX40 agonist biosimilar monoclonal antibody approved by drug regulatory authorities with reference to tavolixizumab. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is tavolixizumab. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is tavolixizumab. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is tavolixizumab.

TABLE 13

Amino acid sequences for OX40 agonist antibodies related to tavolixizumab.

| Identifier | Sequence (One-Letter Amino Acid Symbols) | |
|---|---|---|
| SEQ ID NO: 56 heavy chain for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKRVE PKSCDKTHTC PPCPAPELLG<br>GPSVFLFPPK PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG K | 60<br>120<br>180<br>240<br>300<br>360<br>420<br>451 |
| SEQ ID NO: 57 light chain for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKRTV AAPSVFIFPP<br>SDEQLKSGTA SVVCLLNNFY PREAKVQWKV DNALQSGNSQ ESVTEQDSKD STYSLSSTLT<br>LSKADYEKHK VYACEVTHQG LSSPVTKSFN RGEC | 60<br>120<br>180<br>214 |
| SEQ ID NO: 58 heavy chain variable region for tavolixizumab | QVQLQESGPG LVKPSQTLSL TCAVYGGSFS SGYWNWIRKH PGKGLEYIGY ISYNGITYHN<br>PSLKSRITIN RDTSKNQYSL QLNSVTPEDT AVYYCARYKY DYDGGHAMDY WGQGTLVT | 60<br>118 |
| SEQ ID NO: 59 light chain variable region for tavolixizumab | DIQMTQSPSS LSASVGDRVT ITCRASQDIS NYLNWYQQKP GKAPKLLIYY TSKLHSGVPS<br>RFSGSGSGTD YTLTISSLQP EDFATYYCQQ GSALPWTFGQ GTKVEIKR | 60<br>108 |
| SEQ ID NO: 60 heavy chain CDR1 for tavolixizumab | GSFSSGYWN | 9 |

TABLE 13-continued

Amino acid sequences for OX40 agonist antibodies related to tavolixizumab.

| Identifier | Sequence (One-Letter Amino Acid Symbols) | |
|---|---|---|
| SEQ ID NO: 61 heavy chain CDR2 for tavolixizumab | YIGYISYNGI TYH | 13 |
| SEQ ID NO: 62 heavy chain CDR3 for tavolixizumab | RYKYDYDGGH AMDY | 14 |
| SEQ ID NO: 63 light chain CDR1 for tavolixizumab | QDISNYLN | 8 |
| SEQ ID NO: 64 light chain CDR2 for tavolixizumab | LLIYYTSKLH S | 11 |
| SEQ ID NO: 65 light chain CDR3 for tavolixizumab | QQGSALPW | 8 |

In some embodiments, the OX40 agonist is 11D4, which is a fully human antibody available from Pfizer, Inc. The preparation and properties of 11D4 are described in U.S. Pat. Nos. 7,960,515; 8,236,930; and 9,028,824, the disclosures of which are incorporated by reference herein. The amino acid sequences of 11D4 are set forth in Table 14.

In an embodiment, a OX40 agonist comprises a heavy chain given by SEQ ID NO:66 and a light chain given by SEQ ID NO:67. In an embodiment, a OX40 agonist comprises heavy and light chains having the sequences shown in SEQ ID NO:66 and SEQ ID NO:67, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:66 and SEQ ID NO:67, respectively. In an embodiment, a OX40 agonist comprises heavy and light chains that are each at least 98% identical to the sequences shown in SEQ ID NO:66 and SEQ ID NO:67, respectively. In an embodiment, a OX40 agonist comprises heavy and light chains that are each at least 97% identical to the sequences shown in SEQ ID NO:66 and SEQ ID NO:67, respectively. In an embodiment, a OX40 agonist comprises heavy and light chains that are each at least 96% identical to the sequences shown in SEQ ID NO:66 and SEQ ID NO:67, respectively. In an embodiment, a OX40 agonist comprises heavy and light chains that are each at least 95% identical to the sequences shown in SEQ ID NO:66 and SEQ ID NO:67, respectively.

In an embodiment, the OX40 agonist comprises the heavy and light chain CDRs or variable regions (VRs) of 11D4. In an embodiment, the OX40 agonist heavy chain variable region ($V_H$) comprises the sequence shown in SEQ ID NO:68, and the OX40 agonist light chain variable region ($V_L$) comprises the sequence shown in SEQ ID NO:69, and conservative amino acid substitutions thereof. In an embodiment, a OX40 agonist comprises $V_H$ and $V_L$ regions that are each at least 99% identical to the sequences shown in SEQ ID NO:68 and SEQ ID NO:69, respectively. In an embodiment, a OX40 agonist comprises Vu and $V_L$ regions that are each at least 98% identical to the sequences shown in SEQ ID NO:68 and SEQ ID NO:69, respectively. In an embodiment, a OX40 agonist comprises $V_H$ and $V_L$ regions that are each at least 97% identical to the sequences shown in SEQ ID NO:68 and SEQ ID NO:69, respectively. In an embodiment, a OX40 agonist comprises $V_H$ and $V_L$ regions that are each at least 96% identical to the sequences shown in SEQ ID NO:68 and SEQ ID NO:69, respectively. In an embodiment, a OX40 agonist comprises $V_H$ and $V_L$ regions that are each at least 95% identical to the sequences shown in SEQ ID NO:68 and SEQ ID NO:69, respectively.

In an embodiment, a OX40 agonist comprises heavy chain CDR1, CDR2 and CDR3 domains having the sequences set forth in SEQ ID NO:70, SEQ ID NO:71, and SEQ ID NO:72, respectively, and conservative amino acid substitutions thereof, and light chain CDR1, CDR2 and CDR3 domains having the sequences set forth in SEQ ID NO:73, SEQ ID NO:74, and SEQ ID NO:75, respectively, and conservative amino acid substitutions thereof.

In an embodiment, the OX40 agonist is a OX40 agonist biosimilar monoclonal antibody approved by drug regulatory authorities with reference to 11D4. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 11D4. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 11D4. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 11D4.

In an embodiment, a OX40 agonist comprises a heavy chain given by SEQ ID NO:76 and a light chain given by SEQ ID NO:77. In an embodiment, a OX40 agonist comprises heavy and light chains having the sequences shown in SEQ ID NO:76 and SEQ ID NO:77, respectively, or antigen binding fragments, Fab fragments, single-chain variable fragments (scFv), variants, or conjugates thereof. In an embodiment, a OX40 agonist comprises heavy and light chains that are each at least 99% identical to the sequences shown in SEQ ID NO:76 and SEQ ID NO:77, respectively. In an embodiment, a OX40 agonist comprises heavy and light chains that are each at least 98% identical to the sequences shown in SEQ ID NO:76 and SEQ ID NO:77, respectively. In an embodiment, a OX40 agonist comprises heavy and light chains that are each at least 97% identical to the sequences shown in SEQ ID NO:76 and SEQ ID NO:77, respectively. In an embodiment, a OX40 agonist comprises heavy and light chains that are each at least 96% identical to the sequences shown in SEQ ID NO:76 and SEQ ID NO:77, respectively. In an embodiment, a OX40 agonist comprises

TABLE 14

Amino acid sequences for OX40 agonist antibodies related to 11D4.

| Identifier | Sequence (One-Letter Amino Acid Symbols) | |
|---|---|---|
| SEQ ID NO: 66 heavy chain for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSSAS | 120 |
| | TKGPSVFPLA PCSRSTSEST AALGCLVKDY FPEPVTVSWN SGALTSGVHT FPAVLQSSGL | 180 |
| | YSLSSVVTVP SSNFGTQTYT CNVDHKPSNT KVDKTVERKC CVECPPCPAP PVAGPSVFLF | 240 |
| | PPKPKDTLMI SRTPEVTCVV VDVSHEDPEV QFNWYVDGVE VHNAKTKPRE EQFNSTFRVV | 300 |
| | SVLTVVHQDW LNGKEYKCKV SNKGLPAPIE KTISKTKGQP REPQVYTLPP SREEMTKNQV | 360 |
| | SLTCLVKGFY PSDIAVEWES NGQPENNYKT TPPMLDSDGS FFLYSKLTVD KSRWQQGNVF | 420 |
| | SCSVMHEALH NHYTQKSLSL SPGK | 444 |
| SEQ ID NO: 67 light chain for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIKRTV AAPSVFIFPP | 120 |
| | SDEQLKSGTA SVVCLLNNFY PREAKVQWKV DNALQSGNSQ ESVTEQDSKD STYSLSSTLT | 180 |
| | LSKADYEKHK VYACEVTHQG LSSPVTKSFN RGEC | 214 |
| SEQ ID NO: 68 heavy chain variable region for 11D4 | EVQLVESGGG LVQPGGSLRL SCAASGFTFS SYSMNWVRQA PGKGLEWVSY ISSSSSTIDY | 60 |
| | ADSVKGRFTI SRDNAKNSLY LQMNSLRDED TAVYYCARES GWYLFDYWGQ GTLVTVSS | 118 |
| SEQ ID NO: 69 light chain variable region for 11D4 | DIQMTQSPSS LSASVGDRVT ITCRASQGIS SWLAWYQQKP EKAPKSLIYA ASSLQSGVPS | 60 |
| | RFSGSGSGTD FTLTISSLQP EDFATYYCQQ YNSYPPTFGG GTKVEIK | 107 |
| SEQ ID NO: 70 heavy chain CDR1 for 11D4 | SYSMN | 5 |
| SEQ ID NO: 71 heavy chain CDR2 for 11D4 | YISSSSSTID YADSVKG | 17 |
| SEQ ID NO: 72 heavy chain CDR3 for 11D4 | ESGWYLFDY | 9 |
| SEQ ID NO: 73 light chain CDR1 for 11D4 | RASQGISSWL A | 11 |
| SEQ ID NO: 74 light chain CDR2 for 11D4 | AASSLQS | 7 |
| SEQ ID NO: 75 light chain CDR3 for 11D4 | QQYNSYPPT | 9 |

In some embodiments, the OX40 agonist is 18D8, which is a fully human antibody available from Pfizer, Inc. The preparation and properties of 18D8 are described in U.S. Pat. Nos. 7,960,515; 8,236,930; and 9,028,824, the disclosures of which are incorporated by reference herein. The amino acid sequences of 18D8 are set forth in Table 15.

heavy and light chains that are each at least 95% identical to the sequences shown in SEQ ID NO:76 and SEQ ID NO:77, respectively.

In an embodiment, the OX40 agonist comprises the heavy and light chain CDRs or variable regions (VRs) of 18D8. In an embodiment, the OX40 agonist heavy chain variable region ($V_H$) comprises the sequence shown in SEQ ID NO:78, and the OX40 agonist light chain variable region ($V_L$) comprises the sequence shown in SEQ ID NO:79, and conservative amino acid substitutions thereof. In an embodiment, a OX40 agonist comprises $V_H$ and $V_L$ regions that are each at least 99% identical to the sequences shown in SEQ ID NO:78 and SEQ ID NO:79, respectively. In an embodiment, a OX40 agonist comprises $V_H$ and $V_L$ regions that are each at least 98% identical to the sequences shown in SEQ ID NO:78 and SEQ ID NO:79, respectively. In an embodiment, a OX40 agonist comprises $V_H$ and $V_L$ regions that are each at least 97% identical to the sequences shown in SEQ ID NO:78 and SEQ ID NO:79, respectively. In an embodiment, a OX40 agonist comprises $V_H$ and $V_L$ regions that are each at least 96% identical to the sequences shown in SEQ ID NO:78 and SEQ ID NO:79, respectively. In an embodiment, a OX40 agonist comprises $V_H$ and $V_L$ regions that are each at least 95% identical to the sequences shown in SEQ ID NO:78 and SEQ ID NO:79, respectively.

In an embodiment, a OX40 agonist comprises heavy chain CDR1, CDR2 and CDR3 domains having the sequences set forth in SEQ ID NO:80, SEQ ID NO:81, and SEQ ID NO:82, respectively, and conservative amino acid substitutions thereof, and light chain CDR1, CDR2 and CDR3 domains having the sequences set forth in SEQ ID NO:83, SEQ ID NO:84, and SEQ ID NO:85, respectively, and conservative amino acid substitutions thereof.

In an embodiment, the OX40 agonist is a OX40 agonist biosimilar monoclonal antibody approved by drug regulatory authorities with reference to 18D8. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is 18D8. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is 18D8. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is 18D8.

TABLE 15

Amino acid sequences for OX40 agonist antibodies related to 18D8.

| Identifier | Sequence (One-Letter Amino Acid Symbols) | |
|---|---|---|
| SEQ ID NO: 76<br>heavy chain for<br>18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSSASTKGP SVFPLAPCSR STSESTAALG CLVKDYFPEP VTVSWNSGAL TSGVHTFPAV<br>LQSSGLYSLS SVVTVPSSNF GTQTYTCNVD HKPSNTKVDK TVERKCCVEC PPCPAPPVAG<br>PSVFLFPPKP KDTLMISRTP EVTCVVVDVS HEDPEVQFNW YVDGVEVHNA KTKPREEQFN<br>STFRVVSVLT VVHQDWLNGK EYKCKVSNKG LPAPIEKTIS KTKGQPREPQ VYTLPPSREE<br>MTKNQVSLTC LVKGFYPSDI AVEWESNGQP ENNYKTTPPM LDSDGSFFLY SKLTVDKSRW<br>QQGNVFSCSV MHEALHNHYT QKSLSLSPGK | 60<br>120<br>180<br>240<br>300<br>360<br>420<br>450 |
| SEQ ID NO: 77<br>light chain for<br>18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIKRTVA APSVFIFPPS<br>DEQLKSGTAS VVCLLNNFYP REAKVQWKVD NALQSGNSQE SVTEQDSKDS TYSLSSTLTL<br>SKADYEKHKV YACEVTHQGL SSPVTKSFNR GEC | 60<br>120<br>180<br>213 |
| SEQ ID NO: 78<br>heavy chain<br>variable region<br>for 18D8 | EVQLVESGGG LVQPGRSLRL SCAASGFTFD DYAMHWVRQA PGKGLEWVSG ISWNSGSIGY<br>ADSVKGRFTI SRDNAKNSLY LQMNSLRAED TALYYCAKDQ STADYYFYYG MDVWGQGTTV<br>TVSS | 60<br>120<br>124 |
| SEQ ID NO: 79<br>light chain<br>variable region<br>for 18D8 | EIVVTQSPAT LSLSPGERAT LSCRASQSVS SYLAWYQQKP GQAPRLLIYD ASNRATGIPA<br>RFSGSGSGTD FTLTISSLEP EDFAVYYCQQ RSNWPTFGQG TKVEIK | 60<br>106 |
| SEQ ID NO: 80<br>heavy chain CDR1<br>for 18D8 | DYAMH | 5 |
| SEQ ID NO: 81<br>heavy chain CDR2<br>for 18D8 | GISWNSGSIG YADSVKG | 17 |

TABLE 15-continued

| Amino acid sequences for OX40 agonist antibodies related to 18D8. | | |
|---|---|---|
| Identifier | Sequence (One-Letter Amino Acid Symbols) | |
| SEQ ID NO: 82 heavy chain CDR3 for 18D8 | DQSTADYYFY YGMDV | 15 |
| SEQ ID NO: 83 light chain CDR1 for 18D8 | RASQSVSSYL A | 11 |
| SEQ ID NO: 84 light chain CDR2 for 18D8 | DASNRAT | 7 |
| SEQ ID NO: 85 light chain CDR3 for 18D8 | QQRSNWPT | 8 |

In some embodiments, the OX40 agonist is Hu119-122, which is a humanized antibody available from GlaxoSmithKline plc. The preparation and properties of Hu119-122 are described in U.S. Pat. Nos. 9,006,399 and 9,163,085, and in International Patent Publication No. WO 2012/027328, the disclosures of which are incorporated by reference herein. The amino acid sequences of Hu119-122 are set forth in Table 16.

In an embodiment, the OX40 agonist comprises the heavy and light chain CDRs or variable regions (VRs) of Hu119-122. In an embodiment, the OX40 agonist heavy chain variable region ($V_H$) comprises the sequence shown in SEQ ID NO:86, and the OX40 agonist light chain variable region ($V_L$) comprises the sequence shown in SEQ ID NO:87, and conservative amino acid substitutions thereof. In an embodiment, a OX40 agonist comprises $V_H$ and $V_L$ regions that are each at least 99% identical to the sequences shown in SEQ ID NO:86 and SEQ ID NO:87, respectively. In an embodiment, a OX40 agonist comprises $V_H$ and $V_L$ regions that are each at least 98% identical to the sequences shown in SEQ ID NO:86 and SEQ ID NO:87, respectively. In an embodiment, a OX40 agonist comprises $V_H$ and $V_L$ regions that are each at least 97% identical to the sequences shown in SEQ ID NO:86 and SEQ ID NO:87, respectively. In an embodiment, a OX40 agonist comprises $V_H$ and $V_L$ regions that are each at least 96% identical to the sequences shown in SEQ ID NO:86 and SEQ ID NO:87, respectively. In an embodiment, a OX40 agonist comprises $V_H$ and $V_L$ regions that are each at least 95% identical to the sequences shown in SEQ ID NO:86 and SEQ ID NO:87, respectively.

In an embodiment, a OX40 agonist comprises heavy chain CDR1, CDR2 and CDR3 domains having the sequences set forth in SEQ ID NO:88, SEQ ID NO:89, and SEQ ID NO:90, respectively, and conservative amino acid substitutions thereof, and light chain CDR1, CDR2 and CDR3 domains having the sequences set forth in SEQ ID NO:91, SEQ ID NO:92, and SEQ ID NO:93, respectively, and conservative amino acid substitutions thereof.

In an embodiment, the OX40 agonist is a OX40 agonist biosimilar monoclonal antibody approved by drug regulatory authorities with reference to Hu119-122. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu119-122. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu119-122. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu119-122.

TABLE 16

| Amino acid sequences for OX40 agonist antibodies related to Hu119-122. | | |
|---|---|---|
| Identifier | Sequence (One-Letter Amino Acid Symbols) | |
| SEQ ID NO: 86 heavy chain variable region for Hu119-122 | EVQLVESGGG LVQPGGSLRL SCAASEYEFP SHDMSWVRQA PGKGLELVAA INSDGGSTYY | 60 |
| | PDTMERRFTI SRDNAKNSLY LQMNSLRAED TAVYYCARHY DDYYAWFAYW GQGTMVTVSS | 120 |

TABLE 16-continued

Amino acid sequences for OX40 agonist antibodies related to Hu119-122.

| Identifier | Sequence (One-Letter Amino Acid Symbols) | |
|---|---|---|
| SEQ ID NO: 87 light chain variable region for Hu119-122 | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 88 heavy chain CDR1 for Hu119-122 | SHDMS | 5 |
| SEQ ID NO: 89 heavy chain CDR2 for Hu119-122 | AINSDGGSTY YPDTMER | 17 |
| SEQ ID NO: 90 heavy chain CDR3 for Hu119-122 | HYDDYYAWFA Y | 11 |
| SEQ ID NO: 91 light chain CDR1 for Hu119-122 | RASKSVSTSG YSYMH | 15 |
| SEQ ID NO: 92 light chain CDR2 for Hu119-122 | LASNLES | 7 |
| SEQ ID NO: 93 light chain CDR3 for Hu119-122 | QHSRELPLT | 9 |

In some embodiments, the OX40 agonist is Hu106-222, which is a humanized antibody available from GlaxoSmithKline plc. The preparation and properties of Hu106-222 are described in U.S. Pat. Nos. 9,006,399 and 9,163,085, and in International Patent Publication No. WO 2012/027328, the disclosures of which are incorporated by reference herein. The amino acid sequences of Hu106-222 are set forth in Table 17.

In an embodiment, the OX40 agonist comprises the heavy and light chain CDRs or variable regions (VRs) of Hu106-222. In an embodiment, the OX40 agonist heavy chain variable region ($V_H$) comprises the sequence shown in SEQ ID NO:94, and the OX40 agonist light chain variable region ($V_L$) comprises the sequence shown in SEQ ID NO:95, and conservative amino acid substitutions thereof. In an embodiment, a OX40 agonist comprises $V_H$ and $V_L$ regions that are each at least 99% identical to the sequences shown in SEQ ID NO:94 and SEQ ID NO:95, respectively. In an embodiment, a OX40 agonist comprises $V_H$ and $V_L$ regions that are each at least 98% identical to the sequences shown in SEQ ID NO:94 and SEQ ID NO:95, respectively. In an embodiment, a OX40 agonist comprises $V_H$ and $V_L$ regions that are each at least 97% identical to the sequences shown in SEQ ID NO:94 and SEQ ID NO:95, respectively. In an embodiment, a OX40 agonist comprises $V_H$ and $V_L$ regions that are each at least 96% identical to the sequences shown in SEQ ID NO:94 and SEQ ID NO:95, respectively. In an embodiment, a OX40 agonist comprises $V_H$ and $V_L$ regions that are each at least 95% identical to the sequences shown in SEQ ID NO:94 and SEQ ID NO:95, respectively.

In an embodiment, a OX40 agonist comprises heavy chain CDR1, CDR2 and CDR3 domains having the sequences set forth in SEQ ID NO:96, SEQ ID NO:97, and SEQ ID NO:98, respectively, and conservative amino acid substitutions thereof, and light chain CDR1, CDR2 and CDR3 domains having the sequences set forth in SEQ ID NO:99, SEQ ID NO:100, and SEQ ID NO:101, respectively, and conservative amino acid substitutions thereof.

In an embodiment, the OX40 agonist is a OX40 agonist biosimilar monoclonal antibody approved by drug regulatory authorities with reference to Hu106-222. In an embodiment, the biosimilar monoclonal antibody comprises an OX40 antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is Hu106-222. In some embodiments, the one or more post-translational modifications are selected from one or more of: glycosylation, oxidation, deamidation, and truncation. In some embodiments, the biosimilar is a OX40 agonist antibody authorized or submitted for authorization, wherein the OX40 agonist antibody is provided in a formulation which differs from the formulations of a reference medicinal product or reference biological product, wherein the reference medicinal product or reference biological product is Hu106-222. The OX40 agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is Hu106-222.

TABLE 17

Amino acid sequences for OX40 agonist antibodies related to Hu106-222.

| Identifier | Sequence (One-Letter Amino Acid Symbols) | |
|---|---|---|
| SEQ ID NO: 94 heavy chain variable region for Hu106-222 | QVQLVQSGSE LKKPGASVKV SCKASGYTFT DYSMHWVRQA PGQGLKWMGW INTETGEPTY | 60 |
| | ADDFKGRFVF SLDTSVSTAY LQISSLKAED TAVYYCANPY YDYVSYYAMD YWGQGTTVTV | 120 |
| | SS | 122 |
| SEQ ID NO: 95 light chain variable region for Hu106-222 | DIQMTQSPSS LSASVGDRVT ITCKASQDVS TAVAWYQQKP GKAPKLLIYS ASYLYTGVPS | 60 |
| | RFSGSGSGTD FTFTISSLQP EDIATYYCQQ HYSTPRTFGQ GTKLEIK | 107 |
| SEQ ID NO: 96 heavy chain CDR1 for Hu106-222 | DYSMH | 5 |
| SEQ ID NO: 97 heavy chain CDR2 for Hu106-222 | WINTETGEPT YADDFKG | 17 |
| SEQ ID NO: 98 heavy chain CDR3 for Hu106-222 | PYYDYVSYYA MDY | 13 |
| SEQ ID NO: 99 light chain CDR1 for Hu106-222 | KASQDVSTAV A | 11 |
| SEQ ID NO: 100 light chain CDR2 for Hu106-222 | SASYLYT | 7 |
| SEQ ID NO: 101 light chain CDR3 for Hu106-222 | QQHYSTPRT | 9 |

In some embodiments, the OX40 agonist antibody is MEDI6469 (also referred to as 9B12). MEDI6469 is a murine monoclonal antibody. Weinberg, et al., *J. Immunother.* 2006, 29, 575-585. In some embodiments the OX40 agonist is an antibody produced by the 9B12 hybridoma, deposited with Biovest Inc. (Malvern, MA, USA), as described in Weinberg, et al., *J. Immunother.* 2006, 29, 575-585, the disclosure of which is hereby incorporated by reference in its entirety. In some embodiments, the antibody comprises the CDR sequences of MEDI6469. In some embodiments, the antibody comprises a heavy chain variable region sequence and/or a light chain variable region sequence of MEDI6469.

In an embodiment, the OX40 agonist is L106 BD (Pharmingen Product #340420). In some embodiments, the OX40 agonist comprises the CDRs of antibody L106 (BD Pharmingen Product #340420). In some embodiments, the OX40 agonist comprises a heavy chain variable region sequence and/or a light chain variable region sequence of antibody L106 (BD Pharmingen Product #340420). In an embodiment, the OX40 agonist is ACT35 (Santa Cruz Biotechnology, Catalog #20073). In some embodiments, the OX40 agonist comprises the CDRs of antibody ACT35 (Santa Cruz Biotechnology, Catalog #20073). In some embodiments, the OX40 agonist comprises a heavy chain variable region sequence and/or a light chain variable region sequence of antibody ACT35 (Santa Cruz Biotechnology, Catalog #20073). In an embodiment, the OX40 agonist is the murine monoclonal antibody anti-mCD134/mOX40 (clone OX86), commercially available from InVivoMAb, BioXcell Inc, West Lebanon, NH.

In an embodiment, the OX40 agonist is selected from the OX40 agonists described in International Patent Application Publication Nos. WO 95/12673, WO 95/21925, WO 2006/121810, WO 2012/027328, WO 2013/028231, WO 2013/038191, and WO 2014/148895; European Patent Application EP 0672141; U.S. Patent Application Publication Nos. US 2010/136030, US 2014/377284, US 2015/190506, and US 2015/132288 (including clones 20E5 and 12H3); and U.S. Pat. Nos. 7,504,101, 7,550,140, 7,622,444, 7,696,175, 7,960,515, 7,961,515, 8,133,983, 9,006,399, and 9,163,085, the disclosure of each of which is incorporated herein by reference in its entirety.

In an embodiment, the OX40 agonist is an OX40 agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof. The properties of structures I-A and I-B are described above and in U.S. Pat. Nos. 9,359,420, 9,340,599, 8,921,519, and 8,450,460, the disclosures of which are incorporated by reference herein. Amino acid sequences for the polypeptide domains of structure I-A are given in Table 9. The Fc domain preferably comprises a complete constant domain (amino acids 17-230 of SEQ ID NO:31) the complete hinge domain (amino acids 1-16 of SEQ ID NO:31) or a portion of the hinge domain (e.g., amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides. Likewise, amino acid sequences for the polypeptide domains of structure I-B are given in Table 10. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SEQ ID NO:43 to SEQ ID NO:45.

In an embodiment, an OX40 agonist fusion protein according to structures I-A or I-B comprises one or more OX40 binding domains selected from the group consisting of a variable heavy chain and variable light chain of tavolixizumab, a variable heavy chain and variable light chain of 11D4, a variable heavy chain and variable light chain of 18D8, a variable heavy chain and variable light chain of Hu119-122, a variable heavy chain and variable light chain of Hu106-222, a variable heavy chain and variable light chain selected from the variable heavy chains and variable light chains described in Table 17, any combination of a variable heavy chain and variable light chain of the foregoing, and fragments, derivatives, conjugates, variants, and biosimilars thereof.

In an embodiment, an OX40 agonist fusion protein according to structures I-A or I-B comprises one or more OX40 binding domains comprising an OX40L sequence. In an embodiment, an OX40 agonist fusion protein according to structures I-A or I-B comprises one or more OX40 binding domains comprising a sequence according to SEQ ID NO:102. In an embodiment, an OX40 agonist fusion protein according to structures I-A or I-B comprises one or more OX40 binding domains comprising a soluble OX40L sequence. In an embodiment, a OX40 agonist fusion protein according to structures I-A or I-B comprises one or more OX40 binding domains comprising a sequence according to SEQ ID NO:103. In an embodiment, a OX40 agonist fusion protein according to structures I-A or I-B comprises one or more OX40 binding domains comprising a sequence according to SEQ ID NO:104.

In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:58 and SEQ ID NO:59, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:68 and SEQ ID NO:69, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:78 and SEQ ID NO:79, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:86 and SEQ ID NO:87, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the sequences shown in SEQ ID NO:94 and SEQ ID NO:95, respectively, wherein the $V_H$ and $V_L$ domains are connected by a linker. In an embodiment, an OX40 agonist fusion protein according to structures I-A or I-B comprises one or more OX40 binding domains that is a scFv domain comprising $V_H$ and $V_L$ regions that are each at least 95% identical to the $V_H$ and $V_L$ sequences given in Table 14, wherein the $V_H$ and $V_L$ domains are connected by a linker.

TABLE 18

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 102<br>OX40L | MERVQPLEEN VGNAARPRFE RNKLLLVASV IQGLGLLLCF TYICLHFSAL QVSHRYPRIQ | 60 |
| | SIKVQFTEYK KEKGFILTSQ KEDEIMKVQN NSVIINCDGF YLISLKGYFS QEVNISLHYQ | 120 |
| | KDEEPLFQLK KVRSVNSLMV ASLTYKDKVY LNVTTDNTSL DDFHVNGGEL ILIHQNPGEF | 180 |
| | CVL | 183 |
| SEQ ID NO: 103<br>OX40L soluble domain | SHRYPRIQSI KVQFTEYKKE KGFILTSQKE DEIMKVQNNS VIINCDGFYL ISLKGYFSQE | 60 |
| | VNISLHYQKD EEPLFQLKKV RSVNSLMVAS LTYKDKVYLN VTTDNTSLDD FHVNGGELIL | 120 |
| | IHQNPGEFCV L | 131 |
| SEQ ID NO: 104<br>OX40L soluble domain (alternative) | YPRIQSIKVQ FTEYKKEKGF ILTSQKEDEI MKVQNNSVII NCDGFYLISL KGYFSQEVNI | 60 |
| | SLHYQKDEEP LFQLKKVRSV NSLMVASLTY KDKVYLNVTT DNTSLDDFHV NGGELILIHQ | 120 |
| | NPGEFCVL | 128 |
| SEQ ID NO: 105<br>variable heavy chain for 008 | EVQLVESGGG LVQPGGSLRL SCAASGFTFS NYTMNWVRQA PGKGLEWVSA ISGSGGSTYY | 60 |
| | ADSVKGRFTI SRDNSKNTLY LQMNSLRAED TAVYYCAKDR YSQVHYALDY WGQGTLVTVS | 120 |
| SEQ ID NO: 106<br>variable light chain for 008 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |
| SEQ ID NO: 107<br>variable heavy chain for 011 | EVQLVESGGG VVQPGRSLRL SCAASGFTFS DYTMNWVRQA PGKGLEWVSS ISGGSTYYAD | 60 |
| | SRKGRFTISR DNSKNTLYLQ MNNLRAEDTA VYYCARDRYF RQQNAFDYWG QGTLVTVSSA | 120 |
| SEQ ID NO: 108<br>variable light chain for 011 | DIVMTQSPDS LPVTPGEPAS ISCRSSQSLL HSNGYNYLDW YLQKAGQSPQ LLIYLGSNRA | 60 |
| | SGVPDRFSGS GSGTDFTLKI SRVEAEDVGV YYCQQYYNHP TTFGQGTK | 108 |

TABLE 18-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 109 variable heavy chain for 021 | EVQLVESGGG LVQPRGSLRL SCAASGFTFS SYAMNWVRQA PGKGLEWVAV ISYDGSNKYY | 60 |
| | ADSVKGRFTI SRDNSKNTLY LQMNSLRAED TAVYYCAKDR YITLPNALDY WGQGTLVTVS | 120 |
| SEQ ID NO: 110 variable light chain for 021 | DIQMTQSPVS LPVTPGEPAS ISCRSSQSLL HSNGYNYLDW YLQKPGQSPQ LLIYLGSNRA | 60 |
| | SGVPDRFSGS GSGTDFTLKI SRVEAEDVGV YYCQQYKSNP PTFGQGTK | 108 |
| SEQ ID NO: 111 variable heavy chain for 023 | EVQLVESGGG LVHPGGSLRL SCAGSGFTFS SYAMHWVRQA PGKGLEWVSA IGTGGGTYYA | 60 |
| | DSVMGRFTIS RDNSKNTLYL QMNSLRAEDT AVYYCARYDN VMGLYWFDYW GQGTLVTVSS | 120 |
| SEQ ID NO: 112 variable light chain for 023 | EIVLTQSPAT LSLSPGERAT LSCRASQSVS SYLAWYQQKP GQAPRLLIYD ASNRATGIPA | 60 |
| | RFSGSGSGTD FTLTISSLEP EDFAVYYCQQ RSNWPPAFGG GTKVEIKR | 108 |
| SEQ ID NO: 113 heavy chain variable region | EVQLQQSGPE LVKPGASVKM SCKASGYTFT SYVMHWVKQK PGQGLEWIGY INPYNDGTKY | 60 |
| | NEKFKGKATL TSDKSSSTAY MELSSLTSED SAVYYCANYY GSSLSMDYWG QGTSVTVSS | 119 |
| SEQ ID NO: 114 light chain variable region | DIQMTQTTSS LSASLGDRVT ISCRASQDIS NYLNWYQQKP DGTVKLLIYY TSRLHSGVPS | 60 |
| | RFSGSGSGTD YSLTISNLEQ EDIATYFCQQ GNTLPWTFGG GTKLEIKR | 108 |
| SEQ ID NO: 115 heavy chain variable region | EVQLQQSGPE LVKPGASVKI SCKTSGYTFK DYTMHWVKQS HGKSLEWIGG IYPNNGGSTY | 60 |
| | NQNFKDKATL TVDKSSSTAY MEFRSLTSED SAVYYCARMG YHGPHLDFDV WGAGTTVTVS | 120 |
| | P | 121 |
| SEQ ID NO: 116 light chain variable region | DIVMTQSHKF MSTSLGDRVS ITCKASQDVG AAVAWYQQKP GQSPKLLIYW ASTRHTGVPD | 60 |
| | RFTGGGSGTD FTLTISNVQS EDLTDYFCQQ YINYPLTFGG GTKLEIKR | 108 |
| SEQ ID NO: 117 heavy chain variable region of humanized antibody | QIQLVQSGPE LKKPGETVKI SCKASGYTFT DYSMHWVKQA PGKGLKWMGW INTETGEPTY | 60 |
| | ADDFKGRFAF SLETSASTAY LQINNLKNED TATYFCANPY YDYVSYYAMD YWGHGTSVTV | 120 |
| | SS | 122 |
| SEQ ID NO: 118 heavy chain variable region of humanized antibody | QVQLVQSGSE LKKPGASVKV SCKASGYTFT DYSMHWVRQA PGQGLKWMGW INTETGEPTY | 60 |
| | ADDFKGRFVF SLDTSVSTAY LQISSLKAED TAVYYCANPY YDYVSYYAMD YWGQGTTVTV | 120 |
| | SS | 122 |
| SEQ ID NO: 119 light chain variable region of humanized antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |
| SEQ ID NO: 120 light chain variable region of humanized antibody | DIVMTQSHKF MSTSVRDRVS ITCKASQDVS TAVAWYQQKP GQSPKLLIYS ASYLYTGVPD | 60 |
| | RFTGSGSGTD FTFTISSVQA EDLAVYYCQQ HYSTPRTFGG GTKLEIK | 107 |
| SEQ ID NO: 121 heavy chain variable region of humanized antibody | EVQLVESGGG LVQPGESLKL SCESNEYEFP SHDMSWVRKT PEKRLELVAA INSDGGSTYY | 60 |
| | PDTMERRFII SRDNTKKTLY LQMSSLRSED TALYYCARHY DDYYAWFAYW GQGTLVTVSA | 120 |
| SEQ ID NO: 122 heavy chain variable region of humanized antibody | EVQLVESGGG LVQPGGSLRL SCAASEYEFP SHDMSWVRQA PGKGLELVAA INSDGGSTYY | 60 |
| | PDTMERRFTI SRDNAKNSLY LQMNSLRAED TAVYYCARHY DDYYAWFAYW GQGTMVTVSS | 120 |
| SEQ ID NO: 123 light chain variable region of humanized antibody | DIVLTQSPAS LAVSLGQRAT ISCRASKSVS TSGYSYMHWY QQKPGQPPKL LIYLASNLES | 60 |
| | GVPARFSGSG SGTDFTLNIH PVEEEDAATY YCQHSRELPL TFGAGTKLEL K | 111 |

TABLE 18-continued

Additional polypeptide domains useful as OX40 binding domains in fusion proteins (e.g., structures I-A and I-B) or as scFv OX40 agonist antibodies.

| Identifier | Sequence (One-Letter Amino Acid Symbols) | |
|---|---|---|
| SEQ ID NO: 124 light chain variable region of humanized antibody | EIVLTQSPAT LSLSPGERAT LSCRASKSVS TSGYSYMHWY QQKPGQAPRL LIYLASNLES<br>GVPARFSGSG SGTDFTLTIS SLEPEDFAVY YCQHSRELPL TFGGGTKVEI K | 60<br>111 |
| SEQ ID NO: 125 heavy chain variable region | MYLGLNYVFI VFLLNGVQSE VKLEESGGGL VQPGGSMKLS CAASGFTFSD AWMDWVRQSP<br>EKGLEWVAEI RSKANNHATY YAESVNGRFT ISRDDSKSSV YLQMNSLRAE DTGIYYCTWG<br>EVFYFDYWGQ GTTLTVSS | 60<br>120<br>138 |
| SEQ ID NO: 126 light chain variable region | MRPSIQFLGL LLFWLHGAQC DIQMTQSPSS LSASLGGKVT ITCKSSQDIN KYIAWYQHKP<br>GKGPRLLIHY TSTLQPGIPS RFSGSGSGRD YSFSISNLEP EDIATYYCLQ YDNLLTFGAG<br>TKLELK | 60<br>120<br>126 |

In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, and wherein the additional domain is a Fab or Fc fragment domain. In an embodiment, the OX40 agonist is a OX40 agonistic single-chain fusion polypeptide comprising (i) a first soluble OX40 binding domain, (ii) a first peptide linker, (iii) a second soluble OX40 binding domain, (iv) a second peptide linker, and (v) a third soluble OX40 binding domain, further comprising an additional domain at the N-terminal and/or C-terminal end, wherein the additional domain is a Fab or Fc fragment domain wherein each of the soluble OX40 binding domains lacks a stalk region (which contributes to trimerisation and provides a certain distance to the cell membrane, but is not part of the OX40 binding domain) and the first and the second peptide linkers independently have a length of 3-8 amino acids.

In an embodiment, the OX40 agonist is an OX40 agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein the TNF superfamily cytokine domain is an OX40 binding domain.

In some embodiments, the OX40 agonist is MEDI6383. MEDI6383 is an OX40 agonistic fusion protein and can be prepared as described in U.S. Pat. No. 6,312,700, the disclosure of which is incorporated by reference herein.

In an embodiment, the OX40 agonist is an OX40 agonistic scFv antibody comprising any of the foregoing $V_H$ domains linked to any of the foregoing $V_L$ domains.

In an embodiment, the OX40 agonist is Creative Biolabs OX40 agonist monoclonal antibody MOM-18455, commercially available from Creative Biolabs, Inc., Shirley, NY, USA.

In an embodiment, the OX40 agonist is OX40 agonistic antibody clone Ber-ACT35 commercially available from BioLegend, Inc., San Diego, CA, USA.

I. Optional Cell Viability Analyses

Optionally, a cell viability assay can be performed after the priming first expansion (sometimes referred to as the initial bulk expansion), using standard assays known in the art. Thus, in certain embodiments, the method comprises performing a cell viability assay subsequent to the priming first expansion. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining. The cell viability can also be assayed based on U.S. Ser. No. 15/863,634, incorporated by reference herein in its entirety. Cell viability can also be assayed based on U.S. Patent Publication No. 2018/0280436 or International Patent Publication No. WO/2018/081473, both of which are incorporate herein in their entireties for all purposes.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs, including those discussed above as well as exemplified in FIG. 1, in particular, e.g., FIG. 1B and/or FIG. 1C, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium. In some embodiments, the media in the priming first expansion is serum free. In some embodiments, the media in the second expansion is serum free. In some embodiments, the media in the priming first expansion and the second expansion (also referred to as rapid second expansion) are both serum free. In an embodiment, expanding the number of TILs uses no more than one type of cell culture medium. Any suitable cell culture medium may be used, e.g., AIM-V cell medium (L-glutamine, 50 μM streptomycin sulfate, and 10 μM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell culture medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 8 days, e.g., about 8 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 9 days, e.g., about 7 days, about 8 days, or about 9 days.

In an embodiment, the duration of the method comprising obtaining a tumor tissue sample from the mammal; culturing the tumor tissue sample in a first gas permeable container containing cell medium including IL-2, 1× antigen-presenting feeder cells, and OKT-3 for a duration of about 1 to 7 days, e.g., about 7 days as a priming first expansion; transferring the TILs to a second gas permeable container and expanding the number of TILs in the second gas permeable container containing cell medium including IL-2, 2× antigen-presenting feeder cells, and OKT-3 for a duration of about 7 to 10 days, e.g., about 7 days, about 8 days, about 9 days or about 10 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy,* 2012, 35:283-292.

J. Optional Genetic Engineering of TILs

In some embodiments, the expanded TILs of the present invention are further manipulated before, during, or after an expansion step, including during closed, sterile manufacturing processes, each as provided herein, in order to alter protein expression in a transient manner. In some embodiments, the transiently altered protein expression is due to transient gene editing. In some embodiments, the expanded TILs of the present invention are treated with transcription factors (TFs) and/or other molecules capable of transiently altering protein expression in the TILs. In some embodiments, the TFs and/or other molecules that are capable of transiently altering protein expression provide for altered expression of tumor antigens and/or an alteration in the number of tumor antigen-specific T cells in a population of TILs.

In certain embodiments, the method comprises genetically editing a population of TILs. In certain embodiments, the method comprises genetically editing the first population of TILs, the second population of TILs and/or the third population of TILs.

In some embodiments, the present invention includes genetic editing through nucleotide insertion, such as through ribonucleic acid (RNA) insertion, including insertion of messenger RNA (mRNA) or small (or short) interfering RNA (siRNA), into a population of TILs for promotion of the expression of one or more proteins or inhibition of the expression of one or more proteins, as well as simultaneous combinations of both promotion of one set of proteins with inhibition of another set of proteins.

In some embodiments, the expanded TILs of the present invention undergo transient alteration of protein expression. In some embodiments, the transient alteration of protein expression occurs in the bulk TIL population prior to first expansion, including, for example in the TIL population obtained from for example, Step A as indicated in FIG. 1 (particularly FIG. 1B and/or FIG. 1C). In some embodiments, the transient alteration of protein expression occurs during the first expansion, including, for example in the TIL population expanded in for example, Step B as indicated in FIG. 1 (for example FIG. 1B and/or FIG. 1C). In some embodiments, the transient alteration of protein expression occurs after the first expansion, including, for example in the TIL population in transition between the first and second expansion (e.g. the second population of TILs as described herein), the TIL population obtained from for example, Step B and included in Step C as indicated in FIG. 1. In some embodiments, the transient alteration of protein expression occurs in the bulk TIL population prior to second expansion, including, for example in the TIL population obtained from for example, Step C and prior to its expansion in Step D as indicated in FIG. 1. In some embodiments, the transient alteration of protein expression occurs during the second expansion, including, for example in the TIL population expanded in for example, Step D as indicated in FIG. 1 (e.g. the third population of TILs). In some embodiments, the transient alteration of protein expression occurs after the second expansion, including, for example in the TIL population obtained from the expansion in for example, Step D as indicated in FIG. 1.

In an embodiment, a method of transiently altering protein expression in a population of TILs includes the step of electroporation. Electroporation methods are known in the art and are described, e.g., in Tsong, *Biophys. J.* 1991, 60, 297-306, and U.S. Patent Application Publication No. 2014/0227237 A1, the disclosures of each of which are incorporated by reference herein. In an embodiment, a method of transiently altering protein expression in population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of transiently altering protein expression in a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of transiently altering protein expression in a population of TILs includes the step of transfection using methods described in U.S. Pat. Nos. 5,766,902; 6,025,337; 6,410,517; 6,475,994; and 7,189,705; the disclosures of each of which are incorporated by reference herein.

In some embodiments, transient alteration of protein expression results in an increase in Stem Memory T cells (TSCMs). TSCMs are early progenitors of antigen-experienced central memory T cells. TSCMs generally display the long-term survival, self-renewal, and multipotency abilities that define stem cells, and are generally desirable for the generation of effective TIL products. TSCM have shown enhanced anti-tumor activity compared with other T cell subsets in mouse models of adoptive cell transfer (Gattinoni et al. Nat Med 2009, 2011; Gattinoni, Nature Rev. Cancer, 2012; Cieri et al. Blood 2013). In some embodiments, transient alteration of protein expression results in a TIL population with a composition comprising a high proportion of TSCM. In some embodiments, transient alteration of protein expression results in an at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% increase in TSCM percentage. In some embodiments, transient alteration of protein expression results in an at least a 1-fold, 2-fold, 3-fold, 4-fold, 5-fold, or 10-fold increase in TSCMs in the TIL population. In some embodiments, transient alteration of protein expression results in a TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs. In some embodiments, transient alteration of protein expression results in a therapeutic TIL population with at least at least 5%, at least 10%, at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% TSCMs.

In some embodiments, transient alteration of protein expression results in rejuvenation of antigen-experienced T-cells. In some embodiments, rejuvenation includes, for example, increased proliferation, increased T-cell activation, and/or increased antigen recognition.

In some embodiments, transient alteration of protein expression alters the expression in a large fraction of the T-cells in order to preserve the tumor-derived TCR repertoire. In some embodiments, transient alteration of protein expression does not alter the tumor-derived TCR repertoire. In some embodiments, transient alteration of protein expression maintains the tumor-derived TCR repertoire.

In some embodiments, transient alteration of protein results in altered expression of a particular gene. In some embodiments, the transient alteration of protein expression targets a gene including but not limited to PD-1 (also referred to as PDCD1 or CC279), TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets a gene selected from the group consisting of PD-1, TGFBR2, CCR4/5, CBLB (CBL-B), CISH, CCRs (chimeric co-stimulatory receptors), IL-2, IL-12, IL-15, IL-21, NOTCH 1/2 ICD, TIM3, LAG3, TIGIT, TGFβ, CCR2, CCR4, CCR5, CXCR1, CXCR2, CSCR3, CCL2 (MCP-1), CCL3 (MIP-1α), CCL4 (MIP1-β), CCL5 (RANTES), CXCL1/CXCL8, CCL22, CCL17, CXCL1/CXCL8, VHL, CD44, PIK3CD, SOCS1, and/or cAMP protein kinase A (PKA). In some embodiments, the transient alteration of protein expression targets PD-1. In some embodiments, the transient alteration of protein expression targets TGFBR2. In some embodiments, the transient alteration of protein expression targets CCR4/5. In some embodiments, the transient alteration of protein expression targets CBLB. In some embodiments, the transient alteration of protein expression targets CISH. In some embodiments, the transient alteration of protein expression targets CCRs (chimeric co-stimulatory receptors). In some embodiments, the transient alteration of protein expression targets IL-2. In some embodiments, the transient alteration of protein expression targets IL-12. In some embodiments, the transient alteration of protein expression targets IL-15. In some embodiments, the transient alteration of protein expression targets IL-21. In some embodiments, the transient alteration of protein expression targets NOTCH 1/2 ICD. In some embodiments, the transient alteration of protein expression targets TIM3. In some embodiments, the transient alteration of protein expression targets LAG3. In some embodiments, the transient alteration of protein expression targets TIGIT. In some embodiments, the transient alteration of protein expression targets TGFβ. In some embodiments, the transient alteration of protein expression targets CCR1. In some embodiments, the transient alteration of protein expression targets CCR2. In some embodiments, the transient alteration of protein expression targets CCR4. In some embodiments, the transient alteration of protein expression targets CCR5. In some embodiments, the transient alteration of protein expression targets CXCR1. In some embodiments, the transient alteration of protein expression targets CXCR2. In some embodiments, the transient alteration of protein expression targets CSCR3. In some embodiments, the transient alteration of protein expression targets CCL2 (MCP-1). In some embodiments, the transient alteration of protein expression targets CCL3 (MIP-1α). In some embodiments, the transient alteration of protein expression targets CCL4 (MIP1-β). In some embodiments, the transient alteration of protein expression targets CCL5 (RANTES). In some embodiments, the transient alteration of protein expression targets CXCL1. In some embodiments, the transient alteration of protein expression targets CXCL8. In some embodiments, the transient alteration of protein expression targets CCL22. In some embodiments, the transient alteration of protein expression targets CCL17. In some embodiments, the transient alteration of protein expression targets VHL. In some embodiments, the transient alteration of protein expression targets CD44. In some embodiments, the transient alteration of protein expression targets PIK3CD. In some embodiments, the transient alteration of protein expression targets SOCS1. In some embodiments, the transient alteration of protein expression targets cAMP protein kinase A (PKA).

In some embodiments, the transient alteration of protein expression results in increased and/or overexpression of a chemokine receptor. In some embodiments, the chemokine receptor that is overexpressed by transient protein expression includes a receptor with a ligand that includes but is not limited to CCL2 (MCP-1), CCL3 (MIP-1a), CCL4 (MIP1-β), CCL5 (RANTES), CXCL1, CXCL8, CCL22, and/or CCL17.

In some embodiments, the transient alteration of protein expression results in a decrease and/or reduced expression of PD-1, CTLA-4, TIM-3, LAG-3, TIGIT, TGFβR2, and/or TGFβ (including resulting in, for example, TGFβ pathway blockade). In some embodiments, the transient alteration of protein expression results in a decrease and/or reduced expression of CBLB (CBL-B). In some embodiments, the transient alteration of protein expression results in a decrease and/or reduced expression of CISH.

In some embodiments, the transient alteration of protein expression results in increased and/or overexpression of chemokine receptors in order to, for example, improve TIL trafficking or movement to the tumor site. In some embodiments, the transient alteration of protein expression results in increased and/or overexpression of a CCR (chimeric co-stimulatory receptor). In some embodiments, the transient alteration of protein expression results in increased and/or overexpression of a chemokine receptor selected from the group consisting of CCR1, CCR2, CCR4, CCR5, CXCR1, CXCR2, and/or CSCR3.

In some embodiments, the transient alteration of protein expression results in increased and/or overexpression of an interleukin. In some embodiments, the transient alteration of protein expression results in increased and/or overexpression of an interleukin selected from the group consisting of IL-2, IL-12, IL-15, and/or IL-21.

In some embodiments, the transient alteration of protein expression results in increased and/or overexpression of NOTCH 1/2 ICD. In some embodiments, the transient alteration of protein expression results in increased and/or overexpression of VHL. In some embodiments, the transient alteration of protein expression results in increased and/or overexpression of CD44. In some embodiments, the transient alteration of protein expression results in increased and/or overexpression of PIK3CD. In some embodiments, the transient alteration of protein expression results in increased and/or overexpression of SOCS1, In some embodiments, the transient alteration of protein expression results in decreased and/or reduced expression of cAMP protein kinase A (PKA).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of two molecules selected from the group consisting of PD-1, LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1 and one molecule selected from the group consisting of LAG3, TIM3, CTLA-4, TIGIT, CISH, TGFβR2, PKA, CBLB, BAFF (BR3), and combinations thereof. In some embodiments, the transient alteration of protein expression results in decreased and/or reduced expression of PD-1, LAG-3, CISH, CBLB, TIM3, and combinations thereof. In some embodiments, the transient alteration of protein expression results in decreased and/or reduced expression of PD-1 and one of LAG3, CISH, CBLB, TIM3, and combinations thereof. In some embodiments, the transient alteration of protein expression results in decreased and/or reduced expression of PD-1 and LAG3. In some embodiments, the transient alteration of protein expression results in decreased and/or reduced expression of PD-1 and CISH. In some embodiments, the transient alteration of protein expression results in decreased and/or reduced expression of PD-1 and CBLB. In some embodiments, the transient alteration of protein expression results in decreased and/or reduced expression of LAG3 and CISH. In some embodiments, the transient alteration of protein expression results in decreased and/or reduced expression of LAG3 and CBLB. In some embodiments, the transient alteration of protein expression results in decreased and/or reduced expression of CISH and CBLB. In some embodiments, the transient alteration of protein expression results in decreased and/or reduced expression of TIM3 and PD-1. In some embodiments, the transient alteration of protein expression results in decreased and/or reduced expression of TIM3 and LAG3. In some embodiments, the transient alteration of protein expression results in decreased and/or reduced expression of TIM3 and CISH. In some embodiments, the transient alteration of protein expression results in decreased and/or reduced expression of TIM3 and CBLB.

In some embodiments, an adhesion molecule selected from the group consisting of CCR2, CCR4, CCR5, CXCR2, CXCR3, CX3CR1, and combinations thereof, is inserted by a gammaretroviral or lentiviral method into the first population of TILs, second population of TILs, or harvested population of TILs (e.g., the expression of the adhesion molecule is increased).

In some embodiments, the transient alteration of protein expression results in decreased and/or reduced expression of a molecule selected from the group consisting of PD-1, LAG3, TIM3, CTLA-4, TIGIT, CISH, TGFβR2, PKA, CBLB, BAFF (BR3), and combinations thereof, and increased and/or enhanced expression of CCR2, CCR4, CCR5, CXCR2, CXCR3, CX3CR1, and combinations thereof. In some embodiments, the transient alteration of protein expression results in decreased and/or reduced expression of a molecule selected from the group consisting of PD-1, LAG3, TIM3, CISH, CBLB, and combinations thereof, and increased and/or enhanced expression of CCR2, CCR4, CCR5, CXCR2, CXCR3, CX3CR1, and combinations thereof.

In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

In some embodiments, there is an increase in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is an increase in expression of at least about 65%, about 70%, about 75%, about 80%, about 85%, about 90%, or about 95%. In some embodiments, there is an increase in expression of at least about 75%, about 80%, about 85%, about 90%, or about 95%. In some embodiments, there is an increase in expression of at least about 80%, about 85%, about 90%, or about 95%. In some embodiments, there is an increase in expression of at least about 85%, about 90%, or about 95%. In some embodiments, there is an increase in expression of at least about 80%. In some embodiments, there is an increase in expression of at least about 85%, In some embodiments, there is an increase in expression of at least about 90%. In some embodiments, there is an increase in expression of at least about 95%. In some embodiments, there is an increase in expression of at least about 99%.

In some embodiments, transient alteration of protein expression is induced by treatment of the TILs with transcription factors (TFs) and/or other molecules capable of transiently altering protein expression in the TILs. In some embodiments, the SQZ vector-free microfluidic platform is employed for intracellular delivery of the transcription factors (TFs) and/or other molecules capable of transiently altering protein expression. Such methods demonstrating the ability to deliver proteins, including transcription factors, to a variety of primary human cells, including T cells (Sharei et al. PNAS 2013, as well as Sharei et al. PLOS ONE 2015 and Greisbeck et al. J. Immunology vol. 195, 2015) have been described; see, for example, International Patent Publications WO 2013/059343A1, WO 2017/008063A1, and WO 2017/123663A1, all of which are incorporated by reference herein in their entireties. Such methods as described in International Patent Publications WO 2013/059343A1, WO 2017/008063A1, and WO 2017/123663A1 can be employed with the present invention in order to expose a population of TILs to transcription factors (TFs) and/or other molecules capable of inducing transient protein expression, wherein said TFs and/or other molecules capable of inducing transient protein expression provide for increased expression of tumor antigens and/or an increase in the number of tumor antigen-specific T cells in the population of TILs, thus resulting in reprogramming of the TIL population and an increase in therapeutic efficacy of the reprogrammed TIL population as compared to a non-reprogrammed TIL population. In some embodiments, the reprogramming results in an increased subpopulation of effector T cells and/or central memory T cells relative to the starting or prior population (i.e., prior to reprogramming) population of TILs, as described herein.

In some embodiments, the transcription factor (TF) includes but is not limited to TCF-1, NOTCH 1/2 ICD, and/or MYB. In some embodiments, the transcription factor (TF) is TCF-1. In some embodiments, the transcription factor (TF) is NOTCH 1/2 ICD. In some embodiments, the transcription factor (TF) is MYB. In some embodiments, the transcription factor (TF) is administered with induced pluripotent stem cell culture (iPSC), such as the commercially available KNOCKOUT Serum Replacement (Gibco/ThermoFisher), to induce additional TIL reprogramming. In some embodiments, the transcription factor (TF) is administered with an iPSC cocktail to induce additional TIL reprogramming. In some embodiments, the transcription factor (TF) is administered without an iPSC cocktail. In some embodiments, reprogramming results in an increase in the percentage of TSCMs. In some embodiments, reprogramming results in an increase in the percentage of TSCMs by about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95% TSCMs.

In some embodiments, a method of transient altering protein expression, as described above, may be combined with a method of genetically modifying a population of TILs includes the step of stable incorporation of genes for production of one or more proteins. In certain embodiments, the method comprises a step of genetically modifying a population of TILs. In certain embodiments, the method comprises genetically modifying the first population of TILs, the second population of TILs and/or the third population of TILs. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In some embodiments, transient alteration of protein expression is a reduction in expression induced by self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. In some embodiments, the method comprises transient alteration of protein expression in a population of TILs, comprising the use of self-delivering RNA interference (sdRNA), which is a chemically-synthesized asymmetric siRNA duplex with a high percentage of 2'-OH substitutions (typically fluorine or —$OCH_3$) which comprises a 20-nucleotide antisense (guide) strand and a 13 to 15 base sense (passenger) strand conjugated to cholesterol at its 3' end using a tetraethylenglycol (TEG) linker. Methods of using sdRNA have been described in Khvorova and Watts, *Nat. Biotechnol.* 2017, 35, 238-248; Byrne, et al., *J. Ocul. Pharmacol. Ther.* 2013, 29, 855-864; and Ligtenberg, et al., *Mol. Therapy,* 2018, in press, the disclosures of which are incorporated by reference herein. In an embodiment, delivery of sdRNA to a TIL population is accomplished without use of electroporation, SQZ, or other methods, instead using a 1 to 3 day period in which a TIL population is exposed to sdRNA at a concentration of 1 μM/10,000 TILs in medium. In certain embodiments, the method comprises delivery sdRNA to a TILs population comprising exposing the TILs population to sdRNA at a concentration of 1 μM/10,000 TILs in medium for a period of between 1 to 3 days. In an embodiment, delivery of sdRNA to a TIL population is accomplished using a 1 to 3 day period in which a TIL population is exposed to sdRNA at a concentration of 10 μM/10,000 TILs in medium. In an embodiment, delivery of sdRNA to a TIL population is accomplished using a 1 to 3 day period in which a TIL population is exposed to sdRNA at a concentration of 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium. In an embodiment, delivery of sdRNA to a TIL population is accomplished using a 1 to 3 day period in which a TIL population is exposed to sdRNA at a concentration of between 0.1 μM/10,000 TILs and 50 μM/10,000 TILs in medium, wherein the exposure to sdRNA is performed two, three, four, or five times by addition of fresh sdRNA to the media. Other suitable processes are described, for example, in U.S. Patent Application Publication No. US 2011/0039914 A1, US 2013/0131141 A1, and US 2013/0131142 A1, and U.S. Pat. No. 9,080,171, the disclosures of which are incorporated by reference herein.

In some embodiments, sdRNA is inserted into a population of TILs during manufacturing. In some embodiments, the sdRNA encodes RNA that interferes with NOTCH 1/2 ICD, PD-1, CTLA-4 TIM-3, LAG-3, TIGIT, TGFβ, TGFBR2, cAMP protein kinase A (PKA), BAFF BR3, CISH, and/or CBLB. In some embodiments, the reduction in expression is determined based on a percentage of gene silencing, for example, as assessed by flow cytometry and/or qPCR. In some embodiments, there is a reduction in expression of about 5%, about 10%, about 10%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, there is a reduction in expression of at least about 65%, about 70%, about 75%, about 80%, about 85%, about 90%, or about 95%. In some embodiments, there is a reduction in expression of at least about 75%, about 80%, about 85%, about 90%, or about 95%. In some embodiments, there is a reduction in expression of at least about 80%, about 85%, about 90%, or about 95%. In some embodiments, there is a reduction in expression of at least about 85%, about 90%, or about 95%. In some embodiments, there is a reduction in expression of at least about 80%. In some embodiments, there is a reduction in expression of at least about 85%, In some embodiments, there is a reduction in expression of at least about 90%. In some embodiments, there is a reduction in expression of at least about 95%. In some embodiments, there is a reduction in expression of at least about 99%.

The self-deliverable RNAi technology based on the chemical modification of siRNAs can be employed with the methods of the present invention to successfully deliver the sdRNAs to the TILs as described herein. The combination of backbone modifications with asymmetric siRNA structure and a hydrophobic ligand (see, for example, Ligtenberg, et al., *Mol. Therapy,* 2018 and US20160304873) allow sdRNAs to penetrate cultured mammalian cells without additional formulations and methods by simple addition to the culture media, capitalizing on the nuclease stability of sdRNAs. This stability allows the support of constant levels of RNAi-mediated reduction of target gene activity simply by maintaining the active concentration of sdRNA in the media. While not being bound by theory, the backbone stabilization of sdRNA provides for extended reduction in gene expression effects which can last for months in non-dividing cells.

In some embodiments, over 95% transfection efficiency of TILs and a reduction in expression of the target by various specific sdRNA occurs. In some embodiments, sdRNAs containing several unmodified ribose residues were replaced with fully modified sequences to increase potency and/or the longevity of RNAi effect. In some embodiments, a reduction in expression effect is maintained for 12 hours, 24 hours, 36 hours, 48 hours, 5 days, 6 days, 7 days, or 8 days or more. In some embodiments, the reduction in expression effect decreases at 10 days or more post sdRNA treatment of the TILs. In some embodiments, more than 70% reduction in expression of the target expression is maintained. In some embodiments, more than 70% reduction in expression of the target expression is maintained TILs. In some embodiments, a reduction in expression in the PD-1/PD-L1 pathway allows for the TILs to exhibit a more potent in vivo effect, which is in some embodiments, due to the avoidance of the suppressive effects of the PD-1/PD-L1 pathway. In some embodiments, a reduction in expression of PD-1 by sdRNA results in an increase TIL proliferation.

Small interfering RNA (siRNA), sometimes known as short interfering RNA or silencing RNA, is a double stranded RNA molecule, generally 19-25 base pairs in length. siRNA is used in RNA interference (RNAi), where it interferes with expression of specific genes with complementary nucleotide sequences.

Double stranded DNA (dsRNA) can be generally used to define any molecule comprising a pair of complementary strands of RNA, generally a sense (passenger) and antisense (guide) strands, and may include single-stranded overhang regions. The term dsRNA, contrasted with siRNA, generally refers to a precursor molecule that includes the sequence of an siRNA molecule which is released from the larger dsRNA molecule by the action of cleavage enzyme systems, including Dicer.

sdRNA (self-deliverable RNA) are a new class of covalently modified RNAi compounds that do not require a delivery vehicle to enter cells and have improved pharmacology compared to traditional siRNAs. “Self-deliverable RNA” or “sdRNA” is a hydrophobically modified RNA interfering-antisense hybrid, demonstrated to be highly efficacious in vitro in primary cells and in vivo upon local administration. Robust uptake and/or silencing without toxicity has been demonstrated. sdRNAs are generally asymmetric chemically modified nucleic acid molecules with minimal double stranded regions. sdRNA molecules typically contain single stranded regions and double stranded regions, and can contain a variety of chemical modifications within both the single stranded and double stranded regions of the molecule. Additionally, the sdRNA molecules can be attached to a hydrophobic conjugate such as a conventional and advanced sterol-type molecule, as described herein. sdRNAs and associated methods for making such sdRNAs have also been described extensively in, for example, US20160304873, WO2010033246, WO2017070151, WO2009102427, WO2011119887, WO2010033247A2, WO2009045457, WO2011119852, all of which are incorporated by reference herein in their entireties for all purposes. To optimize sdRNA structure, chemistry, targeting position, sequence preferences, and the like, a proprietary algorithm has been developed and utilized for sdRNA potency prediction (see, for example, US 20160304873). Based on these analyses, functional sdRNA sequences have been generally defined as having over 70% reduction in expression at 1 μM concentration, with a probability over 40%.

In some embodiments, the sdRNA sequences used in the invention exhibit a 70% reduction in expression of the target gene. In some embodiments, the sdRNA sequences used in the invention exhibit a 75% reduction in expression of the target gene.

In some embodiments, the sdRNA sequences used in the invention exhibit an 80% reduction in expression of the target gene. In some embodiments, the sdRNA sequences used in the invention exhibit an 85% reduction in expression of the target gene. In some embodiments, the sdRNA sequences used in the invention exhibit a 90% reduction in expression of the target gene. In some embodiments, the sdRNA sequences used in the invention exhibit a 95% reduction in expression of the target gene. In some embodiments, the sdRNA sequences used in the invention exhibit a 99% reduction in expression of the target gene. In some embodiments, the sdRNA sequences used in the invention exhibit a reduction in expression of the target gene when delivered at a concentration of about 0.25 μM to about 4 μM. In some embodiments, the sdRNA sequences used in the invention exhibit a reduction in expression of the target gene when delivered at a concentration of about 0.25 μM. In some embodiments, the sdRNA sequences used in the invention exhibit a reduction in expression of the target gene when delivered at a concentration of about 0.5 μM. In some embodiments, the sdRNA sequences used in the invention exhibit a reduction in expression of the target gene when delivered at a concentration of about 0.75 μM. In some embodiments, the sdRNA sequences used in the invention exhibit a reduction in expression of the target gene when delivered at a concentration of about 1.0 μM. In some embodiments, the sdRNA sequences used in the invention exhibit a reduction in expression of the target gene when delivered at a concentration of about 1.25 μM. In some embodiments, the sdRNA sequences used in the invention exhibit a reduction in expression of the target gene when delivered at a concentration of about 1.5 μM. In some embodiments, the sdRNA sequences used in the invention exhibit a reduction in expression of the target gene when delivered at a concentration of about 1.75 μM. In some embodiments, the sdRNA sequences used in the invention exhibit a reduction in expression of the target gene when delivered at a concentration of about 2.0 μM. In some embodiments, the sdRNA sequences used in the invention exhibit a reduction in expression of the target gene when delivered at a concentration of about 2.25 μM. In some embodiments, the sdRNA sequences used in the invention exhibit a reduction in expression of the target gene when delivered at a concentration of about 2.5 μM. In some embodiments, the sdRNA sequences used in the invention exhibit a reduction in expression of the target gene when delivered at a concentration of about 2.75 μM. In some embodiments, the sdRNA sequences used in the invention exhibit a reduction in expression of the target gene when delivered at a concentration of about 3.0 μM. In some embodiments, the sdRNA sequences used in the invention exhibit a reduction in expression of the target gene when delivered at a concentration of about 3.25 μM. In some embodiments, the sdRNA sequences used in the invention exhibit a reduction in expression of the target gene when delivered at a concentration of about 3.5 μM. In some embodiments, the sdRNA sequences used in the invention exhibit a reduction in expression of the target gene when delivered at a concentration of about 3.75 μM. In some embodiments, the sdRNA sequences used in the invention exhibit a reduction in expression of the target gene when delivered at a concentration of about 4.0 μM.

In some embodiments, the oligonucleotide agents comprise one or more modification to increase stability and/or effectiveness of the therapeutic agent, and to effect efficient delivery of the oligonucleotide to the cells or tissue to be treated. Such modifications can include a 2'-O-methyl modification, a 2'-O-Fluro modification, a diphosphorothioate modification, 2' F modified nucleotide, a2'-O-methyl modified and/or a 2'deoxy nucleotide. In some embodiments, the oligonucleotide is modified to include one or more hydrophobic modifications including, for example, sterol, cholesterol, vitamin D, naphtyl, isobutyl, benzyl, indol, tryptophane, and/or phenyl. In an additional particular embodiment, chemically modified nucleotides are combination of phosphorothioates, 2'-O-methyl, 2'deoxy, hydrophobic modifications and phosphorothioates. In some embodiments, the sugars can be modified and modified sugars can include but are not limited to D-ribose, 2'-O-alkyl (including 2'-O-methyl and 2'-O-ethyl), i.e., 2'-alkoxy, 2'-amino, 2'-S-alkyl, 2'-halo (including 2'-fluoro), T-methoxyethoxy, 2'-allyloxy (—$OCH_2CH{=}CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., Nucl. Acids. Res. 18:4711 (1992)).

In some embodiments, the double-stranded oligonucleotide of the invention is double-stranded over its entire length, i.e., with no overhanging single-stranded sequence at either end of the molecule, i.e., is blunt-ended. In some embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). In some embodiments, when a single nucleic acid molecule is used a portion of the molecule at either end can remain single-stranded.

In some embodiments, a double-stranded oligonucleotide of the invention contains mismatches and/or loops or bulges, but is double-stranded over at least about 70% of the length of the oligonucleotide. In some embodiments, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In some embodiments, a double-stranded oligonucleotide of the invention is double-stranded over at least about 96%-98% of the length of the oligonucleotide. In some embodiments, the double-stranded oligonucleotide of the invention contains at least or up to 1, 2, 3, 4, 5, 6, 7, 8, 9, 10, 11, 12, 13, 14, or 15 mismatches.

In some embodiments, the oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (-0-$CH_2$—$CH_2$—O—) phosphate ($PO_3^{2-}$), hydrogen phosphonate, or phosphoramidite). "Blocking groups" can also include "end blocking groups" or "exonuclease blocking groups" which protect the 5' and 3' termini of the oligonucleotide, including modified nucleotides and non-nucleotide exonuclease resistant structures.

In some embodiments, at least a portion of the contiguous polynucleotides within the sdRNA are linked by a substitute linkage, e.g., a phosphorothioate linkage.

In some embodiments, chemical modification can lead to at least a 1.5, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 425, 450, 475, 500 enhancements in cellular uptake. In some embodiments, at least one of the C or U residues includes a hydrophobic modification. In some embodiments, a plurality of Cs and Us contain a hydrophobic modification. In some embodiments, at least 10%, 15%, 20%, 30%, 40%, 50%, 55%, 60% 65%, 70%, 75%, 80%, 85%, 90% or at least 95% of the Cs and Us can contain a hydrophobic modification. In some embodiments, all of the Cs and Us contain a hydrophobic modification.

In some embodiments, the sdRNA or sd-rxRNAs exhibit enhanced endosomal release of sd-rxRNA molecules through the incorporation of protonatable amines. In some embodiments, protonatable amines are incorporated in the sense strand (in the part of the molecule which is discarded after RISC loading). In some embodiments, the sdRNA compounds of the invention comprise an asymmetric compound comprising a duplex region (required for efficient RISC entry of 10-15 bases long) and single stranded region of 4-12 nucleotides long; with a 13 nucleotide duplex. In some embodiments, a 6 nucleotide single stranded region is employed. In some embodiments, the single stranded region of the sdRNA comprises 2-12 phosphorothioate internucleotide linkages (referred to as phosphorothioate modifications). In some embodiments, 6-8 phosphorothioate internucleotide linkages are employed. In some embodiments, the sdRNA compounds of the invention also include a unique chemical modification pattern, which provides stability and is compatible with RISC entry.

The guide strand, for example, may also be modified by any chemical modification which confirms stability without interfering with RISC entry. In some embodiments, the chemical modification pattern in the guide strand includes the majority of C and U nucleotides being 2' F modified and the 5' end being phosphorylated.

In some embodiments, at least 30% of the nucleotides in the sdRNA or sd-rxRNA are modified. In some embodiments, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sdRNA or sd-rxRNA are modified. In some embodiments, 100% of the nucleotides in the sdRNA or sd-rxRNA are modified.

In some embodiments, the sdRNA molecules have minimal double stranded regions. In some embodiments the region of the molecule that is double stranded ranges from 8-15 nucleotides long. In some embodiments, the region of the molecule that is double stranded is 8, 9, 10, 11, 12, 13, 14 or 15 nucleotides long. In some embodiments the double stranded region is 13 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. In some embodiments, the single stranded region can be 4, 5, 6, 7, 8, 9, 10, 11 or 12 nucleotides long. In some embodiments, the single stranded region can also be less than 4 or greater than 12 nucleotides long. In certain embodiments, the single stranded region is 6 or 7 nucleotides long.

In some embodiments, the sdRNA molecules have increased stability. In some instances, a chemically modified sdRNA or sd-rxRNA molecule has a half-life in media that is longer than 1, 2, 3, 4, 5, 6, 7, 8, 9, 10, 11, 12, 13, 14, 15, 16, 17, 18, 19, 20, 21, 22, 23, 24 or more than 24 hours, including any intermediate values. In some embodiments, the sd-rxRNA has a half-life in media that is longer than 12 hours.

In some embodiments, the sdRNA is optimized for increased potency and/or reduced toxicity. In some embodiments, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. In some embodiments, reduction in 2'F content of a molecule is predicted to reduce toxicity of the molecule. In some embodiments, the number of phosphorothioate modifications in an RNA molecule can influence the uptake of the molecule into a cell, for example the efficiency of passive uptake of the molecule into a cell. In some embodiments, the sdRNA has no 2'F modification and yet are characterized by equal efficacy in cellular uptake and tissue penetration.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contain 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

The self-deliverable RNAi technology provides a method of directly transfecting cells with the RNAi agent, without the need for additional formulations or techniques. The ability to transfect hard-to-transfect cell lines, high in vivo activity, and simplicity of use, are characteristics of the compositions and methods that present significant functional advantages over traditional siRNA-based techniques, and as such, the sdRNA methods are employed in several embodiments related to the methods of reduction in expression of the target gene in the TILs of the present invention. The sdRNAi methods allows direct delivery of chemically synthesized compounds to a wide range of primary cells and tissues, both ex-vivo and in vivo. The sdRNAs described in some embodiments of the invention herein are commercially available from Advirna LLC, Worcester, MA, USA.

The sdRNA are formed as hydrophobically-modified siRNA-antisense oligonucleotide hybrid structures, and are disclosed, for example in Byrne et al., December 2013, J. Ocular Pharmacology and Therapeutics, 29(10): 855-864, incorporated by reference herein in its entirety.

In some embodiments, the sdRNA oligonucleotides can be delivered to the TILs described herein using sterile electroporation. In certain embodiments, the method comprises sterile electroporation of a population of TILs to deliver sdRNA oligonucleotides.

In some embodiments, the oligonucleotides can be delivered to the cells in combination with a transmembrane delivery system. In some embodiments, this transmembrane delivery system comprises lipids, viral vectors, and the like. In some embodiments, the oligonucleotide agent is a self-delivery RNAi agent, that does not require any delivery agents. In certain embodiments, the method comprises use of a transmembrane delivery system to deliver sdRNA oligonucleotides to a population of TILs.

Oligonucleotides and oligonucleotide compositions are contacted with (e.g., brought into contact with, also referred to herein as administered or delivered to) and taken up by TILs described herein, including through passive uptake by TILs. The sdRNA can be added to the TILs as described herein during the first expansion, for example Step B, after the first expansion, for example, during Step C, before or during the second expansion, for example before or during Step D, after Step D and before harvest in Step E, during or after harvest in Step F, before or during final formulation and/or transfer to infusion Bag in Step F, as well as before any optional cryopreservation step in Step F. Moreover, sdRNA can be added after thawing from any cryopreservation step in Step F. In an embodiment, one or more sdRNAs targeting genes as described herein, including PD-1, LAG-3, TIM-3, CISH, and CBLB, may be added to cell culture media comprising TILs and other agents at concentrations selected from the group consisting of 100 nM to 20 mM, 200 nM to 10 mM, 500 nm to 1 mM, 1 μM to 100 μM, and 1 μM to 100 μM. In an embodiment, one or more sdRNAs targeting genes as described herein, including PD-1, LAG-3, TIM-3, CISH, and CBLB, may be added to cell culture media comprising TILs and other agents at amounts selected from the group consisting of 0.1 μM sdRNA/10,000 TILs/100 μL media, 0.5 μM sdRNA/10,000 TILs/100 μL media, 0.75 μM sdRNA/10,000 TILs/100 μL media, 1 μM sdRNA/10,000 TILs/100 μL media, 1.25 μM sdRNA/10,000 TILs/100 μL media, 1.5 μM sdRNA/10,000 TILs/100 μL media, 2 μM sdRNA/10,000 TILs/100 μL media, 5 μM sdRNA/10,000 TILs/100 μL media, or 10 μM sdRNA/10,000 TILs/100 μL media. In an embodiment, one or more sdRNAs targeting genes as described herein, including PD-1, LAG-3, TIM-3, CISH, and CBLB, may be added to TIL cultures during the pre-REP or REP stages twice a day, once a day, every two days, every three days, every four days, every five days, every six days, or every seven days.

Oligonucleotide compositions of the invention, including sdRNA, can be contacted with TILs as described herein during the expansion process, for example by dissolving sdRNA at high concentrations in cell culture media and allowing sufficient time for passive uptake to occur. In certain embodiments, the method of the present invention comprises contacting a population of TILs with an oligonucleotide composition as described herein. In certain embodiments, the method comprises dissolving an oligonucleotide e.g. sdRNA in a cell culture media and contacting the cell culture media with a population of TILs. The TILs may be a first population, a second population and/or a third population as described herein.

In some embodiments, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see, e.g., WO 90/14074; WO 91/16024; WO 91/17424; U.S. Pat. No. 4,897,355; Bergan et a 1993. Nucleic Acids Research. 21:3567).

In some embodiments, more than one sdRNA is used to reduce expression of a target gene. In some embodiments, one or more of PD-1, TIM-3, CBLB, LAG3 and/or CISH targeting sdRNAs are used together. In some embodiments, a PD-1 sdRNA is used with one or more of TIM-3, CBLB, LAG3 and/or CISH in order to reduce expression of more than one gene target. In some embodiments, a LAG3 sdRNA is used in combination with a CISH targeting sdRNA to reduce gene expression of both targets. In some embodiments, the sdRNAs targeting one or more of PD-1, TIM-3, CBLB, LAG3 and/or CISH herein are commercially available from Advirna LLC, Worcester, MA, USA.

In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, the sdRNA targets a gene selected from the group consisting of PD-1, LAG3, TIM3, CTLA-4, TIGIT, CISH, TGFβR2, PKA, CBLB, BAFF (BR3), and combinations thereof. In some embodiments, one sdRNA targets PD-1 and another sdRNA targets a gene selected from the group consisting of LAG3, TIM3, CTLA-4, TIGIT, CISH, TGFβR2, PKA, CBLB, BAFF (BR3), and combinations thereof. In some embodiments, the sdRNA targets a gene selected from PD-1, LAG-3, CISH, CBLB, TIM3, and combinations thereof. In some embodiments, the sdRNA targets a gene selected from PD-1 and one of LAG3, CISH, CBLB, TIM3, and combinations thereof. In some embodiments, one sdRNA targets PD-1 and one sdRNA targets LAG3. In some embodiments, one sdRNA targets PD-1 and one sdRNA targets CISH. In some embodiments, one sdRNA targets PD-1 and one sdRNA targets CBLB. In some embodiments, one sdRNA targets LAG3 and one sdRNA targets CISH. In some embodiments, one sdRNA targets LAG3 and one sdRNA targets CBLB. In some embodiments, one sdRNA targets CISH and one sdRNA targets CBLB. In some embodiments, one sdRNA targets TIM3 and one sdRNA targets PD-1. In some embodiments, one sdRNA targets TIM3 and one sdRNA targets LAG3. In some embodiments, one sdRNA targets TIM3 and one sdRNA targets CISH. In some embodiments, one sdRNA targets TIM3 and one sdRNA targets CBLB.

As discussed above, embodiments of the present invention provide tumor infiltrating lymphocytes (TILs) that have been genetically modified via gene-editing to enhance their therapeutic effect. Embodiments of the present invention embrace genetic editing through nucleotide insertion (RNA or DNA) into a population of TILs for both promotion of the expression of one or more proteins and inhibition of the expression of one or more proteins, as well as combinations thereof. Embodiments of the present invention also provide methods for expanding TILs into a therapeutic population, wherein the methods comprise gene-editing the TILs. There are several gene-editing technologies that may be used to genetically modify a population of TILs, which are suitable for use in accordance with the present invention.

In some embodiments, the method comprises a method of genetically modifying a population of TILs which include the step of stable incorporation of genes for production of one or more proteins. In an embodiment, a method of genetically modifying a population of TILs includes the step of retroviral transduction. In an embodiment, a method of genetically modifying a population of TILs includes the step of lentiviral transduction. Lentiviral transduction systems are known in the art and are described, e.g., in Levine, et al., *Proc. Nat'l Acad. Sci.* 2006, 103, 17372-77; Zufferey, et al., *Nat. Biotechnol.* 1997, 15, 871-75; Dull, et al., *J. Virology* 1998, 72, 8463-71, and U.S. Pat. No. 6,627,442, the disclosures of each of which are incorporated by reference herein. In an embodiment, a method of genetically modifying a population of TILs includes the step of gamma-retroviral transduction. Gamma-retroviral transduction systems are known in the art and are described, e.g., Cepko and Pear, *Cur. Prot. Mol. Biol.* 1996, 9.9.1-9.9.16, the disclosure of which is incorporated by reference herein. In an embodiment, a method of genetically modifying a population of TILs includes the step of transposon-mediated gene transfer. Transposon-mediated gene transfer systems are known in the art and include systems wherein the transposase is provided as DNA expression vector or as an expressible RNA or a protein such that long-term expression of the transposase does not occur in the transgenic cells, for example, a transposase provided as an mRNA (e.g., an mRNA comprising a cap and poly-A tail). Suitable transposon-mediated gene transfer systems, including the salmonid-type Tel-like transposase (SB or Sleeping Beauty transposase), such as SB10, SB11, and SB100x, and engineered enzymes with increased enzymatic activity, are described in, e.g., Hackett, et al., *Mol. Therapy* 2010, 18, 674-83 and U.S. Pat. No. 6,489,458, the disclosures of each of which are incorporated by reference herein.

In an embodiment, the method comprises a method of genetically modifying a population of TILs e.g. a first population, a second population and/or a third population as described herein. In an embodiment, a method of genetically modifying a population of TILs includes the step of stable incorporation of genes for production or inhibition (e.g., silencing) of one ore more proteins. In an embodiment, a method of genetically modifying a population of TILs includes the step of electroporation. Electroporation methods are known in the art and are described, e.g., in Tsong, *Biophys*. J. 1991, 60, 297-306, and U.S. Patent Application Publication No. 2014/0227237 A1, the disclosures of each of which are incorporated by reference herein. Other electroporation methods known in the art, such as those described in U.S. Pat. Nos. 5,019,034; 5,128,257; 5,137,817; 5,173,158; 5,232,856; 5,273,525; 5,304,120; 5,318,514; 6,010,613 and 6,078,490, the disclosures of which are incorporated by reference herein, may be used. In an embodiment, the electroporation method is a sterile electroporation method. In an embodiment, the electroporation method is a pulsed electroporation method. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse amplitude. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein at least two of the at least three pulses differ from each other in pulse width. In an embodiment, the electroporation method is a pulsed electroporation method comprising the steps of treating TILs with pulsed electrical fields to alter, manipulate, or cause defined and controlled, permanent or temporary changes in the TILs, comprising the step of applying a sequence of at least three single, operator-controlled, independently programmed, DC electrical pulses, having field strengths equal to or greater than 100 V/cm, to the TILs, wherein a first pulse interval for a first set of two of the at least three pulses is different from a second pulse interval for a second set of two of the at least three pulses. In an embodiment, the electroporation method is a pulsed electroporation method comprising the steps of treating TILs with pulsed electrical fields to induce pore formation in the TILs, comprising the step of applying a sequence of at least three DC electrical pulses, having field strengths equal to or greater than 100 V/cm, to TILs, wherein the sequence of at least three DC electrical pulses has one, two, or three of the following characteristics: (1) at least two of the at least three pulses differ from each other in pulse amplitude; (2) at least two of the at least three pulses differ from each other in pulse width; and (3) a first pulse interval for a first set of two of the at least three pulses is different from a second pulse interval for a second set of two of the at least three pulses, such that induced pores are sustained for a relatively long period of time, and such that viability of the TILs is maintained. In an embodiment, a method of genetically modifying a population of TILs includes the step of calcium phosphate transfection. Calcium phosphate transfection methods (calcium phosphate DNA precipitation, cell surface coating, and endocytosis) are known in the art and are described in Graham and van der Eb, *Virology* 1973, 52, 456-467; Wigler, et al., *Proc. Natl. Acad. Sci.* 1979, 76, 1373-1376; and Chen and Okayarea, *Mol. Cell. Biol.* 1987, 7, 2745-2752; and in U.S. Pat. No. 5,593,875, the disclosures of each of which are incorporated by reference herein. In an embodiment, a method of genetically modifying a population of TILs includes the step of liposomal transfection. Liposomal transfection methods, such as methods that employ a 1:1 (w/w) liposome formulation of the cationic lipid N-[1-(2,3-dioleyloxy)propyl]-n,n,n-trimethylammonium chloride (DOTMA) and dioleoyl phophotidylethanolamine (DOPE) in filtered water, are known in the art and are described in Rose, et al., *Biotechniques* 1991, 10, 520-525 and Felgner, et al., *Proc. Natl. Acad. Sci. USA,* 1987, 84, 7413-7417 and in U.S. Pat. Nos. 5,279,833; 5,908,635; 6,056,938; 6,110,490; 6,534,484; and 7,687,070, the disclosures of each of which are incorporated by reference herein. In an embodiment, a method of genetically modifying a population of TILs includes the step of transfection using methods described in U.S. Pat. Nos. 5,766,902; 6,025,337; 6,410,517; 6,475,994; and 7,189,705; the disclosures of each of which are incorporated by reference herein. The TILs may be a first population, a second population and/or a third population of TILs as described herein.

According to an embodiment, the gene-editing process may comprise the use of a programmable nuclease that mediates the generation of a double-strand or single-strand break at one or more immune checkpoint genes. Such programmable nucleases enable precise genome editing by introducing breaks at specific genomic loci, i.e., they rely on the recognition of a specific DNA sequence within the genome to target a nuclease domain to this location and mediate the generation of a double-strand break at the target sequence. A double-strand break in the DNA subsequently recruits endogenous repair machinery to the break site to mediate genome editing by either non-homologous end-joining (NHEJ) or homology-directed repair (HDR). Thus, the repair of the break can result in the introduction of insertion/deletion mutations that disrupt (e.g., silence, repress, or enhance) the target gene product.

Major classes of nucleases that have been developed to enable site-specific genomic editing include zinc finger nucleases (ZFNs), transcription activator-like nucleases (TALENs), and CRISPR-associated nucleases (e.g., CRISPR/Cas9). These nuclease systems can be broadly classified into two categories based on their mode of DNA recognition: ZFNs and TALENs achieve specific DNA binding via protein-DNA interactions, whereas CRISPR systems, such as Cas9, are targeted to specific DNA sequences by a short RNA guide molecule that base-pairs directly with the target DNA and by protein-DNA interactions. See, e.g., Cox et al., *Nature Medicine,* 2015, Vol. 21, No. 2.

Non-limiting examples of gene-editing methods that may be used in accordance with TIL expansion methods of the present invention include CRISPR methods, TALE methods, and ZFN methods, which are described in more detail below. According to an embodiment, a method for expanding TILs into a therapeutic population may be carried out in accordance with any embodiment of the methods described herein (e.g., GEN 3 process) or as described in PCT/US2017/058610, PCT/US2018/012605, or PCT/US2018/012633, wherein the method further comprises gene-editing at least a portion of the TILs by one or more of a CRISPR method, a TALE method or a ZFN method, in order to generate TILs that can provide an enhanced therapeutic effect. According to an embodiment, gene-edited TILs can be evaluated for an improved therapeutic effect by comparing them to nonmodified TILs in vitro, e.g., by evaluating in vitro effector function, cytokine profiles, etc. compared to unmodified TILs. In certain embodiments, the method comprises gene editing a population of TILs using CRISPR, TALE and/or ZFN methods.

In some embodiments of the present invention, electroporation is used for delivery of a gene editing system, such as CRISPR, TALEN, and ZFN systems. In some embodiments of the present invention, the electroporation system is a flow electroporation system. An example of a suitable flow electroporation system suitable for use with some embodiments of the present invention is the commercially-available MaxCyte STX system. There are several alternative commercially-available electroporation instruments which may be suitable for use with the present invention, such as the AgilePulse system or ECM 830 available from BTX-Harvard Apparatus, Cellaxess Elektra (Cellectricon), Nucleofector (Lonza/Amaxa), GenePulser MXcell (BIORAD), iPorator-96 (Primax) or siPORTer96 (Ambion). In some embodiments of the present invention, the electroporation system forms a closed, sterile system with the remainder of the TIL expansion method. In some embodiments of the present invention, the electroporation system is a pulsed electroporation system as described herein, and forms a closed, sterile system with the remainder of the TIL expansion method.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a CRISPR method (e.g., CRISPR/Cas9 or CRISPR/Cpf1). According to particular embodiments, the use of a CRISPR method during the TIL expansion process causes expression of one or more immune checkpoint genes to be silenced or reduced in at least a portion of the therapeutic population of TILs. Alternatively, the use of a CRISPR method during the TIL expansion process causes expression of one or more immune checkpoint genes to be enhanced in at least a portion of the therapeutic population of TILs.

CRISPR stands for "Clustered Regularly Interspaced Short Palindromic Repeats." A method of using a CRISPR system for gene editing is also referred to herein as a CRISPR method. There are three types of CRISPR systems which incorporate RNAs and Cas proteins, and which may be used in accordance with the present invention: Types I, II, and III. The Type II CRISPR (exemplified by Cas9) is one of the most well-characterized systems.

CRISPR technology was adapted from the natural defense mechanisms of bacteria and archaea (the domain of single-celled microorganisms). These organisms use CRISPR-derived RNA and various Cas proteins, including Cas9, to foil attacks by viruses and other foreign bodies by chopping up and destroying the DNA of a foreign invader. A CRISPR is a specialized region of DNA with two distinct characteristics: the presence of nucleotide repeats and spacers. Repeated sequences of nucleotides are distributed throughout a CRISPR region with short segments of foreign DNA (spacers) interspersed among the repeated sequences. In the type II CRISPR/Cas system, spacers are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Target recognition by the Cas9 protein requires a "seed" sequence within the crRNA and a conserved dinucleotide-containing protospacer adjacent motif (PAM) sequence upstream of the crRNA-binding region. The CRISPR/Cas system can thereby be retargeted to cleave virtually any DNA sequence by redesigning the crRNA. The crRNA and tracrRNA in the native system can be simplified into a single guide RNA (sgRNA) of approximately 100 nucleotides for use in genetic engineering. The CRISPR/Cas system is directly portable to human cells by co-delivery of plasmids expressing the Cas9 endo-nuclease and the necessary crRNA components. Different variants of Cas proteins may be used to reduce targeting limitations (e.g., orthologs of Cas9, such as Cpf1).

Non-limiting examples of genes that may be silenced or inhibited by permanently gene-editing TILs via a CRISPR method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a CRISPR method include CCR2, CCR4, CCR5, CXCR2, CXCR3, CX3CR1, IL-2, IL12, IL-15, and IL-21.

Examples of systems, methods, and compositions for altering the expression of a target gene sequence by a CRISPR method, and which may be used in accordance with embodiments of the present invention, are described in U.S. Pat. Nos. 8,697,359; 8,993,233; 8,795,965; 8,771,945; 8,889,356; 8,865,406; 8,999,641; 8,945,839; 8,932,814; 8,871,445; 8,906,616; and 8,895,308, which are incorporated by reference herein. Resources for carrying out CRISPR methods, such as plasmids for expressing CRISPR/Cas9 and CRISPR/Cpf1, are commercially available from companies such as GenScript.

In an embodiment, genetic modifications of populations of TILs, as described herein, may be performed using the CRISPR/Cpf1 system as described in U.S. Pat. No. 9,790,490, the disclosure of which is incorporated by reference herein.

A method for expanding TILs into a therapeutic population may be carried out in accordance with any embodiment of the methods described herein (e.g., process 2A) or as described in PCT/US2017/058610, PCT/US2018/012605, or PCT/US2018/012633, wherein the method further comprises gene-editing at least a portion of the TILs by a TALE method. According to particular embodiments, the use of a TALE method during the TIL expansion process causes expression of one or more immune checkpoint genes to be silenced or reduced in at least a portion of the therapeutic population of TILs. Alternatively, the use of a TALE method during the TIL expansion process causes expression of one or more immune checkpoint genes to be enhanced in at least a portion of the therapeutic population of TILs.

TALE stands for "Transcription Activator-Like Effector" proteins, which include TALENs ("Transcription Activator-Like Effector Nucleases"). A method of using a TALE system for gene editing may also be referred to herein as a TALE method. TALEs are naturally occurring proteins from the plant pathogenic bacteria genus *Xanthomonas*, and contain DNA-binding domains composed of a series of 33-35-amino-acid repeat domains that each recognizes a single base pair. TALE specificity is determined by two hypervariable amino acids that are known as the repeat-variable di-residues (RVDs). Modular TALE repeats are linked together to recognize contiguous DNA sequences. A specific RVD in the DNA-binding domain recognizes a base in the target locus, providing a structural feature to assemble predictable DNA-binding domains. The DNA binding domains of a TALE are fused to the catalytic domain of a type IIS FokI endonuclease to make a targetable TALE nuclease. To induce site-specific mutation, two individual TALEN arms, separated by a 14-20 base pair spacer region, bring FokI monomers in close proximity to dimerize and produce a targeted double-strand break.

Several large, systematic studies utilizing various assembly methods have indicated that TALE repeats can be combined to recognize virtually any user-defined sequence. Custom-designed TALE arrays are also commercially available through Cellectis Bioresearch (Paris, France), Transposagen Biopharmaceuticals (Lexington, KY, USA), and Life Technologies (Grand Island, NY, USA). TALE and TALEN methods suitable for use in the present invention are described in U.S. Patent Application Publication Nos. US 2011/0201118 A1; US 2013/0117869 A1; US 2013/0315884 A1; US 2015/0203871 A1 and US 2016/0120906 A1, the disclosures of which are incorporated by reference herein.

Non-limiting examples of genes that may be silenced or inhibited by permanently gene-editing TILs via a TALE method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a TALE method include CCR2, CCR4, CCR5, CXCR2, CXCR3, CX3CR1, IL-2, IL12, IL-15, and IL-21.

Examples of systems, methods, and compositions for altering the expression of a target gene sequence by a TALE method, and which may be used in accordance with embodiments of the present invention, are described in U.S. Pat. No. 8,586,526, which is incorporated by reference herein.

A method for expanding TILs into a therapeutic population may be carried out in accordance with any embodiment of the methods described herein (e.g., process GEN 3) or as described in PCT/US2017/058610, PCT/US2018/012605, or PCT/US2018/012633, wherein the method further comprises gene-editing at least a portion of the TILs by a zinc finger or zinc finger nuclease method. According to particular embodiments, the use of a zinc finger method during the TIL expansion process causes expression of one or more immune checkpoint genes to be silenced or reduced in at least a portion of the therapeutic population of TILs. Alternatively, the use of a zinc finger method during the TIL expansion process causes expression of one or more immune checkpoint genes to be enhanced in at least a portion of the therapeutic population of TILs.

An individual zinc finger contains approximately 30 amino acids in a conserved ββα configuration. Several amino acids on the surface of the α-helix typically contact 3 bp in the major groove of DNA, with varying levels of selectivity. Zinc fingers have two protein domains. The first domain is the DNA binding domain, which includes eukaryotic transcription factors and contain the zinc finger. The second domain is the nuclease domain, which includes the FokI restriction enzyme and is responsible for the catalytic cleavage of DNA.

The DNA-binding domains of individual ZFNs typically contain between three and six individual zinc finger repeats and can each recognize between 9 and 18 base pairs. If the zinc finger domains are specific for their intended target site then even a pair of 3-finger ZFNs that recognize a total of 18 base pairs can, in theory, target a single locus in a mammalian genome. One method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Alternatively, selection-based approaches, such as oligomerized pool engineering (OPEN) can be used to select for new zinc-finger arrays from randomized libraries that take into consideration context-dependent interactions between neighboring fingers. Engineered zinc fingers are available commercially; Sangamo Biosciences (Richmond, CA, USA) has developed a propriety platform (CompoZr®) for zinc-finger construction in partnership with Sigma-Aldrich (St. Louis, MO, USA).

Non-limiting examples of genes that may be silenced or inhibited by permanently gene-editing TILs via a zinc finger method include PD-1, CTLA-4, LAG-3, HAVCR2 (TIM-3), Cish, TGFβ, PKA, CBL-B, PPP2CA, PPP2CB, PTPN6, PTPN22, PDCD1, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, GUCY1A2, GUCY1A3, GUCY1B2, and GUCY1B3.

Non-limiting examples of genes that may be enhanced by permanently gene-editing TILs via a zinc finger method include CCR2, CCR4, CCR5, CXCR2, CXCR3, CX3CR1, IL-2, IL12, IL-15, and IL-21.

Examples of systems, methods, and compositions for altering the expression of a target gene sequence by a zinc finger method, which may be used in accordance with embodiments of the present invention, are described in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, which are incorporated by reference herein.

Other examples of systems, methods, and compositions for altering the expression of a target gene sequence by a zinc finger method, which may be used in accordance with embodiments of the present invention, are described in Beane, et al., *Mol. Therapy,* 2015, 23 1380-1390, the disclosure of which is incorporated by reference herein.

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). In certain embodiments, the method comprises genetically engineering a population of TILs to include a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19). Aptly, the population of TILs may be a first population, a second population and/or a third population as described herein.

K. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, in "CBER Guidances/Guidelines/Points to Consider" from world wide web <fda.gov/cber/guidelines.htm> and "Guidance for Industry: Use of Sterile Connecting Devices in Blood Bank Practices" from world wide web <fda.gov/BiologicsBloodVaccines/GuidanceComplianceRegulatoryInformation/Guidances/Blood/ucm076779.htm>.

Sterile connecting devices (STCDs) produce sterile welds between two pieces of compatible tubing. This procedure permits sterile connection of a variety of containers and tube diameters. In some embodiments, the closed systems include luer lock and heat sealed systems as described in for example, Example G. In some embodiments, the closed system is accessed via syringes under sterile conditions in order to maintain the sterility and closed nature of the system. In some embodiments, a closed system as described in Example G is employed. In some embodiments, the TILs are formulated into a final product formulation container according to the method described in Example G, section "Final Formulation and Fill".

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

L. Optional Cryopreservation of TILs

Either the bulk TIL population (for example the second population of TILs) or the expanded population of TILs (for example the third population of TILs) can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 1 (in particular, e.g., FIG. 1B and/or FIG. 1C). In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above, and exemplified in Steps A through E as provided in FIG. 1 (in particular, e.g., FIG. 1B and/or FIG. 1C), cryopreservation can occur at numerous points throughout the TIL expansion process. In some embodiments, the expanded population of TILs after the second expansion (as provided for example, according to Step D of FIG. 1 (in particular, e.g., FIG. 1B and/or FIG. 1C) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Example D.

When appropriate, the cells are removed from the freezer and thawed in a 37° C. water bath until approximately 4/5 of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

M. Phenotypic Characteristics of Expanded TILs

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D.

In some embodiments, the marker is selected from the group consisting of CD8 and CD28. In some embodiments, expression of CD8 is examined. In some embodiments, expression of CD28 is examined. In some embodiments, the expression of CD8 and/or CD28 is higher on TILs produced according the current invention process, as compared to other processes (e.g., the Gen 3 process as provided for example in FIG. 1 (in particular, e.g., FIG. 1B and/or FIG. 1C), as compared to the 2A process as provided for example in FIG. 1 (in particular, e.g., FIG. 1B and/or FIG. 1C). In some embodiments, the expression of CD8 is higher on TILs produced according the current invention process, as compared to other processes (e.g., the Gen 3 process as provided for example in FIG. 1 (in particular, e.g., FIG. 1B and/or FIG. 1C), as compared to the 2A process as provided for example in FIG. 1 (in particular, e.g., FIG. 1B and/or FIG. 1C). In some embodiments, the expression of CD28 is higher on TILs produced according the current invention process, as compared to other processes (e.g., the Gen 3 process as provided for example in FIG. 1 (in particular, e.g., FIG. 1B and/or FIG. 1C), as compared to the 2A process as provided for example in FIG. 1 (in particular, e.g., FIG. 1A)). In some embodiments, high CD28 expression is indicative of a younger, more persistent TIL phenotype. In an embodiment, expression of one or more regulatory markers is measured.

In an embodiment, no selection of the first population of TILs, second population of TILs, third population of TILs, or harvested TIL population based on CD8 and/or CD28 expression is performed during any of the steps for the method for expanding tumor infiltrating lymphocytes (TILs) described herein.

In some embodiments, the percentage of central memory cells is higher on TILs produced according the current invention process, as compared to other processes (e.g., the Gen 3 process as provided for example in FIG. 1 (in particular, e.g., FIG. 1B and/or FIG. 1C), as compared to the 2A process as provided for example in FIG. 1 (in particular, e.g., FIG. 1A)). In some embodiments, the memory marker for central memory cells is selected from the group consisting of CCR7 and CD62L.

In some embodiments, the CD4+ and/or CD8+ TIL Memory subsets can be divided into different memory subsets. In some embodiments, the CD4+ and/or CD8+ TILs comprise the naïve (CD45RA+CD62L+) TILS. In some embodiments, the CD4+ and/or CD8+ TILs comprise the central memory (CM; CD45RA−CD62L+) TILs. In some embodiments, the CD4+ and/or CD8+ TILs comprise the effector memory (EM; CD45RA−CD62L−) TILs. In some embodiments, the CD4+ and/or CD8+ TILs comprise the, RA+ effector memory/effector (TEMRA/TEFF; CD45RA+ CD62L+) TILs. In some embodiments, there is a higher % of CD8+ as compared to CD4+ population.

In some embodiments, the TILs express one more markers selected from the group consisting of granzyme B, perforin, and granulysin. In some embodiments, the TILs express granzyme B. In some embodiments, the TILs express perforin. In some embodiments, the TILs express granulysin.

In an embodiment, restimulated TILs can also be evaluated for cytokine release, using cytokine release assays. In some embodiments, TILs can be evaluated for interferon-γ (IFN-γ) secretion. In some embodiments, the IFN-γ secretion is measured by an ELISA assay. In some embodiments, the IFN-γ secretion is measured by an ELISA assay after the rapid second expansion step, after Step D as provided in for example, FIG. 1 (in particular, e.g., FIG. 1B and/or FIG. 1C). In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D in the Gen 3 process as provided in FIG. 1 (in particular, e.g., FIG. 1B and/or FIG. 1C) TILs as compared to for example Step D in the 2A process as provided in FIG. 1 (in particular, e.g., FIG. 1A) is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TILs ex vivo, including TILs produced by the methods of the present invention, including, for example FIG. 1B methods.

In some embodiments, TILs capable of at least one-fold, two-fold, three-fold, four-fold, or five-fold or more IFN-γ secretion are TILs produced by the expansion methods of the present invention, including, for example FIG. 1B and/or FIG. 1C methods. In some embodiments, TILs capable of at least one-fold more IFN-γ secretion are TILs produced by the expansion methods of the present invention, including, for example FIG. 1B and/or FIG. 1C methods. In some embodiments, TILs capable of at least two-fold more IFN-γ secretion are TILs produced by the expansion methods of the present invention, including, for example FIG. 1B and/or FIG. 1C methods. In some embodiments, TILs capable of at least three-fold more IFN-γ secretion are TILs produced by the expansion methods of the present invention, including, for example FIG. 1B and/or FIG. 1C methods. In some embodiments, TILs capable of at least four-fold more IFN-γ secretion are TILs produced by the expansion methods of the present invention, including, for example FIG. 1B and/or FIG. 1C methods. In some embodiments, TILs capable of at least five-fold more IFN-γ secretion are TILs produced by the expansion methods of the present invention, including, for example FIG. 1B and/or FIG. 1C methods.

Figure 12:
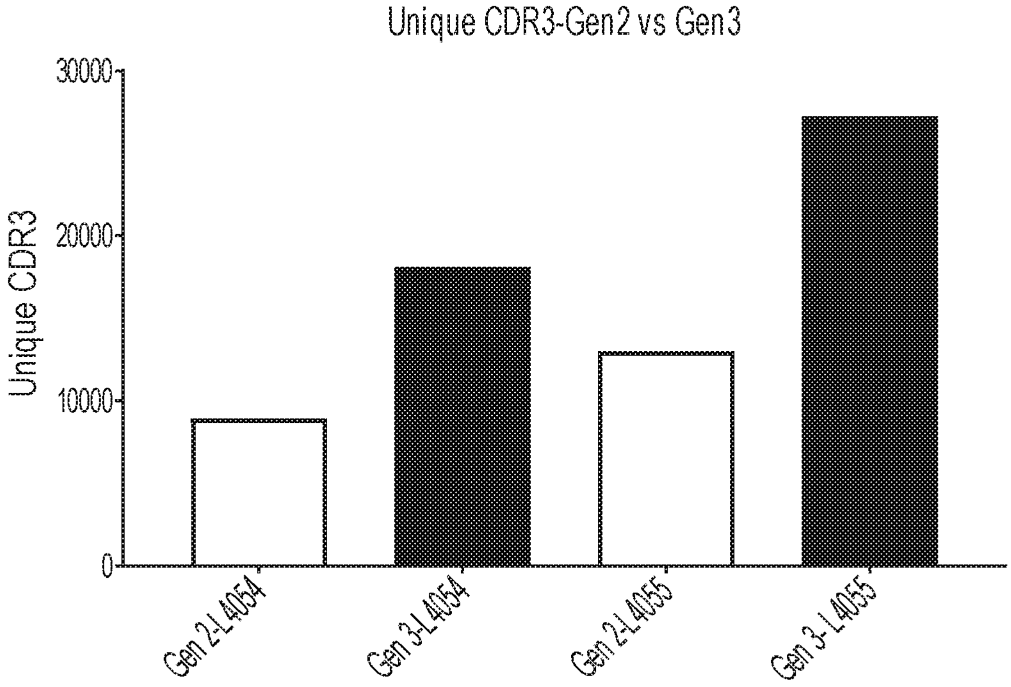
FIG. 12: Unique CDR3 sequence analysis for TIL final product on L4054 and L4055 under Gen 2 and Gen 3 process. Columns show the number of unique TCR B clonotypes identified from $1\times10^6$ cells collected on Harvest Day Gen 2 (e.g., day 22) and Gen 3 process (e.g., day 14-16). Gen 3 shows higher clonal diversity compared to Gen 2 based on the number of unique peptide CDRs within the sample.
Figure 13:
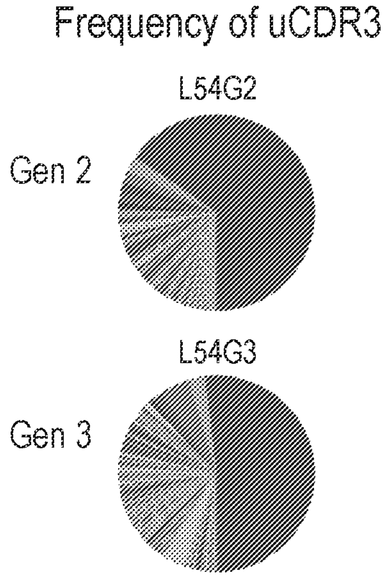
FIG. 13: Frequency of unique CDR3 sequences on L4054 IL harvested final cell product (Gen 2 (e.g., day 22) and Gen 3 process (e.g., day 14-16)).
Figure 14:
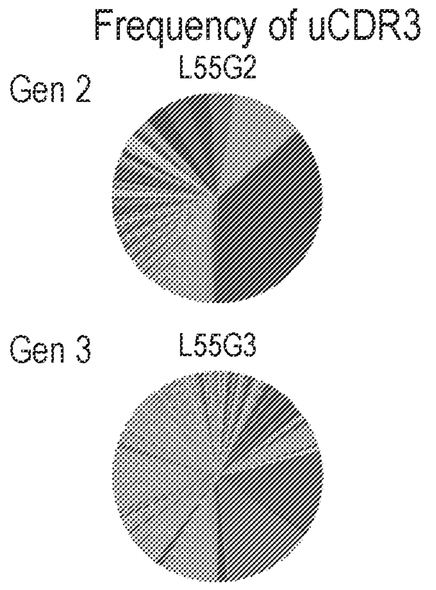
FIG. 14: Frequency of unique CDR3 sequences on L4055 TIL harvested final cell product (Gen 2 (e.g., day 22) and Gen 3 process (e.g., day 14-16)).
Figure 15:
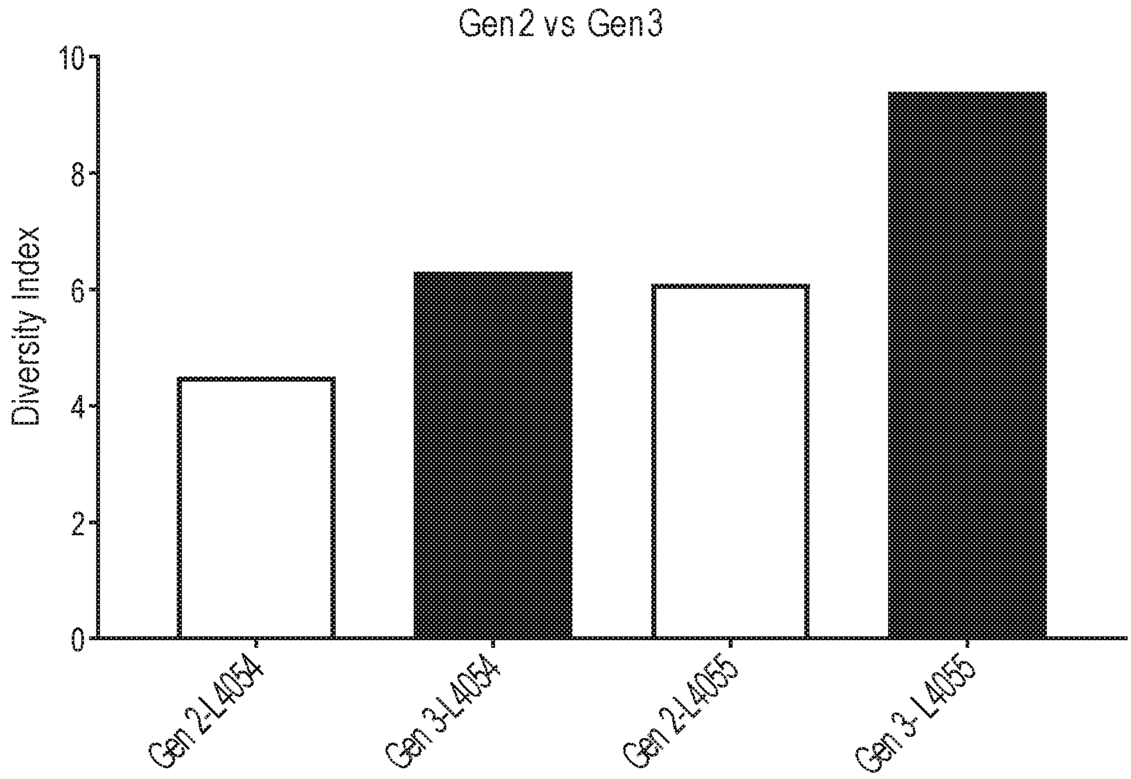
FIG. 15: Diversity Index for TIL final product on L4054 and L4055 under Gen 2 and Gen 3 process. Shanon entropy diversity index is a more reliable and common metric for comparison. Gen 3 L4054 and L4055 showed a slightly higher diversity than Gen 2.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including, for example, methods other than those embodied in FIG. 1 (in particular, e.g., FIG. 1B and/or FIG. 1C). In some embodiments, the TILs obtained by the present method exhibit an increase in the T-cell repertoire diversity as compared to freshly harvested TILs and/or TILs prepared using methods referred to as process 2A, as exemplified in FIG. 1 (in particular, e.g., FIG. 1A). In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β). In some embodiments, the process as described herein (e.g., the Gen 3 process) shows higher clonal diversity as compared to other processes, for example the process referred to as the Gen 2 based on the number of unique peptide CDRs within the sample (see, for example FIGS. 12-14).

In some embodiments, the activation and exhaustion of TILs can be determined by examining one or more markers. In some embodiments, the activation and exhaustion can be determined using multicolor flow cytometry. In some embodiments, the activation and exhaustion of markers include but not limited to one or more markers selected from the group consisting of CD3, PD-1, 2B4/CD244, CD8, CD25, BTLA, KLRG, TIM-3, CD194/CCR4, CD4, TIGIT, CD183, CD69, CD95, CD127, CD103, and/or LAG-3). In some embodiments, the activation and exhaustion of markers include but not limited to one or more markers selected from the group consisting of BTLA, CTLA-4, ICOS, Ki67, LAG-3, PD-1, TIGIT, and/or TIM-3. In some embodiments, the activation and exhaustion of markers include but not limited to one or more markers selected from the group consisting of BTLA, CTLA-4, ICOS, Ki67, LAG-3, CD103+/CD69+, CD103+/CD69−, PD-1, TIGIT, and/or TIM-3. In some embodiments, the T-cell markers (including activation and exhaustion markers) can be determined and/or analyzed to examine T-cell activation, inhibition, or function. In some embodiments, the T-cell markers can include but are not limited to one or more markers selected from the group consisting of TIGIT, CD3, FoxP3, Tim-3, PD-1, CD103, CTLA-4, LAG-3, BTLA-4, ICOS, Ki67, CD8, CD25, CD45, CD4, and/or CD59.

In some embodiments, the phenotypic characterization is examined after cryopreservation.

N. Additional Process Embodiments

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 10 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 2 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 8 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 to 7 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 8 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 8 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 2 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 8 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 2 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 6 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 4 to 5 days.

In some embodiments, the invention provides a method for expanding tumor infiltrating lymphocytes (TILs) into a therapeutic population of TILs comprising: (a) obtaining a first population of TILs from a tumor resected from a subject by processing a tumor sample obtained from the subject into multiple tumor fragments; (b) performing a priming first expansion by culturing the first population of TILs in a cell culture medium comprising IL-2 and OKT-3, wherein the priming first expansion is performed for about 1 to 7 days to obtain the second population of TILs, wherein the second population of TILs is greater in number than the first population of TILs; (c) performing a rapid second expansion by contacting the second population of TILs with a cell culture medium comprising IL-2, OKT-3 and exogenous antigen presenting cells (APCs) to produce a third population of TILs, wherein the rapid second expansion is performed for about 1 to 11 days to obtain the third population of TILs, wherein the third population of TILs is a therapeutic population of TILs; and (d) harvesting the therapeutic population of TILs obtained from step (c). In some embodiments, the step of rapid second expansion is split into a plurality of steps to achieve a scaling up of the culture by: (1) performing the rapid second expansion by culturing the second population of TILs in a small scale culture in a first container, e.g., a G-REX 100MCS container, for a period of about 3 to 4 days, and then (2) effecting the transfer of the second population of TILs from the small scale culture to a second container larger than the first container, e.g., a G-REX 500MCS container, wherein in the second container the second population of TILs from the small scale culture is cultured in a larger scale culture for a period of about 4 to 7 days. In some embodiments, the step of rapid expansion is split into a plurality of steps to achieve a scaling out of the culture by: (1) performing the rapid second expansion by culturing the second population of TILs in a first small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the second population of TILs from the first small scale culture transferred to such second container is cultured in a second small scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 3 to 4 days, and then (2) effecting the transfer and apportioning of the second population of TILs from the first small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the second population of TILs transferred from the small scale culture to such second container is cultured in a larger scale culture for a period of about 4 to 7 days. In some embodiments, the step of rapid expansion is split into a plurality of steps to achieve a scaling out and scaling up of the culture by: (1) performing the rapid second expansion by culturing the second population of TILs in a small scale culture in a first container, e.g., a G-REX 100MCS container, for a period of about 4 days, and then (2) effecting the transfer and apportioning of the second population of TILs from the first small scale culture into and amongst 2, 3 or 4 second containers that are larger in size than the first container, e.g., G-REX 500MCS containers, wherein in each second container the portion of the second population of TILs transferred from the small scale culture to such second container is cultured in a larger scale culture for a period of about 5 days.

In another embodiment, the invention provides the method described in any of the preceding paragraphs as applicable above modified such that in step (b) the primary first expansion is performed by contacting the first population of TILs with a culture medium which further comprises exogenous antigen-presenting cells (APCs), wherein the number of APCs in the culture medium in step (c) is greater than the number of APCs in the culture medium in step (b).

In another embodiment, the invention provides the method described in any of the preceding paragraphs as applicable above modified such that in step (c) the culture medium is supplemented with additional exogenous APCs.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 20:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 10:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 9:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 8:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 7:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 6:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 5:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 4:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 3:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.9:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.8:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.7:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.6:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.5:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.4:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.3:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.2:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2.1:1.

In another embodiment, the invention provides the method described in any of the preceding paragraphs as applicable above modified such that the ratio of number of APCs added in the rapid second expansion to the number of APCs added in step (b) is in a range of from at or about 1.1:1 to at or about 2:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 10:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 5:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 4:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 3:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.9:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.8:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.7:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.6:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.5:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.4:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.3:1.

In another embodiment, the invention provides the method described in any of the preceding paragraph as applicable above modified such that the ratio of number of APCs added in the rapid second expansion to the number of APCs added in step (b) is in a range of from at or about 2:1 to at or about 2.2:1.

In another embodiment, the invention provides the method described in any of the preceding paragraphs as applicable above modified such that the ratio of number of APCs added in the rapid second expansion to the number of APCs added in step (b) is in a range of from at or about 2:1 to at or about 2.1:1.

In another embodiment, the invention provides the method described in any of the preceding paragraphs as applicable above modified such that the ratio of number of APCs added in the rapid second expansion to the number of APCs added in step (b) is at or about 2:1.

In another embodiment, the invention provides the method described in any of the preceding paragraphs as applicable above modified such that the ratio of number of APCs added in the rapid second expansion to the number of APCs added in step (b) is at or about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, or 5:1.

In another embodiment, the invention provides the method described in any of the preceding paragraphs as applicable above modified such that the number of APCs added in the primary first expansion is at or about $1\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3\times10^8$, $3.1\times10^8$, $3.2\times10^8$, $3.3\times10^8$, $3.4\times10^8$ or $3.5\times10^8$ APCs, and such that the number of APCs added in the rapid second expansion is at or about $3.5\times10^8$, $3.6\times10^8$, $3.7\times10^8$, $3.8\times10^8$, $3.9\times10^8$, $4\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, $6\times10^8$, $6.1\times10^8$, $6.2\times10^8$, $6.3\times10^8$, $6.4\times10^8$, $6.5\times10^8$, $6.6\times10^8$, $6.7\times10^8$, $6.8\times10^8$, $6.9\times10^8$, $7\times10^8$, $7.1\times10^8$, $7.2\times10^8$, $7.3\times10^8$, $7.4\times10^8$, $7.5\times10^8$, $7.6\times10^8$, $7.7\times10^8$, $7.8\times10^8$, $7.9\times10^8$, $8\times10^8$, $8.1\times10^8$, $8.2\times10^8$, $8.3\times10^8$, $8.4\times10^8$, $8.5\times10^8$, $8.6\times10^8$, $8.7\times10^8$, $8.8\times10^8$, $8.9\times10^8$, $9\times10^8$, $9.1\times10^8$, $9.2\times10^8$, $9.3\times10^8$, $9.4\times10^8$, $9.5\times10^8$, $9.6\times10^8$, $9.7\times10^8$, $9.8\times10^8$, $9.9\times10^8$ or $1\times10^9$ APCs.

In another embodiment, the invention provides the method described in any of the preceding paragraphs as applicable above modified such that the number of APCs added in the primary first expansion is in the range of at or about $1\times10^8$ APCs to at or about $3.5\times10^8$ APCs, and wherein the number of APCs added in the rapid second expansion is in the range of at or about $3.5\times10^8$ APCs to at or about $1\times10^9$ APCs.

In another embodiment, the invention provides the method described in any of the preceding paragraphs as applicable above modified such that the number of APCs added in the primary first expansion is in the range of at or about $1.5\times10^8$ APCs to at or about $3\times10^8$ APCs, and wherein the number of APCs added in the rapid second expansion is in the range of at or about $4\times10^8$ APCs to at or about $7.5\times10^8$ APCs.

In another embodiment, the invention provides the method described in any of the preceding paragraphs as applicable above modified such that the number of APCs added in the primary first expansion is in the range of at or about $2\times10^8$ APCs to at or about $2.5\times10^8$ APCs, and wherein the number of APCs added in the rapid second expansion is in the range of at or about $4.5\times10^8$ APCs to at or about $5.5\times10^8$ APCs.

In another embodiment, the invention provides the method described in any of the preceding paragraphs as applicable above modified such that at or about $2.5\times10^8$ APCs are added to the primary first expansion and at or about $5\times10^8$ APCs are added to the rapid second expansion.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the multiple tumor fragments are distributed into a plurality of separate containers, in each of which separate containers the first population of TILs is obtained in step (a), the second population of TILs is obtained in step (b), and the third population of TILs is obtained in step (c), and the therapeutic populations of TILs from the plurality of containers in step (c) are combined to yield the harvested TIL population from step (d).

In another embodiment, the invention provides the method described in any of the preceding paragraphs as applicable above modified such that the multiple tumors are evenly distributed into the plurality of separate containers.

In another embodiment, the invention provides the method described in any of the preceding paragraphs as applicable above modified such that the plurality of separate containers comprises at least two separate containers.

In another embodiment, the invention provides the method described in any of the preceding paragraphs as applicable above modified such that the plurality of separate containers comprises from two to twenty separate containers.

In another embodiment, the invention provides the method described in any of the preceding paragraphs as applicable above modified such that the plurality of separate containers comprises from two to fifteen separate containers.

In another embodiment, the invention provides the method described in any of the preceding paragraphs as applicable above modified such that the plurality of separate containers comprises from two to ten separate containers.

In another embodiment, the invention provides the method described in any of the preceding paragraphs as applicable above modified such that the plurality of separate containers comprises from two to five separate containers.

In another embodiment, the invention provides the method described in any of the preceding paragraphs as applicable above modified such that the plurality of separate containers comprises 2, 3, 4, 5, 6, 7, 8, 9, 10, 11, 12, 13, 14, 15, 16, 17, 18, 19, or 20 separate containers.

In another embodiment, the invention provides the method described in any of the preceding paragraphs as applicable above modified such that for each container in which the priming first expansion is performed on a first population of TILs in step (b) the rapid second expansion in step (c) is performed in the same container on the second population of TILs produced from such first population of TILs.

In another embodiment, the invention provides the method described in any of the preceding paragraphs as applicable above modified such that each of the separate containers comprises a first gas-permeable surface area.

In another embodiment, the invention provides the method described in any of the preceding paragraphs as applicable above modified such that the multiple tumor fragments are distributed in a single container.

In another embodiment, the invention provides the method described in any of the preceding paragraphs as applicable above modified such that the single container comprises a first gas-permeable surface area.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in a second container comprising a second gas-permeable surface area.

In another embodiment, the invention provides the method described in any of the preceding paragraphs as applicable above modified such that the second container is larger than the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the second gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the second gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the second gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the second gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the priming first expansion is performed in a first container comprising a first gas-permeable surface area and in step (c) the rapid second expansion is performed in the first container.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein in step (b) the APCs are layered onto the first gas-permeable surface area at an average thickness of at or about one cell layer to at or about three cell layers.

In another embodiment, the invention provides the method described in any of the preceding paragraphs as applicable above modified such that in step (b) the APCs are layered onto the first gas-permeable surface area at an average thickness of at or about 1.5 cell layers to at or about 2.5 cell layers.

In another embodiment, the invention provides the method described in any of the preceding paragraphs as applicable above modified such that in step (b) the APCs are layered onto the first gas-permeable surface area at an average thickness of at or about 2 cell layers.

In another embodiment, the invention provides the method described in any of the preceding paragraphs as applicable above modified such that in step (b) the APCs are layered onto the first gas-permeable surface area at an average thickness of at or about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 cell layers.

In another embodiment, the invention provides the method described in any of the preceding paragraphs as applicable above modified such that in step (c) the APCs are layered onto the first gas-permeable surface area at an average thickness of at or about 3 cell layers to at or about 10 cell layers.

In another embodiment, the invention provides the method described in any of the preceding paragraphs as applicable above modified such that in step (c) the APCs are layered onto the first gas-permeable surface area at an average thickness of at or about 4 cell layers to at or about 8 cell layers.

In another embodiment, the invention provides the method described in any of the preceding paragraphs as applicable above modified such that in step (c) the APCs are layered onto the first gas-permeable surface area at an average thickness of at or about 3, 4, 5, 6, 7, 8, 9 or 10 cell layers.

In another embodiment, the invention provides the method described in any of the preceding paragraphs as applicable above modified such that in step (c) the APCs are layered onto the first gas-permeable surface area at an average thickness of at or about 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9 or 8 cell layers.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:10.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:9.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.1 to at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.2 to at or about 1:8.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.3 to at or about 1:7.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.4 to at or about 1:6.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.5 to at or about 1:5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.6 to at or about 1:4.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.7 to at or about 1:3.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.8 to at or about 1:3.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:1.9 to at or about 1:2.5.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is in the range of at or about 1:2.

In another embodiment, the invention provides the method described in any of the preceding paragraphs as applicable above modified such that in step (b) the primary first expansion is performed by supplementing the cell culture medium of the first population of TILs with additional antigen-presenting cells (APCs), wherein the number of APCs added in step (c) is greater than the number of APCs added in step (b), and wherein the ratio of the average number of layers of APCs layered in step (b) to the average number of layers of APCs layered in step (c) is selected from at or about 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3, 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9, 1:6, 1:6.1, 1:6.2, 1:6.3, 1:6.4, 1:6.5, 1:6.6, 1:6.7, 1:6.8, 1:6.9, 1:7, 1:7.1, 1:7.2, 1:7.3, 1:7.4, 1:7.5, 1:7.6, 1:7.7, 1:7.8, 1:7.9, 1:8, 1:8.1, 1:8.2, 1:8.3, 1:8.4, 1:8.5, 1:8.6, 1:8.7, 1:8.8, 1:8.9, 1:9, 1:9.1, 1:9.2, 1:9.3, 1:9.4, 1:9.5, 1:9.6, 1:9.7, 1:9.8, 1:9.9 or 1:10.

In another embodiment, the invention provides the method described in any of the preceding paragraphs as applicable above modified such that the ratio of the number of TILs in the second population of TILs to the number of TILs in the first population of TILs is at or about 1.5:1 to at or about 100:1.

In another embodiment, the invention provides the method described in any of the preceding paragraphs as applicable above modified such that the ratio of the number of TILs in the second population of TILs to the number of TILs in the first population of TILs is at or about 50:1.

In another embodiment, the invention provides the method described in any of the preceding paragraphs as applicable above modified such that the ratio of the number of TILs in the second population of TILs to the number of TILs in the first population of TILs is at or about 25:1.

In another embodiment, the invention provides the method described in any of the preceding paragraphs as applicable above modified such that the ratio of the number of TILs in the second population of TILs to the number of TILs in the first population of TILs is at or about 20:1.

In another embodiment, the invention provides the method described in any of the preceding paragraphs as applicable above modified such that the ratio of the number of TILs in the second population of TILs to the number of TILs in the first population of TILs is at or about 10:1.

In another embodiment, the invention provides the method described in any of the preceding paragraphs as applicable above modified such that the second population of TILs is at least at or about 50-fold greater in number than the first population of TILs.

In another embodiment, the invention provides the method described in any of the preceding paragraphs as applicable above modified such that the second population of TILs is at least at or about 1-, 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49- or 50-fold greater in number than the first population of TILs.

In another embodiment, the invention provides the method described in any of the preceding paragraphs as applicable above modified such that at or about 2 days or at or about 3 days after the commencement of the second period in step (c), the cell culture medium is supplemented with additional IL-2.

In another embodiment, the invention provides the method described in any of the preceding paragraphs as applicable above modified to further comprise the step of cryopreserving the harvested TIL population in step (d) using a cryopreservation process.

In another embodiment, the invention provides the method described in any of the preceding paragraphs as applicable above modified to comprise performing after step (d) the additional step of (e) transferring the harvested TIL population from step (d) to an infusion bag that optionally contains HypoThermosol.

In another embodiment, the invention provides the method described in any of the preceding paragraphs as applicable above modified to comprise the step of cryopreserving the infusion bag comprising the harvested TIL population in step (e) using a cryopreservation process.

In another embodiment, the invention provides the method described in any of the preceding paragraphs as applicable above modified such that the cryopreservation process is performed using a 1:1 ratio of harvested TIL population to cryopreservation media.

In another embodiment, the invention provides the method described in any of the preceding paragraphs as applicable above modified such that the antigen-presenting cells are peripheral blood mononuclear cells (PBMCs).

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the total number of APCs added to the cell culture in step (b) is $2.5\times10^8$.

In another embodiment, the invention provides the method described in any of the preceding paragraphs as applicable above modified such that the total number of APCs added to the cell culture in step (c) is $5\times10^8$.

In another embodiment, the invention provides the method described in any of the preceding paragraphs as applicable above modified such that the APCs are PBMCs.

In another embodiment, the invention provides the method described in any of the preceding paragraphs as applicable above modified such that the PBMCs are irradiated and allogeneic.

In another embodiment, the invention provides the method described in any of the preceding paragraphs as applicable above modified such that the antigen-presenting cells are artificial antigen-presenting cells.

In another embodiment, the invention provides the method described in any of the preceding paragraphs as applicable above modified such that the harvesting in step (d) is performed using a membrane-based cell processing system.

In another embodiment, the invention provides the method described in any of the preceding paragraphs as applicable above modified such that the harvesting in step (d) is performed using a LOVO cell processing system.

In another embodiment, the invention provides the method described in any of the preceding paragraphs as applicable above modified such that the multiple fragments comprise at or about 5 to at or about 60 fragments per container in step (b).

In another embodiment, the invention provides the method described in any of the preceding paragraphs as applicable above modified such that the multiple fragments comprise at or about 10 to at or about 60 fragments per container in step (b).

In another embodiment, the invention provides the method described in any of the preceding paragraphs as applicable above modified such that the multiple fragments comprise at or about 15 to at or about 60 fragments per container in step (b).

In another embodiment, the invention provides the method described in any of the preceding paragraphs as applicable above modified such that the multiple fragments comprise at or about 20 to at or about 60 fragments per container in step (b).

In another embodiment, the invention provides the method described in any of the preceding paragraphs as applicable above modified such that the multiple fragments comprise at or about 25 to at or about 60 fragments per container in step (b).

In another embodiment, the invention provides the method described in any of the preceding paragraphs as applicable above modified such that the multiple fragments comprise at or about 30 to at or about 60 fragments per container in step (b).

In another embodiment, the invention provides the method described in any of the preceding paragraphs as applicable above modified such that the multiple fragments comprise at or about 35 to at or about 60 fragments per container in step (b).

In another embodiment, the invention provides the method described in any of the preceding paragraphs as applicable above modified such that the multiple fragments comprise at or about 40 to at or about 60 fragments per container in step (b).

In another embodiment, the invention provides the method described in any of the preceding paragraphs as applicable above modified such that the multiple fragments comprise at or about 45 to at or about 60 fragments per container in step (b).

In another embodiment, the invention provides the method described in any of the preceding paragraphs as applicable above modified such that the multiple fragments comprise at or about 50 to at or about 60 fragments per container in step (b).

In another embodiment, the invention provides the method described in any of the preceding paragraphs as applicable above modified such that the multiple fragments comprise at or about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 fragment(s) per container in step (b).

In another embodiment, the invention provides the method described in any of the preceding paragraphs as applicable above modified such that each fragment has a volume of at or about 27 $mm^3$.

In another embodiment, the invention provides the method described in any of the preceding paragraphs as applicable above modified such that each fragment has a volume of at or about 20 $mm^3$ to at or about 50 $mm^3$.

In another embodiment, the invention provides the method described in any of the preceding paragraphs as applicable above modified such that each fragment has a volume of at or about 21 $mm^3$ to at or about 30 $mm^3$.

In another embodiment, the invention provides the method described in any of the preceding paragraphs as applicable above modified such that each fragment has a volume of at or about 22 $mm^3$ to at or about 29.5 $mm^3$.

In another embodiment, the invention provides the method described in any of the preceding paragraphs as applicable above modified such that each fragment has a volume of at or about 23 $mm^3$ to at or about 29 $mm^3$.

In another embodiment, the invention provides the method described in any of the preceding paragraphs as applicable above modified such that each fragment has a volume of at or about 24 $mm^3$ to at or about 28.5 $mm^3$.

In another embodiment, the invention provides the method described in any of the preceding paragraphs as applicable above modified such that each fragment has a volume of at or about 25 $mm^3$ to at or about 28 $mm^3$.

In another embodiment, the invention provides the method described in any of the preceding paragraphs as applicable above modified such that each fragment has a volume of at or about 26.5 $mm^3$ to at or about 27.5 $mm^3$.

In another embodiment, the invention provides the method described in any of the preceding paragraphs as applicable above modified such that each fragment has a volume of at or about 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 $mm^3$.

In another embodiment, the invention provides the method described in any of the preceding paragraphs as applicable above modified such that the multiple fragments comprise at or about 30 to at or about 60 fragments with a total volume of at or about 1300 $mm^3$ to at or about 1500 $mm^3$.

In another embodiment, the invention provides the method described in any of the preceding paragraphs as applicable above modified such that the multiple fragments comprise at or about 50 fragments with a total volume of at or about 1350 $mm^3$.

In another embodiment, the invention provides the method described in any of the preceding paragraphs as applicable above modified such that the multiple fragments comprise at or about 50 fragments with a total mass of at or about 1 gram to at or about 1.5 grams.

In another embodiment, the invention provides the method described in any of the preceding paragraphs as applicable above modified such that the cell culture medium is provided in a container that is a G-container or a Xuri cellbag.

In another embodiment, the invention provides the method described in any of the preceding paragraphs as applicable above modified such that the IL-2 concentration in the cell culture medium is about 10,000 IU/mL to about 5,000 IU/mL.

In another embodiment, the invention provides the method described in any of the preceding paragraphs as applicable above modified such that the IL-2 concentration in the cell culture medium is about 6,000 IU/mL.

In another embodiment, the invention provides the method described in any of the preceding paragraphs as applicable above modified such that the cryopreservation media comprises dimethlysulfoxide (DMSO).

In another embodiment, the invention provides the method described in any of the preceding paragraphs as applicable above modified such that the cryopreservation media comprises 7% to 10% DMSO.

In another embodiment, the invention provides the method described in any of the preceding paragraphs as applicable above modified such that the first period in step (b) is performed within a period of at or about 1 day, 2 days, 3 days, 4 days, 5 days, 6 days, or 7 days.

In another embodiment, the invention provides the method described in any of the preceding paragraphs as applicable above modified such that the second period in step (c) is performed within a period of at or about 1 day, 2 days, 3 days, 4 days, 5 days, 6 days, 7 days, 8 days, 9 days, 10 days or 11 days.

In another embodiment, the invention provides the method described in any of the preceding paragraphs as applicable above modified such that the first period in step (b) and the second period in step (c) are each individually performed within a period of at or about 1 day, 2 days, 3 days, 4 days, 5 days, 6 days, or 7 days.

In another embodiment, the invention provides the method described in any of the preceding paragraphs as applicable above modified such that the first period in step (b) and the second period in step (c) are each individually performed within a period of at or about 5 days, 6 days, or 7 days.

In another embodiment, the invention provides the method described in any of the preceding paragraphs as applicable above modified such that the first period in step (b) and the second period in step (c) are each individually performed within a period of at or about 7 days.

In another embodiment, the invention provides the method described in any of the preceding paragraphs as applicable above modified such that steps (a) through (d) are performed in a total of at or about 14 days to at or about 18 days.

In another embodiment, the invention provides the method described in any of the preceding paragraphs as applicable above modified such that steps (a) through (d) are performed in a total of at or about 15 days to at or about 18 days.

In another embodiment, the invention provides the method described in any of the preceding paragraphs as applicable above modified such that steps (a) through (d) are performed in a total of at or about 16 days to at or about 18 days.

In another embodiment, the invention provides the method described in any of the preceding paragraphs as applicable above modified such that steps (a) through (d) are performed in a total of at or about 17 days to at or about 18 days.

In another embodiment, the invention provides the method described in any of the preceding paragraphs as applicable above modified such that steps (a) through (d) are performed in a total of at or about 14 days to at or about 17 days.

In another embodiment, the invention provides the method described in any of the preceding paragraphs as applicable above modified such that steps (a) through (d) are performed in a total of at or about 15 days to at or about 17 days.

In another embodiment, the invention provides the method described in any of the preceding paragraphs as applicable above modified such that steps (a) through (d) are performed in a total of at or about 16 days to at or about 17 days.

In another embodiment, the invention provides the method described in any of the preceding paragraphs as applicable above modified such that steps (a) through (d) are performed in a total of at or about 14 days to at or about 16 days.

In another embodiment, the invention provides the method described in any of the preceding paragraphs as applicable above modified such that steps (a) through (d) are performed in a total of at or about 15 days to at or about 16 days.

In another embodiment, the invention provides the method described in any of the preceding paragraphs as applicable above modified such that steps (a) through (d) are performed in a total of at or about 14 days.

In another embodiment, the invention provides the method described in any of the preceding paragraphs as applicable above modified such that steps (a) through (d) are performed in a total of at or about 15 days.

In another embodiment, the invention provides the method described in any of the preceding paragraphs as applicable above modified such that steps (a) through (d) are performed in a total of at or about 16 days.

In another embodiment, the invention provides the method described in any of the preceding paragraphs as applicable above modified such that steps (a) through (d) are performed in a total of at or about 17 days.

In another embodiment, the invention provides the method described in any of the preceding paragraphs as applicable above modified such that steps (a) through (d) are performed in a total of at or about 18 days.

In another embodiment, the invention provides the method described in any of the preceding paragraphs as applicable above modified such that steps (a) through (d) are performed in a total of at or about 14 days or less.

In another embodiment, the invention provides the method described in any of the preceding paragraphs as applicable above modified such that steps (a) through (d) are performed in a total of at or about 15 days or less.

In another embodiment, the invention provides the method described in any of the preceding paragraphs as applicable above modified such that steps (a) through (d) are performed in a total of at or about 16 days or less.

In another embodiment, the invention provides the method described in any of the preceding paragraphs as applicable above modified such that steps (a) through (d) are performed in a total of at or about 17 days or less.

In another embodiment, the invention provides the method described in any of the preceding paragraphs as applicable above modified such that steps (a) through (d) are performed in a total of at or about 18 days or less.

In another embodiment, the invention provides the method described in any of the preceding paragraphs as applicable above modified such that the therapeutic population of TILs harvested in step (d) comprises sufficient TILs for a therapeutically effective dosage of the TILs.

In another embodiment, the invention provides the method described in any of the preceding paragraphs as applicable above modified such that the number of TILs sufficient for a therapeutically effective dosage is from at or about $2.3\times10^{10}$ to at or about $13.7\times10^{10}$.

In another embodiment, the invention provides the method described in any of the preceding paragraphs as applicable above modified such that the third population of TILs in step (c) provides for increased efficacy, increased interferon-gamma production, and/or increased polyclonality.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 16 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 17 days.

In another embodiment, the invention provides the method described in any of the preceding paragraphs as applicable above modified such that the third population of TILs in step (c) provides for at least a one-fold to five-fold or more interferon-gamma production as compared to TILs prepared by a process longer than 18 days.

In another embodiment, the invention provides the method described in any of the preceding paragraphs as applicable above modified such that the effector T cells and/or central memory T cells obtained from the third population of TILs step (c) exhibit increased CD8 and CD28 expression relative to effector T cells and/or central memory T cells obtained from the second population of cells step (b).

In another embodiment, the invention provides the method described in any of the preceding paragraphs as applicable above modified such that each container recited in the method is a closed container.

In another embodiment, the invention provides the method described in any of the preceding paragraphs as applicable above modified such that each container recited in the method is a G-container.

In another embodiment, the invention provides the method described in any of the preceding paragraphs as applicable above modified such that each container recited in the method is a GREX-10.

In another embodiment, the invention provides the method described in any of the preceding paragraphs as applicable above modified such that each container recited in the method is a GREX-100.

In another embodiment, the invention provides the method described in any of the preceding paragraphs as applicable above modified such that each container recited in the method is a GREX-500.

In another embodiment, the invention provides the therapeutic population of tumor infiltrating lymphocytes (TILs) made by the method described in any of the preceding paragraphs as applicable above.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs) or OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added antigen-presenting cells (APCs).

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed without any added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process in which the first expansion of TILs is performed with no added antigen-presenting cells (APCs) and no added OKT3.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 16 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 17 days.

In another embodiment, the invention provides a therapeutic population of tumor infiltrating lymphocytes (TILs) prepared from tumor tissue of a patient, wherein the therapeutic population of TILs provides for increased efficacy, increased interferon-gamma production, and/or increased polyclonality compared to TILs prepared by a process by a process longer than 18 days.

In another embodiment, the invention provides for the therapeutic population of TILs described in any of the preceding paragraphs as applicable above that provides for increased interferon-gamma production.

In another embodiment, the invention provides for the therapeutic population of TILs described in any of the preceding paragraphs as applicable above that provides for increased polyclonality.

In another embodiment, the invention provides for the therapeutic population of TILs described in any of the preceding paragraphs as applicable above that provides for increased efficacy.

In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least one-fold more interferon-gamma production as compared to TILs prepared by a process longer than 18 days. In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least two-fold more interferon-gamma production as compared to TILs prepared by a process longer than 18 days. In some embodiments, the TILs are rendered capable of the at least two-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 16 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 17 days. In another embodiment, the invention provides for the therapeutic population of TILs described in any of the preceding paragraphs as applicable above modified such that the therapeutic population of TILs is capable of at least three-fold more interferon-gamma production as compared to TILs prepared by a process longer than 18 days. In some embodiments, the TILs are rendered capable of the at least three-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added antigen-presenting cells (APCs). In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of tumor infiltrating lymphocytes (TILs) that is capable of at least one-fold more interferon-gamma production as compared to TILs prepared by a process in which the first expansion of TILs is performed without any added OKT3. In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least two-fold more interferon-gamma production as compared to TILs prepared by a process in which the first expansion of TILs is performed without any added APCs. In some embodiments, the TILs are rendered capable of the at least two-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least two-fold more interferon-gamma production as compared to TILs prepared by a process in which the first expansion of TILs is performed without any added OKT3. In some embodiments, the TILs are rendered capable of the at least two-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least three-fold more interferon-gamma production as compared to TILs prepared by a process in which the first expansion of TILs is performed without any added APCs. In some embodiments, the TILs are rendered capable of the at least one-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides for a therapeutic population of TILs that is capable of at least three-fold more interferon-gamma production as compared to TILs prepared by a process in which the first expansion of TILs is performed without any added OKT3. In some embodiments, the TILs are rendered capable of the at least three-fold more interferon-gamma production due to the expansion process described herein, for example as described in Steps A through F above or according to Steps A through F above (also as shown, for example, in FIG. 1 (in particular, e.g., FIG. 1B and/or FIG. 1C).

In another embodiment, the invention provides the method described in any of the preceding paragraphs as applicable above modified such that the tumor fragments are small biopsies (including, for example, a punch biopsy), core biopsies, core needle biopsies or fine needle aspirates.

In another embodiment, the invention provides the method described in any of the preceding paragraphs as applicable above modified such that the tumor fragments are core biopsies.

In another embodiment, the invention provides the method described in any of the preceding paragraphs as applicable above modified such that the tumor fragments are fine needle aspirates.

In another embodiment, the invention provides the method described in any of the preceding paragraphs as applicable above modified such that the tumor fragments are small biopsies (including, for example, a punch biopsy).

In another embodiment, the invention provides the method described in any of the preceding paragraphs as applicable above modified such that the tumor fragments are core needle biopsies.

In another embodiment, the invention provides the method described in any of the preceding paragraphs as applicable above modified such that (i) the method comprises obtaining the first population of TILs from one or more small biopsies (including, for example, a punch biopsy), core biopsies, core needle biopsies or fine needle aspirates of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion for a period of about 8 days, and (iv) the method comprises performing the rapid second expansion for a period of about 11 days. In some of the foregoing embodiments, the steps of the method are completed in about 22 days.

In another embodiment, the invention provides the method described in any of the preceding paragraphs as applicable above modified such that (i) the method comprises obtaining the first population of TILs from one or more small biopsies (including, for example, a punch biopsy), core biopsies, core needle biopsies or fine needle aspirates of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion for a period of about 8 days, and (iv) the method comprises performing the rapid second expansion by culturing the culture of the second population of TILs for about 5 days, splitting the culture into up to 5 subcultures and culturing the subcultures for about 6 days. In some of the foregoing embodiments, the up to 5 subcultures are each cultured in a container that is the same size or larger than the container in which the culture of the second population of TILs is commenced in the rapid second expansion. In some of the foregoing embodiments, the culture of the second population of TILs is equally divided amongst the up to 5 subcultures. In some of the foregoing embodiments, the steps of the method are completed in about 22 days.

In another embodiment, the invention provides the method described in any of the preceding paragraphs as applicable above modified such that the first population of TILs is obtained from 1 to about 20 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1 to about 10 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 small biopsies (including, for example, a punch biopsy), core biopsies, core needle biopsies or fine needle aspirates of tumor tissue from the subject.

In another embodiment, the invention provides the method described in any of the preceding paragraphs as applicable above modified such that the first population of TILs is obtained from 1 to about 20 core biopsies of tumor tissue from the subject.

In another embodiment, the invention provides the method described in any of the preceding paragraphs as applicable above modified such that the first population of TILs is obtained from 1 to about 10 core biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 core biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 core biopsies of tumor tissue from the subject.

In another embodiment, the invention provides the method described in any of the preceding paragraphs as applicable above modified such that the first population of TILs is obtained from 1 to about 20 fine needle aspirates of tumor tissue from the subject.

paragraphs as applicable above modified such that the first population of TILs is obtained from 1 to about 10 fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 fine needle aspirates of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 fine needle aspirates of tumor tissue from the subject.

In another embodiment, the invention provides the method described in any of the preceding paragraphs as applicable above modified such that the first population of TILs is obtained from 1 to about 20 core needle biopsies of tumor tissue from the subject.

In another embodiment, the invention provides the method described in any of the preceding paragraphs as applicable above modified such that the first population of TILs is obtained from 1 to about 10 core needle biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 core needle biopsies of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 core needle biopsies of tumor tissue from the subject.

In another embodiment, the invention provides the method described in any of the preceding paragraphs as applicable above modified such that the first population of TILs is obtained from 1 to about 20 small biopsies (including, for example, a punch biopsy) of tumor tissue from the subject.

In another embodiment, the invention provides the method described in any of the preceding paragraphs as applicable above modified such that the first population of TILs is obtained from 1 to about 10 small biopsies (including, for example, a punch biopsy) of tumor tissue from the subject.

In another embodiment, the invention provides the method described in any of the preceding paragraphs as applicable above modified such that the first population of TILs is obtained from 1, 2, 3, 4, 5, 6, 7, 8, 9, 10, 11, 12, 13, 14, 15, 16, 17, 18, 19 or 20 small biopsies (including, for example, a punch biopsy) of tumor tissue from the subject.

In another embodiment, the invention provides the method described in any of the preceding paragraphs as applicable above modified such that the first population of TILs is obtained from 1, 2, 3, 4, 5, 6, 7, 8, 9 or 10 small biopsies (including, for example, a punch biopsy) of tumor tissue from the subject.

In another embodiment, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion step by culturing the first population of TILs in a culture medium comprising IL-2, OKT-3 and antigen presenting cells (APCs) for a period of about 8 days to obtain the second population of TILs, and (iv) the method comprises performing the rapid second expansion step by culturing the second population of TILs in a culture medium comprising IL-2, OKT-3 and APCs for a period of about 11 days. In some of the foregoing embodiments, the steps of the method are completed in about 22 days.

In another embodiment, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising IL-2 for a period of about 3 days prior to performing the step of the priming first expansion, (iii) the method comprises performing the priming first expansion step by culturing the first population of TILs in a culture medium comprising IL-2, OKT-3 and antigen presenting cells (APCs) for a period of about 8 days to obtain the second population of TILs, and (iv) the method comprises performing the rapid second expansion by culturing the culture of the second population of TILs in a culture medium comprising IL-2, OKT-3 and APCs for about 5 days, splitting the culture into up to 5 subcultures and culturing each of the subcultures in a culture medium comprising IL-2 for about 6 days. In some of the foregoing embodiments, the up to 5 subcultures are each cultured in a container that is the same size or larger than the container in which the culture of the second population of TILs is commenced in the rapid second expansion. In some of the foregoing embodiments, the culture of the second population of TILs is equally divided amongst the up to 5 subcultures. In some of the foregoing embodiments, the steps of the method are completed in about 22 days.

In another embodiment, the invention provides the method described in any of the preceding paragraphs as applicable above modified such that (i) the method comprises obtaining the first population of TILs from 1 to about 10 core biopsies of tumor tissue from the subject, (ii) the method comprises performing the step of culturing the first population of TILs in a cell culture medium comprising 6000 IU IL-2/ml in 0.5 L of CM1 culture medium in a G-Rex 100M flask for a period of about 3 days prior to performing the step of the priming first expansion, (iii) the method comprises performing the priming first expansion by adding 0.5 L of CM1 culture medium containing 6000 IU/ml IL-2, 30 ng/ml OKT-3, and about $10^8$ feeder cells and culturing for a period of about 8 days, and (iv) the method comprises performing the rapid second expansion by (a) transferring the second population of TILs to a G-Rex 500MCS flask containing 5 L of CM2 culture medium with 3000 IU/ml IL-2, 30 ng/ml OKT-3, and $5\times10^9$ feeder cells and culturing for about 5 days (b) splitting the culture into up to 5 subcultures by transferring $10^9$ TILs into each of up to 5 G-Rex 500MCS flasks containing 5 L of AIM-V medium with 3000 IU/ml IL-2, and culturing the subcultures for about 6 days. In some of the foregoing embodiments, the steps of the method are completed in about 22 days.

In another embodiment, the invention provides a method of expanding T cells comprising: (a) performing a priming first expansion of a first population of T cells obtained from a donor by culturing the first population of T cells to effect growth and to prime an activation of the first population of T cells; (b) after the activation of the first population of T cells primed in step (a) begins to decay, performing a rapid second expansion of the first population of T cells by culturing the first population of T cells to effect growth and to boost the activation of the first population of T cells to obtain a second population of T cells; and (c) harvesting the second population of T cells. In another embodiment, the step of rapid second expansion is split into a plurality of steps to achieve a scaling up of the culture by: (a) performing the rapid second expansion by culturing the first population of T cells in a small scale culture in a first container, e.g., a G-REX 100MCS container, for a period of about 3 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 4 to 7 days. In another embodiment, the step of rapid expansion is split into a plurality of steps to achieve a scaling out of the culture by: (a) performing the rapid second expansion by culturing the first population of T cells in a first small scale culture in a first container, e.g., a G-REX 100MCS container, for a period of about 3 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 4 to 7 days. In another embodiment, the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid second expansion is split into a plurality of steps to achieve a scaling up of the culture by: (a) performing the rapid second expansion by culturing the first population of T cells in a small scale culture in a first container, e.g., a G-REX 100MCS container, for a period of about 2 to 4 days, and then (b) effecting the transfer of the first population of T cells from the small scale culture to a second container larger than the first container, e.g., a G-REX 500MCS container, and culturing the first population of T cells from the small scale culture in a larger scale culture in the second container for a period of about 5 to 7 days.

In another embodiment, the invention provides the method described in any of the preceding paragraphs as applicable above modified such that the step of rapid expansion is split into a plurality of steps to achieve a scaling out of the culture by: (a) performing the rapid second expansion by culturing the first population of T cells in a first small scale culture in a first container, e.g., a G-REX 100MCS container, for a period of about 2 to 4 days, and then (b) effecting the transfer and apportioning of the first population of T cells from the first small scale culture into and amongst at least 2, 3, 4, 5, 6, 7, 8, 9, 10, 11, 12, 13, 14, 15, 16, 17, 18, 19, or 20 second containers that are equal in size to the first container, wherein in each second container the portion of the first population of T cells from first small scale culture transferred to such second container is cultured in a second small scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 2 to 4 days, and then (b) effecting the transfer and apportioning of the first population of T cells from the small scale culture into and amongst at least 2, 3, 4, 5, 6, 7, 8, 9, 10, 11, 12, 13, 14, 15, 16, 17, 18, 19, or 20 second containers that are larger in size than the first container, e.g., G-REX 500MCS containers, wherein in each second container the portion of the first population of T cells from the small scale culture transferred to such second container is cultured in a larger scale culture for a period of about 5 to 7 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 to 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 5 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 6 days.

In another embodiment, the invention provides the method described in any of the preceding paragraphs as applicable above modified such that the step of rapid expansion is split into a plurality of steps to achieve a scaling out and scaling up of the culture by: (a) performing the rapid second expansion by culturing the first population of T cells in a small scale culture in a first container, e.g., a G-REX 100MCS container, for a period of about 3 to 4 days, and then (b) effecting the transfer and apportioning of the first population of T cells from the small scale culture into and amongst 2, 3 or 4 second containers that are larger in size than the first container, e.g., G-REX 500MCS containers, wherein in each second container the portion of the first population of T cells from the small scale culture transferred to such second container is cultured in a larger scale culture for a period of about 7 days.

In another embodiment, the invention provides the method described in any of the preceding paragraphs as applicable above modified such that the priming first expansion of step (a) is performed during a period of up to 7 days.

In another embodiment, the invention provides the method described in any of the preceding paragraphs as applicable above modified such that the rapid second expansion of step (b) is performed during a period of up to 8 days.

In another embodiment, the invention provides the method described in any of the preceding paragraphs as applicable above modified such that the rapid second expansion of step (b) is performed during a period of up to 9 days.

In another embodiment, the invention provides the method described in any of the preceding paragraphs as applicable above modified such that the rapid second expansion of step (b) is performed during a period of up to 10 days.

In another embodiment, the invention provides the method described in any of the preceding paragraphs as applicable above modified such that the rapid second expansion of step (b) is performed during a period of up to 11 days.

In another embodiment, the invention provides the method described in any of the preceding paragraphs as applicable above modified such that the priming first expansion in step (a) is performed during a period of 7 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days and the rapid second expansion of step (b) is performed during a period of up to 10 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 9 days.

In another embodiment, the invention provides the method described in any of the preceding paragraphs as applicable above modified such that the priming first expansion in step (a) is performed during a period of 7 days or 8 days and the rapid second expansion of step (b) is performed during a period of up to 10 days.

In another embodiment, the invention provides the method described in any of the preceding paragraphs as applicable above modified such that the priming first expansion in step (a) is performed during a period of 8 days and the rapid second expansion of step (b) is performed during a period of up to 9 days.

In another embodiment, the invention provides the method described in any of the preceding paragraphs as applicable above modified such that the priming first expansion in step (a) is performed during a period of 8 days and the rapid second expansion of step (b) is performed during a period of up to 8 days.

In another embodiment, the invention provides the method described in any of the preceding paragraphs as applicable above modified such that in step (a) the first population of T cells is cultured in a first culture medium comprising OKT-3 and IL-2.

In another embodiment, the invention provides the method described in any of the preceding paragraphs as applicable above modified such that the first culture medium comprises 4-1BB agonist, OKT-3 and IL-2.

In another embodiment, the invention provides the method described in any of the preceding paragraphs as applicable above modified such that the first culture medium comprises OKT-3, IL-2 and antigen-presenting cells (APCs).

In another embodiment, the invention provides the method described in any of the preceding paragraphs as applicable above modified such that the first culture medium comprises 4-1BB agonist, OKT-3, IL-2 and antigen-presenting cells (APCs).

In another embodiment, the invention provides the method described in any of the preceding paragraphs as applicable above modified such that in step (b) the first population of T cells is cultured in a second culture medium comprising OKT-3, IL-2 and antigen-presenting cells (APCs).

In another embodiment, the invention provides the method described in any of the preceding paragraphs as applicable above modified such that the second culture medium comprises 4-1BB agonist, OKT-3, IL-2 and antigen-presenting cells (APCs).

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that in step (a) the first population of T cells is cultured in a first culture medium in a container comprising a first gas-permeable surface, wherein the first culture medium comprises 4-1BB agonist, OKT-3, IL-2 and a first population of antigen-presenting cells (APCs), wherein the first population of APCs is exogenous to the donor of the first population of T cells and the first population of APCs is layered onto the first gas-permeable surface, wherein in step (b) the first population of T cells is cultured in a second culture medium in the container, wherein the second culture medium comprises 4-1BB agonist, OKT-3, IL-2 and a second population of APCs, wherein the second population of APCs is exogenous to the donor of the first population of T cells and the second population of APCs is layered onto the first gas-permeable surface, and wherein the second population of APCs is greater than the first population of APCs.

In another embodiment, the invention provides the method described in any of the preceding paragraphs as applicable above modified such that the ratio of the number of APCs in the second population of APCs to the number of APCs in the first population of APCs is about 2:1.

In another embodiment, the invention provides the method described in any of the preceding paragraphs as applicable above modified such that the number of APCs in the first population of APCs is about $2.5\times10^8$ and the number of APCs in the second population of APCs is about $5\times10^8$.

In another embodiment, the invention provides the method described in any of the preceding paragraphs as applicable above modified such that in step (a) the first population of APCs is layered onto the first gas-permeable surface at an average thickness of 2 layers of APCs.

In another embodiment, the invention provides the method described in any of the preceding paragraphs as applicable above modified such that in step (b) the second population of APCs is layered onto the first gas-permeable surface at an average thickness in the range of 4 to 8 layers of APCs.

In another embodiment, the invention provides the method described in any of the preceding paragraphs as applicable above modified such that the ratio of the average number of layers of APCs layered onto the first gas-permeable surface in step (b) to the average number of layers of APCs layered onto the first gas-permeable surface in step (a) is 2:1.

In another embodiment, the invention provides the method described in any of the preceding paragraphs as applicable above modified such that in step (a) the first population of APCs is seeded on the first gas permeable surface at a density in the range of at or about $1.0\times10^6$ APCs/$cm^2$ to at or about $4.5\times10^6$ APCs/$cm^2$.

In another embodiment, the invention provides the method described in any of the preceding paragraphs as applicable above modified such that in step (a) the first population of APCs is seeded on the first gas permeable surface at a density in the range of at or about $1.5\times10^6$ APCs/$cm^2$ to at or about $3.5\times10^6$ APCs/$cm^2$.

In another embodiment, the invention provides the method described in any of the preceding paragraphs as applicable above modified such that in step (a) the first population of APCs is seeded on the first gas permeable surface at a density in the range of at or about $2.0\times10^6$ APCs/$cm^2$ to at or about $3.0\times10^6$ APCs/$cm^2$.

In another embodiment, the invention provides the method described in any of the preceding paragraphs as applicable above modified such that in step (a) the first population of APCs is seeded on the first gas permeable surface at a density of at or about $2.0\times10^6$ APCs/$cm^2$.

In another embodiment, the invention provides the method described in any of the preceding paragraphs as applicable above modified such that in step (b) the second population of APCs is seeded on the first gas permeable surface at a density in the range of at or about $2.5\times10^6$ APCs/$cm^2$ to at or about $7.5\times10^6$ APCs/$cm^2$.

In another embodiment, the invention provides the method described in any of the preceding paragraphs as applicable above modified such that in step (b) the second population of APCs is seeded on the first gas permeable surface at a density in the range of at or about $3.5\times10^6$ APCs/$cm^2$ to at or about $6.0\times10^6$ APCs/$cm^2$.

In another embodiment, the invention provides the method described in any of the preceding paragraphs as applicable above modified such that in step (b) the second population of APCs is seeded on the first gas permeable surface at a density in the range of at or about $4.0\times10^6$ APCs/$cm^2$ to at or about $5.5\times10^6$ APCs/$cm^2$.

In another embodiment, the invention provides the method described in any of the preceding paragraphs as applicable above modified such that in step (b) the second population of APCs is seeded on the first gas permeable surface at a density of at or about $4.0\times10^6$ APCs/$cm^2$.

In another embodiment, the invention provides the method described in any of the preceding paragraphs as applicable above modified such that in step (a) the first population of APCs is seeded on the first gas permeable surface at a density in the range of at or about $1.0\times10^6$ APCs/$cm^2$ to at or about $4.5\times10^6$ APCs/$cm^2$ and in step (b) the second population of APCs is seeded on the first gas permeable surface at a density in the range of at or about $2.5\times10^6$ APCs/$cm^2$ to at or about $7.5\times10^6$ APCs/$cm^2$.

In another embodiment, the invention provides the method described in any of the preceding paragraphs as applicable modified such that in step (a) the first population of APCs is seeded on the first gas permeable surface at a density in the range of at or about $1.5\times10^6$ APCs/$cm^2$ to at or about $3.5\times10^6$ APCs/$cm^2$ and in step (b) the second population of APCs is seeded on the first gas permeable surface at a density in the range of at or about $3.5\times10^6$ APCs/$cm^2$ to at or about $6.0\times10^6$ APCs/$cm^2$.

In another embodiment, the invention provides the method described in any of the preceding paragraphs as applicable above modified such that in step (a) the first population of APCs is seeded on the first gas permeable surface at a density in the range of at or about $2.0\times10^6$ APCs/$cm^2$ to at or about $3.0\times10^6$ APCs/$cm^2$ and in step (b) the second population of APCs is seeded on the first gas permeable surface at a density in the range of at or about $4.0\times10^6$ APCs/$cm^2$ to at or about $5.5\times10^6$ APCs/$cm^2$.

In another embodiment, the invention provides the method described in any of the preceding paragraphs as applicable above modified such that in step (a) the first population of APCs is seeded on the first gas permeable surface at a density of at or about $2.0\times10^6$ APCs/$cm^2$ and in step (b) the second population of APCs is seeded on the first gas permeable surface at a density of at or about $4.0\times10^6$ APCs/$cm^2$.

In another embodiment, the invention provides the method described in any of the preceding paragraphs as applicable above modified such that the APCs are peripheral blood mononuclear cells (PBMCs).

In another embodiment, the invention provides the method described in any of the preceding paragraphs as applicable above modified such that the PBMCs are irradiated and exogenous to the donor of the first population of T cells.

In another embodiment, the invention provides the method described in any of the preceding paragraphs as applicable above modified such that the T cells are tumor infiltrating lymphocytes (TILs).

In another embodiment, the invention provides the method described in any of the preceding paragraphs as applicable above modified such that the T cells are marrow infiltrating lymphocytes (MILs).

In another embodiment, the invention provides the method described in any of the preceding paragraphs as applicable above modified such that the T cells are peripheral blood lymphocytes (PBLs).

In another embodiment, the invention provides the method described in any of the preceding paragraphs as applicable above modified such that the first population of T cells is obtained by separation from the whole blood of the donor.

In another embodiment, the invention provides the method described in any of the preceding paragraphs as applicable above modified such that the first population of T cells is obtained by separation from the apheresis product of the donor.

In another embodiment, the invention provides the method described in any of the preceding paragraphs as applicable above modified such that the first population of T cells is separated from the whole blood or apheresis product of the donor by positive or negative selection of a T cell phenotype.

In another embodiment, the invention provides the method described in any of the preceding paragraphs as applicable above modified such that the T cell phenotype is CD3+ and CD45+.

In another embodiment, the invention provides the method described in any of the preceding paragraphs as applicable above modified such that before performing the priming first expansion of the first population of T cells the T cells are separated from NK cells. In another embodiment, the T cells are separated from NK cells in the first population of T cells by removal of CD3− CD56+ cells from the first population of T cells. In another embodiment, the CD3− CD56+ cells are removed from the first population of T cells by subjecting the first population of T cells to cell sorting using a gating strategy that removes the CD3− CD56+ cell fraction and recovers the negative fraction. In another embodiment, the foregoing method is utilized for the expansion of T cells in a first population of T cells characterized by a high percentage of NK cells. In another embodiment, the foregoing method is utilized for the expansion of T cells in a first population of T cells characterized by a high percentage of CD3− CD56+ cells. In another embodiment, the foregoing method is utilized for the expansion of T cells in tumor tissue characterized by the present of a high number of NK cells. In another embodiment, the foregoing method is utilized for the expansion of T cells in tumor tissue characterized by a high number of CD3− CD56+ cells. In another embodiment, the foregoing method is utilized for the expansion of T cells in tumor tissue obtained from a patient suffering from a tumor characterized by the presence of a high number of NK cells. In another embodiment, the foregoing method is utilized for the expansion of T cells in tumor tissue obtained from a patient suffering from a tumor characterized by the presence of a high number of CD3− CD56+ cells. In another embodiment, the foregoing method is utilized for the expansion of T cells in tumor tissue obtained from a patient suffering from ovarian cancer.

In another embodiment, the invention provides the method described in any of the preceding paragraphs as applicable above modified such that at or about $1\times10^7$ T cells from the first population of T cells are seeded in a container to initiate the primary first expansion culture in such container.

In another embodiment, the invention provides the method described in any of the preceding paragraphs as applicable above modified such that the first population of T cells is distributed into a plurality of containers, and in each container at or about $1\times10^7$ T cells from the first population of T cells are seeded to initiate the primary first expansion culture in such container.

In another embodiment, the invention provides the method described in any of the preceding paragraphs as applicable above modified such that the second population of T cells harvested in step (c) is a therapeutic population of TILs.

In another embodiment, the invention provides the method described in any of the preceding paragraphs as applicable above modified such that the first population of T cells is obtained from one or more small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1 to 20 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1 to 10 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 small biopsies (including, for example, a punch biopsy), core biopsies, core needle biopsies or fine needle aspirates of tumor tissue from the donor.

In another embodiment, the invention provides the method described in any of the preceding paragraphs as applicable above modified such that the first population of T cells is obtained from one or more core biopsies of tumor tissue from the donor.

In another embodiment, the invention provides the method described in any of the preceding paragraphs as applicable above modified such that the first population of T cells is obtained from 1 to 20 core biopsies of tumor tissue from the donor.

In another embodiment, the invention provides the method described in any of the preceding paragraphs as applicable above modified such that the first population of T cells is obtained from 1 to 10 core biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 core biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 core biopsies of tumor tissue from the donor.

In another embodiment, the invention provides the method described in any of the preceding paragraphs as applicable above modified such that the first population of T cells is obtained from one or more fine needle aspirates of tumor tissue from the donor.

In another embodiment, the invention provides the method described in any of the preceding paragraphs as applicable above modified such that the first population of T cells is obtained from 1 to 20 fine needle aspirates of tumor tissue from the donor.

In another embodiment, the invention provides the method described in any of the preceding paragraphs as applicable above modified such that the first population of T cells is obtained from 1 to 10 fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 fine needle aspirates of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 fine needle aspirates of tumor tissue from the donor.

In another embodiment, the invention provides the method described in any of the preceding paragraphs as applicable above modified such that the first population of T cells is obtained from one or more small biopsies (including, for example, a punch biopsy) of tumor tissue from the donor.

In another embodiment, the invention provides the method described in any of the preceding paragraphs as applicable above modified such that the first population of T cells is obtained from 1 to 20 small biopsies (including, for example, a punch biopsy) of tumor tissue from the donor.

In another embodiment, the invention provides the method described in any of the preceding paragraphs as applicable above modified such that the first population of T cells is obtained from 1 to 10 small biopsies (including, for example, a punch biopsy) of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 small biopsies (including, for example, a punch biopsy) of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 small biopsies (including, for example, a punch biopsy) of tumor tissue from the donor.

In another embodiment, the invention provides the method described in any of the preceding paragraphs as applicable above modified such that the first population of T cells is obtained from one or more core needle biopsies of tumor tissue from the donor.

In another embodiment, the invention provides the method described in any of the preceding paragraphs as applicable above modified such that the first population of T cells is obtained from 1 to 20 core needle biopsies of tumor tissue from the donor.

In another embodiment, the invention provides the method described in any of the preceding paragraphs as applicable above modified such that the first population of T cells is obtained from 1 to 10 core needle biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, 10, 11, 12, 13, 14, 15, 16, 17, 18, 19 or 20 core needle biopsies of tumor tissue from the donor.

In another embodiment, the invention provides the method described in any of the preceding paragraphs as applicable above modified such that the first population of T cells is obtained from 1, 2, 3, 4, 5, 6, 7, 8, 9, or 10 core needle biopsies of tumor tissue from the donor.

In another embodiment, the invention provides a method for expanding tumor infiltrating lymphocytes (TILs) into a therapeutic population of TILs comprising: i) obtaining and/or receiving a first population of TILs from a tumor sample obtained from one or more small biopsies, core biopsies, or needle biopsies of a tumor in a subject by culturing the tumor sample in a first cell culture medium comprising IL-2 for about 3 days; (ii) performing a priming first expansion by culturing the first population of TILs in a second cell culture medium comprising IL-2, OKT-3, and antigen presenting cells (APCs) to produce a second population of TILs, wherein the priming first expansion is performed in a container comprising a first gas-permeable surface area, wherein the priming first expansion is performed for first period of about 7 or 8 days to obtain the second population of TILs, wherein the second population of TILs is greater in number than the first population of TILs; (iii) performing a rapid second expansion by supplementing the second cell culture medium of the second population of TILs with additional IL-2, OKT-3, and APCs, to produce a third population of TILs, wherein the number of APCs added in the rapid second expansion is at least twice the number of APCs added in step (ii), wherein the rapid second expansion is performed for a second period of about 11 days to obtain the third population of TILs, wherein the third population of TILs is a therapeutic population of TILs, wherein the rapid second expansion is performed in a container comprising a second gas-permeable surface area; (iv) harvesting the therapeutic population of TILs obtained from step (iii); and (v) transferring the harvested TIL population from step (iv) to an infusion bag.

In another embodiment, the invention provides a method for expanding tumor infiltrating lymphocytes (TILs) into a therapeutic population of TILs comprising: (i) obtaining and/or receiving a first population of TILs from a tumor sample obtained from one or more small biopsies, core biopsies, or needle biopsies of a tumor in a subject by culturing the tumor sample in a first cell culture medium comprising IL-2 for about 3 days; (ii) performing a priming first expansion by culturing the first population of TILs in a second cell culture medium comprising IL-2, OKT-3, and antigen presenting cells (APCs) to produce a second population of TILs, wherein the priming first expansion is performed for first period of about 7 or 8 days to obtain the second population of TILs, wherein the second population of TILs is greater in number than the first population of TILs; (iii) performing a rapid second expansion by contacting the second population of TILs with a third cell culture medium comprising IL-2, OKT-3, and APCs, to produce a third population of TILs, wherein the rapid second expansion is performed for a second period of about 11 days to obtain the third population of TILs, wherein the third population of TILs is a therapeutic population of TILs; and (iv) harvesting the therapeutic population of TILs obtained from step (iii).

In another embodiment, the invention provides the method described in any of the preceding paragraphs as applicable above modified such that after day 5 of the second period the culture is split into 2 or more subcultures, and each subculture is supplemented with an additional quantity of the third culture medium and cultured for about 6 days.

In another embodiment, the invention provides the method described in any of the preceding paragraphs as applicable above modified such that after day 5 of the second period the culture is split into 2 or more subcultures, and each subculture is supplemented with a fourth culture medium comprising IL-2 and cultured for about 6 days.

In another embodiment, the invention provides the method described in any of the preceding paragraphs as applicable above modified such that after day 5 of the second period the culture is split into up to 5 subcultures.

In another embodiment, the invention provides the method described in any of the preceding paragraphs as applicable above modified such that all steps in the method are completed in about 22 days.

In another embodiment, the invention provides a method of expanding T cells comprising: (i) performing a priming first expansion of a first population of T cells from a tumor sample obtained from one or more small biopsies, core biopsies, or needle biopsies of a tumor in a donor by culturing the first population of T cells to effect growth and to prime an activation of the first population of T cells; (ii) after the activation of the first population of T cells primed in step (a) begins to decay, performing a rapid second expansion of the first population of T cells by culturing the first population of T cells to effect growth and to boost the activation of the first population of T cells to obtain a second population of T cells; and (iv) harvesting the second population of T cells. In some embodiments, the tumor sample is obtained from a plurality of core biopsies. In some embodiments, the plurality of core biopsies is selected from the group consisting of 2, 3, 4, 5, 6, 7, 8, 9 and 10 core biopsies.

III. TIL Manufacturing Processes (Process 2A Embodiments with Defined Media)

An exemplary TIL process known as process 2A containing some of these features is depicted in FIGS. 1A and 109 (such a process is also described in International Patent Publication WO/2018/182817.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 109 as Step A) is shortened to 3 to 14 days and the second expansion (including processes referred to as the REP as well as processes shown in FIG. 109 as Step B) is shorted to 7 to 14 days, as discussed in detail below as well as in the examples and figures. In some embodiments, the first expansion (for example, an expansion described as Step B in FIG. 109) is shortened to 11 days and the second expansion (for example, an expansion as described in Step D in FIG. 109) is shortened to 11 days. In some embodiments, the combination of the first expansion and second expansion (for example, expansions described as Step B and Step D in FIG. 109) is shortened to 22 days, as discussed in detail below and in the examples and figures.

The "Step" Designations A, B, C, etc., below are in reference to FIG. 109 and in reference to certain embodiments described herein. The ordering of the Steps below and in FIG. 109 is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer (including, for example, head and neck squamous cell carcinoma (HNSCC)) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 $mm^3$, with from about 2-3 $mm^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 109). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 $mm^3$ and 10 $mm^3$. In some embodiments, the tumor fragment is between about 1 $mm^3$ and 8 $mm^3$. In some embodiments, the tumor fragment is about 1 $mm^3$. In some embodiments, the tumor fragment is about 2 $mm^3$. In some embodiments, the tumor fragment is about 3 $mm^3$. In some embodiments, the tumor fragment is about 4 $mm^3$. In some embodiments, the tumor fragment is about 5 $mm^3$. In some embodiments, the tumor fragment is about 6 $mm^3$. In some embodiments, the tumor fragment is about 7 $mm^3$. In some embodiments, the tumor fragment is about 8 $mm^3$. In some embodiments, the tumor fragment is about 9 $mm^3$. In some embodiments, the tumor fragment is about 10 $mm^3$.

In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 109.

B. Step B: First Expansion

1. Young TILs

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology,* 75:157-167 (2012); Dudley et al., *Clin Cancer Res,* 16:6122-6131 (2010); Huang et al., *J Immunother,* 28(3):258-267 (2005); Besser et al., Clin *Cancer Res,* 19(17):OF1-OF9 (2013); Besser et al., *J Immunother* 32:415-423 (2009); Robbins, et al., *J Immunol* 2004; 173: 7125-7130; Shen et al., *J Immunother,* 30:123-129 (2007); Zhou, et al., *J Immunother,* 28:53-62 (2005); and Tran, et al., *J Immunother,* 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 109. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 109, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 109, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 $mm^3$ and 10 $mm^3$.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-Rex10; Wilson Wolf Manufacturing, New Brighton, MN) (FIG. 1), each flask was loaded with $10\text{-}40\times10^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example 4. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 $cm^2$ gas-permeable silicon bottom (for example, G-Rex10; Wilson Wolf Manufacturing, New Brighton, MN) (FIG. 1), each flask was loaded with 10-40×$10^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples, see, Example 5. In some embodiments, the first expansion occurs in an initial cell culture medium or a first cell culture medium. In some embodiments, the initial cell culture medium or the first cell culture medium comprises IL-2.

Figure 4:
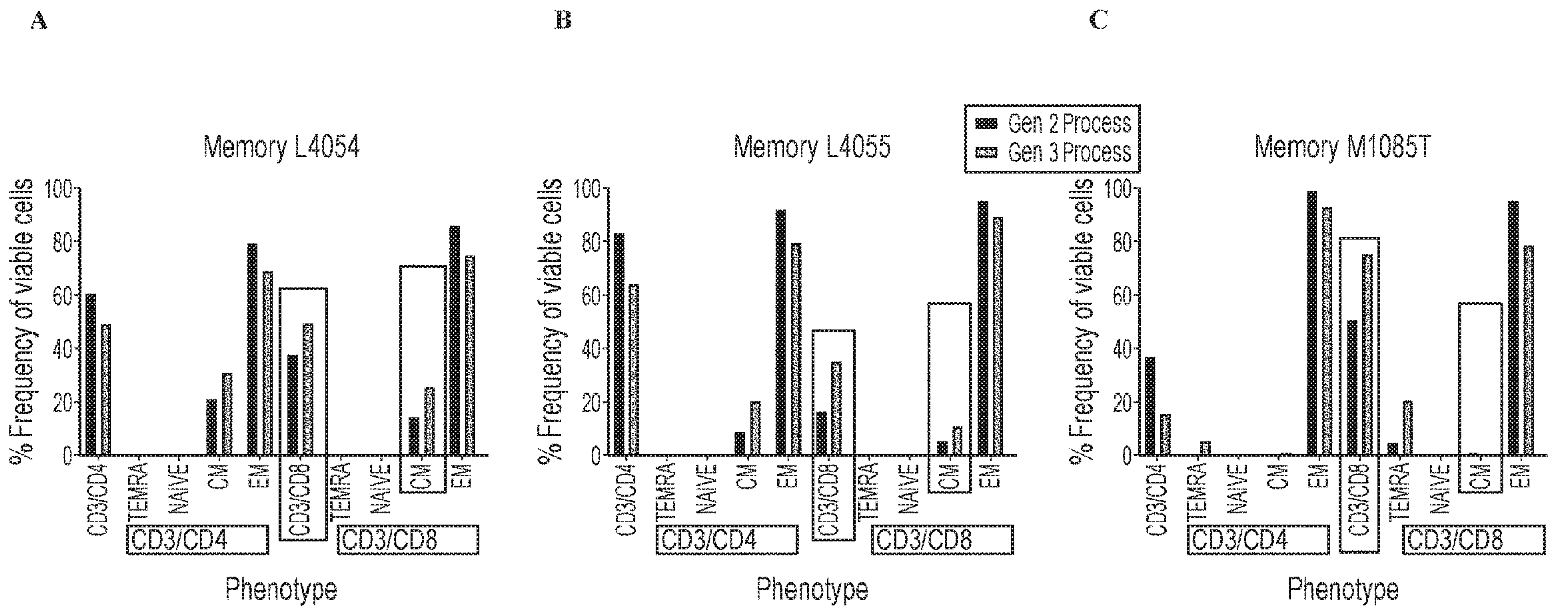
FIG. 4A-4C: A) L4054—Memory markers analysis on TIL product from the Gen 2 and Gen 3 processes. B) L4055—Memory markers analysis on TIL product from the Gen 2 and Gen 3 processes. C) M1085T—Memory markers analysis on TIL product from the Gen 2 and Gen 3 processes.
Figure 5:
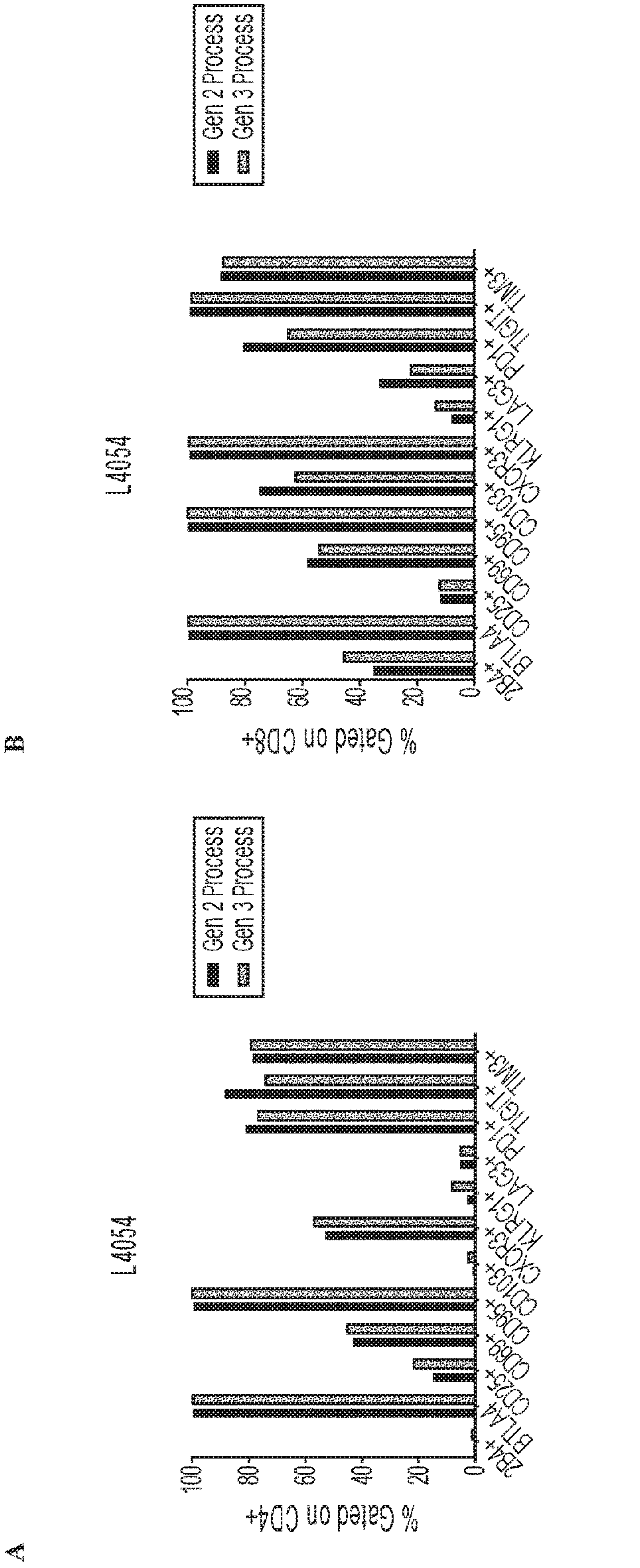
FIG. 5: L4054 Activation and exhaustion markers (A) Gated on CD4+, (B) Gated on CD8+.

In some embodiments, the first expansion (including processes such as for example those described in Step B of FIG. 109, which can include those sometimes referred to as the pre-REP) process is shortened to 3-14 days, as discussed in the examples and figures. In some embodiments, the first expansion (including processes such as for example those described in Step B of FIG. 109, which can include those sometimes referred to as the pre-REP) is shortened to 7 to 14 days, as discussed in the Examples and shown in FIGS. 4 and 5, as well as including for example, an expansion as described in Step B of FIG. 109. In some embodiments, the first expansion of Step B is shortened to 10-14 days, as discussed in the Examples and shown in FIGS. 4 and 5. In some embodiments, the first expansion is shortened to 11 days, as well as including for example, an expansion as described in Step B of FIG. 109.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 109, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 109 and as described herein.

In some embodiments, the first expansion (including processes referred to as the pre-REP; for example, Step B according to FIG. 109) process is shortened to 3 to 14 days, as discussed in the examples and figures. In some embodiments, the first expansion of Step B is shortened to 7 to 14 days, as discussed in the Examples and shown in FIGS. 4 and 5. In some embodiments, the first expansion of Step B is shortened to 10 to 14 days, as discussed in the Examples and shown in FIGS. 4, 5, and 27. In some embodiments, the first expansion is shortened to 11 days.

In some embodiments, the first expansion, for example, Step B according to FIG. 109, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

C. Step C: First Expansion to Second Expansion Transition

In some cases, the bulk TIL population obtained from the first expansion, including for example the TIL population obtained from for example, Step B as indicated in FIG. 109, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 109) are stored until phenotyped for selection. In some embodiments, the TILs obtained from the first expansion (for example, from Step B as indicated in FIG. 109) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 109). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 109, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3''}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR)

(ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine. L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3"}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |

TABLE A-continued

| Concentrations of Non-Trace Element Moiety Ingredients | | | |
|---|---|---|---|
| Ingredient | A preferred embodiment in supplement (mg/L) (About) | Concentration range in 1X medium (mg/L) (About) | A preferred embodiment in 1X medium (mg/L) (About) |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ® I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

D. Step D: Second Expansion

In some embodiments, the TIL cell population is expanded in number after harvest and initial bulk processing for example, after Step A and Step B, and the transition referred to as Step C, as indicated in FIG. 109). This further expansion is referred to herein as the second expansion, which can include expansion processes generally referred to in the art as a rapid expansion process (REP; as well as processes as indicated in Step D of FIG. 109). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 109) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 109). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In a some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT3 antibody. In a some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 109, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 109 and as described herein.

In some embodiments, the second expansion can be conducted in a supplemented cell culture medium comprising IL-2, OKT-3, and antigen-presenting feeder cells. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally 2/3 media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J. Immunother.* 2003, 26, 332-42) or gas permeable cultureware (G-Rex flasks). In some embodiments, the second expansion (including expansions referred to as rapid expansions) is performed in T-175 flasks, and about $1\times10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0\times10^6$ cells/mL.

In an embodiment, the second expansion (which can include expansions referred to as REP, as well as those referred to in Step D of FIG. 109) may be performed in 500 mL capacity gas permeable flasks with 100 cm gas-permeable silicon bottoms (G-Rex 100, commercially available from Wilson Wolf Manufacturing Corporation, New Brighton, MN, USA), $5\times10^6$ or $10\times10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% $CO_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% $CO_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, 2/3 of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the Cellometer K2 Image Cytometer Automatic Cell Counter protocol described, for example, in Example 15.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother,* 31:742-751, and Dudley M E, Wunderlich J R, Shelton T E, et al. 2003, *J Immunother.,* 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1\times10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% $CO_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (including expansions referred to as REP) are performed in 500 mL capacity flasks with 100 $cm^2$ gas-permeable silicon bottoms (G-Rex 100, Wilson Wolf) (FIG. 1), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% $CO_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% $CO_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCR$\alpha/\beta$).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 109, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, the culture medium used in the expansion processes disclosed herein is a serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium, CTSS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium ($\alpha$MEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3"}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium ($\alpha$MEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione. L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3''}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

1. Feeder Cells and Antigen Presenting Cells

In an embodiment, the second expansion procedures described herein (for example including expansion such as those described in Step D from FIG. 109, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, in particular example 14, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion). See, for example, Example 14.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. See, for example, Example 13.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5\times10^9$ feeder cells to about $100\times10^6$ TILs. In another embodiment, the second expansion procedures described herein require a ratio of about $2.5\times10^9$ feeder cells to about $50\times10^6$ TILs. In yet another embodiment, the second expansion procedures described herein require about $2.5\times10^9$ feeder cells to about $25\times10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedures described herein.

In an embodiment, artificial antigen presenting cells are used in the second expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

3. Anti-CD3 Antibodies

In some embodiments, the culture media used in expansion methods described herein (including those referred to as REP, see for example, FIG. 109) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

E. Step E: Harvest TILS

After the second expansion step, cells can be harvested. In some embodiments the TILs are harvested after one, two, three, four or more expansion steps, for example as provided in FIG. 109. In some embodiments the TILs are harvested after two expansion steps, for example as provided in FIG. 109.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 109, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

F. Step F: Final Formulation/Transfer to Infusion Bag

After Steps A through E as provided in an exemplary order in FIG. 109 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

1. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

IV. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$ $4\times10^{12}$ $4\times10^{12}$, $5\times10^{12}$, $6\times10^{12}$, $6\times10^{12}$, $7\times10^{12}$ $8\times10^{12}$ $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

In another embodiment, the invention provides an infusion bag comprising the therapeutic population of TILs described in any of the preceding paragraphs as applicable above.

In another embodiment, the invention provides a tumor infiltrating lymphocyte (TIL) composition comprising the therapeutic population of TILs described in any of the preceding paragraphs as applicable above and a pharmaceutically acceptable carrier.

In another embodiment, the invention provides an infusion bag comprising the TIL composition described in any of the preceding paragraphs as applicable above.

In another embodiment, the invention provides a cryopreserved preparation of the therapeutic population of TILs described in any of the preceding paragraphs as applicable above.

In another embodiment, the invention provides a tumor infiltrating lymphocyte (TIL) composition comprising the therapeutic population of TILs described in any of the preceding paragraphs as applicable above and a cryopreservation media.

In another embodiment, the invention provides the TIL composition described in any of the preceding paragraphs as applicable above modified such that the cryopreservation media contains DMSO.

In another embodiment, the invention provides the TIL composition described in any of the preceding paragraphs as applicable above modified such that the cryopreservation media contains 7-10% DMSO.

In some embodiments, the invention provides the TIL compositions comprising TILs in serum-free medium or a defined medium. In some embodiments, the serum-free or defined medium comprises a basal cell medium and a serum supplement and/or a serum replacement. In some embodiments, the serum-free or defined medium is used to prevent and/or decrease experimental variation due in part to the lot-to-lot variation of serum-containing media.

In some embodiments, the serum-free or defined medium comprises a basal cell medium and a serum supplement and/or serum replacement. In some embodiments, the basal cell medium includes, but is not limited to CTS™ OpTmizer™ T-cell Expansion Basal Medium CTS™ OpTmizer™ T-Cell Expansion SFM, CTS™ AIM-V Medium, CTS™ AIM-V SFM, LymphoONE™ T-Cell Expansion Xeno-Free Medium, Dulbecco's Modified Eagle's Medium (DME), Essential Medium (MEM), Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the serum supplement or serum replacement includes, but is not limited to one or more of CTS™ OpTmizer T-Cell Expansion Serum Supplement, CTS™ Immune Cell Serum Replacement, one or more albumins or albumin substitutes, one or more amino acids, one or more vitamins, one or more transferrins or transferrin substitutes, one or more antioxidants, one or more insulins or insulin substitutes, one or more collagen precursors, one or more antibiotics, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3"}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments the defined medium further comprises L-glutamine, sodium bicarbonate and/or 2-mercaptoethanol.

In some embodiments, the CTS™OpTmizer™ T-cell Immune Cell Serum Replacement is used with conventional growth media, including but not limited to CTS™ OpTmizer™ T-cell Expansion Basal Medium, CTS™ OpTmizer™ T-cell Expansion SFM, CTS™ AIM-V Medium, CST™ AIM-V SFM, LymphoONE™ T-Cell Expansion Xeno-Free Medium, Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the total serum replacement concentration (vol %) in the serum-free or defined medium is from about 1%, 2%, 3%, 4%, 5%, 6%, 7%, 8%, 9%, 10%, 11%, 12%, 13%, 14%, 15%, 16%, 17%, 18%, 19%, or 20% by volume of the total serum-free or defined medium. In some embodiments, the total serum replacement concentration is about 3% of the total volume of the serum-free or defined medium. In some embodiments, the total serum replacement concentration is about 5% of the total volume of the serum-free or defined medium. In some embodiments, the total serum replacement concentration is about 10% of the total volume of the serum-free or defined medium.

In some embodiments, the serum-free or defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM.

In some embodiments, the defined medium is CTS™ OpTmizer™ T-cell Expansion SFM (ThermoFisher Scientific). Any formulation of CTS™ OpTmizer™ is useful in the present invention. CTS™ OpTmizer™ T-cell Expansion SFM is a combination of 1 L CTS™ OpTmizer™ T-cell Expansion Basal Medium and 26 mL CTS™ OpTmizer™ T-Cell Expansion Supplement, which are mixed together prior to use. In some embodiments, the CTS™ OpTmizer™ T-cell Expansion SFM is supplemented with about 3% of the CTS™ Immune Cell Serum Replacement (SR) (ThermoFisher Scientific), along with 2-mercaptoethanol at 55 mM. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific), 55 mM of 2-mercaptoethanol, and 2 mM of L-glutamine, and further comprises about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and 55 mM of 2-mercaptoethanol, and further comprises about 1000 IU/mL to about 6000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 1000 IU/mL to about 8000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 3000 IU/mL of IL-2. In some embodiments, the CTS™OpTmizer™ T-cell Expansion SFM is supplemented with about 3% of the CTS™ Immune Cell Serum Replacement (SR) (ThermoFisher Scientific) and about 2 mM glutamine, and further comprises about 6000 IU/mL of IL-2.

In some embodiments, the serum-free medium or defined medium is supplemented with glutamine (i.e., GlutaMAX®) at a concentration of from about 0.1 mM to about 10 mM, 0.5 mM to about 9 mM, 1 mM to about 8 mM, 2 mM to about 7 mM, 3 mM to about 6 mM, or 4 mM to about 5 mM. In some embodiments, the serum-free medium or defined medium is supplemented with glutamine (i.e., GlutaMAX®) at a concentration of about 2 mM.

In some embodiments, the serum-free medium or defined medium is supplemented with 2-mercaptoethanol at a concentration of from about 5 mM to about 150 mM, 10 mM to about 140 mM, 15 mM to about 130 mM, 20 mM to about 120 mM, 25 mM to about 110 mM, 30 mM to about 100 mM, 35 mM to about 95 mM, 40 mM to about 90 mM, 45 mM to about 85 mM, 50 mM to about 80 mM, 55 mM to about 75 mM, 60 mM to about 70 mM, or about 65 mM. In some embodiments, the serum-free medium or defined medium is supplemented with 2-mercaptoethanol at a concentration of about 55 mM.

In some embodiments, the defined media described in International PCT Publication No. WO/1998/030679, which is herein incorporated by reference, are useful in the present invention. In that publication, serum-free eukaryotic cell culture media are described. The serum-free, eukaryotic cell culture medium includes a basal cell culture medium supplemented with a serum-free supplement capable of supporting the growth of cells in serum-free culture. The serum-free eukaryotic cell culture medium supplement comprises or is obtained by combining one or more ingredients selected from the group consisting of one or more albumins or albumin substitutes, one or more amino acids, one or more vitamins, one or more transferrins or transferrin substitutes, one or more antioxidants, one or more insulins or insulin substitutes, one or more collagen precursors, one or more trace elements, and one or more antibiotics. In some embodiments, the defined medium further comprises L-glutamine, sodium bicarbonate and/or beta-mercaptoethanol. In some embodiments, the defined medium comprises an albumin or an albumin substitute and one or more ingredients selected from group consisting of one or more amino acids, one or more vitamins, one or more transferrins or transferrin substitutes, one or more antioxidants, one or more insulins or insulin substitutes, one or more collagen precursors, and one or more trace elements. In some embodiments, the defined medium comprises albumin and one or more ingredients selected from the group consisting of glycine, L-histidine, L-isoleucine, L-methionine, L-phenylalanine, L-proline, L-hydroxyproline, L-serine, L-threonine, L-tryptophan, L-tyrosine, L-valine, thiamine, reduced glutathione, L-ascorbic acid-2-phosphate, iron saturated transferrin, insulin, and compounds containing the trace element moieties $Ag^{+}$, $Al^{3+}$, $Ba^{2+}$, $Cd^{2+}$, $Co^{2+}$, $Cr^{3''}$, $Ge^{4+}$, $Se^{4+}$, Br, T, $Mn^{2+}$, P, $Si^{4+}$, $V^{5+}$, $Mo^{6+}$, $Ni^{2+}$, $Rb^{+}$, $Sn^{2+}$ and $Zr^{4+}$. In some embodiments, the basal cell media is selected from the group consisting of Dulbecco's Modified Eagle's Medium (DMEM), Minimal Essential Medium (MEM), Basal Medium Eagle (BME), RPMI 1640, F-10, F-12, Minimal Essential Medium (αMEM), Glasgow's Minimal Essential Medium (G-MEM), RPMI growth medium, and Iscove's Modified Dulbecco's Medium.

In some embodiments, the concentration of glycine in the defined medium is in the range of from about 5-200 mg/L, the concentration of L-histidine is about 5-250 mg/L, the concentration of L-isoleucine is about 5-300 mg/L, the concentration of L-methionine is about 5-200 mg/L, the concentration of L-phenylalanine is about 5-400 mg/L, the concentration of L-proline is about 1-1000 mg/L, the concentration of L-hydroxyproline is about 1-45 mg/L, the concentration of L-serine is about 1-250 mg/L, the concentration of L-threonine is about 10-500 mg/L, the concentration of L-tryptophan is about 2-110 mg/L, the concentration of L-tyrosine is about 3-175 mg/L, the concentration of L-valine is about 5-500 mg/L, the concentration of thiamine is about 1-20 mg/L, the concentration of reduced glutathione is about 1-20 mg/L, the concentration of L-ascorbic acid-2-phosphate is about 1-200 mg/L, the concentration of iron saturated transferrin is about 1-50 mg/L, the concentration of insulin is about 1-100 mg/L, the concentration of sodium selenite is about 0.000001-0.0001 mg/L, and the concentration of albumin (e.g., AlbuMAX® I) is about 5000-50,000 mg/L.

In some embodiments, the non-trace element moiety ingredients in the defined medium are present in the concentration ranges listed in the column under the heading "Concentration Range in 1× Medium" in Table A below. In other embodiments, the non-trace element moiety ingredients in the defined medium are present in the final concentrations listed in the column under the heading "A Preferred Embodiment of the 1× Medium" in Table A below. In other embodiments, the defined medium is a basal cell medium comprising a serum free supplement. In some of these embodiments, the serum free supplement comprises non-trace moiety ingredients of the type and in the concentrations listed in the column under the heading "A Preferred Embodiment in Supplement" in Table A below.

TABLE A

Concentrations of Non-Trace Element Moiety Ingredients

| Ingredient | A preferred embodiment in supplement (mg/L) (About) | Concentration range in 1X medium (mg/L) (About) | A preferred embodiment in 1X medium (mg/L) (About) |
|---|---|---|---|
| Glycine | 150 | 5-200 | 53 |
| L-Histidine | 940 | 5-250 | 183 |
| L-Isoleucine | 3400 | 5-300 | 615 |
| L-Methionine | 90 | 5-200 | 44 |
| L-Phenylalanine | 1800 | 5-400 | 336 |
| L-Proline | 4000 | 1-1000 | 600 |
| L-Hydroxyproline | 100 | 1-45 | 15 |
| L-Serine | 800 | 1-250 | 162 |
| L-Threonine | 2200 | 10-500 | 425 |
| L-Tryptophan | 440 | 2-110 | 82 |
| L-Tyrosine | 77 | 3-175 | 84 |
| L-Valine | 2400 | 5-500 | 454 |
| Thiamine | 33 | 1-20 | 9 |
| Reduced Glutathione | 10 | 1-20 | 1.5 |
| Ascorbic Acid-2-$PO_4$ (Mg Salt) | 330 | 1-200 | 50 |
| Transferrin (iron saturated) | 55 | 1-50 | 8 |
| Insulin | 100 | 1-100 | 10 |
| Sodium Selenite | 0.07 | 0.000001-0.0001 | 0.00001 |
| AlbuMAX ®I | 83,000 | 5000-50,000 | 12,500 |

In some embodiments, the osmolarity of the defined medium is between about 260 and 350 mOsmol. In some embodiments, the osmolarity is between about 280 and 310 mOsmol. In some embodiments, the defined medium is supplemented with up to about 3.7 g/L, or about 2.2 g/L sodium bicarbonate. The defined medium can be further supplemented with L-glutamine (final concentration of about 2 mM), one or more antibiotics, non-essential amino acids (NEAA; final concentration of about 100 μM), 2-mercaptoethanol (final concentration of about 100 μM).

In some embodiments, the defined media described in Smith, et al., "Ex vivo expansion of human T cells for adoptive immunotherapy using the novel Xeno-free CTS Immune Cell Serum Replacement," *Clin Transl Immunology,* 4(1) 2015 (doi: 10.1038/cti.2014.31) are useful in the present invention. Briefly, RPMI or CTS™ OpTmizer™ was used as the basal cell medium, and supplemented with either 0, 2%, 5%, or 10% CTS™ Immune Cell Serum Replacement.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME or βME; also known as 2-mercaptoethanol, CAS 60-24-2).

In another embodiment, the invention provides a cryopreserved preparation of the TIL composition described in any of the preceding paragraphs as applicable above.

V. Methods of Treating Patients

Methods of treatment begin with the initial TIL collection and culture of TILs. Such methods have been both described in the art by, for example, Jin et al., *J. Immunotherapy,* 2012, 35(3):283-292, incorporated by reference herein in its entirety. Embodiments of methods of treatment are described throughout the sections below, including the Examples.

The expanded TILs produced according the methods described herein, including, for example as described in Steps A through F above or according to Steps A through F above (also as shown, for example, in FIG. 1 (in particular, e.g., FIG. 1B and/or FIG. 1C) find particular use in the treatment of patients with cancer (for example, as described in Goff, et al., *J Clinical Oncology,* 2016, 34(20):2389-239, as well as the supplemental content; incorporated by reference herein in its entirety. In some embodiments, TIL were grown from resected deposits of metastatic melanoma as previously described (see, Dudley, et al., *J Immunother.,* 2003, 26:332-342; incorporated by reference herein in its entirety). Fresh tumor can be dissected under sterile conditions. A representative sample can be collected for formal pathologic analysis. Single fragments of 2 $mm^3$ to 3 $mm^3$ may be used. In some embodiments, 5, 10, 15, 20, 25 or 30 samples per patient are obtained. In some embodiments, 20, 25, or 30 samples per patient are obtained. In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 pg/mL and twice background. (Goff, et al., *J Immunother.*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 1 (in particular, e.g., FIG. 1B and/or FIG. 1C), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 1 (in particular, e.g., FIG. 1B and/or FIG. 1C), are selected for an additional second expansion according to Step D of FIG. 1 (in particular, e.g., FIG. 1B and/or FIG. 1C).

In some embodiments, the patient is not moved directly to ACT (adoptive cell transfer), for example, in some embodiments, after tumor harvesting and/or a first expansion, the cells are not utilized immediately. In some embodiments, TILs can be cryopreserved and thawed 2 days before administration to a patient. In some embodiments, TILs can be cryopreserved and thawed 1 day before administration to a patient. In some embodiments, the TILs can be cryopreserved and thawed immediately before the administration to a patient.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines can be measured by using standard enzyme-linked immunosorbent assay techniques. A rise in serum IFN-g can be defined as >100 pg/mL and at least 4-fold or at least 3-fold or at least 2-fold or at least 1-fold greater than baseline levels of serum IFN-g. In some embodiments, a rise in serum IFN-g is defined as >1000 pg/mL. In some embodiments, a rise in serum IFN-g is defined as >200 pg/mL. In some embodiments, a rise in serum IFN-g is defined as >250 pg/mL. In some embodiments, a rise in serum IFN-g is defined as >300 pg/mL. In some embodiments, a rise in serum IFN-g is defined as >350 pg/mL. In some embodiments, a rise in serum IFN-g is defined as >400 pg/mL. In some embodiments, a rise in serum IFN-g is defined as >450 pg/mL. In some embodiments, a rise in serum IFN-g is defined as >500 pg/mL. In some embodiments, a rise in serum IFN-g is defined as >550 pg/mL. In some embodiments, a rise in serum IFN-g is defined as >600 pg/mL. In some embodiments, a rise in serum IFN-g is defined as >650 pg/mL. In some embodiments, a rise in serum IFN-g is defined as >700 pg/mL. In some embodiments, a rise in serum IFN-g is defined as >750 pg/mL. In some embodiments, a rise in serum IFN-g is defined as >800 pg/mL. In some embodiments, a rise in serum IFN-g is defined as >850 pg/mL. In some embodiments, a rise in serum IFN-g is defined as >900 pg/mL. In some embodiments, a rise in serum IFN-g is defined as >950 pg/mL. In some embodiments, a rise in serum IFN-g is defined as >1000 pg/mL.

In some embodiments, the TILs produced by the methods provided herein, for example those exemplified in FIG. 1 (in particular, e.g., FIG. 1B and/or FIG. 1C), provide for a surprising improvement in clinical efficacy of the TILs. In some embodiments, the TILs produced by the methods provided herein, for example those exemplified in FIG. 1 (in particular, e.g., FIG. 1B and/or FIG. 1C), exhibit increased clinical efficacy as compared to TILs produced by methods other than those described herein, including, for example, methods other than those exemplified in FIG. 1 (in particular, e.g., FIG. 1B and/or FIG. 1C). In some embodiments, the methods other than those described herein include methods referred to as process 1C and/or Generation 1 (Gen 1). In some embodiments, the increased efficacy is measured by DCR, ORR, and/or other clinical responses. In some embodiments, the TILS produced by the methods provided herein, for example those exemplified in FIG. 1 (in particular, e.g., FIG. 1B and/or FIG. 1C), exhibit a similar time to response and safety profile compared to TILs produced by methods other than those described herein, including, for example, methods other than those exemplified in FIG. 1 (in particular, e.g., FIG. 1B and/or FIG. 1C), for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 1 (in particular, e.g., FIG. 1B and/or FIG. 1C). In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased one-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased two-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased three-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased four-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased five-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 1 (in particular, e.g., FIG. 1B and/or FIG. 1C). In some embodiments, IFN-γ is measured in blood of a subject treated with TILs prepared by the methods of the present invention, including those as described for example in FIG. 1 (in particular, e.g., FIG. 1B and/or FIG. 1C). In some embodiments, IFN-γ is measured in TILs serum of a subject treated with TILs prepared by the methods of the present invention, including those as described for example in FIG. 1 (in particular, e.g., FIG. 1B and/or FIG. 1C).

In some embodiments, the TILs prepared by the methods of the present invention, including those as described for example in FIG. 1 (in particular, e.g., FIG. 1B and/or FIG. 1C), exhibit increased polyclonality as compared to TILs produced by other methods, including those not exemplified in FIG. 1 (in particular, e.g., FIG. 1B and/or FIG. 1C), such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including, for example, methods other than those embodied in FIG. 1 (in particular, e.g., FIG. 1B and/or FIG. 1C). In some embodiments, polyclonality is increased one-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased two-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased ten-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased 100-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased 500-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased 1000-fold as compared to an untreated patient and/or as compared to a patient treated with TILs prepared using other methods than those provide herein including, for example, methods other than those embodied in FIG. 1 (in particular, e.g., FIG. 1B and/or FIG. 1C).

Measures of efficacy can include the disease control rate (DCR) as well as overall response rate (ORR), as known in the art as well as described herein.

1. Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of glioblastoma (GBM), gastrointestinal cancer, melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In some embodiments, the cancer is a hypermutated cancer phenotype. Hypermutated cancers are extensively described in Campbell, et al. (Cell, 171:1042-1056 (2017); incorporated by reference herein in its entirety for all purposes). In some embodiments, a hypermutated tumors comprise between 9 and 10 mutations per megabase (Mb). In some embodiments, pediatric hypermutated tumors comprise 9.91 mutations per megabase (Mb). In some embodiments, adult hypermutated tumors comprise 9 mutations per megabase (Mb). In some embodiments, enhanced hypermutated tumors comprise between 10 and 100 mutations per megabase (Mb). In some embodiments, enhanced pediatric hypermutated tumors comprise between 10 and 100 mutations per megabase (Mb). In some embodiments, enhanced adult hypermutated tumors comprise between 10 and 100 mutations per megabase (Mb). In some embodiments, an ultra-hypermutated tumors comprise greater than 100 mutations per megabase (Mb). In some embodiments, pediatric ultra-hypermutated tumors comprise greater than 100 mutations per megabase (Mb). In some embodiments, adult ultra-hypermutated tumors comprise greater than 100 mutations per megabase (Mb).

In some embodiments, the hypermutated tumors have mutations in replication repair pathways. In some embodiments, the hypermutated tumors have mutations in replication repair associated DNA polymerases. In some embodiments, the hypermutated tumors have microsatellite instability. In some embodiments, the ultra-hypermutated tumors have mutations in replication repair associated DNA polymerases and have microsatellite instability. In some embodiments, hypermutation in the tumor is correlated with response to immune checkpoint inhibitors. In some embodiments, hypermutated tumors are resistant to treatment with immune checkpoint inhibitors. In some embodiments, hypermutated tumors can be treated using the TILs of the present invention. In some embodiments, hypermutation in the tumor is caused by environmental factors (extrinsic exposures). For example, UV light can be the primary cause of the high numbers of mutations in malignant melanoma (see, for example, Pfeifer, G. P., You, Y. H., and Besaratinia, A. (2005). Mutat. Res. 571, 19-31; Sage, E. (1993). Photochem. Photobiol. 57, 163-174.). In some embodiments, hypermutation in the tumor can be caused by the greater than 60 carcinogens in tobacco smoke for tumors of the lung and larynx, as well as other tumors, due to direct mutagen exposure (see, for example, Pleasance, E. D., Stephens, P. J., O'Meara, S., McBride, D. J., Meynert, A., Jones, D., Lin, M. L., Beare, D., Lau, K. W., Greenman, C., et al. (2010). Nature 463, 184-190). In some embodiments, hypermutation in the tumor is caused by dysregulation of apolipoprotein B mRNA editing enzyme, catalytic polypeptide-like (APOBEC) family members, which has been shown to result in increased levels of C to T transitions in a wide range of cancers (see, for example, Roberts, S. A., Lawrence, M. S., Klimczak, L. J., Grimm, S. A., Fargo, D., Stojanov, P., Kiezun, A., Kryukov, G. V., Carter, S. L., Saksena, G., et al. (2013). Nat. Genet. 45, 970-976). In some embodiments, hypermutation in the tumor is caused by defective DNA replication repair by mutations that compromise proofreading, which is performed by the major replicative enzymes Pol3 and Pold1. In some embodiments, hypermutation in the tumor is caused by defects in DNA mismatch repair, which are associated with hypermutation in colorectal, endometrial, and other cancers (see, for example, Kandoth, C., Schultz, N., Cherniack, A. D., Akbani, R., Liu, Y., Shen, H., Robertson, A. G., Pashtan, I., Shen, R., Benz, C. C., et al.; (2013). Nature 497, 67-73; Muzny, D. M., Bainbridge, M. N., Chang, K., Dinh, H. H., Drummond, J. A., Fowler, G., Kovar, C. L., Lewis, L. R., Morgan, M. B., Newsham, I. F., et al.; (2012). Nature 487, 330-337). In some embodiments, DNA replication repair mutations are also found in cancer predisposition syndromes, such as constitutional or biallelic mismatch repair deficiency (CMMRD), Lynch syndrome, and polymerase proofreading-associated polyposis (PPAP).

In an embodiment, the invention includes a method of treating a cancer with a population of TILs, wherein the cancer is a hypermutated cancer. In an embodiment, the invention includes a method of treating a cancer with a population of TILs, wherein the cancer is an enhanced hypermutated cancer. In an embodiment, the invention includes a method of treating a cancer with a population of TILs, wherein the cancer is an ultra-hypermutated cancer.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J. Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 1 (in particular, e.g., FIG. 1B and/or FIG. 1C). In some embodiments, the TILs obtained by the present method provide for increased IFN-γ in the blood of subjects treated with the TILs of the present method as compared subjects treated with TILs prepared using methods referred to as the Gen 3 process, as exemplified FIG. 1 (in particular, e.g., FIG. 1B and/or FIG. 1C) and throughout this application. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased one-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased two-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased three-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased four-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ secretion is increased five-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-γ is measured in blood in a patient treated with the TILs produced by the methods of the present invention. In some embodiments, IFN-γ is measured in serum in a patient treated with the TILs produced by the methods of the present invention.

In some embodiments, the TILs prepared by the methods of the present invention, including those as described for example in FIG. 1 (in particular, e.g., FIG. 1B and/or FIG. 1C), exhibit increased polyclonality as compared to TILs produced by other methods, including those not exemplified in FIG. 1 (in particular, e.g., FIG. 1B and/or FIG. 1C), such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including, for example, methods other than those embodied in FIG. 1 (in particular, e.g., FIG. 1B and/or FIG. 1C). In some embodiments, polyclonality is increased one-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased two-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased ten-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased 100-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased 500-fold as compared to an untreated patient and/or as compared to a patient treated with TILs prepared using other methods than those provide herein including, for example, methods other than those embodied in FIG. 1 (in particular, e.g., FIG. 1B and/or FIG. 1C). In some embodiments, polyclonality is increased 1000-fold as compared to an untreated patient and/or as compared to a patient treated with TILs prepared using other methods than those provide herein including, for example, methods other than those embodied in FIG. 1 (in particular, e.g., FIG. 1B and/or FIG. 1C).

2. Methods of Co-Administration

In some embodiments, the TILs produced as described herein, including, for example TILs derived from a method described in Steps A through F of FIG. 1 (in particular, e.g., FIG. 1B and/or FIG. 1C), can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small-cell lung carcinoma (NSCLC).

3. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 $mg/m^2/d$ for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., Cancer *Immunol. Immunother.* 2011, 60, 75-85, Muranski, et al., *Nat. Clin. Pract. Oncol.,* 2006, 3, 668-681, Dudley, et al., J. *Clin. Oncol.* 2008, 26, 5233-5239, and Dudley, et al., *J. Clin. Oncol.* 2005, 23, 2346-2357, all of which are incorporated by reference herein in their entireties.

In some embodiments, the fludarabine is administered at a concentration of 0.5 μg/mL-10 μg/mL fludarabine. In some embodiments, the fludarabine is administered at a concentration of 1 μg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 μg/mL-10 μg/mL by administration of cyclophosphamide. In some embodiments, mafosfamide, the active form of cyclophosphamide, is obtained at a concentration of 1 μg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 $mg/m^2$/day, 150 $mg/m^2$/day, 175 $mg/m^2$/day, 200 $mg/m^2$/day, 225 $mg/m^2$/day, 250 $mg/m^2$/day, 275 $mg/m^2$/day, or 300 $mg/m^2$/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 $mg/m^2$/day i.v. In some embodiments, the cyclophosphamide treatment is administered for 4 days at 250 $mg/m^2$/day i.v.

In some embodiments, lymphodepletion is performed by administering the fludarabine and the cyclophosphamide together to a patient. In some embodiments, fludarabine is administered at 25 $mg/m^2$/day i.v. and cyclophosphamide is administered at 250 $mg/m^2$/day i.v. over 4 days.

In an embodiment, the lymphodepletion is performed by administration of cyclophosphamide at a dose of 60 $mg/m^2$/day for two days followed by administration of fludarabine at a dose of 25 $mg/m^2$/day for five days.

4. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., *Cancer* 2000, 88, 1703-9, the disclosures of which are incorporated herein by reference. In an embodiment, a decrescendo IL-2 regimen comprises $18\times10^6$ IU/$m^2$ administered intravenously over 6 hours, followed by $18\times10^6$ IU/$m^2$ administered intravenously over 12 hours, followed by $18\times10^6$ IU/$m^2$ administered intravenously over 24 hrs, followed by $4.5\times10^6$ IU/$m^2$ administered intravenously over 72 hours. This treatment cycle may be repeated every 28 days for a maximum of four cycles. In an embodiment, a decrescendo IL-2 regimen comprises 18,000,000 IU/$m^2$ on day 1, 9,000,000 IU/$m^2$ on day 2, and 4,500,000 IU/$m^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

5. Adoptive Cell Transfer

Adoptive cell transfer (ACT) is an effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 1 (in particular, e.g., FIG. 1B and/or FIG. 1C). They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

6. Additional Methods of Treatment

In another embodiment, the invention provides a method for treating a subject with cancer comprising administering to the subject a therapeutically effective dosage of the therapeutic TIL population described in any one of the preceding paragraphs as applicable above.

In another embodiment, the invention provides a method for treating a subject with cancer comprising administering to the subject a therapeutically effective dosage of the TIL composition described in any of the preceding paragraph as applicable above.

In another embodiment, the invention provides the method for treating a subject with cancer described in any of the preceding paragraphs as applicable above modified such that prior to administering the therapeutically effective dosage of the therapeutic TIL population described in any of the preceding paragraphs as applicable above or the therapeutically effective dosage of the TIL composition described in any of the preceding paragraphs as applicable above, a non-myeloablative lymphodepletion regimen has been administered to the subject.

In another embodiment, the invention provides the method for treating a subject with cancer described in any of the preceding paragraph as applicable above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In another embodiment, the invention provides the method for treating a subject with cancer described in any of the preceding paragraphs as applicable above modified to further comprise the step of treating the subject with a high-dose IL-2 regimen starting on the day after administration of the TIL cells to the subject.

In another embodiment, the invention provides the method for treating a subject with cancer described in any of the preceding paragraphs as applicable above modified such that the high-dose IL-2 regimen comprises 600,000 or 720,000 IU/kg administered as a 15-minute bolus intravenous infusion every eight hours until tolerance.

In another embodiment, the invention provides the method for treating a subject with cancer described in any of the preceding paragraphs as applicable above modified such that the cancer is a solid tumor.

In another embodiment, the invention provides the method for treating a subject with cancer described in any of the preceding paragraphs as applicable above modified such that the cancer is melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the method for treating a subject with cancer described in any of the preceding paragraphs as applicable above modified such that the cancer is melanoma, HNSCC, cervical cancers, NSCLC, glioblastoma (including GBM), and gastrointestinal cancer.

In another embodiment, the invention provides the method for treating a subject with cancer described in any of the preceding paragraphs as applicable above modified such that the cancer is melanoma.

In another embodiment, the invention provides the method for treating a subject with cancer described in any of the preceding paragraphs as applicable above modified such that the cancer is HNSCC.

In another embodiment, the invention provides the method for treating a subject with cancer described in any of the preceding paragraphs as applicable above modified such that the cancer is a cervical cancer.

In another embodiment, the invention provides the method for treating a subject with cancer described in any of the preceding paragraphs as applicable above modified such that the cancer is NSCLC.

In another embodiment, the invention provides the method for treating a subject with cancer described in any of the preceding paragraphs as applicable above modified such that the cancer is glioblastoma (including GBM).

In another embodiment, the invention provides the method for treating a subject with cancer described in any of the preceding paragraphs as applicable above modified such that the cancer is gastrointestinal cancer.

In another embodiment, the invention provides the method for treating a subject with cancer described in any of the preceding paragraphs as applicable above modified such that the cancer is a hypermutated cancer.

In another embodiment, the invention provides the method for treating a subject with cancer described in any of the preceding paragraphs as applicable above modified such that the cancer is a pediatric hypermutated cancer.

In another embodiment, the invention provides the therapeutic TIL population described in any one of the preceding paragraphs as applicable above for use in a method for treating a subject with cancer comprising administering to the subject a therapeutically effective dosage of the therapeutic TIL population.

In another embodiment, the invention provides the TIL composition described in any of the preceding paragraphs as applicable above for use in a method for treating a subject with cancer comprising administering to the subject a therapeutically effective dosage of the TIL composition.

In another embodiment, the invention provides the therapeutic TIL population described in any of the preceding paragraphs as applicable above or the TIL composition described in any of the preceding paragraphs as applicable above modified such that prior to administering to the subject the therapeutically effective dosage of the therapeutic TIL population described in any of the preceding paragraphs as applicable above or the TIL composition described in any of the preceding paragraphs as applicable above, a non-myeloablative lymphodepletion regimen has been administered to the subject.

In another embodiment, the invention provides the therapeutic TIL population or the TIL composition described in any of the preceding paragraphs as applicable above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In another embodiment, the invention provides the therapeutic TIL population described in any of the preceding paragraphs as applicable above or the TIL composition described in any of the preceding paragraphs as applicable above modified to further comprise the step of treating patient with a high-dose IL-2 regimen starting on the day after administration of the TIL cells to the patient.

In another embodiment, the invention provides the therapeutic TIL population or the TIL composition described in any of the preceding paragraphs as applicable above modified such that the high-dose IL-2 regimen comprises 600,000 or 720,000 IU/kg administered as a 15-minute bolus intravenous infusion every eight hours until tolerance.

In another embodiment, the invention provides the therapeutic TIL population described in any of the preceding paragraphs as applicable above or the TIL composition described in any of the preceding paragraphs as applicable above modified such that the cancer is a solid tumor.

In another embodiment, the invention provides the therapeutic TIL population described in any of the preceding paragraphs as applicable above or the TIL composition described in any of the preceding paragraphs as applicable above modified such that the cancer is melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the therapeutic TIL population described in any of the preceding paragraphs as applicable above or the TIL composition described in any of the preceding paragraphs as applicable above modified such that the cancer is melanoma, HNSCC, cervical cancers, NSCLC, glioblastoma (including GBM), and gastrointestinal cancer.

In another embodiment, the invention provides the therapeutic TIL population described in any of the preceding paragraphs as applicable above or the TIL composition described in any of the preceding paragraphs as applicable above modified such that the cancer is melanoma.

In another embodiment, the invention provides the therapeutic TIL population or the TIL composition described in any of the preceding paragraphs as applicable above modified such that the cancer is HNSCC.

In another embodiment, the invention provides the therapeutic TIL population or the TIL composition described in any of the preceding paragraphs as applicable above modified such that the cancer is a cervical cancer.

In another embodiment, the invention provides the therapeutic TIL population or the TIL composition described in any of the preceding paragraphs as applicable above modified such that the cancer is NSCLC.

In another embodiment, the invention provides the therapeutic TIL population or the TIL composition described in any of the preceding paragraphs as applicable above modified such that the cancer is glioblastoma (including GBM).

In another embodiment, the invention provides the therapeutic TIL population or the TIL composition described in any of the preceding paragraphs as applicable above modified such that the cancer is gastrointestinal cancer.

In another embodiment, the invention provides the therapeutic TIL population or the TIL composition described in any of the preceding paragraphs as applicable above modified such that the cancer is a hypermutated cancer.

In another embodiment, the invention provides the therapeutic TIL population or the TIL composition described in any of the preceding paragraphs as applicable above modified such that the cancer is a pediatric hypermutated cancer.

In another embodiment, the invention provides the use of the therapeutic TIL population described in any one of the preceding paragraphs as applicable above in a method of treating cancer in a subject comprising administering to the subject a therapeutically effective dosage of the therapeutic TIL population.

In another embodiment, the invention provides the use of the TIL composition described in any of the preceding paragraphs as applicable above in a method of treating cancer in a subject comprising administering to the subject a therapeutically effective dosage of the TIL composition.

In another embodiment, the invention provides the use of the therapeutic TIL population described in any of the preceding paragraphs as applicable above or the TIL composition described in any of the preceding paragraphs as applicable above in a method of treating cancer in a subject comprising administering to the subject a non-myeloablative lymphodepletion regimen and then administering to the subject a therapeutically effective dosage of the therapeutic TIL population described in any of the preceding paragraphs as applicable above or a therapeutically effective dosage of the TIL composition described in any of the preceding paragraphs as applicable above.

In another embodiment, the invention provides the use of the therapeutic TIL population or the TIL composition described in any of the preceding paragraphs as applicable above modified such that prior to administering to the subject the therapeutically effective dosage of the therapeutic TIL population or the therapeutically effective dosage of the TIL composition, a non-myeloablative lymphodepletion regimen has been administered to the subject.

In another embodiment, the invention provides the use of the therapeutic TIL population or the TIL composition described in any of the preceding paragraphs as applicable above modified such that the non-myeloablative lymphodepletion regimen comprises the steps of administration of cyclophosphamide at a dose of 60 $mg/m^2$/day for two days followed by administration of fludarabine at a dose of 25 $mg/m^2$/day for five days.

In another embodiment, the invention provides the use of the therapeutic TIL population described in any of the preceding paragraphs as applicable above or the use of the TIL composition described in any of the preceding paragraphs as applicable above modified to further comprise the step of treating patient with a high-dose IL-2 regimen starting on the day after administration of the TIL cells to the patient.

In another embodiment, the invention provides the use of the therapeutic TIL population or the TIL composition described in any of the preceding paragraphs as applicable above modified such that the high-dose IL-2 regimen comprises 600,000 or 720,000 IU/kg administered as a 15-minute bolus intravenous infusion every eight hours until tolerance.

In another embodiment, the invention provides the use of the therapeutic TIL population or the TIL composition described in any of the preceding paragraphs as applicable above modified such that the cancer is a solid tumor.

In another embodiment, the invention provides the use of the therapeutic TIL population or the TIL composition described in any of the preceding paragraphs as applicable above modified such that the cancer is melanoma, ovarian cancer, endometrial cancer, thyroid cancer, colorectal cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), glioblastoma (including GBM), gastrointestinal cancer, renal cancer, or renal cell carcinoma.

In another embodiment, the invention provides the use of the therapeutic TIL population or the TIL composition described in any of the preceding paragraphs as applicable above modified such that the cancer is melanoma, HNSCC, cervical cancers, NSCLC, glioblastoma (including GBM), and gastrointestinal cancer.

In another embodiment, the invention provides the use of the therapeutic TIL population or the TIL composition described in any of the preceding paragraphs as applicable above modified such that the cancer is melanoma.

In another embodiment, the invention provides the use of the therapeutic TIL population or the TIL composition described in any of the preceding paragraphs as applicable above modified such that the cancer is HNSCC.

In another embodiment, the invention provides the use of the therapeutic TIL population or the TIL composition described in any of the preceding paragraphs as applicable above modified such that the cancer is a cervical cancer.

In another embodiment, the invention provides the use of the therapeutic TIL population or the TIL composition described in any of the preceding paragraphs as applicable above modified such that the cancer is NSCLC.

In another embodiment, the invention provides the use of the therapeutic TIL population or the TIL composition described in any of the preceding paragraphs as applicable above modified such that the cancer is glioblastoma (including GBM).

In another embodiment, the invention provides the use of the therapeutic TIL population or the TIL composition described in any of the preceding paragraphs as applicable above modified such that the cancer is gastrointestinal cancer.

In another embodiment, the invention provides the use of the therapeutic TIL population or the TIL composition described in any of the preceding paragraphs as applicable above modified such that the cancer is a hypermutated cancer.

In another embodiment, the invention provides the use of the therapeutic TIL population or the TIL composition described in any of the preceding paragraphs as applicable above modified such that the cancer is a pediatric hypermutated cancer.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Preparation of Media for Pre-Rep and Rep Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma (HNSCC), ovarian carcinoma, triple-negative breast carcinoma, and lung adenocarcinoma. This media can be used for preparation of any of the TILs described in the present application and Examples.

Preparation of CM1

Removed the following reagents from cold storage and warmed them in a 37° C. water bath: (RPMI1640, Human AB serum, 200 mM L-glutamine). Prepared CM1 medium according to Table 19 below by adding each of the ingredients into the top section of a 0.2 μm filter unit appropriate to the volume to be filtered. Stored at 4° C.

TABLE 19

| Preparation of CM1 | | | |
|---|---|---|---|
| Ingredient | Final concentration | Final Volume 500 ml | Final Volume IL |
| RPMI1640 | NA | 450 ml | 900 ml |
| Human AB serum, heat-inactivated 10% | 50 ml | 100 ml | |
| 200 mM L-glutamine | 2 mM | 5 ml | 10 ml |
| 55 mM BME | 55 μM | 0.5 ml | 1 ml |
| 50 mg/ml gentamicin sulfate | 50 μg/ml | 0.5 ml | 1 ml |

On the day of use, prewarmed required amount of CM1 in 37° C. water bath and add 6000 IU/ml IL-2.

Additional supplementation—as needed according to Table 20.

TABLE 20

| Additional supplementation of CM1, as needed. | | | |
|---|---|---|---|
| Supplement | Stock concentration | Dilution | Final concentration |
| GlutaMAX ™ | 200 mM | 1:100 | 2 mM |
| Penicillin/streptomycin | 10,000 U/ml penicillin 10,000 μg/ml streptomycin | 1:100 | 100 U/ml penicillin 100 μg/ml streptomycin |
| Amphotericin B | 250 μg/ml | 1:100 | 2.5 μg/ml |

Preparation of CM2

Removed prepared CM1 from refrigerator or prepare fresh CM1 as per Table 19 above. Removed AIM-V® from refrigerator and prepared the amount of CM2 needed by mixing prepared CM1 with an equal volume of AIM-V® in a sterile media bottle. Added 3000 IU/ml IL-2 to CM2 medium on the day of usage. Made sufficient amount of CM2 with 3000 IU/ml IL-2 on the day of usage. Labeled the CM2 media bottle with its name, the initials of the preparer, the date it was filtered/prepared, the two-week expiration date and stored at 4° C. until needed for tissue culture.

Preparation of CM3

Prepared CM3 on the day it was required for use. CM3 was the same as AIM-V® medium, supplemented with 3000 IU/ml IL-2 on the day of use. Prepared an amount of CM3 sufficient to experimental needs by adding IL-2 stock solution directly to the bottle or bag of AIM-V. Mixed well by gentle shaking. Labeled bottle with "3000 IU/ml IL-2" immediately after adding to the AIM-V. If there was excess CM3, stored it in bottles at 4° C. labeled with the media name, the initials of the preparer, the date the media was prepared, and its expiration date (7 days after preparation). Discarded media supplemented with IL-2 after 7 days storage at 4° C.

Preparation of CM4

CM4 was the same as CM3, with the additional supplement of 2 mM GlutaMAX™ (final concentration). For every 1 L of CM3, added 10 ml of 200 mM GlutaMAX™. Prepared an amount of CM4 sufficient to experimental needs by adding IL-2 stock solution and GlutaMAX™ stock solution directly to the bottle or bag of AIM-V. Mixed well by gentle shaking. Labeled bottle with "3000 IL/nil IL-2 and GlutaMAX" immediately after adding to the AIM-V. If there was excess CM4, stored it in bottles at 4° C. labeled with the media name, "GlutaMAX", and its expiration date (7 days after preparation). Discarded media supplemented with IL-2 after 7-days storage at 4° C.

Example 2: Use of IL-2, IL-15, and IL-21 Cytokine Cocktail

This example describes the use of IL-2, IL-15, and IL-21 cytokines, which serve as additional T cell growth factors, in combination with the TIL process of Examples A to G.

Using the processes described herein, TILs were grown from colorectal, melanoma, cervical, triple negative breast, lung and renal tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR Vβ repertoire. IL-15 and IL-21 are described elsewhere herein and in Gruijl et al., IL-21 promotes the expansion of CD27+CD28+ tumor infiltrating lymphocytes with high cytotoxic potential and low collateral expansion of regulatory T cells, Santegoets, S. J., J Transl Med., 2013, 11:37.

The results showed that enhanced TIL expansion (>20%), in both $CD4^+$ and $CD8^+$ cells in the IL-2, IL-15, and IL-21 treated conditions were observed in multiple histologies relative to the IL-2 only conditions. There was a skewing towards a predominantly $CD8^+$ population with a skewed TCR Vβ repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 3: Preparation of IL-2 Stock Solution (Cellgenix)

This Example describes the process of dissolving purified, lyophilized recombinant human interleukin-2 into stock samples suitable for use in further tissue culture protocols, including all of those described in the present application and Examples, including those that involve using rhIL-2.

Procedure

Prepared 0.2% Acetic Acid solution (HAc). Transferred 29 mL sterile water to a 50 mL conical tube. Added 1 mL 1N acetic acid to the 50 mL conical tube. Mixed well by inverting tube 2-3 times. Sterilized the HAc solution by filtration using a Steriflip filter Prepared 1% HSA in PBS. Added 4 mL of 25% HSA stock solution to 96 mL PBS in a 150 mL sterile filter unit. Filtered solution. Stored at 4° C. For each vial of rhIL-2 prepared, fill out forms.

Prepared rhIL-2 stock solution (6×10$^6$ IU/mL final concentration). Each lot of rhIL-2 was different and required information found in the manufacturer's Certificate of Analysis (COA), such as: 1) Mass of rhIL-2 per vial (mg), 2) Specific activity of rhIL-2 (IU/mg) and 3) Recommended 0.2% HAc reconstitution volume (mL).

Calculated the volume of 1% HSA required for rhIL-2 lot by using the equation below:

$$\left(\frac{\text{Vial Mass (mg)} \times \text{Biological Activity}\left(\frac{IU}{\text{mg}}\right)}{6\times 10^{6}\ \frac{IU}{\text{mL}}}\right) - HAc\ vol\ (\text{mL}) = 1\%\ HSA\ vol\ (\text{mL})$$

For example, according to CellGenix's rhIL-2 lot 10200121 COA, the specific activity for the 1 mg vial is 25×10$^6$ IU/mg. It recommends reconstituting the rhIL-2 in 2 mL 0.2% HAc.

$$\left(\frac{1\ \text{mg}\times 25\times 10^{6}\ \frac{IU}{\text{mg}}}{6\times 10^{6}\ \frac{IU}{\text{mL}}}\right) - 2\ \text{mL} = 2.167\ \text{mL}\ HSA$$

Wiped rubber stopper of IL-2 vial with alcohol wipe. Using a 16G needle attached to a 3 mL syringe, injected recommended volume of 0.2% HAc into vial. Took care to not dislodge the stopper as the needle is withdrawn. Inverted vial 3 times and swirled until all powder was dissolved. Carefully removed the stopper and set aside on an alcohol wipe. Added the calculated volume of 1% HSA to the vial.

Storage of rhIL-2 solution. For short-term storage (<72 hrs), stored vial at 4° C. For long-term storage (>72 hrs), aliquoted vial into smaller volumes and stored in cryovials at −20° C. until ready to use. Avoided freeze/thaw cycles. Recorded expiration date of 6 months after date of preparation. Rh-IL-2 labels included vendor and catalog number, lot number, expiration date, operator initials, concentration and volume of aliquot.

Example 4: Cryopreservation Process

This example describes the cryopreservation process method for TILs prepared with the abbreviated, closed procedure described in Example G using the CryoMed Controlled Rate Freezer, Model 7454 (Thermo Scientific).

The equipment used was as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provided for a 0.5° C. rate from nucleation to −20° C. and 1° C. per minute cooling rate to −80° C. end temperature. The program parameters were as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Example 5: Gen 3 Exemplary Process

The example provides a comparison between the Gen 2 and Gen 3 processes. This example describes the development of a robust TIL expansion platform. The modifications to the Gen 2 process reduce risk and streamline the manufacturing process by reducing the number of operator interventions, reduce the overall time of manufacturing, optimize the use of reagents, and facilitate a flexible semi-closed and semi-automated cell production process amenable to high-throughput manufacturing on a commercial scale.

Process Gen 2 and Gen 3 TILs are composed of autologous TIL derived from an individual patient through surgical resection of a tumor and then expanded ex vivo. The Priming First Expansion step of the Gen 3 process was a cell culture in the presence of interleukin-2 (IL-2) and the monoclonal antibody OKT3, which targets the T-cell co-receptor CD3 on a scaffold of irradiated peripheral blood mononuclear cells (PBMCs).

The manufacture of Gen 2 TIL products consisted of two phases: 1) pre-Rapid Expansion (Pre-REP) and 2) Rapid Expansion Protocol (REP). During the Pre-REP resected tumors were cut up into ≤50 fragments 2-3 mm in each dimension which were cultured with serum-containing culture medium (RPMI 1640 media containing 10% HuSAB supplemented) and 6,000 IU/mL of Interleukin-2 (IL-2) for a period of 11 days. On day 11 TIL were harvested and introduced into the large-scale secondary REP expansion. The REP consists of activation of ≤200×10$^6$ of the viable cells from pre-REP in a co-culture of 5×10$^9$ irradiated allogeneic PBMCs feeder cells loaded with 150 μg of monoclonal anti-CD3 antibody (OKT3) in a 5 L volume of CM2 supplemented with 3000 IU/mL of rhIL-2 for 5 days. On day 16 the culture is volume reduced 90% and the cell fraction is split into multiple G-REX-500 flasks at ≥1×10$^9$ viable lymphocytes/flask and QS to 5 L with CM4. TIL are incubated an additional 6 days. The REP is harvested on day 22, washed, formulated, and cryo-preserved prior to shipping at −150° C. to the clinical site for infusion.

The manufacture of Gen 3 TIL products consisted of three phases: 1) Priming First Expansion Protocol 2) Rapid Second Expansion Protocol (also referred to as rapid expansion phase or REP) and 3) Subculture Split. To effect the Priming First Expansion TIL propagation, resected tumor was cut up into ≤120 fragments 2-3 mm in each dimension. On day 0 of the Priming First Expansion, a feeder layer of approximately 2.5×10$^8$ allogeneic irradiated PBMCs feeder cells loaded with OKT-3 was established on a surface area of approximately 100 cm$^2$ in each of 3 100 MCS vessels. The tumor fragments were distributed among and cultured in the 3 100 MCS vessels each with 500 mL serum-containing CM1 culture medium and 6,000 IU/mL of Interleukin-2 (IL-2) and 15 μg OKT-3 for a period of 7 days. On day 7, REP was initiated by incorporating an additional feeder cell layer of approximately 5×10$^8$ allogeneic irradiated PBMCs feeder cells loaded with OKT-3 into the tumor fragmented culture phase in each of the 3 100 MCS vessels and culturing with 500 mL CM2 culture medium and 6,000 IU/mL IL-2 and 30 μg OKT-3. The REP initiation was enhanced by activating the entire Priming First Expansion culture in the same vessel using closed system fluid transfer of OKT3 loaded feeder cells into the 100MCS vessel. For Gen 3, the TIL scale up or split involved process steps where the whole cell culture was scaled to a larger vessel through closed system fluid transfer and was transferred (from 100 M flask to a 500 M flask) and additional 4 L of CM4 media was added. The REP cells were harvested on day 16, washed, formulated, and cryo-preserved prior to shipping at −150° C. to the clinical site for infusion.

Overall, the Gen 3 process is a shorter, more scalable, and easily modifiable expansion platform that will accommodate to fit robust manufacturing and process comparability.

TABLE 21

Comparison of Exemplary Gen 2 and Exemplary Gen 3 manufacturing process.

| Step | Process (Gen 2) | Process (Gen 3) |
|---|---|---|
| Pre REP-day 0 | Up to 50 fragments/1-G-Rex 100MCS - 11 days<br>In 1 L of CM1 media + IL-2 (6000 IU/mL) | Whole tumor up to 120 fragments divided evenly among up to 3 flasks. 1 flask: 1-60 fragments<br>2 flasks: 61-89 fragments<br>3 flasks 90-120 fragments<br>7 days in 200-500 mL of CM1 media + IL-2 (6000 IU/mL)<br>2.5 × 10$^8$ feeder cells/flask<br>Optionally 15 μg OKT-3/flask |
| REP Initiation | Direct to REP- Day 11- <200e$^6$ TIL<br>(1)G-Rex 500MCS in 5 L CM2 media<br>IL-2 (3000 IU/mL)<br>5 × 10$^9$ feeder cells<br>150 μg OKT-3 | Direct to REP- Day 7-all cells TIL- same G-Rex 100MCS<br>Add 500 mL CM2 media<br>IL-2 (6000 IU/mL)<br>5 × 10$^8$ feeder cells/flask<br>30 μg OKT-3/flask |
| TIL propagation or Scale up | Volume reduce and split cell fraction in up to 5 G-REX 500MCS<br>4.5 L CM4 media + IL-2 (3000 IU/mL)<br>≥1 × 10$^9$ TVC/flask<br>Split day 16 | Each G-REX 100MCS(1 L) transfers to 1 G-REX 500MCS<br>Add 4 L CM4 media + IL-2 (3000 IU/mL)<br>Scale up on day 9 to 11 |
| Harvest | Harvest day 22,<br>LOVO-automated cell washer | Harvest day 16<br>LOVO-automated cell washer |
| Final formulation | Cryopreserved Product<br>300 IU/mL IL2-CS10 in $LN_2$,<br>multiple aliquots | Cryopreserved product<br>300 IU/mL IL-2-CS10 in $LN_2$,<br>multiple aliquots |
| Process time | 22 days | 16 days |

On day 0, for both processes, the tumor was washed 3 times and the fragments were randomized and divided into two pools; one pool per process. For the Gen 2 Process, the fragments were transferred to one GREX 100MCS flask with 1 L of CM1 media containing 6,000 IU/mL rhIL-2. For the Gen 3 Process, fragments were transferred to one GREX100MCS flask with 200-500 mL of CM1 containing 6,000 IU/mL rhIL-2, optionally 15 OKT-3 and $2.5\times10^8$ feeder cells.

Seeding of TIL for Rep initiation day occurred on different days according to each process. For the Gen 2 Process, in which the G-REX 100MCS flask was 90% volume reduced, collected cell suspension was transferred to a new G-REX 500MCS to start REP initiation on day 11 in CM2 media containing IL-2 (3000 IU/mL), plus 5e9 feeder cells and OKT-3 (30 ng/mL). Cells were expanded and split on day 16 into multiple GREX 500 MCS flasks with CM4 media with IL-2 (3000 IU/mL) per protocol. The culture was then harvested and cryopreserved on day 22 per protocol.

For the Gen 3 process, the REP initiation occurred on day 7, in which the same G-REX 100MCS used for REP initiation. Briefly, 200-500 mL of CM2 media containing IL-2 (6000 IU/mL) and $5\times10^8$ feeder cells with 30 μg OKT-3 was added to each flask. On day 9-11 the culture was scaled up. The entire volume of the G-Rex100M (1 L) was transferred to a G-REX 500MCS and 4 L of CM4 containing IL-2 (3000 IU/mL) was added. Flasks were incubated 5 days. Cultures were harvested and cryopreserved on Day 16.

In particular, seeding of TIL for Rep initiation day occurred on different days according to each process. For the Gen 2 Process, in which the G-REX 100MCS flask was 90% volume reduced, collected cell suspension was transferred to a new G-Rex 500MCS to start REP initiation on day 11 in CM2 media containing IL-2 (3000 IU/mL) plus 5e9 feeder cells and OKT-3 (30 ng/mL). Cells were expanded and split on day 16 into multiple G-Rex 500 MCS flasks with CM4 media containing IL-2 (3000 IU/mL) per protocol. The culture was then harvested and cryopreserved on day 22 per protocol.

In particular, seeding for the Gen 3 process, the REP initiation occurred on day 7, in which the same G-Rex 100MCS used for REP initiation. Briefly, 800 mL of CM2 media containing IL-2 (6000 IU/mL) and 1e9 feeder cells with 30 ug OKT-3 was added to each flask. On day 11 the culture was scaled-up for the three runs. The entire volume of the G-Rex100MCS was transferred to a G-Rex 500MCS and 4 L of CM4 containing IL-2 (3000 IU/mL) was added. Flasks were incubated 5 days. Cultures were harvested and cryopreserved on Day 16.

Three different tumors were included in the comparison, two lung tumors (L4054 and L4055) and one melanoma tumor (M1085T).

CM1 (culture media 1), CM2 (culture media 2), and CM4 (culture media 4) media were prepared in advance and held at 4° C. for L4054 and L4055. CM1 and CM2 media were prepared without filtration to compare cell growth with and without filtration of media.

Media was warmed at 37° C. up to 24 hours in advance for L4055 tumor on REP initiation and scale-up.

Results Summary

Gen 3 fell within 30% of Gen 2 for total viable cells achieved. Gen 3 final product exhibited higher production of INF-γ after restimulation. Gen 3 final product exhibited increased clonal diversity as measured by total unique CDR3 sequences present. Gen 3 final product exhibited longer mean telomere length.

Results Achieved

Cell Count and % Viability:

Pre REP and REP expansion on Gen 2 and Gen 3 processes followed details described above.

Table 22: Pre-REP cell counts. For each tumor, the two pools contained equal number of fragments. Due to the small size of tumors, the maximum number of fragments per flask was not achieved. Total pre-REP cells (TVC) were harvested and counted at day 11 for the Gen 2 process and at day 7 for the Gen 3 process. To compare the two pre-REP arms, the cell count was divided over the number of fragments provided in the culture in order to calculate an average of viable cells per fragment. As indicated in the table below, the Gen 2 process consistently grew more cells per fragment compared to the Gen 3 Process. An extrapolated calculation of the number of TVC expected for Gen 3 process at day 11, which was calculated dividing the pre-REP TVC by 7 and then multiply by 11.

TABLE 22 pre-REP cell counts

| | Tumor ID | | | | | |
|---|---|---|---|---|---|---|
| | L4054 | | L4055* | | M1085T | |
| Process | Gen 2 | Gen 3 | Gen 2 | Gen 3 | Gen 2 | Gen 3 |
| pre-REP TVC | 1.42E+08 | 4.32E+07 | 2.68E+07 | 1.38E+07 | 1.23E+07 | 3.50E+06 |
| Number of fragments | 21 | 21 | 24 | 24 | 16 | 16 |
| Average TVC per fragment at pre-REP harvest | 6.78E+06 | 2.06E+06 | 1.12E+06 | 5.75E+05 | 7.66E+05 | 2.18E+05 |

*L4055, unfiltered media.

Table 23: Total viable cell count and fold expansion on TIL final product: For the Gen 2 and Gen 3 processes, TVC was counted per process condition and percent viable cells was generated for each day of the process. On harvest, day 22 (Gen 2) and day 16 (Gen 3) cells were collected and the TVC count was established. The TVC was then divided by the number of fragments provided on day 0, to calculate an average of viable cells per fragment. Fold expansion was calculated by dividing harvest TVC by over the REP initiation TVC. As exhibited in the table, comparing Gen 2 and the Gen 3, fold expansions were similar for L4054; in the case of L4055, the fold expansion was higher for the Gen 2 process. Specifically, in this case, the media was warmed up 24 in advance of REP initiation day. A higher fold expansion was also observed in Gen 3 for M1085T. An extrapolated calculation of the number of TVC expected for Gen 3 process at day 22, which was calculated dividing the REP TVC by 16 and then multiply by 22.

TABLE 23

Total viable cell count and fold expansion on TIL final product

| | Tumor ID | | | | | |
|---|---|---|---|---|---|---|
| | L4054 | | L4055* | | M1085T | |
| Process | Gen 2 | Gen 3 | Gen 2 | Gen 3 | Gen 2 | Gen 3 |
| # Fragments | 21 | 21 | 24 | 24 | 16 | 16 |
| TVC at REP initiation | 1.42E+08 | 4.32E+07 | 2.68E+07 | 1.38E+07 | 1.23E+07 | 3.50E+06 |
| TVC at Scale-up (including feeders) | 3.36E+09 | 9.35E+08 | 3.49E+09 | 8.44E+08 | 1.99E+09 | 3.25E+08 |
| TVC at Harvest | 6.67E+10 | 1.84E+10 | 5.52E+10 | 8.76E+09 | 1.13E+10 | 7.68E+09 |
| Fold Expansion REP Harvest/ REP initiation | 468.4 | 425.9 | 2056.8 | 634.6 | 925.0 | 2197.2 |
| TVC/fragment (at REP Harvest) | 3.18E+09 | 8.77E+08 | 2.30E+09 | 3.65E+08 | 7.09E+08 | 4.80E+08 |

*L4055, unfiltered media.

Table 24: % Viability of TIL final product: Upon harvest, the final TIL REP products were compared against release criteria for % viability. All of the conditions for the Gen 2 and Gen 3 processes surpassed the 70% viability criterion and were comparable across processes and tumors.

TABLE 24

% Viability of REP

| | Tumor ID | | | | | |
|---|---|---|---|---|---|---|
| | L4054 | | L4055* | | M1085T | |
| Process | Gen 2 | Gen 3 | Gen 2 | Gen 3 | Gen 2 | Gen 3 |
| REP initiation | 98.23% | 97.97% | 97.43% | 92.03% | 81.85% | 68.27% |
| Scale up | 94.00% | 93.57% | 90.50% | 95.93% | 78.55% | 71.15% |
| Harvest | 87.95% | 89.85% | 87.50% | 86.70% | 86.10% | 87.45% |

*L4055, unfiltered media.

Table 25: Estimate cell count per additional flask for Gen 3 process. Due to the number of fragments per flask below the maximum required number, an estimated cell count at harvest day was calculated for each tumor. The estimation was based on the expectation that clinical tumors were large enough to seed 2 or 3 flasks on day 0.

TABLE 25

| Extrapolated estimate cell count calculation to full scale 2 and 3 flask on Gen 3 Process | | | | | | |
|---|---|---|---|---|---|---|
| | Tumor ID | | | | | |
| | L4054 | | L4055 | | M1085T | |
| Gen 3 Process | 2 flasks | 3 Flasks | 2 flasks | 3 Flasks | 2 flasks | 3 Flasks |
| Estimate Harvest | 3.68E+10 | 5.52E+10 | 1.75E+10 | 2.63E+10 | 1.54E+10 | 2.30E+10 |

Immunophenotyping:

Phenotypic Markers Comparison on TIL Final Product:

Three tumors L4054, L4055, and M1085T underwent TIL expansion in both the Gen 2 and Gen 3 processes. Upon harvest, the REP TIL final products were subjected to flow cytometry analysis to test purity, differentiation, and memory markers. For all the conditions the percentage of TCR a/b+ cells was over 90%.

Figure 3:
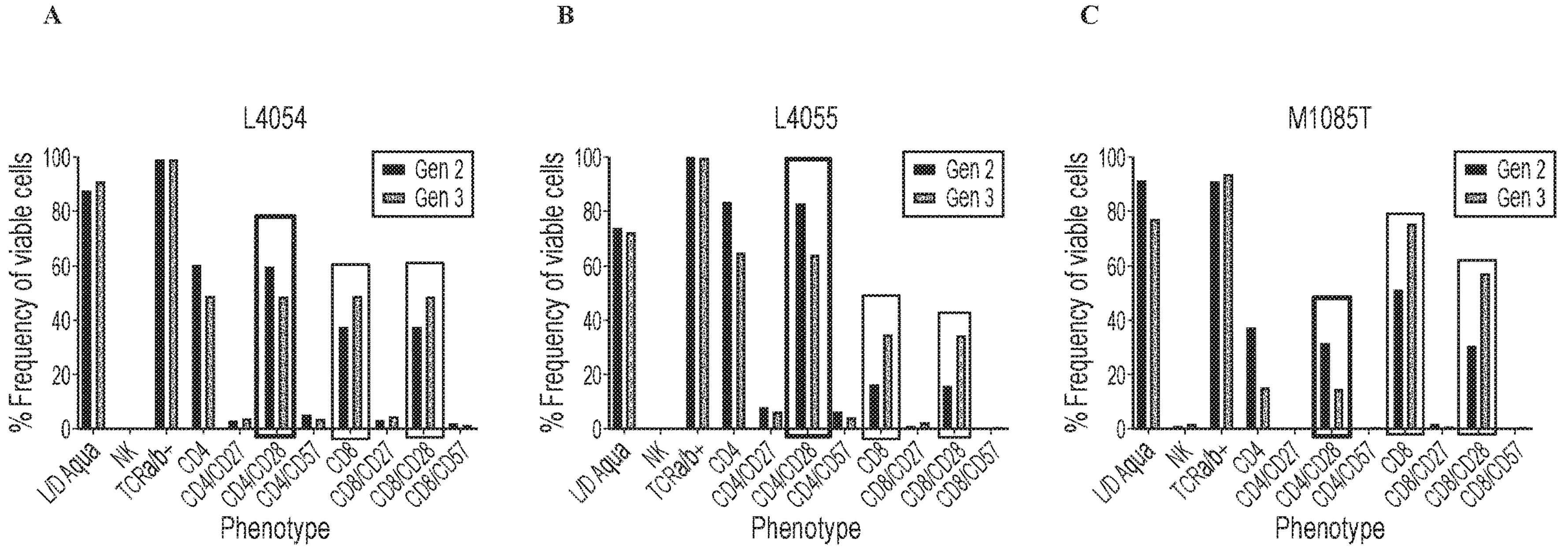
FIG. 3A-3C: A) L4054—Phenotypic characterization on TIL product on Gen 2 and Gen 3 process. B) L4055—Phenotypic characterization on TIL product on Gen 2 and Gen 3 process. C) M1085T—Phenotypic characterization on TIL product on Gen 2 and Gen 3 process.

TIL harvested from the Gen 3 process showed a higher expression of CD8 and CD28 compared to TIL harvested from the Gen 2 process. The Gen 2 process showed a higher percentage of CD4+. See, FIG. 3 (A, B, C).

Memory Markers Comparison on TIL Final Product:

TIL harvested from the Gen 3 process showed a higher expression on central memory compartments compared to TIL from the Gen 2 process. See, FIG. 4 (A, B, C).

Figure 6:
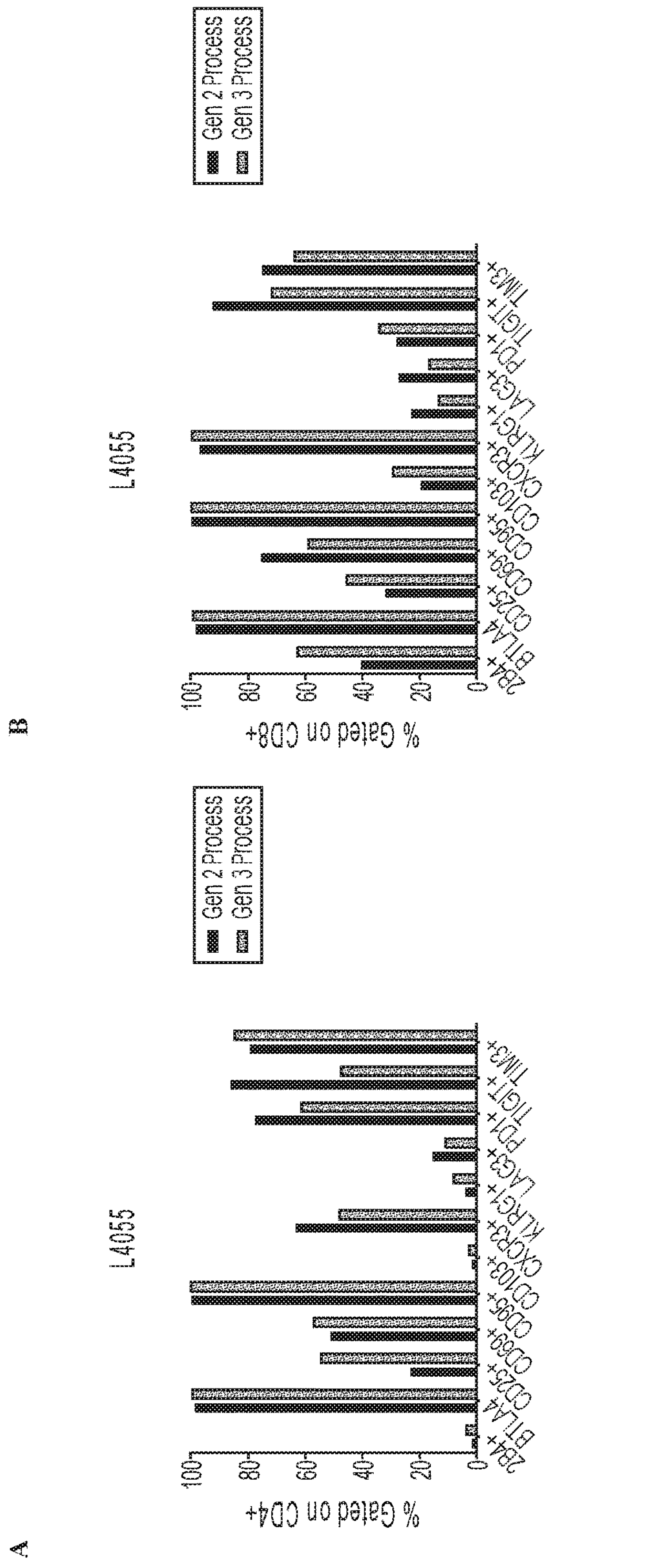
FIG. 6: L4055 Activation and exhaustion markers (A) Gated on CD4+, (B) Gated on CD8+.

Activation and Exhaustion Markers Comparison on TIL Final Product:

Activation and exhaustion marker were analyzed in TIL from two, tumors L4054 and L4055 to compare the final TIL product by from the Gen 2 and Gen 3 TIL expansion processes. Activation and exhaustion markers were comparable between the Gen 2 and Gen 3 processes. See, FIG. 5 (A, B); FIG. 6 (A, B).

Interferon Gamma Secretion Upon Restimulation:

On harvest day, day 22 for Gen 2 and day 16 for Gen 3, TIL underwent an overnight restimulation with coated anti-CD3 plates for L4054 and L4055. The restimulation on M1085T was performed using anti-CD3, CD28, and CD137 beads. Supernatant was collected after 24 hours of the restimulation in all conditions and the supernatant was frozen. IFNγ analysis by ELISA was assessed on the supernatant from both processes at the same time using the same ELISA plate. Higher production of IFNγ from the Gen 3 process was observed in the three tumors analyzed. See, FIG. 7 (A, B, C).

Figure 8:
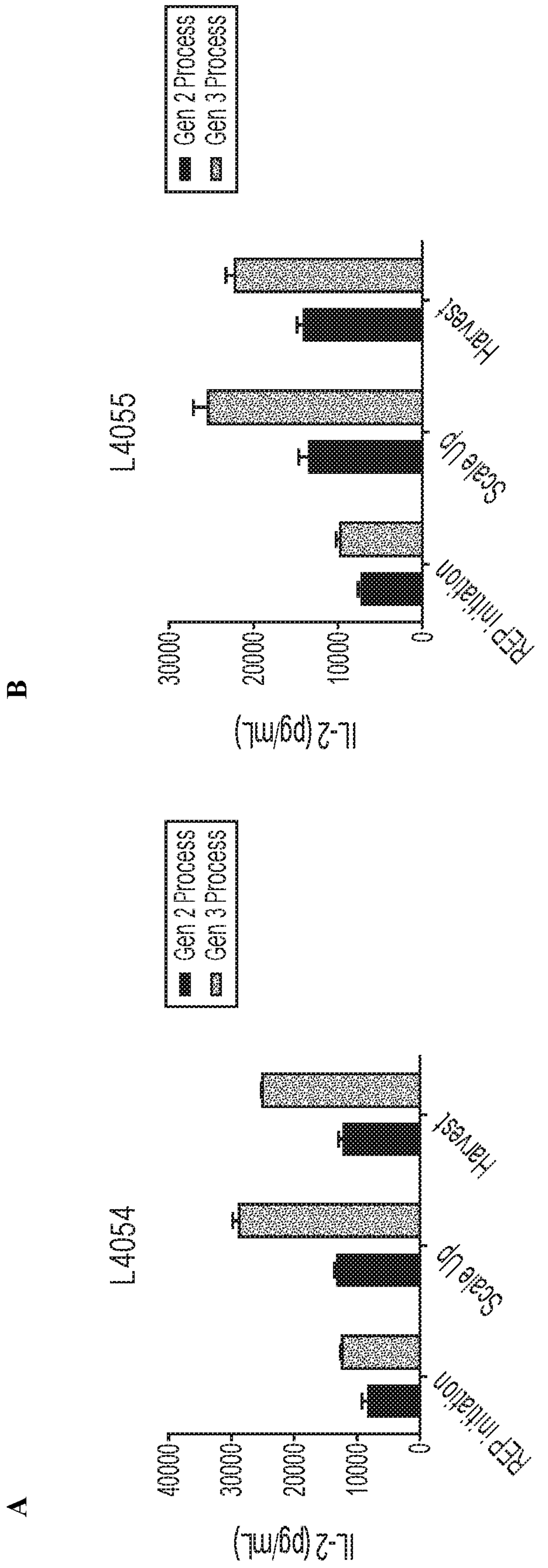
FIG. 8: ELISA analysis of IL-2 concentration in cell culture supernatant: (A) L4054 and (B) L4055. Each bar represented here is mean+SEM for IL-2 levels on spent media. Optical density measured at 450 nm.

Measurement of IL-2 Levels in Culture Media:

To compare the IL-2 consumption between Gen 2 and Gen 3 process, cell supernatant was collected on REP initiation, scale up, and harvest day, on tumor L4054 and L4055. The quantity of IL-2 in cell culture supernatant was measured by Quantitate ELISA Kit from R&D. The general trend indicates that the IL-2 concentration remains higher in the Gen 3 process when compared to the Gen 2 process. This is likely due to the higher concentration of IL-2 on REP initiation (6000 IU/mL) for Gen 3 coupled with the carry-over of the media throughout the process. See, FIG. 8 (A, B).

Metabolic Substrate and Metabolite Analysis

Figure 9:
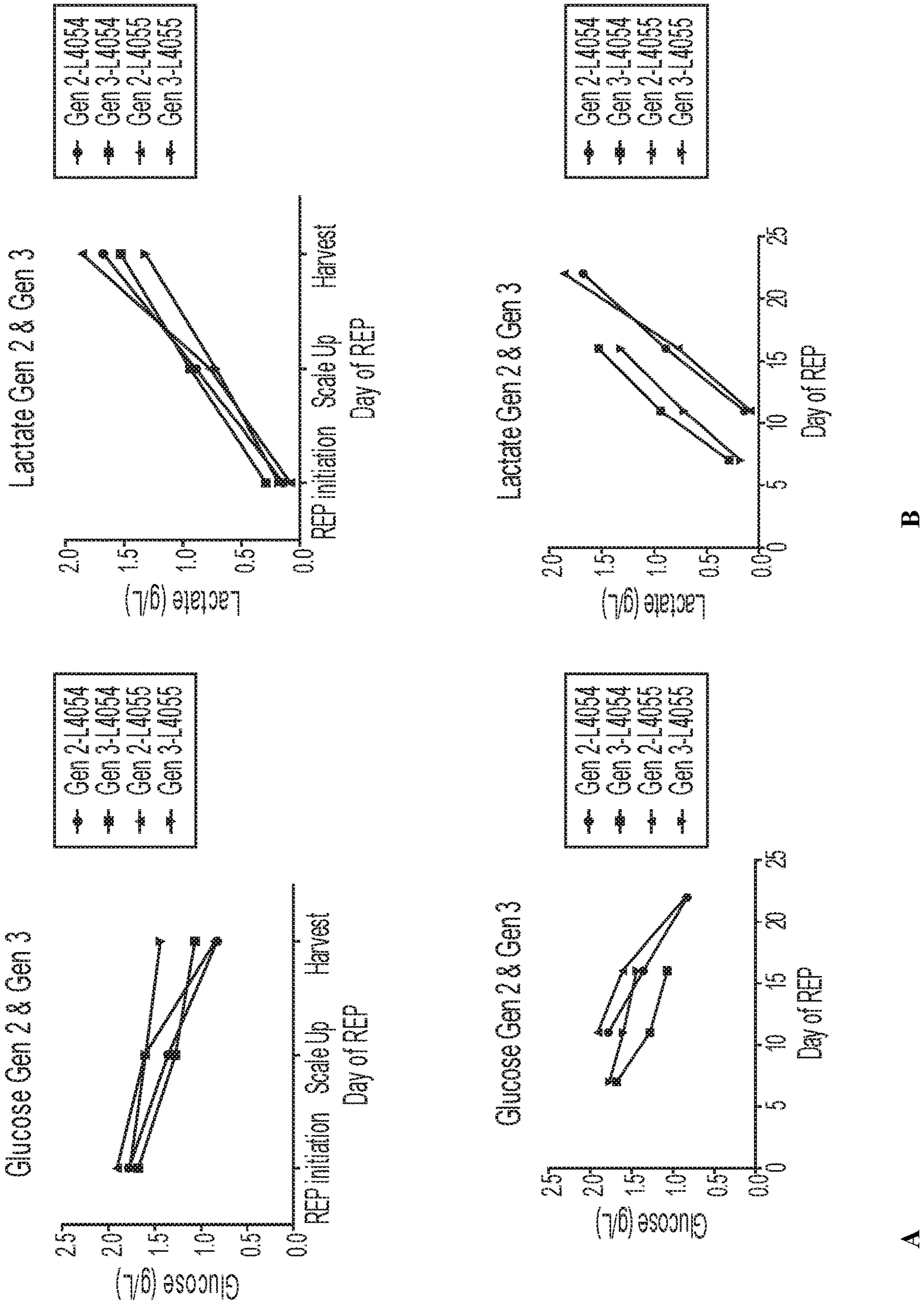
FIG. 9: Quantification of glucose and lactate (g/L) in spent media: (A) Glucose and (B) Lactate: In the two tumor lines, and in both processes, a decrease in glucose was observed throughout the REP expansion. Conversely, as expected, an increase in lactate was observed. Both the decrease in glucose and the increase in lactate were comparable between the Gen 2 and Gen 3 processes.
Figure 11:
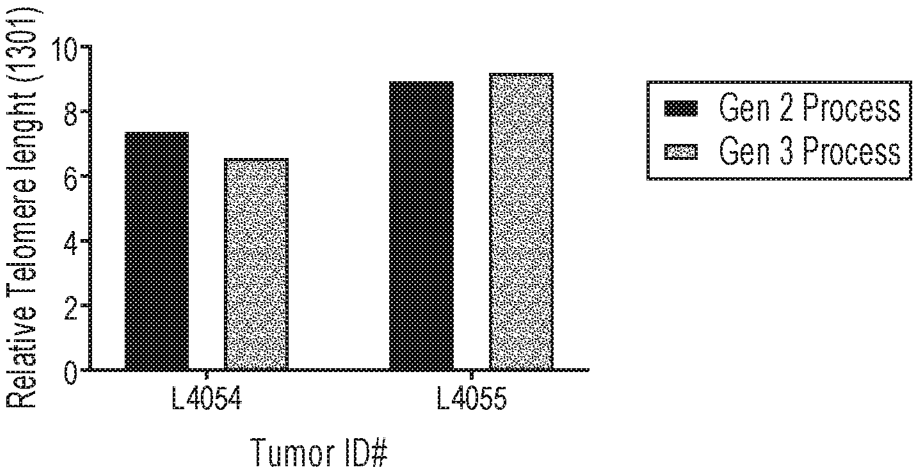
FIG. 11: Telomere length analysis. The relative telomere length (RTL) value indicates that the average telomere fluorescence per chromosome/genome in Gen 2 and Gen 3 process of the telomere fluorescence per chromosome/genome in the control cells line (1301 Leukemia cell line) using DAKO kit.

The levels of metabolic substrates such as D-glucose and L-glutamine were measured as surrogates of overall media consumption. Their reciprocal metabolites, such lactic acid and ammonia, were measured. Glucose is a simple sugar in media that is utilized by mitochondria to produce energy in the form of ATP. When glucose is oxidized, lactic acid is produced (lactate is an ester of lactic acid). Lactate is strongly produced during the cells exponential growth phase. High levels of lactate have a negative impact on cell culture processes. See, FIG. 9 (A, B).

Spent media for L4054 and L4055 was collected at REP initiation, scale up, and harvest days for both process Gen 2 and Gen 3. The spent media collection was for Gen 2 on Day 11, day 16 and day 22; for Gen 3 was on day 7, day 11 and day 16. Supernatant was analyzed on a CEDEX Bio-analyzer for concentrations of glucose, lactic acid, glutamine, glutamax, and ammonia.

L-glutamine is an unstable essential amino acid required in cell culture media formulations. Glutamine contains an amine, and this amide structural group can transport and deliver nitrogen to cells. When L-glutamine oxidizes, a toxic ammonia by-product is produced by the cell. To counteract the degradation of L-glutamine the media for the Gen 2 and Gen 3 processes was supplemented with Glutamax, which is more stable in aqueous solutions and does not spontaneously degrade. In the two tumor lines, the Gen 3 arm (16-day process) showed a decrease in L-glutamine and Glutamax during the process and an increase in ammonia throughout the REP. In the Gen 2 arm (22-day process) a constant concentration of L-glutamine and Glutamax, and a slight increase in the ammonia production was observed. The Gen 2 and Gen 3 processes were comparable at harvest day (22 for Gen 2; 16 for Gen 3) for ammonia and showed a slight difference in L-glutamine degradation. See, FIG. 10 (A, B, C).

Telomere Repeats by Flow-FISH:

Flow-FISH technology was used to measure the average length of the telomere repeat on L4054 and L4055 under Gen 2 and Gen 3 process. The determination of a relative telomere length (RTL) was calculated using Telomere PNA kit/FITC for flow cytometry analysis from DAKO. Gen 3 showed comparable telomere length to Gen 2.

CD3 Analysis

To determine the clonal diversity of the cell products generated in each process, TIL final product harvested for L4054 and L4055, were sampled and assayed for clonal diversity analysis through sequencing of the CDR3 portion of the T-cell receptors.

Table 26: Comparison of Gen 2 and Gen3 of percentage shared unique CDR3 sequences on L4054 on TIL harvested cell product. 199 sequences are shared between Gen 3 and Gen 2 final product, corresponding to 97.07% of top 80% of unique CDR3 sequences from Gen 2 shared with Gen 3 final product.

TABLE 26

Comparison of shared uCDR3 sequences between Gen 2 and Gen 3 processes on L4054.

| | # uCDR3 (% Overlap) | | | |
|---|---|---|---|---|
| | All uCDR3's | | Top 80% uCDR3's | |
| | Gen 2 | Gen 3 | Gen 2 | Gen 3 |
| Gen 2-L4054 | 8915 | 4355 (48.85%) | 205 | 199 (97.07%) |
| Gen 3-L4054 | — | 18130 | — | 223 |

Table 27: Comparison of Gen 2 and Gen3 of percentage shared unique CDR3 sequences on L4055 on TIL harvested cell product. 1833 sequences are shared between Gen 3 and Gen 2 final product, corresponding to 99.45% of top 80% of unique CDR3 sequences from Gen 2 shared with Gen 3 final product.

TABLE 27

Comparison of shared uCDR3 sequences between Gen 2 and Gen 3 processes on L4055.

| | # uCDR3 (% Overlap) | | | |
|---|---|---|---|---|
| | All uCDR3's | | Top 80% uCDR3's | |
| | Gen 2 | Gen 3 | Gen 2 | Gen 3 |
| Gen 2-L4055 | 12996 | 6599 (50.77%) | 1843 | 1833 (99.45%) |
| Gen 3-L4055 | — | 27246 | — | 2616 |

CM1 and CM2 media was prepared in advanced without filtration and held at 4° C. until use for tumor L4055 to use on Gen 2 and Gen 3 process.

Media was warmed up at 37° C. for 24 hours in advance for tumor L4055 on REP initiation day for Gen 2 and Gen 3 process.

LDH was not measured in the supernatants collected on the processes.

M1085T TIL cell count was executed with K2 cellometer cell counter.

On tumor M1085T, samples were not available such as supernatant for metabolic analysis, TIL product for activation and exhaustion markers analysis, telomere length and CD3-TCR vb Analysis.

Conclusions

This example compares 3 independent donor tumors tissue in terms of functional quality attributes, plus extended phenotypic characterization and media consumption among Gen 2 and Gen 3 processes.

Gen 2 and Gen 3 pre-REP and REP expansion comparison were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

An extrapolated cell number was calculated for the Gen 3 process that assumed the pre-REP harvest occurred at day 11 instead of day 7 and the REP Harvest at Day 22 instead of day 16. Both cases showed closer numbers of TVC using the Gen 3 process as compared to the Gen 2 process, which indicated that the early activation allowed for an overall better performance on TIL growth. See, Table 4 and 5, bottom row.

In the case of extrapolated value for extra flasks (2 or 3) on Gen 3 process assuming a bigger size of tumor processed, and reaching the maximum number of fragments required per process as described. It was observed that a similar dose can be reachable on TVC at Day 16 Harvest for Gen 3 process compared to Gen 2 process at Day 22. This observation is important and indicates an early activation of the culture can allow better performance of TIL in less processing time.

Gen 2 and Gen 3 pre-REP and REP expansion comparisons were evaluated in terms of total viable cells generated and viability of the total nucleated cell population. TVC cell doses at harvest day was not comparable between Gen 2 (22 days) and Gen 3 (16 days). Gen 3 cell doses were lower than Gen 2 at around 40% of total viable cells collected at harvest.

In terms of phenotypic characterization, a higher CD8+ and CD28+ expression was observed on three tumors on Gen 3 process compared to Gen 2 process. This data indicates the Gen 3 process has improved attributes of final TIL product compared to Gen 2.

Gen 3 process showed slightly higher central memory compartments compared to Gen 2 process.

Gen 2 and Gen 3 process showed comparable activation and exhaustion markers, despite the shorter duration of the Gen 3 process.

IFN gamma (IFNγ) production was 3 times higher on Gen 3 final product compared to Gen 2 in the three tumors analyzed. This data indicates the Gen 3 process generated a highly functional and more potent TIL product as compared to the Gen 2 process, possibly due to the higher expression of CD8 and CD28 expression on Gen 3. IFN-γ production was 3 times higher on Gen 3 final product compared to Gen 2 in the three tumors analyzed suggesting the Gen 3 process generated highly functional TIL. Phenotypic characterization suggested positive trends in Gen 3 toward CD8+, CD28+ expression on three tumors compared to Gen 2 process.

Telomere length on TIL final product between Gen 2 and Gen 3 were comparable.

Glucose and Lactate levels were comparable between Gen 2 and Gen 3 final product, suggesting the levels of nutrients on the media of Gen 3 process were not affected due to the non-execution of volume reduction removal in each day of the process and less volume media overall in the process, compared to Gen 2.

Overall Gen 3 process showed a reduction almost two times of the processing time compared to Gen 2 process, which would yield a substantial reduction on the cost of goods (COGs) for TIL product expanded by the Gen 3 process.

IL-2 consumption indicates a general trend of IL-2 consumption on Gen 2 process, and in Gen 3 process IL-2 was higher due to the non-removal of the old media.

The Gen 3 process showed a higher clonal diversity measured by CDR3 TCRab sequence analysis.

The addition of feeders and OKT-3 on day 0 of the pre-REP allowed an early activation of TIL and overall a better growth TIL performance using the Gen 3 process.

Table 28 describes various embodiments and outcomes for the Gen 3 process as compared to the current Gen 2 process:

TABLE 28

| Exemplary Gen 3 process. | | |
|---|---|---|
| Step | Process Gen 2 | Process Gen 3-Optimized |
| Pre REP-day 0 | ≤50 fragments<br>1X G-Rex 100MCS<br>1 L media<br>IL-2 (6000 IU/mL)<br>11 days | ≤240 fragments<br>≤60 fragments/flask<br>≤4 flasks<br>≤2 L media (500 mL/flask)<br>IL-2 (6000 IU/mL)<br>2.5 × $10^8$ feeder cells/flask<br>15 μg OKT3/flask |
| REP Initiation | Fresh TIL direct to REP<br>Day 11<br>≤200e$^6$ viable cells<br>5 × $10^9$ feeder cells<br>G-Rex 500MCS<br>5 L CM2 media + IL-2 (3000 IU/mL)<br>150 μg OKT3 | Fresh TIL direct to REP<br>Day 7<br>Activate entire culture<br>5 × $10^8$ feeder cells<br>30 μg OKT3/flask<br>G-Rex 100MCS<br>500 mL media + IL-2(6000 IU/mL) |
| TIL Sub-culture or Scale up | ≤5 G-REX 500MCS<br>≤1 × 10 viable cells/flask<br>5 L/flask<br>Day 16 | ≤4 G-REX 500MCS<br>Scale up entire culture<br>4 L/flask<br>Day 10-11 |
| Harvest | Harvest Day 22,<br>LOVO-automated cell washer<br>2 wash cycles | Harvest Day 16<br>LOVO-automated cell washer<br>5 wash cycles |
| Final formulation | Cryopreserved Product<br>300 IU/mL IL2-CS10 in $LN_2$,<br>multiple aliquots | Cryopreserved product<br>300 IU/mL IL-2-CS10 in $LN_2$,<br>multiple aliquots |
| Process time | 22 days | 16 days |

Example 6: An Exemplary Embodiment of Selecting and Expanding PBLS from PBMCS in CLL Patients PBMCs are collected from patients and either frozen for later use, or used fresh. Enough volume of peripheral blood is collected to yield at least about 400,000,000 ($400\times10^6$) PBMCs for starting material in the method of the present invention. On Day 0 of the method, IL-2 at $6\times10^6$ IU/mL is either prepared fresh or thawed, and stored at 4° C. or on ice until ready to use. 200 mL of CM2 medium is prepared by combining 100 mL of CM1 medium (containing GlutaMAX®), then diluting it with 100 mL (1:1) with AIM-V to make CM2. The CM2 is protected from light, and sealed tightly when not in use.

All of the following steps are performed under sterile cell culture conditions. An aliquot of CM2 is warmed in a 50 mL conical tube in a 37° C. water bath for use in thawing and/or washing a frozen PBMC sample. If a frozen PBMC sample is used, the sample is removed from freezer storage and kept on dry ice until ready to thaw. When ready to thaw the PBMC cryovial, 5 mL of CM2 medium is placed in a sterile 50 mL conical tube. The PBMC sample cryovial is placed in a 37° C. water bath until only a few ice crystals remain. Warmed CM2 medium is added, dropwise, to the sample vial in a 1:1 volume ratio of sample:medium (about 1 mL). The entire contents is removed from the cryovial and transferred to the remaining CM2 medium in the 50 mL conical tube. An additional 1-2 mL of CM2 medium is used to rinse the cryovial and the entire contents of the cryovial is removed and transferred to the 50 mL conical tube. The volume in the conical tube is then adjusted with additional CM2 medium to 15 mL, and swirled gently to rinse the cells. The conical tube is then centrifuged at 400 g for 5 minutes at room temperature in order to collect the cell pellet.

The supernatant is removed from the pellet, the conical tube is capped, and then the cell pellet is disrupted by, for example, scraping the tube along a rough surface. About 1 mL of CM2 medium is added to the cell pellet, and the pellet and medium are aspirated up and down 5-10 times with a pipette to break up the cell pellet. An additional 3-5 mL of CM2 medium is added to the tube and mixed via pipette to suspend the cells. At this point, the volume of the cell suspension is recorded. Remove 100 μL of the cell suspension from the tube for cell counting with an automatic cell counter, for example, a Nexcelom Cellometer K2. Determine the number of live cells in the sample and record.

Reserve a minimum of $5\times10^6$ cells for phenotyping and other characterization experiments. Spin the reserved cells at 400 g for 5 minutes at room temperature to collect the cell pellet. Resuspend the cell pellet in freezing medium (sterile, heat-inactivated FBS containing 20% DMSO). Freeze one or two aliquots of the reserved cells in freezing medium, and slow-freeze the aliquots in a cell freezer (Mr. Frosty™) in a −80° C. freezer. Transfer to liquid nitrogen storage after a minimum of 24 hours at −80° C.

For the following steps, use pre-cooled solutions, work quickly, and keep the cells cold. The next step is to purify the T-cell fraction of the PBMC sample. This is completed using a Pan T-cell Isolation Kit (Miltenyi, catalog #130-096-535). Prepare the cells for purification by washing the cells with a sterile-filtered wash buffer containing PBS, 0.5% BSA, and 2 mM EDTA at pH 7.2. The PBMC sample is centrifuged at 400 g for 5 minutes to collect the cell pellet. The supernatant is aspirated off and the cell pellet is resuspended in 40 uL of wash buffer for every $10^7$ cells. Add 10 μL of Pan T Cell Biotin-Antibody Cocktail for every $10^7$ cells. Mix well and incubate for 5 minutes in refrigerator or on ice. Add 30 μL of wash buffer for every $10^7$ cells. Add 20 uL of Pan T-cell MicroBead Cocktail for every $10^7$ cells. Mix well and incubate for 10 minutes in refrigerator or on ice. Prepare an LS column and magnetically separate cells from the microbeads. The LS column is placed in the QuadroMACS magnetic field. The LS column is washed with 3 mL of cold wash buffer, and the wash is collected and discarded. The cell suspension is applied to the column and the flow-through (unlabeled cells) is collected. This flow-through is the enriched T-cell fraction (PBLs). Wash the column with 3 mL of wash buffer and collect the flow-through in the same tube as the initial flow-through. Cap the tube and place on ice. This is the T-cell fraction, or PBLs. Remove the LS column from the magnetic field, wash the column with 5 mL of wash buffer, and collect the non-T-cell fraction (magnetically labeled cells) into another tube. Centrifuge both fractions at 400 g for 5 minutes to collect the cell pellets. Supernatants are aspirated from both samples, disrupt the pellet, and resuspend the cells in 1 mL of CM2 medium supplemented with 3000 IU/mL IL-2 to each pellet, and pipette up and down 5-10 times to break up the pellets. Add 1-2 mL of CM2 to each sample, and mix each sample well, and store in tissue culture incubator for next steps. Remove about a 50 μL aliquot from each sample, count cells, and record count and viability.

The T-cells (PBLs) are then cultured with Dunabeads™ Human T-Expander CD3/CD28. A stock vial of Dynabeads is vortexed for 30 seconds at medium speed. A required aliquot of beads is removed from the stock vial into a sterile 1.5 mL microtube. The beads are washed with bead wash solution by adding 1 mL of bead wash to the 1.5 mL microtube containing the beads. Mix gently. Place the tube onto the DynaMag™-2 magnet and let sit for 30 minutes while beads draw toward the magnet. Aspirate the wash solution off the beads and remove tube from the magnet. 1 mL of CM2 medium supplemented with 3000 IU/mL IL-2 is added to the beads. The entire contents of the microtube is transferred to a 15 or 50 mL conical tube. Bring the beads to a final concentration of about 500,000/mL using CM2 medium with IL-2.

The T-cells (PBLs) and beads are cultured together as follows. On day 0: In a G-Rex 24 well plate, in a total of 7 mL per well, add 500,000 T-cells, 500,000 CD3/CD28 Dynabeads, and CM2 supplemented with IL-2. The G-Rex plate is placed into a humidified 37° C., 5% $CO_2$ incubator until the next step in the process (on Day 4). Remaining cells are frozen in CS10 cryopreservation medium using a Mr. Frosty™ cell freezer. The non-T-cell fraction of cells are frozen in CS10 cryopreservation medium using a Mr. Frosty cell freezer. On day 4, medium is exchanged. Half of the medium (about 3.5 mL) is removed from each well of the G-rex plate. A sufficient volume (about 3.5 mL) of CM4 medium supplemented with 3000 IU/mL IL-2 warmed to 37° C. is added to replace the medium removed from each sample well. The G-rex plate is returned to the incubator.

On day 7, cells are prepared for expansion by REP. The G-rex plate is removed from the incubator and half of medium is removed from each well and discarded. The cells are resuspended in the remaining medium and transferred to a 15 mL conical tube. The wells are washed with 1 mL each of CM4 supplemented with 3000 IU/mL IL-2 warmed to 37° C. and the wash medium is transferred to the same 15 mL tube with the cells. A representative sample of cells is removed and counted using an automated cell counter. If there are less than $1\times10^6$ live cells, the Dynabead expansion process at Day 0 is repeated. The remainder of the cells are frozen for back-up expansion or for phenotyping and other characterization studies. If there are $1\times10^6$ live cells or more, the REP expansion is set up in replicate according to the protocol from Day 0. Alternatively, with enough cells, the expansion may be set up in a G-rex 10M culture flask using $10\text{-}15\times10^6$ PBLs per flask and a 1:1 ratio of Dynabeads: PBLs in a final volume of 100 mL/well of CM4 medium supplemented with 3000 IU/mL IL-2. The plate and/or flask is returned to the incubator. Excess PBLs may be aliquotted and slow-frozen in a Mr. Frosty™ cell freezer in a −80° C. freezer, and the transferred to liquid nitrogen storage after a minimum of 24 hours at −80° C. These PBLs may be used as back-up samples for expansion or for phenotyping or other characterization studies.

On Day 11, the medium is exchanged. Half of the medium is removed from either each well of the G-rex plate or the flask and replaced with the same amount of fresh CM4 medium supplemented with 3000 IU/mL IL-2 at 37° C.

On Day 14, the PBLs are harvested. If the G-rex plate is used, about half of the medium is removed from each well of the plate and discarded. The PBLs and beads are suspended in the remaining medium and transferred to a sterile 15 mL conical tube (Tube 1). The wells are washed with 1-2 mL of fresh AIM-V medium warmed to 37° C., and the wash is transferred to Tube 1. Tube 1 is capped and placed in the DynaMag™-15 Magnet for 1 minute to allow the beads to be drawn to the magnet. The cell suspension is transferred into a new 15 mL tube (Tube 2), and the beads are washed with 2 mL of fresh AIM-V at 37° C. Tube 1 is placed back in the magnet for an additional 1 minute, and the wash medium is then transferred to Tube 2. The wells may be combined if desired, after the final washing step. Remove a representative sample of cells and count, record count and viability. Tubes may be placed in the incubator while counting. Additional AIM-V medium may be added to the Tube 2 if cells appear very dense. If a flask is used, the volume in the flask should be reduced to about 10 mL. The contents of the flask is mixed and transferred to a 15 mL conical tube (Tube A). The flask is washed with 2 mL of the AIM-V medium as described above and the wash medium is also transferred to Tube A. Tube A is capped and placed in the DynaMag™-15 Magnet for 1 minute to allow the beads to be drawn to the magnet. The cell suspension is transferred into a new 15 mL tube (Tube B), and the beads are washed with 2 mL of fresh AIM-V at 37° C. Tube A is placed back in the magnet for an additional 1 minute, and the wash medium is then transferred to Tube B. The wells may be combined if desired, after the final washing step. Remove a representative sample of cells and count, record count and viability. Tubes may be placed in the incubator while counting. Additional AIM-V medium may be added to the Tube B if cells appear very dense. Cells may be used fresh or frozen in CS10 preservation medium at desired concentrations.

Example 7: An Exemplary Embodiment of Expanding T Cells from Hematopoietic Malignances Using Gen 3 Expansion Platform At Day 0, a T cell fraction (CD3+,CD45+) is isolated from an apheresis product enriched for lymphocytes, whole blood, or tumor digest (fresh or thawed) using positive or negative selection methods, i.e removing the T-cells using a T-cell marker (CD2, CD3, etc, or removing other cells leaving T-cells), or gradient centrifugation.

The Gen 3.1 process is commenced by seeding $\sim1\times10^7$ cells/flask according to Gen3 process described herein.

At Day 7, the cells are reactivated per the Gen 3.1 process.

At Day 9-11, the cells are scaled up per the Gen 3.1 process.

At Day 14-16, the cells are harvested per the Gen 3.1 process.

Figure 42:
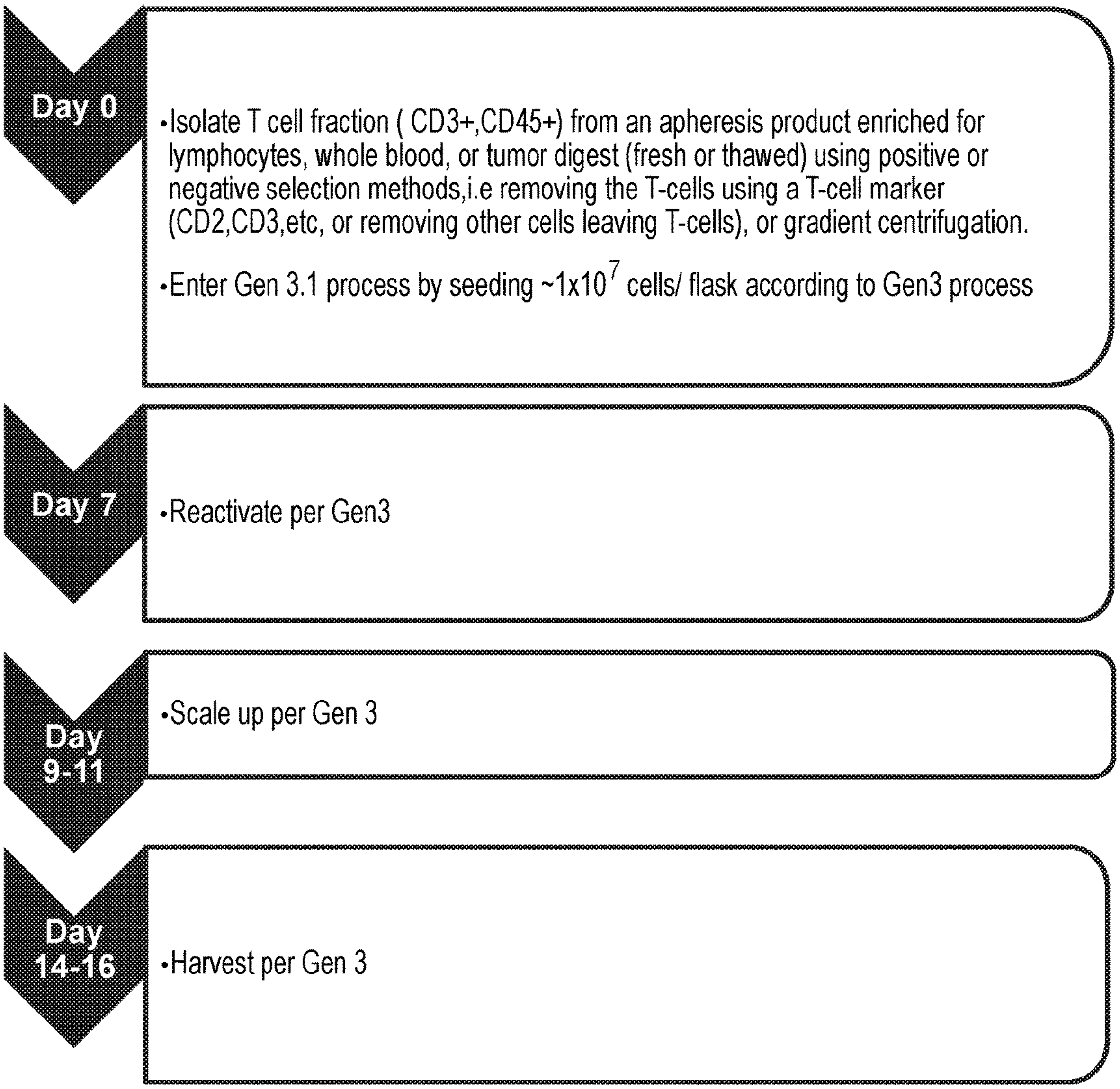
FIG. 42: Schematic of an exemplary embodiment for expanding TILs from hematopoietic malignancies using the Gen 3 process. At Day 0, a T cell fraction (CD3+, CD45+) is isolated from an apheresis product enriched for lymphocytes, whole blood, or tumor digest (fresh or thawed) using positive or negative selection methods, i.e., removing the T-cells using a T-cell marker (CD2, CD3, etc., or removing other cells leaving T-cells), or gradient centrifugation.
Figure 43:
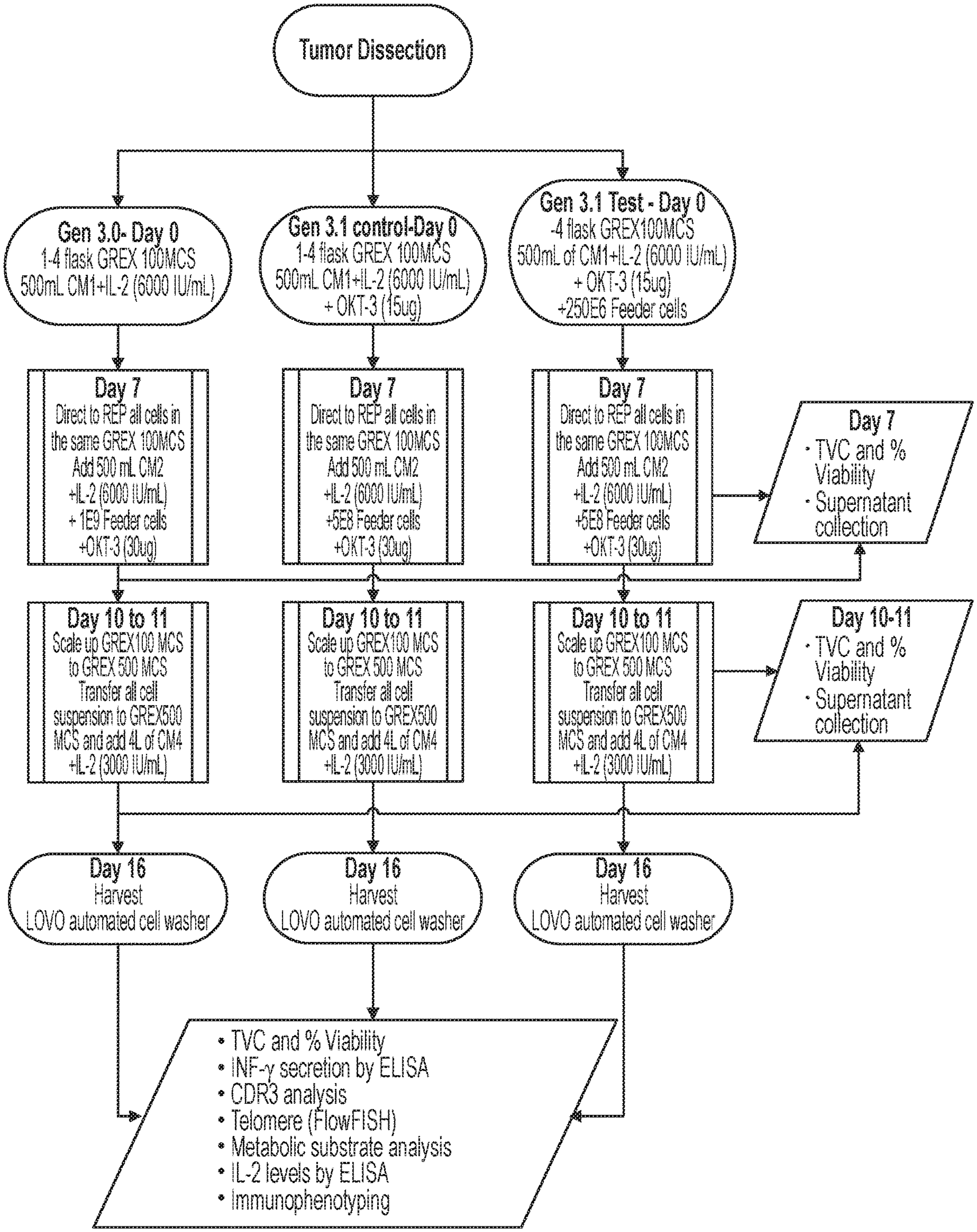
FIG. 43: Schematic of an exemplary embodiment of the Gen 3 process (a 16-day process).
Figure 46:
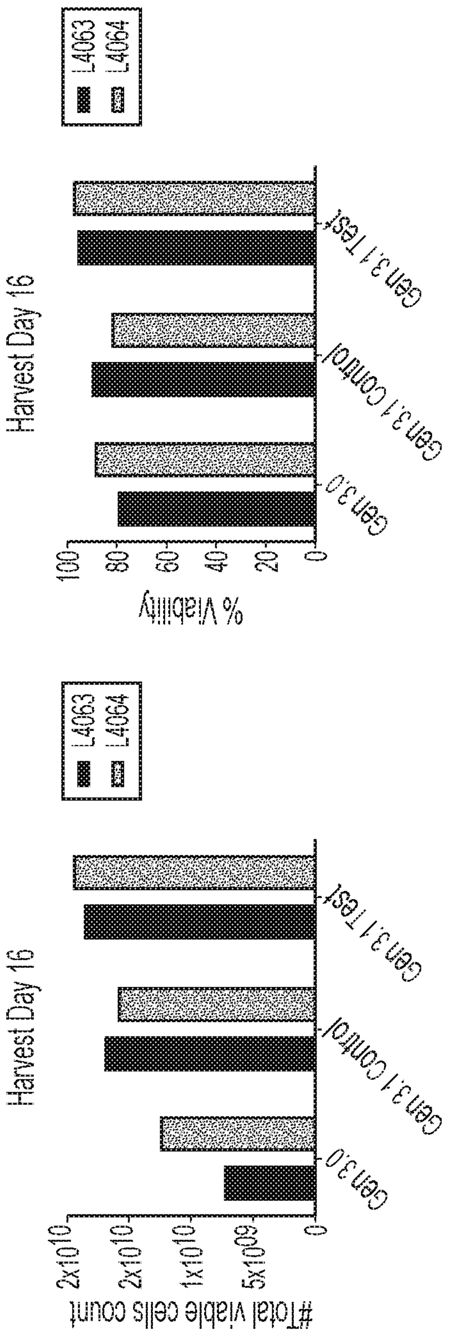
FIG. 46: Bar graph depicting total viable cell count (TVC) and percent viability for exemplary embodiments of the Gen 3 process (Gen 3.0, Gen 3.1 Control, Gen 3.1 Test), a 16-day process.
Figure 47:
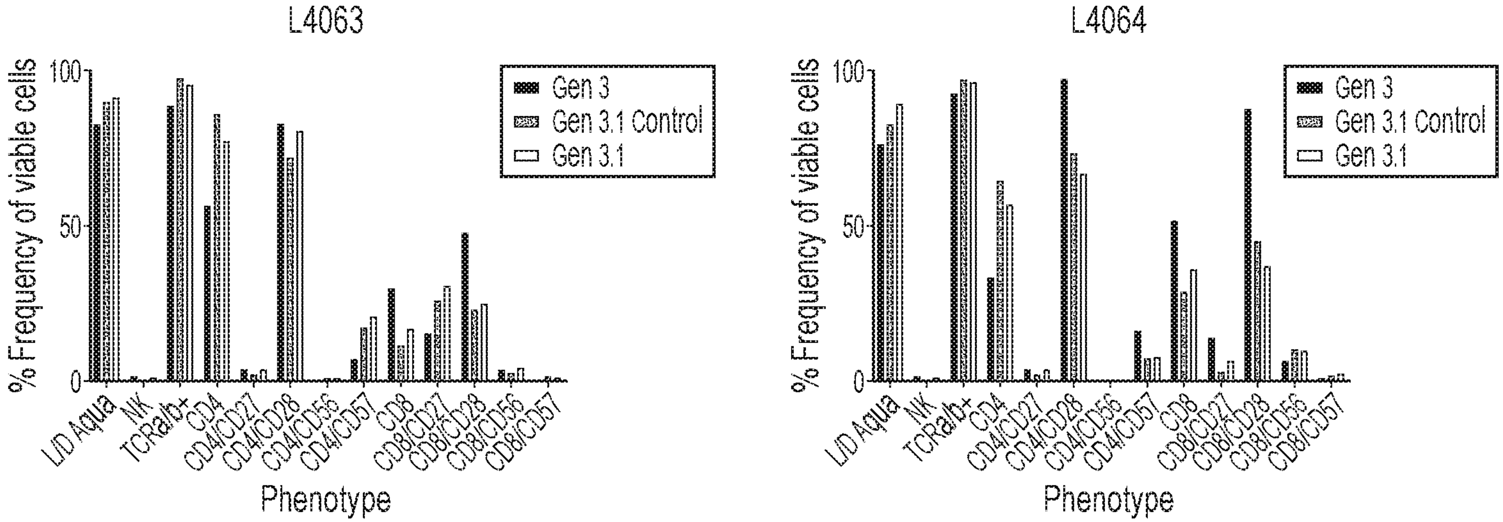
FIG. 47: Provides data showing that exemplary embodiments of the Gen 3 process (Gen 3.0, Gen 3.1 Control and Gen 3.1 Test) yielded cells that showed comparable CD28, CD27 and CD57 expression.
Figure 48:
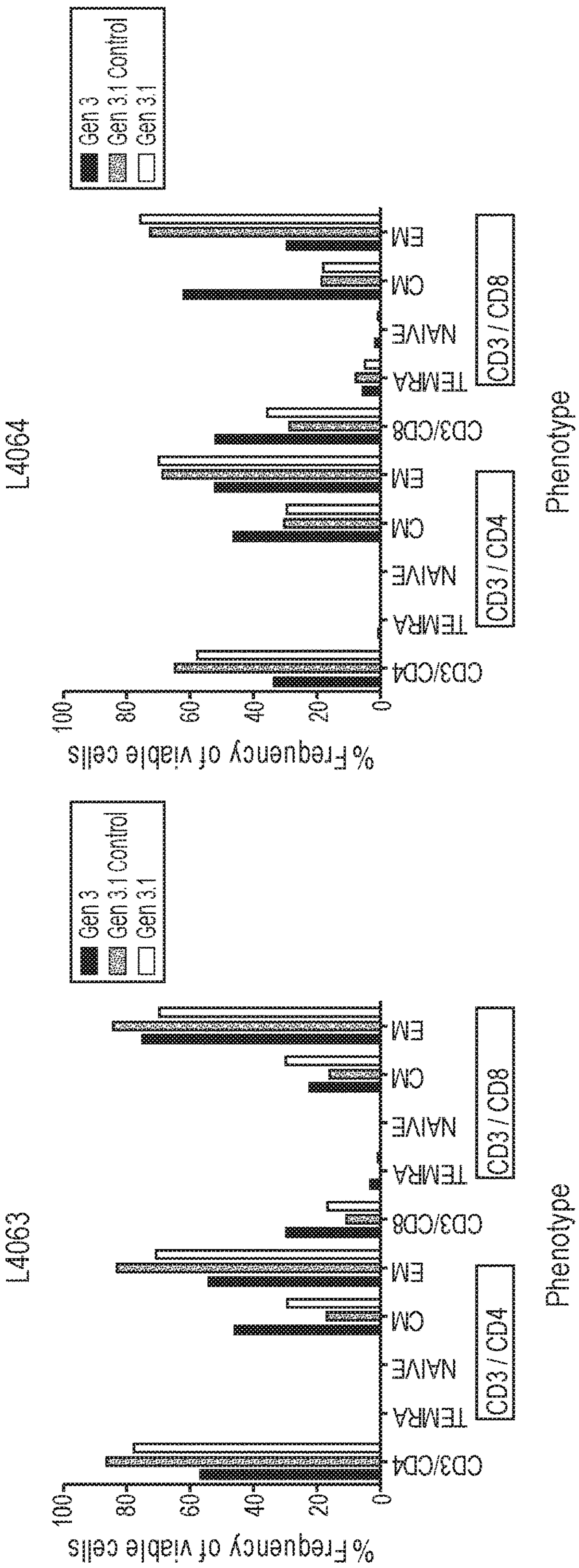
FIG. 48: Provides data showing TIL memory statuses were comparable across cells yielded by exemplary embodiments of the Gen 3 process (Gen 3.0, Gen 3.1 Control, and Gen 3.1 Test). Memory statuses of REP TIL are depicted as follows: CD4+ or CD8+ TIL Memory subsets were divided into different memory subsets. Naïve (CD45RC=CD62L+), CM: Central memory (CD45RA−CD62L+), EM: Effector memory (CD45RA−CD62L−), TEMRA/TEFF: RA+ Effector memory/Effectors (CD45RA+CD62L+). Bar graph presented are percentage positive CD45+/−CD62L+/− when gated on CD4+ or CD8+.
Figure 49:
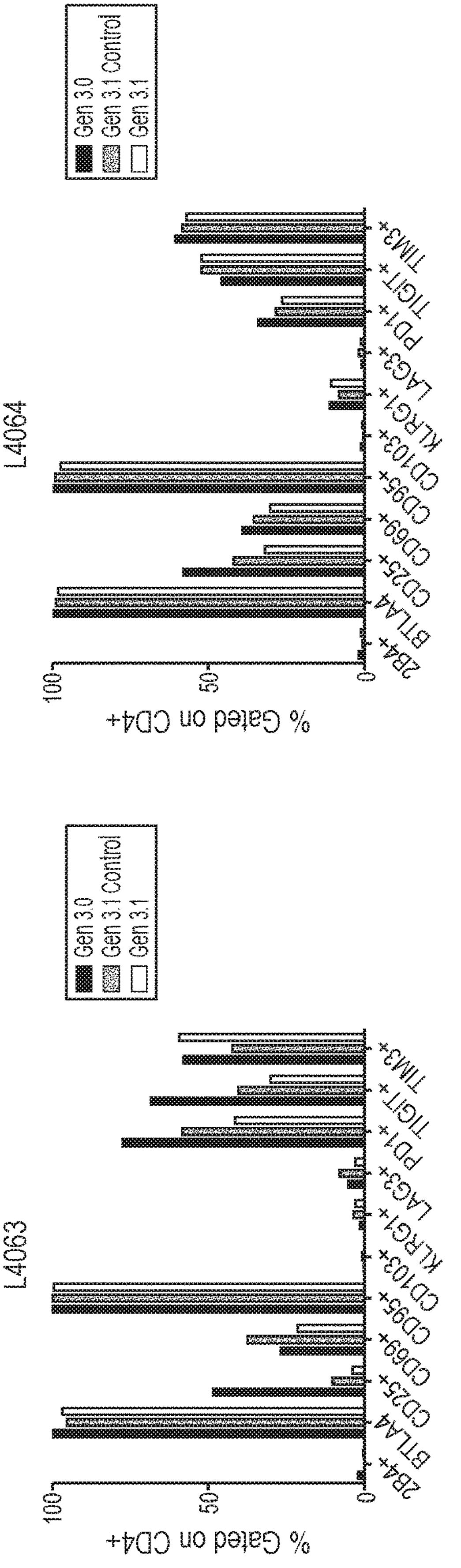
FIG. 49: Provides data showing TIL activation/exhaustion markers were comparable across cells yielded by exemplary embodiments of the Gen 3 process (Gen 3.0, Gen 3.1 Control, and Gen 3.1 Test) when gated on CD4+. Activation and exhaustion of REP TIL were determined by multicolor flow cytometry. Harvested TIL samples were stained with flow cytometry antibodies (CD3-BUV395, PD-1-BV421, 2B4/CD244-PB, CD8-BB515, CD25-BUV563, BTLA-PE, KLRG1-PE-Dazzle 594, TIM-3-BV650, CD194/CCR4-APC, CD4-VioGreen, TIGIT-PerCP-eFluor 710, CD183-BV711, CD69-APC-R700, CD95-BUV737, CD127-PE-Cy7, CD103-BV786, LAG-3-APC-eFluor 780). Bar graph presented are percentage of CD4+ or CD8+ TIL of REP TIL.
Figure 50:
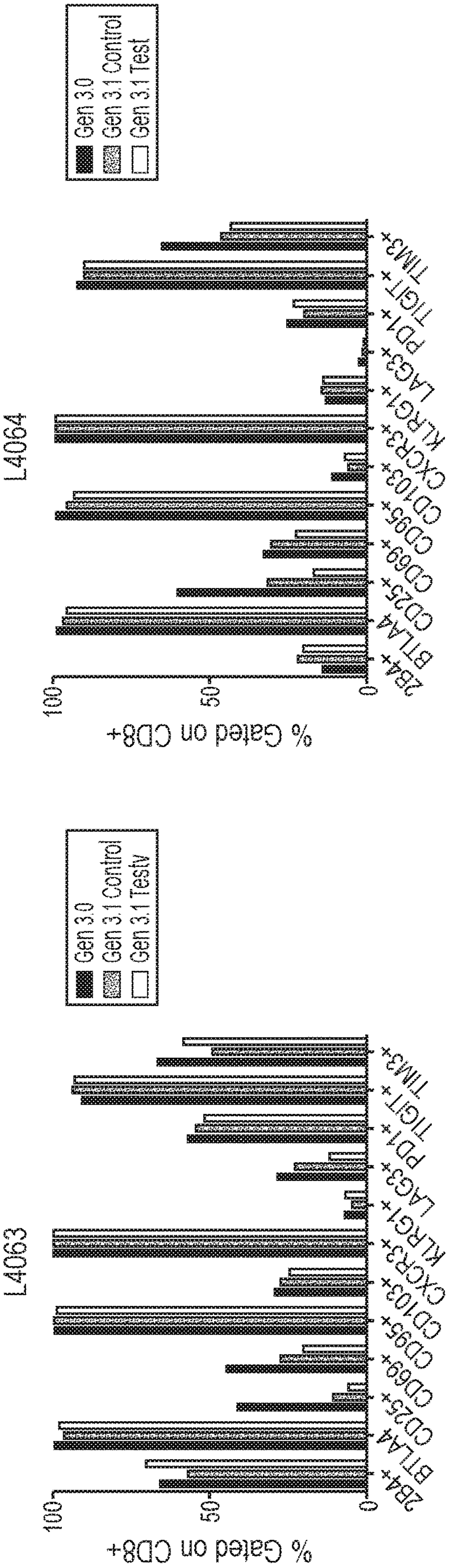
FIG. 50: Provides data showing TIL activation/exhaustion markers were comparable across cells yielded by exemplary embodiments of the Gen 3 process (Gen 3.0, Gen 3.0, Gen 3.1 Control and Gen 3.1) when gated on CD8+. Activation and exhaustion of REP TIL were determined by multicolor flow cytometry. TIL Harvested samples were stained with flow cytometry antibodies (CD3-BUV395, PD-1-BV421, 2B4/CD244-PB, CD8-BB515, CD25-BUV563, BTLA-PE, KLRG1-PE-Dazzle 594, TIM-3-BV650, CD194/CCR4-APC, CD4-VioGreen, TIGIT-PerCP-eFluor 710, CD183-BV711, CD69-APC-R700, CD95-BUV737, CD127-PE-Cy7, CD103-BV786, LAG-3-APC-eFluor 780). Bar graph presented are percentage of CD4+ or CD8+ TIL of REP TIL.
Figure 51:
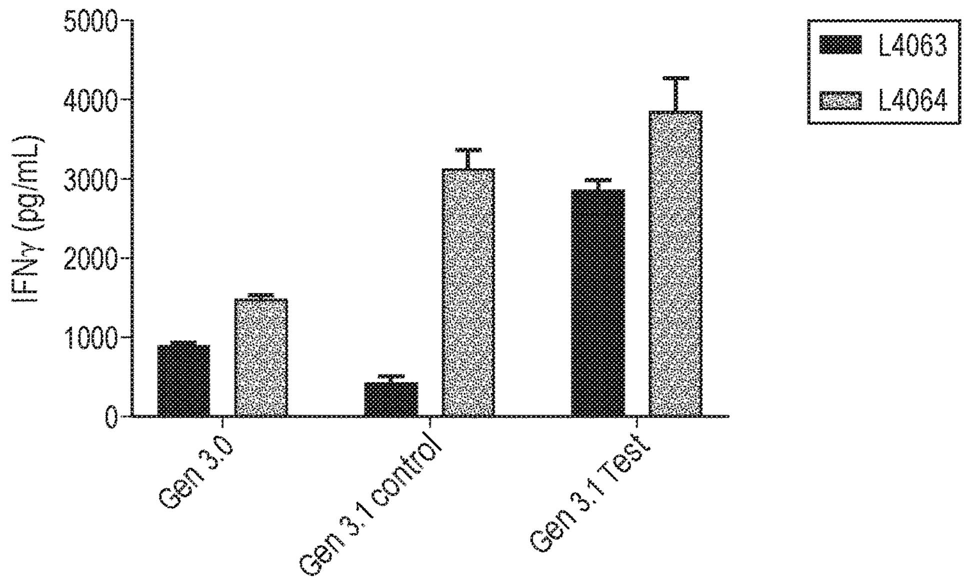
FIG. 51: Provides data showing higher production of IFN-γ exhibited by Gen 3.1 final product. IFNγ analysis ELISA was assessed in the culture frozen supernatant to compare both processes. For each tumor overnight stimulation with coated anti-CD3 plate, using fresh TIL product on each Harvest day. Each bar represents here are IFN-γ levels of stimulated, unstimulated and media control.
Figure 52:
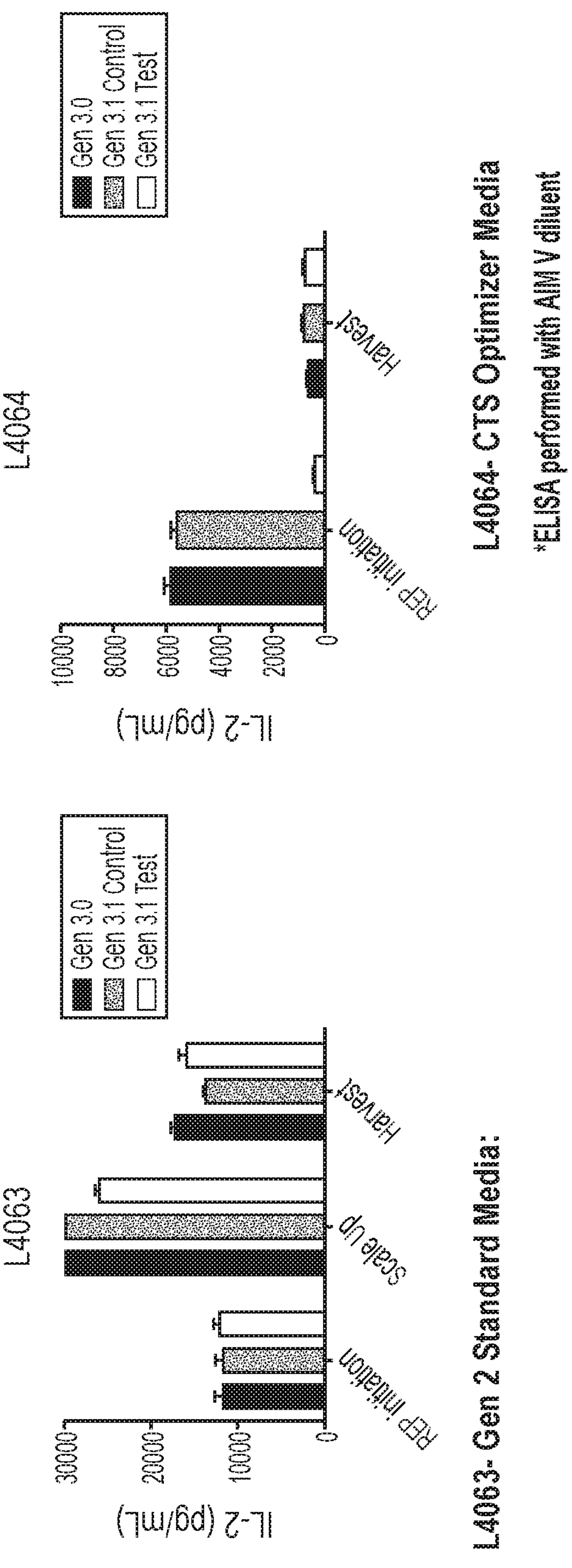
FIG. 52: Provides data showing that IL-2 concentration on supernatant were comparable across exemplary embodiments of the Gen 3 process (Gen 3.0, Gen 3.1 Control, Gen 3.1 Test) using Standard media. Left panel: L4063-Gen 2 Standard Media. Right panel: L4064-CTS Optimizer Media. *ELISA performed with AIM V diluent
Figure 53:
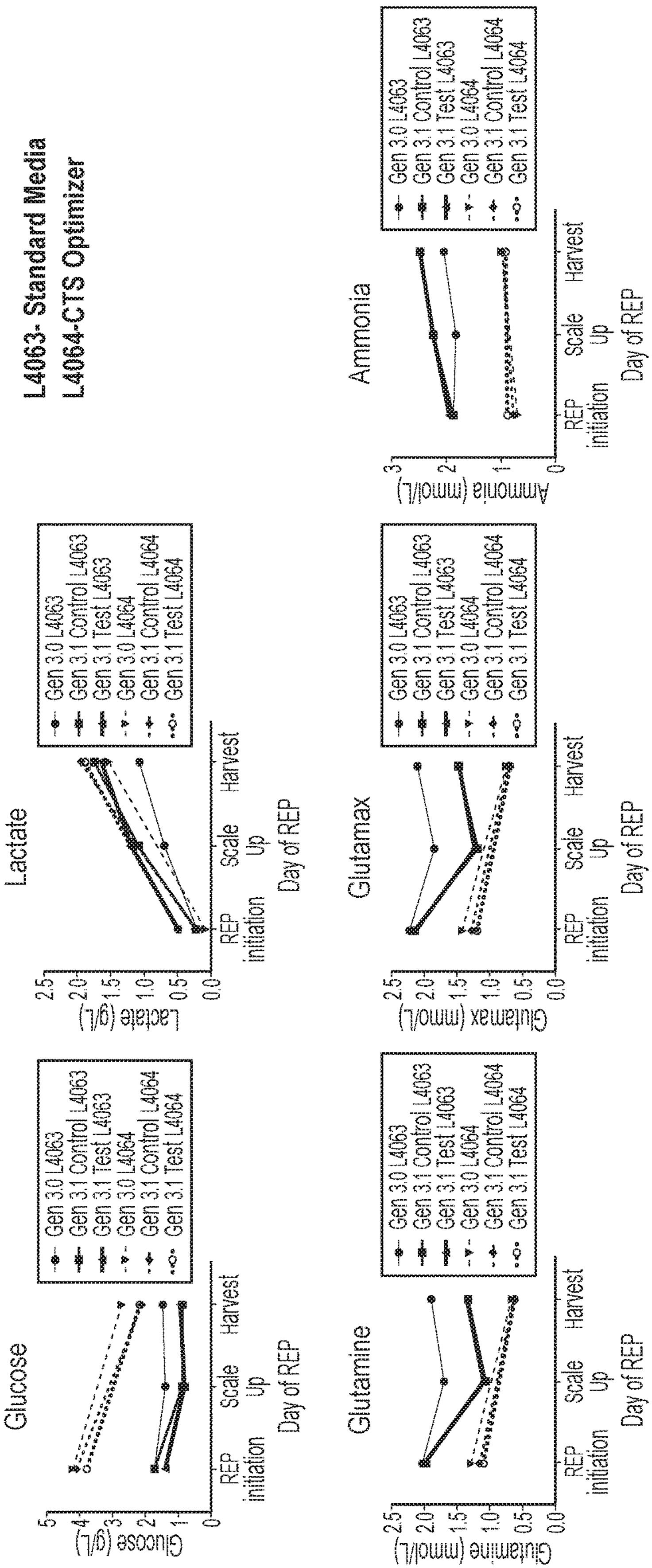
FIG. 53: Provides data showing that metabolite concentrations were comparable on supernatant supernatants across exemplary embodiments of the Gen 3 process (Gen 3.0, Gen 3.1 Control, Gen 3.1 Test). L4063 TILs were expanded in standard media. L4064 TILs were expanded in CTS Optimizer media.
Figure 54:
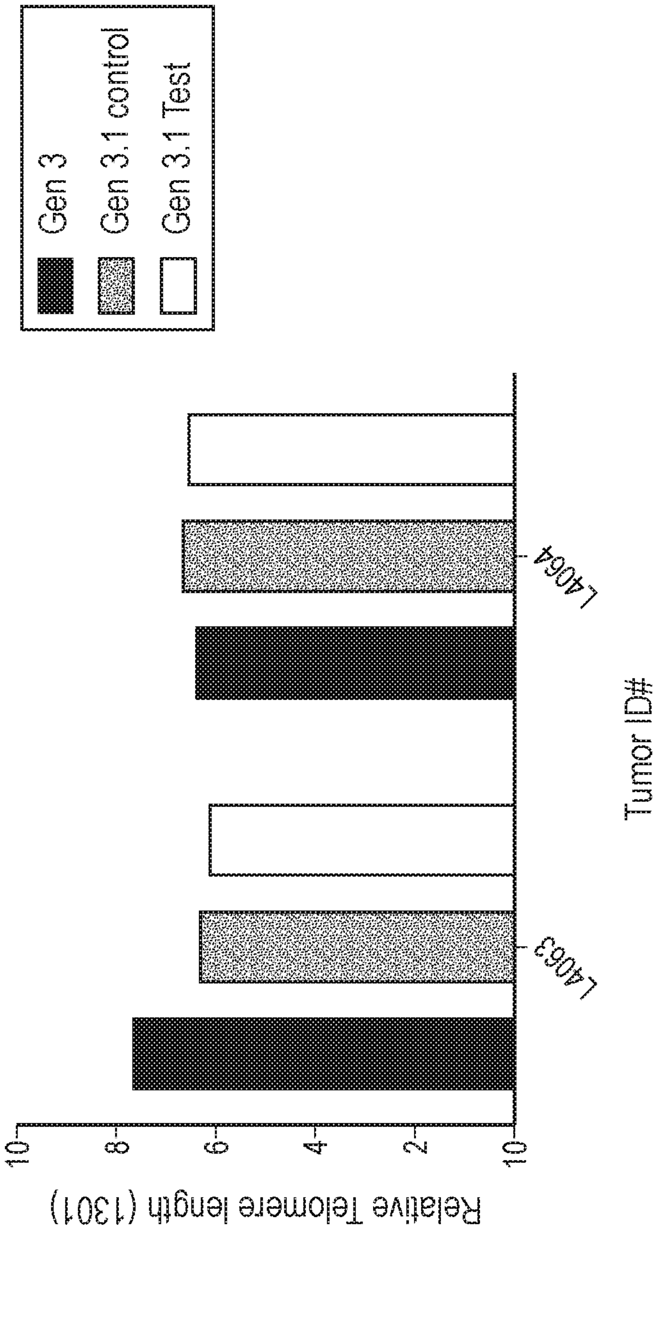
FIG. 54: Telomere length analysis on exemplary embodiments of the Gen 3 process (Gen 3.0, Gen 3.1 Control, Gen 3.1 Test). Telomere length analysis for cells yielded by tumor identification numbers L4063 and L4064: the relative telomere length (RTL) value indicates the average telomere fluorescence per chromosome/genome in cells produced by the Gen 3.0, Gen 3.1 Control and Gen 3.1 Test processes over the telomere fluorescence per chromosome/genome in the control cells line (1301 Leukemia cell line) using DAKO kit.
Figure 55:
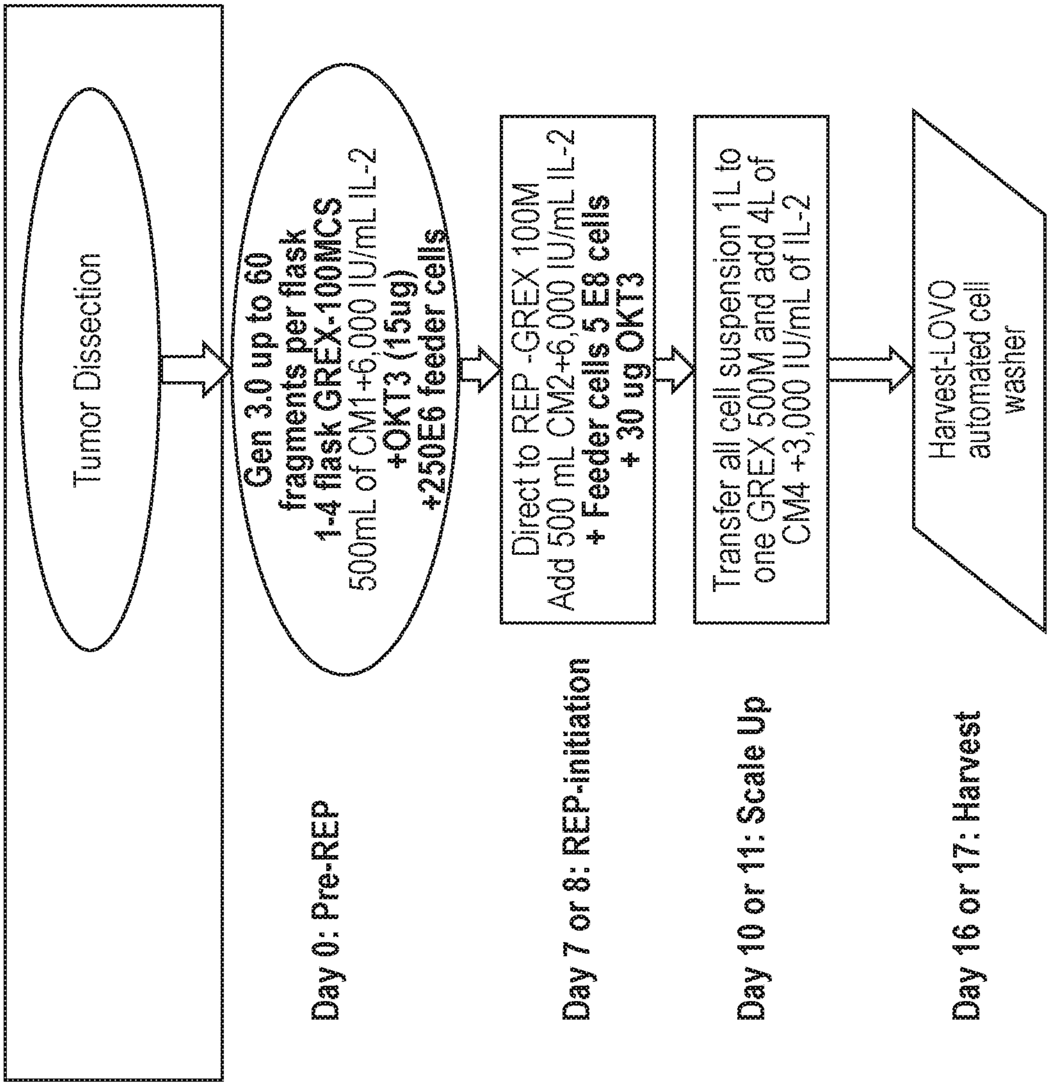
FIG. 55: Schematic of an exemplary embodiment of the Gen 3.1 Test (Gen 3.1 optimized) process (a 16-17 day process).
Figure 56:
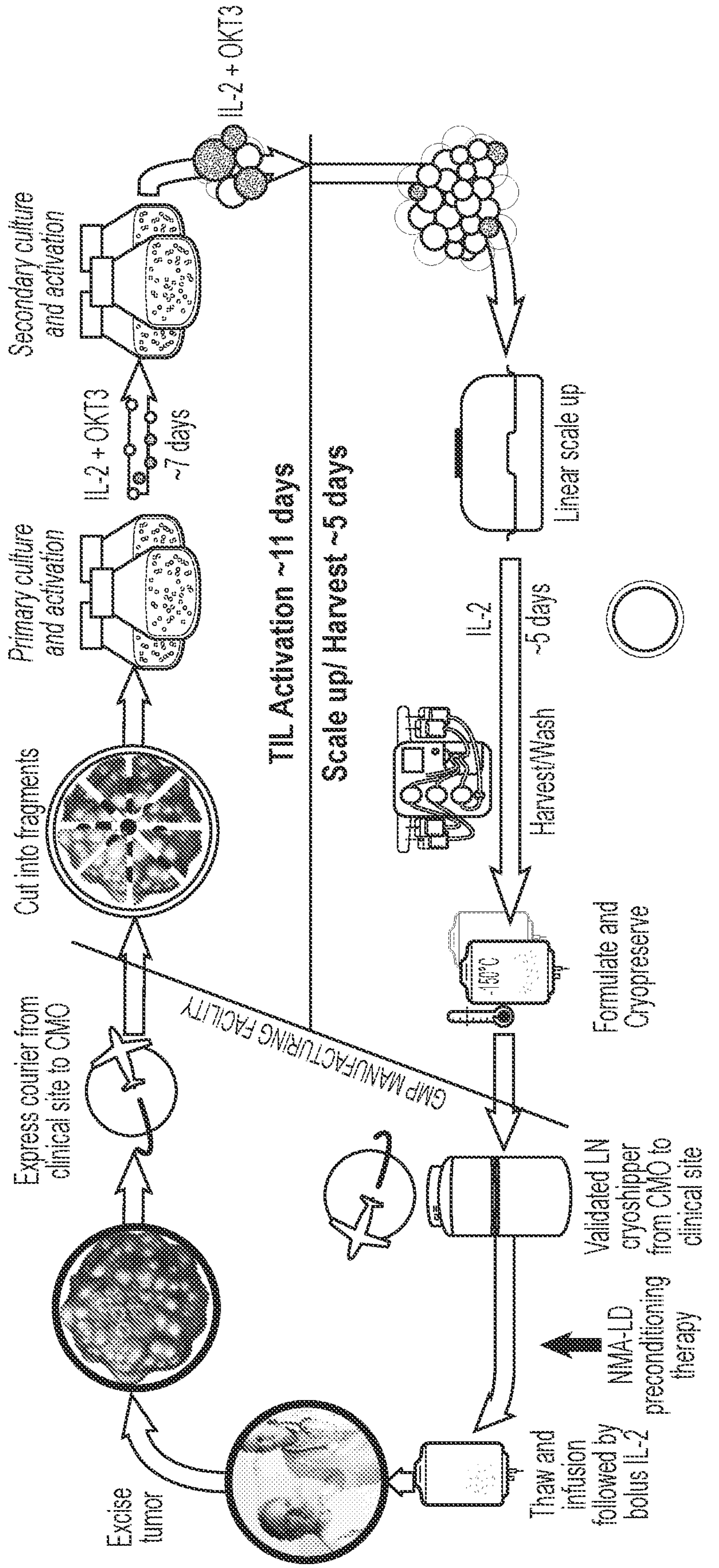
FIG. 56: Schematic of an exemplary embodiment of the Gen 3 process (a 16-day process).
Figure 59:
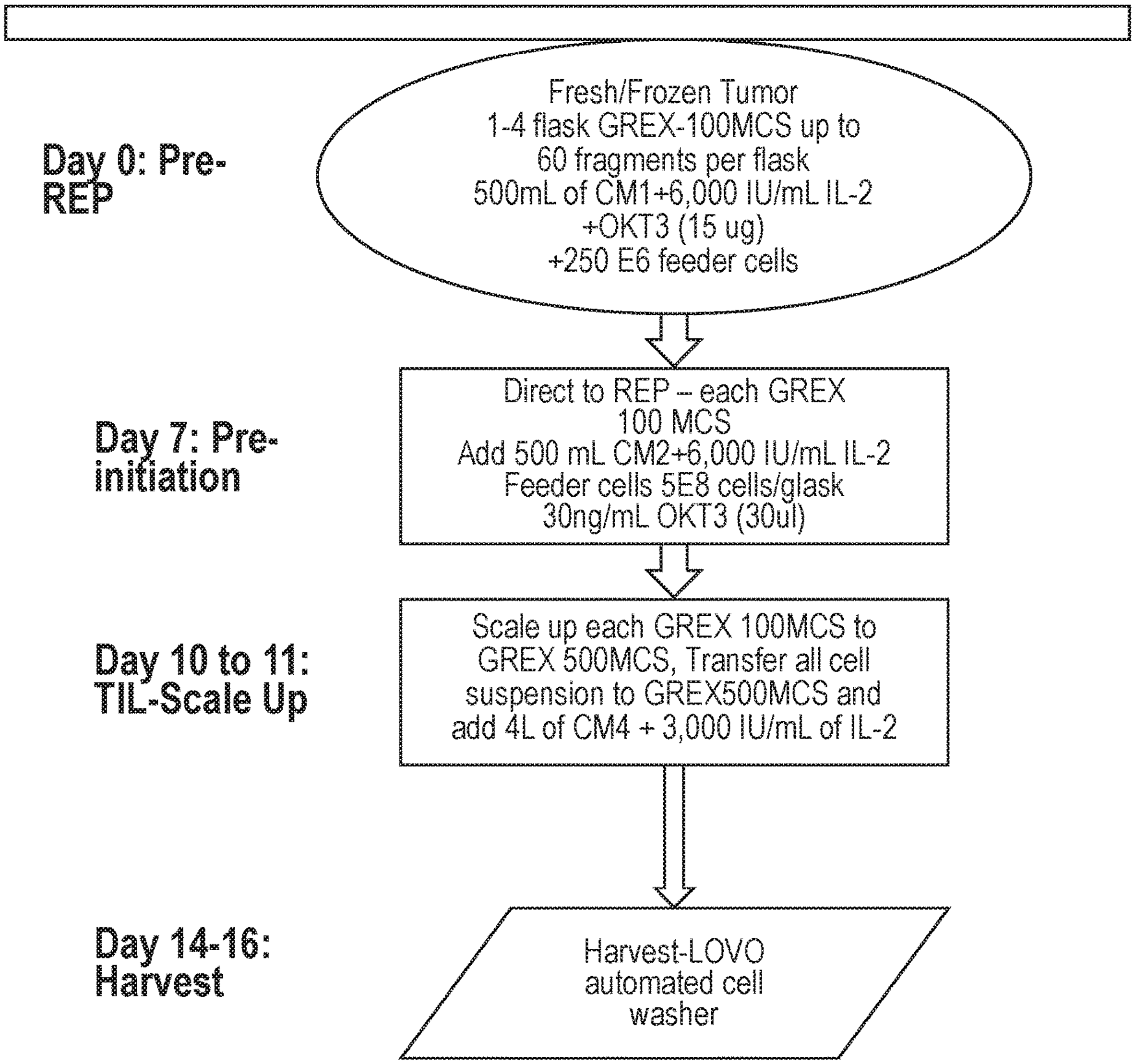
FIG. 59: Schematic of an exemplary embodiment of the Gen 3 process (a 14-16 day process).
Figure 67A:
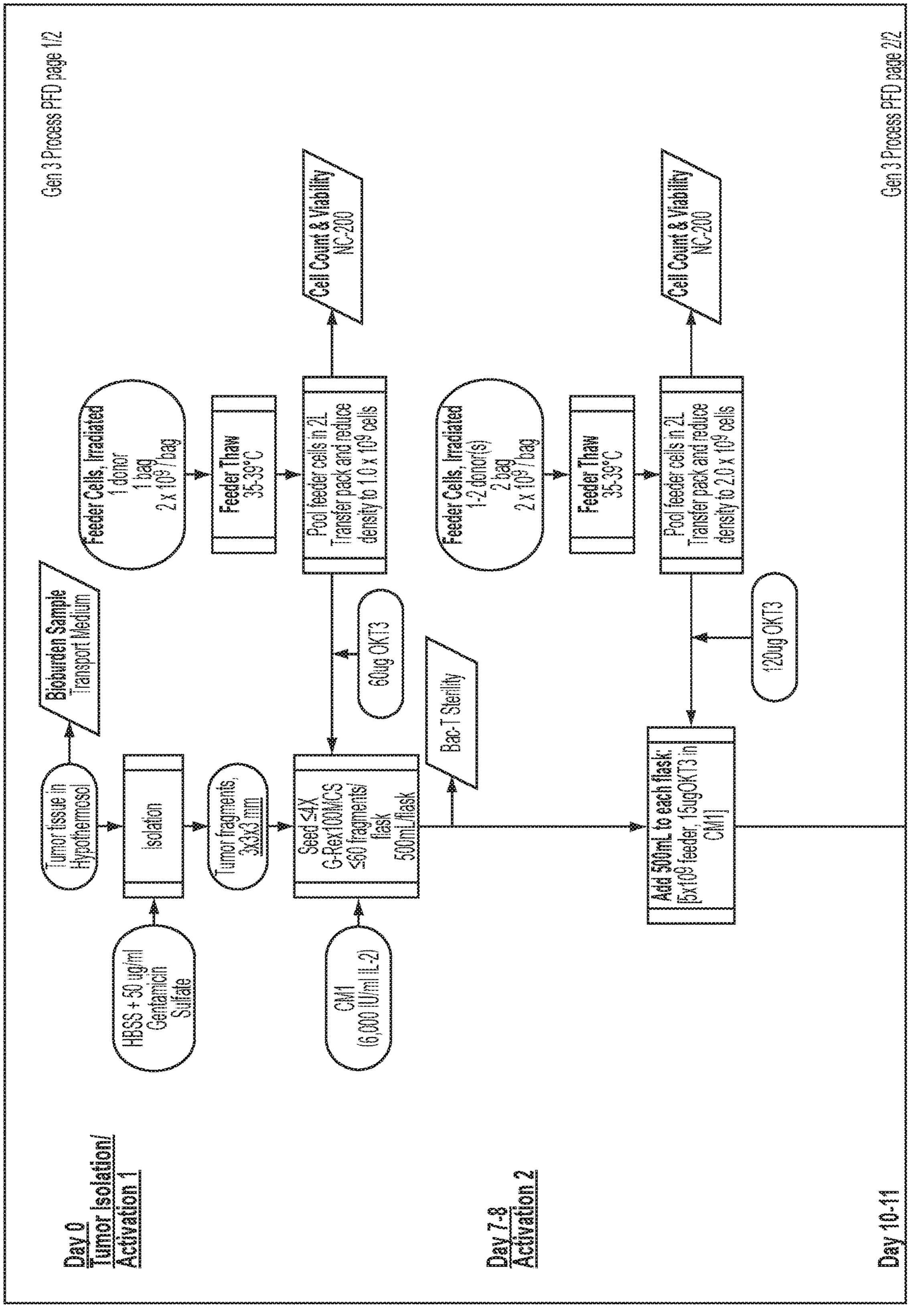
FIG. 67A-67B: Schematic of an exemplary embodiment of the Gen 3 process (a 16 day process).
Figure 67B:
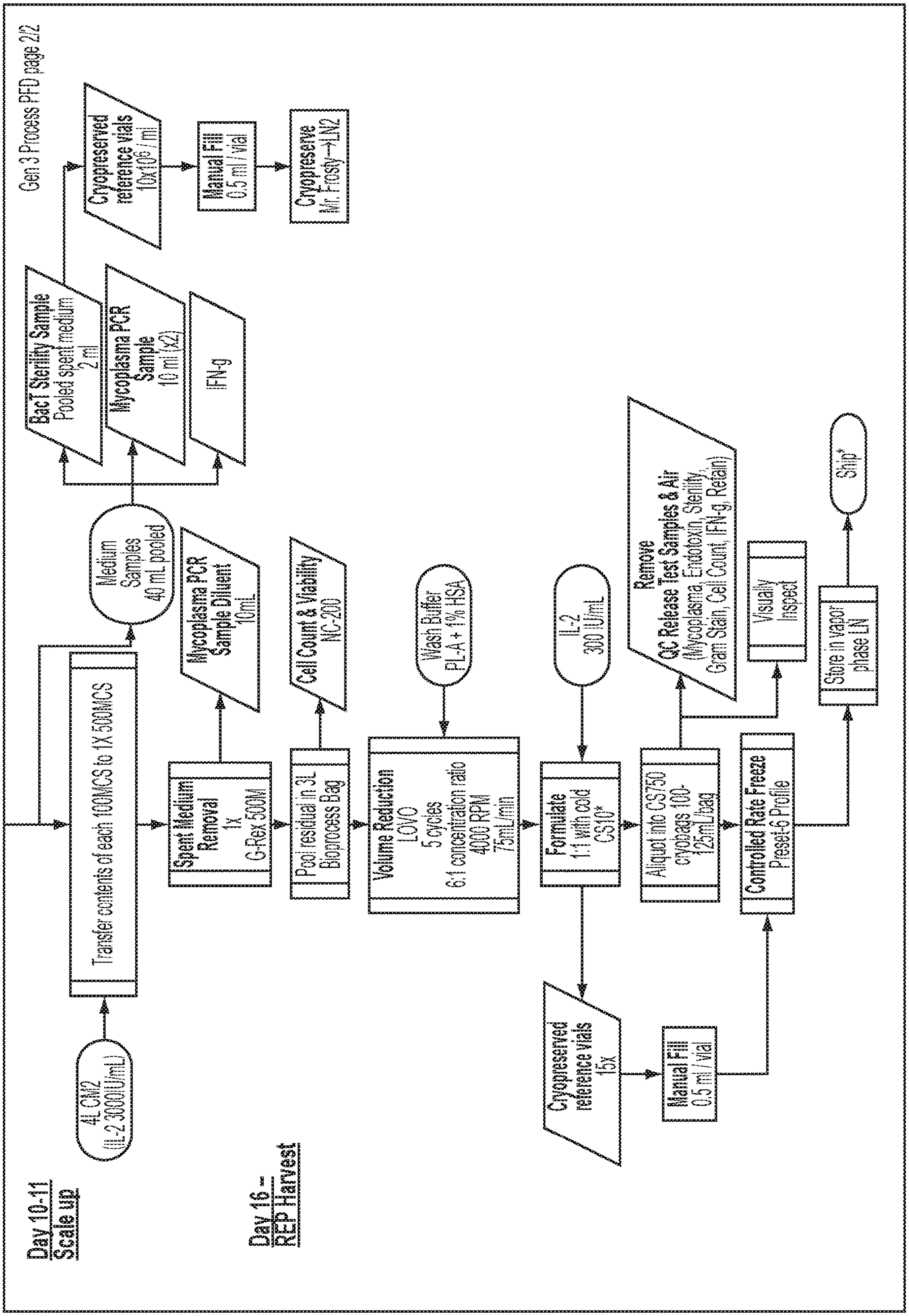
Figure 68:
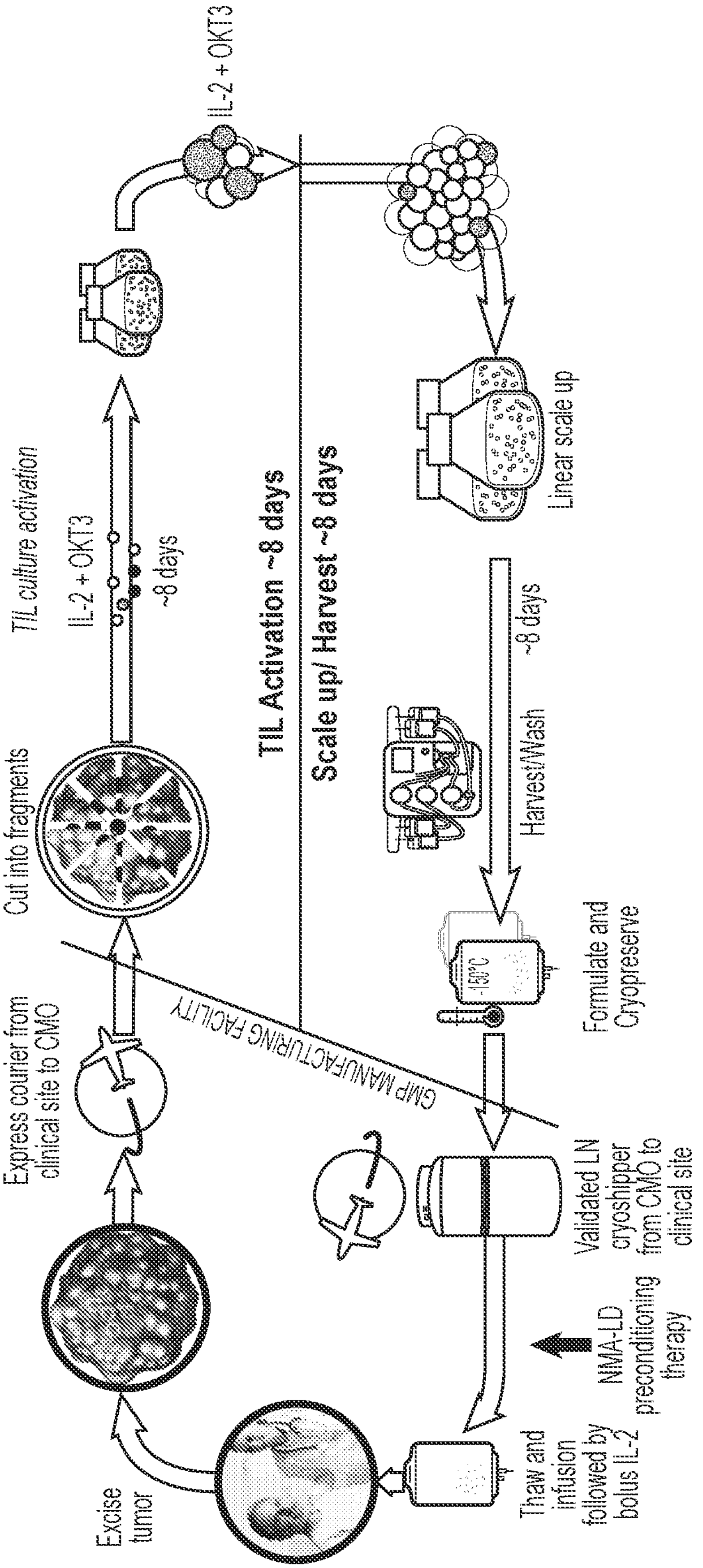
FIG. 68: Schematic of an exemplary embodiment of the Gen 3 process (a 16 day process).
Figure 72:
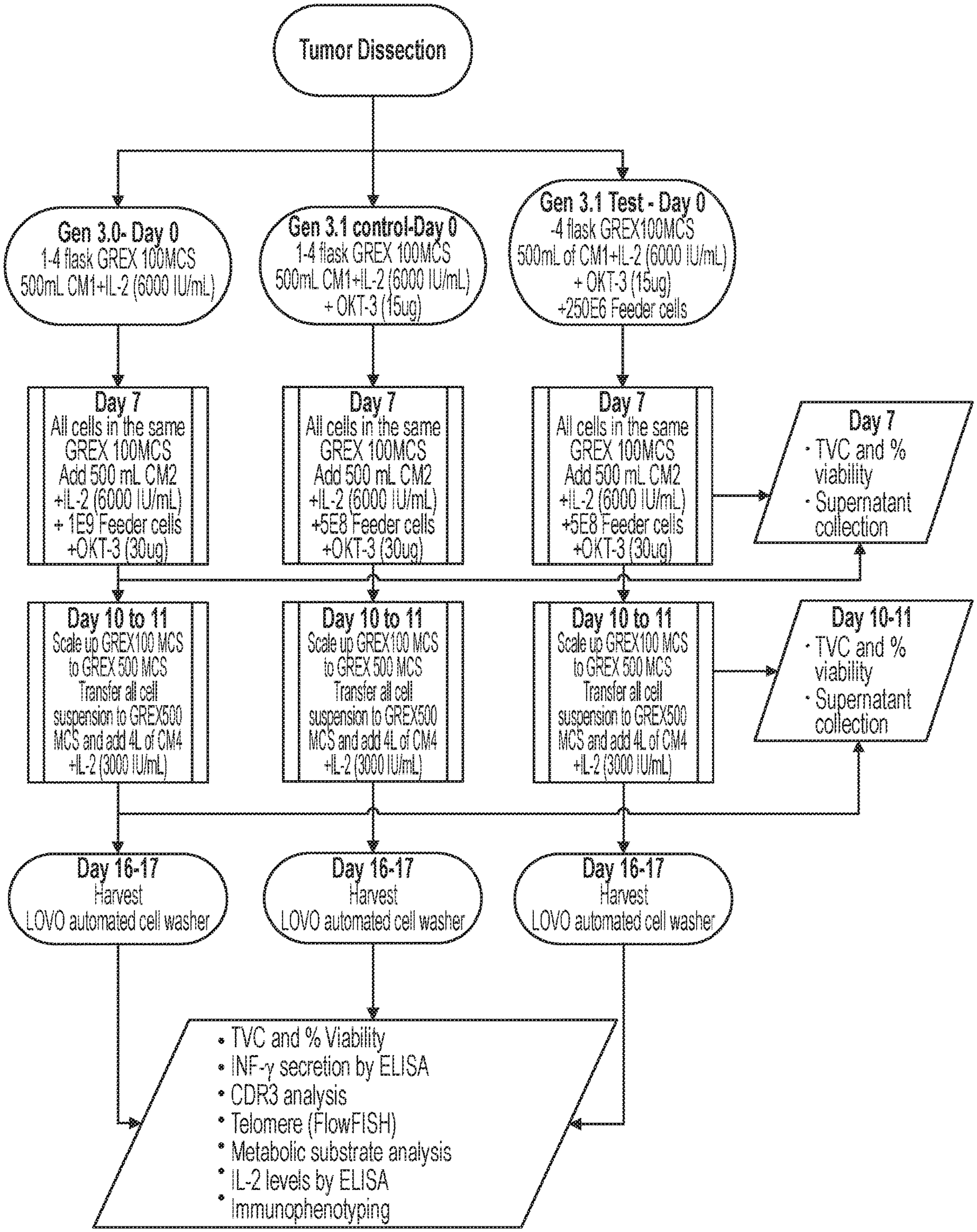
FIG. 72: Gen 3 embodiment flow chart comparison (Gen 3.0, Gen 3.1 control, Gen 3.1 Test).

FIG. 42 provides a schematic diagram of an exemplary embodiment for expanding TILs from hematopoietic malignancies using the Gen 3 process.

Example 8: An Exemplary Embodiment of the Gen 3 Expansion Platform at Day 0

Prepared tumor wash media. Media warmed prior to start. Added 5 mL of gentamicin (50 mg/mL) to the 500 mL bottle of HBSS. Added 5 mL of Tumor Wash Media to a 15 mL conical to be used for OKT3 dilution. Store at room temperature (RT)

Prepared feeder cell bags. Sterilely transferred feeder cells to feeder cell bags and stored at 37° C. until use or freeze. Counted feeder cells if at 37° C. Thawed and then counted feeder cells if frozen.

Optimal range for the feeder cell concentration is between $5\times10^4$ and $5\times10^6$ cells/mL. Prepared four conical tubes with 4.5 mL of AIM-V. Added 0.5 mL of cell fraction for each cell count.

If total viable feeder cell number was $>1\times10^9$ cells, proceeded to the next step to adjust the feeder cell concentration. Calculated the volume of feeder cells to remove from the first feeder cell bag in order to add $1\times10^9$ cells to a second feeder cell bag.

Using the p1000 micropipette, transferred 900 μl of Tumor Wash Media to the OKT3 aliquot (100 μL). Using a syringe and sterile technique, drew up 0.6 mL of OKT3 and added into the second feeder cell bag. Adjusted media volume to a total volume of 2 L. Transferred the second feeder cells bag to the incubator.

OKT3 formulation details: OKT3 may be aliquoted and frozen in original stock concentration from the vial (1 mg/mL) in 100 ul aliquots. ~10× aliquots per 1 mL vial. Stored at −80 C. Day 0: 15 ug/flask, i.e. 30 ng/mL in 500 mL~60 ul max ~1 aliquot.

Prepared tumor samples. Obtained 6-well plate and 100 mm petri dishes (4 total). Labeled the 6 well plate 'Excess Tumor Pieces'. Labeled one each of the four 100 mm petri dishes as 'Wash_01', 'Wash_02', 'Wash_03', 'Wash_04', and 'Holding'.

Added 5 mL of Tumor Wash Medium into all wells of the 6-well plate labelled Excess Tumor Pieces. Kept the Tumor Wash Medium available for further use in keeping the tumor hydrated during dissection.

Added 50 mL of Tumor Wash Medium to each 100 mm petri dish labelled Wash_01, Wash_02, Wash_03, and Holding (Wash_04). Using a marker, label each petri dish as Dissection 1 through Dissection 4. Incubated the tumor at ambient temperature in Wash_01 for ≥3 min. Incubated the tumor at ambient temperature in Wash_02 for ≥3 min. Incubated the tumor at ambient temperature in Wash_03 for ≥3 min. Wash_04 was for holding the tumor after three washes were completed. After washes were completed, moved tumor to the 'Holding' dish to ensure tissue stays hydrated.

While tumor incubations were in progress, transferred 10 mL of tumor shipping medium into a tube labelled Tumor Shipping Medium. Drew 10 mL of the Tumor Shipping Medium into a syringe and inoculated one each anaerobic and aerobic sterility bottle with 5 mL of tumor shipping medium.

Placed ruler under the petri dish lid for the entirety of the dissection process. Measured and recorded length of the tumor and the number of fragments. Dissected the tumor into four intermediate pieces or group into four groups of equivalent volume and conserving the tumor structure of each intermediate piece. Keep tumor pieces hydrated.

Transferred any intermediate tumor pieces not being actively dissected to the Holding dish to keep the tissue hydrated.

Dissected the tumor into 27 $mm^3$ fragments (3×3×3 mm), using the ruler under the Dissection dish lid as a reference. Dissected intermediate fragment until 60 fragments were reached. Counted total number of final fragments and prepared G-Rex 100MCS flasks according to the number of final fragments generated (generally 60 fragments per flask).

Retained favorable tissue fragments in the conical tubes labeled as Fragments Tube 1 through Fragments Tube 4. Calculated the number of G-Rex 100MCS flasks to seed with feeder cell suspension according to the number of fragments tubes originated.

Removed feeder cells bag from the incubator and seed the G-Rex 100MCS. Label as D0 (Day 0).

Tumor Fragment Addition Culture in G-Rex100MCS

Under sterile conditions, unscrewed the cap of the G-Rex 100MCS labelled Tumor Fragments Culture (D0) 1 and the 50 mL conical tube labelled Fragments Tube. Swirled the opened Fragments Tube 1 and, at the same time, slightly lifted the cap of the G-Rex100MCS. Added the medium with the fragments to the G-Rex100MCS while being swirled. Recorded the number of fragments transferred into the G-Rex100MCS.

Once the fragments were located at the bottom of the GREX flask, drew 7 mL of media and created seven 1 mL aliquots-5 mL for extended characterization and 2 mL for sterility samples. Stored the 5 aliquots (final fragment culture supernatant) for extended characterization at −20° C. until needed.

Inoculated one anaerobic BacT/Alert bottle and one aerobic BacT/Alert bottle each with 1 mL of final fragment culture supernatant. Repeat for each flask sampled.

Example 9: An Exemplary Embodiment of the Gen 3 Expansion Platform at Day 7-8

Prepared feeder cell bags. Thawed feeder bags for 3-5 minutes in 37° C. water bath when frozen. Counted feeder cells if frozen.

Optimal range for the feeder cell concentration is between $5\times10^4$ and $5\times10^6$ cells/mL. Prepared four conical tubes with 4.5 mL of AIM-V. Added 0.5 mL of cell fraction for each cell count into a new cryovial tube. Mixed the samples well and proceeded with the cell count.

If total viable feeder cell number was $\geq2\times10^9$ cells, proceeded to the next step to adjust the feeder cell concentration. Calculated the volume of feeder cells to remove from the first feeder cell bag in order to add $2\times10^9$ cells to the second feeder cell bag.

Using the p1000 micropipette, transfer 900 ul of HBSS to a 1004, OKT3 aliquot. Mix by pipetting up and down 3 times. Prepared two aliquots.

OKT3 formulation details: OKT3 may be aliquoted and frozen in original stock concentration from the vial (1 mg/mL) in 100 ul aliquots. ~10× aliquots per 1 mL vial. Stored at −80 C. Day 7/8: 30 ug/flask, i.e. 60 ng/mL in 500 mL~120 ul max ~2 aliquots.

Using a syringe and sterile technique, drew up 0.6 mL of OKT3 and added into the feeder cell bag, ensuring all added. Adjusted media volume to a total volume of 2 L. Repeated with second OKT3 aliquot and added to the feeder cell bag. Transferred the second feeder cells bag to the incubator.

Prepare G-Rex100MCS Flask with Feeder Cell Suspension

Recorded the number of G-Rex 100MCS flasks to process according to the number of G-Rex flasks generated on Day 0. Removed G-Rex flask from incubator and removed second feeder cells bag from incubator.

Removal of Supernatant Prior to Feeder Cell Suspension Addition:

Connected one 10 mL syringe to the G-Rex100 flask and drew up 5 mL of media. Created five 1 mL aliquots-5 mL for extended characterization and stored the 5 aliquots (final fragment culture supernatant) for extended characterization at −20° C. until requested by sponsor. Labeled and repeated for each G-Rex100 flask.

5-20×1 mL samples for characterization, dependeding on number of flasks:

5 mL=1 flask
10 mL=2 flasks
15 mL=3 flasks
20 mL=4 flasks

Continued seeding feeder cells into the G-Rex100 MCS and repeated for each G-Rex100 MCS flask. Using sterile transfer methods, gravity transferred 500 mL of the second feeder cells bag by weight (assume 1g=1 mL) into each G-Rex 100MCS flask and recorded amount. Labeled as Day 7 culture and repeated for each G-Rex100 flask. Transferred G-Rex 100MCS flasks to the incubator.

Example 10: An Exemplary Embodiment of the Gen 3 Expansion Platform at Day 10-11

Removed the first G-Rex 100MCS flask and using sterile conditions removed 7 mL of Pre-process Culture Supernatant using a 10 mL syringe. Created seven 1 mL aliquots-5 mL for extended characterization and 2 mL for sterility samples.

Mixed the flask carefully and using a new 10 mL syringe remove 10 mL supernatant and transfer to a 15 mL tube labelled as D10/11 *Mycoplasma* Supernatant.

Mixed the flask carefully by swirling gently to bring the cells into suspension. Using a new syringe, removed the volume below according to the number of flasks to be processed and add to a 50 mL conical tube. The samples drawn from each flask were kept separate and not pooled.

1 flask=40 mL
2 flasks=20 mL/flask
3 flasks=13.3 mL/flask
4 flasks=10 mL/flask

Labeled each conical tube Day 10/11 QC Sample Flask #. Stored in the incubator until needed in section 14. Repeat for each flask.

A total of 40 mL should be pulled from all flasks and pooled in a 50 mL conical tube labeled 'Day 10/11 QC Sample' and stored in the incubator until needed. Performed a cell count and allocated the cells.

Stored the 5 aliquots (pre-process culture supernatant) for extended characterization at ≤−20° C. until needed. Inoculated one anaerobic BacT/Alert bottle and one aerobic BacT/Alert bottle each with 1 mL of pre-process culture supernatant.

Continued with cell suspension transferred to the G-Rex 500MCS and repeated for each G-Rex 100MCS. Using sterile conditions, transferred the contents of each G-Rex 100MCS into a G-Rex 500MCS, monitoring about 100 mL of fluid transfer at a time. Stopped transfer when the volume of the G-Rex 100MCS was reduced to 500 mL (or in some cases about 100 mL).

During transfer step, used 10 mL syringe and drew 10 mL of cell suspension into the syringe from the G-Rex 100MCS. Followed the instructions according to the number of flasks in culture. If only 1 flask: Removed 20 mL total using two syringes. If 2 flasks: removed 10 mL per flask. If 3 flasks: removed 7 mL per flask. If 4 flasks: removed 5 mL per flask. Transferred the cell suspension to one common 50 mL conical tube. Keep in the incubator until the cell count step and QC sample. Total number of cells needed for QC was ~20e6 cells: 4×0.5 mL cell counts (cell counts were undiluted first).

Cells needed for assays:

10e6 cells minimum for IFN-G assay

1e6 cells for *mycoplasma*

5e6 cells flow CD3+/CD45+

Transferred the G-Rex 500MCS flasks to the incubator.

Prepared QC Samples

Needed at least $15\times10^8$. Assays included: Cell count and viability; *Mycoplasma* ($1\times10^6$ cells/average viable concentration) Flow cytometry and phenotyping ($5\times10^6$ cells/average viable concentration) and IFN-g assay ($5\times10^6$ cells-$1\times10^6$ cells; $8\text{-}10\times10^6$ cells are required for the IFN-γ assay.

Calculated the volume of cells fraction for cryopreservation at $10\times10^6$ cells/mL and calculated the number of vials to prepare.

Example 11: An Exemplary Embodiment of Gen 3 Expansion Platform Day 16-17

Wash Buffer Preparation (1% HAS PLasmalyte A)

Transferred HSA and PLasmalyte to 5 L bag to make LOVO wash buffer. Using sterile conditions, transferred a total volume of 125 mL of 25% HSA to the 5 L bag. Stored at room temperature.

Removed and transferred 10 mL or 40 mL of wash buffer in the 'IL-2 $6\times10^4$ IU/mL' tube (10 mL if IL-2 was prepared in advance or 40 mL if IL-2 was prepared fresh). When the IL-2 was prepared fresh: Mixed the LOVO wash buffer bag and using an appropriately sized syringe, remove and transferred 40 mL of wash buffer into the 'IL-2 $6\times10^4$ IU/mL' tube. When the IL-2 was prepared in advance the IL-2 was $6\times10^4$ IU/mL aliquot.

Calculated volume of reconstituted IL-2 to add to Plasmalyte+1% HSA: volume of reconstituted IL-2=(Final concentration of IL-2× Final volume)/specific activity of the IL-2 (based on standard assay and manufacturing protocol). The Final Concentration of IL-2 was $6\times10^4$ IU/mL. The final volume was 40 mL.

Removed calculated initial volume of IL-2 needed of reconstituted IL-2 and transfer to the 'IL-2 $6\times10^4$ IU/mL' tube. Added 1004, of IL-2 $6\times10^6$ IU/mL from the aliquot prepared in advance to the tube labelled 'IL-2 $6\times10^4$ IU/mL' containing 10 mL of LOVO wash buffer.

Removed about 4500 mL of supernatant from the G-Rex 500MCS flasks. Swirled the remaining supernatant and transferred cells to the Cell Collection Pool bag. Repeated with all G-Rex 500MCS flasks.

Removed 60 mL of supernatant and add to supernatant tubes for quality control assays, including *mycoplasma* detection. Stored at +2-8° C.

Cell Collection

Counted cells. Prepare four 15 mL conicals with 4.5 mL of AIM-V. These may be prepared in advance. Optimal range=is between $5\times10^4$ and $5\times10^6$ cells/mL. (1:10 dilution was recommended). For 1:10 dilution, to 4500 μL of AIM V prepared previously, add 500 μL of CF. Recorded dilution factor.

$$\text{Calculated the } TC \text{ (Total Cells) pre} - LOVO \text{ (live + dead)} = \text{Average Total Cell Concentration } (TC\ conc \text{ pre } LOVO) \text{ (live + dead)} \times \text{Volume of Source bag}$$

$$\text{Calculated the } TVC \text{ (Total Viable Cells) pre} - LOVO\ (live) = \text{Average Total Viable Cell Concentration } (TVC \text{ pre } LOVO)\text{(live)} \times \text{Volume of } LOVO \text{ Source Bag}$$

When the total cell (TC) number was $>5\times10^9$, remove $5\times10^8$ cells to be cryopreserved as MDA retention samples. $5\times10^8$÷avg TC concentration (step 14.44)=volume to remove When the total cell (TC) number was $\leq5\times10^9$, remove $4\times10^6$ cells to be cryopreserved as MDA retention samples. $4\times10^6$÷avg TC concentration=volume to remove.

Used an appropriately sized syringe to remove the required volume from the LOVO Source Bag. Retained in incubator until cryopreservation steps.

When the total cell number was determined, the number of cells to remove should allow retention of $150\times10^9$ viable cells. Confirm TVC pre-LOVO $5\times10^8$ or $4\times10^6$ or not applicable. Calculated the volume of cells to remove.

Calculated the remaining Total Cells Remaining in Bag. Calculated the TC (Total Cells) pre-LOVO. [Avg. Total cell concentration X Remaining Volume=TC pre-LOVO Remaining]

According to the Total number of cells remaining, selected the corresponding process in the following table:

| Total cells: | Retentate (mL) |
|---|---|
| $0 < \text{Total cells} \leq 31\times10^9$ | 115 |
| $31\times10^9 < \text{Total cells} \leq 71\times10^9$ | 165 |
| $71\times10^9 < \text{Total Cells} \leq 110\times10^9$ | 215 |
| $110\times10^9 < \text{Total Cells} \leq 115\times10^9$ | 265 |

Chose the volume of IL-2 to add corresponding to the used process. Volume calculated as: Retentate Volume×2×300 IU/mL=IU of IL-2 required. IU of IL-2 required/$6\times10^4$IU/mL=Volume of IL-2 to add Post LOVO bag. Recorded all volumes added. Obtained samples in cryovial for further analyses.

Mixed the cell product well. Sealed all bags for further processing, included cryopreservation when applicable.

Performed Enodxoton, IFN-γ, sterility, and other assays as needed on cryovial samples obtained.

Example 12: Exemplary Gen 3 Process (Also Referred to as Gen 3.1)

Purpose

This example describes further studies regarding the “Comparability between the Gen 2 and Gen 3 processes for TIL expansion”. The Gen 3 process was modified to include an activation step early in the process with the goal of increasing the final total viable cell (TVC) output to be comparable (or better) to that in Gen 2, while maintaining the phenotypic and functional profiles as previously seen.

Scope

Assessed TVC output through introduction of an activation step to the cultured tumor fragments on Day 0.

Demonstrated comparability in terms of functional and extended phenotypic characterization with the Gen 3 standard, as well as a control arm, across two independent patient tumors.

Analyzed media consumption and metabolite production to confirm processing parameters were maintained at physiologic conditions.

All runs for this example were performed at full-scale platform using commercial donor tumor tissue as the starting material.

Information

The Process Gen 3 embodiment was modified as a further embodiment and is referred to herein in this example as Gen 3.1.

Gen 3.1 TIL manufacturing concept has four operator interventions:

1. Tumor Fragment Isolation and Activation: On Day 0 of the process the tumor was dissected and the final fragments generated awe-3×3 mm each (up to 240 fragments total) and cultured in 1-4 G-Rex100MCS flasks. Each flask contained up to 60 fragments, 500 mL of CM1 or DM1 media, and supplemented with 6,000 IU rhIL-2, 15 μg OKT3, and $2.5\times10^8$ irradiated allogeneic mononuclear cells. The culture was incubated at 37° C. for 6-8 days.
2. TIL Culture Reactivation: On Day 7-8 the culture was supplemented through slow addition of CM2 or DM1 media supplemented with 6,000 IU rhIL-2, 30 μg OKT3, and $5\times10^8$ irradiated allogeneic mononuclear cells in both cases. Care was taken to not disturb the existing cells at the bottom of the flask. The culture was incubated at 37° C. for 3-4 days.
3. Culture Scale Up: Occurs on day 10-11. During the culture scale-up, the entire contents of the G-Rex100MCS was transferred to a G-Rex500MCS flask containing 4 L of CM4 or DM2 supplemented with 3,000 IU/mL of IL-2 in both cases. Flasks were incubated at 37° C. for 5-6 days until harvest.
4. Harvest/Wash/Formulate: On day 16-17 the flasks are volume reduced and pooled. Cells were concentrated and washed with PlasmaLyte A pH 7.4 containing 1% HSA. The washed cell suspension was formulated at a 1:1 ratio with CryoStor10 and supplemented with rhIL-2 to a final concentration of 300 IU/mL.

The DP was cryopreserved with a controlled rate freeze and stored in vapor phase liquid nitrogen. *Complete Standard TIL media 1, 2, or 4 (CM1, CM2, CM4) could be substituted for CTS™OpTmizer™ T-Cell serum free expansion Medium, referred to as Defined Medium (DM1 or DM2), as noted above. For process overview, see for example, FIGS. 70 and 71.

Process Description

On day 0, the tumor was washed 3 times, then fragmented in 3×3×3 final fragments. Once the whole tumor was fragmented, then the final fragments were randomized equally and divided into three pools. One randomized fragment pool was introduced to each arm, adding the same number of fragments per the three experimental matrices.

Tumor L4063 expansion was performed with Standard Media and tumor L4064 expansion was performed with Defined Media (CTS OpTmizer) for the entire TIL expansion process. Components of the media are described herein.

- CM1 Complete Media 1: RPMI+ Glutamine supplemented with 2 mM Glutamax, 10% Human AB Serum, Gentamicin (50 ug/mL), 2-Mercaptoethanol (55 uM). Final media formulation supplemented with 6000 IU/mL IL-2
- CM2 Complete Media 2: 50% CM1 medium+50% AIM-V medium. Final media formulation supplemented with 6000 IU/mL IL-2

CM4 Complete Media 4: AIM-V supplemented with Glutamax (2 mM). Final media formulation supplemented with 3000 IU/mL IL-2

CTS OpTmizer CTS™OpTmizer™ T-Cell Expansion Basal Medium supplemented with CTS™ OpTmizer™ T-Cell Expansion Supplement (26 mL/L).

DM1: CTS™OpTmizer™ T-Cell Expansion Basal Medium supplemented with CTS™ OpTmizer™ T-Cell Expansion Supplement (26 mL/L), and CTS™ Immune Cell SR (3%), with Glutamax (2 mM). Final formulation supplemented with 6,000 IU/mL of IL-2.

DM2: CTS™OpTmizer™ T-Cell Expansion Basal Medium supplemented with CTS™ OpTmizer™ T-Cell Expansion Supplement (26 mL/L), and CTS™ Immune Cell SR (3%), with Glutamax (2 mM). Final formulation supplemented with 3,000 IU/mL of IL-2.

All types of media used, i.e., Complete (CM) and Defined (DM) media, were prepared in advance, held at 4° C. degree until the day before use, and warmed at 37° C. in an incubator for up to 24 hours in advance prior to process day.

TIL Culture Reactivation occurred on Day 7 for both tumors. Scale-up occurred on day 10 for L4063 and day 11 for L4064. Both cultures were harvested and cryopreserved on Day 16.

Expected Results

Gen 3.1 may reach a higher total viable cells number at harvest on day 16-17 compared to Gen 3.0.

Gen 3.1 may produce similar levels of IFNγ after restimulation, relative to Gen 3.0.

Gen 3.1 and Gen 3.0 may have a similar clonal diversity, measured by total unique CDR3 sequences present in the final TIL product.

Phenotypic characteristics in the Gen 3.1 process may be similar to Gen 3.0.

Results Achieved

Cells counted and % viability for Gen 3.0 and Gen 3.1 processes were determined. Expansion in all the conditions followed details described in this example.

Total Viable Cell Counts and Fold Expansion

For each tumor, the fragments were divided into three pools of equal numbers. Due to the small size of the tumors, the maximum number of fragments per flask was not achieved. For the three different processes, the total viable cells and cell viability were assessed for each condition. Cell counts were determined as TVC on day 7 for reactivation, TVC on day 10 (L4064) or day 11 (L4063) for scale-up, and TVC at harvest on day 16/17.

Cell counts for Day 7 and Day 10/11 were taken FIO. Fold expansion was calculated by dividing the harvest day 16/17 TVC by the day 7 reactivation day TVC. To compare the three arms, the TVC on harvest day was divided by the number of fragments added in the culture on Day 0 in order to calculate an average of viable cells per fragment.

Cell counts and viability assays were performed for L4063 and L4064. As indicated in FIG. 73, the Gen 3.1—Test process yielded more cells per fragment than the Gen 3.0 Process on both tumors.

FIG. 74: Total viable cell count and fold expansion

% Viability During the Process

On reactivation, scale up and harvest the percent viability was performed on all conditions. On day 16/17 harvest, the final TVC were compared against release criteria for % viability. All of the conditions assessed surpassed the 70% viability criterion and were comparable across processes and tumors as is shown in FIG. 74.

Immunophenotyping

Phenotypic characterization on TIL final product.

The final products were subjected to flow cytometry analysis to test purity, differentiation, and memory markers. Percent populations were consistent for TCRα/β, CD4+ and CD8+ cells for all conditions.

Extended phenotypic analysis of REP TIL was performed. TIL product showed a higher percentage of CD4+ cells for Gen 3.1 conditions compared to Gen 3.0 on both tumors, and higher percentage of CD28+ cells from CD8+ population for Gen 3.0 compared to Gen 3.1 conditions on both conditions.

TIL harvested from the Gen 3.0 and Gen 3.1 processes showed comparable phenotypic markers as CD27 and CD56 expression on CD4+ and CD8+ cells, and a comparable CD28 expression on CD4+ gated cells population. FIG. 75 shows the phenotypic markers of the final TIL product for Gen 3.0 and Gen 3.1 processes. FIG. 75: Phenotypic characterization of final TIL product for L4063 and L4064.

Memory Markers Comparison on TIL Final Product:

FIG. 76 shows the memory markers of TIL final product that were determined by multicolor flow cytometry. Frozen samples of TIL harvested on day 16 were stained for analysis. TIL memory status was comparable between Gen 3.0 and Gen 3.1 processes. FIG. 76: Memory marker analysis of TIL product for L4063 and L4064.

Activation and Exhaustion Markers Comparison on TIL Final Product:

FIGS. 77 and 78 show the activation and exhaustion of TIL final product that were determined by multicolor flow cytometry. Activation and exhaustion markers were comparable between the Gen 3.0 and Gen 3.1 processes gated on CD4+ (FIG. 77) and CD8+ (FIG. 78) cells. FIG. 77: Activation and exhaustion markers gated on CD4+ cells for L4063 and L4064. Table 78: Activation and exhaustion markers gated on CD8+ cells for L4063 and L4064.

Interferon Gamma Secretion Upon Restimulation:

Harvested TIL underwent an overnight restimulation with coated anti-CD3 plates for L4063 and L4064. Higher production of IFNγ from the Gen 3.1 process was observed in the two tumors analyzed compared to Gen 3.0 process. The IFNγ production on each condition is shown in FIG. 79. FIG. 79: IFN-γ production (pg/mL) for final product on processes Gen 3.0 and Gen 3.1.

Measurement of IL-2 Levels in Culture Media

To compare the levels of IL-2 consumption between all of the conditions and processes, cell supernatants were collected at initiation of reactivation on Day 7, at scale-up Day 10 (L4064)/11 (L4063), and at harvest Day 16/17, and frozen. The supernatants were subsequently thawed and then analyzed. The quantity of IL-2 in cell culture supernatant was measured by the manufacturer protocol. Data are shown in FIG. 80.

Overall Gen 3 and Gen 3.1 processes were comparable in terms of IL-2 consumption during the complete process assessed across same media conditions. FIG. 80: IL-2 concentration (pg/mL) analysis on spent media collected for L4063 and L4064.

Metabolite Analysis

Spent media supernatants was collected from L4063 and L4064 at reactivation initiation on day 7, scale-up on day 10 (L4064) or day 11 (L4063), and at harvest on days 16/17 for L4063 and L4064, for every condition. Supernatants were analyzed on a CEDEX Bio-analyzer for concentrations of glucose, lactate, glutamine, glutamax, and ammonia. FIG. 81 shows the concentration of glucose in spent media collected for Gen 3.0 and Gen 3.1 processes for L4063 and L4064 tumors.

Defined media has a higher glucose concentration of 4.5 g/L compared to complete media (2 g/L). Overall, the concentration and consumption of glucose were comparable for Gen 3.0 and Gen 3.1 processes within each media type. FIG. 81: Concentration of glucose (g/L) in spent media for L4063 and L4064.

An increase in lactate was observed for both tumors, L4063 and L4064, for all test conditions. The increase in lactate was comparable between the Gen 3.0 and Gen 3.1 conditions and between the two media used for reactivation expansion (complete media for L4063 and defined media for L4064).

FIG. 82 shows the concentration of lactate on spent media collected for Gen 3.0 and Gen 3.1 processes conditions for both tumors L4063 and L4064. FIG. 82: Concentration of lactate (g/L) in spent media for L4063 and L4064.

In the case of L4063, the standard basal media contained 2 mM L-glutamine and was supplemented with 2 mM glutamax to compensate for the natural degradation of L-glutamine in culture conditions to L-glutamate and ammonia.

For L4064 tumor, defined (serum free) media used did not contain L-glutamine on the basal media, and was supplemented only with glutamax to a final concentration of 2 mM. Glutamax is a dipeptide of L-alanine and L-glutamine, is more stable then L-glutamine in aqueous solutions and does not spontaneously degrade into glutamate and ammonia. Instead, the dipeptide is gradually dissociated into the individual amino acids, thereby maintaining a lower but sufficient concentration of L-glutamine to sustain robust cell growth. FIG. 83 and FIG. 84 shows the concentration of glutamine and glutamax respectively on spent media collected on Gen 3.0 and Gen 3.1 processes conditions for both tumors L4063 and L4064.

For L4063, the concentration of glutamine and glutamax slightly decreased on the scale-up day, but at harvest day showed an increase to similar or closer levels compared to reactivation day. For L4064, glutamine and glutamax concentration showed a slight degradation in a similar rate between different conditions, during the whole process. FIG. 83: Concentration of glutamine (mmol/L) in spent media for L4063 and L4064. FIG. 84: Concentration of glutamax (mmol/L) in spent media for L4063 and L4064.

FIG. 85 shows the concentration of ammonia on spent media collected for Gen 3.0 and Gen 3.1 processes for both tumors L4063 and L4064. As expected, ammonia concentrations were higher for L4063 (grown in standard media containing 2 mM glutamine+2 mM glutamax) than L4064 (grown in defined media containing 2 mM glutamax). Further, as expected, there was a gradual increase or accumulation of ammonia over the course of the culture. There were no differences in ammonia concentrations across the three different test conditions. FIG. 85: Concentration of Ammonia (mmol/L) in spent media for L4063 and L4064.

Telomere Repeats by Flow-FISH:

Flow-FISH technology was used to measure the average length of the telomere repeat on L4063 and L4064 under Gen 3 and Gen 3.1 processes. The determination of a relative telomere length (RTL) was calculated using Telomere PNA kit/FITC for flow cytometry analysis from DAKO. Telomere assay was performed.

Telomere length in samples of L4063 an L4064, were compared to a control cell line (1301 leukemia). The control cell line is a tetraploid cell line having long stable telomeres, that allows calculation of a relative telomere length. Gen 3 and Gen 3.1 processes assessed in both tumors showed comparable telomere length as shown in FIG. 86. FIG. 86: Summary of Relative Telomere Length (RTL) Compared to the Control (1301) Cell Line.

TCR Vβ Repertoire Analysis

To determine the clonal diversity of the cell products generated in each process, TIL final products were assayed for clonal diversity analysis through sequencing of the CDR3 portion of the T-cell receptors.

Three parameters were compared between the three conditions:

Diversity index of Unique CDR3 (uCDR3)

% shared uCDR3

For the top 80% of uCDR3:

Compare the % shared uCDR3 copies

Compare the frequency of unique clonotypes

FIG. 87: TCR Vβ repertoire summary for L4063 and L4064. Describes the clonality of TIL for final TIL product on tumor L4063 and L4064 on Gen 3 and Gen 3.1 conditions as measured by the TCR Vβ repertoire.

FIG. 89: Comparison between Gen 3 and Gen3.1 Control and Gen 3.1 Test, percentage shared unique CDR3 sequences on L4063 on TIL harvested cell product for: 975 sequences are shared between Gen 3 and Gen 3.1 Test final product, equivalent to 88% of top 80% of unique CDR3 sequences from Gen 3 shared with Gen 3.1 Test final product.

FIG. 88: L4063 Frequency comparison of unique CDR3 sequences on TIL harvested final cell product between Gen 3.0 and Gen 3.1 processes.

FIG. 90: Comparison between Gen 3 and Gen3.1 Control and Gen 3.1 Test, percentage shared unique CDR3 sequences on L4064 on TIL harvested cell product for: 2163 sequences are shared between Gen 3 and Gen 3.1 Test final product, equivalent to 87% of top 80% of unique CDR3 sequences from Gen 3 shared with Gen 3.1 Test final product.

FIG. 91: L4064 Frequency comparison of unique CDR3 sequences on TIL harvested final cell product between Gen 3.0 and Gen 3.1 processes.

The number of unique CD3 sequences identified from $1\times10^6$ cells collected on Harvest day 16, for the different processes. Gen 3.1 Test condition showed a slightly higher clonal diversity compared to Gen 3.0 based on the number of unique peptide CDRs within the sample.

Shanon entropy diversity index is a more reliable and common metric for comparison, for Gen 3.1 conditions on both tumors showed slightly higher diversity than Gen 3 process, suggesting that TCR Vβ repertoire for Gen 3.1 Test condition is more polyclonal than the Gen 3.0 process.

Additionally, the TCR Vβ repertoire for Gen 3.1 Test condition showed more than 87% overlap with the corresponding repertoire for Gen 3.0 process on both tumor L4063 and L4064.

Additional Information

The value of IL-2 concentration on spent media for Gen 3.1 Test L4064 on reactivation day was below to the expected value (similar to Gen 3.1 control and Gen 3.0 condition).

The low value could be due to a pipetting error, but because of the minimal sample taken it was not possible to repeat the assay.

Spent media from scale up day 10/11 on sample L4064 was not collected, and not included in the analysis of IL-2 concentration and metabolite analysis on supernatant.

Conclusions

Gen 3.1 test condition including feeders and OKT-3 on Day 0 showed a higher TVC of cell doses at Harvest day 16 compared to Gen 3.0 and Gen 3.1 control. TVC on the final product for Gen 3.1 test condition was around 2.5 times higher than Gen 3.0.

Gen 3.1 test condition with the addition of OKT-3 and feeders on day 0, for both tumors L4063 and L4064, reached a maximum capacity of the flask at harvest. Under these conditions, if a maximum of 4 flasks on day 0 is initiated, the final cell dose could be between 80-100E+09 TILs.

All the quality attributes such as phenotypic characterization including purity, exhaustion, activation and memory markers on final TIL product were maintained and comparable between Gen 3.1 Test and Gen 3.0 process. Telomere length on TIL final product and IL-2 consumption on spent media were comparable between Gen 3.0 and Gen 3.1 processes.

IFN gamma production on final TIL product was 3 times higher on Gen 3.1 with feeder and OKT-3 addition on day 0, compared to Gen 3.0 in the two tumors analyzed, suggesting Gen 3.1 process generated a potent TIL product.

No differences observed in glucose or lactate levels across test conditions. No differences observed on glutamine and ammonia between Gen 3.0 and Gen 3.1 processes across media conditions. The low levels of glutamine on the media are not limiting cell growth and suggest the addition of glutamax only in media is sufficient to give the nutrients needed to make cells proliferate.

The scale up day for L4063 and L4064 was on day 11 and day 10 respectively and did not show major differences in terms of cell number reached on the harvest day of the process and metabolite consumption was comparable in both cases during the whole process. This observation suggests of Gen 3.0 optimized process can have flexibility on processing days, thereby facilitating flexibility in the manufacturing schedule.

Gen 3.1 process with feeder and OKT-3 addition on day 0 showed a higher clonal diversity measured by CDR3 TCRab sequence analysis compared to Gen 3.0.

FIG. 92 describes an embodiment of the Gen 3 process (Gen 3 Optimized process). Standard media and CTS Optimizer serum free media can be used for Gen 3 Optimized process TIL expansion. In case of CTS Optimizer serum free media is recommended to increase the glutamax on the media to final concentration 4 mM.

Feasibility and Comparability:

Feasibility:

Feasibility was established for all study conditions in all experiments. Across all the experiments and conditions and between the donor tumor tissue, all the experiments were performed utilizing the same lots of critical raw material such as IL-2, Human Serum-AB, allogeneic feeder cells, OKT-3.

Comparability:

Comparability was determined by the ability of any arm of the study to meet release criteria of our clinical product according to LFP-002 Autologous Tumor infiltrating Lymphocytes (TIL) cryopreserved Day 22, as outlined in FIG. 93.

Example 13: Tumor Expansion Processes with Defined Medium

The processes disclosed in Examples 5 through 12 are performed with substituting the CM1 and CM2 media with a defined medium according to the present invention (e.g., CTS™ OpTmizer™ T-Cell Expansion SFM, ThermoFisher, including for example DM1 and DM2).

Example 14: Expansion of Tumor Infiltrating Lymphocytes from Tissue Core Biopsy from a Subject with Pancreatic Cancer This example describes a study performed to expand TILS from a pancreatic cancer tumor core biopsy obtained from a patient (P7055). The example provides an exemplary embodiment for a method for expanding TILS from samples of tissue core biopsies.

A pancreatic tumor core biopsy including 3 tumor fragments was obtained and processed according to the Gen 2-like tumor processing method outlined below. FIG. 111 depicts the process steps of an exemplary Gen 2-like protocol.

Day 0—Tumor Processing

The tumor core biopsy was received and washed as described herein on Day 0 of the method. The length and theoretical mass of the tissue core was measured using a ruler and recorded.

Day 0—Gen 2-Like (Pre-REP)

A G-Rex 100M was labeled with the “Tumor ID, Gen 2, initials, media formulation, and date”. 0.5 L of CM1+6000 IU/mL IL-2 that was warmed to 37° C. (for at least 24-30 h) was added to the G-Rex 100M. A 6 well plate was used and 5 mL of tumor wash buffer was added to three wells labeled “#1,” “#2,” and “#3”. Briefly, all the contents of the core biopsy container solution were transferred to a petri dish (such as a 100 mm or 150 mm).

The sample was washed three times by transferring the core biopsy specimen to well 1 using a pasteur pipette. The sample was incubated for 3 min. Then, the specimens were transferred to well #2 for 3 min and then transferred the specimens to well #3 for 3 min.

Using a transfer pipette or forceps, the biopsy specimens were added directly from well #3 into the labeled G-Rex 100M containing 0.5 L of CM1+6000 IU/mL IL-2 prepared in step above. The G-Rex 100M was placed into 37° C./5% $CO_2$ incubator until Day 11.

Day 3—Gen 2-Like (Pre-REP Harvest/Activation)

Day 3 of the Gen 2-like process was performed as follows. Feeder cells (allogenic PBMC feeder cells) were prepared from a pooled population of PBMCs from 2 or more different donors. Feeder cells were minimally manipulated and frozen until needed. 2×1 mL vials of feeders (allogenic PBMCfeeder cells) were thawed and pipetted into 48 mL of CM-1+6000 IU/mL IL-2 that was warmed to 37° C.

The PBMC feeders were mixed well using a serological pipette and 4×1 mL aliquots were removed. The thawed feeders were counted at no dilution according to standard procedures known to those of skill in the art. Next, the volume required for 100e6 PBMC feeders was calculated according to the equation: 100e6/average live cell concentration=Volume required for 100e6 PBMC.

The G-Rex 100M flask(s) containing the Pre-REP culture were removed from the incubator and placed into a Biological Safety Cabinet (BSC).

The calculated volume from above and 30 μL of stock OKT3 (30 ng/mL) was added to each G-Rex 100M flask containing 500 mL CM1+6000 IU/mL IL-2. Quantity sufficient (QS) total volume to 1 L: 500 mL−calculated volume of PPBMCs added to each flask=total volume of CM1+6000 IU/mL IL-2 was added to flask.

Day 11—Gen 2-Like (REP)

Day 11 of the Gen 2-like process was performed as follows. For the Pre-REP TIL Harvest, an open system flask was used. The G-Rex 100M flask containing the culture was removed from the incubator and 2×1 mL aliquots of supernatant were removed for metabolite analysis and stored in −80° C. A sterile 150 mL bottle was weighed and the weight was recorded. About 900 mL of supernatant was aspirated from G-Rex 100M flask. A serological pipette was used to transfer the Pre-REP TIL culture into the weighed sterile 150 mL flask.

The Pre-REP TIL culture was mixed well with serological pipette and 4×1 mL aliquots were collected for cell counting. Four cell counts were performed at no dilution as per standard procedures known to those skilled in the art. The Pre-REP TIL culture was placed to the incubator while the counts were performed.

Cells exceeding the maximum amount (200e6 TILS) to be seeded into the REP culture were removed from the Pre-REP TIL culture using a 100 mL syringe with an Ashton pipette. 200e6 TILS were transferred into an EV-1000N bag via the blue NIS port.

The EV-1000N bag containing the Pre-REP TIL was sterile welded onto the RED line of the G-Rex 500MCS and the TILS were gravity drained into the flask. After draining, the red line was heat sealed off.

5e9 PBMC feeder cells were thawed as described above. After performing 4 cell counts, the volume of the feeder culture was adjusted based on the cell count in order to add 5e9 feeder cells into the EV1000N Feeder bag. After the feeder cells were added, 150 uL of OKT3 was added to the Feeder bag. The Feeder bag was sterile welded to the red line of the G-Rex 500MCS and the 5e9 feeder cells were gravity drained into the G-Rex. 4.5 L of CM2 and 3,000 IU/mL IL-2 were added to the G-Rex 500MCS.

Day 16—Gen 2-Like (Split)

Day 16 of the Gen 2-like process was performed according to the Gen 2 Day 16 method (see, e.g., Table 21 of Example 5).

Firstly, 2×1 mL aliquots of supernatant were drawn for metabolite analysis and stored in −80° C. Briefly, the volume was reduced and the REP cell culture was split into up to 5 G-REX 500MCS. In each G-REX 500MCS, the culture volume was 4.5 L CM4 media+IL-2 (3000 IU/mL) and ≥$1\times10^9$ TVC/flask.

Day 22—Gen 2-Like (Harvest)

Day 22 of the Gen 2-like process was performed according to the Gen 2 Day 22 method (see, e.g., Table 21 of Example 5).

The Day 22 cells were harvested, processed through the LOVO (TIL Harvest 2cy), and frozen in 30×1 mL cryovials (in 1:1 CS10/PLLA 1% HSA) using the CRF Program #1. In some cases, only 1 flask was present and any additional daughter flasks were extrapolated for the hypothetical yield. 10e6 post-LOVO cells were saved for Identity staining prior to freezing. Before discarding supernatant waste, 2×1 mL aliquots of supernatant were removed for metabolite analysis and stored in −80° C.

Results

The TVC count on Day 11 (Activation) yielded 47.3e6 cells. The TVC count on Day 22 (REP) Post LOVO yielded 10.4e9 cells with 93% viability. As such, there were 8.4 cell doublings from Day 11 to Day 22 of the Gen 2-like process.

Example 15: Gen 2-Like and Gen 3 Processes for Expansion of Tumor Infiltrating Lymphocytes from Tissue Core Biopsies This example describes a study comparing TIL expansion from pancreatic cancer tumor core biopsy samples using a Gen 2-like process and a Gen 3 process. The study utilizes a tumor core biopsy from a patient with pancreatic cancer (P7057). This tumor sample includes 3 cores and TIL products are produced according to the Gen 2-like process described herein. The study also utilizes a tumor core biopsy from a patient with pancreatic cancer (P7058). This tumor sample includes 8 cores and TIL products are produced from 4 cores according to the Gen 2-like process and 4 cores according to the Gen 3 process described herein.

Introduction

Core needle biopsies are standard preliminary diagnostic procedures used to sample aberrant tissue growths when diagnosing cancer. The procedure utilizes large gauge (18, 16, 14, etc.) needles percutaneously to sample the suspicious area, which are then further analyzed and tested to determine if the tissue is cancerous. As core needle biopsy does not require incision or surgery, it is a far less intrusive means of obtaining tumor samples. It is therefore desirable to see if core biopsies could be used as an alternative to resected tumor for starting material in the TIL manufacturing processes outlined.

Background

Two manufacturing processes (Gen 2 and Gen 3) have been developed, and are in use in clinical manufacturing, for the ex vivo expansion of autologous tumor infiltrating lymphocytes (TIL) derived from newly resected tumors. The Gen 2 and Gen 3 processes utilize the same bioreactors (G-Rex100 MCS and G-Rex500 MCS). The Gen 2 process includes a Pre-Rapid Expansion Protocol (pre-REP) step, and this step has bee replaced by an Activation step in the Gen 3 process. Rapid expansion (REP) and scale-up of TIL culture in both Gen 2 and Gen 3 cell culture expansion processes are performed in the presence of interleukin-2 (IL-2), the monoclonal antibody OKT3, and irradiated peripheral blood mononuclear cells (“feeders”), all of which promote TIL expansion. The Gen 3 has a shorter process duration than the Gen 2 process. The Gen 2 and Gen 3 processes were used as the design basis for a process for core needle biopsies.

Purpose

This purpose of this study is to develop a TIL manufacturing process using core biopsy specimen as a starting material. The design of this manufacturing process is based on the designs of the Gen 2-like and Gen 3 clinical manufacturing processes outlined herein.

Scope

The full-scale studies are performed using the Gen 2-like process and Gen 3 processes (see, e.g., Examples above). There are two changes in the Gen 2-like process compared to the Gen 2 process including 3-days Pre-REP (vs 11 days for Gen 2), and an Activation step on Day 3 by adding Feeders and OKT-3 on Day 3.

The major process design differences between Gen 2-like and Gen 3 are as follows. The presence of a Pre-Rapid Expansion Protocol (Pre-REP) in the Gen 2-like process in which the cells extravasate out from the core tissue or biopsy over a 3-day incubation period in the presence of IL-2, but in the absence of OKT-3 and feeder cells. The corresponding step in the Gen 3 process combines the extravasation of TIL from the tumor in combination with their activation by the addition of OKT-3, and feeder cells at Day 0.

Rapid Expansion Protocol in the Gen 2 process includes single activation using addition of OKT3, Feeders to the pre-REP TIL over a period of 11 days with the split on Day 16. The corresponding REP in the Gen 3 process also uses OKT3 and feeders added on Day 7/8 with the scale up on Day 11.

Gen 2 process uses G-Rex 100 MCS for Pre-REP and G-Rex 500 MCS for REP. Gen 3 process uses G-Rex 100 MCS for Activation and Reactivation and G-Rex 500 MCS for Scale up.

The Gen 3 process duration is 16-17 days versus 22 days for the Gen 2 process (e.g., Gen 3 is 5-6 days shorter than Gen 2).

The Gen 3 process uses defined medium (i.e., no human AB serum) while the Gen 2 process uses complete medium containing human AB serum.

FIG. 111 provides a comparison of the Gen 2-like and Gen 3 processes described herein.

Procedures

This section of the example outlines the Gen 2-like process to be utilized to produce TIL product from cores from the pancreatic tumor core biopsy sample P7057. The Gen 2-like process and the Gen 3 process described below are used to produce TIL product from cores from the pancreatic tumor core biopsy sample P7058.

This study utilizes tissue cores/biopsy tumor samples sourced from commercial vendors, collaborators, or partners. Allogeneic PBMC feeder cells are pooled from 2 or more different donors. Feeder cells are minimally manipulated and added directly to the TIL culture in the cryopreservation matrix consisting of mononuclear cells suspended in CS10.

Overview of Gen 2-Like Process

Day 0—Gen 2-Like (Tumor Processing)

Tumor processing of the Gen 2-like method is performed as follows. The tumor core biopsies are received and are washed 3 times. The length and theoretical mass of each tissue core is measured using a ruler and is recorded.

Day 0—Gen 2-Like (Pre-REP)

On Day 0 of the Gen 2-like process, the Pre-REP phase is initiated as follows. Label G-Rex 100M with "Tumor ID, Gen 2, initials, media formulation, and date". Add 0.5 L of CM1+6000 IU/mL IL-2 that is warmed to 37° C. (for at least 24-30 h) to a G-Rex 100M. Use a 6 well plate and add 5 mL of tumor wash buffer to 3 wells labeled 1, 2, and 3. Briefly, transfer all the contents of the core biopsy container solution to a petri dish (100 mm or 150 mm). Wash the sample 3 times by transferring the core biopsy specimen to well 1 using a pasteur pipette. Incubate for 3 min. Then transfer the specimens to well 2 for 3 min and then transfer the specimens to well 3 for 3 min. Using a transfer pipette or forceps, add the biopsy specimens directly from well 3 into the labeled G-Rex 100M containing 0.5 L of CM1+6000 IU/mL IL-2 prepared in step above. Place G-Rex 100M into 37° C./5% $CO_2$ incubator until Day 11.

Day 3—Gen 2-Like (Pre-REP Harvest/Activation)

On Day 3 of the Gen 2-like process, the Pre-REP harvest/activation is performed as follows. Thaw 2×1 mL vials of PBMC and pipette into 48 mL of CM-1+6000 IU/mL IL-2 that is warmed to 37° C. Mix well by serological pipette and remove 4×1 mL aliquots and count thawed feeders as per standard methods at no dilution. Calculate the volume required for 100e6 PBMC: (100e6/average live cell concentration=Volume required for 100e6 PBMC). Remove G-Rex 100M flask(s) containing culture from incubator and place into BSC. Add calculated volume from above and 30 μL of stock OKT3 (30 ng/mL) to each flask containing 500 mL CM1+6000 IU/mL IL-2 QS total volume to 1 L: 500 mL−volume added in 10.5.6.=total volume of CM1+6000 IU/mL IL-2 was added to flask.

Day 11—Gen 2-Like (REP)

On Day 11 of the Gen 2-like process, the REP phase is initiated as per the Gen 2 Day 11 process, with the exception of Pre-REP TIL harvest and seeding into the G-Rex 500MCS. For Pre-REP TIL Harvest, an open system flask is used. Remove flask from incubator and remove 2×1 mL aliquots of supernatant for metabolite analysis and store in −80° C. Weigh a sterile 150 mL bottle and record weight. Aspirate ~900 mL of supernatant. Use a serological pipette to transfer the Pre-REP TIL into the weighed sterile 150 mL flask. Mix well with serological pipette and obtain 4×1 mL aliquots for cell counting. Perform 4 cell counts at no dilution on NC-200 as standard methods. Keep Pre-REP TIL in incubator while cell counting is performed.

If necessary, remove an appropriate volume from the flask to leave 200e6 TIL (the maximum amount to be seeded into the REP) and use a 100 mL syringe with an Ashton pipette to transfer the remaining TIL (200e6 TIL) into an EV-1000N bag via the blue NIS port. Sterile weld EV-1000N bag containing Pre-REP TIL onto the RED line of the G-Rex 500MCS and gravity drain the TIL into the flask. After draining, heat seal red line off.

Thaw 5e9 feeders according to method described above. After performing 4 cell counts, adjust the volume if necessary to achieve 5e9 cells in the EV1000N Feeder bag. Add 150 uL of OKT3 to the Feeder bag. Sterile weld the Feeder bag to the red line of the G-Rex 500MCS and gravity drain the 5e9 feeders into the G-Rex. Add 4.5 L of CM2+3000 IU/mL IL-2 to the G-Rex 500MCS.

Day 16—Gen 2-Like (Split)

On Day 16 of the Gen 2-like process the split step is performed per the Gen 2 Day 16 step (see, Table 21 of Example 5). Draw 2×1 mL aliquots of supernatant were removed for metabolite analysis and store in −80° C. Day 16 of the Gen 2-like process is performed as per the Gen 2 Day 16 process, with the exception as follows. If only 1 flask is moved forward for the scale up/split, the number of daughter flasks is added in at harvest to extrapolate for the full scale. For example, if 5 flasks is needed, only 1 is moved forward and the final product TVC is multiplied by 5 to extrapolate for the expected full-scale yield.

Day 22—Gen 2-Like (Harvest)

On Day 22 of the Gen-2 like process the harvest step is performed per the Gen 2 Day 22 process (see, e.g., Table 21 of Example 5). The Day 22 cells for Gen 2-like is harvested, processed through the LOVO cell processing system, and frozen in 30×1 mL cryovials (in 1:1 CS10/PLLA 1% HSA). In some cases, only 1 flask is present and any additional daughter flasks are extrapolated for the hypothetical yield. 10e6 post-LOVO cells are saved for identity staining prior to freezing. Before discarding supernatant waste, 2×1 mL aliquots of supernatant are removed for metabolite analysis and stored in −80° C.

Overview of Gen 3 Process

Day 0—Gen 3 (Tumor Processing)

Tumor processing of the Gen 3 method is performed as outlined herein. The tumor core biopsies are received and are washed 3 times. The length and theoretical mass of each tissue core is measured using a ruler and is recorded.

Day 0—Gen 3 (Activation)

Day 0 of Gen 3 is performed according to process outlined (see, e.g., Examples 5-8). Allot the remaining biopsy specimens as mentioned above into a G-Rex 100M flask containing 500 mL of DM+6000 IU/mL IL-2 that is warmed to 37° C. For each flask used, thaw 4×1 mL vials of irradiated PBMC in a 37° C. water bath. Use a transfer pipette to transfer the PBMCs to a 50 mL conical tube with 46 mL warm DM+6000 IU/mL IL-2. Mix well by serological pipette and remove 4×1 mL aliquots and count at a 1:10 dilution on NC-200 as per protocol described herein. Calculate the volume required for 250e6 PBMC: (250e6/average concentration=Volume required for 250e6 PBMC). Add the calculated volume from previous step to each flask containing 500 mL DM+6000 IU/mL IL-2 and tumor fragments. Add 15 uL of stock OKT-3 (1 mg/mL) to each flask containing 500 mL DM+6000 IU/mL IL-2, tumor fragments, and PBMC feeders. Label each flask with "Tumor ID, Gen 3, flask number, initials, date". Place into 37° C./5% $CO_2$ incubator until Day 8.

Day 7/8—Gen 3 (Reactivation)

Day 7/8 of the Gen 3 process is performed as described, e.g., in Examples 5-9. Remove G-Rex 100M flask(s) containing culture from incubator and place into BSC. Remove 2×1 mL aliquots of supernatant for metabolite analysis and store in −80° C. Add 500 mL of DM+6000 IU/mL IL-2 that is warmed to 37° C. to G-Rex 100M flask. Add 25 mL of DM+6000 IU/mL IL-2 that is warmed to 37° C. to a 50 mL conical tube. Thaw 1×25 mL bag of PBMC in a 37° C. water bath, spike the bag with a plasma extension set, draw the 25 mL with a syringe, and dispense into the prepared 50 mL conical tube. Perform 4 cell counts at either a 1:10 (100 uL PBMC in 900 uL AIM-V) or a 1:100 (make a 1:10 as described and then transfer 100 uL to another 900 uL of AIM-V) count thawed feeders as per standard methods. Calculate the volume required for 500e6 PBMC: (500e6/average concentration=Volume required for 500e6 PBMC). Add the calculated volume of PBMC the steps above to the G-Rex 100M containing 1L DM+6000 IU/mL IL-2 and core biopsies. Add 30 uL of stock OKT3 (30 ng/mL) to the flask. Place flask in 37° C./5% $CO_2$ incubator.

Day 10/11—Gen 3 (Scale-Up)

Day 10/11 Scale up for the Gen 3 process is performed as described, e.g., in Examples 5-10. Flask(s) from incubator are removed and 2×1 mL aliquots of supernatant are removed for metabolite analysis and stored in −80° C. Sterile weld a fluid transfer set onto the RED line of a G-Rex 500MCS, thread the fluid transfer set through the Baxter pump, and aseptically connect an Ashton pipette to the other end inside of a BSC. Transfer ~700 mL of media from the G-Rex 100MCS to the G-Rex 500MCS, stop pump, swirl to disturb cell layer, and transfer remaining cell culture to the G-Rex 500MCS. After all TIL are transferred, sterile weld the RED line of the G-Rex onto a 5 L or 10 L bag of DM+3K IU/mL IL-2 that is warmed to 37° C. Gravity drain the media up to the 5 L mark of the G-Rex 500MCS. After draining is complete, return flask to incubator.

Day 16/17—Gen 3 (Harvest)

Day 16/17 of the Gen 3 process was performed as described, e.g., in Examples 5-1. The Day 17 cells for Gen 3 are harvested, processed through the LOVO (TIL Harvest 5cy), and frozen in 30×1 mL cryovials (in a 1:1 ratio of CS10:Plasmalyte with 1% HSA) using the CRF Program #1. In some cases, only 1 or 2 flasks are present for harvest, depending on the number of fragments seeded in day 0. 10e6 post-LOVO cells are saved for Purity staining prior to freezing.

Final Product and Starting Material Characterization:

The starting materials and final TIL products manufactured according to the Gen 2-like and Gen 3 processes can be evaluated. The identity (% CD45+/CD3+) is measured on fresh TIL product before freezing using standard protocols. For instance, TIL function in terms of Interferon-gamma production and Granzyme B release is measured. Stimulation of TIL is measured according to IFN-gamma release. Stimulation of TIL is measured according to Granzyme B release via ELISA. CD107a phenotype, extended phenotype, surface antigen staining of TIL using a differentiation panel and/or activation/exhaustion panel can be assessed. TCRvβ Sequencing can be performed. Telomerase activity and telomere length can be performed. Metabolites can be measured in the culture supernatant by CEDEX Bio-analyzer.

Expected Results or Acceptance Criteria

The expected results of the Pre-REP cells and Final Product from the Gen 2-like process as well as the Final Product of the Gen 3 process are provided in Tables 30 and 31.

TABLE 30

| Pre-REP testing and expected results for Gen 2-like process | | |
|---|---|---|
| Test Type | Method | Acceptance Criteria |
| Cell Count/Viability | Fluorescence | >5 × 10e6 Viable cells |

TABLE 31

| Final Product Testing and Acceptance Criteria (Gen 2-like and Gen 3 Processes) | | |
|---|---|---|
| Test Type | Method | Acceptance Criteria |
| Release Testing | | |
| Cell viability | Fluorescence | ≥70% |
| Total Viable Cell Count | Fluorescence | 1e9 to 150e9 |
| Identity (% CD45+/CD3+) | Flow Cytometry | Gen 2-like: ≥90% CD45+CD3+ TIL for all Indications Gen 3: ≥90% CD45+CD3+ TIL for Non-Ovarian ≥85% CD45+CD3+ TIL for Ovarian |
| Interferon-gamma production (Stimulated − Unstimulated) | Stimulation and ELISA | ≥500 pg/mL |

In some embodiments, frozen final product testing is performed on the products produced in the method described herein, such as the GEN 2-like and Gen 3 methods. In some embodiments, the testing comprises assessment of one or more of the following: differentiation, activation and exhaustion markers, granzyme B, CD107A, TCR vβ sequencing, telomere length, telomerase activity, and metabolites. In some instances, differentiation is evaluated by flow cytometry, for example by flow cytometry of a TIL 1 panel. In some instances, activation and exhaustion markers is evaluated by flow cytometry, for example by flow cytometry of a TIL 2 panel. In some instances, granzyme B is evaluated by bead stimulation and ELISA. In some instances, CD107A is evaluated by mitogen stimulation and intracellular flow cytometry. In some instances, TCR vβ sequencing is performed by deep sequencing. In some instances, telomere length is measured using a TAT assay. In some instances, telomerase activity is determined by Q-TRAP. In some instances, telomere length is measured using a TAT assay. In some instances, metabolite is determined using a CEDEX metabolite analyzer.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A method for expanding tumor infiltrating lymphocytes (TILs) into a therapeutic population of TILs comprising:

(a) adding into a first closed container in a closed system a plurality of tumor fragments comprising a first population of TILs obtained by processing a sample of tumor tissue resected from a subject with cancer into the plurality of tumor fragments;

(b) performing a priming first expansion by culturing the first population of TILs in a cell culture medium comprising IL-2, optionally OKT-3, and optionally antigen presenting cells (APCs) to produce a second population of TILs, wherein the priming first expansion is performed in the first closed container comprising a first gas-permeable surface area, wherein the priming first expansion is performed for a first period of about 3 to 7 or 8 days to obtain the second population of TILs, wherein the second population of TILs is greater in number than the first population of TILs;

(c) performing a rapid second expansion by supplementing the cell culture medium of the second population of TILs with additional IL-2, OKT-3, and APCs, to produce a third population of TILs, optionally wherein the number of APCs added in the rapid second expansion is at least twice the number of APCs added in step (b), wherein the rapid second expansion is performed for a second period of about 7 to 11 days to obtain the third population of TILs, wherein the third population of TILs is a therapeutic population of TILs, wherein the rapid second expansion is performed in a second closed container comprising a second gas-permeable surface area;

(d) harvesting the therapeutic population of TILs obtained from step (c); and (e) transferring the harvested TIL population from step (d) to an infusion bag.

2. The method of claim 1, wherein the step of the priming first expansion comprises culturing the first population of TILs in a cell culture medium comprising IL-2, APCs, and optionally OKT-3 to produce the second population of TILs, wherein a ratio of the number of APCs in the rapid second expansion to the number of APCs in the priming first expansion is in a range of from about 2:1 to about 20:1, from about 2:1 to about 5:1, from about 2:1 to about 3:1, or from about 2:1 to about 10:1.

3. The method of claim 1, wherein the step of the priming first expansion comprises culturing the first population of TILs in a cell culture medium comprising IL-2, APCs, and optionally OKT-3 to produce the second population of TILs, wherein a ratio of the number of APCs in the rapid second expansion to the number of APCs in the priming first expansion is about 2:1.

4. The method of claim 1, wherein the step of the priming first expansion comprises culturing the first population of TILs in a cell culture medium comprising IL-2, APCs, and optionally OKT-3 to produce the second population of TILs, wherein the number of APCs per unit gas-permeable surface area in the priming first expansion is in a range of about $1.0\times10^6$ APCs/cm$^2$ to about $4.5\times10^6$ APCs/cm$^2$, and wherein the number of APCs per unit gas-permeable surface area in the rapid second expansion is in a range of about $2.5\times10^6$ APCs/cm$^2$ to about $7.5\times10^6$ APCs/cm$^2$; or wherein the number of APCs per unit gas-permeable surface area in the priming first expansion is in a range of about $1.5\times10^6$ APCs/cm$^2$ to about $3.5\times10^6$ APCs/cm$^2$, or about $2.0\times10^6$ APCs/cm$^2$ to about $3.0\times10^6$ APCs/cm$^2$, and wherein the number of APCs per unit gas-permeable surface area in the rapid second expansion is in a range of about $3.5\times10^6$ APCs/cm$^2$ to about $6.0\times10^6$ APCs/cm$^2$, or about $4.0\times10^6$ APCs/cm$^2$ to about $5.5\times10^6$ APCs/cm$^2$; or wherein the number of APCs in the first closed container in the priming first expansion is in a range of about $1\times10^8$ APCs to about $3.5\times10^8$ APCs, or about $1.5\times10^8$ APCs to about $3\times10^8$ APCs, or about $2\times10^8$ APCs to about $2.5\times10^8$ APCs, and wherein the number of APCs in the second closed container in the rapid second expansion is in a range of about $3.5\times10^8$ APCs to about $1\times10^9$ APCs, or about $4\times10^8$ APCs to about $7.5\times10^8$ APCs, or about $4.5\times10^8$ APCs to about $5.5\times10^8$ APCs.

5. The method of claim 1, wherein a total number of about $2.5\times10^8$ APCs are added to the priming first expansion and a total number of about $5\times10^8$ APCs are added to the rapid second expansion, wherein optionally the second population of TILs is at least 50-fold greater in number than the first population of TILs.

6. The method of claim 1, wherein a ratio of the number of TILs in the second population of TILs to the number of TILs in the first population of TILs is about 1.5:1 to about 100:1, about 50:1, about 25:1, about 20:1 or about 10:1.

7. The method of claim 1, wherein after 2 to 3 days in the step of the rapid second expansion, the cell culture medium is supplemented with additional IL-2, optionally wherein the method further comprises cryopreserving the harvested TIL population in the step of harvesting the therapeutic population of TILs using a cryopreservation process.

8. The method according to claim 1, further comprising a step of cryopreserving the infusion bag.

9. The method according to claim 8, wherein the step of cryopreserving the infusion bag is performed using a 1:1 ratio of harvested TIL population to cryopreservation media, optionally wherein the cryopreservation media comprises 7% to 10% DMSO.

10. The method according to claim 1, wherein the antigen-presenting cells are peripheral blood mononuclear cells (PBMCs) or artificial antigen-presenting cells, optionally wherein the PBMCs are irradiated and allogeneic.

11. The method according to claim 1, wherein in the step of the priming first expansion the cell culture medium comprises peripheral blood mononuclear cells (PBMCs), and wherein the total number of PBMCs added to the cell culture medium in the step of the priming first expansion is about $2.5\times10^8$ PBMCs and/or wherein in the step of the rapid second expansion the APCs in the cell culture medium are PBMCs, and wherein the total number of PBMCs added to the cell culture medium in the step of the rapid second expansion is about $5\times10^8$.

12. The method according to claim 1, wherein the plurality of tumor fragments comprise about 60 fragments per container in the step of the priming first expansion, wherein each fragment has a volume of about 27 mm$^3$, optionally wherein the multiple fragments comprise about 30 to about 60 fragments with a total volume of about 1300 mm$^3$ to about 1500 mm$^3$ or the multiple fragments comprise about 50 fragments with a total volume of about 1350 mm$^3$, optionally wherein the multiple fragments comprise about 50 fragments with a total mass of about 1 gram to about 1.5 grams.

13. The method according to claim 1, wherein the IL-2 concentration in the priming first expansion, or the rapid second expansion, is about 10,000 IU/mL to about 5,000 IU/mL, or about 6,000 IU/mL.

14. The method according to claim 1, wherein the priming first expansion is performed within a period of 5 days, 6 days, or 7 days.

15. The method according to claim 1, wherein the rapid second expansion is performed within a period of 7 days, 8 days, or 9 days.

16. The method according to claim 1, wherein the priming first expansion and the rapid second expansion are each individually performed within a period of 7 days.

17. The method according to claim 1, wherein steps of the priming first expansion through the harvesting of the therapeutic population of TILs are performed within a period of about 14 days to about 16 days, about 15 days to about 16 days, about 14 days, about 15 days, or about 16 days.

18. The method according to claim 1, further comprising a step of cryopreserving the harvested therapeutic population of TILs using a cryopreservation process, wherein steps of the priming first expansion through the harvesting of the therapeutic population of TILs and cryopreservation are performed within a period of about 14 days to about 16 days.

19. The method according to claim 1, wherein the therapeutic population of TILs harvested in the step of harvesting of the therapeutic population of TILs comprises sufficient TILs for a therapeutically effective dosage of the TILs, wherein optionally the number of TILs sufficient for a therapeutically effective dosage is from about $2.3\times10^{10}$ TILs to about $13.7\times10^{10}$ TILs, from about $7.5\times10^9$ TILs to about $100\times10^9$ TILs, or from about $1\times10^9$ TILs to about $1\times10^{11}$ TILs.

20. The method of claim 1, wherein the third population of TILs in the step of the rapid second expansion provides for increased efficacy, increased interferon-gamma production, and/or increased polyclonality, compared to the first and/or second population of TILs.

21. The method of claim 1, wherein the third population of TILs in the step of the rapid second expansion provides for at least a one-fold to five-fold or more interferon-gamma production as compared to TILs prepared by a process longer than 18 days.

22. The method of claim 1, wherein effector T cells and/or central memory T cells obtained from the third population of TILs in the step of the rapid second expansion exhibit increased CD8 and CD28 expression relative to effector T cells and/or central memory T cells obtained from the second population of TILs in the step of the priming first expansion.

* * * * *